US012709641B2

(12) United States Patent
Carter et al.

(10) Patent No.: US 12,709,641 B2

(45) **Date of Patent: *Aug. 18, 2026**

(54) TAU BINDING COMPOUNDS

(71) Applicant: VOYAGER THERAPEUTICS, INC., Lexington, MA (US)

(72) Inventors: Todd Carter, Winchester, MA (US); Jinzhao Hou, Lexington, MA (US); Vinodhbabu Kurella, Woburn, MA (US); Allan D. Capili, Somerville, MA (US); Wencheng Liu, Cambridge, MA (US); Hiu Yan Chung, Boston, MA (US); Jerrah Holth, Sudbury, MA (US); Dillon Kavanagh, Cambridge, MA (US); Maneesha Anand Paranjpe, Burlington, MA (US)

(73) Assignee: VOYAGER THERAPEUTICS, INC., Lexington, MA (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/046,293

(22) Filed: Oct. 13, 2022

(65) Prior Publication Data

US 2023/0192830 A1 Jun. 22, 2023

Related U.S. Application Data

(63) Continuation of application No. PCT/US2021/027346, filed on Apr. 14, 2021.

(Continued)

(51) Int. Cl.

| | |
|---|---|
| ***C07K 16/18*** | (2006.01) |
| ***A61K 39/00*** | (2006.01) |

(Continued)

(52) U.S. Cl.

CPC .......... *C07K 16/18* (2013.01); *A61K 39/3955* (2013.01); *A61K 45/06* (2013.01);

(Continued)

(58) Field of Classification Search

CPC combination set(s) only.

See application file for complete search history.

(56) References Cited

U.S. PATENT DOCUMENTS

| | | |
|---|---|---|
| 7,176,290 B2 | 2/2007 | Mandelkow et al. |
| 8,609,097 B2 | 12/2013 | Bohrmann et al. |

(Continued)

FOREIGN PATENT DOCUMENTS

| | | |
|---|---|---|
| EP | 2625198 B1 | 7/2015 |
| EP | 2899208 A1 | 7/2015 |

(Continued)

OTHER PUBLICATIONS

Hasegawa, M. et al. "Characterization of mAb AP422, a novel phosphorylation-dependent monoclonal antibody against tau protein," FEBS Letters vol. 384, 1 (1996): 25-30.

(Continued)

*Primary Examiner* — Jeffrey Stucker

*Assistant Examiner* — Laura Ann Essex

(74) *Attorney, Agent, or Firm* — K&L Gates LLP

(57) ABSTRACT

The present disclosure provides anti-tau antibodies and vectorization thereof (e.g., into AAV particles). Also provided are methods of using anti-tau antibodies and/or AAV particles for prevention, treatment, and/or diagnosis of neurological indications.

43 Claims, 3 Drawing Sheets

Specification includes a Sequence Listing.

Kabat – Heavy chains

| Chain | 1 5 10 15 20 25 30 35 40 45 50 55 60 65 70 75 80 85 90 95 100 105 110 115 |
|---|---|
| Consensus | z#zLzzpGtz##+pg t# LtC+#Sg#t#t ##M%##+z+pg g#z##g #npnnggt- nz+#+ +%t#t#-+tttt%##z#tt%ttz-t%##### gtgtg#%- %gzgtt t |
| 2: LP004_VH | QVQLQQPGAELVKPGASVKLSCKASDYTFTNYWMHWVKQRPGRGLEWIGRIDPNSGGTRYNEKFKNKATLTVDKPSSTAYMHLSSLTSEDSAVYYCAGDEDWGTGTTVTVSS |
| 4: LP009_VH | EVQLVESGGALVQPGGSLSLSCAASGFTFTDYYMSWVRQPPGKALEWLALIRNKANGFTTEYSASVKGRFTISRDNSQSILLFQMNDLRADDSATYYCVRDINWGQGTTLTVSS |
| 6: LP022_VH | QVQLQQPGTELVKPGSSVNLSCKASGFTFTRYWMHWVKERPGHGLEWIGNINPNNGGTDFNEKFKNKATLTVHKSSTTVFIQLSSLTSEDSAVYYCARGTGTGAMDYWGQGTSVT |
| 8: LP023_VH | QVQLQQPGTELVKPGASVKLSCKASGYTFTEYWMHWVKQRPGHGLEWIGKINPNNGGDYNEKFKSKATLTVDKSSTTAYLQLSSLTSEDSAVYYCARGTGTGAMDYWGQGTSVT |
| 10: LP024_VH | QVQLQQPGTELVKPGASVKLSCKASGYTFTREWMHWVKQRPGQGLEWIGNINPNNGGTDNNERFKSKATLTVDRSSSTAYMQLSSLTSEDSAVYYCARGTGTGAMDYWGQGTSVT |
| 12: LP052_VH | QITLKESGPGILQSSQTLSLTCSFSGFSLSTSAMGVSWIRQPSGEGLEWLAHIYWDDDKRYNPSLKSRLTISKDTSRNQVFLKITSVDTADTATYYCARERRGYGMDYWGQGTSV |

Related U.S. Application Data

(60) Provisional application No. 63/162,976, filed on Mar. 18, 2021, provisional application No. 63/010,261, filed on Apr. 15, 2020.

(51) Int. Cl.
*A61K 39/395* (2006.01)
*A61K 45/06* (2006.01)
*A61P 25/28* (2006.01)

(52) U.S. Cl.
CPC ........ *A61P 25/28* (2018.01); *A61K 2039/505* (2013.01); *C07K 2317/14* (2013.01); *C07K 2317/22* (2013.01); *C07K 2317/24* (2013.01); *C07K 2317/31* (2013.01); *C07K 2317/34* (2013.01); *C07K 2317/54* (2013.01); *C07K 2317/55* (2013.01); *C07K 2317/565* (2013.01); *C07K 2317/622* (2013.01); *C07K 2317/76* (2013.01); *C07K 2317/92* (2013.01)

(56) References Cited

U.S. PATENT DOCUMENTS 8,697,076 B2 4/2014 Binder et al.
8,703,137 B2 4/2014 Chain
9,290,567 B2 3/2016 Bohrmann et al.
9,304,138 B2 4/2016 Pfeifer et al.
9,540,434 B2 1/2017 Pfeifer et al.
9,562,091 B2 2/2017 Grueninger et al.
9,598,485 B2 3/2017 Ayalon et al.
9,657,091 B2 5/2017 Pfeifer et al.
9,862,763 B2 1/2018 Dengl et al.
10,066,010 B2 9/2018 Pfeifer et al.
10,087,245 B2 10/2018 Lafaye et al.
10,100,104 B2 10/2018 Pfeifer et al.
10,196,439 B2 2/2019 Pedersen et al.
10,251,952 B2 4/2019 Bader et al.
10,400,018 B2 9/2019 Griswold-Prenner et al.
10,465,000 B2 11/2019 Grueninger et al.
10,538,582 B2 1/2020 Lafaye et al.
10,556,950 B2 2/2020 Eguchi et al.
10,562,962 B2 2/2020 Pedersen et al.
10,591,492 B2 3/2020 Kolb et al.
10,822,402 B2 11/2020 Dengl et al.
10,889,638 B2 1/2021 Barbour et al.
10,894,822 B2 1/2021 Chain
10,894,829 B2 1/2021 Eguchi et al.
10,934,348 B2 3/2021 Pedersen et al.
10,976,325 B2 4/2021 Kolb et al.
10,995,137 B2 5/2021 Pedersen et al.
11,124,563 B2 9/2021 Lafaye et al.
11,155,609 B2 10/2021 Chain et al.
11,326,182 B2 5/2022 Paul et al.
11,859,200 B2 1/2024 Nonnenmacher et al.
12,291,565 B2 5/2025 Liu et al.
2007/0280935 A1 12/2007 Bohrmann et al.
2010/0135991 A1* 6/2010 Huang ............... C07K 16/3061 424/139.1
2015/0086564 A1* 3/2015 Lambeau ............... C07K 16/40 530/389.1
2015/0183854 A1 7/2015 Mori et al.
2021/0070847 A1 3/2021 Giasson et al.
2021/0130449 A1 5/2021 Barbour et al.
2021/0179699 A1 6/2021 Chain
2021/0206843 A1 7/2021 Pedersen et al.
2021/0380677 A1 12/2021 Eguchi et al.
2021/0403541 A1 12/2021 Baker et al.
2022/0018857 A1 1/2022 Kolb et al.
2022/0064272 A1 3/2022 Chain et al.
2022/0096657 A1 3/2022 Paul et al.
2022/0146535 A1 5/2022 Chai et al.
2022/0339270 A1 10/2022 Liu et al.
2022/0389449 A1 12/2022 Paul et al.
2023/0075314 A1 3/2023 Hou et al.
2023/0192830 A1 6/2023 Carter et al.
2023/0203102 A1 6/2023 Nonnenmacher et al.
2024/0000971 A1 1/2024 Carter et al.
2024/0059766 A1 2/2024 Kurella et al.
2024/0200097 A1 6/2024 Nonnenmacher et al.
2025/0034559 A1 1/2025 Nonnenmacher et al.
2025/0282854 A1 9/2025 Liu et al.

FOREIGN PATENT DOCUMENTS

EP 2764022 B9 2/2017
EP 2670434 B1 12/2018
EP 3135689 B1 12/2018
EP 2834270 B1 10/2019
EP 2857039 B1 11/2019
EP 3164152 B1 2/2020
EP 3313877 B1 6/2020
EP 3662931 A1 6/2020
WO 2004016655 A1 2/2004
WO 2010142423 A2 12/2010
WO 2012045882 A2 4/2012
WO 2012054588 A2 4/2012
WO 2012106363 A2 8/2012
WO 2012149365 A2 11/2012
WO 2013041962 A1 3/2013
WO 2013050567 A1 4/2013
WO 2013151762 A1 10/2013
WO 2013180238 A1 12/2013
WO 2014011972 A1 1/2014
WO 2014028777 A2 2/2014
WO 2014096321 A1 6/2014
WO 2014100600 A2 6/2014
WO 2014150877 A2 9/2014
WO 2014152157 A2 9/2014
WO 2014165271 A2 10/2014
WO 2015091656 A1 6/2015
WO 2015114538 A1 8/2015
WO 2015120364 A1 8/2015
WO 2015122922 A1 8/2015
WO 2015142668 A1 9/2015
WO 2015197735 A1 12/2015
WO 2015197820 A1 12/2015
WO 2015197823 A2 12/2015
WO 2015200806 A2 12/2015
WO 2016079597 A1 5/2016
WO 2016137811 A1 9/2016
WO 2016196726 A1 12/2016
WO 2016207245 A1 12/2016
WO 2017005732 A1 1/2017
WO 2017005734 A1 1/2017
WO 2017009308 A2 1/2017
WO 2017189959 A1 11/2017
WO 2017189963 A1 11/2017
WO 2017191559 A1 11/2017
WO 2017191560 A1 11/2017
WO 2017191561 A1 11/2017
WO 2018071831 A1 4/2018
WO 2018106776 A2 6/2018
WO 2018106781 A1 6/2018
WO 2018127519 A1 7/2018
WO 2018154390 A1 8/2018
WO 2018170351 A1 9/2018
WO 2018178077 A1 10/2018
WO 2019077500 A1 4/2019
WO 2019094595 A2 5/2019
WO 2019110571 A1 6/2019
WO 2019171258 A1 9/2019
WO 2019171259 A1 9/2019
WO 2020097561 A1 5/2020
WO 2020180819 A1 9/2020
WO 2020201828 A1 10/2020
WO 2020223276 A1 11/2020
WO 2020242963 A1 12/2020
WO 202126279 A1 2/2021
WO 2021024209 A1 2/2021
WO 2021110995 A1 6/2021
WO 2021202777 A1 10/2021
WO 2021205359 A1 10/2021
WO 2021230987 A1 11/2021

(56) References Cited

FOREIGN PATENT DOCUMENTS

| | | | |
|---|---|---|---|
| WO | 2021262791 | A1 | 12/2021 |
| WO | 2022013286 | A1 | 1/2022 |
| WO | 2022098699 | A1 | 5/2022 |
| WO | 2022132923 | A1 | 6/2022 |
| WO | 2022144406 | A1 | 7/2022 |
| WO | 2023060269 | A1 | 4/2023 |
| WO | 2023091948 | A1 | 5/2023 |
| WO | 2023092004 | A1 | 5/2023 |
| WO | 2023201207 | A1 | 10/2023 |
| WO | 2023235791 | A1 | 12/2023 |
| WO | 2023250388 | A1 | 12/2023 |
| WO | 2024059739 | A1 | 3/2024 |
| WO | 2024229389 | A1 | 11/2024 |
| WO | 2025122634 | A1 | 6/2025 |

OTHER PUBLICATIONS

International Search Report and Written Opinion in International Patent Application No. PCT/US2021/027346 dated Sep. 10, 2021.

Ji, C. & Sigurdsson, E. M. "Current Status of Clinical Trials on Tau Immunotherapies," Drugs vol. 81, 10 (2021): 1135-1152.

Lichtenberg-Kraag, B. et al. "Phosphorylation-dependent epitopes of neurofilament antibodies on tau protein and relationship with Alzheimer tau," Proceedings of the National Academy of Sciences of the United States of America vol. 89, 12 (1992): 5384-8.

Liu, W. et al. "Efficacy evaluation of a novel vectorized anti-tau antibody, targeting a C-terminal phospho-tau epitope, using systemic dosing of a blood brain barrier penetrant AAV capsid in mouse models of tauopathies," Alzheimer's & Dementia: The Journal of the Alzheimer's Association vol. 18 (Suppl. 10) e062924 (2022).

Liu, W. et al. "Efficacy of a Novel Vectorized Antibody Targeting the C-Terminal Domain of Tau, Antibody 1, using Systemic Dosing of a Blood Brain Barrier Penetrant AAV Capsid in Mouse Models of Tauopathies," Molecular Therapies vol. 30, 4S1 (2022): 483, Abstract 1031.

Liu, W. et al. "Efficacy of a Novel Vectorized Antibody Targeting the C-Terminal Domain of Tau, Antibody 1, using Systemic Dosing of a Blood Brain Barrier Penetrant AAV Capsid in Mouse Models of Tauopathies," Poster presented at: American Society of Gene + Cell Therapy; May 16-19, 2022; Washington DC.

Liu, W. et al. "Efficacy of a Novel Vectorized Antibody Targeting the C-terminal Domain of Tau, Using Systemic Dosing of a Blood Brain Barrier Penetrant AAV Capsid in Mouse Models of Tauopathies," Poster presented at: Alzheimer's Association International Conference ; Jul. 31-Aug. 4, 2022; San Diego, CA.

Liu, W. et al. "Identification and Characterization of Novel Anti-tau Antibodies that Inhibit Tau-seed Mediated Pathology in a P301S Tauopathy Mouse Model of Alzheimer's Disease and Tauopathies," Poster presented at: Alzheimer's Association International Conference; Jul. 31-Aug. 4, 2022; San Diego, CA.

Liu, W. et al. "Identification and characterization of novel anti-tau antibodies that inhibit tau-seed mediated pathology in a P301S tauopathy mousemodel Alzheimer's Disease and tauopathies," Alzheimer's & Dementia: The Journal of the Alzheimer's Association vol. 18 (Suppl. 10) e062878 (2022).

Troquier, L. et al. "Targeting phospho-Ser422 by active Tau Immunotherapy in the THYTau22 mouse model: a suitable therapeutic approach," Current Alzheimer Research vol. 9, 4 (2012): 397-405.

Butler, M. et al. "Study Design of a Multiple Ascending Intravenous Dose Study Evaluating the Safety, Tolerability, and Pharmacokinetics of VY7523 in Participants with Early Alzheimer's Disease." Voyager Therapeutics, Inc., Poster, CTAD 2025: Clinical Trials on Alzheimer's Disease Conference, San Diego, CA, USA, Dec. 1, 2025, 1 page.

International Search Report and Written Opinion in International Patent Application No. PCT/US2023/074239 dated Jan. 17, 2024.

International Search Report and Written Opinion in International Patent Application No. PCT/US2024/058486 dated Mar. 12, 2025.

Ising, C. et al. "AAV-mediated expression of anti-tau scFvs decreases tau accumulation in a mouse model of tauopathy." The Journal of Experimental Medicine vol. 214, 5 (2017): 1227-1238.

Liu, W. et al. "AAV Gene Delivery of the Anti-Tau Antibody PHF1 Reduces Brain Tau Pathology in P301L Mice," Molecular Therapy vol. 23, Supplement 1 (2015): S237, Abstract 596.

Liu, W. et al. "Discrimination of Anti-tau Antibodies Targeting Different tau Epitopes by a P301S Mouse Hippocampal Seeding Model of Tauopathy." Voyager Therapeutics Inc., AD /PD 2025: Advances in Science & Therapy, Apr. 1-5, 2025, Vienna, Austria.

Lombana, T.N. et al. "Optimizing antibody expression by using the naturally occurring framework diversity in a live bacterial antibody display system." Scientific Reports vol. 5: 17488. Dec. 3, 2015.

Ratti, E. et al. "Results of a Phase 1, randomized, placebo-controlled, double-blind study to evaluate the safety, tolerability, and pharmacokinetics of ascending single IV doses of VY7523, a tau-targeting therapeutic, in healthy adult participants." Voyager Therapeutics, Inc., Presentation, CTAD 2025: Clinical Trials on Alzheimer's Disease Conference, San Diego, CA, USA, Dec. 4, 2025, 10 pages.

Sadhu, C. et al. "Pharmacokinetics and Pharmacodynamics of an Antibody Targeting Pathological Tau for the Treatment of Alzheimer's Disease: Nonclinical Studies in P301S Mice and Cynomolgus Macaques." Voyager Therapeutics, Inc., Poster, Alzheimer's Association International Conference, Jul. 28-Aug. 1, 2024, Philadelphia, PA, USA, 1 page.

Vandermeeren, M. et al. "Anti-Tau Monoclonal Antibodies Derived from Soluble and Filamentous Tau Show Diverse Functional Properties in vitro and in vivo." Journal of Alzheimer's Disease : JAD vol. 65,1 (2018): 265-281.

Voyager Therapeutics Inc. "Voyager Presents Robust Preclinical Data from Tau Targeting Gene Therapy and Antibody Programs at AD/PD™ 2025." Mar. 31, 2025 (Globe Newswire).

Voyager Therapeutics Inc. "Voyager Reports Positive Topline Data for Single Ascending Dose (SAD) Trial of Anti-Tau Antibody VY7523 and Initiates Multiple Ascending Dose (MAD) Trial in Alzheimer's Disease." Mar. 3, 2025 (Globe Newswire).

Voyager Therapeutics Inc. "VY7523-102: Randomized, Placebo-Controlled, Double-Blind, Multiple Ascending Dose Study in Participants with Early Alzheimer's Disease." NIH, ClinicalTrials.gov ID NCT06874621, Study Details, Last Update Posted Mar. 18, 2025.

Courade, Jean-Philippe et al. "Epitope determines efficacy of therapeutic anti-Tau antibodies in a functional assay with human Alzheimer Tau." Acta Neuropathologica, vol. 136,5 (2018): 729-745.

Li, M. et al. "Patent Technology for Anti-Tau Antibodies in the Diagnosis or Treatment of AD." China Science and Technology Information, No. 15 (2019): 33-35.

Malia, T. J. et al. "Epitope mapping and structural basis for the recognition of phosphorylated tau by the anti-tau antibody AT8." Proteins, vol. 84,4 (2016): 427-34.

* cited by examiner

FIG. 1A

Kabat – Light chains

| Chain | 1 5 10 15 20 25 30 35 40 45 50 55 60 65 70 75 80 85 90 95 100 105 110 |
| --- | --- |
| Consensus | -##MtQtP%tLp#S#G- #t#tC+tSzt##%tng%t %%#%%z pgztp #%%# %t tg p- %gttgtgt- t# #t #z%z-#g###%%zgt# p t gggt z |
| 1: LP004_VL | DIQMTQSPASLSASVGETVTITCRASGNIHNYLAWYQQRQGKSPQLLVYNAKTLPDGVPSRFSGSGSGTQYSLKINSLQPEDFGSYCCQHFWSTPLTFGAGTKLELK |
| 3: LP009_VL | DIVMSQSPSSLAVSVGEKVTMSCKSSQSLLYSTNQENYLAWYQQKPGQSPKLLIYWASSRESGVPDRFTGSGSGTDFTLTISSVKAEDLAVYYCQQYYSYPRTFGGGTKLEIK |
| 5: LP022_VL | DVVMTQTPLSLPVSLGDQASISCRSSQSLVHNNGITYLYWYLQKPGQSPKLLIYRVSNRFSGVPDRFGGSGSGTDFTLKISRVEAEDLGVYFCFQGTHVPRTFGGGTKLEIK |
| 7: LP023_VL | DVVMTQTPLSLPVSLGDHASISCRSSQSLVHSNGITHLYWYLQRPGQTPKLLIYRVSNRFSGVPDRFSGSGSGTDFTLKISSVEAEDLGVYFCFQGTHVPRTFGGGTKLEIE |
| 9: LP024_VL | DVVMTQTPLSLPVSLGDQASISCRSSQSLVHSNGNTHLYWYLQKPGQSPKLLIYRVSSRFSGVPDRFSGSGSGTDFTLKISRVEAEDLGVYFCFQGTHVPRTFGGGTKLEIK |
| 11: LP052_VL | SIVMTQTPKFLLVSAGDRVTITCKASQSVSNDVAWYQQKPGQSPKLLIYYASNRCTGVPDRFTGSGYGTDFTFTISTVQAEDLAVYFCQQDYRSPLTFGAGTKLELK |

FIG. 1B

Kabat – Heavy chains

| Chain | 1 5 10 15 20 25 30 35 40 45 50 55 60 65 70 75 80 85 90 95 100 105 110 115 |
| --- | --- |
| Consensus | z#zLzzpGtz##+pg t# LtC+#Sg#t#t ##M%##+z+pg g#z##g #npnnggt- nz+#+ +%t#t#-+tttt%##z#tt%ttz-t%##### gtgtg#%- %gzgtt t |
| 2: LP004_VH | QVQLQQPGAELVKPGASVKLSCKASDYTFTNYWMHWVKQRPGRGLEWIGRIDPNSGGTRYNEKFKNKATLTVDKPSSTAYMHLSSLTSEDSAVYYCAGDFDVWGTGTTVTVSS |
| 4: LP009_VH | EVQLVESGGALVQPGGSLSLSCAASGFTFTDYYMSWVRQPPGKALEWLALIRNKAKGFTTEYSASVKGRFTISRDNSQSILLFQMNDLRADDSATYYCVRDINYWGQGTTLTVSS |
| 6: LP022_VH | QVQLQQPGTELVKPGSSVNLSCKASGFTFTRYWMHWVKERPGHGLEWIGNINPNNGGTDFNEKFKNKATLTVHKSSTTVFIQLSSLTSEDSAVYYCARGTGTGAMDYWGQGTSVT |
| 8: LP023_VH | QVQLQQPGTELVKPGASVKLSCKASGYTFTIFWMHWVKQRPGHGLEWIGKINPNNGGGDYNEKFKSKATLTVDKSSTTAYLQLSSLTSEDSAVYYCARGTGTGAMDYWGQGTSVT |
| 10: LP024_VH | QVQLQQPGTELVKPGASVKLSCKASGYTFTREWMHWVKQRPGQGLEWIGNINPNNGGTDNNERFKSKATLTVDRSSSTAYMQLSSLTSEDSAVYYCARGTGTGAMDYWGQGTSVT |
| 12: LP052_VH | QITLKESGPGILQSSQTLSLTCSFSGFSLSTSAMGVSWIRQPSGEGLEWLAHIYWDDDKRYNPSLKSRLTISKDTSRNQVFLKITSVDTADTATYYCARRRRGYGMDYWGQGTSV |

FIG. 2A

Chothia – Light chains

| Chain | 1 5 10 15 20 25 30 35 40 45 50 55 60 65 70 75 80 85 90 95 100 105 110 |
| --- | --- |
| Consensus | -##MtQtP%tLp#S#G- #t#tC+tSzt##%tng%t %%#%%z pgztp #%%# %t tg p- %gttgtgt- t# #t #z%z-#g###%%zgt# p t gggt z |
| 1: LP004_VL | DIQMTQSPASLSASVGETVTITCRASGNIHNYLAWYQQRQGKSPQLLVYNAKTLPDGVPSRFSGSGSGTQYSLKINSLQPEDFGSYCCQHFWSTPLTFGAGTKLELK |
| 3: LP009_VL | DIVMSQSPSSLAVSVGEKVTMSCKSSQSLLYSTNQENYLAWYQQKPGQSPKLLIYWASSRESGVPDRFTGSGSGTDFTLTISSVKAEDLAVYYCQQYYSYPRTFGGGTKLEIK |
| 5: LP022_VL | DVVMTQTPLSLPVSLGDQASISCRSSQSLVHNNGITYLYWYLQKPGQSPKLLIYRVSNRFSGVPDRFGGSGSGTDFTLKISRVEAEDLGVYFCFQGTHVPRTFGGGTKLEIK |
| 7: LP023_VL | DVVMTQTPLSLPVSLGDHASISCRSSQSLVHSNGITHLYWYLQRPGQTPKLLIYRVSNRFSGVPDRFSGSGSGTDFTLKISSVEAEDLGVYFCFQGTHVPRTFGGGTKLEIE |
| 9: LP024_VL | DVVMTQTPLSLPVSLGDQASISCRSSQSLVHSNGNTHLYWYLQKPGQSPKLLIYRVSSRFSGVPDRFSGSGSGTDFTLKISRVEAEDLGVYFCFQGTHVPRTFGGGTKLEIK |
| 11: LP052_VL | SIVMTQTPKFLLVSAGDRVTITCKASQSVSNDVAWYQQKPGQSPKLLIYYASNRCTGVPDRFTGSGYGTDFTFTISTVQAEDLAVYFCQQDYRSPLTFGAGTKLELK |

FIG. 2B

Chothia – Heavy chains

| Chain | 1 5 10 15 20 25 30 35 40 45 50 55 60 65 70 75 80 85 90 95 100 105 110 115 |
| --- | --- |
| Consensus | z#zLzzpGtz##+pg t# LtC+#Sg#t#t ##M%##+z+pg g#z##g #npnnggt- nz+#+ +%t#t#-+tttt%##z#tt%ttz-t%##### gtgtg#%- %gzgtt t |
| 2: LP004_VH | QVQLQQPGAELVKPGASVKLSCKASDYTFTNYWMHWVKQRPGRGLEWIGRIDPNSGGTRYNEKFKNKATLTVDKPSSTAYMHLSSLTSEDSAVYYCAGDFDVWGTGTTVTVSS |
| 4: LP009_VH | EVQLVESGGALVQPGGSLSLSCAASGFTFTDYYMSWVRQPPGKALEWLALIRNKAKGFTTEYSASVKGRFTISRDNSQSILLFQMNDLRADDSATYYCVRDINYWGQGTTLTVSS |
| 6: LP022_VH | QVQLQQPGTELVKPGSSVNLSCKASGFTFTRYWMHWVKERPGHGLEWIGNINPNNGGTDFNEKFKNKATLTVHKSSTTVFIQLSSLTSEDSAVYYCARGTGTGAMDYWGQGTSVT |
| 8: LP023_VH | QVQLQQPGTELVKPGASVKLSCKASGYTFTIEWMHWVKQRPGHGLEWIGKINPNNGGGDYNEKFKSKATLTVDKSSTTAYLQLSSLTSEDSAVYYCARGTGTGAMDYWGQGTSVT |
| 10: LP024_VH | QVQLQQPGTELVKPGASVKLSCKASGYTFTRFWMHWVKQRPGQGLEWIGNINPNNGGTDNNERFKSKATLTVDRSSSTAYMQLSSLTSEDSAVYYCARGTGTGAMDYWGQGTSVT |
| 12: LP052_VH | QITLKESGPGILQSSQTLSLTCSFSGFSLSTSAMGVSWIRQPSGEGLEWLAHIYWDDDKRYNPSLKSRLTISKDTSRNQVFLKITSVDTADTATYYCARRRRGYGMDYWGQGTSV |

FIG. 3A

IMGT – Light chains

| Chain | 1 5 10 15 20 25 30 35 40 45 50 55 60 65 70 75 80 85 90 95 100 105 110 |
| --- | --- |
| Consensus | -##MtQtP%tLp#S#G- #t#tC+tSzt##%tng%t %%#%%z pgztp #%%# %t tg p- %gttgtgt- t# #t #z%z-#g###%%zgt# p t gggt z |
| 1: LP004_VL | DIQMTQSPASLSASVGETVTITCRASGNIHNYLAWYQQRQGKSPQLLVYNAKTLPDGVPSRFSGSGSGTQYSLKINSLQPEDFGSYCCQHFWSTPLTFGAGTKLELK |
| 3: LP009_VL | DIVMSQSPSSLAVSVGEKVTMSCKSSQSLLYSTNQENYLAWYQQKPGQSPKLLIYWASSRESGVPDRFTGSGSGTDFTLTISSVKAEDLAVYYCQQYYSYPRTFGGGTKLEIK |
| 5: LP022_VL | DVVMTQTPLSLPVSLGDQASISCRSSQSLVHNNGITYLYWYLQKPGQSPKLLIYRVSNRFSGVPDRFGGSGSGTDFTLKISRVEAEDLGVYFCFQGTHVPRTFGGGTKLEIK |
| 7: LP023_VL | DVVMTQTPLSLPVSLGDHASISCRSSQSLVHSNGITHLYWYLQRPGQTPKLLIYRVSNRFSGVPDRFSGSGSGTDFTLKISSVEAEDLGVYFCFQGTHVPRTFGGGTKLEIE |
| 9: LP024_VL | DVVMTQTPLSLPVSLGDQASISCRSSQSLVHSNGNTHLYWYLQKPGQSPKLLIYRVSSRFSGVPDRFSGSGSGTDFTLKISRVEAEDLGVYFCFQGTHVPRTFGGGTKLEIK |
| 11: LP052_VL | SIVMTQTPKFLLVSAGDRVTITCKASQSVSNDVAWYQQKPGQSPKLLIYYASNRCTGVPDRFTGSGYGTDFTFTISTVQAEDLAVYFCQQDYRSPLTFGAGTKLELK |

FIG. 3B

IMGT – Heavy chains

| Chain | 1 5 10 15 20 25 30 35 40 45 50 55 60 65 70 75 80 85 90 95 100 105 110 115 |
| --- | --- |
| Consensus | z#zLzzpGtz##+pg t# LtC+#Sg#t#t ##M%##+z+pg g#z##g #npnnggt- nz+#+ +%t#t#-+tttt%##z#tt%ttz-t%##### gtgtg#%- %gzgtt t |
| 2: LP004_VH | QVQLQQPGAELVKPGASVKLSCKASDYTFTNYWMHWVKQRPGRGLEWIGRIDPNSGGTRYNEKFKNKATLTVDKPSSTAYMHLSSLTSEDSAVYYCAGDFDVWGTGTTVTVSS |
| 4: LP009_VH | EVQLVESGGALVQPGGSLSLSCAASGFTFTDYYMSWVRQPPGKALEWLALIRNKAKGFTTEYSASVKGRFTISRDNSQSILLFQMNDLRADDSATYYCVRDINYWGQGTTLTVSS |
| 6: LP022_VH | QVQLQQPGTELVKPGSSVNLSCKASGFTFTRYWMHWVKERPGHGLEWIGNINPNNGGTDFNEKFKNKATLTVHKSSTTVFIQLSSLTSEDSAVYYCARGTGTGAMDYWGQGTSVT |
| 8: LP023_VH | QVQLQQPGTELVKPGASVKLSCKASGYTFTIEWMHWVKQRPGHGLEWIGKINPNNGGGDYNEKFKSKATLTVDKSSTTAYLQLSSLTSEDSAVYYCARGTGTGAMDYWGQGTSVT |
| 10: LP024_VH | QVQLQQPGTELVKPGASVKLSCKASGYTFTREWMHWVKQRPGQGLEWIGNINPNNGGTDNNERFKSKATLTVDRSSSTAYMQLSSLTSEDSAVYYCARGTGTGAMDYWGQGTSVT |
| 12: LP052_VH | QITLKESGPGILQSSQTLSLTCSFSGFSLSTSAMGVSWIRQPSGEGLEWLAHIYWDDDKRYNPSLKSRLTISKDTSRNQVFLKITSVDTADTATYYCARRRRGYGMDYWGQGTSV |

TAU BINDING COMPOUNDS

REFERENCE TO RELATED APPLICATIONS

This application is a continuation of International Application No. PCT/US2021/027346, filed on Apr. 14, 2021, which claims the benefit of the filing date of U.S. Provisional Patent Application Nos. 63/010,261, filed on Apr. 15, 2020, and 63/162,976, filed on Mar. 18, 2021, the entire contents of the above-referenced applications, including any sequences in the listings and drawings, are incorporated herein by reference.

SEQUENCE LISTING

The instant application contains a Sequence Listing which has been filed electronically in XML format and is hereby incorporated by reference in its entirety. Said XML copy, created on Dec. 16, 2025, is named V2071-1308USCON1_SL and is 1,371,717 bytes in size.

FIELD OF THE DISCLOSURE

The present disclosure presents tau binding compounds and adeno-associated virus (AAV) particles comprising the same.

BACKGROUND OF THE INVENTION

Tauopathies are a group of neurodegenerative diseases characterized by the dysfunction and/or aggregation of the microtubule associated protein tau. Tau is normally a very soluble protein known to associate with microtubules based on the extent of its phosphorylation. Tau is considered a critical component of intracellular trafficking processes, particularly in neuronal cells, given their unique and extended structure. Hyperphosphorylation of tau depresses its binding to microtubules and microtubule assembly activity. Further, hyperphosphorylation of tau renders it prone to misfolding and aggregation. In tauopathies, the tau becomes hyperphosphorylated, misfolds and aggregates as neurofibrillary tangles (NFT) of paired helical filaments (PHF), twisted ribbons or straight filaments. These NFT are largely considered indicative of impending neuronal cell death and thought to contribute to widespread neuronal cell loss, leading to a variety of behavioral and cognitive deficits.

A genetically defined tauopathy was described when mutations in the tau gene were shown to lead to an autosomal dominantly inherited tauopathy known as frontotemporal dementia and parkinsonism linked to chromosome 17 (FTDP-17). This provided evidence that changes in tau could lead to neurodegenerative changes in the brain. These molecules are considered to be more amyloidogenic, meaning they are more likely to become hyperphosphorylated and more likely to aggregate into NFT (Hutton, M. et al., 1998, Nature 393(6686):702-5).

Several approaches have been proposed for therapeutically interfering with progression of tau pathology and preventing the subsequent molecular and cellular consequences. Given that NFT are composed of hyperphosphorylated, misfolded and aggregated forms of tau, interference at each of these stages provides targets that can be pursued. Introducing agents that limit phosphorylation, block misfolding or prevent aggregation are promising strategies. It has also been suggested that introduction of anti-tau antibodies can prevent the trans-neuronal spread of tau pathology.

There remains a need for anti-tau antibodies for use in tauopathy treatment, diagnostics, and other applications. The present disclosure addresses this need with related compounds and methods described herein.

SUMMARY OF THE INVENTION

The present disclosure pertains at least in part to compositions and methods for modulating the level of tau, e.g., aggregation and or distribution of tau, and/or delivery, e.g., vectorized delivery of an antibody that binds to tau, e.g., an anti-tau antibody, e.g., an anti-tau antibody described herein. In some embodiments, the level of tau, e.g., aggregation or distribution, is reduced or inhibited using an anti-tau antibody described herein or an isolated, e.g., recombinant, AAV particle comprising a viral genome encoding an anti-tau antibody. e.g., an anti-tau antibody described herein. In some embodiments, the degradation of tau is increased using an anti-tau antibody described herein or an isolated, e.g., recombinant, AAV particle comprising a viral genome encoding an anti-tau antibody, e.g., an anti-tau antibody described herein. Such inhibition and/or degradation can be useful in treating disorders related to expression of tau and/or neurological disorders, such as tauopathies.

Accordingly, in one aspect, the present disclosure provides an isolated, e.g., recombinant antibody that binds to tau, comprising a heavy chain variable region (VH) comprising one, two, or three of a heavy chain complementary determining region 1 (HC CDR1), a heavy chain complementary determining region 2 (HC CDR2), and/or a heavy chain complementary determining region 3 (HC CDR3) of any of the HC CDR sequences of Table 1, 6, 2A-2C, 4, or 5; and/or a light chain variable region (VL) comprising one, two, or three of a light chain complementary determining region 1 (LC CDR1), a light chain complementary determining region 2 (LC CDR2), and/or a light chain complementary determining region 3 (LC CDR3) of any of the LC CDR sequences of Table 1, 6, 2A-2B, 4, or 5.

In another aspect, the present disclosure provides an isolated, e.g., recombinant antibody that binds to human tau, wherein the antibody binds the same or substantially the same epitope as a reference antibody, the reference antibody comprises a VH comprising an HC CDR1, an HC CDR2, and an HC CDR3 and a VL comprising a light LC CDR1, a LC CDR2, and a LC CDR3, wherein: the HC CDR1, HC CDR2, HC CDR3, LC CDR1, LC CDR2, and LC CDR3 comprise the amino acid sequence of SEQ ID NO: 315, 341, 410, 474, 529, and 571, respectively; the HC CDR1, HC CDR2, HC CDR3, LC CDR1, LC CDR2, and LC CDR3 comprise the amino acid sequence of SEQ ID NO: 314, 341, 410, 1154, 529, and 571, respectively; or the HC CDR1, HC CDR2, HC CDR3, LC CDR1, LC CDR2, and LC CDR3 comprise the amino acid sequence of SEQ ID NO: 316, 341, 410, 475, 530, and 571, respectively.

In another aspect, the present disclosure provides an isolated, e.g., recombinant, antibody that binds to human tau, wherein the antibody competes for binding with a reference antibody, wherein the reference antibody comprises a VH comprising an HC CDR1, an HC CDR2, and an HC CDR3 and a VL comprising a light LC CDR1, a LC CDR2, and a LC CDR3, wherein: the HC CDR1, HC CDR2, HC CDR3, LC CDR1, LC CDR2, and LC CDR3 comprise the amino acid sequence of SEQ ID NO: 315, 341, 410, 474, 529, and 571, respectively: the HC CDR1, HC CDR2, HC CDR3, LC CDR1, LC CDR2, and LC CDR3 comprise the amino acid sequence of SEQ ID NO: 314, 341, 410, 1154, 529, and 571, respectively; or the HC CDR1, HC CDR2, HC CDR3, LC CDR1, LC CDR2, and LC CDR3 comprise the amino acid sequence of SEQ ID NO: 316, 341, 410, 475, 530, and 571, respectively.

In yet another aspect, the present disclosure provides an isolated, e.g., recombinant, antibody that binds to a region of a human tau protein comprising residues 409-436, numbered according to SEQ ID NO: 920. In some embodiments, the antibody comprises a VH comprising an HC CDR1, an HC CDR2, and an HC CDR3 wherein: the HC CDR1, HC CDR2, HC CDR3 comprise the amino acid sequence of SEQ ID NOs: 1180, 341, and 410, respectively; the HC CDR1, HC CDR2, HC CDR3 comprise the amino acid sequence of $X_1X_2$WMH wherein $X_1$ is R or I and $X_2$ is Y or F. SEQ ID NO: 1184, and SEQ ID NO: 410, respectively; or the HC CDR1, HC CDR2, HC CDR3 comprise the amino acid sequence of SEQ ID NOs: 1186, 1187, and 1167, respectively. In some embodiments, the antibody comprises a VL comprising an LC CDR1, an LC CDR2, and an LC CDR3 wherein: the LC CDR1, LC CDR2, and LC CDR3 comprise the amino acid sequence of SEQ ID NOs: 1181, 1182, and 571, respectively; the LC CDR1, LC CDR2, and LC CDR3 comprise the amino acid sequence of SEQ ID NOs: 1185, 1182, and 571, respectively; or the LC CDR1, LC CDR2, and LC CDR3 comprise the amino acid sequence of SEQ ID NO: 1188, RVS, and SEQ ID NO: 571, respectively.

In yet another aspect, the present disclosure provides an antibody that binds, e.g., directly or indirectly, to a region of a human tau protein comprising residues 32-49, 55-76, 159-194, 185-200, 219-247, 381-426, and/or 409-436, numbered according to SEQ ID NO: 920.

In yet another aspect, the present disclosure provides an isolated, e.g., recombinant, nucleic acid that encodes an antibody described herein, e.g., an antibody comprising VH comprising one, two, or three of an HC CDR1, an HC CDR2, and/or an HC CDR3 of any of the HC CDR sequences of Table 1, 6, 2A-2C, 4, or 5; and/or a VL comprising one, two, or three of an LC CDR1, an LC CDR2, and/or an LC CDR3 of any of the LC CDR sequences of Table 1, 6, 2A-2C, 4, or 5.

In yet another aspect, the present disclosure provides a viral genome comprising a promoter operably linked to a nucleic acid encoding an antibody that binds to tau (e.g., an anti-tau antibody described herein). In some embodiments, the viral genome further comprises an internal terminal repeat (ITR) sequence (e.g., an ITR region described herein), an enhancer (e.g., an enhancer described herein), an intron region (e.g., an intron region described herein) and/or an exon region (e.g., an exon region described herein), a poly A signal region (e.g., a poly A signal sequence described herein), and/or an encoded miR binding site.

In yet another aspect, the present disclosure provides an isolated, e.g., recombinant, AAV particle comprising a capsid protein and a viral genome comprising nucleic acid encoding an antibody that binds to tau (e.g., an anti-tau antibody described herein). In some embodiments, the capsid protein comprises an AAV capsid protein, e.g., a wild-type AAV capsid protein or a functional variant thereof. In some embodiments, the capsid protein comprises, or is chosen from, an AAV9 capsid protein (e.g., a wild-type AAV9 capsid protein), a VOY101 capsid protein, a PHP.N capsid protein, or a PHP.B capsid protein, or a functional variant thereof.

In yet another aspect, the present disclosure provides method of delivering an exogenous antibody molecule that binds to tau (e.g., an anti-tau antibody molecule described herein), to a subject. The method comprising administering an effective amount of an AAV particle or a plurality of AAV particles, described herein, said AAV particle comprising a viral genome described herein.

In yet another aspect, the present disclosure provides a method of treating a subject having or being diagnosed as having a neurological disorder, a tauopathy, and/or a disease associated with expression of tau. The method comprising administering to the subject an effective amount of an AAV particle or a plurality of AAV particles, described herein, comprising a viral genome described herein.

In some embodiments, the present disclosure provides an antibody that includes (1) a heavy chain variable domain (VH), wherein the VH includes: a complementarity determining region (CDR) H1 that includes an amino acid sequence selected from the group consisting of SEQ ID NOs: 296-339, or a fragment thereof; a CDRH2 that includes an amino acid sequence selected from the group consisting of SEQ ID NOs: 340-391, or a fragment thereof; and a CDRH3 that includes an amino acid sequence selected from the group consisting of SEQ ID NOs: 392-456, or a fragment thereof; and (2) a light chain variable domain (VL), wherein the VL includes: a CDRL1 that includes an amino acid sequence selected from the group consisting of SEQ ID NOs: 457-514, or a fragment thereof; a CDRL2 that includes an amino acid sequence selected from the group consisting of SEQ ID NOS: 515-553, or a fragment thereof; and a CDRL3 that includes an amino acid sequence selected from the group consisting of SEQ ID NOs: 554-600, or a fragment thereof. The antibody may include a set of variable domain CDR amino acid sequences, wherein the variable domain CDR amino acid sequence set is selected from Table 6.

The VH may include: a framework region (FR) H1 that includes an amino acid sequence selected from the group consisting of SEQ ID NOs: 601-643, or a fragment thereof; a FRH2 that includes an amino acid sequence selected from the group consisting of SEQ ID NOs: 644-696, or a fragment thereof; a FRH3 that includes an amino acid sequence selected from the group consisting of SEQ ID NOs: 697-766, or a fragment thereof; and a FRH4 that includes an amino acid sequence selected from the group consisting of SEQ ID NOs: 767-775, or a fragment thereof.

The VL may include: a FRL1 that includes an amino acid sequence selected from the group consisting of SEQ ID NOs: 776-822, or a fragment thereof; a FRL2 that includes an amino acid sequence selected from the group consisting of SEQ ID NOs: 823-857, or a fragment thereof; a FRL3 that includes an amino acid sequence selected from the group consisting of SEQ ID NOs: 858-904, or a fragment thereof; and a FRL4 that includes an amino acid sequence selected from the group consisting of SEQ ID NOs: 905-919, or a fragment thereof.

The VH may include an amino acid sequence selected from the group consisting of SEQ ID NOs: 1-74; and/or an amino acid sequence that is encoded by a nucleic acid sequence selected from the group consisting of SEQ ID NOs: 147-220.

The VL may include an amino acid sequence selected from the group consisting of SEQ ID NOs: 75-146; and/or an amino acid sequence that is encoded by a nucleic acid sequence selected from the group consisting of SEQ ID NOs: 221-295.

The antibody may include a variable domain pair selected from Table 3.

The CDRH1 may include an amino acid sequence selected from the group consisting of GFTFTRY (SEQ ID NO: 314), GYTFTIF (SEQ ID NO: 315), and GYTFTRF (SEQ ID NO: 316). The CDRH2 may include the amino acid sequence of NPNNGG (SEQ ID NO: 341). The CDRH3 may include the amino acid sequence of GTGTGAMDY (SEQ ID NO: 410).

The CDRL1 may include an amino acid sequence selected from the group consisting of RSSQSLVHNNGITYLY (SEQ ID NO: 1154), RSSQSLVHSNGITHLY (SEQ ID NO: 474), and RSSQSLVHSNGNTHLY (SEQ ID NO: 475). The CDRL2 may include an amino acid sequence selected from the group consisting of RVSNRFS (SEQ ID NO: 529), and RVSSRFS (SEQ ID NO: 530). The CDRL3 may include the amino acid sequence of FQGTHVPRT (SEQ ID NO: 571).

The CDRH1 may include an amino acid sequence selected from the group consisting of GFSLSTSAM (SEQ ID NO: 325), GFSLNTSGM (SEQ ID NO: 326), GFSLSTSGM (SEQ ID NO: 321), and GFSLSTFGM (SEQ ID NO: 327). The CDRH2 may include the amino acid sequence of YWDDD (SEQ ID NO: 362). The CDRH3 may include an amino acid sequence selected from the group consisting of RRRGYGMDY (SEQ ID NO: 435), RVRGYGMDY (SEQ ID NO: 437), RVRYYAMDY (SEQ ID NO: 438), RKRSYGMDY (SEQ ID NO: 440), RSRRGNYDY (SEQ ID NO: 421), and RGYYSNGNYFDY (SEQ ID NO: 432).

The CDRL1 may include an amino acid sequence selected from the group consisting of KASQSVSNDVA (SEQ ID NO: 495), KSSQSLLNSGNQKNYLA (SEQ ID NO: 496), KSSQSLLSSGNQKNYLA (SEQ ID NO: 497), KSSQSLLDSDGKTYLN (SEQ ID NO: 484), and SASSSISSTYLH (SEQ ID NO: 493). The CDRL2 may include an amino acid sequence selected from the group consisting of YASNRCT (SEQ ID NO: 540), GTSTRES (SEQ ID NO: 542), GASTRES (SEQ ID NO: 543), LVSKLDS (SEQ ID NO: 532), and RTSNLAS (SEQ ID NO: 538). The CDRL3 may include an amino acid sequence selected from the group consisting of QQDYRSPLT (SEQ ID NO: 587), QNDHSHPYT (SEQ ID NO: 588), WQGTHFPQT (SEQ ID NO: 576), and QQGSSIPRYT (SEQ ID NO: 585).

Antibodies of the present disclosure may include a format selected from the group consisting of a monoclonal antibody, a multispecific antibody, a chimeric antibody, an antibody mimetic, a single chain Fv (scFv) format, and an antibody fragment. The antibody may include an antibody class selected from the group consisting of IgA, IgD, IgE, IgG, and IgM. The antibody may include a mouse IgG, wherein the mouse IgG includes an isotype selected from the group consisting of IgG1, IgG2a, IgG2b, IgG2c, and IgG3. The antibody may include a human IgG, wherein the human IgG includes an isotype selected from the group consisting of IgG1, IgG2, IgG3, and IgG4. The antibody may include one or more human constant domain. The one or more human constant domain may include a human IgG constant domain. The antibody may include a humanized antibody.

Antibodies of the present disclosure may bind to a tau protein epitope. The tau protein epitope may include or may be included within an amino acid sequence selected from the group consisting of SEQ ID NOs: 920-926. The antibody may compete for binding to the tau protein epitope with an antibody selected from one or more of AT100, AT120, PT3, C10.2, PT76, IPN002, 6C5, and UCB D. The tau protein epitope may include residues 409-436 of human tau (SEQ ID NO: 920). The tau protein epitope may include residues 413-430 of human tau (SEQ ID NO: 920). Antibody binding to the tau protein epitope may exhibit a $K_D$ of from about 0.1 nM to about 0.5 nM. The tau protein epitope may include residues 55-76, 159-194, 219-247, and/or 381-426 of human tau (SEQ ID NO: 920). The tau protein epitope may include residues 57-72, 175-191, 223-238, and/or 383-400 of human tau (SEQ ID NO: 920). The tau protein epitope may include residues 223-238 of human tau (SEQ ID NO: 920). Antibody binding to the tau protein epitope may exhibit a $K_D$ of from about 0.5 nM to about 5 nM. The tau protein epitope may include a region formed by a complex of at least two tau proteins. The antibody may bind to enriched paired helical filament tau protein (ePHF) with a half maximal effective concentration (EC50) of from about 0.01 nM to about 100 nM. The antibody may not bind to non-pathological tau. The antibody may bind to pathological tau. The antibody may inhibit tau aggregation with a half maximal inhibitory concentration (IC50) of from about 1 nM to about 30 nM as determined by immunodepletion assay. The immunodepletion assay may be carried out with tau RD Biosensor cells.

In some embodiments, the present disclosure provides an antibody that competes for binding with a second antibody to a tau protein epitope, wherein the tau protein epitope includes one or more of residues 32-49, 55-76, 57-72, 159-194, 175-191, 185-200, 219-247, 223-238, 381-426, 383-400, 409-436, and 413-430 of human tau (SEQ ID NO: 920). The tau protein epitope may include one or more of residues 409-436 and 413-430 of human tau (SEQ ID NO: 920). The second antibody may include a variable domain pair selected from the group consisting of: a VH with the amino acid sequence of SEQ ID NO: 21 and a VL with the amino acid sequence of SEQ ID NO: 93; a VH with the amino acid sequence of SEQ ID NO: 22 and a VL with the amino acid sequence of SEQ ID NO: 94; and a VH with the amino acid sequence of SEQ ID NO: 23 and a VL with the amino acid sequence of SEQ ID NO: 95.

Antibodies of the present disclosure may include a conjugate. The conjugate may include a therapeutic agent. The conjugate may include a detectable label.

In some embodiments, the present disclosure provides a construct encoding an antibody disclosed herein.

In some embodiments, the present disclosure provides a method of treating a therapeutic indication in a subject by administering an antibody disclosed herein to the subject. The therapeutic indication may be a neurological indication. The neurological indication may be a neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, or progressive subcortical gliosis.

In some embodiments, the present disclosure provides a method of diagnosing a therapeutic indication in a subject through the use of an antibody disclosed herein. The therapeutic indication may include a neurological indication. The neurological indication may be a neurodegenerative disease, AD, FTDP-17, FTLD, FTD, CTE, PSP, Down's syndrome, Pick's disease, CBD, corticobasal syndrome, ALS, a prion disease, CJD, multiple system atrophy, tangle-only dementia, stroke, or progressive subcortical gliosis. The antibody may be used to detect pathological tau in a subject tissue. The subject tissue may include CNS tissue. The subject tissue may be a thin tissue section. The thin tissue section may be a cryopreserved tissue section.

In some embodiments, the tau binding compounds or antibodies of the present disclosure may be encoded in an adeno-associated virus (AAV) viral genome. In some embodiments, the AAV viral genome may comprise one or more nucleic acid sequences encoding an antibody described herein, or a fragment thereof.

In some embodiments, the viral genome may comprise a 5' inverted terminal repeat (ITR) sequence region selected from SEQ ID NO: 1035 and 1036, a promoter sequence region selected from 1039-1050, a polyadenylation (polyA) sequence region selected from 1134-1136, and a 3' ITR selected from SEQ ID NO: 1037 and 1038.

In some embodiments, the viral genome may comprise one or more exon sequence regions selected from SEQ ID NO: 1051-1055, one or more intron sequence regions selected from SEQ ID NO: 1056-1070, one or more signal sequence regions selected from SEQ ID NO: 1071-1089, one or more tag sequence regions selected from SEQ ID NO: 1127-1133, and/or one or more filler sequence regions selected from SEQ ID NO: 1137 and 1138.

In some embodiments, the viral genome may have a first nucleic acid sequence and a second nucleic acid sequence wherein the first nucleic acid sequence encodes a VH and the second nucleic acid sequence encodes a VL. In some embodiments, the viral genome encodes a VH having an amino acid sequence selected from SEQ ID NO: 1-74. In some embodiments, the viral genome encodes a VL having an amino acid sequence selected from SEQ ID NO: 75-146. In some embodiments, the viral genome encodes a VH and VL pair selected from the pairings shown in Table 3.

In some embodiments, the first and second nucleic acid sequences of the viral genome are separated by one or more linker sequences, wherein the linker sequence(s) may be selected from SEQ ID NO: 1090-1126.

In some embodiments, the viral genome comprises a VH nucleic acid sequence selected from SEQ ID NO: 147-220. In some embodiments, the viral genome comprises a VL nucleic acid sequence selected from SEQ ID NO: 221-295.

In some embodiments, the viral genome may encode one or more CDR sequences having an amino acid sequence selected from SEQ ID NO: 296-600. In some embodiments, the viral genome may encode a set of CDRs selected from the CDR sets outlined in Table 6. In some embodiments, the viral genome may encode a CDR set pair selected from those outlined in Table 6.

In some embodiments, the viral genome may encode one or more FR amino acid sequence selected from SEQ ID NO: 601-919.

In some embodiments, the viral genome encodes from 5' to 3', an antibody heavy chain, one or more linker sequences, and an antibody light chain. In other embodiments, the viral genome encodes from 5' to 3', an antibody light chain, one or more linker sequences and an antibody heavy chain.

In some embodiments, an AAV viral genome described herein may be incorporated into an AAV particles.

In some embodiments, the AAV particle comprises an AAV capsid protein chosen from VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP. AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP. AAVPHP.B-TMP, AAVPHP.B-TTP, AAVPHP.S/G2A12, AAVG2A15/G2A3 (G2A3), AAVG2B4 (G2B4), AAVG2B5 (G2B5), AAVPHP.N (PHP.N), PHP.S. AAV1, AAV2, AAV2 variant, AAV2/3 variant, AAV4, AAV5, AAV6, AAV7, AAV8, AAV9.47, AAV9 (hu14), AAV9, AAV9 K449R, AAV10, AAV11, AAV12, AAVrh8, AAVrh10, AAVDJ, AAVDJ8, AAV2.BR1, or AAV2G9 capsid protein, or a functional variant thereof.

In certain embodiments, the AAV particle comprises a VOY101 capsid. In some embodiments, the VOY101 capsid amino acid sequence is given by SEQ ID NO: 1023.

In some embodiments, the viral genome of an AAV particle described herein may further comprise a nucleotide sequence encoding a miR binding site, e.g., a miR binding site that modulates, e.g., reduces, expression of the payload encoded by the viral genome in a cell or tissue where the corresponding miRNA is expressed.

In some embodiments, the viral genome of an AAV particle may further comprise at least 1-5 copies of an encoded miR binding site, e.g., at least 1, 2, 3, 4, or 5 copies. In some embodiments, the viral genome may comprise at least 3 copies of an encoded miR binding site, optionally wherein all three copies are for the same miR binding site or at least one, two, or all of the copies are for different miR binding sites.

In some embodiments, the viral genome may further comprise a nucleotide sequence encoding a miR122 binding site, a miR183 binding site, a miR-142-3p, or a combination thereof.

In some embodiments, the viral genome comprises an encoded miR122 binding site having the nucleotide sequence of SEQ ID NO: 1029, or a nucleotide sequence substantially identical (e.g., having at least 70%, 75%, 80%, 85%, 90%, 92%, 95%, 97%, 98%, or 99% sequence identity) thereto; or a nucleic acid sequence having at least one, two, three, four, five, six, or seven modifications but no more than ten modifications of SEQ ID NO: 1029.

In some embodiments, the viral genome comprises an encoded miR183 binding site having the nucleotide sequence of SEQ ID NO: 1032, or a nucleotide sequence substantially identical (e.g., having at least 70%, 75%, 80%, 85%, 90%, 92%, 95%, 97%, 98%, or 99% sequence identity) thereto; or a nucleic acid sequence having at least one, two, three, four, five, six, or seven modifications but no more than ten modifications of SEQ ID NO: 1032.

In some embodiments, the viral genome comprises an encoded miR-142-3p binding site having the nucleotide sequence of SEQ ID NO: 1031, or a nucleotide sequence substantially identical (e.g., having at least 70%, 75%, 80%, 85%, 90%, 92%, 95%, 97%, 98%, or 99% sequence identity) thereto; or a nucleic acid sequence having at least one, two, three, four, five, six, or seven modifications but no more than ten modifications of SEQ ID NO: 1031.

In some embodiments, the viral genome comprises at least 4 copies of an encoded miR binding site, optionally wherein all four copies comprise the same miR binding site or at least one, two, three, or all of the copies comprise a different miR binding site.

In some embodiments, the AAV particles disclosed herein may be formulated into a pharmaceutical composition.

The present disclosure provides a method of producing an antibody in a subject by administering a pharmaceutical composition to the subject.

The present disclosure also provides methods for preventing or treating a tauopathy in a subject by administering a therapeutically effective amount of a pharmaceutical composition described herein to a subject. The pharmaceutical composition may be administered by any route of administration including, but not limited to, intravenous, intramuscular, intraparenchymal, intracerebroventricular, intracisterna magna (ICM), intrathecal, or a combination thereof.

The tauopathy that may be treated by the methods and/or compositions of the present disclosure include, but are not limited to, AD, FTDP-17, FTLD, FTD, CTE, PSP, Down's syndrome, Pick's disease, CBD, Corticobasal syndrome, ALS, Prion diseases, CJD, Multiple system atrophy. Tangle-only dementia, and Progressive subcortical gliosis.

Those skilled in the art will recognize or be able to ascertain using no more than routine experimentation, many equivalents to the specific embodiments of the invention described herein. Such equivalents are intended to be encompassed by the following enumerated embodiment.

Enumerated Embodiments

E1. An isolated, e.g., recombinant, antibody that binds to human tau, wherein the antibody binds the same or substantially the same epitope as a reference antibody, the reference antibody comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and a light chain variable region (VL) comprising a light chain complementary determining region 1 (LC CDR1), a light chain complementary determining region 2 (LC CDR2), and a light chain complementary determining region 3 (LC CDR3), wherein:
- (i) the HC CDR1, HC CDR2, HC CDR3, LC CDR1, LC CDR2, and LC CDR3 comprise the amino acid sequence of SEQ ID NO: 315, 341, 410, 474, 529, and 571, respectively;
- (ii) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; or,
- (iii) the HC CDR1, HC CDR2, HC CDR3, LC CDR1, LC CDR2, and LC CDR3 comprise the amino acid sequence of SEQ ID NO: 316, 341, 410, 475, 530, and 571, respectively.

E2. An isolated, e.g., recombinant, antibody that binds to human tau, wherein the antibody competes for binding with a reference antibody, wherein the reference antibody comprises a heavy chain variable region (VH) comprising a heavy chain complementary determining region 1 (HC CDR1), a heavy chain complementary determining region 2 (HC CDR2), and a heavy chain complementary determining region 3 (HC CDR3) and a light chain variable region (VL) comprising a light chain complementary determining region 1 (LC CDR1), a light chain complementary determining region 2 (LC CDR2), and a light chain complementary determining region 3 (LC CDR3), wherein:
- (i) the HC CDR1, HC CDR2, HC CDR3, LC CDR1, LC CDR2, and LC CDR3 comprise the amino acid sequence of SEQ ID NO: 315, 341, 410, 474, 529, and 571, respectively;
- (ii) the HC CDR1, HC CDR2, HC CDR3, LC CDR1, LC CDR2, and LC CDR3 comprise the amino acid sequence of SEQ ID NO: 314, 341, 410, 1154, 529, and 571, respectively; or,
- (iii) the HC CDR1, HC CDR2, HC CDR3, LC CDR1, LC CDR2, and LC CDR3 comprise the amino acid sequence of SEQ ID NO: 316, 341, 410, 475, 530, and 571, respectively.

E3. The antibody of embodiment E1 or E2, wherein the reference antibody comprises:
- (i) a VH comprising the amino acid sequence of SEQ ID NO: 22 and a VL comprising the amino acid sequence of SEQ ID NO: 94;
- (ii) a VH comprising the amino acid sequence of SEQ ID NO: 21 and a VL comprising the amino acid sequence of SEQ ID NO: 93; or,
- (iii) a VH comprising the amino acid sequence of SEQ ID NO: 23 and a VL comprising the amino acid sequence of SEQ ID NO: 95.

E4. The antibody of any one of embodiments E1-E3, wherein the antibody binds an epitope that overlaps the epitope recognized by the reference antibody.

E5. The antibody of any one of embodiments E1-E4, wherein the antibody binds to a region of a human tau protein comprising residues 409-436, numbered according to SEQ ID NO: 920.

E6. The antibody of any one of embodiments E1-E5, wherein the antibody binds to a region of a human tau protein comprising residues 413-430, numbered according to SEQ ID NO: 920.

E7. The antibody of any one of embodiments E1-E6, which binds to a tau protein with a dissociation constant ($K_D$) of about 0.1 to about 10 nM, or about 0.2-5 nM.

E8. The antibody of any one of embodiments E1-E7, wherein the antibody comprises a heavy chain variable region comprising at least one, two, or three of an HC CDR1, an HC CDR2, and an HC CDR3 comprising the amino acid sequences of:
- (i) SEQ ID NOs: 1180, 341, and 410, respectively;
- (ii) $X_1X_2$WMH wherein $X_1$ is R or I and $X_2$ is Y or F, SEQ ID NO: 1184, and SEQ ID NO: 410, respectively; or
- (iii) SEQ ID NOs: 1186, 1187, and 1167, respectively.

E9. The antibody of any one of embodiments E1-E8, wherein the antibody comprises a light chain variable region (VL) comprising one, two, or three of an LC CDR1, an LC CDR2, and/or an LC CDR3 of:
- (i) SEQ ID NOs: 1181, 1182, and 571, respectively;
- (ii) SEQ ID NOs: 1185, 1182, and 571, respectively; or,
- (iii) SEQ ID NO: 1188, RVS, and SEQ ID NO: 571, respectively.

E10. The antibody of any one of embodiments E1-E9, wherein the antibody comprises:
- (i) the HC CDR1, HC CDR2, HC CDR3, LC CDR1, LC CDR2, and LC CDR3 comprise the amino acid sequence of SEQ ID NO: 315, 341, 410, 474, 529, and 571, respectively;
- (ii) the HC CDR1, HC CDR2, HC CDR3, LC CDR1, LC CDR2, and LC CDR3 comprise the amino acid sequence of SEQ ID NO: 1147, 1148, 410, 474, 529, and 571, respectively; or
- (iii) the HC CDR1, HC CDR2, HC CDR3, LC CDR1, LC CDR2, and LC CDR3 comprise the amino acid sequence of SEQ ID NO: 1168, SEQ ID NO: 1169, SEQ ID NO: 1167, SEQ ID NO: 1170, RVS, and SEQ ID NO: 571, respectively.

E11. The antibody of any one of embodiments E1-E9, wherein the antibody comprises:
- (i) the HC CDR1, HC CDR2, HC CDR3, LC CDR1, LC CDR2, and LC CDR3 comprise the amino acid sequence of SEQ ID NO: 314, 341, 410, 1154, 529, and 571, respectively;
- (ii) the HC CDR1, HC CDR2, HC CDR3, LC CDR1, LC CDR2, and LC CDR3 comprise the amino acid sequence of SEQ ID NO: 1144, 1145, 410, 1146, 529, and 571, respectively; or (iii) the HC CDR1, HC CDR2, HC CDR3, LC CDR1, LC CDR2, and LC CDR3 comprise the amino acid sequence of SEQ ID NO: 1165, SEQ ID NO: 1166, SEQ ID NO: 1167, SEQ ID NO: 473, RVS, and SEQ ID NO: 571, respectively.

E12. The antibody of any one of embodiments E1-E9, wherein the antibody comprises:

(i) the HC CDR1, HC CDR2, HC CDR3, LC CDR1, LC CDR2, and LC CDR3 comprise the amino acid sequence of SEQ ID NO: 316, 341, 410, 475, 530, and 571, respectively;

(ii) the HC CDR1, HC CDR2, HC CDR3, LC CDR1, LC CDR2, and LC CDR3 comprise the amino acid sequence of SEQ ID NO: 1149, 1150, 410, 475, 530, and 571, respectively; or (iii) the HC CDR1, HC CDR2, HC CDR3, LC CDR1, LC CDR2, and LC CDR3 comprise the amino acid sequence of SEQ ID NO: 1171, SEQ ID NO: 1166, SEQ ID NO: 1167, SEQ ID NO: 1172, RVS, and SEQ ID NO: 571, respectively.

E13. The antibody of any one of embodiments E1-E12, wherein the antibody comprises:

(i) a VH comprising the amino acid sequence of SEQ ID NO: 21-23, or an amino acid sequence having at least 70%, 75%, 80%, 85%, 90%, 92%, 95%, 96%, 97%, 98%, or 99% sequence identity thereto; and/or (ii) a VL comprising the amino acid sequence of SEQ ID NO: 93-95, or an amino acid sequence having at least 70%, 75%, 80%, 85%, 90%, 92%, 95%, 96%, 97%, 98%, or 99% sequence identity thereto.

E14. An isolated, e.g., recombinant, antibody that binds to a region of a human tau protein comprising residues 409-436, numbered according to SEQ ID NO: 920, and wherein the antibody comprises:

(i) a VH comprising an HC CDR1, an HC CDR2, and an HC CDR3 wherein:

(a) the HC CDR1, HC CDR2, HC CDR3 comprise the amino acid sequence of SEQ ID NOs: 1180, 341, and 410, respectively;

(b) the HC CDR1, HC CDR2, HC CDR3 comprise the amino acid sequence of $X_1X_2$WMH wherein $X_1$ is R or I and $X_2$ is Y or F, SEQ ID NO: 1184, and SEQ ID NO: 410, respectively; or (c) the HC CDR1, HC CDR2, HC CDR3 comprise the amino acid sequence of SEQ ID NOs: 1186, 1187, and 1167, respectively; and (ii) a VL comprising an LC CDR1, an LC CDR2, and an LC CDR3 wherein:

(a) the LC CDR1, LC CDR2, LC CDR3 comprise the amino acid sequence of SEQ ID NOs: 1181, 1182, and 571, respectively;

(b) the LC CDR1, LC CDR2, LC CDR3 comprise the amino acid sequence of SEQ ID NOs: 1185, 1182, and 571, respectively; or, (c) the LC CDR1, LC CDR2, LC CDR3 comprise the amino acid sequence of SEQ ID NO: 1188, RVS, and SEQ ID NO: 571, respectively.

E15. An antibody that binds, e.g., directly or indirectly, to a region of a human tau protein comprising residues 32-49, 55-76, 159-194, 185-200, 219-247, 381-426, and/or 409-436, numbered according to SEQ ID NO: 920.

E16. The antibody of embodiment E14 or E15, which binds a region of a human tau protein comprising residues 55-76, 159-194, 219-247, and/or 381-426, numbered according to SEQ ID NO: 920.

E17. The antibody of embodiment E14 or E15, which binds a region of a human tau protein comprising residues 57-72, 175-191, 223-238, and/or 383-400, numbered according to SEQ ID NO: 920.

E18. The antibody of embodiment E14 or E15, which binds a region of a human tau protein comprising residues 223-238, numbered according to SEQ ID NO: 920.

E19. The antibody of any one of embodiments E14-E17, which binds a conformational epitope comprising residues 55-76, 159-194, 219-247, and 381-426, numbered according to SEQ ID NO: 920.

E20. The antibody of any one of embodiments E15-E19, comprising:

(i) a VH comprising an HC CDR1, an HC CDR2, and an HC CDR3 comprising the amino acid sequence of SEQ ID NOs: 325, 362, and 435, respectively; and/or a VL comprising an LC CDR1, an LC CDR2, and an LC CDR3 comprising the amino acid sequence of SEQ ID NOs: 495, 540, and 587, respectively;

(ii) a VH comprising an HC CDR1, an HC CDR2, and an HC CDR3 comprising the amino acid sequence of SEQ ID NOs: 1152, 1153, and 435, respectively; and/or a VL comprising an LC CDR1, an LC CDR2, and an LC CDR3 comprising the amino acid sequence of SEQ ID NOs: 495, 540, and 587, respectively (iii) a VH comprising an HC CDR1, an HC CDR2, and an HC CDR3 comprising the amino acid sequence of SEQ ID NOs: 1173, 1174, and 1175, respectively; and/or a VL comprising an LC CDR1, an LC CDR2, and an LC CDR3 comprising the amino acid sequence of SEQ ID NO: 1176, YAS, and SEQ ID NO: 587, respectively.

E21. The antibody of any one of embodiments E14-E20, which binds to a tau protein with a dissociation constant ($K_D$) of about 0.1 to about 1 nM.

E22. An isolated, e.g., recombinant, antibody that binds to tau, comprising:

(i) a heavy chain variable region (VH) comprising one, two, or three of an HC CDR1, an HC CDR2, and/or an HC CDR3 of any of the HC CDR sequences of Table 1, 6, 2A-2C, 4, or 5; and/or (ii) a light chain variable region (VL) comprising one, two, or three of an LC CDR1, an LC CDR2, and/or an LC CDR3 of any of the LC CDR sequences of Table 1, 6, 2A-2C, 4, or 5.

E23. The antibody of embodiment E22, comprising a VH comprising the HC CDR1, the HC CDR2, and the HC CDR3 of any one of the antibodies in Table 1, 6, 2A-2C, 4, or 5.

E24. The antibody of embodiment E22 or E23, comprising a VL comprising the LC CDR1, the LC CDR2, and the LC CDR3 of any one of the antibodies in Table 1, 6, 2A-2C, 4, or 5.

E25. The antibody of any one of embodiments E22-E24, comprising a VH comprising the HC CDR1, the HC CDR2, and the HC CDR3 of any one of the antibodies in Table 1, 6, 2A-2C, 4, or 5; and a VL comprising the LC CDR1, the LC CDR2, and the LC CDR3 of said any one of the antibodies in Table 1, 6, 2A-2C, 4, or 5.

E26. The antibody of any one of embodiments E22-E25, comprising:

(i) an HC CDR1, an HC CDR2, and an HC CDR3 comprising the amino acid sequence of SEQ ID NO: 931 or 932, 341, and 410, respectively; and/or (ii) an LC CDR1, an LC CDR2, and an LC CDR3 comprising the amino acid sequence of SEQ ID NO: 933 or 934, 935 or 936, and 571, respectively.

E27. The antibody of any one of embodiments E22-E26, comprising:

(i) an HC DR1, an HC CDR2, and an HC CDR3 comprising the amino acid sequence of SEQ ID NOs: 1180, 341, and 410, respectively; and/or an LC CDR1, an LC CDR2, and an LC CDR3 comprising the amino acid sequence of SEQ ID NOs: 1181, 1182, and 571, respectively;

(ii) an HC DR1, an HC CDR2, and an HC CDR3 comprising the amino acid sequence of $X_1X_2$WMH wherein $X_1$ is R or I and $X_2$ is Y or F, SEQ ID NO: 1184, and SEQ ID NO: 410, respectively; and/or an LC CDR1, an LC CDR2, and an LC CDR3 comprising the amino acid sequence of SEQ ID NOs: 1185, 1182, and 571, respectively; or (iii) an HC DR1, an HC CDR2, and an HC CDR3 comprising the amino acid sequence of SEQ ID NOs: 1186, 1187, and 1167, respectively; and/or an LC CDR1, an LC CDR2, and an LC CDR3 comprising the amino acid sequence of SEQ ID NO: 1188, RVS, and SEQ ID NO: 571, respectively.

E28. The antibody of any one of embodiments E22-E27, comprising:

(i) an HC CDR1, an HC CDR2, and an HC CDR3 comprising the amino acid sequence of SEQ ID NOs: 315, 341, and 410, respectively; and/or an LC CDR1, an LC CDR2, and an LC CDR3 comprising the amino acid sequence of SEQ ID NOs: 474, 529, and 571, respectively;

(ii) an HC CDR1, an HC CDR2, and an HC CDR3 comprising the amino acid sequence of SEQ ID NOs: 1147, 1148, and 410, respectively; and/or an LC CDR1, an LC CDR2, and an LC CDR3 comprising the amino acid sequence of SEQ ID NOs: 474, 529, and 571, respectively; or (iii) an HC CDR1, an HC CDR2, and an HC CDR3 comprising the amino acid sequence of SEQ ID NOs: 1168, 1169, and 1167, respectively; and/or an LC CDR1, an LC CDR2, and an LC CDR3 comprising the amino acid sequence of SEQ ID NO: 1170, RVS, and SEQ ID NO: 571, respectively.

E29. The antibody of any one of embodiments E22-E27, comprising:

(i) an HC CDR1, an HC CDR2, and an HC CDR3 comprising the amino acid sequence of SEQ ID NOs: 314, 341, and 410, respectively; and/or an LC CDR1, an LC CDR2, and an LC CDR3 comprising the amino acid sequence of SEQ ID NOs: 1154, 529, and 571, respectively;

(ii) an HC CDR1, an HC CDR2, and an HC CDR3 comprising the amino acid sequence of SEQ ID NO: 1144, 1145, and 410, respectively; and/or an LC CDR1, an LC CDR2, and an LC CDR3 comprising the amino acid sequence of SEQ ID NO: 1146, 529, and 571, respectively; or (iii) an HC CDR1, an HC CDR2, and an HC CDR3 comprising the amino acid sequence of SEQ ID NOs: 1165, 1166, and 1167, respectively; and/or an LC CDR1, an LC CDR2, and an LC CDR3 comprising the amino acid sequence of SEQ ID NO: 473, RVS, and SEQ ID NO: 571, respectively.

E30. The antibody of any one of embodiments E22-E27, comprising:

(i) an HC CDR1, an HC CDR2, and an HC CDR3 comprising the amino acid sequence of SEQ ID NOs: 316, 341, and 410, respectively; and/or an LC CDR1, an LC CDR2, and an LC CDR3 comprising the amino acid sequence of SEQ ID NOs: 475, 530, and 571, respectively;

(ii) an HC CDR1, an HC CDR2, and an HC CDR3 comprising the amino acid sequence of SEQ ID NO: 1149, 1150, and 410, respectively; and/or an LC CDR1, an LC CDR2, and an LC CDR3 comprising the amino acid sequence of SEQ ID NO: 475, 1151, and 571, respectively; or (iii) an HC CDR1, an HC CDR2, and an HC CDR3 comprising the amino acid sequence of SEQ ID NOs: 1171, 1166, and 1167, respectively; and/or an LC CDR1, an LC CDR2, and an LC CDR3 comprising the amino acid sequence of SEQ ID NO: 1172, RVS, and SEQ ID NO: 571, respectively.

E31. The antibody of any one of embodiments E22-E27, comprising:

(i) an HC CDR1, an HC CDR2, and an HC CDR3 comprising the amino acid sequence of SEQ ID NOs: 325, 362, and 435, respectively; and/or an LC CDR1, an LC CDR2, and an LC CDR3 comprising the amino acid sequence of SEQ ID NOs: 495, 540, and 587, respectively;

(ii) an HC CDR1, an HC CDR2, and an HC CDR3 comprising the amino acid sequence of SEQ ID NO: 1152, 1153, and 435, respectively; and/or an LC CDR1, an LC CDR2, and an LC CDR3 comprising the amino acid sequence of SEQ ID NO: 495, 540, and 587, respectively; or (iii) an HC CDR1, an HC CDR2, and an HC CDR3 comprising the amino acid sequence of SEQ ID NOs: 1173, 1174, and 1175, respectively; and/or an LC CDR1, an LC CDR2, and an LC CDR3 comprising the amino acid sequence of SEQ ID NO: 1176, YAS, and SEQ ID NO: 587, respectively.

E32. The antibody of any one of embodiments E22-E27, comprising:

(i) an HC CDR1, an HC CDR2, and an HC CDR3 comprising the amino acid sequence of SEQ ID NOs: 304, 347, and 400, respectively; and/or an LC CDR1, an LC CDR2, and an LC CDR3 comprising the amino acid sequence of SEQ ID NOs: 464, 523, and 562, respectively;

(ii) an HC CDR1, an HC CDR2, and an HC CDR3 comprising the amino acid sequence of SEQ ID NO: 1142, 1143, and 400, respectively; and/or an LC CDR1, an LC CDR2, and an LC CDR3 comprising the amino acid sequence of SEQ ID NO: 464, 523, and 562, respectively; or (iii) an HC CDR1, an HC CDR2, and an HC CDR3 comprising the amino acid sequence of SEQ ID NOs: 1160, 1161, and 1162, respectively; and/or an LC CDR1, an LC CDR2, and an LC CDR3 comprising the amino acid sequence of SEQ ID NO: 1163, WAS, and SEQ ID NO: 562, respectively.

E33. The antibody of any one of embodiments E22-E27, comprising:

(i) an HC CDR1, an HC CDR2, and an HC CDR3 comprising the amino acid sequence of SEQ ID NOs: 299, 343, and 395, respectively; and/or an LC CDR1, an LC CDR2, and an LC CDR3 comprising the amino acid sequence of SEQ ID NOs: 460, 518, and 557, respectively;

(ii) an HC CDR1, an HC CDR2, and an HC CDR3 comprising the amino acid sequence of SEQ ID NO: 1140, 1141, and 395, respectively; and/or an LC CDR1, an LC CDR2, and an LC CDR3 comprising the amino acid sequence of SEQ ID NO: 460, 518, and 557, respectively; or (iii) an HC CDR1, an HC CDR2, and an HC CDR3 comprising the amino acid sequence of SEQ ID NOs: 1155, 1156, and 1157, respectively; and/or an LC CDR1, an LC CDR2, and an LC CDR3 comprising the amino acid sequence of SEQ ID NO: 1158, NAK, and SEQ ID NO: 557, respectively.

E34. The antibody of any one of the preceding embodiments, comprising:

(i) one, two, three, or all of a heavy chain framework region 1 (FRH1), a heavy chain framework region 2 (FRH2), a heavy chain framework region 3 (FRH3), and/or a heavy chain framework region 4 (FRH4) comprising the amino sequence of any of the heavy chain framework regions of the antibodies provided in Table 7 or 4; or (ii) one, two, three, or all of a heavy chain framework region 1 (FRH1), a heavy chain framework region 2 (FRH2), a heavy chain framework region 3 (FRH3), and/or a heavy chain framework region 4 (FRH4) comprising an amino acid sequence having at least one, two, or three but no more than four modifications, e.g., substitutions, relative to the amino acid sequence of any of the heavy chain framework regions of the antibodies provided in Table 7 or 4.

E35. The antibody of any one of the preceding embodiments, comprising:

(i) one, two, three, or all of an FRH1 comprising the amino acid sequence of SEQ ID NO: 603, an FRH2 comprising the amino acid sequence of SEQ ID NO: 664, an FRH3 comprising the amino acid sequence of SEQ ID NO: 718, and/or an FRH4 comprising the amino acid sequence of SEQ ID NO: 771; or an amino acid sequence having at least one, two, or three but no more than four modifications, e.g., substitutions, relative to each of the amino acid sequences of SEQ ID NO: 603, 664, 718, and/or 771;

(ii) one, two, three, or all of an FRH1 comprising the amino acid sequence of SEQ ID NO: 619, an FRH2 comprising the amino acid sequence of SEQ ID NO: 663, an FRH3 comprising the amino acid sequence of SEQ ID NO: 717, and/or an FRH4 comprising the amino acid sequence of SEQ ID NO: 771; or an amino acid sequence having at least one, two, or three but no more than four modifications, e.g., substitutions, relative to each of the amino acid sequences of SEQ ID NO: 619, 663, 717, and/or 771;

(iii) one, two, three, or all of an FRH1 comprising the amino acid sequence of SEQ ID NO: 603, an FRH2 comprising the amino acid sequence of SEQ ID NO: 665, an FRH3 comprising the amino acid sequence of SEQ ID NO: 719, and/or an FRH4 comprising the amino acid sequence of SEQ ID NO: 771; or an amino acid sequence having at least one, two, or three but no more than four modifications, e.g., substitutions, relative to each of the amino acid sequences of SEQ ID NO: 603, 665, 719, and/or 771;

(iv) one, two, three, or all of an FRH1 comprising the amino acid sequence of SEQ ID NO: 633, an FRH2 comprising the amino acid sequence of SEQ ID NO: 682, an FRH3 comprising the amino acid sequence of SEQ ID NO: 745, and/or an FRH4 comprising the amino acid sequence of SEQ ID NO: 771; or an amino acid sequence having at least one, two, or three but no more than four modifications, e.g., substitutions, relative to each of the amino acid sequences of SEQ ID NO: 663, 682, 745, and/or 771.

(v) one, two, three, or all of an FRH1 comprising the amino acid sequence of SEQ ID NO: 608, an FRH2 comprising the amino acid sequence of SEQ ID NO: 652, an FRH3 comprising the amino acid sequence of SEQ ID NO: 705, and/or an FRH4 comprising the amino acid sequence of SEQ ID NO: 767; or an amino acid sequence having at least one, two, or three but no more than four modifications, e.g., substitutions, relative to each of the amino acid sequences of SEQ ID NO: 608, 652, 705, and/or 767; or, (vi) one, two, three, or all of an FRH1 comprising the amino acid sequence of SEQ ID NO: 604, an FRH2 comprising the amino acid sequence of SEQ ID NO: 647, an FRH3 comprising the amino acid sequence of SEQ ID NO: 700, and/or an FRH4 comprising the amino acid sequence of SEQ ID NO: 770; or an amino acid sequence having at least one, two, or three but no more than four modifications, e.g., substitutions, relative to each of the amino acid sequences of SEQ ID NO: 604, 647, 700, and/or 770.

E36. The antibody of any one of the preceding embodiments, comprising:

(i) one, two, three, or all of a light chain framework region 1 (FRL1), a light chain framework region 2 (FRL2), a light chain framework region 3 (FRL3), and/or a light chain framework region 4 (FRL4) comprising the amino sequence of any of the light chain framework regions of the antibodies provided in Table 7 or 4; or (ii) one, two, three, or all of a light chain framework region 1 (FRL1), a light chain framework region 2 (FRL2), a light chain framework region 3 (FRL3), and/or a light chain framework region 4 (FRL4) comprising an amino acid sequence having at least one, two, or three but no more than four modifications, e.g., substitutions, relative to the amino acid sequence of any of the light chain framework regions of the antibodies provided in Table 7 or 4.

E37. The antibody of any one of the preceding embodiments, comprising:

(i) one, two, three, or all of an FRL1 comprising the amino acid sequence of SEQ ID NO: 793, an FRL2 comprising the amino acid sequence of SEQ ID NO: 836, an FRL3 comprising the amino acid sequence of SEQ ID NO: 874, and/or an FRL4 comprising the amino acid sequence of SEQ ID NO: 910; or an amino acid sequence having at least one, two, or three but no more than four modifications, e.g., substitutions, relative to each of the amino acid sequences of SEQ ID NO: 793, 836, 874, and/or 910;

(ii) one, two, three, or all of an FRL1 comprising the amino acid sequence of SEQ ID NO: 1178, an FRL2 comprising the amino acid sequence of SEQ ID NO: 831, an FRL3 comprising the amino acid sequence of SEQ ID NO: 1179, and/or an FRL4 comprising the amino acid sequence of SEQ ID NO: 906; or an amino acid sequence having at least one, two, or three but no more than four modifications, e.g., substitutions, relative to each of the amino acid sequences of SEQ ID NO: 1178, 831, 1179, and/or 906;

(iii) one, two, three, or all of an FRL1 comprising the amino acid sequence of SEQ ID NO: 787, an FRL2 comprising the amino acid sequence of SEQ ID NO: 831, an FRL3 comprising the amino acid sequence of SEQ ID NO: 870, and/or an FRL4 comprising the amino acid sequence of SEQ ID NO: 906, or an amino acid sequence having at least one, two, or three but no more than four modifications, e.g., substitutions, relative to each of the amino acid sequences of SEQ ID NO: 787, 831, 870, and/or 906; or (iv) one, two, three, or all of an FRL1 comprising the amino acid sequence of SEQ ID NO: 807, an FRL2 comprising the amino acid sequence of SEQ ID NO: 830, an FRL3 comprising the amino acid sequence of SEQ ID NO: 888, and/or an FRL4 comprising the amino acid sequence of SEQ ID NO: 908; or an amino acid sequence having at least one, two, or three but no more than four modifications, e.g., substitutions, relative to each of the amino acid sequences of SEQ ID NO: 807, 830, 888, and/or 908.

(v) one, two, three, or all of an FRL1 comprising the amino acid sequence of SEQ ID NO: 783, an FRL2 comprising the amino acid sequence of SEQ ID NO: 830, an FRL3 comprising the amino acid sequence of SEQ ID NO: 866, and/or an FRL4 comprising the amino acid sequence of SEQ ID NO: 906; or an amino acid sequence having at least one, two, or three but no more than four modifications, e.g., substitutions, relative to each of the amino acid sequences of SEQ ID NO: 783, 830, 866, and/or 906; or, (vi) one, two, three, or all of an FRL1 comprising the amino acid sequence of SEQ ID NO: 779, an FRL2 comprising the amino acid sequence of SEQ ID NO: 825, an FRL3 comprising the amino acid sequence of SEQ ID NO: 861, and/or an FRL4 comprising the amino acid sequence of SEQ ID NO: 908; or an amino acid sequence having at least one, two, or three but no more than four modifications, e.g., substitutions, relative to each of the amino acid sequences of SEQ ID NO: 779, 825, 861, and/or 908.

E38. The antibody of any one of embodiments E22-E37, comprising a VH comprising:

(i) the amino acid sequence of any VH provided in Table 3 or 4, or an amino acid sequence having at least 70%, 75%, 80%, 85%, 90%, 92%, 95%, 96%, 97%, 98%, or 99% sequence identity thereto;

(ii) an amino acid sequence having at least one, two or three modifications, but not more than 30, 20 or 10 modifications of the amino acid sequence of any VH provided in Table 3 or 4; or (iii) an amino acid sequence encoded by a nucleotide sequence of any VH provided in Table 3 or 4, or a nucleotide sequence having at least 70%, 75%, 80%, 85%, 90%, 92%, 95%, 96%, 97%, 98%, or 99% sequence identity thereto.

E39. The antibody of any one of embodiments E22-E38, comprising a VH comprising:

(i) the amino acid sequence of SEQ ID NO: 4, 9, 21-23, or 51, or an amino acid sequence having at least 70%, 75%, 80%, 85%, 90%, 92%, 95%, 96%, 97%, 98%, or 99% sequence identity thereto;

(ii) an amino acid sequence having at least one, two or three modifications, but not more than 30, 20 or 10 modifications of the amino acid sequence of SEQ ID NO: 4, 9, 21-23, or 51; or, (iii) an amino acid sequence encoded by the nucleotide sequence of SEQ ID NO: 150, 155, 167-169, or 197, or a nucleotide sequence having at least 70%, 75%, 80%, 85%, 90%, 92%, 95%, 96%, 97%, 98%, or 99% sequence identity thereto.

E40. The isolated antibody of any of the preceding embodiments, comprising a VH comprising, from N-terminus to C-terminus:

(i) an FRH1 comprising the amino acid sequence of any FRH1 of an antibody in Table 7;

(ii) an HC CDR1 comprising the amino acid sequence of the HC CDR1 of the antibody in Table 6 or 5;

(iii) an FRH2 comprising the amino acid sequence of the FRH2 of the antibody in Table 7 or 4;

(iv) an HC CDR2 comprising the amino acid sequence of the HC CDR2 of the antibody in Table 6 or 5;

(v) an FRH3 comprising the amino acid sequence of the FRH3 of the antibody in Table 7 or 4;

(vi) an HC CDR3 comprising the amino acid sequence of the HC CDR3 of the antibody in Table 6, or 5; and (vii) an FRH4 comprising the amino acid sequence of the FRH4 of the antibody in Table 7 or 4.

E41. The antibody of any one of the preceding embodiments comprising a VH comprising, from N-terminus to C-terminus, an FRH1, an HC CDR1, an FRH2, an HC CDR2, an FRH3, an HC CDR3, and an FRH4, wherein:

(i) the FRH1, HC CDR1, FRH2, HC CDR2, FRH3, HC CDR3, FRH4 comprise the amino acid sequences of SEQ ID NO: 603, 315, 664, 341, 718, 410, and 771, respectively;

(ii) the FRH1, HC CDR1, FRH2, HC CDR2, FRH3, HC CDR3, FRH4 comprise the amino acid sequences of SEQ ID NO: 619, 314, 663, 341, 717, 410, and 771, respectively;

(iii) the FRH1, HC CDR1, FRH2, HC CDR2, FRH3, HC CDR3, FRH4 comprise the amino acid sequences of SEQ ID NO: 603, 316, 665, 341, 719, 410, and 771, respectively;

(vi) the FRH1, HC CDR1, FRH2, HC CDR2, FRH3, HC CDR3, FRH4 comprise the amino acid sequences of SEQ ID NO: 663, 325, 682, 362, 745, 435, and 771, respectively.

(v) the FRH1, HC CDR1, FRH2, HC CDR2, FRH3, HCDR3, FRH4 comprise the amino acid sequences of SEQ ID NO: 608, 304, 652, 347, 705, 400, and 767, respectively; or, (vi) the FRH1, HC CDR1, FRH2, HC CDR2, FRH3, HC CDR3, FRH4 comprise the amino acid sequences of SEQ ID NO: 604, 299, 647, 343, 700, 395, and 770, respectively.

E42. The antibody of any one of embodiments E22-E41, wherein the nucleotide sequence encoding the VH comprises a nucleotide sequence of any VH provided in Table 3 or 4, or a nucleotide sequence having at least 70%, 75%, 80%, 85%, 90%, 92%, 95%, 96%, 97%, 98%, or 99% sequence identity thereto.

E43. The antibody of any one of embodiments E22-E42, wherein the nucleotide sequence encoding the VH comprises the nucleotide sequence of SEQ ID NO: 150, 155, 167-169, or 197, or a nucleotide sequence having at least 70%, 75%, 80%, 85%, 90%, 92%, 95%, 96%, 97%, 98%, or 99% sequence identity thereto.

E44. The antibody of any one of embodiments E22-E43, comprising a VL comprising:

(i) the amino acid sequence of any VL provided in Table 3 or 4, or an amino acid sequence having at least 70%, 75%, 80%, 85%, 90%, 92%, 95%, 96%, 97%, 98%, or 99% sequence identity thereto;

(ii) an amino acid sequence having at least one, two or three modifications, but not more than 30, 20 or 10 modifications of the amino acid sequence of any VL provided in Table 3 or 4; or (iii) an amino acid sequence encoded by a nucleotide sequence of any VL provided in Table 3 or 4, or a nucleotide sequence having at least 70%, 75%, 80%, 85%, 90%, 92%, 95%, 96%, 97%, 98%, or 99% sequence identity thereto.

E45. The antibody of any one of embodiments E22-E44, comprising a VL comprising:

(i) the amino acid sequence of SEQ ID NO: 78, 83, 93-95, or 122, or an amino acid sequence having at least 70%, 75%, 80%, 85%, 90%, 92%, 95%, 96%, 97%, 98%, or 99% sequence identity thereto;

(ii) an amino acid sequence having at least one, two or three modifications, but not more than 30, 20 or 10 modifications of the amino acid sequence of SEQ ID NO: 78, 83, 93-95, or 122; or (iii) an amino acid sequence encoded by the nucleotide sequence of SEQ ID NO: 224, 229, 241-243, or 270, or a nucleotide sequence having at least 70%, 75%, 80%, 85%, 90%, 92%, 95%, 96%, 97%, 98%, or 99% sequence identity thereto.

E46. The antibody of any of the preceding embodiments, comprising a VL comprising from N-terminus to C-terminus:

(i) an FRL1 comprising the amino acid sequence of any FRL1 of an antibody in Table 7 or 4;

(ii) an LC CDR1 comprising the amino acid sequence of the LC CDR1 of the antibody in Table 6 or 5;

(iii) an FRL2 comprising the amino acid sequence of the FRL2 of the antibody in Table 7 or 4;

(iv) an LC CDR2 comprising the amino acid sequence of the LC CDR2 of the antibody in Table 6 or 5;

(v) an FRL3 comprising the amino acid sequence of the FRL3 of the antibody in Table 7 or 4;

(vi) an LC CDR3 comprising the amino acid sequence of the LC CDR3 of the antibody in Table 6 or 5; and (vii) an FRL4 comprising the amino acid sequence of the FRL4 of the antibody in Table 7 or 4.

E47. The antibody of any one of the preceding embodiments comprising a VL comprising, from N-terminus to C-terminus, an FRL1, an LC CDR1, an FRL2, an LC CDR2, an FRL3, an LC CDR3, and an FRL4, wherein:

(i) the FRL1, LC CDR1, FRL2, LC CDR2, FRL3, LC CDR3, FRL4 comprise the amino acid sequences of SEQ ID NO: 793, 474, 836, 529, 874, 571, and 910, respectively;

(ii) the FRL1, LC CDR1, FRL2, LC CDR2, FRL3, LC CDR3, FRL4 comprise the amino acid sequences of SEQ ID NO: 1178, 1154, 831, 529, 1179, 571, and 906, respectively;

(iii) the FRL1, LC CDR1, FRL2, LC CDR2, FRL3, LC CDR3, FRL4 comprise the amino acid sequences of SEQ ID NO: 787, 475, 831, 530, 870, 571, and 906, respectively;

(iv) the FRL1, LC CDR1, FRL2, LC CDR2, FRL3, LC CDR3, FRL4 comprise the amino acid sequences of SEQ ID NO: 807, 495, 830, 540, 888, 587, and 908, respectively.

(v) the FRL1, LC CDR1, FRL2, LC CDR2, FRL3, LC CDR3, FRL4 comprise the amino acid sequences of SEQ ID NO: SEQ ID NO: 783, 464, 830, 523, 866, 562, and 906, respectively; or, (vi) the FRL1, LC CDR1, FRL2, LC CDR2, FRL3, LC CDR3, FRL4 comprise the amino acid sequences of SEQ ID NO: 779, 460, 825, 518, 861, 557, and 908, respectively.

E48. The antibody of any one of embodiments E22-E47, wherein the nucleotide sequence encoding the VL comprises a nucleotide sequence of any VL provided in Table 3 or 4, or a nucleotide sequence having at least 70%, 75%, 80%, 85%, 90%, 92%, 95%, 96%, 97%, 98%, or 99% sequence identity thereto.

E49. The antibody of any one of embodiments E22-E48, wherein the nucleotide sequence encoding the VL comprises the nucleotide sequence of SEQ ID NO: 224, 229, 241-243, or 270, or a nucleotide sequence having at least 70%, 75%, 80%, 85%, 90%, 92%, 95%, 96%, 97%, 98%, or 99% sequence identity thereto.

E50. The antibody of any one of the preceding embodiments, comprising:

(i) a VH comprising:

(a) the amino acid sequence of any VH provided in Table 3 or 4, or an amino acid sequence having at least 70%, 75%, 80%, 85%, 90%, 92%, 95%, 96%, 97%, 98%, or 99% sequence identity thereto;

(b) an amino acid sequence having at least one, two or three modifications, but not more than 30, 20 or 10 modifications of the amino acid sequence of any VH provided in Table 3 or 4; or (c) an amino acid sequence encoded by a nucleotide sequence of any VH provided in Table 3 or 4, or a nucleotide sequence having at least 70%, 75%, 80%, 85%, 90%, 92%, 95%, 96%, 97%, 98%, or 99% sequence identity thereto; and (ii) a VL comprising:

(a) the amino acid sequence of any VL provided in Table 3 or 4, or an amino acid sequence having at least 70%, 75%, 80%, 85%, 90%, 92%, 95%, 96%, 97%, 98%, or 99% sequence identity thereto;

(b) an amino acid sequence having at least one, two or three modifications, but not more than 30, 20 or 10 modifications of the amino acid sequence of any VL provided in Table 3 or 4; or (c) an amino acid sequence encoded by a nucleotide sequence of any VL provided in Table 3 or 4, or a nucleotide sequence having at least 70%, 75%, 80%, 85%, 90%, 92%, 95%, 96%, 97%, 98%, or 99% sequence identity thereto.

E51. The antibody of any one of the preceding embodiments, comprising the amino acid sequence of any VH of an antibody provided in Table 3 and 4, and the amino acid sequence of the VL of the antibody provided in Table 3 or 4.

E52. The antibody of any one of embodiments E22-E28 and E34-E51, comprising:

(i) a VH comprising the amino acid sequence of SEQ ID NO: 22, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 94, or an amino acid sequence having at least 70%, 75%, 80%, 85%, 90%, 92%, 95%, 96%, 97%, 98%, or 99% sequence identity thereto.

E53. The antibody of any one of embodiments E22-E27, E29, and E34-E51, comprising:

(i) a VH comprising the amino acid sequence of SEQ ID NO: 21, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 93, or an amino acid sequence having at least 70%, 75%, 80%, 85%, 90%, 92%, 95%, 96%, 97%, 98%, or 99% sequence identity thereto.

E54. The antibody of any one of embodiments E22-E27, E30, and E34-E51, comprising:

(i) a VH comprising the amino acid sequence of SEQ ID NO: 23, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 95, or an amino acid sequence having at least 70%, 75%, 80%, 85%, 90%, 92%, 95%, 96%, 97%, 98%, or 99% sequence identity thereto.

E55. The antibody of any one of embodiments E22-E27, E31, and E44-E51, comprising:

(i) a VH comprising the amino acid sequence of SEQ ID NO: 51, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 122, or an amino acid sequence having at least 70%, 75%, 80%, 85%, 90%, 92%, 95%, 96%, 97%, 98%, or 99% sequence identity thereto.

E56. The antibody of any one of embodiments E22-E27, E32, and E44-E51, comprising:

(i) a VH comprising the amino acid sequence of SEQ ID NO: 9, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 83, or an amino acid sequence having at least 70%, 75%, 80%, 85%, 90%, 92%, 95%, 96%, 97%, 98%, or 99% sequence identity thereto.

E57. The antibody of any one of embodiments E22-E27, and E33-E51, comprising:

(i) a VH comprising the amino acid sequence of SEQ ID NO: 4, or an amino acid sequence having at least 70%, 75%, 80%, 85%, 90%, 92%, 95%, 96%, 97%, 98%, or 99% sequence identity thereto; and (ii) a VL comprising the amino acid sequence of SEQ ID NO: 78, or an amino acid sequence having at least 70%, 75%, 80%, 85%, 90%, 92%, 95%, 96%, 97%, 98%, or 99% sequence identity thereto.

E58. The antibody of any one of the preceding embodiments, wherein the nucleotide sequence encoding the antibody comprises:

(i) the nucleotide sequence of SEQ ID NO: 150, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 224, or a nucleotide sequence having at least 70%, 75%, 80%, 85%, 90%, 92%, 95%, 96%, 97%, 98%, or 99% sequence identity thereto;

(ii) the nucleotide sequence of SEQ ID NO: 155, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 229, or a nucleotide sequence having at least 70%, 75%, 80%, 85%, 90%, 92%, 95%, 96%, 97%, 98%, or 99% sequence identity thereto;

(iii) the nucleotide sequence of SEQ ID NO: 167, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 241, or a nucleotide sequence having at least 70%, 75%, 80%, 85%, 90%, 92%, 95%, 96%, 97%, 98%, or 99% sequence identity thereto;

(iv) the nucleotide sequence of SEQ ID NO: 168, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 242, or a nucleotide sequence having at least 70%, 75%, 80%, 85%, 90%, 92%, 95%, 96%, 97%, 98%, or 99% sequence identity thereto;

(v) the nucleotide sequence of SEQ ID NO: 169, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 243, or a nucleotide sequence having at least 70%, 75%, 80%, 85%, 90%, 92%, 95%, 96%, 97%, 98%, or 99% sequence identity thereto; or (vi) the nucleotide sequence of SEQ ID NO: 197, or a nucleotide sequence having at least 70%, 75%, 80%, 85%, 90%, 92%, 95%, 96%, 97%, 98%, or 99% sequence identity thereto, and/or the nucleotide sequence of SEQ ID NO: 270, or a nucleotide sequence having at least 70%, 75%, 80%, 85%, 90%, 92%, 95%, 96%, 97%, 98%, or 99% sequence identity thereto.

E59. The antibody of any one of the preceding embodiments, which is a full length antibody, a bispecific antibody, an Fab, an $F(ab')_2$, an Fv, or a single chain Fv fragment (scFv).

E60. The antibody of any one of the preceding embodiments, comprising a heavy chain constant region selected from human IgG1, human IgG2, human IgG3, human IgG4, murine IgG1, murine IgG2a, murine IgG2b, murine IgG2c, and murine IgG3; and/or a light chain constant region chosen from the light chain constant regions of kappa or lambda.

E61. The antibody of any one of the preceding embodiments, comprising a heavy chain constant region comprising an amino acid of a heavy chain constant region provided in Table X, or an amino acid sequence having at least 70%, 75%, 80%, 85%, 90%, 92%, 95%, 96%, 97%, 98%, or 99% sequence identity thereto, and/or a light chain constant region comprising the amino acid sequence of a light chain constant region provided in Table X, or an amino acid sequence having at least 70%, 75%, 80%, 85%, 90%, 92%, 95%, 96%, 97%, 98%, or 99% sequence identity thereto.

E62. The antibody of any one of the preceding embodiments, wherein the nucleotide sequence encoding the heavy chain constant region comprises the nucleotide sequence of a heavy chain constant region provided in Table X, or a nucleotide sequence having at least 70%, 75%, 80%, 85%, 90%, 92%, 95%, 96%, 97%, 98%, or 99% sequence identity thereto, and/or the nucleotide sequence encoding the light chain constant region comprises the nucleotide sequence of a light chain constant region provided in Table X, or a nucleotide sequence having at least 70%, 75%, 80%, 85%, 90%, 92%, 95%, 96%, 97%, 98%, or 99% sequence identity thereto.

E63. The antibody of any one of the preceding embodiments, comprising:

(i) a VH comprising the amino acid sequence of any VH provided in Table 3 or 4, or an amino acid sequence having at least 70%, 75%, 80%, 85%, 90%, 92%, 95%, 96%, 97%, 98%, or 99% sequence identity thereto, and a heavy chain constant region comprising the amino acid sequence of an amino acid of a heavy chain constant region provided in Table X, or an amino acid sequence having at least 70%, 75%, 80%, 85%, 90%, 92%, 95%, 96%, 97%, 98%, or 99% sequence identity thereto; and/or (ii) a VL comprising the amino acid sequence of any VL provided in Table 3 or 4, or an amino acid sequence having at least 70%, 75%, 80%, 85%, 90%, 92%, 95%, 96%, 97%, 98%, or 99% sequence identity thereto, and a light chain constant region comprising the amino acid sequence of an amino acid of a light chain constant region provided in Table X, or an amino acid sequence having at least 70%, 75%, 80%, 85%, 90%, 92%, 95%, 96%, 97%, 98%, or 99% sequence identity thereto.

E64. The antibody of any one of the preceding embodiments, comprising:

(i) a VH comprising the amino acid sequence of SEQ ID NO: 4, 9, 21-23, or 51, or an amino acid sequence having at least 70%, 75%, 80%, 85%, 90%, 92%, 95%, 96%, 97%, 98%, or 99% sequence identity thereto, and a heavy chain constant region comprising the amino acid sequence of an amino acid of a heavy chain constant region provided in Table X, or an amino acid sequence having at least 70%, 75%, 80%, 85%, 90%, 92%, 95%, 96%, 97%, 98%, or 99% sequence identity thereto; and/or;

(ii) a VL comprising the amino acid sequence of SEQ ID NO: 78, 83, 93-95, or 122, or an amino acid sequence having at least 70%, 75%, 80%, 85%, 90%, 92%, 95%, 96%, 97%, 98%, or 99% sequence identity thereto, and a light chain constant region comprising the amino acid sequence of an amino acid of a light chain constant region provided in Table X, or an amino acid sequence having at least 70%, 75%, 80%, 85%, 90%, 92%, 95%, 96%, 97%, 98%, or 99% sequence identity thereto.

E65. The antibody of any one of the preceding embodiments, which antibody binds the C-terminus of a tau protein, e.g., residues 409-436 numbered according to SEQ ID NO: 920.

E66. The antibody of any one of the preceding embodiments, which antibody binds a microtubule binding domain of a tau protein.

E67. The antibody of any one of the preceding embodiments, which antibody binds a proline rich domain of a tau protein.

E68. The antibody of any one of the preceding embodiments, which antibody binds to a tau protein with a dissociation constant ($K_D$) of less than about 120 nM, e.g., measured by Octet, e.g., as described in Example 8.

E69. The antibody of any one of the preceding embodiments, which antibody binds to a tau protein with a $K_D$ of about 0.1 nM to about 0.5 nM.

E70. The antibody of any one of the preceding embodiments, which antibody is capable of binding to a tau protein with a $K_D$ of about 0.5 nM to about 5 nM.

E71. The antibody of any one of the preceding embodiments, which antibody is capable of binding to a tau protein with a $K_D$ of about 5 nM to about 30 nM.

E72. The antibody of any one of the preceding embodiments, which antibody binds a tau protein which comprises at least one, two, three or more phosphorylated residues, e.g., residue T212, T217, S396, S404, S409, or combination thereof, numbered according to SEQ ID NO: 920.

E73. The antibody of any one of the preceding embodiments, which antibody binds enriched paired helical filament tau protein (ePHF), e.g., at a half maximal effective concentration (EC50) of from about 0.01 nM to about 100 nM.

E74. The antibody of any one of the preceding embodiments, which antibody reduces, e.g., inhibits, aggregation of tau.

E75. The antibody of any one of the preceding embodiments, which antibody inhibits aggregation of tau at a half maximal inhibitory concentration (IC50) of from about 1 nM to about 30 nM, e.g., as measured by an immunodepletion assay (e.g., with tau RD Biosensor cells), e.g., as described in Example 6.

E76. The antibody of any one of the preceding embodiments, which binds an epitope comprising a region formed by a complex of at least two tau proteins, e.g., a tau dimer.

E77. An antibody that competes for binding to tau with the antibody of any one of the preceding embodiments.

E78. An antibody that binds to the same epitope as, substantially the same epitope as, or an epitope that overlaps with, the epitope of the antibody of any one of the preceding embodiments.

E79. An isolated, e.g., recombinant, nucleic acid encoding the antibody of any one of the preceding embodiments.

E80. An isolated, e.g., recombinant, nucleic acid encoding an antibody that binds to tau, wherein the antibody comprises:

(i) a heavy chain variable region (VH) comprising at least one, two, or three of an HC CDR1, an HC CDR2, and/or an HC CDR3 of an antibody in Table 1, 6, 2A-2C, 4, or 5; and/or (ii) a light chain variable region (VL) comprising at least one, two, or three of an LC CDR1, an LC CDR2, and/or an LC CDR3 of the antibody in Table 1, 6, 2A-2C, 4, or 5.

E81. The nucleic acid of embodiment E80, wherein:

(i) the HC CDR1, HC CDR2, HC CDR3, LC CDR1, LC CDR2, and LC CDR3 comprise the amino acid sequence of SEQ ID NO: 315, 341, 410, 474, 529, and 571, respectively;

(ii) the HC CDR1, HC CDR2, HC CDR3, LC CDR1, LC CDR2, and LC CDR3 comprise the amino acid sequence of SEQ ID NO: 314, 341, 410, 1154, 529, and 571, respectively;

(iii) the HC CDR1, HC CDR2, HC CDR3, LC CDR1, LC CDR2, and LC CDR3 comprise the amino acid sequence of SEQ ID NO: 316, 341, 410, 475, 530, and 571, respectively;

(iv) the HC CDR1, HC CDR2, HC CDR3, LC CDR1, LC CDR2, and LC CDR3 comprise the amino acid sequence of SEQ ID NO: 325, 362, 435, 495, 540, and 587, respectively;

(v) the HC CDR1, HC CDR2, HC CDR3, LC CDR1, LC CDR2, and LC CDR3 comprise the amino acid sequence of SEQ ID NO: 304, 347, 400, 464, 523, and 562, respectively; or, (vi) the HC CDR1, HC CDR2, HC CDR3, LC CDR1, LC CDR2, and LC CDR3 comprise the amino acid sequence of SEQ ID NO: 299, 343, 395, 460, 518, and 557, respectively.

E82. The nucleic acid of embodiment E80, wherein the antibody comprises:

(i) a VH comprising the amino acid sequence of any VH provided in Table 3 or 4, an amino acid sequence having at least 70%, 75%, 80%, 85%, 90%, 92%, 95%, 96%, 97%, 98%, or 99% sequence identity to any VH provided in Table 3 or 4, or an amino acid sequence having at least one, two or three modifications, but not more than 30, 20 or 10 modifications of the amino acid sequence of any VH provided in Table 3 or 4; and/or (ii) a VL comprising the amino acid sequence of any VL provided in Table 3 or 4; an amino acid sequence having at least 70%, 75%, 80%, 85%, 90%, 92%, 95%, 96%, 97%, 98%, or 99% sequence identity to any VL provided in Table 3 or 4; or an amino acid sequence having at least one, two or three modifications, but not more than 30, 20 or 10 modifications of the amino acid sequence of any VL provided in Table 3 or 4.

E83. The nucleic acid of any one of embodiments E80-E82, wherein the antibody comprises:

(i) a VH comprising the amino acid sequence of SEQ ID NO: 4, 9, 21-23, or 51, or an amino acid sequence having at least 70%, 75%, 80%, 85%, 90%, 92%, 95%, 96%, 97%, 98%, or 99% sequence identity thereto; or an amino acid sequence having at least one, two or three modifications, but not more than 30, 20 or 10 modifications of the amino acid sequence of SEQ ID NO: 4, 9, 21-23, or 51; and/or (ii) a VL comprising the amino acid sequence of SEQ ID NO: 78, 83, 93-95, or 122, or an amino acid sequence having at least 70%, 75%, 80%, 85%, 90%, 92%, 95%, 96%, 97%, 98%, or 99% sequence identity thereto; or an amino acid sequence having at least one, two or three modifications, but not more than 30, 20 or 10 modifications of the amino acid sequence of SEQ ID NO: 78, 83, 93-95, or 122.

E84. The nucleic acid of any one embodiments E80-E83, wherein the antibody comprises:

(i) a heavy chain constant region comprising an amino acid of a heavy chain constant region provided in Table X, or an amino acid sequence having at least 70%, 75%, 80%, 85%, 90%, 92%, 95%, 96%, 97%, 98%, or 99% sequence identity thereto; and/or (ii) a light chain constant region comprising the amino acid sequence of a light chain constant region provided in Table X, or an amino acid sequence having at least 70%, 75%, 80%, 85%, 90%, 92%, 95%, 96%, 97%, 98%, or 99% sequence identity thereto.

E85. The nucleic acid of any one of embodiments E80-E84, comprising:

(i) the nucleotide sequence of any VH provided in Table 3 or 4, or a nucleotide sequence having at least 70%, 75%, 80%, 85%, 90%, 92%, 95%, 96%, 97%, 98%, or 99% sequence identity thereto; and/or (ii) the nucleotide sequence of any VL provided in Table 3 or 4, or a nucleotide sequence having at least 70%, 75%, 80%, 85%, 90%, 92%, 95%, 96%, 97%, 98%, or 99% sequence identity thereto.

E86. The nucleic acid of any one of embodiments E80-E85, comprising:

(i) the nucleotide sequence of SEQ ID NO: 150, 155, 167-169, or 197, or a nucleotide sequence having at least 70%, 75%, 80%, 85%, 90%, 92%, 95%, 96%, 97%, 98%, or 99% sequence identity thereto; and/or (ii) the nucleotide sequence of SEQ ID NO: 224, 229, 241-243, or 270, or a nucleotide sequence having at least 70%, 75%, 80%, 85%, 90%, 92%, 95%, 96%, 97%, 98%, or 99% sequence identity thereto.

E87. The isolated nucleic acid sequence of any one of embodiments E79-E86, wherein the nucleic acid sequence encoding the heavy chain variable region and/or the light chain variable region is codon-optimized.

E88. An isolated, e.g., recombinant, antibody encoded by the nucleic acid of any one of embodiments E79-E87.

E89. A vector comprising the nucleic acid of any one of embodiments E79-E87, or a nucleic acid encoding the antibody of any one of embodiments E1-E78 and E88.

E90. A host cell comprising the nucleic acid of any one of embodiments E79-E87, a nucleic acid encoding the antibody of any one of embodiments E1-E78 and E88, or the vector (e.g., expression vector) of embodiment E89.

E91. The host cell of embodiment E90, wherein the host cell is an insect cell, bacterial cell, or a mammalian cell.

E92. A method of producing an antibody, the method comprising culturing the host cell of embodiment E90 or E91, under conditions suitable for gene expression.

E93. An isolated nucleic acid encoding a payload, wherein the encoded payload comprises the antibody of any one of embodiments E1-E78 and E88.

E94. The nucleic acid of embodiment E93, further encoding a signal sequence, optionally wherein the nucleotide sequence encoding the signal sequence comprises the nucleotide sequence of any of the signal sequences listed in Table 14, or a nucleotide sequence with at least 95% sequence identity thereto.

E95. The nucleic acid of any one of embodiments E93-E94, further encoding a second signal sequence, optionally wherein the nucleotide sequence encoding the signal sequence comprises the nucleotide sequence of any of the signal sequences listed in Table 14, or a nucleotide sequence with at least 95% sequence identity thereto.

E96. The nucleic acid of any one of embodiments E93-E95, wherein the:

(i) the nucleotide sequence encoding the signal sequence is located 5' relative to the nucleotide sequence encoding the VH; and/or (ii) the nucleotide sequence encoding the signal sequence is located 5' relative to the nucleotide sequence encoding the VL.

E97. The nucleic acid of any one of embodiments E93-E96, wherein the sequences of the encoded VH and VL are connected directly, e.g., without a linker.

E98. The nucleic acid of any one of embodiments E93-E97, wherein the sequences of the encoded VH and VL are connected via a linker.

E99. The nucleic acid of embodiment E98, wherein the linker comprises the nucleotide sequence of any of the linker sequences provided in Table 15, or a nucleotide sequence with at least 95% sequence identity thereto.

E100. The nucleic acid of any one of embodiments E93-E99, wherein the encoded payload is a full length antibody, a bispecific antibody, an Fab, an $F(ab')_2$, an Fv, a single chain Fv fragment (scFv), single domain antibody, or a camelid antibody.

E101. A viral genome comprising a promoter operably linked to the nucleic acid encoding a payload comprising the antibody of any one of embodiments E1-E78 and E88.

E102. The viral genome of embodiment E101, wherein the promoter:
  (i) is chosen from human elongation factor 1α-subunit (EF1α), cytomegalovirus (CMV) immediate-early enhancer and/or promoter, chicken β-actin (CBA) and its derivative CAG. β glucuronidase (GUSB), or ubiquitin C (UBC), neuron-specific enolase (NSE), platelet-derived growth factor (PDGF), platelet-derived growth factor B-chain (PDGF-β), intercellular adhesion molecule 2 (ICAM-2), synapsin (Syn), methyl-CpG binding protein 2 (MeCP2), Ca2+/calmodulin-dependent protein kinase II (CaMKII), metabotropic glutamate receptor 2 (mGluR2), neurofilament light (NFL) or heavy (NFH), β-globin minigene nβ2, preproenkephalin (PPE), enkephalin (Enk) and excitatory amino acid transporter 2 (EAAT2), glial fibrillary acidic protein (GFAP), myelin basic protein (MBP), or a fragment, e.g., a truncation, or a functional variant thereof; and/or
  (ii) comprises the nucleotide sequence of any of the promoter sequences provided in Table 11, or a nucleotide sequence at least 95% identical thereto.

E103. The viral genome of any one of embodiments E101-E102, which further comprises an enhancer, optionally wherein the enhancer is a CMV immediate-early (CMVie) enhancer.

E104. The viral genome of any one of embodiments E101-E103, which further comprises a polyadenylation (polyA) signal region.

E105. The viral genome of embodiment E104, wherein the polyA signal region comprises the nucleotide sequence of any of SEQ ID NO: 1134-1136, or a nucleotide sequence with at least 95% identity thereto.

E106. The viral genome of any one of embodiments E101-E105, further comprising an inverted terminal repeat (ITR) sequence.

E107. The viral genome of embodiment E106, wherein:
  (i) the ITR sequence is positioned 5' relative to the encoded payload; and/or
  (ii) the ITR sequence is positioned 3' relative to the encoded payload.

E108. The viral genome of any one of embodiments E101-E107, which comprises an ITR sequence positioned 5' relative to the encoded payload and an ITR sequence positioned 3' relative to the encoded payload.

E109. The viral genome of any one of embodiments E101-E108, wherein the ITR sequence comprises a nucleotide sequence of any one of SEQ ID NOs: 1035-1038, or a nucleotide sequence with at least 80%, 85%, 90%, or 95% sequence identity thereto.

E110. The viral genome of any one of embodiments E101-E109, further comprising an intron region.

E111. The viral genome of embodiment E110, wherein the intron region comprises a nucleotide sequence of any of the intron regions listed in Table 13, or a nucleotide sequence with at least 95% identity thereto.

E112. The viral genome of any one of embodiments E101-E111, comprising at least one, two, or three intron regions.

E113. The viral genome of any one of embodiments E101-E112, further comprising an exon region.

E114. The viral genome of embodiment E113, wherein the exon region comprises the nucleotide sequence of any of the exon sequences in Table 12, or a nucleotide sequence with at least 95% identity thereto.

E115. The viral genome of any one of embodiments E101-E114, comprising at least one, two, or three exon regions.

E116. The viral genome of any one of embodiments E101-E115, which further comprises a Kozak sequence, optionally wherein the Kozak sequence comprises the nucleotide sequence of GCCGCCACCATG (SEQ ID NO: 1079) or GAGGAGCCACC (SEQ ID NO: 1089).

E117. The viral genome of any one of embodiments E101-E116, which further comprises a nucleotide sequence encoding a miR binding site, e.g., a miR binding site that modulates, e.g., reduces, expression of the payload encoded by the viral genome in a cell or tissue where the corresponding miRNA is expressed.

E118. The viral genome of embodiment E117, which comprises at least 1-5 copies of an encoded miR binding site, e.g., at least 1, 2, 3, 4, or 5 copies.

E119. The viral genome of any one of embodiments E117-E118, which comprises at least 3 copies of an encoded miR binding sites, optionally wherein all three copies comprise the same miR binding site, or at least one, two, or all of the copies comprise a different miR binding site.

E120. The viral genome of any one of embodiments E117-E119, which comprises at least 4 copies of an encoded miR binding site, optionally wherein all four copies comprise the same miR binding site, or at least one, two, three, or all of the copies comprise a different miR binding site.

E121. The viral genome of any one of embodiments E117-E120, wherein the encoded miR binding site comprises a miR122 binding site, a miR183 binding site, a miR-142-3p, or a combination thereof, optionally wherein:
  (i) the encoded miR122 binding site comprises the nucleotide sequence of SEQ ID NO: 1029, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1029;
  (ii) the encoded miR183 binding site comprises the nucleotide sequence of SEQ ID NO: 1032, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1032; and/or
  (iii) the encoded miR-142-3p binding site comprises the nucleotide sequence of SEQ ID NO: 1031, or a nucleotide sequence substantially identical (e.g., having at least 70%, 75%, 80%, 85%, 90%, 92%, 95%, 97%, 98%, or 99% sequence identity) thereto; or a nucleotide sequence having at least one, two, three, four, five, six, or seven modifications, but no more than ten modifications of SEQ ID NO: 1031.

E122. The viral genome of any one of embodiments E101-E121, which is single stranded.

E123. The viral genome of any one of embodiments E101-E122, which further comprises a nucleotide sequence encoding a Rep protein, e.g., a non-structural protein, wherein the Rep protein comprises a Rep78 protein, a Rep68, Rep52 protein, and/or a Rep40 protein.

E124. The viral genome of embodiment E123, wherein the Rep78 protein, the Rep68 protein, the Rep52 protein, and/or the Rep40 protein are encoded by at least one Rep gene.

E125. The viral genome of any one of embodiments E101-E124, which further comprises a nucleic acid sequence encodes a capsid protein, e.g., a structural protein, wherein the capsid protein comprises a VP1 polypeptide, a VP2 polypeptide, and/or a VP3 polypeptide.

E126. The viral genome of embodiment E125, wherein the VP1 polypeptide, the VP2 polypeptide, and/or the VP3 polypeptide are encoded by at least one Cap gene.

E127. A vector comprising the viral genome of any one embodiments E101-E126.

E128. An isolated, e.g., recombinant AAV particle comprising:

(i) a capsid protein, and, (ii) the nucleic acid of any one of embodiments E79-E87 and E93-E100, or the viral genome of any one of embodiments E101-E126.

E129. The isolated AAV particle of embodiment E128, wherein:

(i) the capsid protein comprises the amino acid sequence of SEQ ID NO: 1003, or an amino acid sequence with at least 80% (e.g., at least about 85, 90, 95, 96, 97, 98, or 99%) sequence identity thereto;

(ii) the capsid protein comprises an amino acid sequence having at least one, two or three modifications but not more than 30, 20 or 10 modifications of the amino acid sequence of SEQ ID NO: 1003;

(iii) the capsid protein comprises the amino acid sequence of SEQ ID NO: 1011, or an amino acid sequence with at least 80% (e.g., at least about 85, 90, 95, 96, 97, 98, or 99%) sequence identity thereto;

(iv) the capsid protein comprises an amino acid sequence having at least one, two or three modifications but not more than 30, 20 or 10 modifications of the amino acid sequence of SEQ ID NO: 1011;

(v) the capsid protein comprises an amino acid sequence encoded by the nucleotide sequence of SEQ ID NO: 1002, or a sequence with at least 80% (e.g., at least about 85, 90, 95, 96, 97, 98, or 99%) sequence identity thereto; and/or (vi) the nucleotide sequence encoding the capsid protein comprises the nucleotide sequence of SEQ ID NO: 1002, or a sequence with at least 80% (e.g., at least about 85, 90, 95, 96, 97, 98, or 99%) sequence identity thereto.

E130. The isolated AAV particle of embodiment E128 or E129, wherein the capsid protein comprises:

(i) an amino acid substitution at position K449, e.g., a K449R substitution, numbered according to SEQ ID NO:1003;

(ii) an insert comprising the amino acid sequence of TLAVPFK (SEQ ID NO: 1151), optionally wherein the insert is present immediately subsequent to position 588, relative to a reference sequence numbered according to SEQ ID NO: 1003;

(iii) an amino acid other than "A" at position 587 and/or an amino acid other than "Q" at position 588, numbered according to SEQ ID NO: 1003; and/or (iv) the amino acid substitution of A587D and/or Q588G, numbered according to SEQ ID NO: 1003.

E131. The AAV particle of any one of embodiments E128-E130, wherein the capsid protein comprises (i) the amino acid substitution of K449R numbered according to SEQ ID NO: 1003; and (ii) an insert comprising the amino acid sequence of TLAVPFK (SEQ ID NO: 1151), optionally wherein the insert is present immediately subsequent to position 588 of SEQ ID NO: 1003.

E132. The AAV particle of any one of embodiments E128-E130, wherein the capsid protein comprises (i) the amino acid substitution of K449R numbered according to SEQ ID NO: 1003; (ii) an insert comprising the amino acid sequence of TLAVPFK (SEQ ID NO: 1151), optionally wherein the insert is present immediately subsequent to position 588, relative to a reference sequence numbered according to SEQ ID NO: 1003; and (iii) the amino acid substitutions of A587D and Q588G, numbered according to SEQ ID NO: 1003.

E133. The AAV particle of any one of embodiments E128-E130, wherein the capsid protein comprises (i) an insert comprising the amino acid sequence of TLAVPFK (SEQ ID NO: 1151), optionally wherein the insert is present immediately subsequent to position 588, relative to a reference sequence numbered according to SEQ ID NO: 1003; and (ii) the amino acid substitutions of A587D and Q588G, numbered according to SEQ ID NO: 1003.

E134. The AAV particle of any one of embodiments E128-E133, wherein the capsid protein comprises any of the capsid proteins listed in Table 9 or a functional variant thereof.

E135. The AAV particle of any one of embodiments E128-E134, wherein the capsid protein comprises a VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP, AAVPHP.B-SNP(3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP. AAVPHP.B-TMP, AAVPHP.B-TTP. AAVPHP.S/G2A12, AAVG2A15/G2A3 (G2A3), AAVG2B4 (G2B4), AAVG2B5 (G2B5), AAVPHP.N (PHP.N), PHP.S. AAV1, AAV2, AAV2 variant, AAV2/3 variant, AAV4, AAV5, AAV6, AAV7, AAV8, AAV9.47, AAV9 (hu14), AAV9, AAV9 K449R, AAV10, AAV11, AAV12, AAVrh8, AAVrh10, AAVDJ, AAVDJ8, or AAV2G9 capsid protein, or a functional variant thereof.

E136. The AAV particle of any of embodiments E128-E135, wherein the capsid protein comprises a VOY101 capsid protein.

E137. The AAV particle of embodiment E136, wherein the capsid protein comprises:

(i) the amino acid sequence of SEQ ID NO: 1023, or an amino acid sequence substantially identical (e.g., having at least 70%, 75%, 80%, 85%, 90%, 92%, 95%, 97%, 98%, or 99% sequence identity) thereto;

(ii) an amino acid sequence comprising at least one, two, or three modifications but no more than 30, 20, or 10 modifications, e.g., substitutions, relative to the amino acid sequence of SEQ ID NO: 1023; or, (iii) an amino acid sequence encoded by the nucleotide sequence of SEQ ID NO: 1022 or a nucleotide sequence substantially identical (e.g., having at least 70%, 75%, 80%, 85%, 90%, 92%, 95%, 97%, 98%, or 99% sequence identity) thereto.

E138. The AAV particle of embodiment E136 or E137, wherein the nucleotide sequence encoding the capsid protein comprises the nucleotide sequence of SEQ ID NO: 1022, or a nucleotide sequence substantially identical (e.g., having at least 70%, 75%, 80%, 85%, 90%, 92%, 95%, 97%, 98%, or 99% sequence identity) thereto.

E139. The AAV particle of any one of embodiments E128-E138, wherein the capsid protein comprises:

(i) a VP1 polypeptide, VP2 polypeptide, VP3 polypeptide, or a combination thereof;

(ii) the amino acid sequence corresponding to positions 138-743, e.g., a VP2, of SEQ ID NO: 1023, or a sequence with at least 80% (e.g., at least about 85, 90, 92, 95, 96, 97, 98, or 99%) sequence identity thereto;

(iii) the amino acid sequence corresponding to positions 203-743, e.g., a VP3, of SEQ ID NO: 1023, or a sequence with at least 80% (e.g., at least about 85, 90, 92, 95, 96, 97, 98, or 99%) sequence identity thereto; and/or (iv) the amino acid sequence corresponding to positions 1-743, e.g., a VP1, of SEQ ID NO: 1023, or a sequence with at least 80% (e.g., at least about 85, 90, 92, 95, 96, 97, 98, or 99%) sequence identity thereto.

E140. A host cell comprising the nucleic acid of any one of embodiments E79-E87 and E93-E100, the viral genome of any one of embodiments E101-E126, or the AAV particle of any one of embodiments E128-E139, optionally wherein the host cell is an insect cell, a bacterial cell or a mammalian cell.

E141. A nucleic acid encoding the viral genome of any one of embodiments E101-E126, and a backbone region suitable for replication of the viral genome in a cell, e.g., a bacterial cell (e.g., wherein the backbone region comprises one or both of a bacterial origin of replication and a selectable marker).

E142. A method of making a viral genome, the method comprising:

(i) providing the nucleic acid molecule comprising the viral genome of any one of embodiments E101-E126; and (ii) excising the viral genome from the backbone region, e.g., by cleaving the nucleic acid molecule at upstream and downstream of the viral genome.

E143. A method of making an isolated, e.g., recombinant, AAV particle, the method comprising (i) providing a host cell comprising the viral genome of embodiment E140; and (ii) incubating the host cell under conditions suitable to enclose the viral genome in a capsid protein, e.g., a VOY101 capsid protein;

thereby making the isolated AAV particle.

E144. The method of embodiment E143, further comprising, prior to step (i), introducing a first nucleic acid molecule comprising the viral genome into the host cell.

E145. The method of embodiment E143 or E144, wherein the host cell comprises a second nucleic acid encoding a capsid protein, e.g., a VOY101 capsid protein.

E146. The method of any one of embodiments E143-E144, wherein the second nucleic acid molecule is introduced into the host cell prior to, concurrently with, or after the first nucleic acid molecule.

E147. A pharmaceutical composition comprising the antibody of any one of embodiments E1-E78 and E88, an AAV particle of any one of embodiments E128-E139, or an AAV particle comprising the viral genome of any one of embodiments E101-E126, or the isolated nucleic acid of any one of embodiments E79-E87 and E93-E100, and a pharmaceutically acceptable excipient.

E148. A method of delivering an exogenous antibody that binds to tau, to a subject, comprising administering an effective amount of the pharmaceutical composition of embodiment S1, the antibody of any one of embodiments E1-E78 and E88, an AAV particle, e.g., a plurality of AAV particles, of any one of embodiments E128-E139, or an AAV particle, e.g., a plurality of AAV particles, comprising the viral genome of any one of embodiments E101-E126, or the isolated nucleic acid of any one of embodiments E79-E87 and E93-E100.

E149. The method of embodiment E148, wherein the subject has, has been diagnosed with having, or is at risk of having a disease associated with expression of tau.

E150. The method of embodiment E148 or E149, wherein the subject has, has been diagnosed with having, or is at risk of having a neurological, e.g., neurodegenerative disorder.

E151. The method of embodiment E148, E149, or E150, wherein the subject has, has been diagnosed with having, or is at risk of having a tauopathy.

E152. A method of treating a subject having or diagnosed with having a disease associated with expression of tau comprising administering to the subject an effective amount of the pharmaceutical composition of embodiment E147, the antibody of any one of embodiments E1-E78 and E88, an AAV particle, e.g., a plurality of AAV particles, of any one of embodiments E128-E139, or an AAV particle, e.g., a plurality of AAV particles, comprising the viral genome of any one of embodiments E101-E126, or the isolated nucleic acid of any one of embodiments E79-E87 and E93-E100.

E153. A method of treating a subject having or diagnosed with having a neurological, e.g., neurodegenerative disorder, comprising administering to the subject an effective amount of the pharmaceutical composition of embodiment E147, the antibody of any one of embodiments E1-E78 and E88, an AAV particle, e.g., a plurality of AAV particles, of any one of embodiments E128-E139, or an AAV particle, e.g., a plurality of AAV particles, comprising the viral genome of any one of embodiments E101-E126, or the isolated nucleic acid of any one of embodiments E79-E87 and E93-E100.

E154. A method of treating a subject having or diagnosed with having a tauopathy comprising administering to the subject an effective amount of the pharmaceutical composition of embodiment E147, the antibody of any one of embodiments E1-E78 and E88, an AAV particle, e.g., a plurality of AAV particles, of any one of embodiments E128-E139, or an AAV particle, e.g., a plurality of AAV particles, comprising the viral genome of any one of embodiments E101-E126, or the isolated nucleic acid of any one of embodiments E79-E87 and E93-E100.

E155. The method of any one of embodiments E152-E154, wherein the disease associated with Tau expression, the neurological disorder, or the tauopathy comprises AD, FTDP-17, FTLD, FTD, CTE, PSP, Down's syndrome, Pick's disease, CBD, Corticobasal syndrome, ALS, Prion diseases, CJD, Multiple system atrophy, Tangle-only dementia, or Progressive subcortical gliosis.

E156. The method of any one of embodiments E152-E155, where treating comprises prevention of progression of the disease in the subject.

E157. The method of any one of embodiments E152-E156, wherein the subject is a human.

E158. The method of any one of embodiments E152-E157, wherein the AAV particle is administered to the subject intravenously, intramuscularly, via intraparenchymal administration, intracerebroventricularly, via intra-cisterna *magna* (ICM) injection, intrathecally, via focused ultrasound (FUS), e.g., coupled with the intravenous administration of microbubbles (FUS-MB), or MRI-guided FUS coupled with intravenous administration.

E159. The method of any one of embodiments E152-E158, wherein the AAV particle is administered to the subject intravenously.

E160. The method of any one of embodiments E152-E158, wherein the AAV particle is administered to the subject via intra-cisterna *magna* injection (ICM).

E161. The method of any one of embodiments E152-E160, further comprising evaluating, e.g., measuring, the level of antibodies generated in a subject, e.g., in a cell or tissue of the subject.

E162. The method of any one of embodiments E152-E161, wherein the administration results in the generation of 0.001 μg/mL to 100 mg/mL of antibodies in the subject, e.g., in a cell or tissue of the subject.

E163. The method of embodiment E162, wherein the cell is a neuronal cell.

E164. The method of embodiment E162, wherein the tissue is a central nervous system tissue, e.g., a brain tissue.

E165. The method of any one of embodiments E152-E164, further comprising performing a blood test, an imaging test, a CNS biopsy sample, or an aqueous cerebral spinal fluid biopsy.

E166. The method of any one of embodiments E161-E165, wherein measuring the level of antibodies is performed prior to, during, or subsequent to treatment with the AAV particle, e.g., plurality of AAV particles.

E167. The method of any one of embodiments E152-E166, wherein the subject has a level of antibodies that is a greater than a reference level, e.g., a subject that has not received treatment, e.g., has not been administered the AAV particle or plurality of AAV particles.

E168. The method of any one of embodiments E152-E167, wherein the plurality of AAV particles are administered at a dose of about $1\times10^6$ VG/mL to about $1\times10^{16}$ VG/mL or about 0.0001 mg/kg to about 100 mg/kg.

E169. The method of any one of embodiments E152-E168, further comprising administration of an additional therapeutic agent and/or therapy suitable for treatment or prevention of a disorder associated with tau expression, a neurological, e.g., neurodegenerative, disorder.

E170. The method of embodiment E169, wherein the additional therapeutic agent and/or therapy comprises a cholinesterase inhibitor (e.g., donepezil, rivastigmine, and/or galantamine), an N-methyl D-aspartate (NMDA) antagonist (e.g., memantine), an antipsychotic drug, an anti-anxiety drug, an anticonvulsant, a dopamine agonist (e.g., pramipexole, ropinirole, rotigotine, and/or apomorphine), an MAO B inhibitor (e.g., selegiline, rasagiline, and/or safinamide), catechol O-methyltransferase (COMT) inhibitors (entacapone, opicapone, and/or tolcapone), anticholinergics (e.g., benztropine and/or trihexyphenidyl), amantadine, carbidopa-levodopa, deep brain simulation (DBS), or a combination thereof.

E171. The antibody of any one of embodiments E1-E78 and E88, the nucleic acid of any one of embodiments E79-E87 and E93-E100, the viral genome of any one of embodiments E101-E126, the pharmaceutical composition of embodiment E147, or the AAV particle of any one of embodiments E128-E139, for use in the manufacture of a medicament.

E172. The antibody of any one of embodiments E1-E78 and E88, the nucleic acid of any one of embodiments E79-E87 and E93-E100, the viral genome of any one of embodiments E101-E126, the pharmaceutical composition of embodiment E147, or the AAV particle of any one of embodiments E128-E139, for use in the treatment of a disease associated with tau expression.

E173. The antibody of any one of embodiments E1-E78 and E88, the nucleic acid of any one of embodiments E79-E87 and E93-E100, the viral genome of any one of embodiments E101-E126, the pharmaceutical composition of embodiment E147, or the AAV particle of any one of embodiments E128-E139, for use in the treatment of a neurological, e.g., neurodegenerative, disorder.

E174. The antibody of any one of embodiments E1-E78 and E88, the nucleic acid of any one of embodiments E79-E87 and E93-E100, the viral genome of any one of embodiments E101-E126, the pharmaceutical composition of embodiment E147, or the AAV particle of any one of embodiments E128-E139, for use in the treatment of a tauopathy.

E175. Use of an effective amount of the antibody of any one of embodiments E1-E78 and E88, the nucleic acid of any one of embodiments E79-E87 and E93-E100, the viral genome of any one of embodiments E101-E126, the pharmaceutical composition of embodiment E147, or the AAV particle of any one of embodiments E128-E139, in the manufacture of a medicament for the treatment of a disease associated with tau expression, a neurological, e.g., neurodegenerative, disorder, or a tauopathy in a subject.

BRIEF DESCRIPTIONS OF THE DRAWINGS

FIGS. 1A-1B show alignment of variable light chain or VL (FIG. 1A) and variable heavy chain or VH (FIG. 1B) regions of selected antibodies V0004, V0009, V0022, V0023, V0024 and V0052, with the CDR sequences highlighted according to the Kabat numbering system. The corresponding framework region sequences under the Kabat numbering system, including FRH1-FRH4 and FRL1-FRL4, are defined by the boundaries of the CDR regions. FIG. 1A shows from top to bottom: SEQ ID NO: 1215, SEQ ID NO: 1216, SEQ ID NO: 1217, SEQ ID NO: 1218, SEQ ID NO: 1219, and SEQ ID NO: 1220. FIG. 1B shows from top to bottom: SEQ ID NO: 1221, SEQ ID NO: 1222, SEQ ID NO: 1223, SEQ ID NO: 1224, SEQ ID NO: 1225, and SEQ ID NO: 1226.

FIGS. 2A-2B show alignment of variable light chain (FIG. 2A) and variable heavy chain (FIG. 2B) regions of selected antibodies V0004, V0009, V0022, V0023, V0024 and V0052, with CDR sequences highlighted according to the Chothia numbering system. The corresponding framework region sequences under the Chothia numbering system, including FRH1-FRH4 and FRL1-FRL4, are defined by the boundaries of the CDR regions. FIG. 2A shows from top to bottom: SEQ ID NO: 1215, SEQ ID NO: 1216, SEQ ID NO: 1217, SEQ ID NO: 1218, SEQ ID NO: 1219, and SEQ ID NO: 1220. FIG. 2B shows from top to bottom: SEQ ID NO: 1221, SEQ ID NO: 1222, SEQ ID NO: 1223, SEQ ID NO: 1224, SEQ ID NO: 1225, and SEQ ID NO: 1226.

FIGS. 3A-3B show alignment of variable light chain (FIG. 3A) and variable heavy chain (FIG. 3B) regions of selected antibodies V0004, V0009, V0022, V0023, V0024 and V0052, with CDR sequences highlighted according to IMGT numbering system. The corresponding framework region sequences under the IMGT numbering system, including FRH1-FRH4 and FRL1-FRL4, are defined by the boundaries of the CDR regions. FIG. 3A shows from top to bottom: SEQ ID NO: 1215, SEQ ID NO: 1216, SEQ ID NO: 1217, SEQ ID NO: 1218, SEQ ID NO: 1219, and SEQ ID NO: 1220. FIG. 3B shows from top to bottom: SEQ ID NO: 1221, SEQ ID NO: 1222, SEQ ID NO: 1223, SEQ ID NO: 1224, SEQ ID NO: 1225, and SEQ ID NO: 1226.

DETAILED DESCRIPTION OF THE INVENTION

I. Compositions

In some embodiments, the present disclosure provides compositions that interact with human microtubule associated protein tau. Such compositions may be antibodies that bind tau protein epitopes, referred to herein as "anti-tau antibodies." Dysfunction and/or aggregation of tau is found in a class of neurodegenerative diseases referred to as tauopathies. Tau hyperphosphorylation leads to aggregation and depressed tau-dependent microtubule assembly. In tauopathies, the tau aggregates form paired helical filaments (PHF) found in neurofibrillary tangles (NFTs). These aggregates lead to neuronal loss and cognitive decline. Anti-tau antibodies of the present disclosure may be useful for treating and/or diagnosing tauopathies, as well as other applications described herein.

Antibodies

In some embodiments, compounds (e.g., anti-tau antibodies) and compositions of the present disclosure include antibodies or fragments thereof. In some embodiments, the antibody described herein bind tau. For example, the antibody binds to an epitope, e.g., a confirmation epitope, phosphorylated epitope, or a linear epitope, on tau, e.g., as described herein.

As used herein, the term "antibody" is referred to in the broadest sense and specifically covers various embodiments including, but not limited to monoclonal antibodies, polyclonal antibodies, multispecific antibodies (e.g. bispecific antibodies formed from at least two intact antibodies), single chain Fv (scFv) formats, and antibody fragments (such as Fab, F(ab'), F(ab')$_2$, Fv, etc.), so long as they exhibit a desired functional or biological activity. Antibodies are primarily amino acid-based molecules but may also include one or more modifications (including, but not limited to the addition of sugar moieties, fluorescent moieties, chemical tags, etc.).

Antibodies (including antigen-binding fragments thereof) of the present disclosure may include, but are not limited to, polyclonal, monoclonal antibodies, multispecific antibodies, bispecific antibodies, trispecific antibodies, human antibodies, humanized antibodies, chimeric antibodies, single chain antibodies, diabodies, linear antibodies, Fab fragments, F(ab') fragments, F(ab')$_2$ fragments, Fv fragments, fragments produced by a Fab expression library, variable domains, anti-idiotypic (anti-Id) antibodies (including, e.g., anti-Id antibodies to antibodies of the invention), intracellularly made antibodies (i.e., intrabodies), codon-optimized antibodies, scFv fragments, tandem scFv antibodies, bispecific T-cell engagers, mAb2 antibodies, chimeric antigen receptors (CAR), tetravalent bispecific antibodies, biosynthetic antibodies, native antibodies, miniaturized antibodies, unibodies, maxibodies, and epitope-binding fragments of any of the above.

In some embodiments, the antibody comprises at least one immunoglobulin variable domain sequence. An antibody may include, for example, full-length, mature antibodies and antigen-binding fragments of an antibody. For example, an antibody can include a heavy (H) chain variable domain sequence (abbreviated herein as VH), and a light (L) chain variable domain sequence (abbreviated herein as VL). In another example, an antibody includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA. IgM, IgD, and IgE, and from any subclass (e.g., human IgG1, IgG2, IgG3, and IgG4, and murine IgG1, IgG2a, IgG2b, IgG2c, and IgG3) of antibodies. The antibodies of the present disclosure can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

In some embodiments, an antibody of the present disclosure comprises a functional fragment or variant thereof. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function).

As used herein, the term "antibody fragment" refers to a portion of an intact antibody or fusion-protein thereof, in some cases including at least one antigen binding region. Examples of antigen-binding fragments include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci.

USA 85:5879-5883); and (viii) a single domain antibody. These antibody fragments are obtained using conventional techniques known to those with skill in the art, and the fragments are screened for utility in the same manner as are intact antibodies. An antibody fragment can also be incorporated into single domain antibodies, maxibodies, minibodies, nanobodies, intrabodies, diabodies, triabodies, tetrabodies, v-NAR and bis-scFv (see, for example, Hollinger and Hudson, Nature Biotechnology 23:1126-1136, 2005). "In some embodiments, papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an $F(ab')_2$ fragment that has two antigen-binding sites and is still capable of cross-linking antigen. Antibodies of the present disclosure may include one or more of these fragments and may, for example, be generated through enzymatic digestion of whole antibodies or through recombinant expression.

In some embodiments, the antibody can be single domain antibody. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

"Native antibodies" are usually heterotetrameric glycoproteins of about 150,000 Daltons, composed of two identical light (L) chains and two identical heavy (H) chains. Genes encoding antibody heavy and light chains are known and segments making up each have been well characterized and described (Matsuda, F. et al., 1998. The Journal of Experimental Medicine. 188(11); 2151-62 and Li, A. et al., 2004. Blood. 10 (12:4602-9, the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. In some embodiments, the VH and VL regions of the antibody described herein can be subdivided into regions of hypervariability, termed complementarity determining regions (CDR), interspersed with regions that are more conserved, termed framework regions (FR).

As used herein, the term "hypervariable region" refers to a region within a variable domain that includes amino acid residues responsible for antigen binding. The amino acids present within the hypervariable regions determine the structure of the complementarity determining regions (CDRs) that become part of the antigen-binding site of the antibody.

As used herein, the term "CDR" refers to a region of an antibody that includes a structure that is complimentary to its target antigen or epitope. CDR regions generally confer antigen specificity and binding affinity. Other portions of the variable domain, not interacting with the antigen, are each referred to as a "framework region" (FR). The antigen-binding site (also known as the antigen combining site or paratope) includes the amino acid residues necessary to interact with a particular antigen. The exact residues making up the antigen-binding site may be determined by CDR analysis.

As used herein, the term "CDR analysis" refers to any process used to determine which antibody variable domain residues make up the CDRs. The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196: 901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). CDR analysis may be conducted by co-crystallography with bound antigen. In some embodiments, CDR analysis may include computational assessments based on comparisons with other antibodies (Strohl, W. R. Therapeutic Antibody Engineering. Woodhead Publishing, Philadelphia PA. 2012. Ch. 3, p 47-54, the contents of which are herein incorporated by reference in their entirety). CDR analysis and/or the precise amino acid sequence boundaries may include the use of numbering schemes including, but not limited to, those taught by Kabat [Wu, T. T. et al., 1970, JEM, 132(2):211-50 and Johnson, G. et al., 2000, Nucleic Acids Res. 28(1): 214-8, the contents of each of which are herein incorporated by reference in their entirety], Chothia [Chothia and Lesk, J. Mol. Biol. 196, 901 (1987), Chothia et al., Nature 342, 877 (1989), and Al-Lazikani, B. et al., 1997, J. Mol. Biol. 273(4):927-48, the contents of each of which are herein incorporated by reference in their entirety], Lefranc (Lefranc, M. P. et al., 2005, Immunome Res. 1:3), and Honegger (Honegger, A. and Pluckthun, A. 2001. J. Mol. Biol. 309(3):657-70, the contents of which are herein incorporated by reference in their entirety). In some embodiments, the CDRs defined according the Chothia number scheme are also sometimes referred to as hypervariable loops.

For example, under Kabat, the CDR amino acid residues in the heavy chain variable domain (VH) are numbered 31-35 (HCDR1), 50-65 (HCDR2), and 95-102 (HCDR3);

and the CDR amino acid residues in the light chain variable domain (VL) are numbered 24-34 (LCDR1), 50-56 (LCDR2), and 89-97 (LCDR3).

Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

For certain antibodies of the invention, equivalent CDR sequences and framework region sequences, based on the Kabat, Chothia, and IMGT numbering systems, can be readily obtained based at least on Tables and sequences described herein, which provide SEQ ID NOs: for the equivalent CDR regions based on the Kabat, Chothia, and IMGT numbering systems, respectively. Also see FIGS. 1A-3B.

In general, the VH and VL domains have three CDRs each. VL CDRs are referred to herein as CDRL1, CDRL2 and CDRL3, in order of occurrence when moving from N- to C-terminus along the variable domain polypeptide. VH CDRs are referred to herein as CDRH1, CDRH2 and CDRH3, in order of occurrence when moving from N- to C-terminus along the variable domain polypeptide. Each of the CDRs have favored canonical structures with the exception of the CDRH3, which includes amino acid sequences that may be highly variable in sequence and length between antibodies resulting in a variety of three-dimensional structures in antigen-binding domains (Nikoloudis, D. et al., 2014. Peer J. 2:e456). In some cases, CDRH3s may be analyzed among a panel of related antibodies to assess antibody diversity. Various methods of determining CDR sequences are known in the art and may be applied to known antibody sequences (Strohl, W. R. Therapeutic Antibody Engineering. Woodhead Publishing, Philadelphia PA. 2012. Ch. 3, p 47-54, the contents of which are herein incorporated by reference in their entirety).

In some embodiments, the VH and VL domains each have four framework regions (FRs) located before, after, and between CDR regions. VH framework regions are referred to herein as FRH1, FRH2, FRH3, and FRH4 and VL framework regions are referred to herein as FRL1, FRL2, FRL3, and FRL4. In some embodiments, on VH domains, FRs and CDRs are in the order of FRH1-CDRH1-FRH2-CDRH2-FRH3-CDRH3-FRH4, from N-terminus to C-terminus. In some embodiments, on VL domains, FRs and CDRs are in the order of FRL1-CDRL1-FRL2-CDRL2-FRL3-CDRL3-FRL4, from N-terminus to C-terminus.

In some embodiments, the antigen binding domain of the antibodies of the present disclosure is the part of the antibody that comprises determinants that form an interface that binds to the tau polypeptide or an epitope thereof. With respect to proteins (or protein mimetics), the antigen-binding site typically includes one or more loops (of at least four amino acids or amino acid mimics) that form an interface that binds to the tau polypeptide. Typically, the antigen-binding site of an antibody includes at least one or two CDRs and/or hypervariable loops, or more typically at least three, four, five or six CDRs and/or hypervariable loops.

In yet other embodiments, the antibody has a heavy chain constant region chosen from, e.g., the heavy chain constant regions of IgG1, IgG2, IgG3, IgG4, IgM, IgA1, IgA2, IgD, and IgE; particularly, chosen from, e.g., the human heavy chain constant regions of IgG1, IgG2, IgG3, and IgG4, or the murine heavy chain constant regions of IgG1, IgG2a. IgG2b, IgG2c, and IgG3. In another embodiment, the antibody has a light chain constant region chosen from, e.g., the (e.g., murine or human) light chain constant regions of kappa or lambda.

The constant region can be altered, e.g., mutated, to modify the properties of the antibody (e.g., to increase or decrease one or more of: Fc receptor binding, antibody glycosylation, the number of cysteine residues, effector cell function, and/or complement function). In some embodiments the antibody has: effector function; and can fix complement. In other embodiments the antibody does not recruit effector cells; or fix complement. In other embodiments, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

As used herein, the term "Fv" refers to an antibody fragment that includes the minimum fragment on an antibody needed to form a complete antigen-binding site. These regions consist of a dimer of one heavy chain and one light chain variable domain in tight, non-covalent association. Fv fragments can be generated by proteolytic cleavage, but are largely unstable. Recombinant methods are known in the art for generating stable Fv fragments, typically through insertion of a flexible linker between the light chain variable domain and the heavy chain variable domain (to form a single chain Fv (scFv)] or through the introduction of a disulfide bridge between heavy and light chain variable domains (Strohl, W. R. Therapeutic Antibody Engineering. Woodhead Publishing, Philadelphia PA. 2012. Ch. 3, p 46-47, the contents of which are herein incorporated by reference in their entirety).

Antibody "light chains" from any vertebrate species can be assigned to one of two clearly distinct types, called kappa and lambda based on amino acid sequences of their constant domains. Depending on the amino acid sequence of the constant domain of their heavy chains, antibodies can be assigned to different classes.

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen. In some embodiments, antibodies of the present disclosure are prepared as scFvFc antibodies. The term "scFvFc" refers to an antibody format which includes the fusion of one or more scFv with an antibody Fc domain.

The term "chimeric antibody" refers to an antibody with portions derived from two or more sources. Chimeric antibodies may include portions derived from different species. For example, chimeric antibodies may include antibodies with mouse variable domains and human constant domains. Further examples of chimeric antibodies and methods for producing them include any of those described in Morrison, S. L., *Transfectomas provide novel chimeric antibodies*. Science. 1985 Sep. 20; 229(4719):1202-7; Gillies, S. D. et al., *High-level expression of chimeric antibodies using adapted cDNA variable region cassettes*. J Immunol Methods. 1989 Dec. 20; 125(1-2):191-202.; and U.S. Pat. Nos. 5,807,715; 4,816,567; and 4,816,397, the contents of each of which are incorporated herein by reference in their entirety.

The term "diabodies" refers to small antibody fragments with two antigen-binding sites, which fragments include a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993), the contents of each of which are incorporated herein by reference in their entirety.

The term "intrabody" refers to a form of antibody that is not secreted from a cell in which it is produced, but instead targets one or more intracellular protein(s). Intrabodies may be used to affect a multitude of cellular processes including, but not limited to intracellular trafficking, transcription, translation, metabolic processes, proliferative signaling and cell division. In some embodiments, methods of the present invention may include intrabody-based therapies. In some such embodiments, variable domain sequences and/or CDR sequences disclosed herein may be incorporated into one or more constructs for intrabody-based therapy. In some cases, intrabodies of the invention may target one or more glycated intracellular proteins or may modulate the interaction between one or more glycated intracellular protein and an alternative protein.

The term "chimeric antigen receptor" or "CAR" as used herein, refers to artificial receptors that are engineered to be expressed on the surface of immune effector cells resulting in specific targeting of such immune effector cells to cells expressing entities that bind with high affinity to the artificial receptors. CARs may be designed to include one or more segments of an antibody, antibody variable domain and/or antibody CDR, such that when such CARs are expressed on immune effector cells, the immune effector cells bind and clear any cells that are recognized by the antibody portions of the CARs. In some cases, CARs are designed to specifically bind cancer cells, leading to immune-regulated clearance of the cancer cells.

The antibody of the invention can be a monoclonal antibody or a polyclonal antibody. The term "monoclonal antibody" as used herein refers to an antibody obtained from a population of substantially homogeneous cells (or clones), i.e.g., the individual antibodies making up the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method.

In some embodiments, the antibody comprises an amino acid sequence of an antibody in which the variable region, or a portion thereof, e.g., the CDRs, are generated in a non-human organism, e.g., a rat or mouse. Antibodies comprising chimeric, CDR-grafted, and humanized antibodies are within the invention. Antibodies comprising the sequences of antibodies generated in a non-human organism, e.g., a rat or mouse, and then modified, e.g., in the variable framework or constant region, to decrease antigenicity in a human are within the invention.

The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

Antibodies of the present disclosure may be from any animal origin including mammals, birds, reptiles, and insects. Mammalian antibodies may be, for example, of human, murine (e.g., mouse or rat), donkey, sheep, rabbit, goat, guinea pig, camel, bovine, or horse origin.

In some embodiments, antibodies of the present disclosure may be antibody mimetics. The term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, DARPins, Fynomers and Kunitz and domain peptides. In other embodiments, antibody mimetics may include one or more non-peptide region.

As used herein, the term "antibody variant" refers to a biomolecule resembling an antibody in structure, sequence and/or function, but including some differences in their amino acid sequence, composition or structure as compared to another antibody or a native antibody.

Multispecific Antibodies

In some embodiments, the antibody is a multispecific antibody, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a multispecific antibody comprises a third, fourth or fifth immunoglobulin variable domain. In some embodiments, a multispecific antibody is a bispecific antibody, a trispecific antibody, or tetraspecific antibody. In some embodiments, the anti-tau antibody is a multispecific antibody.

In some embodiments, a multispecific antibody is a bispecific antibody. A bispecific antibody has specificity for no more than two antigens. A bispecific antibody is characterized by a first immunoglobulin variable domain sequence which has binding specificity for a first epitope and a second immunoglobulin variable domain sequence that has binding specificity for a second epitope. In some embodiments, the first and second epitopes are on the same antigen, e.g., the same protein (or subunit of a multimeric protein). In some embodiments, the first and second epitopes overlap. In some embodiments, the first and second epitopes do not overlap. In some embodiments, the first and second epitopes are on different antigens, e.g., the different proteins (or different subunits of a multimeric protein). In some embodiments, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In some embodiments, a bispecific antibody comprises a half antibody having binding specificity for a first epitope and a half antibody having binding specificity for a second epitope. In some embodiments, a bispecific antibody comprises a half antibody, or fragment thereof, having binding specificity for a first epitope and a half antibody, or fragment thereof, having binding specificity for a second epitope. In some embodiments, a bispecific antibody comprises a scFv, or fragment thereof, have binding specificity for a first epitope and a scFv, or fragment thereof, have binding specificity for a second epitope. In some embodiment, the anti-tau antibody is a bispecific antibody.

In some embodiments, the sequences of the antibody of the present disclosure can be generated from bispecific or heterodimeric antibody produced using protocols known in the art; including but not limited to, for example, the "knob in a hole" approach described in, e.g., U.S. Pat. No. 5,731, 168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/ 131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhydryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582, 996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also disclosed creating bispecific, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620.

Antibody Development

Antibodies according to the present disclosure may be developed using methods standard in the art. Two primary antibody preparation technologies are immunization and antibody display technology. In either case, desired antibodies are identified from a larger pool of candidates based on affinity for a specific target or epitope. An immune response is characterized by the reaction of the cells, tissues and/or organs of an organism to the presence of a foreign entity. Such an immune response typically leads to the production by the organism of one or more antibodies against the foreign entity, e.g., antigen or a portion of the antigen.

Antigens

Antibodies may be developed (e.g., through immunization) or selected (e.g., from pool of candidates), for example, using any naturally occurring or synthetic antigen. As used herein, an "antigen" is an entity which induces or evokes an immune response in an organism and may also refer to an antibody binding partner. An immune response is characterized by the reaction of the cells, tissues and/or organs of an organism to the presence of a foreign entity. Such an immune response typically leads to the production by the organism of one or more antibodies against the foreign entity. In some embodiments, antigens include tau proteins.

As used herein, the term "tau protein" refers to proteins or protein complexes that include microtubule-associated protein tau or peptide fragments thereof. Tau proteins may include enriched paired helical filament tau protein (ePHF), also referred to as "sarkosyl insoluble tau." or fragments thereof. Tau proteins may include one or more phosphorylated residues. Such phosphorylated residues may correspond to tau proteins associated with disease (also referred to herein as "pathological tau").

Immunization

In some embodiments, antibodies may be prepared by immunizing a host with an antigen of interest. Host animals (e.g., mice, rabbits, goats, or llamas) may be immunized with an antigenic protein to elicit lymphocytes that specifically bind to the antigen. Lymphocytes may be collected and fused with immortalized cell lines to generate hybridomas which can be cultured in a suitable culture medium to promote growth (e.g., see Kohler, G. et al., Continuous cultures of fused cells secreting antibody of predefined specificity. Nature. 1975 Aug. 7; 256(5517):495-7, the contents of which are herein incorporated by reference in their entirety). Alternatively, lymphocytes may be immunized in vitro.

Lymphocytes may be fused with immortalized cell lines using suitable fusing agents (e.g., polyethylene glycol) to form a hybridoma cell (e.g., see Goding, J. W., Monoclonal Antibodies: Principles and Practice. Academic Press. 1986; 59-1031, the contents of which are herein incorporated by reference in their entirety). Immortalized cell lines may be transformed mammalian cells, particularly myeloma cells of rodent, rabbit, bovine, or human origin. In some embodiments, rat or mouse myeloma cell lines are employed. Hybridoma cells may be cultured in suitable culture media, typically including one or more substances that inhibit the growth or survival of unfused cells. For example, parental cells lacking the enzyme hypoxanthine guanine phosphoribosyl transferase (HGPRT or HPRT) may be used and culture media for resulting hybridoma cells may be supplemented with hypoxanthine, aminopterin, and thymidine ("HAT medium") to prevent growth of HGPRT-deficient (unfused) cells.

Desirable properties for immortalized cell lines may include, but are not limited to, efficient fusing, supportive of high level antibody expression by selected antibody-producing cells, and sensitivity to unfused cell-inhibitory media (e.g., HAT media). In some embodiments, immortalized cell lines are murine myeloma lines. Such cell lines may be obtained, for example, from the Salk Institute Cell Distribution Center (San Diego, CA) or the American Type Culture Collection, (Manassas, VA). Human myeloma and mouse-human heteromyeloma cell lines may also be used for the production of human monoclonal antibodies (e.g., see Kozbor, D. et al., A human hybrid myeloma for production of human monoclonal antibodies. J Immunol. 1984 December; 133(6):3001-5 and Brodeur, B. et al., Monoclonal Antibody Production Techniques and Applications. Marcel Dekker, Inc., New York. 1987; 33:51-63, the contents of each of which are herein incorporated by reference in their entireties).

Hybridoma cell culture media may be assayed for the presence of monoclonal antibodies with desired binding specificity. Assays may include, but are not limited to, immunoprecipitation assay, in vitro binding assay, radioimmunoassay (RIA), surface plasmon resonance (SPR) assay, and/or enzyme-linked immunosorbent assay (ELISA). In some embodiments, binding specificity of monoclonal antibodies may be determined by Scatchard analysis (Munson, P. J. et al., Ligand: a versatile computerized approach for characterization of ligand-binding systems. Anal Biochem. 1980 Sep. 1; 107(1):220-39, the contents of which are herein incorporated by reference in their entirety).

Antibodies produced by cultured hybridomas may be analyzed to determine binding specificity for target antigens. Once antibodies with desirable characteristics are identified, corresponding hybridomas may be subcloned through limiting dilution procedures and grown by standard methods. Antibodies produced by hybridomas may be isolated and purified using standard immunoglobulin purification procedures such as, for example, protein A-Sepharose, hydroxyapatite chromatography, gel electrophoresis, dialysis, or affinity chromatography. Alternatively, hybridoma cells may be grown in vivo as ascites in a mammal. In some embodiments, antibodies may be isolated directly from serum of immunized hosts.

In some embodiments, recombinant versions of antibodies generated through immunization may be prepared. Such antibodies may be prepared using genomic antibody sequences from selected hybridomas. Hybridoma genomic antibody sequences may be obtained by extracting RNA molecules from antibody-producing hybridoma cells and producing cDNA by reverse transcriptase polymerase chain reaction (PCR). PCR may be used to amplify cDNA using primers specific for antibody heavy and light chains. PCR products may then be subcloned into plasmids for sequence analysis. Antibodies may be produced by insertion of resulting antibody sequences into expression vectors. Some recombinant antibodies may be prepared using synthetic nucleic acid constructs that encode amino acid sequences corresponding to amino acid sequences obtained from isolated hybridoma antibodies.

Antibody Display

In some embodiments, antibodies may be developed using antibody display technologies. "Display technology" refers to systems and methods for expressing amino acid-based candidate compounds in a format where they are linked with nucleic acids encoding them and are accessible to a target or ligand. Candidate compounds are expressed at the surface of a host capsid or cell in most systems, however, some host-free systems (e.g., ribosomal display) exist. Display technologies may be used to generate display "libraries," which include sets of candidate compound library members. Display libraries with antibodies (or variants or fragments thereof) as library members are referred to herein as "antibody display libraries." Antibodies may be designed, selected, or optimized by screening target antigens using antibody display libraries. Antibody display libraries may include millions to billions of members, each expressing unique antibody domains. Antibody fragments displayed may be scFv antibody fragments, which are fusion proteins of $V_H$ and $V_L$ antibody domains joined by a flexible linker. Display libraries may include antibody fragments with differing levels of diversity between variable domain framework regions and CDRs. Display library antibody fragment CDRs may include unique variable loop lengths and/or sequences. Antibody variable domains or CDRs obtained from display library selection may be directly incorporated into antibody sequences for recombinant antibody production or mutated and utilized for further optimization through in vitro affinity maturation.

Antibody display libraries may include antibody phage display libraries. Antibody phage display libraries utilize phage virus particles as hosts with millions to billions of members, each expressing unique antibody domains. Such libraries may provide richly diverse sources that may be used to select potentially hundreds of antibody fragments with diverse levels of affinity for one or more antigens of interest (McCafferty, et al., 1990. Nature. 348:552-4; Edwards, B. M. et al., 2003. JMB. 334: 103-18; Schofield, D. et al., 2007. Genome Biol. 8, R254 and Pershad, K. et al., 2010. Protein Engineering Design and Selection. 23:279-88; the contents of each of which are herein incorporated by reference in their entirety). Antibody fragments displayed may be scFv antibody fragments. Phage display library members may be expressed as fusion proteins, linked to viral coat proteins (e.g. the N-terminus of the viral pIII coat protein). $V_L$ chains may be expressed separately for assembly with $V_H$ chains in the periplasm prior to complex incorporation into viral coats. Precipitated library members may be sequenced from the bound phage to obtain cDNA encoding desired antibody domains.

In some embodiments, antibody display libraries may be generated using yeast surface display technology. Antibody yeast display libraries are made up of yeast cells with surface displayed antibodies or antibody fragments. Antibody yeast display libraries may include antibody variable domains expressed on the surface of *Saccharomyces cerevisiae* cells. Yeast display libraries may be developed by displaying antibody fragments of interest as fusion proteins with yeast surface proteins (e.g. Aga2p protein). Yeast cells displaying antibodies or antibody fragments with affinity for a specific target may be isolated according to standard methods. Such methods may include, but are not limited to, magnetic separation and flow cytometry.

Recombinant Synthesis

Antibodies of the present disclosure may be prepared using recombinant DNA technology and related processes. Constructs (e.g., DNA expression plasmids) encoding antibodies may be prepared and used to synthesize full antibodies or portions thereof. In some embodiments, DNA sequences encoding antibody variable domains of the present disclosure may be inserted into expression vectors (e.g., mammalian expression vectors) encoding other antibody domains and used to prepare antibodies with the inserted variable domains. DNA sequences encoding antibody variable domains may be inserted downstream of upstream expression vector regions with promoter/enhancer elements and/or encoding immunoglobulin signal sequences. DNA sequences encoding antibody variable domains may be inserted upstream of downstream expression vector regions encoding immunoglobulin constant domains. Encoded constant domains may be from any class (e.g., IgG, IgA, IgD, IgE, and IgM) or species (e.g., human, mouse, rabbit, rat, and non-human primate). In some embodiments, encoded constant domains encode human IgG (e.g., IgG1, IgG2, IgG3, or IgG4) constant domains. In some embodiments, encoded constant domains encode mouse IgG (e.g., IgG1, IgG2a, IgG2b, IgG2c, or IgG3) constant domains.

Expression vectors encoding antibodies of the present disclosure may be used to transfect cells for antibody production. Such cells may be mammalian cells. Cell lines with stable transfection of antibody expression vectors may be prepared and used to establish stable cell lines. Cell lines producing antibodies may be expanded for expression of antibodies which may be isolated or purified from cell culture media.

Antibody Characterization

In some embodiments, antibodies of the present disclosure may be identified, selected, or excluded based on different characteristics. Such characteristics may include, but are not limited to, physical and functional characteristics. Physical characteristics may include features of antibody structures [e.g., amino acid sequence or residues; secondary, tertiary, or quaternary protein structure; post-translational modifications (e.g., glycosylations); chemical bonds, and stability]. Functional characteristics may include, but are not limited to, antibody affinity (i.e., for specific epitopes and/or antigens) and antibody activity (e.g., antibody ability to activate or inhibit a target, process, or pathway).

Antibody Binding and Affinity

In some embodiments, antibodies of the present disclosure may be identified, selected, or excluded based on binding and/or level of affinity for specific epitopes and/or antigens. Antibody binding and/or affinity level may be assessed with different antigen formats. In some embodiments, antibody affinity for different antigen formats may be tested in vitro (e.g., by ELISA). Anti-tau antibody in vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples used for anti-tau antibody testing may include brain samples or fractions from non-diseased human subjects. In some embodiments, brain samples or fractions from wild type and/or Tau knockout mouse strains may be used as control samples.

In vitro affinity testing may be carried out (e.g., by ELISA) using recombinant or isolated protein antigens. For example, recombinant or isolated ePHF may be used for anti-tau antibody affinity testing. In some embodiments, anti-tau antibodies of the present disclosure may exhibit a half maximal effective concentration (EC50) of from about 0.01 nM to about 100 nM for binding to ePHF when assessed by ELISA. In some embodiments, the exhibited EC50 may be less than about 50 nM, less than about 20 nM, less than about 10 nM, or less than about 1 nM. In some embodiments, anti-tau antibodies of the present disclosure may exhibit an EC50 of from about 0.01 nM to about 100 nM for binding to any of the antigens listed in Table 8, or an epitope that includes or is included within any of the antigens (including, but not limited to conformational epitopes), when assessed by ELISA. In some embodiments, the exhibited EC50 may be less than about 50 nM, less than about 20 nM, less than about 10 nM, or less than about 1 nM.

In some embodiments, anti-tau antibodies of the present disclosure bind to pathological tau, but do not bind to non-pathological tau. Such antibodies may be referred to herein as being "selective" for pathological forms of tau. In some embodiments, anti-tau antibodies of the present disclosure bind to tau tangles.

In some embodiments, antibody affinity analysis may be used to identify, select, or exclude polyspecific antibodies. As used herein, the term "polyspecific antibody" refers to an antibody with affinity for more than one epitope or antigen. In some embodiments, polyspecific antibodies may be identified, selected, or excluded based on relative affinity for each epitope or antigen recognized. For example, a polyspecific antibody may be selected for use or further development based on higher affinity for one epitope or antigen over a second epitope or antigen for which the polyspecific antibody demonstrates affinity.

In some embodiments, anti-tau antibodies may be tested for competition with other anti-tau antibodies. Such testing may be carried out to provide information on the specific epitope recognized by an antibody and may yield information related to level of epitope affinity in comparison to the competing antibody. In some embodiments, anti-tau antibodies used in antibody binding and/or affinity analysis may include anti-tau antibody PT3, as described in U.S. Pat. No. 9,371,376; anti-tau antibody C10.2, as described in U.S. Pat.

No. 10,196,439 (referred to as antibody "C10-2," therein); anti-tau antibody IPN002, as described in U.S. Pat. No. 10,040,847; anti-tau antibody AT8 (ThermoFisher, Waltham, MA); anti-tau antibody AT100 (ThermoFisher, Waltham, MA); anti-tau antibody AT120 as described in U.S. Pat. No. 5,843,779; or anti-tau antibody PT76, as described in Vandermeeren, M. et al., J Alzheimers Dis. 2018; 65(1):265-281.

Antibody Activity

In some embodiments, antibodies of the present disclosure may be identified, selected, or excluded based on their ability to promote or reduce a certain activity. Antibody activity may be assessed using analytical assays. Such assays may be selected or designed to detect, screen, measure, and/or rank antibodies based on such antibody activity.

Anti-tau antibodies may be characterized by ability to inhibit tau aggregation. Inhibition may be based on physical disruption of tau aggregation or may be based on anti-tau antibody-dependent depletion (immunodepletion) of tau protein. Characterization based on tau aggregation inhibition may be assessed using one or more assays of tau aggregation. In some embodiments, anti-tau antibodies may be characterized by tau seeding assay. Tau seeding assays typically involve in vitro initiation of tau aggregation and assessment of aggregation inhibition by candidate compounds being tested. Tau seeding assays may be carried out using tau aggregation biosensor cells. Tau aggregation biosensor cells yield a detectable signal (e.g., a fluorescent signal) in response to tau aggregation. Tau aggregation biosensor cells may be cultured with recombinant or isolated tau or with samples from high tau brain tissues or fluids (to promote tau aggregation) and treated with or without candidate compounds to assess tau aggregation inhibition. In some embodiments, anti-tau antibodies may be used to deplete tau from media prior to incubation with biosensor cells. Aggregation levels with depleted media may be compared to aggregation levels with non-depleted media to assess anti-tau antibody inhibitory function. Tau aggregation biosensor cells may include, but are not limited to, tau RD Biosensor cells. In some embodiments, neurons expressing human tau may be used.

In some embodiments, anti-tau antibodies of the present disclosure may inhibit tau aggregation with a half maximal inhibitory concentration (IC50) of from about 1 nM to about 30 nM as determined by immunodepletion assay (e.g., using tau RD Biosensor cells).

Antibody Structure and Variations

Antibodies of the present disclosure may exist as a whole polypeptide, a plurality of polypeptides or fragments of polypeptides, which independently may be encoded by one or more nucleic acids, a plurality of nucleic acids, fragments of nucleic acids or variants of any of the aforementioned.

As used herein, "polypeptide" means a polymer of amino acid residues (natural or unnatural) linked together most often by peptide bonds. The term, as used herein, refers to proteins, polypeptides, and peptides of any size, structure, or function. Polypeptides smaller than about 50 amino acids may be referred to using the term "peptide." Peptides may be at least about 2, 3, 4, or at least 5 amino acid residues long. Polypeptides of the present disclosure may include gene products, naturally occurring polypeptides, synthetic polypeptides, homologs, orthologs, paralogs, fragments, or other equivalents, variants, and analogs of the foregoing. Polypeptides may be single molecules or may be multi-molecular complexes such as dimers, trimers, or tetramers. Polypeptides may also include single chain or multichain polypeptides, which may be associated or linked. Polypeptides may include amino acid polymers in which one or more amino acid residues are artificial chemical analogues of corresponding naturally occurring amino acids.

The term "polypeptide variant" refers to molecules which differ in their amino acid sequence from a native or reference sequence. Amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphorylated threonine and/or phosphorylated serine. Alternatively, variant mimics may result in deactivation or in an inactivated product containing the mimic, e.g., phenylalanine may act as an inactivating substitution for tyrosine; or alanine may act as an inactivating substitution for serine.

The term "amino acid sequence variant" refers to molecules with some differences in their amino acid sequences as compared to a native or starting sequence. The amino acid sequence variants may possess substitutions, deletions, and/or insertions at certain positions within the amino acid sequence. "Native" or "starting" sequence should not be confused with a wild type sequence. As used herein, a native or starting sequence is a relative term referring to an original molecule against which a comparison may be made. "Native" or "starting" sequences or molecules may represent the wild-type (that sequence found in nature) but do not have to be the wild-type sequence.

Ordinarily, variants will possess at least 70%, at least 75%, at least 80%, at least 85%, at least 90%, at least 95%, at least 96%, at least 97%, at least 98%, at least 99%, at least 99.5% at least 99.8%, or at least 99.9% sequence identity as compared to a native sequence.

By "homologs" as it applies to amino acid sequences is meant the corresponding sequence of other species having substantial identity to a second sequence of a second species.

"Analogs" is meant to include polypeptide variants which differ by one or more amino acid alterations, e.g., substitutions, additions or deletions of amino acid residues that still maintain the properties of the parent polypeptide.

The present disclosure contemplates variants and derivatives of antibodies presented herein. These include substitutional, insertional, deletion and covalent variants and derivatives. For example, sequence tags or amino acids, such as one or more lysines, may be added to antibody peptide sequences (e.g., at the N-terminal or C-terminal ends). Sequence tags may be used for peptide purification or localization. Lysines may be used to increase peptide solubility or to allow for biotinylation. Alternatively, amino acid residues located at the carboxy and amino terminal regions of the amino acid sequence of a peptide or polypeptide may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides, are those with one or more amino acids in the native or starting amino acid sequence removed. Ordinarily, deletional variants will have one or more amino acids deleted in a particular region of the molecule.

As used herein, the term "derivative" is used synonymously with the term "variant" and refers to a molecule that has been modified or changed in any way relative to a reference molecule or starting molecule. In some embodiments, derivatives include native or starting polypeptides that have been modified with an organic proteinaceous or non-proteinaceous derivatizing agent, and post-translational modifications. Covalent modifications are traditionally introduced by reacting targeted amino acid residues of a polypeptide with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of antibodies for immunoaffinity purification.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in polypeptides used in accordance with the present disclosure.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

Covalent derivatives specifically include fusion molecules in which polypeptides are covalently bonded to non-proteinaceous polymers. Non-proteinaceous polymers may include hydrophilic synthetic polymers, i.e., polymers not otherwise found in nature. However, polymers which exist in nature and are produced by recombinant or in vitro methods are useful, as are polymers which are isolated from nature. Hydrophilic polyvinyl polymers may include polyvinylalcohol and/or polyvinylpyrrolidone. Particularly useful are polyvinylalkylene ethers such a polyethylene glycol and polypropylene glycol. Polypeptides may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337, the contents of each of which are herein incorporated by reference in their entirety.

As used herein when referring to polypeptides the term "loop" refers to a structural feature of a peptide or polypeptide which reverses the direction of the backbone of a peptide or polypeptide and includes four or more amino acid residues. Oliva et al. have identified at least 5 classes of polypeptide loops (J. Mol Biol 266 (4): 814-830; 1997, the contents of which are herein incorporated by reference in their entirety).

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to include an odd number of amino acids, a half-loop of the odd-numbered loop will include the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural and/or functional characteristics or properties (e.g., binding capacity), e.g., serving as a site for protein-protein interactions.

As used herein when referring to polypeptides, the term "site" is synonymous with "amino acid residue" and "amino acid side chain." A site represents a position on a polypeptide that may be modified, manipulated, altered, derivatized or varied within the polypeptide.

As used herein the terms "termini or terminus" when referring to polypeptides refers to an extremity of a peptide or polypeptide. Such extremity is not limited only to the first or final site of the peptide or polypeptide but may include additional amino acids in the terminal regions. Polypeptide based molecules of the present disclosure may be characterized as having both an N-terminus (terminated by an amino acid with a free amino group) and a C-terminus (terminated by an amino acid with a free carboxyl group). Proteins of the present disclosure are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Antibody Modification

Antibodies may be modified to obtain variants with one or more altered properties. Such properties may include or relate to antibody structure, function, affinity, specificity, protein folding, stability, manufacturing, expression, and/or immunogenicity (i.e., immune reactions in subjects being treated with such antibodies). In some embodiments, antibody fragments or variants may be used to modify another antibody or may be incorporated into a synthetic antibody.

Antibody modification may include amino acid sequence modifications. Such modifications may include, but are not limited to, amino acid deletions, additions, and/or substitutions. Modifications may be informed by amino acid sequence analysis. Such analysis may include alignment of amino acid sequences between different antibodies or antibody variants. Two or more antibodies may be compared to identify residues or regions suitable for modification. Compared antibodies may include those binding to the same epitope. Compared antibodies may bind to different epitopes (separate or overlapping) of the same protein or target (e.g., to identify residues or regions conferring specificity to specific epitopes). Comparisons may include light and/or heavy chain sequence variation analysis, CDR sequence variation analysis, germline sequence analysis, and/or framework sequence analysis. Information obtained from such analysis may be used to identify amino acid residues, segments of amino acids, amino acid side chains, CDR lengths, and/or other features or properties that are conserved or variable among antibodies binding to the same or different epitopes.

In some embodiments, modified versions of anti-tau antibodies described above may be prepared by adding, deleting, or substituting one or more CDR amino acid residues.

In some embodiments, anti-tau antibodies may be modified by amino acid sequence alignment of antibodies binding to similar targets and preparing modified antibodies with one or more amino acid deletions, substitutions, or insertions based on analysis of the aligned sequences.

The present disclosure includes amino acid consensus sequences for CDR region sequences, showing specific amino acids (shown in square brackets) that may be modified or amino acid residue positions that may be more generally deleted or substituted (shown using variable "X") in antibody amino acid sequences, e.g. as described in Table 1A or Z.

Related CDR sequences that can appear in the same VH and/or VL sequences of an antibody are grouped together in the same row. For example, an antibody of the invention may comprise one each of CDRH1-CDRH3 and CDRL1-CDRL3, wherein said CDRH1-CDRH3 and CDRL1-CDRL3 are represented by SEQ ID NOs: 928, 930, 409, 472, 525, and 570, respectively.

In addition, in Table 5, for example, each odd numbered rows below the table heading, and the even numbered rows immediately therebelow, are related (if not identical) consensus sequences (e.g., SEQ ID NOs: 927 and 928 are related, SEQ ID NOs: 933 and 934 are related). It is contemplated that an antibody of the invention may comprise one each of CDRH1-CDRH3 and CDRL1-CDRL3, wherein each of said CDRH1-CDRH3 and CDRL1-CDRL3 can be independently represented by one of the two related consensus sequences. For example, an antibody of the invention may comprise one each of CDRH1-CDRH3 and CDRL1-CDRL3, wherein said CDRH1-CDRH3 and CDRL1-CDRL3 are represented by SEQ ID NOs: 931, 341, 410, 934, 935, and 571, respectively.

Furthermore, amino acid at each X position or Xi position (where i=1, 2, 3, . . . ) may be any naturally occurring amino acids, or may be a selected subset of amino acids as specified in each consensus sequence X/Xi position. It is contemplated that any one or more of the enumerated specific amino acids at each X or Xi positions can be eliminated as a permissible value for the X or Xi position.

CDR Consensus Sequences

| CDRH1 | CDRH2 | CDRH3 | CDRL1 | CDRL2 | CDRL3 |
|---|---|---|---|---|---|
| GYTFTS [Y/N] (SEQ ID NO: 927) | NPNNS [D/E] (SEQ ID NO: 929) | ANYYGGSQFAY (SEQ ID NO: 409) | RSSQSLVHSNGKTYLH (SEQ ID NO: 472) | KVSNRFS (SEQ ID NO: 525) | SQSTHVPFT (SEQ ID NO: 570) |
| GYTFTSX (SEQ ID NO: 928),<br>X = any; e.g., Y, F, N, Q | NPNNSX (SEQ ID NO: 930)<br>X = any, e.g., negatively charged | ANYYGGSQFAY (SEQ ID NO: 409) | RSSQSLVHSNGKTYLH (SEQ ID NO: 472) | KVSNRFS (SEQ ID NO: 525) | SQSTHVPFT (SEQ ID NO: 570) |
| G [F/Y] TFT [R/I] [Y/F] (SEQ ID NO: 931) | NPNNGG (SEQ ID NO: 341) | GTGTGAMDY (SEQ ID NO: 410) | RSSQSLVH [N/S] NG [I/N] T [H/Y] LY (SEQ ID NO: 933) | RVS [N/S] RFS (SEQ ID NO: 935) | FQGTHVPRT (SEQ ID NO: 571) |
| G-X1-TFT-X2-X3 (SEQ ID NO: 932),<br>X1 = any; e.g., F, Y<br>X2 = any; e.g., R, K, H, A, V, I, L<br>X3 = any; e.g., Y, F | NPNNGG (SEQ ID NO: 341) | GTGTGAMDY (SEQ ID NO: 410) | RSSQSLVH-X1-NG-X2-T-X3-LY (SEQ ID NO: 934),<br>X1 = any; e.g., N, Q, S, T<br>X2 = any; e.g., A, V, I, L, N, Q<br>X3 = any; e.g., H, R, K, Y, F | RVSXRFS (SEQ ID NO: 936),<br>X = any; e.g., N, Q, S, T | FQGTHVPRT (SEQ ID NO: 571) |
| G [F/Y] TFT [R/I/D] [Y/F] (SEQ ID NO: 937) | NPNNG [G/E] (SEQ ID NO: 939) | G [T/R] G [T/M] G [—/Y] [—/Y] A [M/L] DY (SEQ ID NO: 941) | [R/G] [S/A] S [Q/E] [S/N] [L/V] [V/Y] [H/G] [S/A/N] [N/T/L] [G/N] [I/N/absent] [T/absent] [H/Y/absent] [L/absent] [Y/absent] | [R/G] [V/A] [S/T] [N/T/S] [R/L] [F/A] [S/D] | [F/Q] [G/N] [G/V] [T/L] [H/T] [V/I] P [R/W] T |
| G-X1-TFT-X2-X3 (SEQ ID NO: 938),<br>X1 = any; e.g., F, Y<br>X2 = any; e.g., R, K, H, G, A, V, I, L, D, E<br>X3 = any; e.g., Y, F | NPNNGX (SEQ ID NO: 940)<br>X = any; e.g., G, A, V, I, L, E, D | G-X1-G-X2-G-X3-X4-A-X5-DY (SEQ ID NO: 942),<br>X1 = any; e.g., T, S, R, K, H<br>X2 = any; e.g., T, S, M, A, V, I, L<br>X3 = any or absent; e.g., Y, F, — | X1-X2-S-X3-X4-X5-X6-X7-X8-X9-X10-X11-X12-X13-X14-X15,<br>X1 = any; e.g., R, K, H, G, A, V, I, L<br>X2 = any; e.g., S, T, A, V, I, L<br>X3 = any; e.g., Q, N, E, D<br>X4 = any; e.g., S, T, N, Q | X1-X2-X3-X4-X5-X6-X7,<br>X1 = any; e.g., R, K, H, G, A<br>X2 = any; e.g., A, V, I, L<br>X3 = any; e.g., S, T<br>X4 = any; e.g., N, Q, T, S | X1-X2-X3-X4-X5-X6-P-X7-T,<br>X1 = any; e.g., F, Y, Q, N<br>X2 = any; e.g., G, A, N, Q<br>X3 = any; e.g., G, A, V, I, L<br>X4 = any; e.g., T, S, A, V, I, L<br>X5 = any; e.g., H, K, R, T, |

-continued

| CDR Consensus Sequences | | | | | |
|---|---|---|---|---|---|
| CDRH1 | CDRH2 | CDRH3 | CDRL1 | CDRL2 | CDRL3 |
| | | X4 = any or absent; e.g., Y, F, —<br>X5 = any; e.g., M, A, I, L, V | X5 = any; e.g., A, V, I, L<br>X6 = any; e.g., A, V, I, L, Y, F<br>X7 = any; e.g., H, R, K, G, A<br>X8 = any; e.g., S, T, A, V, I, L, N, Q<br>X9 = any; e.g., N, Q, T, S, A, V, I, L, M<br>X10 = any; e.g., G, A, N, Q<br>X11 = any or absent; e.g., A, V, I, L, N, Q, —<br>X12 = any or absent; e.g., T, S, —<br>X13 = any or absent; e.g., R, K, H, Y, F, —<br>X14 = any or absent; e.g., A, V, I, L, —<br>X15 = any or absent; e.g., Y, F, — | X5 = any; e.g., R, K, H, A, V, I, L<br>X6 = any; e.g., F, Y, A, V, I, L, G<br>X7 = any; e.g., S, T, D, E | S<br>X6 = any; e.g., A, V, I, L<br>X7 = any; e.g., R, K, H, W, F, Y |
| GY [S/T] FT [D/E] Y (SEQ ID NO: 949) | [F/Y] PG [S/R] [D/G][S/N] | P [T/A] [V/I/Y] [V/Y] [A/S] [R/K] DYAM [D/E] Y (SEQ ID NO: 953) | RSSQSIV [Y/H] [S/R/T] NGNTYLE (SEQ ID NO: 955) | KVSNRFS (SEQ ID NO: 525) | FQGSHVP [Y/F] T (SEQ ID NO: 957) |
| GY-X1-FT-X2-Y (SEQ ID NO: 950),<br>X1 = any; e.g., S, T<br>X2 = any; e.g., D, E, S, T | X1-PG-X2-X3-X4,<br>X1 = any; e.g., F, Y<br>X2 = any; e.g., S, T, R, K, H<br>X3 = any; e.g., D, E, G, A<br>X4 = any; e.g., S, T, N, Q | P-X1-X2-X3-X4-X5-DYAM-X6-Y (SEQ ID NO: 954),<br>X1 = any; e.g., T, S, A, V, I, L<br>X2 = any; e.g., A, V, I, L, Y, F<br>X3 = any; e.g., A, V, I, L, Y, F<br>X4 = any; e.g., A, V, I, L, S, T<br>X5 = any; e.g., R, K, H<br>X6 = any; e.g., D, E | RSSQSIV-X1-X2-NGNTYLE (SEQ ID NO: 956),<br>X1 = any; e.g., Y, F, H, R, K<br>X2 = any; e.g., S, T, R, K, H | KVSNRFS (SEQ ID NO: 525) | FQGSHVPXT (SEQ ID NO: 958),<br>X = any; e.g., Y, F |
| GY [S/T] FT [D/E/S] Y (SEQ ID NO: 959) | [F/Y] P [G/S] [S/R/N] [D/G] [S/G/N] | [P/S] [T/A/S] [V/I/Y] [V/Y] [A/S/G] [R/K] DYAM [D/E] Y (SEQ ID NO: 962) | RSSQSIV [Y/H] [S/R/T] NGNTYLE (SEQ ID NO: 955) | KVSNRFS (SEQ ID NO: 525) | FQGSHVP [Y/F] T (SEQ ID NO: 957) |
| GY-X1-FT-X2-Y (SEQ ID NO: 950),<br>X1 = any; e.g., S, T<br>X = any; e.g., D, E, S, T | X1-P-X2-X3-X4-X5,<br>X1 = any; e.g., F, Y<br>X2 = any; e.g., S, T, G, A, V, I, L<br>X3 = any; e.g., S, T, R, K, H, N, Q<br>X4 = any; e.g., D, E, G, A<br>X5 = any; e.g., S, T, G, A, N, Q | X1-X2-X3-X4-X5-X6-DYAM-X7-Y (SEQ ID NO: 963),<br>X1 = any; e.g., P, S, T, A, V, I, L<br>X2 = any; e.g., T, S, A, V, I, L<br>X3 = any; e.g., A, V, I, L, Y, F<br>X4 = any; e.g., A, V, I, L, Y, F<br>X5 = any; e.g., A, V, I, L, S, T, G<br>X6 = any; e.g., R, K, H<br>X7 = any; e.g., E, D | RSSQSIV-X1-X2-NGNTYLE (SEQ ID NO: 956),<br>X1 = any; e.g., Y, F, H, R, K<br>X2 = any; e.g., S, T, R, K, H | KVSNRFS (SEQ ID NO: 525) | FQGSHVPXT (SEQ ID NO: 958),<br>X = any; e.g., F, Y |
| GFSL [S/N] T [S/F] [A/G] M (SEQ ID NO: 964) | YWDDD (SEQ ID NO: 362) | R [R/V/K] R [G/Y/S] Y [G/A] MDY (SEQ ID NO: 966) | K [A/S] SQS [V/L] [S/L] [N/S] [—/S] [—/G] [—/N] [—/Q] [—/K] [—/N] [D/Y] [V/L] A (SEQ ID NO: 968) | [Y/G] [A/T] S [N/T] R [C/E] [T/S] | Q [Q/N] D [Y/H] [R/S] [S/H] P [L/Y] T (SEQ ID NO: 972) |
| GFSL-X1-T-X2-X3-M (SEQ ID NO: 965),<br>X1 = any; e.g., S, T, N, Q<br>X2 = any; e.g., S, T, F, Y<br>X3 = any; e.g., A, V, I, L, G | YWDDD (SEQ ID NO: 362) | R-X1-R-X2-Y-X3-MDY (SEQ ID NO: 967),<br>X1 = any; e.g., R, K, H, A, V, I, L<br>X2 = any; e.g., A, V, I, L, G, S, T, Y, F<br>X3 = any; e.g., A, V, I, L, G | K-X1-SQS-X2-X3-X4-X5-X6-X7-X8-X9-X10-X11-X12-A (SEQ ID NO: 969),<br>X1 = any; e.g., A, V, I, L, S, T<br>X2 = any; e.g., A, V, I, L<br>X3 = any; e.g., S, T, A, V, I, L<br>X4 = any; e.g., S, T, N, Q<br>X5 = any or absent; e.g., S, T, — | X1-X2-S-X3-R-X4-X5,<br>X1 = any; e.g., Y, F, G, A, V, I, L<br>X2 = any; e.g., A, V, I, L, T, S<br>X3 = any; e.g., N, Q, T, S<br>X4 = any; e.g., C, E, D, S<br>X5 = any; e.g., T, S | Q-X1-D-X3-X4-X5-P-X6-T (SEQ ID NO: 973),<br>X1 = any; e.g., Q, N<br>X2 = any; e.g., Y, F, H, K, R<br>X3 = any; e.g., R, K, H, S, T<br>X4 = any; e.g., S, T, H, K, R<br>X5 = any; e.g., A, V, I, L, Y, F |

-continued

| CDR Consensus Sequences | | | | | |
|---|---|---|---|---|---|
| CDRH1 | CDRH2 | CDRH3 | CDRL1 | CDRL2 | CDRL3 |
| | | | X6 = any or absent; e.g., G, A, V, I, L, —<br>X7 = any or absent; e.g., N, Q, —<br>X8 = any or absent; e.g., N, Q, —<br>X9 = any or absent; e.g., K, R, H, —<br>X10 = any or absent; e.g., N, Q, —<br>X11 = any; e.g., D, E, Y, F<br>X12 = any; e.g., A, V, I, L | | |
| GFSL [S/N] T [S/F] [A/G] M (SEQ ID NO: 964) | YWDDD (SEQ ID NO: 362) | R [R/V/K/S/G] [Y/R] [Y/—] [S/—] [—/N] [G/S/Y/R] [Y/N/G] [G/A/Y/N] [M/F/Y] DY | [K/S] [S/A] S [Q/S] S [L/I/V] [L/S] [N/S/D] [D/S/T] [V/G/D/Y] [N/G/—] [Q/—] [K/—] [N/T/—] [Y/—] [L/—] [A/H/N] | [Y/G/L/R] [A/T/V] S [N/T/K] [R/L] [C/E/D/A] [T/S] | [W/Q] [Q/N] [G/D] [T/S/Y/H] [H/S/R] [F/I/S/H] P [Q/R/L/Y] [—/Y] T |
| GFSL-X1-T-X2-X3-M (SEQ ID NO: 965),<br>X1 = any; e.g., S, T, N, Q<br>X2 = any; e.g., S, T, F, Y<br>X3 = any; e.g., A, V, I, L, G | YWDDD (SEQ ID NO: 362) | R-X1-X2-X3-X4-X5-X6-X7-X8-X9-DY,<br>X1 = any; e.g., R, K, H, A, V, I, L, S, T, G<br>X2 = any; e.g., Y, F, R, K, H<br>X3 = any or absent; e.g., Y, F, —<br>X4 = any or absent; e.g., S, T, —<br>X5 = any or absent; e.g., N, Q, —<br>X6 = any; e.g., G, A, V, I, L, S, T, Y, F, R, K, H<br>X7 = any; e.g., Y, F, N, Q, G, A, V, I, L<br>X8 = any; e.g., G, A, V, I, L, N, Q, Y, F<br>X9 = any; e.g., M, Y, F | X1-X2-S-X3-S-X4-X5-X6-X7-X8-X9-X10-X11-X12-X13-X14-X15,<br>X1 = any; e.g., K, R, H, S, T<br>X2 = any; e.g., S, T, A, V, I, L<br>X3 = any; e.g., Q, N, S, T<br>X4 = any; e.g., A, V, I, L<br>X5 = any; e.g., A, V, I, L, S, T<br>X6 = any; e.g., N, Q, S, T, D, E<br>X7 = any; e.g., D, E, S, T<br>X8 = any; e.g., A, V, I, L, G, D, E, Y, F<br>X9 = any or absent; e.g., N, Q, G, A, —<br>X10 = any or absent; e.g., Q, N, —<br>X11 = any or absent; e.g., K, R, H, —<br>X12 = any or absent; e.g., N, Q, T, S, —<br>X13 = any or absent; e.g., Y, F, —<br>X14 = any or absent; e.g., A, V, I, L, —<br>X15 = any; e.g., A, V, I, L, H, R, K, N, Q | X1-X2-S-X3-X4-X5-X6,<br>X1 = any; e.g., Y, F, G, A, V, I, L, R, K, H<br>X2 = any; e.g., A, V, I, L, S, T<br>X3 = any; e.g., N, Q, T, S, K, R, H<br>X4 = any; e.g., R, K, H, A, V, I, L<br>X5 = any; e.g., C, S, E, D, A, V, I, L<br>X6 = any; e.g., T, S | X1-X2-X3-X4-X5-X6-P-X7-X8-T,<br>X1 = any; e.g., Q, N, W, F, Y<br>X2 = any; e.g., Q, N<br>X3 = any; e.g., D, E, G, A, V, I, L<br>X4 = any; e.g., T, S, Y, F, H, K, R<br>X5 = any; e.g., H, R, K, S, T<br>X6 = any; e.g., F, Y, A, V, I, L, S, T, H, K, R<br>X7 = any; e.g., Q, N, R, K, H, L, V, A, I, Y, F<br>X8 = any or absent; e.g., Y, F, — |

*In the table above, "—" in the bracket means the residue can be absent.

TABLE 1

| Consensus CDRs for exemplary anti-tau antibodies V0022, V0023 and V0024 | | |
|---|---|---|
| SEQ ID NO | Description | Sequence |
| SEQ ID NO: 1180 (Chothia) | HCDR1 | $GX_1TFTX_2X_3$, wherein<br>$X_1$ is For Y;<br>$X_2$ is R or I; and<br>$X_3$ is Y or F |
| SEQ ID NO: 341 (Chothia) | HCDR2 | NPNNGG |
| SEQ ID NO: 410 (Chothia) | HCDR3 | GTGTGAMDY |
| SEQ ID NO: 1181 (Chothia) | LCDR1 | $RSSQSLVHX_1NGX_2TX_3LY$, wherein<br>$X_1$ is N or S;<br>$X_2$ is I or N; and<br>$X_3$ is Y or H |
| SEQ ID NO: 1182 (Chothia) | LCDR2 | $RVSX_1RFS$, wherein<br>$X_1$ is N or S |
| SEQ ID NO: 571 (Chothia) | LCDR3 | FQGTHVPRT |
| (Kabat) | HCDR1 | $X_1X_2WMH$, wherein<br>$X_1$ is R or I; and<br>$X_2$ is Y or F |
| SEQ ID NO: 1184 (Kabat) | HCDR2 | $X_1INPNNGGX_2DX_3NEX_4FKX_5$, wherein<br>$X_1$ is Nor K;<br>$X_2$ is T or G;<br>$X_3$ is F, Y, or N;<br>$X_4$ is Kor R; and<br>$X_5$ is N or S; |
| SEQ ID NO: 410 (Kabat) | HCDR3 | GTGTGAMDY |

TABLE 1-continued

Consensus CDRs for exemplary anti-tau antibodies V0022, V0023 and V0024

| SEQ ID NO | Description | Sequence |
|---|---|---|
| SEQ ID NO: 1185 (Kabat) | LCDR1 | RSSQSLVHX$_1$NGX$_2$TX$_3$LY, wherein X$_1$ is N or S; X$_2$ is I or N; and X$_3$ is Y or H |
| SEQ ID NO: 1182 (Kabat) | LCDR2 | RVSX$_1$RFS, wherein X$_1$ is N or S |
| SEQ ID NO: 571 (Kabat) | LCDR3 | FQGTHVPRT |
| SEQ ID NO: 1186 (IMGT) | HCDR1 | GX$_1$TFTX$_2$X$_3$W, wherein X$_1$ is For Y; X$_2$ is R or I; and X$_3$ is Y or F |
| SEQ ID NO: 1187 (IMGT) | HCDR2 | INPNNGG X$_1$, wherein X$_1$ is T or G |
| SEQ ID NO: 1167 (IMGT) | HCDR3 | ARGTGTGAMDY |
| SEQ ID NO: 1188 (IMGT) | LCDR1 | QSLVHX$_1$NGX$_2$TX$_3$, wherein X$_1$ is N or S; X$_2$ is I or N; and X$_3$ is Y or H |
| (IMGT) | LCDR2 | RVS |
| SEQ ID NO: 571 (IMGT) | LCDR3 | FQGTHVPRT |

In some embodiments, anti-tau antibodies of the present disclosure may include a CDRH1 that includes the amino acid sequence GYTFTS [Y/N] (SEQ ID NO: 927), or a CDRH1 that includes the amino acid sequence GYTFTSX (SEQ ID NO: 928), wherein X may be any amino acid, e.g., X is Y/F/N/Q; a CDRH2 that includes the amino acid sequence NPNNS [D/E] (SEQ ID NO: 929), or a CDRH2 that includes the amino acid sequence NPNNSX (SEQ ID NO: 930), wherein X may be any amino acid, e.g., an amino acid with a negatively charged side chain; and a CDRH3 that includes the amino acid sequence ANYYGGSQFAY (SEQ ID NO: 409); a CDRL1 that includes the amino acid sequence RSSQSLVHSNGKTYLH (SEQ ID NO: 472); a CDRL2 that includes the amino acid sequence KVSNRFS (SEQ ID NO: 525); and/or a CDRL3 that includes the amino acid sequence SQSTHVPFT (SEQ ID NO: 570).

In some embodiments, anti-tau antibodies include a CDRH1 that includes the amino acid sequence G [F/Y] TFT [R/I] [Y/F] (SEQ ID NO: 931), or a CDRH1 that includes the amino acid sequence G-X1-TFT-X2-X3 (SEQ ID NO: 932), wherein each of X1, X2, and X3 may be any amino acid, e.g., X1 and/or X3 may be an amino acid with a hydrophobic and/or aromatic side chain, such as F or Y, and/or X2 may be a positively charged residue (such as R. K. H) or a residue with aliphatic side chain (such as A, V, I, or L); a CDRH2 that includes the amino acid sequence NPNNGG (SEQ ID NO: 341); a CDRH3 that includes the amino acid sequence GTGTGAMDY (SEQ ID NO: 410); a CDRL1 that includes the amino acid sequence RSSQSLVH [N/S] NG [IN] T [H/Y] LY (SEQ ID NO: 933), or a CDRL1 that includes the amino acid sequence RSSQSLVH-X1-NG-X2-T-X3-LY (SEQ ID NO: 934), where X1, X2, and X3 may be any amino acid, e.g., X1 is Q/N/S/T and/or X2 is A/V/I/L/Q/N and/or X3 is H/R/K/Y/F; a CDRL2 that includes the amino acid sequence RVS [N/S] RFS (SEQ ID NO: 935), or a CDRL2 that includes the amino acid sequence RVSXRFS (SEQ ID NO: 936), where X may be any amino acid, e.g., X is Q/N/S/T; and/or a CDRL3 that includes the amino acid sequence FQGTHVPRT (SEQ ID NO: 571).

In some embodiments, anti-tau antibodies include a CDRH1 that includes the amino acid sequence G [F/Y] TFT [R/I/D] [Y/F] (SEQ ID NO: 937), or a CDRH1 that includes the amino acid sequence G-X1-TFT-X2-X3 (SEQ ID NO: 938), where X1, X2 and X3 may be any amino acid, e.g., X1 and X3 are each independently F/Y and/or X2 is any residue (such as R/K/H/D/E/G/A/I/L/V); a CDRH2 that includes the amino acid sequence NPNNG [G/E] (SEQ ID NO: 939), or a CDRH2 that includes the amino acid sequence NPNNGX (SEQ ID NO: 940), where X may be any amino acid, e.g., E/D/G/A/V/I/L; a CDRH3 that includes the amino acid sequence of G [T/R] G [T/M] G [absent/Y] [absent/Y] A [M/L] DY (SEQ ID NO: 941), or a CDRH3 that includes the amino acid sequence G-X1-G-X2-G-X3-X4-A-X5-DY (SEQ ID NO: 942), where each of X1-X5 may be any amino acid and/or where X3 and/or X4 may be absent, e.g., X1 is S/T/R/K/H and/or X2 is S/T/V/L/A/I/M and/or X3 and X4 are each independently Y/F/absent and/or X5 is A/V/I/L/M; a CDRL1 that includes the amino acid sequence [R/G] [S/A] S [Q/E] [S/N] [L/V] [V/Y] [H/G] [S/A/N] [N/T/L] [G/N] [I/N/absent] [T/absent] [H/Y/absent] [L/absent] [Y/absent], or a CDRL1 that includes the amino acid sequence X1-X2-S-X3-X4-X5-X6-X7-X8-X9-X10-X11-X12-X13-X14-X15, where X1-X15 may be any amino acid and/or where X11, X12, X13, X14, and/or X15 may be absent, e.g., X1 is R/K/H/G/A/V/I/L and/or X2 is S/T/A/V/I/L and/or X3 is Q/N/E/D and/or X4 is S/T/N/Q and/or X5 is L/V/A/I and/or X6 is A/V/I/L/Y/F and/or X7 is H/R/K/G/A and/or X8 is S/T/A/V/I/L/N/Q and/or X9 is N/Q/A/I/L/V/M/S/T and/or X10 is G/A/N/Q and/or X11 is Q/N/A/V/I/L/absent and/or X12 is T/S/absent and/or X13 is H/R/K/Y/F/absent and/or X14 is A/V/I/L/absent and/or X15 is Y/F/absent; a CDRL2 consensus sequence with from about 3 to about 7 amino acids with an amino acid sequence of [R/G] [V/A]S/T]N/T/S] [R/L] [F/A] [S/D], or a CDRL2 that includes the amino acid sequence X1-X2-X3-X4-X5-X6-X7, where X1, X2, X3, X4, X5, X6, and X7 may be any amino acid, e.g., X1 is R/K/H/G/A and/or X2 is V/A/I/L and/or X3 is S/T and/or X4 is N/Q/T/S and/or X5 is R/K/H/A/V/I/L and/or X6 is F/Y/A/V/I/L/G and/or X7 is S/T/D/E; and/or a CDRL3 that includes the amino acid sequence [F/Q] [G/N] [G/V] [T/L] [H/T] [V/I] P [R/W] T, or a CDRL3 that includes the amino acid sequence X1-X2-X3-X4-X5-X6-P-X7-T, where X1, X2, X3, X4, X5, X6, and X7 may be any amino acid, e.g., X1 is F/Y/Q/N and/or X2 is G/A/Q/N and/or X3 is G/A/V/I/L and/or X4 is T/S/A/V/I/L and/or X5 is H/R/K/T/S and/or X6 is V/I/A/L and/or X7 is R/K/H/W/F/Y.

In some embodiments, anti-tau antibodies include a CDRH1 that includes the amino acid sequence GY [S/T] FT [D/E] Y (SEQ ID NO: 949), or a CDRH1 that includes the amino acid sequence GY-X1-FT-X2-Y (SEQ ID NO: 950), where X1 and X2 may be any amino acid, e.g., X1 is S/T and/or X2 is D/E/S/T; a CDRH2 that includes the amino acid sequence [F/Y] PG [S/R] [D/G] [S/N], or a CDRH2 that includes the amino acid sequence X1-PG-X2-X3-$X_4$, where X1-X4 may be any amino acid, e.g., X1 is F/Y and/or X2 is S/T/R/K/H and/or X3 is D/E/G/A and/or X4 is S/T/N/Q; a CDRH3 that includes the amino acid sequence P [T/A] [V/V/Y] [V/Y] [A/S] [R/K] DYAM [D/E] Y (SEQ ID NO: 953), or a CDRH3 that includes the amino acid sequence P-X1-X2-X3-X4-X5-DYAM-X6-Y (SEQ ID NO: 954), where X1-X6 may be any amino acid, e.g., X1 is T/S/A/V/I/L and/or X2 is V/I/A/L/Y/F and/or X3 is V/I/A/L/Y/F and/or X4 is A/V/I/L/S/T and/or X5 is R/K/H and/or X6 is D/E; a CDRL1 that includes the amino acid sequence RSSQSIV [Y/H] [S/R/T] NGNTYLE (SEQ ID NO: 955), or a CDRL1 that includes the amino acid sequence RSSQSIV- X1-X2-NGNTYLE (SEQ ID NO: 956), where X1 and X2 may be any amino acid, e.g., X1 is Y/F/H/R/K and/or X2 is S/T/R/K/H; a CDRL2 that includes the amino acid sequence KVSNRFS (SEQ ID NO: 525); and/or a CDRL3 that includes the amino acid sequence FQGSHVP [Y/F]T (SEQ ID NO: 957), or a CDRL3 that includes the amino acid sequence FQGSHVPXT (SEQ ID NO: 958), wherein X may be any amino acid, e.g., X is Y/F.

In some embodiments, anti-tau antibodies include a CDRH1 that includes the amino acid sequence GY [S/T] FT [D/E/S] Y (SEQ ID NO: 959), or a CDRH1 that includes the amino acid sequence GY-X1-FT-X2-Y (SEQ ID NO: 950), where X1 and X2 may be any amino acid, e.g., X1 is S/T and/or X2 is E/D/S/T; a CDRH2 that includes the amino acid sequence [F/Y] P [G/S] [S/R/N] [D/G] [S/G/N], or a CDRH2 that includes the amino acid sequence X1-P-X2-X3-X4-X5, where X1-X5 may be any amino acid, e.g., X1 is F/Y and/or X2 is S/T/G/A/V/I/L and/or X3 is S/T/R/K/H/N/Q and/or X4 is D/E/G/A and/or X5 is S/T/N/Q/G/A; a CDRH3 that includes the amino acid sequence [P/S] [T/A/S] [V/V/Y] [V/Y] [A/S/G] [R/K] DYAM [D/E] Y (SEQ ID NO: 962), or a CDRH3 that includes the amino acid sequence X1-X2-X3-X4-X5-X6-DYAM-X7-Y (SEQ ID NO: 963), where X1-X7 may be any amino acid, e.g., X1 is S/T/P/A/I/L/V and/or X2 is T/S/A/V/I/L and/or X3 is A/V/I/L/Y/F and/or X4 is A/V/I/L/Y/F and/or X5 is A/V/I/L/G/S/T and/or X6 is R/K/H and/or X7 is E/D; a CDRL1 that includes the amino acid sequence RSSQSIV [Y/H] [S/R/T] NGNTYLE (SEQ ID NO: 955), or a CDRL1 that includes the amino acid sequence RSSQSIV-X1-X2-NGNTYLE (SEQ ID NO: 956), where X1 and X2 may be any amino acid, e.g., X1 is Y/F/H/R/K and/or X2 is S/T/R/K/H; a CDRL2 that includes the amino acid sequence KVSNRFS (SEQ ID NO: 525); and/or a CDRL3 that includes the amino acid sequence FQGSHVP [Y/F]T (SEQ ID NO: 957), or a CDRL3 that includes the amino acid sequence FQGSHVPXT (SEQ ID NO: 958), wherein X may be any amino acid, e.g., X is F/Y.

In some embodiments, anti-tau antibodies include a CDRH1 that includes the amino acid sequence GFSL [S/N] T [S/F] [A/G] M (SEQ ID NO: 964), or a CDRH1 that includes the amino acid sequence GFSL-X1-T-X2-X3-M (SEQ ID NO: 965), where X1-X3 may be any amino acid, e.g., X1 is S/T/N/Q and/or X2 is S/T/F/Y and/or X3 is A/V/I/L/G; a CDRH2 that includes the amino acid sequence YWDDD (SEQ ID NO: 362); a CDRH3 that includes the amino acid sequence R [R/V/K] R [G/Y/S] Y [G/A] MDY (SEQ ID NO: 966), or a CDRH3 that includes the amino acid sequence R-X1-R-X2-Y-X3-MDY (SEQ ID NO: 967), where X1-X3 may be any amino acid, e.g., X1 is R/K/H/A/V/I/L and/or X2 is G/A/V/I/L/S/T/Y/F and/or X3 is A/V/I/L/G; a CDRL1 that includes the amino acid sequence K [A/S] SQS [V/L] [S/L] [N/S] [absent/S] [absent/G] [absent/N] [absent/Q] [absent/K] [absent/N] [D/Y] [V/L] A (SEQ ID NO: 968), or a CDRL1 that includes the amino acid sequence K-X1-SQS-X2-X3-X4-X5-X6-X7-X8-X9-X10-X11-X12-A (SEQ ID NO: 969), where X1-X12 may be any amino acid and/or where one or more of X5-X10 may be absent, e.g., X1 is S/T/A/V/I/L and/or X2 is A/V/I/L and/or X3 is S/T/A/V/I/L and/or X4 is N/Q/S/T and/or X5 is S/T/absent and/or X6 is G/A/V/I/L/absent and/or X7 is N/Q/absent and/or X8 is N/Q/absent and/or X9 is K/R/H/absent and/or X10 is N/Q/absent and/or X11 is E/D/Y/F and/or X12 is A/V/I/L; a CDRL2 that includes the amino acid sequence [Y/G] [A/T] S [N/T] R [C/E] [T/S], or a CDRL2 that includes the amino acid sequence X1-X2-S-X3-R-X4-X5, where X1-X5 may be any amino acid, e.g., X1 is Y/F/G/A/V/I/L and/or X2 is A/V/I/L/T/S and/or X3 is N/Q/T/S and/or X4 is C/S/E/D and/or X5 is T/S; and/or a CDRL3 that includes the amino acid sequence Q [Q/N] D [Y/H] [R/S] [S/H] P [L/Y] T (SEQ ID NO: 972), or a CDRL3 that includes the amino acid sequence Q-X1-D-X3-X4-X5-P-X6-T (SEQ ID NO: 973), where X1-X6 may be any amino acid, e.g., X1 is Q/N and/or X2 is Y/F/H/R/K and/or X3 is R/K/H/S/T and/or X4 is S/T/H/K/R and/or A/V/I/L/Y/F.

In some embodiments, anti-tau antibodies include a CDRH1 that includes the amino acid sequence GFSL [S/N] T [S/F] [A/G] M (SEQ ID NO: 964), or a CDRH1 that includes the amino acid sequence GFSL-X1-T-X2-X3-M (SEQ ID NO: 965), where X1-X3 may be any amino acid, e.g., X1 is S/T/N/Q and/or X2 is S/T/F/Y and/or X3 is G/A/I/L/V; a CDRH2 that includes the amino acid sequence YWDDD (SEQ ID NO: 362); a CDRH3 that includes the amino acid sequence R [R/V/K/S/G] [Y/R] [Y/absent] [S/absent] [absent/N] [G/S/Y/R] [Y/N/G] [G/A/Y/N] [M/F/Y] DY, or a CDRH3 that includes the amino acid sequence R-X1-X2-X3-$X_4$-X5-X6-X7-X8-X9-DY, where each of X1-X9 may be any amino acid and/or where one or more of X3-X5 may be absent, e.g., X1 is R/K/H/A/V/I/L/G/S/T and/or X2 is Y/F/R/K/H and/or X3 is Y/F/absent and/or X4 is S/T/absent and/or X5 is N/Q/absent and/or X6 is G/A/V/I/L/S/T/Y/F/R/K/H and/or X7 is Y/F/N/Q/G/A/V/I/L and/or X8 is G/A/V/I/L/Y/F/N/Q and/or X9 is M/F/Y; a CDRL1 that includes the amino acid sequence [K/S] [S/A] S [Q/S] S [L/V/V] [L/S] [N/S/D] [D/S/T] [V/G/D/Y] [N/G/absent] [Q/absent] [K/absent] [N/T/absent] [Y/absent] [L/absent] [A/H/N], or a CDRL1 that includes the amino acid sequence X1-X2-S-X3-S-X4-X5-X6-X7-X8-X9-X10-X11-X12-X13-X14-X15, where each of X1-X15 may be any amino acid and/or where one or more of X9-X14 may be absent, e.g., X1 is K/R/H/S/T and/or X2 is S/T/A/V/I/L and or X3 is Q/N/S/T and/or X4 is L/I/V/A and/or X5 is A/V/I/L/S/T and/or X6 is N/Q/S/T/D/E and/or X7 is D/E/S/T and/or X8 is G/A/V/I/L/D/E/Y/F and/or X9 is N/Q/G/A/absent and/or X10 is Q/N/absent and/or X11 is K/R/H/absent and/or X12 is N/Q/T/S/absent and/or X13 is Y/F/absent and/or X14 is A/V/I/L/absent and/or X15 is A/V/I/L/H/K/R/N/Q; a CDRL2 that includes the amino acid sequence [Y/G/L/R] [A/T/V] S [N/T/K] [R/L] [C/E/D/A] [T/S], or a CDRL2 that includes the amino acid sequence X1-X2-S-X3-X4-X5-X6, where X1-X6 may be any amino acid, e.g., X1 is Y/F/G/A/V/I/L/R/K/H and/or X2 is A/V/I/L/T/S and/or X3 is N/Q/T/S/K/R/H and/or X4 is R/K/H/A/V/I/L and/or X5 is C/S/E/D/A/V/I/L and/or X6 is T/S; and/or a CDRL3 that includes the amino acid sequence [W/Q] [Q/N] [G/D] [T/S/Y/H] [H/S/R] [F/V/S/H] P [Q/R/L/Y] [absent/Y] T, or a CDRL3 that includes the amino acid sequence X1-X2-X3-$X_4$-X5-X6-P-X7-X8-T, where each of X1-X8 may be any amino acid and/or where X8 may be absent, e.g., X1 is Q/N/W/F/Y and/or X2 is Q/N and/or X3 is G/A/V/I/L/D/E and/or X4 is T/S/Y/F/H/K/R and/or X5 is H/K/R/S/T and/or X6 is F/Y/A/V/I/L/S/T/H/K/R and/or X7 is Q/N/R/K/H/A/V/I/L/Y/F and/or X8 is Y/F/absent.

Functional Modifications

In some embodiments, antibodies of the present disclosure may be modified to optimize one or more functional properties (e.g., antibody affinity or activity). Non-limiting examples of antibody functional properties include epitope or antigen affinity, ability to mobilize or immobilize targets, and ability to activate or inhibit a target, process, or pathway. In some embodiments, functional properties include or relate to ability to modulate protein-protein interactions, protein aggregation, enzyme activity, receptor-ligand interactions, cellular signaling pathways, proteolytic cascades, and/or biological or physiological responses.

Antibody modifications may optimize antibodies by modulating epitope affinity. Such modifications may be carried out by affinity maturation. Affinity maturation technology is used to identify sequences encoding CDRs with highest affinity for target antigens. In some embodiments, antibody display technologies (e.g., phage or yeast) may be used. Such methods may include mutating nucleotide sequences encoding parental antibodies being optimized. Nucleotide sequences may be mutated randomly as a whole or to vary expression at specific amino acid residues to create millions to billions of variants. Sites or residues may be selected for mutation based on sequences or amino acid frequencies observed in natural human antibody repertoires. Variants may be subjected to repeated rounds of affinity screening [e.g., using display library screening technologies, surface plasmon resonance technologies, fluorescence-associated cell sorting (FACS) analysis, enzyme-linked immunosorbent assay (ELISA), etc.] for target antigen binding. Repeated rounds of selection, mutation, and expression may be carried out to identify antibody fragment sequences with highest affinity for target antigens. Such sequences may be directly incorporated into antibody sequences for production. In some cases, the goal of affinity maturation is to increase antibody affinity by at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100 fold, at least 500-fold, at least 1,000-fold, or more than 1,000-fold as compared to the affinity of an original or starting antibody. In cases where affinity is less than desired, the process may be repeated.

In some embodiments, antibody affinity may be assessed with different antigen formats. In some embodiments, antibody affinity for different antigen formats may be tested in vitro (e.g., by ELISA). In vitro testing may be carried out using brain samples or fractions. Such samples or fractions may be obtained from subjects with AD (e.g., human AD patients). In some embodiments, brain samples or fractions may be obtained from non-human subjects. Such non-human subjects may include non-human animals used in AD disease model studies (e.g., mice, rats, and primates). In some embodiments, brain samples or fractions used for antibody affinity testing may be derived from TG4510/P301S mouse strains. Antibody affinity may be compared against control samples lacking the particular antigen for which affinity is being analyzed. In some embodiments, control samples may include brain samples or fraction from non-diseased human subjects. In some embodiments, brain samples or fractions from wild type and/or Tau knockout mouse strains may be used as control samples. In vitro affinity testing may be carried out (e.g., by ELISA) using recombinant or isolated protein antigens. In some embodiments, recombinant or isolated ePHF is used for antibody affinity testing. In some embodiments, antigens listed in Table 8 may be used.

In some embodiments, antibody affinity analysis may be used to modulate antibody polyspecificity (e.g., to reduce or enhance antibody polyspecificity). Such modulation may include modulating relative affinity for two or more epitopes or antigens. For example, antibodies may be optimized for higher affinity for one epitope or antigen over a second epitope or antigen.

Antibodies may be modified to optimize antibody functional properties. Such functional properties may be assessed or engineered based on analytical assay results relating to one or more antibody functional properties. Assays may be used to screen multiple antibodies to identify or rank antibodies based on functional criteria. Anti-tau antibodies may be modified to optimize tau aggregation inhibition. Such inhibition may be based on physical disruption of tau aggregation or may be based on the ability of anti-tau antibodies to deplete tau protein from assay samples. Optimization based on tau aggregation inhibition may be assessed using one or more assays of tau aggregation (e.g., by tau seeding assay).

Production Modifications

In some embodiments, modifications may be made to optimize antibody production. Such modifications may include or relate to one or more of protein folding, stability, expression, and/or immunogenicity. Modifications may be carried out to address one or more antibody features negatively impacting production. Such features may include, but are not limited to, unpaired cysteines or irregular disulfides; glycosylation sites (e.g., N-linked NXS/T sites); acid cleavage sites, amino acid oxidation sites, conformity with mouse germline sequences; asparagine deamidation sites; aspartate isomerization sites; N-terminal pyroglutamate formation sites; and aggregation-prone amino acid sequence regions (e.g., within CDR sequences).

In some embodiments, antibodies of the present disclosure may be prepared using recombinant DNA technology (e.g., see U.S. Pat. No. 4,816,567, which is hereby incorporated by reference in its entirety). Antibody-encoding DNA may be isolated and sequenced using conventional procedures (e.g., by using oligonucleotide probes that are capable of binding specifically to genes encoding the heavy and light chains of murine antibodies). In some embodiments, hybridoma cells may be used as a preferred source of DNA. Once isolated, the DNA can be placed into expression vectors, which are then transfected into host cells. Host cells may include, but are not limited to HEK293 cells, HEK293T cells, simian COS cells, Chinese hamster ovary (CHO) cells, and myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide.

Antibody Humanization

In some embodiments, anti-tau antibodies of the present disclosure may be prepared as humanized antibodies. "Humanized" antibodies are chimeric antibodies that contain minimal sequences (e.g., variable domains or CDRs) derived from non-human immunoglobulins (e.g., murine immunoglobulins). Humanized antibodies may be prepared from human (recipient) immunoglobulins in which residues from the hypervariable regions are replaced by hypervariable region residues from one or more non-human "donor" antibodies (e.g., mouse, rat, rabbit, or nonhuman primate). Donor antibodies may be selected based on desired specificity, affinity, and/or capacity. Humanized antibodies may include one or more back-mutation that includes the reversion of one or more amino acids back to amino acids found in a donor antibody. Conversely, residues from donor antibodies included in humanized antibodies may be mutated to match residues present in human recipient antibodies. Back-mutations may be introduced to reduce human immune response to the humanized antibodies. In some embodiments, back-mutations are introduced to avoid issues with antibody manufacturing (e.g., protein aggregation or post-translational modification).

For construction of expression plasmids encoding fully humanized antibodies with human constant regions, DNA sequences encoding antibody variable regions may be inserted into expression vectors (e.g., mammalian expression vectors) between an upstream promoter/enhancer and immunoglobulin signal sequence and a downstream immunoglobulin constant region gene. DNA samples may then be transfected into mammalian cells for antibody production. Constant domains from any class of human antibody may be used. There are five major classes of intact human antibodies: IgA, IgD, IgE, IgG, and IgM, and several of these may be further divided into subclasses (isotypes), e.g., IgG1 (human and murine), IgG2 (human), IgG2a (murine), IgG2b (murine), IgG2c (murine), IgG3 (human and murine), IgG4 (human), IgA (murine), IgAQ1 (human), and IgA2 (human).

Cell lines with stable transfection of DNA encoding humanized antibodies may be prepared and used to establish stable cell lines. Cell lines producing humanized antibodies may be expanded for expression of humanized antibodies that may be harvested and purified from cell culture media.

In some embodiments, humanized antibodies of the present disclosure may have cross-reactivity with non-human species. Species cross-reactivity may allow antibodies to be used in different animals for various purposes. For example, cross-reactive antibodies may be used in pre-clinical animal studies to provide information about antibody efficacy and/or toxicity. Non-human species may include, but are not limited to, mouse, rat, rabbit, dog, pig, goat, sheep, and nonhuman primates (e.g., Cynomolgus monkeys).

Antibody Conjugates

In some embodiments, antibodies of the present disclosure may be or be prepared as antibody conjugates. As used herein, the term "conjugate" refers to any agent, cargo, or chemical moiety that is attached to a recipient entity or the process of attaching such an agent, cargo, or chemical moiety. As used herein, the term "antibody conjugate" refers to any antibody with an attached agent, cargo, or chemical moiety. Conjugates utilized to prepare antibody conjugates may include therapeutic agents. Such therapeutic agents may include drugs. Antibody conjugates that include a conjugated drug are referred to herein as "antibody drug conjugates." Antibody drug conjugates may be used to direct conjugated drugs to specific targets based on the affinity of associated antibodies for proteins or epitopes associated with such targets. Such antibody drug conjugates may be used to localize biological activity associated with such conjugated drugs to targeted cells, tissues, organs, or other targeted entities. In some embodiments, conjugates utilized to prepare antibody conjugates include detectable labels. Antibodies may be conjugated with detectable labels for purposes of detection. Such detectable labels may include, but are not limited to, radioisotopes, fluorophores, chromophores, chemiluminescent compounds, enzymes, enzyme co-factors, dyes, metal ions, ligands, biotin, avidin, streptavidin, haptens, quantum dots, or any other detectable labels known in the art or described herein.

Conjugates may be attached to antibodies directly or via a linker. Direct attachment may be by covalent bonding or by non-covalent association (e.g., ionic bonds, hydrostatic bonds, hydrophobic bonds, hydrogen bonds, hybridization, etc.). Linkers used for conjugate attachment may include any chemical structure capable of connecting an antibody to a conjugate. In some embodiments, linkers include polymeric molecules (e.g., nucleic acids, polypeptides, polyethylene glycols, carbohydrates, lipids, or combinations thereof). Antibody conjugate linkers may be cleavable (e.g., through contact with an enzyme, change in pH, or change in temperature).

Exemplary Anti-Tau Antibodies

In some embodiments, the anti-tau antibody comprises at least one antigen-binding domain, e.g., a variable region or antigen binding fragment thereof, from an antibody described herein, e.g., antibody chosen from V0001-V0065, V1001-V1005, or V2001-V2005, e.g., as described in Tables 1, 3, 6, 2A-2C, 4, or 5, or a sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain variable region from an antibody described herein, e.g., chosen from V0001-V0065, V1001-V1005, or V2001-V2005, e.g., as described in Table 3, 6, or 4, or a sequence substantially identical (e.g., having at least about 70%, 75%, 80%, 85%, 90%, 92%, 95%, 97%, 98%, or 99% sequence identity) to any of the aforesaid sequences. In some embodiments, the heavy chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 3, 6, or 4.

In some embodiments, the nucleotide sequence encoding the anti-tau antibody comprises the nucleotide sequence of a heavy chain variable region from an antibody described herein, e.g., chosen from V0001-V0065, V1001-V1005, or V2001-V2005, e.g., as described in Table 3 or 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a light chain variable region from an antibody described herein, e.g., chosen from V0001-V0065, V1001-V1005, or V2001-V2005, e.g., as described in Table 3, 6, or 4, or a sequence substantially identical (e.g., having at least about 70%, 75%, 80%, 85%, 90%, 92%, 95%, 97%, 98%, or 99% sequence identity) to any of the aforesaid sequences. In some embodiments, the light chain variable region comprises an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 3, 6, or 4.

In some embodiments, the nucleotide sequence encoding the anti-tau antibody comprises the nucleotide sequence of a light chain variable region from an antibody described herein, e.g., chosen from V0001-V0065, V1001-V1005, or V2001-V2005, e.g., as described in Table 3 or 4, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain variable region and a light chain variable region from an antibody described herein, e.g., chosen from V0001-V0065, V1001-V1005, or V2001-V2005, e.g., as described in Table 3, 6, or 4, or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a heavy chain variable region provided in Table 3, 6, or 4; and a light chain variable region comprising an amino acid sequence having at least one, two, or three modifications (e.g., substitutions, e.g., conservative substitutions), but not more than 30, 20, or 10 modifications (e.g., substitutions, e.g., conservative substitutions) of an amino acid sequence of a light chain variable region provided in Table 3, 6, or 4.

In some embodiments, the anti-tau antibody comprises a heavy chain constant region, e.g., a human IgG1, IgG2, IgG3, or IgG4 constant regions, or a murine IgG1, IgG2A, IgG2B, IgG2C, or IgG3 constant regions. In some embodiments, the heavy chain constant comprises an amino acid sequence set forth in Table X, or a sequence substantially identical (e.g., having at least about 70%, 75%, 80%, 85%, 90%, 92%, 95%, 97%, 98%, or 99% sequence identity) to any of the aforesaid sequences. In some embodiments, a nucleic acid encoding the heavy chain constant region comprises a nucleotide sequence set forth in Table X, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a light chain constant region, e.g., a kappa light chain constant region, e.g., a human kappa or lambda light chain constant region or a murine kappa or lambda light chain constant region. In some embodiments, the light chain constant comprises an amino acid sequence set forth in Table X, or a sequence substantially identical (e.g., having at least about 70%, 75%, 80%, 85%, 90%, 92%, 95%, 97%, 98%, or 99% sequence identity) to any of the aforesaid sequences. In some embodiments, nucleic acid encoding the light chain constant region comprises a nucleotide sequence set forth in Table X, or a nucleotide sequence substantially identical (e.g., having at least about 70%, 75%, 80%, 85%, 90%, 92%, 95%, 97%, 98%, or 99% sequence identity) to any of the aforesaid sequences.

In some embodiments, the anti-tau antibody comprises a heavy chain constant region and a light chain constant region. In some embodiments, the heavy chain constant region and the light chain constant region comprise an amino acid sequence set forth in Table X, or a sequence substantially identical (e.g., having at least about 80%, 85%, 90%, 92%, 95%, 97%, 98%, or 99% sequence identity) thereto. In some embodiments, the nucleotide sequence encoding the anti-tau antibody comprises the nucleotide sequence of a heavy chain constant region and the nucleotide sequence of a kappa or lambda light chain constant region. In some embodiments, the nucleotide sequence encoding the heavy chain constant region and light chain constant region comprise a nucleotide sequence set forth in Table X, or a nucleotide sequence substantially identical (e.g., having at least about 80%, 85%, 90%, 92%, 95%, 97%, 98%, or 99% sequence identity) thereto.

In some embodiments, the anti-tau antibody comprises a heavy chain variable region and a constant region, a light chain variable region and a constant region, or both, comprising an amino acid sequence of Table 3, 6, or 4 for variable region, and an amino acid sequence of Table X for constant region; or is encoded by a nucleic acid sequence of Table 3, 6, or 4, and X; or a sequence substantially identical (e.g., having at least about 80%, 85%, 90%, 92%, 95%, 97%, 98%, or 99% sequence identity) to any of the aforesaid sequences.

In some embodiments, the anti-tau antibody comprises at least one, two, three, or four framework regions from a heavy chain variable region of an antibody described herein, e.g., chosen from V0001-V0065, V1001-V1005, or V2001-V2005, e.g., as described in Table 7 or 4, or a sequence substantially identical (e.g., having at least about 70%, 75%, 80%, 85%, 90%, 92%, 95%, 97%, 98%, or 99% sequence identity) to any of the aforesaid sequences. In some embodiments, one or more of the framework regions (or collectively all of the framework regions) have one, two, three, four, five, or more changes, e.g., amino acid substitutions, insertions, or deletions, relative to the amino acid sequence shown in Table 7 or 4. In some embodiments, the anti-tau antibody includes a substitution in a heavy chain framework region, e.g., one or more substitutions in a FRH1, FRH2, FRH3, and/or FRH4 of the heavy chain.

In some embodiments, the anti-tau antibody comprises at least one, two, three, or four framework regions from a light chain variable region of an antibody described herein, e.g., chosen from V0001-V0065, V1001-V1005, or V2001-V2005, e.g., as described in Table 7 or 4, or a sequence substantially identical (e.g., having at least about 70%, 75%, 80%, 85%, 90%, 92%, 95%, 97%, 98%, or 99% sequence identity) to any of the aforesaid sequences. In some embodiments, one or more of the framework regions (or collectively all of the framework regions) have one, two, three, four, five, or more changes, e.g., amino acid substitutions, insertions, or deletions, relative to the amino acid sequence shown in Table 7 or 4. In some embodiments, the anti-tau antibody includes a substitution in a light chain framework region, e.g., one or more substitutions in a FRL1, FRL2, FRL3, and/or FRL4 of the light chain.

In some embodiments, the anti-tau antibody comprises at least one, two, or three complementarity determining regions (CDRs) from a heavy chain variable region comprising an amino acid sequence in Table 2A-2C, 3, 6, 4, or 5, or is encoded by a nucleic acid sequence in Table 4; or a sequence substantially identical (e.g., having at least about 70%, 75%, 80%, 85%, 90%, 92%, 95%, 97%, 98%, or 99% sequence identity) to any of the aforesaid sequences. In some embodiments, one or more of the CDRs (or collectively all of the CDRs) have one, two, three, four, five or more changes, e.g., amino acid substitutions, insertions, or deletions, relative to the amino acid sequence shown in Table 2A-2C, 6, 4, or 5, or encoded by a nucleotide sequence shown in Table 4. In some embodiments, the encoded anti-tau antibody includes a substitution in a heavy chain CDR, e.g., one or more substitutions in a CDR1, CDR2 and/or CDR3 of the heavy chain.

In some embodiments, the anti-tau antibody comprises at least one, two, or three complementarity determining regions (CDRs) from a light chain variable region comprising an amino acid sequence in Table 2A-2C, 6, 4, or 5, or is encoded by a nucleic acid sequence in Table 4; or a sequence substantially identical (e.g., having at least about 80%, 85%, 90%, 92%, 95%, 97%, 98%, or 99% sequence identity) to any of the aforesaid sequences. In some embodiments, one or more of the CDRs (or collectively all of the CDRs) have one, two, three, four, five or more changes, e.g., amino acid substitutions, insertions, or deletions, relative to the amino acid sequence shown in Table 2A-2C, 6, 4, or 5, or encoded by a nucleotide sequence shown in Table 4. In some embodiments, the anti-tau antibody includes a substitution in a light chain CDR, e.g., one or more substitutions in a CDR1, CDR2 and/or CDR3 of the light chain.

In some embodiments, the anti-tau antibody comprises at least one, two, three, four, five or six CDRs (or collectively all of the CDRs) from a heavy and light chain variable region comprising an amino acid sequence shown in Table 2A-2C, 6, 4, or 5, or is encoded by a nucleotide sequence shown in Table 4. In some embodiments, one or more of the CDRs (or collectively all of the CDRs) have one, two, three, four, five, six or more changes, e.g., amino acid substitutions, insertions, or deletions, relative to the CDRs shown in Table 2A-2C, 6, 4, or 5, or encoded by a nucleotide sequence shown in Table 4.

In some embodiments, the anti-tau antibody comprises all three CDRs from a heavy chain variable region, all three CDRs from light chain variable region, or both (e.g., all six CDRs from a heavy chain variable region and a light chain variable region) comprising an amino acid sequence shown in Table 2A-2C, 6, 4, or 5, or is encoded by a nucleotide sequence shown in Table 4.

In some embodiments, an anti-tau antibody of the present disclosure may include CDRs identified through CDR analysis of variable domain sequences presented herein via co-crystallography with bound antigen; by computational assessments based on comparisons with other antibodies (e.g., see Strohl, W. R. Therapeutic Antibody Engineering. Woodhead Publishing, Philadelphia PA. 2012. Ch. 3, p 47-54); or Kabat, Chothia, Al-Lazikani, Lefranc, or Honegger numbering schemes, as described previously.

TABLE 2A

CDR sequences of selected antibodies based on Kabat numbering system

| Ab ID | HC CDR1 | HC CDR2 | HC CDR3 | LC CDR1 | LC CDR2 | LC CDR3 |
|---|---|---|---|---|---|---|
| V0004 | NYWMH (SEQ ID NO: 1140) | RIDPNSGGTR YNEKFKN (SEQ ID NO: 1141) | DFDV (SEQ ID NO: 395) | RASGNIHN YLA (SEQ ID NO: 460) | NAKTLPD (SEQ ID NO: 518) | QHFWSTPLT (SEQ ID NO: 557) |
| V0009 | DYYMS (SEQ ID NO: 1142) | LIRNKAKGFT TEYSASVKG (SEQ ID NO: 1143) | DINY (SEQ ID NO: 400) | KSSQSLLY STNQENYL A (SEQ ID NO: 464) | WASSRES (SEQ ID NO: 523) | QQYYSYPRT (SEQ ID NO: 562) |
| V0022 | RYWMH (SEQ ID NO: 1144) | NINPNNGGTD FNEKFKN (SEQ ID NO: 1145) | GTGTGAMD Y (SEQ ID NO: 410) | RSSQSLVH NNGITYLY (SEQ ID NO: 1146) | RVSNRFS (SEQ ID NO: 529) | FQGTHVPRT (SEQ ID NO: 571) |
| V0023 | IFWMH (SEQ ID NO: 1147) | KINPNNGGGD YNEKFKS (SEQ ID NO: 1148) | GTGTGAMD Y (SEQ ID NO: 410) | RSSQSLVH SNGITHLY (SEQ ID NO: 474) | RVSNRFS (SEQ ID NO: 529) | FQGTHVPRT (SEQ ID NO: 571) |
| V0024 | RFWMH (SEQ ID NO: 1149) | NINPNNGGTD NNERFKS (SEQ ID NO: 1150) | GTGTGAMD Y (SEQ ID NO: 410) | RSSQSLVH SNGNTHLY (SEQ ID NO: 475) | RVSSRFS (SEQ ID NO: 530) | FQGTHVPRT (SEQ ID NO: 571) |
| V0052 | TSAMGVS (SEQ ID NO: 1152) | HIYWDDDKRY NPSLKS (SEQ ID NO: 1153) | RRRGYGMD Y (SEQ ID NO: 435) | KASQSVSN DVA (SEQ ID NO: 495) | YASNRCT (SEQ ID NO: 540) | QQDYRSPLT (SEQ ID NO: 587) |

TABLE 2B

CDR sequences of selected antibodies based on Chothia numbering system

| Ab ID | HC CDR1 | HC CDR2 | HC CDR3 | LC CDR1 | LC CDR2 | LC CDR3 |
|---|---|---|---|---|---|---|
| V0004 | DYTFTNY (SEQ ID NO: 299) | DPNSGG (SEQ ID NO: 343) | DFDV (SEQ ID NO: 395) | RASGNIHN YLA (SEQ ID NO: 460) | NAKTLPD (SEQ ID NO: 518) | QHFWSTPLT (SEQ ID NO: 557) |
| V0009 | GFTFTDY (SEQ ID NO: 304) | RNKAKGFT (SEQ ID NO: 347) | DINY (SEQ ID NO: 400) | KSSQSLLY STNQENYL A (SEQ ID NO: 464) | WASSRES (SEQ ID NO: 523) | QQYYSYPRT (SEQ ID NO: 562) |
| V0022 | GFTFTRY (SEQ ID NO: 314) | NPNNGG (SEQ ID NO: 341) | GTGTGAMD Y (SEQ ID NO: 410) | RSSQSLVH NNGITYLY (SEQ ID NO: 1154) | RVSNRFS (SEQ ID NO: 529) | FQGTHVPRT (SEQ ID NO: 571) |
| V0023 | GYTFTIF (SEQ ID NO: 315) | NPNNGG (SEQ ID NO: 341) | GTGTGAMD Y (SEQ ID NO: 410) | RSSQSLVH SNGITHLY (SEQ ID NO: 474) | RVSNRFS (SEQ ID NO: 529) | FQGTHVPRT (SEQ ID NO: 571) |

TABLE 2B-continued

CDR sequences of selected antibodies based on Chothia numbering system

| Ab ID | HC CDR1 | HC CDR2 | HC CDR3 | LC CDR1 | LC CDR2 | LC CDR3 |
|---|---|---|---|---|---|---|
| V0024 | GYTFTRF (SEQ ID NO: 316) | NPNNGG (SEQ ID NO: 341) | GTGTGAMDY (SEQ ID NO: 410) | RSSQSLVHSNGNTHLY (SEQ ID NO: 475) | RVSSRES (SEQ ID NO: 530) | FQGTHVPRT (SEQ ID NO: 571) |
| V0052 | GFSLSTSAM (SEQ ID NO: 325) | YWDDD (SEQ ID NO: 362) | RRRGYGMDY (SEQ ID NO: 435) | KASQSVSNDVA (SEQ ID NO: 495) | YASNRCT (SEQ ID NO: 540) | QQDYRSPLT (SEQ ID NO: 587) |

TABLE 2C

CDR sequences of selected antibodies based on IMGT numbering system

| Ab ID | HC CDR1 | HC CDR2 | HC CDR3 | LC CDR1 | LC CDR2 | LC CDR3 |
|---|---|---|---|---|---|---|
| V0004 | DYTFTNYW (SEQ ID NO: 1155) | IDPNSGGT (SEQ ID NO: 1156) | AGDFDV (SEQ ID NO: 1157) | GNIHNY (SEQ ID NO: 1158) | NAK | QHFWSTPLT (SEQ ID NO: 557) |
| V0009 | GFTFTDYY (SEQ ID NO: 1160) | IRNKAKGFTT (SEQ ID NO: 1161) | VRDINY (SEQ ID NO: 1162) | QSLLYSTNQENY (SEQ ID NO: 1163) | WAS | QQYYSYPRT (SEQ ID NO: 562) |
| V0022 | GFTFTRYW (SEQ ID NO: 1165) | INPNNGGT (SEQ ID NO: 1166) | ARGTGTGAMDY (SEQ ID NO: 1167) | QSLVHNNGITY (SEQ ID NO: 473) | RVS | FQGTHVPRT (SEQ ID NO: 571) |
| V0023 | GYTFTIFW (SEQ ID NO: 1168) | INPNNGGG (SEQ ID NO: 1169) | ARGTGTGAMDY (SEQ ID NO: 1167) | QSLVHSNGITH (SEQ ID NO: 1170) | RVS | FQGTHVPRT (SEQ ID NO: 571) |
| V0024 | GYTFTRFW (SEQ ID NO: 1171) | INPNNGGT (SEQ ID NO: 1166) | ARGTGTGAMDY (SEQ ID NO: 1167) | QSLVHSNGNTH (SEQ ID NO: 1172) | RVS | FQGTHVPRT (SEQ ID NO: 571) |
| V0052 | GFSLSTSAMG (SEQ ID NO: 1173) | IYWDDDK (SEQ ID NO: 1174) | ARRRRGYGMDY (SEQ ID NO: 1175) | QSVSND (SEQ ID NO: 1176) | YAS | QQDYRSPLT (SEQ ID NO: 587) |

TABLE 3

Amino acid and nucleotide sequences of the heavy and light chain variable regions of exemplary anti-Tau antibodies

| ID# | VH SEQ ID NO amino acid | VH SEQ ID NO nucleotide | VL SEQ ID NO amino acid | VL SEQ ID NO nucleotide |
|---|---|---|---|---|
| V0001 | 1 | 147 | 75 | 221 |
| V0002 | 2 | 148 | 76 | 222 |
| V0003 | 3 | 149 | 77 | 223 |
| V0004 | 4 | 150 | 78 | 224 |
| V0005 | 5 | 151 | 79 | 225 |
| V0006 | 6 | 152 | 80 | 226 |
| V0007 | 7 | 153 | 81 | 227 |
| V0008 | 8 | 154 | 82 | 228 |
| V0009 | 9 | 155 | 83 | 229 |
| V00010 | 10 | 156 | 84 | 230 |
| V00011 | 11 | 157 | 85 | 231 |
| V00012 | 12 | 158 | 86 | 232 |
| V00014 | 13 | 159 | 87 | 233 |
| V00015 | 14 | 160 | 87 | 234 |
| V00016 | 15 | 161 | 88 | 235 |
| V00017 | 16 | 162 | 88 | 236 |
| V00018 | 17 | 163 | 89 | 237 |
| V00019 | 18 | 164 | 90 | 238 |
| V0020 | 19 | 165 | 91 | 239 |
| V0021 | 20 | 166 | 92 | 240 |
| V0022 | 21 | 167 | 93 | 241 |
| V0023 | 22 | 168 | 94 | 242 |
| V0024 | 23 | 169 | 95 | 243 |
| V0025 | 24 | 170 | 96 | 244 |
| V0026 | 25 | 171 | 97 | 245 |
| V0027 | 26 | 172 | 98 | 246 |
| V0028 | 27 | 173 | 99 | 247 |
| V0029 | 28 | 174 | 100 | 248 |
| V0030 | 29 | 175 | 101 | 249 |
| V0031 | 30 | 176 | 102 | 250 |
| V0032 | 31 | 177 | 103 | 251 |
| V0033 | 32 | 178 | 104 | 252 |
| V0034 | 33 | 179 | 105 | 253 |
| V0035 | 34 | 180 | 106 | 254 |

TABLE 3-continued

Amino acid and nucleotide sequences of the heavy and light chain variable regions of exemplary anti-Tau antibodies

| ID# | VH SEQ ID NO amino acid | VH SEQ ID NO nucleotide | VL SEQ ID NO amino acid | VL SEQ ID NO nucleotide |
|---|---|---|---|---|
| V0036 | 35 | 181 | 107 | 255 |
| V0037 | 36 | 182 | 108 | 256 |
| V0038 | 37 | 183 | 109 | 257 |
| V0039 | 38 | 184 | 110 | 258 |
| V0040 | 39 | 185 | 111 | 259 |
| V0041 | 40 | 186 | 112 | 260 |
| V0042 | 41 | 187 | 113 | 261 |
| V0043 | 42 | 188 | 114 | 262 |
| V0044 | 43 | 189 | 115 | 263 |
| V0045 | 44 | 190 | 116 | 264 |
| V0046 | 45 | 191 | 117 | 265 |
| V0047 | 46 | 192 | 118 | 266 |
| V0048 | 47 | 193 | 119 | 267 |
| V0049 | 48 | 194 | 120 | 268 |
| V0050 | 49 | 195 | 121 | 269 |
| V0051 | 50 | 196 | 121 | 269 |
| V0052 | 51 | 197 | 122 | 270 |
| V0053 | 52 | 198 | 123 | 271 |
| V0054 | 53 | 199 | 124 | 272 |
| V0055 | 54 | 200 | 125 | 273 |
| V0056 | 55 | 201 | 126 | 274 |
| V0057 | 56 | 202 | 125 | 275 |
| V0058 | 57 | 203 | 127 | 276 |
| V0059 | 58 | 204 | 128 | 277 |
| V0060 | 59 | 205 | 129 | 278 |
| V0061 | 60 | 206 | 130 | 279 |
| V0062 | 61 | 207 | 131 | 280 |
| V0063 | 62 | 208 | 132 | 281 |
| V0064 | 63 | 209 | 133 | 282 |
| V0065 | 64 | 210 | 134 | 283 |
| V1001 | 65 | 211 | 135 | 284 |
| V1002 | 66 | 212 | 136 | 285 |
| V1003 | 67 | 213 | 137 | 286 |
| V1004 | 68 | 214 | 138 | 287 |
| V1005 | 69 | 215 | 139 | 288 |
| V1006 | 69 | 215 | 140 | 289 |
| V1007 | 69 | 215 | 141 | 290 |
| V2001 | 70 | 216 | 142 | 291 |
| V2002 | 71 | 217 | 143 | 292 |
| V2003 | 72 | 218 | 144 | 293 |
| V2004 | 73 | 219 | 145 | 294 |
| V2005 | 74 | 220 | 146 | 295 |

TABLE 4

Exemplary anti-tau antibodies

| Ab ID | SEQ ID NO | Description | Sequence |
|---|---|---|---|
| V0004 | 299 | HC CDR1 (Chothia) | DYTFTNY |
| | 343 | HC CDR2 (Chothia) | DPNSGG |
| | 395 | HC CDR3 (Chothia) | DFDV |
| | 1140 | HC CDR1 (Kabat) | NYWMH |
| | 1141 | HC CDR2 (Kabat) | RIDPNSGGTRYNEKFKN |
| | 395 | HC CDR3 (Kabat) | DFDV |
| | 1155 | HC CDR1 (IMGT) | DYTFTNYW |
| | 1156 | HC CDR2 (IMGT) | IDPNSGGT |
| | 1157 | HC CDR3 (IMGT) | AGDFDV |

TABLE 4-continued

Exemplary anti-tau antibodies

| Ab ID | SEQ ID NO | Description | Sequence |
|---|---|---|---|
| | 604 | FR H1 (corresponding to the Chothia CDR definition) | QVQLQQPGAELVKPGASVKLSCKAS |
| | 647 | FR H2 (corresponding to the Chothia CDR definition) | WMHWVKQRPGRGLEWIGRI |
| | 700 | FR H3 (corresponding to the Chothia CDR definition) | TRYNEKFKNKATLTVDKPSSTAYMHLSSLTSEDSAVYYCAG |
| | 770 | FR H4 (corresponding to the Chothia CDR definition) | WGTGTTVTVSS |
| | 4 | VH | QVQLQQPGAELVKPGASVKLSCKASDYTFTNYWMHWVKQRPGRGLEWIGRIDPNSGGTRYNEKFKNKATLTVDKPSSTAYMHLSSLTSEDSAVYYCAGDFDVWGTGTTVTVSS |
| | 150 | DNA VH | CAGGTCCAACTGCAGCAGCCTGGGGCTGAGCTTGTGAAGCCTGGGGCTTCAGTGAAGCTGTCCTGCAAGGCTTCTGACTACACCTTCACCAACTACTGGATGCACTGGGTGAAGCAGAGGCCTGGACGAGGCCTTGAGTGGATAGGAAGGATTGATCCTAATAGTGGTGGTACTAGGTACAATGAGAAGTTCAAGAACAAGGCCACACTGACTGTTGACAAACCCTCCAGCACAGCCTACATGCATCTCAGCAGCCTGACATCTGAGGACTCTGCGGTCTATTATTGTGCAGGGGACTTCGATGTCTGGGGCACAGGGACCACGGTCACCGTCTCCTCA |
| | 460 | LC CDR1 (Chothia) | RASGNIHNYLA |
| | 518 | LC CDR2 (Chothia) | NAKTLPD |
| | 557 | LC CDR3 (Chothia) | QHFWSTPLT |
| | 460 | LC CDR1 (Kabat) | RASGNIHNYLA |
| | 518 | LC CDR2 (Kabat) | NAKTLPD |
| | 557 | LC CDR3 (Kabat) | QHFWSTPLT |
| | 1158 | LC CDR1 (IMGT) | GNIHNY |
| | | LC CDR2 (IMGT) | NAK |
| | 557 | LC CDR3 (IMGT) | QHFWSTPLT |
| | 779 | FR L1 (corresponding to the Chothia CDR definition) | DIQMTQSPASLSASVGETVTITC |
| | 825 | FR L2 (corresponding to the Chothia CDR definition) | WYQQRQGKSPQLLVY |

TABLE 4-continued

Exemplary anti-tau antibodies

| Ab ID | SEQ ID NO | Description | Sequence |
|---|---|---|---|
| | 861 | FR L3 (corresponding to the Chothia CDR definition) | GVPSRFSGSGSGTQYSLKINSLQPEDFGSYCC |
| | 908 | FR L4 (corresponding to the Chothia CDR definition) | FGAGTKLELK |
| | 78 | VL | DIQMTQSPASLSASVGETVTITCRASGNIHNYLAWYQQRQGKSPQLLVYNAKTLPDGVPSRFSGSGSGTQYSLKINSLQPEDFGSYCCQHFWSTPLTFGAGTKLELK |
| | 224 | DNA VL | GACATCCAGATGACTCAGTCTCCAGCCTCCCTATCTGCATCTGTGGGAGAAACTGTCACCATCACATGTCGAGCAAGTGGGAATATTCACAATTATTTAGCATGGTATCAGCAGAGACAGGGAAAATCTCCTCAGCTCCTGGTCTATAATGCAAAAACCTTACCAGATGGTGTGCCATCAAGGTTCAGTGGCAGTGGATCAGGAACACAATATTCTCTCAAGATCAACAGCCTGCAGCCTGAAGATTTTGGGAGTTATTGCTGTCAACATTTTTGGAGTACTCCGCTCACGTTCGGTGCTGGGACCAAGTTGGAGCTGAAA |
| V0009 | 304 | HC CDR1 (Chothia) | GFTFTDY |
| | 347 | HC CDR2 (Chothia) | RNKAKGFT |
| | 400 | HC CDR3 (Chothia) | DINY |
| | 1142 | HC CDR1 (Kabat) | DYYMS |
| | 1143 | HC CDR2 (Kabat) | LIRNKAKGFTTEYSASVKG |
| | 400 | HC CDR3 (Kabat) | DINY |
| | 1160 | HC CDR1 (IMGT) | GFTFTDYY |
| | 1161 | HC CDR2 (IMGT) | IRNKAKGFTT |
| | 1162 | HC CDR3 (IMGT) | VRDINY |
| | 608 | FR H1 (corresponding to the Chothia CDR definition) | EVQLVESGGALVQPGGSLSLSCAAS |
| | 652 | FR H2 (corresponding to the Chothia CDR definition) | YMSWVRQPPGKALEWLALI |
| | 705 | FR H3 (corresponding to the Chothia CDR definition) | TEYSASVKGRFTISRDNSQSILLFQMNDLRADDSATYYCVR |
| | 767 | FR H4 (corresponding to the Chothia CDR definition) | WGQGTTLTVSS |
| | 9 | VH | EVQLVESGGALVQPGGSLSLSCAASGFTFTDYYMSWVRQPPGKALEWLALIRNKAKGFTTEYSASVKGRFTISRDNSQSILLFQMNDLRADDSATYYCVRDINYWGQGTTLTVSS |
| | 155 | DNA VH | GAGGTGCAGCTGGTGGAGTCTGGAGGAGCCTTGGTACAGCCTGGGGGTTCTCTGAGTCTCTCCTGTGCAGCTTCTGGATTCACCTTCACTGATTACTACATGAGCTGGGTCCGCCAGCCTCCAGGGAAGGCACTTGAGTGGCTGGCTTTGATTAGAAACAAAGCTAAAGGTTTCACAACAGAATACAGTGCATCTGTGAAGGGTCGGTTCACCATCTCCAGAGATAATTCCCAAAGCATCCTCCTTTTTCAAATGAATGACCTGAGAGCTGACGACAGTGCCACTTATTACTGTGTAAGAGATATAAACTACTGGGGCCAAGGCACCACTCTCACAGTCTCCTCA |
| | 464 | LC CDR1 (Chothia) | KSSQSLLYSTNQENYLA |
| | 523 | LC CDR2 (Chothia) | WASSRES |
| | 562 | LC CDR3 (Chothia) | QQYYSYPRT |
| | 464 | LC CDR1 (Kabat) | KSSQSLLYSTNQENYLA |
| | 523 | LC CDR2 (Kabat) | WASSRES |
| | 562 | LC CDR3 (Kabat) | QQYYSYPRT |
| | 1163 | LC CDR1 (IMGT) | QSLLYSTNQENY |
| | | LC CDR2 (IMGT) | WAS |
| | 562 | LC CDR3 (IMGT) | QQYYSYPRT |
| | 783 | FR L1 (corresponding to the Chothia CDR definition) | DIVMSQSPSSLAVSVGEKVTMSC |
| | 830 | FR L2 (corresponding to the Chothia CDR definition) | WYQQKPGQSPKLLIY |
| | 866 | FR L3 (corresponding to the Chothia CDR definition) | GVPDRFTGSGSGTDFTLTISSVKAEDLAVYYC |
| | 906 | FR L4 (corresponding to the Chothia CDR definition) | FGGGTKLEIK |
| | 83 | VL | DIVMSQSPSSLAVSVGEKVTMSCKSSQSLLYSTNQENYLAWYQQKPGQSPKLLIYWASSRESGVPDRFTGSGSGTDFTLTISSVKAEDLAVYYCQQYYSYPRTFGGGTKLEIK |
| | 229 | DNA VL | GACATTGTGATGTCACAGTCTCCATCCTCCCTAGCTGTGTCAGTTGGAGAGAAGGTTACTATGAGCTGCAAGTCCAGTCAGAGCCTTTTATATAGTACCAATCAAGAGAACTACTTGGCCTGGTACCAGCAGAAACCAGGGCAGTCTCCTAAACTGCTGATTTACTGGGCATCCTCTAGGGAATCTGGGGTCCCTGATCGCTTTACAGGCAGTGGATCTGGGACAGATTTCACTCTCACCATCAGCAGTGTGAAGGCTGAAGACCTGGCAGTTTATTACT |

TABLE 4-continued

Exemplary anti-tau antibodies

| Ab ID | SEQ ID NO | Description | Sequence |
|---|---|---|---|
| | | | GTCAGCAATATTATAGCTATC CTCGGACGTTCGGTGGAGGCA CCAAGCTGGAAATCAAA |
| V0022 | 314 | HC CDR1 (Chothia) | GFTFTRY |
| | 341 | HC CDR2 (Chothia) | NPNNGG |
| | 410 | HC CDR3 (Chothia) | GTGTGAMDY |
| | 1144 | HC CDR1 (Kabat) | RYWMH |
| | 1145 | HC CDR2 (Kabat) | NINPNNGGTDFNEKFKN |
| | 410 | HC CDR3 (Kabat) | GTGTGAMDY |
| | 1165 | HC CDR1 (IMGT) | GFTFTRYW |
| | 1166 | HC CDR2 (IMGT) | INPNNGGT |
| | 1167 | HC CDR3 (IMGT) | ARGTGTGAMDY |
| | 619 | FR H1 (corresponding to the Chothia CDR definition) | QVQLQQPGTELVKPGSSVNLSCKAS |
| | 663 | FR H2 (corresponding to the Chothia CDR definition) | WMHWVKERPGHGLEWIGNI |
| | 717 | FR H3 (corresponding to the Chothia CDR definition) | TDFNEKFKNKATLTVHKSSTT VFIQLSSLTSEDSAVYYCAR |
| | 771 | FR H4 (corresponding to the Chothia CDR definition) | WGQGTSVTVSS |
| | 21 | VH | QVQLQQPGTELVKPGSSVNLSC KASGFTFTRYWMHWVKERPGH GLEWIGNINPNNGGTDFNEKFK NKATLTVHKSSTTVFIQLSSL TSEDSAVYYCARGTGTGAMD YWGQGTSVTVSS |
| | 167 | DNA VH | CAGGTCCAACTGCAGCAGCCT GGGACTGAACTGGTGAAGCCTG GGTCTTCAGTGAACCTGTCCTG CAAGGCTTCTGGCTTCACCTT CACCAGGTACTGGATGCACTG GGTGAAGGAGAGGCCTGGACAT GGCCTTGAGTGGATTGGAAATA TTAATCCTAACAATGGTGGTA CTGACTTCAATGAGAAGTTCA AGAACAAGGCCACACTGACTGT ACACAAGTCCTCCACCACAGTC TTCATCCAACTCAGCAGCCTG ACATCTGAGGACTCTGCGGTCT ATTATTGTGCAAGAGGAACTG GGACGGGAGCTATGGACTACT GGGGTCAAGGAACCTCAGTCAC CGTCTCCTCA |
| | 1154 | LC CDR1 (Chothia) | RSSQSLVHNNGITYLY |
| | 529 | LC CDR2 (Chothia) | RVSNRFS |
| | 571 | LC CDR3 (Chothia) | FQGTHVPRT |
| | 1146 | LC CDR1 (Kabat) | RSSQSLVHNNGITYLY |
| | 529 | LC CDR2 (Kabat) | RVSNRFS |
| | 571 | LC CDR3 (Kabat) | FQGTHVPRT |
| | 473 | LC CDR1 (IMGT) | QSLVHNNGITY |
| | | LC CDR2 (IMGT) | RVS |
| | 571 | LC CDR3 (IMGT) | FQGTHVPRT |
| | 1178 | FR L1 (corresponding to the Chothia CDR definition) | DVVMTQTPLSLPVSLGDQASISC |
| | 831 | FR L2 (corresponding to the Chothia CDR definition) | WYLQKPGQSPKLLIY |
| | 1179 | FR L3 (corresponding to the Chothia CDR definition) | GVPDRFGGSGSGTDFTLK ISRVEAEDLGVYFC |
| | 906 | FR L4 (corresponding to the Chothia CDR definition) | FGGGTKLEIK |
| | 93 | VL | DVVMTQTPLSLPVSLGDQASIS CRSSQSLVHNNGITYLYWYLQ KPGQSPKLLIYRVSNRFSGVPD RFGGSGSGTDFTLKISRVEAE DLGVYFCFQGTHVPRTFGGG TKLEIK |
| | 241 | DNA VL | GATGTTGTGATGACCCAAACT CCACTCTCCCTGCCTGTCAGTC TTGGAGATCAAGCTTCCATCT CTTGCAGATCTAGTCAGAGCCT TGTACACAACAATGGAATCA CCTATTTATATTGGTACCTGCAG AAGCCAGGCCAGTCTCCAAAG CTCCTGATCTACAGGGTTTCCA ACCGATTTTCTGGGGTCCCAG ACAGGTTCGGTGGCAGTGGATC AGGGACAGATTTCACACTCAAG ATCAGCAGAGTGGAGGCTGAG GATCTGGGAGTTTATTTCTGCT TTCAAGGTACACATGTTCCTC GGACGTTCGGTGGAGGCACCA AGCTGGAAATCAAA |
| V0023 | 315 | HC CDR1 (Chothia) | GYTFTIF |
| | 341 | HC CDR2 (Chothia) | NPNNGG |
| | 410 | HC CDR3 (Chothia) | GTGTGAMDY |
| | 1147 | HC CDR1 (Kabat) | IFWMH |
| | 1148 | HC CDR2 (Kabat) | KINPNNGGGDYNEKFKS |
| | 410 | HC CDR3 (Kabat) | GTGTGAMDY |
| | 1168 | HC CDR1 (IMGT) | GYTFTIFW |
| | 1169 | HC CDR2 (IMGT) | INPNNGGG |
| | 1167 | HC CDR3 (IMGT) | ARGTGTGAMDY |
| | 603 | FR H1 (corresponding to the Chothia CDR definition) | QVQLQQPGTELVKPGASVKLSCKAS |

TABLE 4-continued

| Exemplary anti-tau antibodies | | | |
|---|---|---|---|
| Ab ID | SEQ ID NO | Description | Sequence |
| | 664 | FR H2 (corresponding to the Chothia CDR definition) | WMHWVKQRPGHGLEWIGKI |
| | 718 | FR H3 (corresponding to the Chothia CDR definition) | GDYNEKFKSKATLTVDKSSTTAYLQLSSLTSEDSAVYYCAR |
| | 771 | FR H4 (corresponding to the Chothia CDR definition) | WGQGTSVTVSS |
| | 22 | VH | QVQLQQPGTELVKPGASVKLSCKASGYTFTIFWMHWVKQRPGHGLEWIGKINPNNGGGDYNEKFKSKATLTVDKSSTTAYLQLSSLTSEDSAVYYCARGTGTGAMDYWGQGTSVTVSS |
| | 168 | DNA VH | CAGGTCCAACTGCAGCAGCCTGGGACTGAACTGGTGAAGCCTGGGGCTTCAGTGAAGCTGTCCTGCAAGGCTTCTGGCTACACCTTCACCATCTTCTGGATGCACTGGGTGAAGCAGAGGCCTGGACATGGCCTTGAGTGGATTGGAAAGATTAATCCTAACAATGGAGGTGGTGACTACAATGAGAAATTCAAGAGTAAGGCCACATTGACTGTAGACAAATCCTCCACCACAGCCTACTTGCAGCTCAGCAGCCTGACATCTGAGGACTCTGCGGTCTATTATTGTGCAAGAGGAACTGGGACGGGAGCTATGGACTACTGGGGTCAAGGAACCTCAGTCACCGTCTCCTCA |
| | 474 | LC CDR 1 (Chothia) | RSSQSLVHSNGITHLY |
| | 529 | LC CDR2 (Chothia) | RVSNRFS |
| | 571 | LC CDR3 (Chothia) | FQGTHVPRT |
| | 474 | LC CDR1 (Kabat) | RSSQSLVHSNGITHLY |
| | 529 | LC CDR2 (Kabat) | RVSNRFS |
| | 571 | LC CDR3 (Kabat) | FQGTHVPRT |
| | 1170 | LC CDR1 (IMGT) | QSLVHSNGITH |
| | | LC CDR2 (IMGT) | RVS |
| | 571 | LC CDR3 (IMGT) | FQGTHVPRT |
| | 793 | FR L1 (corresponding to the Chothia CDR definition) | DVVMTQTPLSLPVSLGDHASISC |
| | 836 | FR L2 (corresponding to the Chothia CDR definition) | WYLQRPGQTPKLLIY |
| | 874 | FR L3 (corresponding to the Chothia CDR definition) | GVPDRFSGSGSGTDFTLKISSVEAEDLGVYFC |
| | 910 | FR L4 (corresponding to the Chothia CDR definition) | FGGGTKLEIE |
| | 94 | VL | DVVMTQTPLSLPVSLGDHASISCRSSQSLVHSNGITHLYWYLQRPGQTPKLLIYRVSNRFSGVPDRFSGSGSGTDFTLKISSVEAEDLGVYFCFQGTHVPRTFGGGTKLEIE |
| | 242 | DNA VL | GATGTTGTGATGACCCAAACTCCACTCTCCCTGCCTGTCAGTCTTGGAGATCACGCTTCCATCTCTTGCAGATCTAGTCAGAGCCTTGTACACAGCAATGGAATCACCCATTTATATTGGTACCTGCAGAGGCCAGGCCAGACTCCAAAGCTCCTGATCTACAGGGTTTCCAACCGATTTTCTGGGGTCCCAGACAGGTTCAGTGGCAGTGGATCAGGGACAGATTTCACACTCAAGATCAGCAGCGTGGAGGCTGAGGATCTGGGAGTTTATTTCTGCTTTCAAGGTACACATGTTCCTCGGACGTTCGGTGGAGGCACCAAGCTGGAAATCGAA |
| V0024 | 316 | HC CDR1 (Chothia) | GYTFTRF |
| | 341 | HC CDR2 (Chothia) | NPNNGG |
| | 410 | HC CDR3 (Chothia) | GTGTGAMDY |
| | 1149 | HC CDR1 (Kabat) | RFWMH |
| | 1150 | HC CDR2 (Kabat) | NINPNNGGTDNNERFKS |
| | 410 | HC CDR3 (Kabat) | GTGTGAMDY |
| | 1171 | HC CDR1 (IMGT) | GYTFTRFW |
| | 1166 | HC CDR2 (IMGT) | INPNNGGT |
| | 1167 | HC CDR3 (IMGT) | ARGTGTGAMDY |
| | 603 | FR H1 (corresponding to the Chothia CDR definition) | QVQLQQPGTELVKPGASVKLSCKAS |
| | 665 | FR H2 (corresponding to the Chothia CDR definition) | WMHWVKQRPGQGLEWIGNI |
| | 719 | FR H3 (corresponding to the Chothia CDR definition) | TDNNERFKSKATLTVDRSSSTAYMQLSSLTSEDSAVYYCAR |
| | 771 | FR H4 (corresponding to the Chothia CDR definition) | WGQGTSVTVSS |
| | 23 | VH | QVQLQQPGTELVKPGASVKLSCKASGYTFTRFWMHWVKQRPGQGLEWIGNINPNNGGTDNNERFKSKATLTVDRSSSTAYMQLSSLTSEDSAVYYCARGTGTGAMDYWGQGTSVTVSS |
| | 169 | DNA VH | CAGGTCCAACTGCAGCAGCCTGGGACTGAACTGGTGAAGCCTGGGGCTTCAGTGAAGCTGTCCTGCAAGGCTTCTGGCTACACCTT |

TABLE 4-continued

| Exemplary anti-tau antibodies | | | |
|---|---|---|---|
| Ab ID | SEQ ID NO | Description | Sequence |
| | | | CACCAGGTTCTGGATGCACTGGGTGAAGCAGAGGCCTGGACAAGGCCTTGAGTGGATTGGAAATATTAATCCTAACAATGGTGGTACTGACAATAATGAGAGGTTCAAGAGCAAGGCCACACTGACTGTAGACAGATCCTCCAGCACAGCCTACATGCAGCTCAGCAGCCTGACATCTGAGGACTCTGCGGTCTATTATTGTGCAAGAGGAACTGGGACGGGAGCTATGGACTACTGGGGTCAAGGAACCTCAGTCACCGTCTCCTCA |
| | 475 | LC CDR 1 (Chothia) | RSSQSLVHSNGNTHLY |
| | 530 | LC CDR2 (Chothia) | RVSSRES |
| | 571 | LC CDR3 (Chothia) | FQGTHVPRT |
| | 475 | LC CDR1 (Kabat) | RSSQSLVHSNGNTHLY |
| | 530 | LC CDR2 (Kabat) | RVSSRFS |
| | 571 | LC CDR3 (Kabat) | FQGTHVPRT |
| | 1172 | LC CDR1 (IMGT) | QSLVHSNGNTH |
| | | LC CDR2 (IMGT) | RVS |
| | 571 | LC CDR3 (IMGT) | FQGTHVPRT |
| | 787 | FR L1 (corresponding to the Chothia CDR definition) | DVVMTQTPLSLPVSLGDQASISC |
| | 831 | FR L2 (corresponding to the Chothia CDR definition) | WYLQKPGQSPKLLIY |
| | 870 | FR L3 (corresponding to the Chothia CDR definition) | GVPDRFSGSGSGTDFTLKISRVEAEDLGVYFC |
| | 906 | FR L4 (corresponding to the Chothia CDR definition) | FGGGTKLEIK |
| | 95 | VL | DVVMTQTPLSLPVSLGDQASISCRSSQSLVHSNGNTHLYWYLQKPGQSPKLLIYRVSSRFSGVPDRFSGSGSGTDFTLKISRVEAEDLGVYFCFQGTHVPRTFGGGTKLEIK |
| | 243 | DNA VL | GATGTGGTGATGACCCAAACTCCACTCTCCCTGCCTGTCAGTCTTGGAGATCAGGCTTCCATCTCTTGCAGATCTAGTCAGAGCCTTGTACACAGCAATGGAAACACCCATTTATATTGGTACCTGCAGAAGCCAGGCCAGTCTCCAAAGCTCCTGATCTACAGGGTTTCCAGCCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTTCTGCTTTCAGGGTACACATGTTCCTCGGACGTTCGGTGGAGGCACCAAGCTGGAAATCAAA |

TABLE 4-continued

| Exemplary anti-tau antibodies | | | |
|---|---|---|---|
| Ab ID | SEQ ID NO | Description | Sequence |
| V0052 | 325 | HC CDR1 (Chothia) | GFSLSTSAM |
| | 362 | HC CDR2 (Chothia) | YWDDD |
| | 435 | HC CDR3 (Chothia) | RRRGYGMDY |
| | 1152 | HC CDR1 (Kabat) | TSAMGVS |
| | 1153 | HC CDR2 (Kabat) | HIYWDDDKRYNPSLKS |
| | 435 | HC CDR3 (Kabat) | RRRGYGMDY |
| | 1173 | HC CDR1 (IMGT) | GFSLSTSAMG |
| | 1174 | HC CDR2 (IMGT) | IYWDDDK |
| | 1175 | HC CDR3 (IMGT) | ARRRRGYGMDY |
| | 633 | FR H1 (corresponding to the Chothia CDR definition) | QITLKESGPGILQSSQTLSLTCSFS |
| | 682 | FR H2 (corresponding to the Chothia CDR definition) | GVSWIRQPSGEGLEWLAHI |
| | 745 | FR H3 (corresponding to the Chothia CDR definition) | KRYNPSLKSRLTISKDTSRNQVFLKITSVDTADTATYYCAR |
| | 771 | FR H4 (corresponding to the Chothia CDR definition) | WGQGTSVTVSS |
| | 51 | VH | QITLKESGPGILQSSQTLSLTCSFSGFSLSTSAMGVSWIRQPSGEGLEWLAHIYWDDDKRYNPSLKSRLTISKDTSRNQVFLKITSVDTADTATYYCARRRRGYGMDYWGQGTSVTVSS |
| | 197 | DNA VH | CAGATTACTCTGAAAGAGTCTGGCCCTGGGATATTGCAGTCCTCCCAGACCCTCAGTCTGACTTGTTCTTTCTCTGGGTTTTCACTGAGCACTTCTGCTATGGGTGTGAGTTGGATTCGTCAGCCTTCAGGAGAGGGTCTGGAGTGGCTGGCACACATTTACTGGGATGATGACAAGCGCTATAACCCATCCCTGAAGAGCCGGCTCACAATCTCCAAGGATACCTCCAGAAACCAGGTATTCCTCAAGATCACCAGTGTGGACACTGCAGATACTGCCACATACTACTGTGCTCGAAGAAGGAGGGGGTATGGTATGGACTACTGGGGTCAAGGAACCTCAGTCACCGTCTCCTCA |
| | 495 | LC CDR 1 (Chothia) | KASQSVSNDVA |
| | 540 | LC CDR2 (Chothia) | YASNRCT |
| | 587 | LC CDR3 (Chothia) | QQDYRSPLT |
| | 495 | LC CDR1 (Kabat) | KASQSVSNDVA |
| | 540 | LC CDR2 (Kabat) | YASNRCT |
| | 587 | LC CDR3 (Kabat) | QQDYRSPLT |

TABLE 4-continued

| Exemplary anti-tau antibodies | | | |
|---|---|---|---|
| Ab ID | SEQ ID NO | Description | Sequence |
| | 1176 | LC CDR1 (IMGT) | QSVSND |
| | | LC CDR2 (IMGT) | YAS |
| | 587 | LC CDR3 (IMGT) | QQDYRSPLIT |
| | 807 | FR L1 (corresponding to the Chothia CDR definition) | SIVMTQTPKFLLVSAGDRVTITC |
| | 830 | FR L2 (corresponding to the Chothia CDR definition) | WYQQKPGQSPKLLIY |
| | 888 | FR L3 (corresponding to the Chothia CDR definition) | GVPDRFTGSGYGTDFT FTISTVQAEDLAVYFC |

TABLE 4-continued

| Exemplary anti-tau antibodies | | | |
|---|---|---|---|
| Ab ID | SEQ ID NO | Description | Sequence |
| | 908 | FR L4 (corresponding to the Chothia CDR definition) | FGAGTKLELK |
| | 122 | VL | SIVMTQTPKFLLVSAGDRVTITCK ASQSVSNDVAWYQQKPGQS PKLLIYYASNRCTGVPDRFTGSG YGTDFTFTISTVQAEDLAVY FCQQDYRSPLTFGAGTKLELK |
| | 270 | DNA VL | AGTATTGTGATGACCCAGACTCC CAAATTCCTGCTTGTATCAG CAGGAGACAGGGTTACCATAAC CTGCAAGGCCAGTCAGAGTGT GAGTAATGATGTAGCTTGGTACC AACAGAAGCCAGGGCAGTCT CCTAAACTGCTAATATACTATGC ATCCAATCGCTGCACTGGAG TCCCTGATCGCTTCACTGGCAG TGGATATGGGACGGATTTCAC TTTCACCATCAGCACTGTACAG GCTGAAGACCTGGCAGTTTAT TTCTGTCAGCAGGATTATAGGT CTCCGCTCACGTTCGGTGCTG GGACCAAGCTGGAGCTGAAA |

TABLE 6

Exemplary heavy and light chain CDR amino acid sequences of anti-tau antibodies

| ID# | CDRH1 SEQ ID NO | CDRH2 SEQ ID NO | CDRH3 SEQ ID NO | CDRL1 SEQ ID NO | CDRL2 SEQ ID NO | CDRL3 SEQ ID NO |
|---|---|---|---|---|---|---|
| V0001 | 296 | 340 | 392 | 457 | 515 | 554 |
| V0002 | 297 | 341 | 393 | 458 | 516 | 555 |
| V0003 | 298 | 342 | 394 | 459 | 517 | 556 |
| V0004 | 299 | 343 | 395 | 460 | 518 | 557 |
| V0005 | 300 | 344 | 396 | 461 | 519 | 558 |
| V0006 | 301 | 345 | 397 | 462 | 520 | 559 |
| V0007 | 302 | 346 | 398 | 463 | 521 | 560 |
| V0008 | 303 | 345 | 399 | 457 | 522 | 561 |
| V0009 | 304 | 347 | 400 | 464 | 523 | 562 |
| V00010 | 305 | 348 | 401 | 465 | 524 | 563 |
| V00011 | 306 | 349 | 402 | 466 | 525 | 564 |
| V00012 | 307 | 350 | 403 | 467 | 526 | 565 |
| V00014 | 308 | 351 | 404 | 468 | 525 | 566 |
| V00015 | 309 | 341 | 405 | 468 | 525 | 566 |
| V00016 | 310 | 352 | 406 | 469 | 524 | 567 |
| V00017 | 310 | 353 | 406 | 469 | 524 | 567 |
| V00018 | 311 | 354 | 407 | 470 | 527 | 568 |
| V00019 | 312 | 355 | 408 | 471 | 527 | 569 |
| V0020 | 308 | 356 | 409 | 472 | 525 | 570 |
| V0021 | 313 | 357 | 409 | 472 | 525 | 570 |
| V0022 | 314 | 341 | 410 | 1154 | 529 | 571 |
| V0023 | 315 | 341 | 410 | 474 | 529 | 571 |
| V0024 | 316 | 341 | 410 | 475 | 530 | 571 |
| V0025 | 317 | 358 | 410 | 476 | 531 | 571 |
| V0026 | 318 | 359 | 411 | 477 | 525 | 572 |
| V0027 | 319 | 360 | 412 | 478 | 525 | 573 |
| V0028 | 320 | 361 | 413 | 479 | 525 | 573 |
| V0029 | 321 | 362 | 414 | 480 | 529 | 574 |
| V0030 | 308 | 363 | 415 | 480 | 525 | 572 |
| V0031 | 308 | 363 | 416 | 479 | 525 | 572 |
| V0032 | 297 | 364 | 417 | 481 | 525 | 572 |
| V0033 | 308 | 365 | 418 | 482 | 532 | 575 |
| V0034 | 308 | 366 | 419 | 483 | 532 | 576 |
| V0035 | 308 | 367 | 420 | 482 | 532 | 576 |
| V0036 | 321 | 362 | 421 | 484 | 532 | 576 |
| V0037 | 308 | 368 | 422 | 484 | 532 | 577 |
| V0038 | 308 | 369 | 423 | 485 | 526 | 578 |

TABLE 6-continued

| Exemplary heavy and light chain CDR amino acid sequences of anti-tau antibodies | | | | | | |
|---|---|---|---|---|---|---|
| ID# | CDRH1 SEQ ID NO | CDRH2 SEQ ID NO | CDRH3 SEQ ID NO | CDRL1 SEQ ID NO | CDRL2 SEQ ID NO | CDRL3 SEQ ID NO |
| V0039 | 308 | 370 | 423 | 486 | 526 | 578 |
| V0040 | 301 | 371 | 424 | 487 | 533 | 579 |
| V0041 | 301 | 371 | 424 | 487 | 534 | 579 |
| V0042 | 322 | 372 | 425 | 488 | 535 | 580 |
| V0043 | 323 | 373 | 426 | 488 | 535 | 581 |
| V0044 | 322 | 374 | 427 | 489 | 536 | 581 |
| V0045 | 322 | 375 | 428 | 490 | 535 | 582 |
| V0046 | 306 | 376 | 429 | 491 | 525 | 583 |
| V0047 | 306 | 377 | 430 | 468 | 525 | 583 |
| V0048 | 321 | 378 | 431 | 492 | 537 | 584 |
| V0049 | 321 | 362 | 432 | 493 | 538 | 585 |
| V0050 | 297 | 341 | 433 | 494 | 539 | 586 |
| V0051 | 324 | 362 | 434 | 494 | 539 | 586 |
| V0052 | 325 | 362 | 435 | 495 | 540 | 587 |
| V0053 | 321 | 362 | 436 | 496 | 541 | 588 |
| V0054 | 326 | 362 | 437 | 496 | 542 | 588 |
| V0055 | 321 | 362 | 438 | 496 | 543 | 588 |
| V0056 | 321 | 362 | 439 | 496 | 543 | 588 |
| V0057 | 321 | 362 | 438 | 496 | 543 | 588 |
| V0058 | 327 | 362 | 440 | 497 | 543 | 588 |
| V0059 | 328 | 348 | 441 | 498 | 544 | 589 |
| V0060 | 329 | 348 | 441 | 499 | 544 | 589 |
| V0061 | 330 | 379 | 442 | 500 | 545 | 590 |
| V0062 | 331 | 380 | 443 | 501 | 546 | 583 |
| V0063 | 332 | 381 | 444 | 502 | 547 | 572 |
| V0064 | 330 | 382 | 445 | 503 | 546 | 591 |
| V0065 | 333 | 383 | 446 | 504 | 548 | 592 |
| V1001 | 334 | 384 | 447 | 505 | 549 | 593 |
| V1002 | 335 | 385 | 448 | 506 | 550 | 594 |
| V1003 | 334 | 386 | 449 | 507 | 549 | 593 |
| V1004 | 334 | 387 | 450 | 507 | 549 | 595 |
| V1005 | 336 | 388 | 451 | 508 | 551 | 596 |
| V1006 | 336 | 388 | 451 | 509 | 551 | 596 |
| V1007 | 336 | 388 | 451 | 509 | 551 | 596 |
| V2001 | 337 | 389 | 452 | 510 | 525 | 597 |
| V2002 | 338 | 390 | 453 | 511 | 552 | 597 |
| V2003 | 306 | 391 | 454 | 512 | 532 | 598 |
| V2004 | 339 | 361 | 455 | 513 | 553 | 599 |
| V2005 | 308 | 361 | 456 | 514 | 553 | 600 |

TABLE 7

| Exemplary FR amino acid sequences of anti-tau antibodies | | | | | | | | |
|---|---|---|---|---|---|---|---|---|
| ID# | FRH1 SEQ ID NO | FRH2 SEQ ID NO | FRH3 SEQ ID NO | FRH4 SEQ ID NO | FRL1 SEQ ID NO | FRL2 SEQ ID NO | FRL3 SEQ ID NO | FRL4 SEQ ID NO |
| V0001 | 601 | 644 | 697 | 767 | 776 | 823 | 858 | 905 |
| V0002 | 602 | 645 | 698 | 768 | 777 | 823 | 859 | 906 |
| V0003 | 603 | 646 | 699 | 769 | 778 | 824 | 860 | 907 |
| V0004 | 604 | 647 | 700 | 770 | 779 | 825 | 861 | 908 |
| V0005 | 605 | 648 | 701 | 768 | 780 | 826 | 862 | 908 |
| V0006 | 606 | 649 | 702 | 768 | 781 | 827 | 863 | 906 |
| V0007 | 607 | 650 | 703 | 771 | 782 | 828 | 864 | 908 |
| V0008 | 606 | 651 | 704 | 771 | 777 | 829 | 865 | 909 |
| V0009 | 608 | 652 | 705 | 767 | 783 | 830 | 866 | 906 |
| V00010 | 609 | 653 | 706 | 767 | 784 | 830 | 867 | 906 |
| V00011 | 610 | 654 | 707 | 770 | 785 | 831 | 868 | 906 |
| V00012 | 611 | 655 | 708 | 767 | 786 | 832 | 869 | 906 |
| V00014 | 612 | 656 | 709 | 771 | 787 | 831 | 870 | 906 |
| V00015 | 613 | 657 | 710 | 768 | 787 | 831 | 870 | 906 |
| V00016 | 614 | 658 | 711 | 771 | 788 | 830 | 871 | 906 |
| V00017 | 614 | 659 | 712 | 771 | 788 | 830 | 871 | 906 |
| V00018 | 615 | 660 | 713 | 768 | 789 | 833 | 872 | 906 |
| V00019 | 616 | 661 | 714 | 768 | 789 | 833 | 872 | 906 |
| V0020 | 617 | 662 | 715 | 768 | 790 | 834 | 870 | 905 |
| V0021 | 618 | 662 | 716 | 768 | 791 | 834 | 870 | 905 |
| V0022 | 619 | 663 | 717 | 771 | 1178 | 831 | 1179 | 906 |
| V0023 | 603 | 664 | 718 | 771 | 793 | 836 | 874 | 910 |
| V0024 | 603 | 665 | 719 | 771 | 787 | 831 | 870 | 906 |

TABLE 7-continued

| Exemplary FR amino acid sequences of anti-tau antibodies | | | | | | | | |
|---|---|---|---|---|---|---|---|---|
| ID# | FRH1 SEQ ID NO | FRH2 SEQ ID NO | FRH3 SEQ ID NO | FRH4 SEQ ID NO | FRL1 SEQ ID NO | FRL2 SEQ ID NO | FRL3 SEQ ID NO | FRL4 SEQ ID NO |
| V0025 | 603 | 665 | 720 | 771 | 787 | 831 | 875 | 906 |
| V0026 | 620 | 666 | 721 | 771 | 794 | 831 | 868 | 906 |
| V0027 | 620 | 667 | 722 | 771 | 794 | 831 | 868 | 905 |
| V0028 | 620 | 668 | 723 | 771 | 794 | 831 | 868 | 905 |
| V0029 | 621 | 669 | 724 | 768 | 794 | 831 | 876 | 911 |
| V0030 | 603 | 665 | 725 | 771 | 794 | 831 | 868 | 906 |
| V0031 | 603 | 665 | 726 | 771 | 795 | 837 | 868 | 906 |
| V0032 | 622 | 670 | 727 | 771 | 794 | 831 | 868 | 906 |
| V0033 | 623 | 671 | 728 | 767 | 796 | 838 | 877 | 908 |
| V0034 | 623 | 672 | 729 | 768 | 797 | 839 | 878 | 906 |
| V0035 | 624 | 671 | 729 | 768 | 798 | 840 | 878 | 906 |
| V0036 | 625 | 673 | 730 | 767 | 797 | 839 | 878 | 906 |
| V0037 | 626 | 674 | 731 | 767 | 797 | 839 | 878 | 906 |
| V0038 | 627 | 675 | 732 | 772 | 799 | 841 | 869 | 906 |
| V0039 | 627 | 675 | 733 | 772 | 800 | 841 | 879 | 912 |
| V0040 | 628 | 676 | 734 | 773 | 779 | 842 | 880 | 909 |
| V0041 | 628 | 676 | 735 | 771 | 779 | 843 | 880 | 906 |
| V0042 | 629 | 677 | 736 | 767 | 801 | 830 | 881 | 913 |
| V0043 | 630 | 678 | 737 | 768 | 802 | 830 | 882 | 908 |
| V0044 | 629 | 677 | 738 | 768 | 803 | 844 | 883 | 908 |
| V0045 | 629 | 677 | 739 | 767 | 801 | 830 | 883 | 914 |
| V0046 | 610 | 679 | 740 | 771 | 787 | 831 | 884 | 906 |
| V0047 | 610 | 679 | 740 | 771 | 787 | 831 | 870 | 90€ |
| V0048 | 631 | 680 | 741 | 767 | 804 | 845 | 885 | 915 |
| V0049 | 631 | 673 | 742 | 767 | 805 | 845 | 886 | 906 |
| V0050 | 632 | 681 | 743 | 771 | 806 | 846 | 887 | 916 |
| V0051 | 631 | 673 | 744 | 771 | 806 | 846 | 887 | 916 |
| V0052 | 633 | 682 | 745 | 771 | 807 | 830 | 888 | 90 |
| V0053 | 631 | 673 | 746 | 771 | 808 | 833 | 871 | 906 |
| V0054 | 631 | 683 | 747 | 771 | 808 | 833 | 871 | 906 |
| V0055 | 631 | 673 | 745 | 771 | 808 | 833 | 871 | 906 |
| V0056 | 631 | 673 | 748 | 771 | 809 | 833 | 871 | 906 |
| V0057 | 631 | 673 | 749 | 771 | 808 | 833 | 871 | 90€ |
| V0058 | 631 | 673 | 730 | 771 | 808 | 833 | 871 | 906 |
| V0059 | 609 | 653 | 750 | 767 | 789 | 847 | 889 | 906 |
| V0060 | 609 | 653 | 751 | 767 | 810 | 847 | 889 | 906 |
| V0061 | 634 | 684 | 752 | 767 | 811 | 848 | 890 | 906 |
| V0062 | 610 | 685 | 753 | 770 | 792 | 849 | 891 | 906 |
| V0063 | 635 | 686 | 754 | 76" | 812 | 850 | 892 | 906 |
| V0064 | 604 | 687 | 755 | 771 | 792 | 851 | 893 | 908 |
| V0065 | 626 | 688 | 756 | 768 | 813 | 852 | 894 | 906 |
| V1001 | 636 | 689 | 757 | 768 | 814 | 853 | 895 | 917 |
| V1002 | 637 | 690 | 758 | 771 | 815 | 854 | 896 | 90€ |
| V1003 | 638 | 691 | 759 | 774 | 816 | 853 | 897 | 90 |
| V1004 | 636 | 689 | 760 | 768 | 817 | 853 | 898 | 908 |
| V1005 | 639 | 692 | 761 | 771 | 818 | 855 | 899 | 908 |
| V1006 | 639 | 692 | 761 | 771 | 819 | 855 | 899 | 908 |
| V1007 | 639 | 692 | 761 | 771 | 819 | 856 | 900 | 908 |
| V2001 | 640 | 679 | 762 | 771 | 794 | 831 | 868 | 906 |
| V2002 | 640 | 693 | 763 | 771 | 820 | 831 | 901 | 906 |
| V2003 | 641 | 694 | 764 | 768 | 821 | 839 | 902 | 906 |
| V2004 | 642 | 695 | 765 | 767 | 797 | 857 | 903 | 918 |
| V2005 | 643 | 696 | 766 | 775 | 822 | 839 | 904 | 919 |

TABLE X

| Constant Regions of Heavy Chains and Light Chains | | |
|---|---|---|
| SEQ ID NO | Description | Sequence |
| 1189 | Constant Region of Heavy Chain, secreted form & membrane-bound form (mIgG1) | AKTTPPSVYPLAPGSAAQTNSMVTLGCLV KGYFPEPVTVTWNSGSLSSGVHTFPAVLQ SDLYTLSSSVTVPSSPRPSETVTCNVAHPA SSTKVDKKIVPRDCGCKPCICTVPEVSS VFIFPPKPKDVLTITLTPKVTCVVVDISKD DPEVQFSWFVDDVEVHTAQTQPREEQFN STFRSVSELPIMHQDWLNGKEFKCRVNS AAFPAPIEKTISKTKGRPKAPQVYTIPPPK EQMAKDKVSLTCMITDFFPEDITVEWQW NGQPAENYKNTQPIMNINGSYFVYSKLNVQ KSNWEAGNTFTCSVLHEGLHNHHTEK SLSHSPGK |
| 1190 | | AKTTPPSVYPLAPGSAAQTNSMVTLGCL VKGYFPEPVTVTWNSGSLSSGVHTFPAVLQ SDLYTLSSSVTVPSSPRPSETVTCNVAHPAS STKVDKKIVPRDCGCKPCICTVPEVSS |

TABLE X-continued

Constant Regions of Heavy Chains and Light Chains

| SEQ ID NO | Description | Sequence |
|---|---|---|
| | | VFIFPPKPKDVLTITLTPKVTCVVVDISKDDPEVQFSWFVDDVEVHTAQTQPREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQPIMNINGSYFVYSKLNVQKSNWEAGNTFTCSVLHEGLHNHHTEKSLSHSPGLQLDETCAEAQDGELDGLWTTITIFISLFLLSVCYSAAVTLFKVKWIFSSVVELKQTLVPEYKNMIGQAP |
| 1191 | Constant Region of murine Heavy Chain, (mIgG2A) | AKTTAPSVYPLAPVCGDTTGSSVTLGCLVKGYFPEPVTLTWNSGSLSSGVHTFPAVLQSDLYTLSSSVTVISSTWPSQSITCNVAHPASSTKVDKKIEPRGPTIKPCPPCKCPAPNLLGGPSVFIFPPKIKDVLMISLSPIVTCVVVDVSEDDPDVQISWFVNNVEVHTAQTQTHREDYNSTLRVVSALPIQHQDWMSGKEFKCKVNNKDLPAPIERTISKPKGSVRAPQVYVLPPPEEEMTKKQVTLTCMVTDFMPEDIYVEWTNNGKTELNYKNTEPVLDSDGSYFMYSKLRVEKKNWVERNSYSCSVVHEGLHNHHTTKSFSRTPGK |
| 1192 | DNA Constant Region of Heavy Chain (mIgG2A) | GCTAAAACAACAGCCCCATCGGTCTATCCACTGGCCCCTGTGTGTGGAGATACAACTGGCTCCTCGGTGACTCTAGGATGCCTGGTCAAGGGTTATTTCCCTGAGCCAGTGACCTTGACCTGGAACTCTGGATCCCTGTCCAGTGGTGTGCACACCTTCCCAGCTGTCCTGCAGTCTGACCTCTACACCCTCAGCAGCTCAGTGACTGTAACCTCGAGCACCTGGCCCAGCCAGTCCATCACCTGCAATGTGGCCCACCCGGCAAGCAGCACCAAGGTGGACAAGAAAATTGAGCCCAGAGGGCCCACAATCAAGCCCTGTCCTCCATGCAAATGCCCAGCACCTAACCTCTTGGGTGGACCATCCGTCTTCATCTTCCCTCCAAAGATCAAGGATGTACTCATGATCTCCCTGAGCCCCATAGTCACATGTGTGGTGGTGGATGTGAGCGAGGATGACCCAGATGTCCAGATCAGCTGGTTTGTGAACAACGTGGAAGTACACACAGCTCAGACACAAACCCATAGAGAGGATTACAACAGTACTCTCCGGGTGGTCAGTGCCCTCCCCATCCAGCACCAGGACTGGATGAGTGGCAAGGAGTTCAAATGCAAGGTCAACAACAAAGACCTCCCAGCGCCCATCGAGAGAACCATCTCAAAACCCAAAGGGTCAGTAAGAGCTCCACAGGTATATGTCTTGCCTCCACCAGAAGAAGAGATGACTAAGAAACAGGTCACTCTGACCTGCATGGTCACAGACTTCATGCCTGAAGACATTTACGTGGAGTGGACCAACAACGGGAAAACAGAGCTAAACTACAAGAACACTGAACCAGTCCTGGACTCTGATGGTTCTTACTTCATGTACAGCAAGCTGAGAGTGGAAAAGAAGAACTGGGTGGAAAGAAATAGCTACTCCTGTTCAGTGGTCCACGAGGGTCTGCACAATCACCACACGACTAAGAGCTTCTCCCGGACTCCGGGTAAA |
| 1193 | Constant Region of Heavy Chain, secreted form (mIgG2A) | AKTTAPSVYPLVPVCGGTTGSSVTLGCLVKGYFPEPVTLTWNSGSLSSGVHTFPALLQSGLYTLSSSVTVTSNTWPSQTITCNVAHPASSTKVDKKIEPRVPITQNPCPPHQRVPPCAAPDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPSPIEKTISKPRGPVRAPQVYVLPPPAEEMTKKEFSLTCMITGFLPAEIAVDWTSNGRTEQNYKNTATVLDSDGSYFMYSKLRVQKSTWERGSLFACSVVHEVLHNHLTTKTISRSLGK |
| 1194 | Constant Region of murine Heavy Chain, secreted form (mIgG2B) | KTTPPSVYPLAPGCGDTTGSSVTLGCLVKGYFPESVTVTWNSGSLSSSVHTFPALLQSGLYTMSSSVTVPSSTWPSQTVTCSVAHPASSTTVDKKLEPSGPISTINPCPPCKECHKCPAPNLEGGPSVFIFPPNIKDVLMISLTPKVTCVVVDVSEDDPDVQISWFVNNVEVHTAQTQTHREDYNSTIRVVSTLPIQHQDWMSGKEFKCKVNNKDLPSPIERTISKIKGLVRAPQVYILPPPAEQLSRKDVSLTCLVVGENPGDISVEWTSNGHTEENYKDTAPVLDSDGSYFIYSKLNMKTSKWEKTDSFSCNVRHEGLKNYYLKKTISRSPGLDLDDICAEAKDGELDGLWTTITIFISLFLLSVCYSASVTLFKVKWIFSSVVELKQKISPDYRNMIGQGA |
| 1195 | Constant Region of murine Heavy Chain, (mIgG2B) | KTTAPSVYPLAPVCGGTTGSSVTLGCLVKGYFPEPVTLTWNSGSLSSGVHTFPALLQSGLYTLSSSVTVTSNTWPSQTITCNVAHPASSTKVDKKIEPRVPITQNPCPPLKECPPCAAPDLLGGPSVFIFPPKIKDVLMISLSPMVTCVVVDVSEDDPDVQISWFVNNVEVHTAQTQTHREDYNSTLRVVSALPIQHQDWMSGKEFKCKVNNRALPSPIEKTISKPRGPVRAPQVYVLPPPAEEMTKKEFSLTCMITGFLPAEIAVDWTSNGRTEQNYKNTATVLDSDGSYFMYSKLRVQKSTWERGSLFACSVVHEGLHNHLTTKTISRSLGLDLDDVCTEAQDGELDGLWTTITIFISLFLLSVCYSASVTLFKVKWIFSSVVELKQKISPDYRNMIGQGA |
| 1196 | Constant Region of murine Heavy Chain, secreted form (mIgG3) | TTTAPSVYPLVPGCSDTSGSSVTLGCLVKGYFPEPVTVKWNYGALSSGVRTVSSVLQSGFYSLSSLVTVPSSTWPSQTVICNVAHPASKTELIKRIEPRIPKPSTPPGSSCPPGNILGGPSVFIFPPKPKDALMISLTPKVTCVVVDVSEDDPDVHVSWFVDNKEVHTAWTQPREAQYNSTFRVVSALPIQHQDWMRGKEFKCKVNNKALPAPIERTISKPKGRAQTPQVYTIPPPREQMSKKKVSLTCLVTNFFSEAISVEWERNGELEQDYKNTPPILDSDGTYFLYSKLTVDTDSWLQGEIFTCSVVHEALHNHHTQKNLSRSPELELNETCAEAQDGELDGLWTTITIFISLFLLSVCYSASVTLFKVKWIFSSVVQVKQTAIPDYRNMIGQGA |
| 1197 | Constant Region of Murine Kappa Light Chain | ADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSENRNEC |
| 1198 | DNA Constant Region of Murine Kappa Light Chain | GCAGATGCTGCACCAACTGTATCCATCTTCCCACCATCCAGTGAGCAGTTAACATCTGGAGGTGCCTCAGTCGTGTGCTTCTTGAACAACTTCTACCCCAAAGACATCAATGTCAAGTGGAAGATTGATGGCAGTGAACGACAAAATGGCGTCCTGAACAGTTGGACTGATCAGGACAGCAAAGACAGCACCTACAGCATGAGCAGCACCCTCACGTTGACCAAGGACGAGTATGAACGACATAACAGCTATACCTGTGAGGCCACTCACAAGACATCAACTTCACCCATTGTCAAGAGCTTCAACAGGAATGAGTGT |
| 1199 | Constant Region of murine Lambda | QPKSSPSVTLFPPSSEELETNKATLVCTITDFYPGVVTVDWKVDGTPVTQGMETTQPSKQSNNKYMASSYLTLTARAWERHSSYSCQVTHEGHTVEKSLSRADCS |
| 1200 | Light Chain (subclasses 1, 2, and 3) | QPKSTPTLTVFPPSSEELKENKATLVCLISNFSPSGVTVAWKANGTPITQGVDTSNPTKEGNKFMASSFLHLTSDQWRSHNSFTCQVTHEGDTVEKSLSPAECL |
| 1201 | | QPKSTPTLTMFPPSPEELQENKATLVCLISNFSPSGVTVAWKANGTPITQGVDTSNPTKEDNKYMASSFLHLTSDQWRSHNSFTCQVTHEGDTVEKSLSPAECL |
| 1202 | Constant Region of human Heavy Chain (hIgG1) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVY |

TABLE X-continued

Constant Regions of Heavy Chains and Light Chains

| SEQ ID NO | Description | Sequence |
|---|---|---|
| | | TLPPSREEMTKNQVSLTCLVKGFYPSDIA VEWESNGQPENNYKTTPPVLDSDGSFFLY SKLTVDKSRWQQGNVFSCSVMHEALHN HYTQKSLSLSPG |
| 1203 | DNA Constant Region of human Heavy Chain (hIgG1) | GCCAGCACAAAAGGGCCCAGTGTGTTCC CGCTCGCACCAAGCAGCAAATCAACGTCAG GCGGCACAGCCGCGTTGGGTTGCCTTGTA AAAGACTACTTCCCAGAACCAGTTACGGT GTCATGGAACAGTGGTGCACTCACGAGCG GCGTTCATACCTTCCCCGCCGTACTTCAG AGTTCAGGTCTTTACTCACTTTCCAGCGT GGTCACAGTACCGTCAAGCTCTCTTGGAA CACAGACATATATCTGTAACGTAAATCAT AAGCCTAGCAATACCAAAGTCGATAAACG AGTGGAACCCAAGAGTTGTGATAAAACCC ACACCTGTCCCCCTTGCCCGGCACCGGAA CTGCTGGGTGGTCCATCAGTATTCTTGTT TCCGCCTAAGCCAAAGGACACACTGATGA TATCCAGAACTCCAGAGGTTACGTGCGTA GTCGTGGACGTCAGTCATGAAGACCCCGA AGTTAAGTTCAACTGGTACGTGGATGGTG TGGAAGTACATAATGCGAAGACGAAACCC AGGGAAGAACAATATAACTCAACTTATAG GGTAGTCAGCGTCTTGACTGTACTTCACC AAGATTGGTTGAATGGCAAAGAGTACAAA TGCAAGGTAAGCAACAAAGCATTGCCTGC GCCAATCGAAAAGACTATCTCAAAAGCAA AGGGCCAGCCACGCGAACCACAAGTGTAT ACATTGCCGCCCAGTCGGGAAGAAATGAC GAAAAATCAAGTCAGTCTCACATGCCTCG TGAAAGGATTTTATCCCTCTGACATAGCT GTGGAGTGGGAAAGTAATGGCCAACCCGA AAATAATTACAAAACGACGCCTCCCGTTT TGGACTCAGATGGGAGTTTTTTCCTTTAC AGTAAGCTGACGGTTGACAAAAGCAGGTG GCAACAAGGGAACGTCTTTTCTTGTAGTG TGATGCATGAGGCGCTCCACAATCATTAC ACTCAAAAAATCCTTGAGCCTGTCTCCAGGC |
| 1204 | Constant Region of Heavy Chain (hIgG2) | ASTKGPSVFPLAPCSRSTSESTAALGCLVKD YFPEPVTVSWNSGALTSGVHTFPAVLQ SSGLYSLSSVVTVPSSNFGTQTYTCNVDHK PSNTKVDKTVERKCCVECPPCPAPPVAG PSVFLFPPKPKDTLMISRTPEVTCVVVDVSH EDPEVQFNWYVDGVEVHNAKTKPREEQ FNSTFRVVSVLTVVHQDWLNGKEYKCKVS NKGLPAPIEKTISKTKGQPREPQVYTLPP SREEMTKNQVSLTCLVKGFYPSDISVEWE SNGQPENNYKTTPPMLDSDGSFFLYSKLT VDKSRWQQGNVFSCSVMHEALHNHYTQ KSLSLSPGK |
| 1205 | Constant Region of Heavy Chain (hIgG3) | ASTKGPSVFPLAPCSRSTSGGTAALGCLVK DYFPEPVTVSWNSGALTSGVHTFPAVLQ SSGLYSLSSVVTVPSSSLGTQTYTCNVNH KPSNTKVDKRVELKTPLGDTTHTCPRCPE PKSCDTPPPCPRCPEPKSCDTPPPCPRCPEP KSCDTPPPCPRCPAPELLGGPSVFLFP PKPKDTLMISRTPEVTCVVVDVSHEDPEV QFKWYVDGVEVHNAKTKPREEQYNSTFRV VSVLTVLHQDWLNGKEYKCKVSNKALP APIEKTISKTKGQPREPQVYTLPPSREEMTK NQVSLTCLVKGFYPSDIAVEWESSGQPEN NYNTTPPMLDSDGSFFLYSKLTVDKSRWQ QGNIFSCSVMHEALHNRFTQKSLSLSPGK |
| 1206 | Constant Region of human Heavy Chain (hIgG4) | ASTKGPSVFPLAPCSRSTSESTAALGCLVK DYFPEPVTVSWNSGALTSGVHTFPAVLQ SSGLYSLSSVVTVPSSSLGTKTYTCNVDHK PSNTKVDKRVESKYGPPCPSCPAPEFLG GPSVFLFPPKPKDTLMISRTPEVTCVVVDV SQEDPEVQFNWYVDGVEVHNAKTKPREE QFNSTYRVVSVLTVLHQDWLNGKEYKCK VSNKGLPSSIEKTISKAKGQPREPQVYTLP PSQEEMTKNQVSLTCLVKGFYPSDIAVE |

TABLE X-continued

Constant Regions of Heavy Chains and Light Chains

| SEQ ID NO | Description | Sequence |
|---|---|---|
| | | WESNGQPENNYKTTPPVLDSDGSFFLYSRL TVDKSRWQEGNVFSCSVMHEALHNHYT QKSLSLSLGK |
| 1207 | Constant Region of human Light | GQPKANPTVTLFPPSSEELQANKATLVCL ISDFYPGAVTVAWKADGSPVKAGVETTKP SKQSNNKYAASSYLSLTPEQWKSHRSY SCQVTHEGSTVEKTVAPTECS |
| 1208 | Chain (hIgG Lambda, subclasses | GQPKAAPSVTLFPPSSEELQANKATLVCL ISDFYPGAVTVAWKADSSPVKAGVETTTP SKQSNNKYAASSYLSLTPEQWKSHR SYSCQVTHEGSTVEKTVAPTECS |
| 1209 | 1, 2, 3, 6, and 7) | GQPKAAPSVTLFPPSSEELQANKATLVCL ISDFYPGAVTVAWKADSSPVKAGVETTTP SKQSNNKYAASSYLSLTPEQWKSHKSYS CQVTHEGSTVEKTVAPTECS |
| 1210 | | GQPKAAPSVTLFPPSSEELQANKATLVC LISDFYPGAVKVAWKADGSPVNTGVETTTP SKQSNNKYAASSYLSLTPEQWKSHRSY SCQVTHEGSTVEKTVAPAECS |
| 1211 | | GQPKAAPSVTLFPPSSEELQANKATLVCL VSDFNPGAVTVAWKADGSPVKVGVETTKP SKQSNNKYAASSYLSLTPEQWKSHRS YSCRVTHEGSTVEKTVAPAECS |
| 1212 | Constant Region of human Light Chain (hIgG Kappa) | TVAAPSVFIFPPSDEQLKSGTASVVCLLN NFYPREAKVQWKVDNALQSGNSQESVTEQ DSKDSTYSLSSTLTLSKADYEKHKVYA CEVTHQGLSSPVTKSENRGEC |
| 1213 | DNA Constant Region of human Light Chain (hIgG kappa) | ACTGTCGCAGCACCTTCTGTCTTCATCT TTCCGCCAAGCGATGAACAGTTGAAATCTG GAACAGCGTCCGTGGTGTGCCTGCTCAA CAACTTCTATCCTCGGGAAGCGAAGGTGCA ATGGAAGGTAGATAATGCTCTTCAGAG TGGCAATTCCCAAGAGTCAGTTACGGAGCAA GATAGCAAGGACAGCACGTATTCCCTGT CTAGTACGTTGACTCTTTCCAAGGCTGACT ATGAAAAGCACAAGGTGTATGCCTGTG AAGTAACCCACCAAGGTCTCTCAAGTCCTGT AACTAAGAGCTTTAATCGAGGAGAATGC |

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 299, 343, and 395, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 460, 518, and 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 299, 343, 395, 460, 518, and 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 299, 343, 395, 460, 518, or 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1140, 1141, and 395, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 460, 518, and 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1140, 1141, 395, 460, 518, and 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1140, 1141, 395, 460, 518, and 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1155, 1156, and 1157, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1158, NAK, and SEQ ID NO: 557, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1155, SEQ ID NO: 1156, SEQ ID NO: 1157, SEQ ID NO: 1158, NAK, and SEQ ID NO: 557, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1155, SEQ ID NO: 1156, SEQ ID NO: 1157, SEQ ID NO: 1158, NAK, and SEQ ID NO: 557.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 304, 347, and 400, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 464, 523, and 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 304, 347, 400, 464, 523, and 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 304, 347, 400, 464, 523, and 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1142, 1143, and 400, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 464, 523, and 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1142, 1143, 400, 464, 523, and 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1142, 1143, 400, 464, 523, and 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1160, 1161, and 1162, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1163, WAS, and SEQ ID NO: 562, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1160, SEQ ID NO: 1161, SEQ ID NO: 1162, SEQ ID NO: 1163, WAS, and SEQ ID NO: 562, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1160, SEQ ID NO: 1161, SEQ ID NO: 1162, SEQ ID NO: 1163, WAS, and SEQ ID NO: 562.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 314, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1154, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 314, 341, 410, 1154, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 314, 341, 410, 1154, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1144, 1145, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1146, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1144, 1145, 410, 1146, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1144, 1145, 410, 1146, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1165, 1166, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 473, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: SEQ ID NO: 1165, SEQ ID NO: 1166, SEQ ID NO: 1167, SEQ ID NO: 473, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1165, SEQ ID NO: 1166, SEQ ID NO: 1167, SEQ ID NO: 473, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 315, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 474, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 315, 341, 410, 474, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 315, 341, 410, 474, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1147, 1148, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 474, 529, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1147, 1148, 410, 474, 529, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1147, 1148, 410, 474, 529, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1168, 1169, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1170, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1168, SEQ ID NO: 1169, SEQ ID NO: 1167, SEQ ID NO: 1170, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1168, SEQ ID NO: 1169, SEQ ID NO: 1167, SEQ ID NO: 1170, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 316, 341, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 475, 530, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 316, 341, 410, 475, 530, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 316, 341, 410, 475, 530, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1149, 1150, and 410, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 475, 530, and 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1149, 1150, 410, 475, 530, and 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1149, 1150, 410, 475, 530, and 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1171, 1166, and 1167, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1172, RVS, and SEQ ID NO: 571, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1171, SEQ ID NO: 1166, SEQ ID NO: 1167, SEQ ID NO: 1172, RVS, and SEQ ID NO: 571, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1171, SEQ ID NO: 1166, SEQ ID NO: 1167, SEQ ID NO: 1172, RVS, and SEQ ID NO: 571.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 325, 362, and 435, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 495, 540, and 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 325, 362, 435, 495, 540, and 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 325, 362, 435, 495, 540, and 587.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1152, 1153, and 435, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 495, 540, and 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1152, 1153, 435, 495, 540, and 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1152, 1153, 435, 495, 540, and 587.

In some embodiments, the anti-tau antibody comprises at least one, two, three, or all of a heavy chain complementary determining region 1 (HC CDR1), a HC CDR2, and/or a HC CDR3, wherein the HC CDR1, HC CDR2, and HC CDR3 sequences comprise the sequences of SEQ ID NO: 1173, 1174, and 1175, respectively. In some embodiments, the anti-tau antibody comprises at least one, two, three, or all of a LC CDR1, a LC CDR2 and/or an LC CDR3, wherein the LC CDR1, LC CDR2, and LC CDR3 sequences comprise the sequences of SEQ ID NO: 1176, YAS, and SEQ ID NO: 587, respectively. In some embodiments, the anti-tau antibody comprises a HC CDR1, a HC CDR2, a HC CDR3, a LC CDR1, a LC CDR2 and an LC CDR3, wherein the HC CDR1, HC CDR2, HC CDR3, LC CDR1, LC CDR2, and LC CDR3 sequences comprise the sequences of SEQ ID NO: 1173, SEQ ID NO: 1174, SEQ ID NO: 1175, SEQ ID NO: 1176, YAS, and SEQ ID NO: 587, respectively. In some embodiments, one or more of the CDRs (or collectively all of the CDRs) have one, two, three, four, five or more changes, e.g., amino acid substitutions, insertions, or deletions, relative to the amino acid sequence of any of SEQ ID NO: 1173, SEQ ID NO: 1174, SEQ ID NO: 1175, SEQ ID NO: 1176, YAS, and SEQ ID NO: 587.

In some embodiments, the anti-tau antibody comprises a heavy chain variable region comprising the amino acid sequence of SEQ ID NO: 4; or encoded by the nucleotide sequence of SEQ ID NO: 150; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 78; or encoded by the nucleotide sequence of SEQ ID NO: 224; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 4 and 78, respectively; or encoded by the nucleotide sequences of SEQ ID NO: 150 and 224, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 150, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 224, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 9; or encoded by the nucleotide sequence of SEQ ID NO: 155; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 83; or encoded by the nucleotide sequence of SEQ ID NO: 229; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 9 and 83, respectively; or encoded by the nucleotide sequences of SEQ ID NO: 155 and 229, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 155, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 229, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 21; or encoded by the nucleotide sequence of SEQ ID NO: 167; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 93; or encoded by the nucleotide sequence of SEQ ID NO: 241; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 21 and 93, respectively; or encoded by the nucleotide sequences of SEQ ID NO: 167 and 241, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 167, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 241, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 22; or encoded by the nucleotide sequence of SEQ ID NO: 168; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 94; or encoded by the nucleotide sequence of SEQ ID NO: 242; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 22 and 94, respectively; or encoded by the nucleotide sequences of SEQ ID NO: 168 and 242, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 168, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 242, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 23; or encoded by the nucleotide sequence of SEQ ID NO: 169; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 95; or encoded by the nucleotide sequence of SEQ ID NO: 243; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 23 and 95, respectively; or encoded by the nucleotide sequences of SEQ ID NO: 169 and 243, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 169, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 243, or a sequence substantially identical (e.g., having at least about 80%, 85%, 90%, 92%, 95%, 97%, 98%, or 99% sequence identity).

In some embodiments, the anti-tau antibody comprises a heavy chain variable region comprising the amino acid sequence of SEQ ID NO: 51; or encoded by the nucleotide sequence of SEQ ID NO: 197; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a light chain variable region comprising the amino acid sequence of SEQ ID NO: 122; or encoded by the nucleotide sequence of SEQ ID NO: 270; or a sequence substantially identical (e.g., having at least about 70%, 75%, 80%, 85%, 90%, 92%, 95%, 97%, 98%, or 99% sequence identity) to any of the aforesaid sequences. In some embodiments, the anti-tau antibody comprises a heavy chain variable region and a light chain variable region comprising the amino acid sequences of SEQ ID NO: 51 and 122, respectively; or encoded by the nucleotide sequences of SEQ ID NO: 197 and 270, respectively; or a sequence substantially identical (e.g., having at least about 70%, 75%, 80%, 85%, 90%, 92%, 95%, 97%, 98%, or 99% sequence identity) to any of the aforesaid sequences. In some embodiments, the nucleotide sequence encoding the heavy chain variable region of the anti-tau antibody comprises the nucleotide sequence of SEQ ID NO: 197, or a sequence substantially identical (e.g., having at least about 80%, 85%, 90%, 92%, 95%, 97%, 98%, or 99% sequence identity); and/or the nucleotide sequence encoding the light chain variable region comprises the nucleotide sequence of SEQ ID NO: 270, or a sequence substantially identical (e.g., having at least about 80%, 85%, 90%, 92%, 95%, 97%, 98%, or 99% sequence identity).

In some embodiments, the anti-tau antibody comprises a VH and/or VL encoded by a codon-optimized nucleic acid sequence. Codon-optimization may be achieved by any method known to one with skill in the art such as, but not limited to, by a method according to Genescript, EMBOSS, Bioinformatics, NUS, NUS2, Geneinfinity, IDT, NUS3, GregThatcher, Insilico, Molbio, N2P, Snapgene, and/or VectorNTI.

Anti-tau antibodies according to the present disclosure may be prepared using any of the antibody sequences (e.g., variable domain amino acid sequences, variable domain amino acid sequence pairs, CDR amino acid sequences, variable domain CDR amino acid sequence sets, variable domain CDR amino acid sequence set pairs, and/or framework region amino acid sequences) presented herein, any may be prepared, for example, as monoclonal antibodies, multispecific antibodies, chimeric antibodies, antibody mimetics, scFvs, or antibody fragments.

In some embodiments, anti-tau antibodies using any of the antibody sequences presented herein may be prepared as IgA, IgD, IgE, IgG, or IgM antibodies. When prepared as mouse IgG antibodies, anti-tau antibodies may be prepared as IgG1, IgG2a, IgG2b, IgG2c, or IgG3 isotypes. When prepared as human IgG antibodies, anti-tau antibodies may be prepared as IgG1, IgG2, IgG3, or IgG4 isotypes. Anti-tau antibodies prepared as human or humanized antibodies may include one or more human constant domains.

This present disclosure provides in some embodiments, a nucleic acid (e.g., an isolated nucleic acid) encoding any of the above described antibodies, and viral genomes, vectors, AAV particles, and cells comprising the same.

Tau Protein Antigens

In some embodiments, anti-tau antibodies bind to tau protein antigens, e.g., an epitope on a tau protein. Tau protein antigens may include human microtubule-associated protein tau, isoform 2 (SEQ ID NO: 920) or fragments thereof. Tau protein antigens may include ePHF or fragments thereof. Tau protein antigens may include one or more phosphorylated residues. Such phosphorylated residues may correspond to those found with pathological tau. In some embodiments tau protein antigens include any of those listed in Table 8. In the Table, phosphorylated residues associated with each antigen are double-underlined. In some embodiments, tau proteins may include variants (e.g., phosphorylated or unphosphorylated variants) or fragments of the sequences listed.

TABLE 8

Tau protein antigen sequences

| Antigen | Sequence | SEQ ID NO |
|---|---|---|
| human microtubule-associated protein tau, isoform 2 | MAEPRQEFEVMEDHAGTYGLGDRKD QGGYTMHQDQEGDTDAGLKESPLQ TPTEDGSEEPGSETSDAKSTPTAEDVT APLVDEGAPGKQAAAQPHTEIP EGTTAEEAGIGDTPSLEDEAAGHVTQ ARMVSKSKDGTGSDDKKAKGADG KTKIATPRGAAPPGQKGQANATRIP AKIPPAPKTPPSSGEPPKSGDRSG YSSPGSPGTPGSRSRIPSLPTPPTREP KKVAVVRTPPKSPSSAKSRLQT APVPMPDLKNVKSKIGSTENLKHQP GGGKVQIINKKLDLSNVQSKCGSK DNIKHVPGGGSVQIVYKPVDLSKVT SKCGSLGNIHHKPGGGQVEVKSEK LDFKDRVQSKIGSLDNITHVPGGGN KKIETHKLTFRENAKAKTDHGAEI VYKSPVVSGDTSPRHLSNVSSTGSI DMVDSPQLATLADEVSASLAKQGL | 920 |
| PT3 epitope peptide (pT212/pT217) | TPGSRSRTPSLPTPPTREPK | 921 |
| Peptide 5 (pT212/pS214/pT217) | GTPGSRSRTPSLPTPPTRE | 922 |
| Peptide 12 (pS396/pS404/pS409) | RENAKAKTDHGAEIVYKSP VVSGDTSPRHLSNVSSTG | 923 |
| Peptide 1 (AT120 epitope) | PTREPKKV | 924 |
| 6C5 epitope peptide | ARMVSKS | 925 |
| UCB D & PT76 epitope peptide | SPSSAKSRLQTAPVPMPDLKNVKS | 926 |

In some embodiments, anti-tau antibodies of the present disclosure bind to tau protein epitopes on tau protein antigens described herein. Such tau protein epitopes may include or be included within a tau protein antigen amino acid sequence listed in Table 8. In some embodiments, anti-tau antibodies of the present disclosure bind to tau protein epitopes that include a region formed by a complex of at least two tau proteins.

In some embodiments, disclosed herein is an encoded an antibody that competes for binding to tau with the aforesaid antibodies. In some embodiments, disclosed herein is an antibody that binds to the same epitope as, substantially the same epitope as, an epitope that overlaps with, or an epitope that substantially overlaps with, the epitope of the aforesaid anti-tau antibody.

In some embodiment, compete or cross-compete refers to the ability of an antibody to interfere with binding of an anti-tau antibody, e.g., an anti-tau antibody provided herein, to a target, e.g., tau protein. The interference with binding can be direct or indirect (e.g., through an allosteric modulation of the antibody or the target). The extent to which an antibody is able to interfere with the binding of another antibody to the target, and therefore whether it can be said to compete, can be determined using a competition binding assay, for example, a FACS assay, an ELISA or BIACORE assay. In some embodiments, a competition binding assay is a quantitative competition assay. In some embodiments, a first anti-tau antibody is said to compete for binding to the target with a second anti-tau antibody when the binding of the first antibody to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

In some embodiments, an epitope comprises the moieties of an antigen (e.g., a tau protein antigen) that specifically interact with an antibody. Such moieties, referred to herein as epitopic determinants, typically comprise, or are part of, elements such as amino acid side chains or sugar side chains. An epitopic determinate can be defined by methods known in the art or disclosed herein, e.g., by crystallography or by hydrogen-deuterium exchange. At least one or some of the moieties on the antibody, that specifically interact with an epitopic determinant, are typically located in a CDR(s). Typically, an epitope has a specific three dimensional structural characteristics. Typically, an epitope has specific charge characteristics. Some epitopes are linear epitopes while others are conformational epitopes.

In an embodiment, an epitopic determinant is a moiety on the antigen, e.g., such as amino acid side chain or sugar side chain, or part thereof, which, when the antigen and antibody are co-crystallized, is within a predetermined distance, e.g., within 5 Angstroms, of a moiety on the antibody, referred to herein as a crystallographic epitopic determinant. In some embodiments, the crystallographic epitopic determinants of an epitope are collectively referred to as a crystallographic epitope.

A first antibody binds the same epitope as a second antibody (e.g., a reference antibody, e.g., an antibody disclosed herein) if the first antibody specifically interacts with the same epitopic determinants on the antigen as does the second or reference antibody, e.g., when interaction is measured in the same way for both the antibody and the second or reference antibody. Epitopes that overlap share at least one epitopic determinant. A first antibody binds an overlapping epitope with a second antibody (e.g., a reference antibody, e.g., an antibody disclosed herein) when both antibodies specifically interact with a common epitopic determinant. A first and a second antibody (e.g., a reference antibody, e.g., an antibody disclosed herein) bind substantially overlapping epitopes if at least half of the epitopic determinants of the second or reference antibody are found as epitopic determinants in the epitope of the first antibody. A first and a second antibody (e.g., a reference antibody, e.g., an antibody disclosed herein) bind substantially the same epitope if the first antibody binds at least half of the core epitopic determinants of the epitope of the second or reference antibody, wherein the core epitopic determinants are defined by crystallography.

Epitope Specificity

Antibodies of the present disclosure may bind to tau protein epitopes, which may include or be included within the residues of SEQ ID NOs: 920-926. Antibodies may compete for binding to tau protein epitopes with other anti-tau antibodies, including, but not limited to, AT100, AT120, PT3, C10.2, PT76, IPN002, 6C5, and UCB D. Tau protein epitopes may include C-terminal residues 409-436 of human tau (SEQ ID NO: 920). Such epitopes may include residues 413-430 of human tau (SEQ ID NO: 920). Antibody binding to such residues may exhibit a $K_D$ of from about 0.1 nM to about 0.5 nM. In some embodiments, tau protein epitopes may include residues 55-76, 159-194, 219-247, and/or 381-426 of human tau (SEQ ID NO: 920). Such epitopes may include residues 57-72, 175-191, 223-238, and/or 383-400 of human tau (SEQ ID NO: 920). Antibodies binding to such residues may exhibit a $K_D$ of from about 0.5 nM to about 5 nM.

In some embodiments, the present disclosure provides antibodies that compete for binding with second antibodies to tau protein epitopes. Such epitopes may include one or more of residues 32-49, 55-76, 57-72, 159-194, 175-191, 185-200, 219-247, 223-238, 381-426, 383-400, 409-436, and 413-430 of human tau (SEQ ID NO: 920).

Tau protein epitopes may include one or more of residues 409-436 and 413-430 of human tau (SEQ ID NO: 920). Second antibodies competing for binding to such epitopes may include variable domain pairs selected from the group consisting of: a VH with the amino acid sequence of SEQ ID NO: 21 and a VL with the amino acid sequence of SEQ ID NO: 93; a VH with the amino acid sequence of SEQ ID NO: 22 and a VL with the amino acid sequence of SEQ ID NO: 94; and a VH with the amino acid sequence of SEQ ID NO: 23 and a VL with the amino acid sequence of SEQ ID NO: 95.

Antibodies competing for tau epitope binding with such second antibodies may include a CDRH1 that includes the amino acid sequence of G [F/Y] TFT [R/I] [Y/F] (SEQ ID NO: 931), or more generally G-X1-TFT-X2-X3 (SEQ ID NO: 932), where X1, X2, and X3 may be any amino acid, e.g., X1 and/or X3 may be an amino acid with a hydrophobic and/or aromatic side chain, such as F or Y, and/or X2 may be a positively charged residue (such as R. K. H) or a residue with aliphatic side chain (such as A. V. I, or L); a CDRH2 that includes the amino acid sequence NPNNGG (SEQ ID NO: 341); a CDRH3 that includes the amino acid sequence GTGTGAMDY (SEQ ID NO: 410); a CDRL1 that includes the amino acid sequence RSSQSLVH [N/S] NG [I/N] T [H/Y] LY (SEQ ID NO: 933), or more generally RSSQSLVH-X1-NG-X2-T-X3-LY (SEQ ID NO: 934), where X1, X2, and $X_3$ may be any amino acid, e.g., X1 is Q/N/S/T and/or X2 is A/V/I/L/Q/N and/or X3 is H/R/K/Y/F; a CDRL2 that includes the amino acid sequence RVS [N/S] RFS (SEQ ID NO: 935), or more generally RVSXRFS (SEQ ID NO: 936), where X may be any amino acid, e.g., X1 is Q/N/S/T; and/or a CDRL3 that includes the amino acid sequence FQGTHVPRT (SEQ ID NO: 571).

In some embodiments, the CDRH1 may include the amino acid sequence G[F/Y]TFT[R/I][Y/F] (SEQ ID NO: 931). The CDRH2 may include the amino acid sequence NPNNGG (SEQ ID NO: 341). The CDRH3 may include the amino acid sequence GTGTGAMDY (SEQ ID NO: 410). The CDRL1 may include the amino acid sequence RSSQSLVH [N/S] NG [IN] T [H/Y] LY (SEQ ID NO: 933). The CDRL2 may include the amino acid sequence RVS [N/S] RFS (SEQ ID NO: 935). The CDRL3 may include the amino acid sequence FQGTHVPRT (SEQ ID NO: 571).

In some embodiments, tau protein epitopes may include one or more of residues 57-72, 175-191, 223-238, and 383-400 of human tau (SEQ ID NO: 920). Second antibodies competing for binding to such epitopes may include variable domain pairs selected from the group consisting of: a VH with the amino acid sequence of SEQ ID NO: 51 and a VL with the amino acid sequence of SEQ ID NO: 122; a VH with the amino acid sequence of SEQ ID NO: 53 and a VL with the amino acid sequence of SEQ ID NO: 124; a VH with the amino acid sequence of SEQ ID NO: 54 and a VL with the amino acid sequence of SEQ ID NO: 125; a VH with the amino acid sequence of SEQ ID NO: 56 and a VL with the amino acid sequence of SEQ ID NO: 125; a VH with the amino acid sequence of SEQ ID NO: 57 and a VL with the amino acid sequence of SEQ ID NO: 126; a VH with the amino acid sequence of SEQ ID NO: 35 and a VL with the amino acid sequence of SEQ ID NO: 107; and a VH with the amino acid sequence of SEQ ID NO: 48 and a VL with the amino acid sequence of SEQ ID NO: 120.

Antibodies competing for tau epitope binding with such second antibodies may include a CDRH1 that includes the amino acid sequence of GFSL [S/N] T [S/F] [A/G] M (SEQ ID NO: 964), or more generally GFSL-X1-T-X2-X3-M (SEQ ID NO: 965), where X1-X3 may be any amino acid, e.g., X1 is S/T/N/Q and/or X2 is S/T/F/Y and/or X3 is G/A/I/L/V; a CDRH2 that includes the amino acid sequence YWDDD (SEQ ID NO: 362); a CDRH3 that includes the amino acid sequence R [R/V/K/S/G] [Y/R] [Y/absent] [S/absent] [absent/N] [G/S/Y/R] [Y/N/G] [G/A/Y/N] [M/F/Y] DY, or more generally R-X1-X2-X3-X4-X5-X6-X7-X8-X9-DY, where each of X1-X9 may be any amino acid and/or where one or more of X3-X5 may be absent, e.g., X1 is R/K/H/A/V/I/L/G/S/T and/or X2 is Y/F/R/K/H and/or X3 is Y/F/absent and/or X4 is S/T/absent and/or X5 is N/Q/absent and/or X6 is G/A/V/I/L/S/T/Y/F/R/K/H and/or X7 is Y/F/N/Q/G/A/V/I/L and/or X8 is G/A/V/I/L/Y/F/N/Q and/or X9 is M/F/Y: a CDRL1 that includes the amino acid sequence [K/S] [S/A] S [Q/S] S [L/V/V] [L/S] [N/S/D] [D/S/T] [V/G/D/Y] [N/G/absent] [Q/absent] [K/absent] [N/T/absent] [Y/absent] [L/absent] [A/H/N], or more generally X1-X2-S-X3-S-X4-X5-X6-X7-X8-X9-X10-X11-X12-X13-X14-X15, where each of X1-X15 may be any amino acid and/or where one or more of X9-X14 may be absent, e.g., X1 is K/R/H/S/T and/or X2 is S/T/A/V/I/L and or X3 is Q/N/S/T and/or X4 is L/I/V/A and/or X5 is A/V/I/L/S/T and/or X6 is N/Q/S/T/D/E and/or X7 is D/E/S/T and/or X8 is G/A/V/I/L/D/E/Y/F and/or X9 is N/Q/G/A/absent and/or X10 is Q/N/absent and/or X11 is K/R/H/absent and/or X12 is N/Q/T/S/absent and/or X13 is Y/F/absent and/or X14 is A/V/I/L/absent and/or X15 is A/V/I/L/H/K/R/N/Q; a CDRL2 that includes the amino acid sequence [Y/G/L/R] [A/T/V] S [N/T/K] [R/L] [C/E/D/A] [T/S], or more generally X1-X2-S-X3-X4-X5-X6, where X1-X6 may be any amino acid, e.g., X1 is Y/F/G/A/V/I/L/R/K/H and/or X2 is A/V/I/L/T/S and/or X3 is N/Q/T/S/K/R/H and/or X4 is R/K/H/A/V/I/L and/or X5 is C/S/E/D/A/V/I/L and/or X6 is T/S; and/or a CDRL3 that includes the amino acid sequence [W/Q] [Q/N] [G/D] [T/S/Y/H] [H/S/R] [F/I/S/H] P [Q/R/L/Y] [absent/Y] T, or more generally X1-X2-X3-X4-X5-X6-P-X7-X8-T, where each of X1-X8 may be any amino acid and/or where X8 may be absent, e.g., $X_1$ is Q/N/W/F/Y and/or X2 is Q/N and/or X3 is G/A/V/I/L/D/E and/or X4 is T/S/Y/F/H/K/R and/or X5 is H/K/R/S/T and/or X6 is F/Y/A/V/I/L/S/T/H/K/R and/or X7 is Q/N/R/K/H/A/V/I/L/Y/F and/or X8 is Y/F/absent.

The CDRH1 may include the amino acid sequence GFSL [S/N] T [S/F] [A/G] M (SEQ ID NO: 964). The CDRH2 may include the amino acid sequence YWDDD (SEQ ID NO: 362). The CDRH3 may include the amino acid sequence R [R/V/K/S/G] [Y/R] [Y/absent] [S/absent] [absent/N] [G/S/Y/R] [Y/N/G] [G/A/Y/N] [M/F/Y] DY. The CDRL1 may include the amino acid sequence [K/S] [S/A] S [Q/S] S [L/I/V] [L/S] [N/S/D] [D/S/T] [V/G/D/Y] [N/G/absent] [Q/absent] [K/absent] [N/T/absent] [Y/absent] [L/absent] [A/H/N]. The CDRL2 may include the amino acid sequence [Y/G/L/R] [A/T/V] S [N/T/K] [R/L] [C/E/D/A] [T/S]. The CDRL3 may include the amino acid sequence [W/Q] [Q/N] [G/D] [T/S/Y/H] [H/S/R] [F/I/S/H] P [Q/R/L/Y] [absent/Y] T.

II. Vectorization

According to the present disclosure, compositions for delivering anti-tau antibodies or functional variants thereof by adeno-associated virus particles (AAVs) are provided. In some embodiments, an AAV particle, e.g., an AAV particle as described herein, or plurality of particles, may be provided, e.g., delivered, via any of several routes of administration, to a cell, tissue, organ, or organism, in vivo, ex vivo, or in vitro.

As used herein, an "AAV particle" is a virus which comprises a capsid and a viral genome with at least one payload region and at least one inverted terminal repeat (ITR) region.

As used herein, "viral genome" or "vector genome" refers to the nucleic acid sequence(s) encapsulated in an AAV particle. Viral genomes comprise at least one payload region encoding polypeptides, e.g., antibodies, antibody-based compositions or fragments thereof.

As used herein, a "payload" or "payload region" is any nucleic acid molecule which encodes one or more polypeptides. At a minimum, a payload region comprises nucleic acid sequences that encode an antibody, an antibody-based composition, or a fragment thereof, but may also optionally comprise one or more functional or regulatory elements to facilitate transcriptional expression and/or polypeptide translation.

In some embodiments, AAV particles, viral genomes and/or payloads, and the methods of their use may be as described in WO2017189963 or WO2020223276, the contents of each of which are herein incorporated by reference in their entirety.

The nucleic acid sequences, viral genomes, and polypeptides disclosed herein may be engineered to contain modular elements and/or sequence motifs assembled to enable expression of an antibody or functional variant thereof, e.g., an antibody described herein. In some embodiments, the nucleic acid sequence encodes an antibody comprising one or more of the CDRs (e.g., heavy chain and/or light chain CDRs) of an antibody, a variable heavy (VH) chain region and/or variable light (VL) chain region, a heavy and/or light chain constant region, or a combination thereof. In some embodiments, the nucleic acid sequence encoding the antibody may also encode a linker, e.g., such that the VH/heavy chain and the VL/light chain of the antibody are connected via a linker. In some embodiments, the viral genome may further comprise a promoter region, an intron, a Kozak sequence, an enhancer, or a polyadenylation sequence. The order of expression, structural position, or concatemer count (e.g., the VH, VL, heavy chain, light chain, and/or linker) may be different within or among different payload regions. The identity, position and number of linkers expressed by payload regions may also vary. In some embodiments, the payload is a region comprising one or more humanized antibody sequences, such as but not limited to, a humanized antibody VL, light chain domain and/or a humanized antibody VH, heavy chain domain, or fragments thereof.

In some embodiments, the present disclosure provides methods for delivering an antibody (e.g., an anti-tau antibody described herein) and/or a nucleic acid sequence encoding an antibody (e.g., an anti-tau antibody described herein) comprised within the viral genome comprised within a recombinant, AAV particle (e.g., an AAV particle described herein) to a cell, tissue, organ, or subject.

Adeno-Associated Viruses (AAVs) and AAV Particles

In some embodiments, adeno-associated viruses (AAV) are small non-enveloped icosahedral capsid viruses of the Parvoviridae family characterized by a single stranded DNA viral genome. Parvoviridae family viruses consist of two subfamilies: Parvovirinae, which infect vertebrates, and Densovirinae, which infect invertebrates. The Parvoviridae family comprises the Dependovirus genus which includes AAV. In some embodiments, the AAV is capable of replication in vertebrate hosts including, but not limited to, human, primate, bovine, canine, equine, and ovine species.

The parvoviruses and other members of the Parvoviridae family are generally described in Kenneth I. Berns, "Parvoviridae: The Viruses and Their Replication," Chapter 69 in FIELDS VIROLOGY (3d Ed. 1996), the contents of which are incorporated by reference in their entirety.

AAV have proven to be useful as a biological tool due to their relatively simple structure, their ability to infect a wide range of cells (including quiescent and dividing cells) without integration into the host genome and without replicating, and their relatively benign immunogenic profile. The genome of the virus may be manipulated to contain a minimum of components for the assembly of a functional recombinant virus, or viral particle, which is loaded with or engineered to target a particular tissue and express or deliver a desired payload.

The wild-type AAV vector genome is a linear, single-stranded DNA (ssDNA) molecule approximately 5,000 nucleotides (nt) in length. Inverted terminal repeats (ITRs) traditionally cap the viral genome at both the 5' and the 3' end, providing origins of replication for the viral genome. While not wishing to be bound by theory, an AAV viral genome typically comprises two ITR sequences. These ITRs have a characteristic T-shaped hairpin structure defined by a self-complementary region (145nt in wild-type AAV) at the 5' and 3' ends of the ssDNA which form an energetically stable double stranded region. The double stranded hairpin structures comprise multiple functions including, but not limited to, acting as an origin for DNA replication by functioning as primers for the endogenous DNA polymerase complex of the host viral replication cell.

The wild-type AAV viral genome further comprises nucleotide sequences for two open reading frames, one for the four non-structural Rep proteins (Rep78, Rep68, Rep52, Rep40, encoded by Rep genes) and one for the three capsid, or structural, proteins (VP1, VP2, VP3, encoded by capsid genes or Cap genes). The Rep proteins are important for replication and packaging, while the capsid proteins are assembled to create the protein shell of the AAV, or AAV capsid. Alternative splicing and alternate initiation codons and promoters result in the generation of four different Rep proteins from a single open reading frame and the generation of three capsid proteins from a single open reading frame. Though it varies by AAV serotype, as a non-limiting example, for AAV9/hu.14 (SEQ ID NO: 123 of U.S. Pat. No. 7,906,111, the contents of which are herein incorporated by reference in their entirety) VP1 refers to amino acids 1-736, VP2 refers to amino acids 138-736, and VP3 refers to amino acids 203-736. In other words, VP1 is the full-length capsid sequence, while VP2 and VP3 are shorter components of the whole. As a result, changes in the sequence in the VP3 region, are also changes to VP1 and VP2, however, the percent difference as compared to the parent sequence will be greatest for VP3 since it is the shortest sequence of the three. Though described here in relation to the amino acid sequence, the nucleic acid sequence encoding these proteins can be similarly described. Together, the three capsid proteins assemble to create the AAV capsid protein. While not wishing to be bound by theory, the AAV capsid protein typically comprises a molar ratio of 1:1:10 of VP1: VP2: VP3. As used herein, an "AAV serotype" is defined primarily by the AAV capsid. In some instances, the ITRs are also specifically described by the AAV serotype (e.g., AAV2/9).

For use as a biological tool, the wild-type AAV viral genome can be modified to replace the rep/cap sequences with a nucleic acid sequence comprising a payload region with at least one ITR region. Typically, in recombinant AAV viral genomes there are two ITR regions. The rep/cap sequences can be provided in trans during production to generate AAV particles.

In addition to the encoded heterologous payload. AAV vectors may comprise the viral genome, in whole or in part, of any naturally occurring and/or recombinant AAV serotype nucleotide sequence or variant. AAV variants may have sequences of significant homology at the nucleic acid (genome or capsid) and amino acid levels (capsids), to produce constructs which are generally physical and functional equivalents, replicate by similar mechanisms, and assemble by similar mechanisms. Chiorini et al., J. Vir. 71: 6823-33 (1997); Srivastava et al., J. Vir. 45:555-64 (1983); Chiorini et al., J. Vir. 73:1309-1319 (1999); Rutledge et al., J. Vir. 72:309-319 (1998); and Wu et al., J. Vir. 74: 8635-47 (2000), the contents of each of which are incorporated herein by reference in their entirety.

In some embodiments, AAV particles of the present disclosure are recombinant AAV viral vectors which are replication defective and lacking sequences encoding functional Rep and Cap proteins within their viral genome. These defective AAV vectors may lack most or all parental coding sequences and essentially carry only one or two AAV ITR sequences and the nucleic acid of interest for delivery to a cell, a tissue, an organ, or an organism.

In some embodiments, the viral genome of the AAV particles of the present disclosure comprise at least one control element which provides for the replication, transcription, and translation of a coding sequence encoded therein. Not all of the control elements need always be present as long as the coding sequence is capable of being replicated, transcribed, and/or translated in an appropriate host cell. Non-limiting examples of expression control elements include sequences for transcription initiation and/or termination, promoter and/or enhancer sequences, efficient RNA processing signals such as splicing and polyadenylation signals, sequences that stabilize cytoplasmic mRNA, sequences that enhance translation efficacy (e.g., Kozak consensus sequence), sequences that enhance protein stability, and/or sequences that enhance protein processing and/or secretion.

According to the present disclosure, AAV particles for use in therapeutics and/or diagnostics comprise a virus that has been distilled or reduced to the minimum components necessary for transduction of a nucleic acid payload or cargo of interest. In this manner, AAV particles are engineered as vehicles for specific delivery while lacking the deleterious replication and/or integration features found in wild-type viruses.

AAV vectors of the present disclosure may be produced recombinantly and may be based on adeno-associated virus (AAV) parent or reference sequences. As used herein, a "vector" is any molecule or moiety which transports, transduces, or otherwise acts as a carrier of a heterologous molecule such as the nucleic acids described herein.

In addition to single stranded AAV viral genomes (e.g., ssAAVs), the present disclosure also provides for self-complementary AAV (scAAVs) viral genomes. scAAV vector genomes contain DNA strands which anneal together to form double stranded DNA. By skipping second strand synthesis, scAAVs allow for rapid expression in the transduced cell.

In some embodiments, the AAV particle of the present disclosure is an scAAV.

In some embodiments, the AAV particle of the present disclosure is an ssAAV.

Methods for producing and/or modifying AAV particles are disclosed in the art such as pseudotyped AAV vectors (PCT Patent Publication Nos. WO200028004; WO200123001; WO2004112727; WO2005005610; and WO2005072364, the content of each of which is incorporated herein by reference in its entirety).

AAV particles may be modified to enhance the efficiency of delivery. Such modified AAV particles can be packaged efficiently and be used to successfully infect the target cells at high frequency and with minimal toxicity. In some embodiments, the capsids of the AAV particles are engineered according to the methods described in US Publication Number US20130195801, the contents of which are incorporated herein by reference in their entirety.

In some embodiments, the AAV particles comprising a payload region encoding the polypeptides may be introduced into mammalian cells.

AAV Serotypes

In some embodiments, the AAV particle, e.g., an AAV particle for the vectorized delivery of an antibody described herein (e.g., an anti-tau antibody), may comprise or be derived from any natural or recombinant AAV serotype. AAV particles of the present disclosure may comprise or be derived from any natural or recombinant AAV serotype. According to the present disclosure, the AAV particles may utilize or be based on a serotype or include a peptide selected from any of the following VOY101, VOY201, AAVPHP.B (PHP.B), AAVPHP.A (PHP.A), AAVG2B-26, AAVG2B-13, AAVTH1.1-32, AAVTH1.1-35, AAVPHP.B2 (PHP.B2), AAVPHP.B3 (PHP.B3), AAVPHP.N/PHP.B-DGT, AAVPHP.B-EST, AAVPHP.B-GGT, AAVPHP.B-ATP, AAVPHP.B-ATT-T, AAVPHP.B-DGT-T, AAVPHP.B-GGT-T, AAVPHP.B-SGS, AAVPHP.B-AQP, AAVPHP.B-QQP. AAVPHP.B-SNP (3), AAVPHP.B-SNP, AAVPHP.B-QGT, AAVPHP.B-NQT, AAVPHP.B-EGS, AAVPHP.B-SGN, AAVPHP.B-EGT, AAVPHP.B-DST, AAVPHP.B-DST, AAVPHP.B-STP, AAVPHP.B-PQP, AAVPHP.B-SQP, AAVPHP.B-QLP, AAVPHP.B-TMP, AAVPHP.B-TTP, AAVPHP.S/G2A12, AAVG2A15/G2A3 (G2A3), AAVG2B4 (G2B4), AAVG2B5 (G2B5), PHP.S. AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9 K449R, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu. 16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu. 10, AAVhu.11, AAVhu. 13, AAVhu. 15, AAVhu. 16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AA Vhu.45, AAVhu.46, AAVhu.47, AAVhu.48, AAVhu.48R1, AAVhu.48R2, AAVhu.48R3, AA Vhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu. 14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-MI, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, and/or AAVF9/HSC9 and variants thereof.

In some embodiments, the AAV serotype may be, or have a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV9 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1 (US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh. 10 (SEQ ID NO: 9 and 25 of US20150159173), rh. 13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu. 13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch.5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have a mutation in the AAV9 sequence as described by N Pulicherla et al. (Molecular Therapy 19(6):1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T: Thr). As another non-limiting example, may comprise three mutations: (1) K406R where lysine (K: Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have a mutation in the AAV2 sequence to generate AAV2G9 as described in International Publication No. WO2014144229 and herein incorporated by reference in its entirety.

In some embodiments, the AAV serotype may be, or have a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu. 10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu. 17 (SEQ ID NO: 4 of WO2005033321), AAV33.4/hu.15 (SEQ ID No: 50 of WO2005033321), AAV33.8/hu. 16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu. 1 (SEQ ID No: 46 of WO2005033321), AAVH-5/hu.3 (SEQ ID No: 44 of WO2005033321), AAVhu.1 (SEQ ID NO: 144 of WO2005033321), AAVhu. 10 (SEQ ID NO: 156 of WO2005033321), AAVhu.11 (SEQ ID NO: 153 of WO2005033321), AAVhu.12 (WO2005033321 SEQ ID NO: 59), AAVhu. 13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu. 19 (SEQ ID NO: 133 of WO2005033321), AAVhu.2 (SEQ ID NO: 143 of WO2005033321), AAVhu.20 (SEQ ID NO: 134 of WO2005033321), AA Vhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AA Vhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AA Vpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO: 37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh. 12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151,154, 158, 161, 162, 165-183, 202, 204-212, 215, 219, 224-236, of WO2005033321, the contents of which are herein incorporated by reference in their entirety.

In some embodiments, the AAV serotype may be, or have a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO: 50 of U.S. Pat. No. 9,233,131), AAVhEr1.7 (SEQ ID NO:51 of U.S. Pat. No. 9,233,131), AAVhEr1.36 (SEQ ID NO: 52 of U.S. Pat. No. 9,233,131), AAVhEr2.29 (SEQ ID NO:53 of U.S. Pat. No. 9,233,131), AAVhEr2.4 (SEQ ID NO: 54 of U.S. Pat. No. 9,233,131), AAVhEr2.16 (SEQ ID NO:55 of U.S. Pat. No. 9,233,131), AAVhEr2.30 (SEQ ID NO: 56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have a sequence as described in United States Patent Publication No. US20150376607, the contents of which are herein incorporated by reference in their entirety, such as, but not limited to, AAV-PAEC (SEQ ID NO: 1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO: 10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO: 17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO: 24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use may be from a variety of species. In some embodiments, the AAV may be an avian AAV (AAAV). The AAAV serotype may be, or have a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In some embodiments, the AAV may be a bovine AAV (BAAV). The BAAV serotype may be, or have a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In some embodiments, the AAV may be a caprine AAV. The caprine AAV serotype may be, or have a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments the AAV may be engineered as a hybrid AAV from two or more parental serotypes. In some embodiments, the AAV may be AAV2G9 which comprises sequences from AAV2 and AAV9. The AAV2G9 AAV serotype may be, or have a sequence as described in United States Patent Publication No. US20160017005, the contents of which are herein incorporated by reference in its entirety.

In some embodiments, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but are not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A: Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T;

R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N4981), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734,809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: X and X of U.S. Pat. No. 8,734,809), AAV CLv-R9 (SEQ ID NO: X and X of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No.

8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734,809), or variants or derivatives thereof.

In some embodiments, the AAV serotype may be, or have a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-MI (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In some embodiments, the AAV particle may have, or may be a serotype selected from any of those found in Table 9.

In some embodiments, the AAV capsid may comprise a sequence, fragment or variant thereof, of any of the sequences in Table 9.

In some embodiments, the AAV capsid may be encoded by a sequence, fragment or variant as described in Table 9.

In any of the DNA and RNA sequences referenced and/or described herein, the single letter symbol has the following description: A for adenine; C for cytosine; G for guanine; T for thymine; U for Uracil; W for weak bases such as adenine or thymine; S for strong nucleotides such as cytosine and guanine; M for amino nucleotides such as adenine and cytosine; K for keto nucleotides such as guanine and thymine; R for purines adenine and guanine; Y for pyrimidine cytosine and thymine; B for any base that is not A (e.g., cytosine, guanine, and thymine); D for any base that is not C (e.g., adenine, guanine, and thymine); H for any base that is not G (e.g., adenine, cytosine, and thymine); V for any base that is not T (e.g., adenine, cytosine, and guanine); N for any nucleotide (which is not a gap); and Z is for zero.

In any of the amino acid sequences referenced and/or described herein, the single letter symbol has the following description: G (Gly) for Glycine; A (Ala) for Alanine; L (Leu) for Leucine; M (Met) for Methionine; F (Phe) for Phenylalanine; W (Trp) for Tryptophan; K (Lys) for Lysine; Q (Gln) for Glutamine; E (Glu) for Glutamic Acid; S (Ser) for Serine; P (Pro) for Proline; V (Val) for Valine; I (Ile) for Isoleucine; C (Cys) for Cysteine; Y (Tyr) for Tyrosine; H (His) for Histidine; R (Arg) for Arginine; N (Asn) for Asparagine; D (Asp) for Aspartic Acid; T (Thr) for Threonine; B (Asx) for Aspartic acid or Asparagine; J (Xle) for Leucine or Isoleucine; O (Pyl) for Pyrrolysine; U (Sec) for Selenocysteine; X (Xaa) for any amino acid; and Z (Glx) for Glutamine or Glutamic acid.

TABLE 9

AAV Serotypes

| Serotype | SEQ ID NO | Reference Information |
| --- | --- | --- |
| AAV1 (nt) | 982 | US20030138772 SEQ ID NO: 6 |
| AAV1 (aa) | 983 | US20160017295 SEQ ID NO: 1, US20030138772 SEQ ID NO: 64, US20150159173 SEQ ID NO: 27, US20150315612 SEQ ID NO: 219, US7198951 SEQ ID NO: 5 |
| AAV2 (nt) | 984 | US20150159173 SEQ ID NO: 7, US20150315612 SEQ ID NO: 211 |
| AAV2 (aa) | 985 | US20030138772 SEQ ID NO: 70, US20150159173 SEQ ID NO: 23, US20150315612 SEQ ID NO: 221, US20160017295 SEQ ID NO: 2, US6156303 SEQ ID NO: 4, US7198951 SEQ ID NO: 4, WO2015121501 SEQ ID NO: 1 |
| AAV3 (nt) | 986 | US20030138772 SEQ ID NO: 8 |
| AAV3 (aa) | 987 | US20030138772 SEQ ID NO: 71, US20150159173 SEQ ID NO: 28, US20160017295 SEQ ID NO: 3, US7198951 SEQ ID NO: 6 |
| AAV4 (nt) | 988 | US20140348794 SEQ ID NO: 1 |
| AAV4 (nt) | 989 | WO2016065001 SEQ ID NO: 49 |
| AAV4 (aa) | 990 | US20030138772 SEQ ID NO: 63, US20160017295 SEQ ID NO: 4, US20140348794 SEQ ID NO: 4 |
| AAV5 (nt) | 991 | US7427396 SEQ ID NO: 1 |
| AAV5 (aa) | 992 | US20160017295 SEQ ID NO: 5, US7427396 SEQ ID NO: 2, US20150315612 SEQ ID NO: 216 |
| AAV6 (nt) | 993 | US6156303 SEQ ID NO: 2 |
| AAV6 (nt) | 994 | US20150315612 SEQ ID NO: 203 |
| AAV6 (aa) | 995 | US20030138772 SEQ ID NO: 65, US20150159173 SEQ ID NO: 29, US20160017295 SEQ ID NO: 6, US6156303 SEQ ID NO: 7 |
| AAV7 (nt) | 996 | US20150159173 SEQ ID NO: 14 |
| AAV7 (nt) | 997 | US20030138772 SEQ ID NO: 1, US20150315612 SEQ ID NO: 180 |

TABLE 9-continued

| AAV Serotypes | | |
|---|---|---|
| Serotype | SEQ ID NO | Reference Information |
| AAV7 (aa) | 998 | US20030138772 SEQ ID NO: 2, US20150159173 SEQ ID NO: 30, US20150315612 SEQ ID NO: 181, US20160017295 SEQ ID NO: 7 |
| AAV8 (nt) | 999 | US20030138772 SEQ ID NO: 4, US20150315612 SEQ ID NO: 182 |
| AAV8 (nt) | 1000 | US20150159173 SEQ ID NO: 15 |
| AAV8 (aa) | 1001 | US20030138772 SEQ ID NO: 95, US20140359799 SEQ ID NO: 1, US20150159173 SEQ ID NO: 31, US20160017295 SEQ ID NO: 8, US7198951 SEQ ID NO: 7, US20150315612 SEQ ID NO: 223 |
| AAV9/hu.14 (nt) | 1002 | SEQ ID NO: 3; US7906111 |
| AAV9/hu.14 (aa) | 1003 | SEQ ID NO: 123; US7906111 |
| AAV PHP.B (nt) | 1004 | SEQ ID NO: 9; WO2015038958 |
| AAV PHP.B (aa) (K449R) | 1005 | SEQ ID NO: 8; WO2015038958 |
| AAVG2B-13 | 1006 | SEQ ID NO: 12; WO2015038958 |
| AAVTH1.1-32 | 1007 | SEQ ID NO: 14; WO2015038958 |
| AAVTH1.1-35 | 1008 | SEQ ID NO: 15; WO2015038958 |
| PHP.N/PHP.B-DGT | 1009 | SEQ ID NO: 46; WO2017100671 |
| PHP.S/G2A12 | 1010 | SEQ ID NO: 47; WO2017100671 |
| AAV9/hu.14 K449R | 101 | SEQ ID NO: 45; WO2017100671 |
| AAVrh10 (nt) (referred to as clone 44.2) | 1012 | US20030138772 SEQ ID NO: 59 |
| AAVrh10 (aa) (referred to as clone 44.2) | 1013 | US20030138772 SEQ ID NO: 81 |
| AAV-DJ (nt) | 1014 | US20140359799 SEQ ID NO: 3, US7588772 SEQ ID NO: 2 |
| AAV-DJ (aa) | 1015 | US20140359799 SEQ ID NO: 2, US7588772 SEQ ID NO: 1 |
| AAV-DJ8 (2 mutations) | 1016 | US7588772; Grimm et al 2008 |
| AAV-DJ8 (3 mutations) | 1017 | US7588772; Grimm et al 2008 |
| rh74 (nt) | 1018 | US9434928B2 SEQ ID NO: 1; US2015023924A1 SEQ ID NO: 2 |
| rh74 (aa) | 1019 | US9434928B2 SEQ ID NO: 2; US2015023924A1 SEQ ID NO: 1 |
| AAV10 (aa) | 1020 | WO2015121501 SEQ ID NO: 9 |
| AAV10 (aa) | 1021 | WO2015121501 SEQ ID NO: 8 |
| VQY101 (nt) | 1022 | — |
| VQY101 (aa) | 1023 | — |
| VQY201 (nt) | 1024 | — |
| VQY201 (aa) | 1025 | — |
| AAV2 variant (aa) | 1026 | WO2018071831 SEQ ID NO: 358 |
| AAV2/3 variant (aa) | 1027 | WO2018071831 SEQ ID NO: 513 |
| AAV2/3 variant (aa) | 1028 | WO2018071831 SEQ ID NO: 575 |

In some embodiments the AAV serotype is VOY101, or a variant thereof. In some embodiments, the VOY101 capsid comprises the amino acid sequence SEQ ID NO: 1023. In some embodiments, the VOY101 amino acid sequence is encoded by a nucleotide sequence comprising SEQ ID NO: 1022. In some embodiments, the VOY101 capsid comprises an amino acid sequence at least 70% identical to SEQ ID NO: 1023, such as, 70%, 75%, 80%, 85%, 90%, 91%, 92%, 93%, 94%, 95%, 96%, 97%, 98%, 99%, or greater than 99%. In some embodiments, the VOY101 capsid comprises a nucleotide sequence at least 70% identical to SEQ ID NO: 1022, such as, 70%, 75%, 80%, 85%, 90%, 91%, 92%, 93%, 94%, 95%, 96%, 97%, 98%, 99%, or greater than 99%.

In some embodiments, the AAV serotype is VOY201, or a variant thereof. In some embodiments, the VOY201 capsid comprises the amino acid sequence SEQ ID NO: 1025. In some embodiments, the VOY201 amino acid sequence is encoded by a nucleotide sequence comprising SEQ ID NO: 1024. In some embodiments, the VOY201 capsid comprises an amino acid sequence at least 70% identical to SEQ ID NO: 1025, such as, 70%, 75%, 80%, 85%, 90%, 91%, 92%, 93%, 94%, 95%, 96%, 97%, 98%, 99%, or greater than 99%. In some embodiments, the VOY201 capsid comprises a nucleotide sequence at least 70% identical to SEQ ID NO: 1024, such as, 70%, 75%, 80%, 85%, 90%, 91%, 92%, 93%, 94%, 95%, 96%, 97%, 98%, 99%, or greater than 99%.

In some embodiments, the AAV serotype is PHP.B, or a variant thereof. In some embodiments, the PHP.B capsid comprises the amino acid sequence SEQ ID NO: 1005. In some embodiments, the PHP.B amino acid sequence is encoded by a nucleotide sequence comprising SEQ ID NO: 1004. In some embodiments, the PHP.B capsid comprises an amino acid sequence at least 70% identical to SEQ ID NO: 1005, such as, 70%, 75%, 80%, 85%, 90%, 91%, 92%, 93%, 94%, 95%, 96%, 97%, 98%, 99%, or greater than 99%. In some embodiments, the PHP.B capsid comprises a nucleotide sequence at least 70% identical to SEQ ID NO: 1004, such as, 70%, 75%, 80%, 85%, 90%, 91%, 92%, 93%, 94%, 95%, 96%, 97%, 98%, 99%, or greater than 99%.

In some embodiments, the AAV serotype is PHP.N, or a variant thereof. In some embodiments, the PHP.N capsid comprises the amino acid sequence SEQ ID NO: 1009. In some embodiments, the PHP.N capsid comprises an amino acid sequence at least 70% identical to SEQ ID NO: 1009, such as, 70%, 75%, 80%, 85%, 90%, 91%, 92%, 93%,94%, 95%, 96%, 97%, 98%, 99%, or greater than 99%.

In some embodiments the AAV serotype is AAV9, or a variant thereof. In some embodiments, the AAV9 capsid comprises the amino acid sequence SEQ ID NO: 1003. In some embodiments, the AAV9 amino acid sequence is encoded by a nucleotide sequence comprising SEQ ID NO: 1002. In some embodiments, the AAV9 capsid comprises an amino acid sequence at least 70% identical to SEQ ID NO: 1003, such as, 70%, 75%, 80%, 85%, 90%, 91%, 92%, 93%, 94%, 95%, 96%, 97%, 98%, 99%, or greater than 99%. In some embodiments, the AAV9 capsid comprises a nucleotide sequence at least 70% identical to SEQ ID NO: 1002, such as, 70%, 75%, 80%, 85%, 90%, 91%, 92%, 93%, 94%, 95%,96%, 97%, 98%, 99%, or greater than 99%.

In some embodiments, the capsid protein comprises an insert comprising the amino acid sequence of TLAVPFK (SEQ ID NO: 1151). In some embodiments, the insert is present immediately subsequent to position 588, relative to a reference sequence numbered according to SEQ ID NO: 1003. In some embodiments, the capsid protein comprises the amino acid substitutions of A587D and Q588G, numbered according to SEQ ID NO: 1003.

In some embodiments, the capsid protein comprises the amino acid substitution of K449R, numbered according to SEQ ID NO: 1003; and an insert comprising the amino acid sequence of TLAVPFK (SEQ ID NO: 1151), wherein the insert is present immediately subsequent to position 588, relative to a reference sequence numbered according to SEQ ID NO: 1003.

In some embodiments, the capsid protein comprises the amino acid substitution of K449R, numbered according to SEQ ID NO: 1003; an insert comprising the amino acid sequence of TLAVPFK (SEQ ID NO: 1151), wherein the insert is present immediately subsequent to position 588, relative to a reference sequence numbered according to SEQ ID NO: 1003; and the amino acid substitutions of A587D and Q588G, numbered according to SEQ ID NO: 1003.

In some embodiments, the capsid protein comprises an insert comprising the amino acid sequence of TLAVPFK (SEQ ID NO: 1151), wherein the insert is present immediately subsequent to position 588, relative to a reference sequence numbered according to SEQ ID NO: 1003; and the amino acid substitutions of A587D and Q588G, numbered according to SEQ ID NO: 1003.

In some embodiments, the AAV serotype is AAV9 K449R, or a variant thereof. In some embodiments, the AAV9 K449R capsid comprises the amino acid sequence SEQ ID NO: 1011. In some embodiments, the AAV9 K449R capsid comprises an amino acid sequence at least 70% identical to SEQ ID NO: 1011, such as, 70%, 75%, 80%, 85%, 90%, 91%, 92%, 93%, 94%, 95%, 96%, 97%, 98%, 99%, or greater than 99%.

In some embodiments, the AAV capsid allows for blood brain barrier penetration following intravenous administration. Non-limiting examples of such AAV capsids include AAV9, AAV9 K449R, VOY101, VOY201, or AAV capsids comprising a peptide insert such as, but not limited to, AAVPHP.N (PHP.N), AAVPHP.B (PHP.B), PHP.S, G2A3, G2B4, G2B5, G2A12, G2A15, PHP.B2, PHP.B3, or AAVPHP.A (PHP.A).

In some embodiments, the AAV capsid is suitable for intramuscular administration and/or transduction of muscle fibers. Non-limiting examples of such AAV capsids include AAV2, AAV3, AAV8 and variants thereof such as, but not limited to, AAV2 variants, AAV2/3 variants, AAV8 variants, and/or AAV2/3/8 variants.

In some embodiments, the AAV serotype is an AAV2 variant. As a non-limiting example, the AAV serotype is an AAV2 variant comprising SEQ ID NO: 1026 or a fragment or variant thereof. As a non-limiting example, the AAV serotype is at least 70% identical to SEQ ID NO: 1026, such as, 70%, 75%, 80%, 85%, 90%, 91%, 92%, 93%, 94%, 95%,96%, 97%, 98%, 99%, or greater than 99%.

In some embodiments, the AAV serotype is an AAV2/3 variant. As a non-limiting example, the AAV serotype is an AAV2/3 variant comprising SEQ ID NO: 1027 or a fragment or variant thereof. As a non-limiting example, the AAV serotype is an AAV2/3 variant which is at least 70% identical to SEQ ID NO: 1027, such as, 70%, 75%, 80%, 85%, 90%, 91%, 92%, 939%, 94%, 95%, 96%, 97%, 98%, 99%, or greater than 99%. As a non-limiting example, the AAV serotype is an AAV2/3 variant comprising SEQ ID NO: 1028 or a fragment or variant thereof. As a non-limiting example, the AAV serotype is an AAV2/3 variant which is at least 70% identical to SEQ ID NO: 1028, such as, 70%, 75%, 80%, 85%, 90%, 91%, 92%, 93%, 94%, 95%, 96%, 97%, 98%, 99%, or greater than 99%.

In some embodiments, the AAV serotype may comprise a capsid amino acid sequence with 50%, 51%, 52%, 53%, 54%, 55%, 56%, 57%, 58%, 59%, 60%, 61%, 62%, 63%, 64%, 65%, 669%, 67%, 68%, 69%, 70%, 71%, 72%, 73%, 74%, 75%, 76%, 77%,78%. 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein.

In some embodiments, the AAV serotype may be encoded by a capsid nucleic acid sequence with 50%, 51%, 52%, 53%, 54%, 55%, 56%, 57%, 58%, 59%, 60%, 61%,62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any of those described herein.

In some embodiments, the AAV serotype is selected for use due to its tropism for cells of the central nervous system. In some embodiments, the cells of the central nervous system are neurons. In another embodiment, the cells of the central nervous system are astrocytes.

In some embodiments, the AAV serotype is selected for use due to its tropism for cells of the muscle(s).

In some embodiments, the initiation codon for translation of the AAV VP1 capsid protein may be CTG, TTG, or GTG as described in U.S. Pat. No. 8,163,543, the contents of which are herein incorporated by reference in their entirety.

The present disclosure refers to structural capsid proteins (including VP1, VP2 and VP3) which are encoded by capsid (Cap) genes. These capsid proteins form an outer protein structural shell (i.e. capsid) of a viral vector such as AAV. VP capsid proteins synthesized from Cap polynucleotides generally include a methionine as the first amino acid in the peptide sequence (Met1), which is associated with the start codon (AUG or ATG) in the corresponding Cap nucleotide sequence. However, it is common for a first-methionine (Met1) residue or generally any first amino acid (AA1) to be cleaved off after or during polypeptide synthesis by protein processing enzymes such as Met-aminopeptidases. This "Met/AA-clipping" process often correlates with a corresponding acetylation of the second amino acid in the polypeptide sequence (e.g., alanine, valine, serine, threonine, etc.). Met-clipping commonly occurs with VP1 and VP3 capsid proteins but can also occur with VP2 capsid proteins.

Where the Met/AA-clipping is incomplete, a mixture of one or more (one, two or three) VP capsid proteins comprising the viral capsid may be produced, some of which may include a Met1/AA1 amino acid (Met+/AA+) and some of which may lack a Met1/AA1 amino acid as a result of Met/AA-clipping (Met−/AA−). For further discussion regarding Met/AA-clipping in capsid proteins, see Jin, et al. Direct Liquid Chromatography/Mass Spectrometry Analysis for Complete Characterization of Recombinant Adeno-Associated Virus Capsid Proteins. *Hum Gene Ther Methods.* 2017 Oct. 28(5):255-267; Hwang, et al. N-Terminal Acetylation of Cellular Proteins Creates Specific Degradation Signals. Science. 2010 Feb. 19, 327(5968): 973-977; the contents of which are each incorporated herein by reference in its entirety.

According to the present disclosure, references to capsid proteins is not limited to either clipped (Met−/AA−) or unclipped (Met+/AA+) and may, in context, refer to independent capsid proteins, viral capsids comprised of a mixture of capsid proteins, and/or polynucleotide sequences (or fragments thereof) which encode, describe, produce or result in capsid proteins of the present disclosure. A direct reference to a "capsid protein" or "capsid polypeptide" (such as VP1, VP2 or VP2) may also comprise VP capsid proteins which include a Met1/AA1 amino acid (Met+/AA+) as well as corresponding VP capsid proteins which lack the Met1/AA1 amino acid as a result of Met/AA-clipping (Met−/AA−).

Further according to the present disclosure, a reference to a specific SEQ ID NO: (whether a protein or nucleic acid) which comprises or encodes, respectively, one or more capsid proteins which include a Met1/AA1 amino acid (Met+/AA+) should be understood to teach the VP capsid proteins which lack the Met1/AA1 amino acid as upon review of the sequence, it is readily apparent any sequence which merely lacks the first listed amino acid (whether or not Met1/AA1).

As a non-limiting example, reference to a VP1 polypeptide sequence which is 736 amino acids in length and which includes a "Met1" amino acid (Met+) encoded by the AUG/ATG start codon may also be understood to teach a VP1 polypeptide sequence which is 735 amino acids in length and which does not include the "Met1" amino acid (Met−) of the 736 amino acid Met+ sequence. As a second non-limiting example, reference to a VP1 polypeptide sequence which is 736 amino acids in length and which includes an "AA1" amino acid (AA1+) encoded by any NNN initiator codon may also be understood to teach a VP1 polypeptide sequence which is 735 amino acids in length and which does not include the "AA1" amino acid (AA1−) of the 736 amino acid AA1+ sequence.

References to viral capsids formed from VP capsid proteins (such as reference to specific AAV capsid serotypes), can incorporate VP capsid proteins which include a Met1/AA1 amino acid (Met+/AA1+), corresponding VP capsid proteins which lack the Met1/AA1 amino acid as a result of Met/AA1-clipping (Met−/AA1−), and combinations thereof (Met+/AA1+ and Met−/AA1−).

As a non-limiting example, an AAV capsid serotype can include VP1 (Met+/AA1+), VP1 (Met−/AA1−), or a combination of VP1 (Met+/AA1+) and VP1 (Met−/AA1−). An AAV capsid serotype can also include VP3 (Met+/AA1+), VP3 (Met−/AA1−), or a combination of VP3 (Met+/AA1+) and VP3 (Met−/AA1−); and can also include similar optional combinations of VP2 (Met+/AA1) and VP2 (Met−/AA1−).

AAV Particles Comprising Anti-Tau Antibody Payloads

AAV particles as described herein may be used for the delivery of an antibody payload (e.g., anti-tau antibody) to a target tissue (e.g., CNS). In some embodiments, a viral genome encoding an anti-tau antibody polypeptide may be packaged into a viral particle, e.g., an AAV particle. A target cell transduced with a viral particle comprising one or more anti-tau antibody polynucleotides may express the encoded antibody or antibodies in a single cell.

In some embodiments, the AAV particles comprising anti-tau antibody polynucleotide sequences which comprise a nucleic acid sequence encoding at least one antibody heavy and/or light chain may be introduced into mammalian cells.

The AAV viral genomes encoding anti-tau antibody polypeptides described herein may be useful in the fields of human disease, viruses, infections veterinary applications and a variety of in vivo and in vitro settings. In some embodiments, the AAV viral genomes encoding anti-tau antibody polypeptides are used for the prevention and/or treatment of a tauopathy.

A viral genome of an AAV particle as described herein, comprises a nucleic acid sequence encoding a payload, and at least one ITR. In some embodiments, a viral genome comprises two ITR sequences, one at each of the 5' and 3' ends. Further, a viral genome of the AAV particles described herein may comprise nucleic acid sequences for additional components, such as, but not limited to, a regulatory element (e.g., promoter), untranslated regions (UTR), a polyadenylation sequence (polyA), a filler sequence, an intron, and/or a linker sequence for enhanced expression. These viral genome components can be selected and/or engineered to further tailor the specificity and efficiency of expression of a given payload in a target tissue.

The viral genome of the AAV particles of the present disclosure may comprise any combination of the sequence regions described in Tables 10-18 encapsulated in any of the capsids listed in Table 9 or described herein.

In some embodiments, the viral genome may comprise at least one sequence region as described in Tables 10-18. The regions may be located before or after any of the other sequence regions described herein. Viral genomes may further comprise more than one copy of one or more sequence regions as described in Tables 10-18.

Viral Genome Component: Inverted Terminal Repeats (ITRs)

In some embodiments, the viral genome may comprise at least one inverted terminal repeat (ITR) region. In some embodiments, the viral genome comprises at least one ITR region and a nucleic acid encoding a payload, e.g., an antibody molecule (e.g., an anti-tau antibody molecule). In some embodiments, viral genome comprises two ITRs. In some embodiments, the two ITRs flank the nucleic acid encoding the transgene at the 5' and 3' ends. In some embodiments, the ITR functions as an origin of replication comprising recognition sites for replication. In some embodiments, the ITRs comprise sequence regions which can be complementary and symmetrically arranged. In some embodiments, the ITR incorporated into viral genome may be comprised of naturally occurring nucleic acid sequences or recombinantly derived nucleic acid sequences.

In some embodiments, the ITR may be of the same AAV serotype as the capsid, e.g., a capsid protein selected from any of the AAV serotypes listed in Table 9, or a functional variant thereof. In some embodiments, the ITR may be of a different AAV serotype than the capsid protein. In some embodiments, the AAV particle comprises a viral genome comprising two ITRs wherein the two ITRs of viral genome are of the same AAV serotype. In other embodiments, the two ITRs of a viral genome are of different AAV serotypes. In some embodiments both ITRs of the viral genome of the AAV particle are AAV2 ITRs or a functional variant thereof.

The ITR region(s) may, independently, have a length such as, but not limited to, about 100 to about 150 nucleotides in length. An ITR may be about 100-180 nucleotides in length, e.g., about 100-115, about 100-120, about 100-130, about 100-140, about 100-150, about 100-160, about 100-170, about 100-180, about 110-120, about 110-130, about 110-140, about 110-150, about 110-160, about 110-170, about 110-180, about 120-130, about 120-140, about 120-150, about 120-160, about 120-170, about 120-180, about 130-140, about 130-150, about 130-160, about 130-170, about 130-180, about 140-150, about 140-160, about 140-170, about 140-180, about 150-160, about 150-170, about 150-180, about 160-170, about 160-180, or about 170-180 nucleotides in length. In some embodiments, the ITR comprises about 120-140 nucleotides in length, e.g., about 130 nucleotides in length. In some embodiments, the ITR comprises about 140-150 nucleotides in length, about 141 nucleotides in length. In some embodiments, the viral genome comprises an ITR region comprising the nucleotide sequence of any of the sequences provided in Table 10 or a nucleotide sequence with at least 70%, 75%, 80%, 85%, 90%, 95% or 99% sequence identity thereto. In some embodiments, the viral genome comprises two ITR regions comprising the nucleotide sequence of any of the sequences provided in Table 10 or a nucleotide sequence with at least 70%, 75%, 80%, 85%, 90%, 95% or 99% sequence identity thereto, wherein the first and second ITR comprise the same sequence or wherein the first and second ITR comprise different sequences.

As a non-limiting example, the viral genome comprises a 5' ITR that is about 141 nucleotides in length. As a non-limiting example, the viral genome comprises a 5' ITR that is about 130 nucleotides in length. As a non-limiting example, the viral genome comprises a 3' ITR that is about 141 nucleotides in length. As a non-limiting example, the viral genome comprises a 3' ITR that is about 130 nucleotides in length. In some embodiments, the AAV particles comprise two ITRs and one ITR is 141 nucleotides in length and the other ITR is 130 nucleotides in length.

In some embodiments, the AAV particle viral genome comprises a 5' inverted terminal repeat (5' ITR) sequence region. In some embodiments, the viral genome comprises a 3' inverted terminal repeat (3' ITR) sequence region. Non-limiting examples of 5' ITR and 3' ITR sequence regions are described in Table 10.

TABLE 10

Inverted Terminal Repeat (ITR) Sequence Regions

| Sequence Region Name | Sequence Length | SEQ ID NO |
|---|---|---|
| ITR1 | 130 | 1035 |
| ITR2 | 141 | 1036 |
| ITR3 | 130 | 1037 |
| ITR4 | 141 | 1038 |

In some embodiment, the viral genome comprises an ITR provided in Table 10. In some embodiments, the viral genome comprises an ITR chosen from any one of ITR1-ITR4 or a functional variant thereof. In some embodiments, the viral genome may have an ITR that comprises ITR1. In some embodiments, the viral genome may have an ITR that comprises ITR2. In some embodiments, the viral genome may have an ITR that comprises ITR3. In some embodiments, the viral genome may have an ITR that comprises ITR4.

In some embodiments, the ITR comprises the nucleotide sequence of any one of SEQ ID NOs: 1035-1038, or a sequence with at least 70%, 75%, 80%, 85%, 90%, 95% or 99% sequence identity thereto. In some embodiments, the ITR comprises the nucleotide sequence of SEQ ID NO: 1035 or a nucleotide sequence with at least 70%, 75%, 80%, 85%, 90%, 95% or 99% sequence identity thereto. In some embodiments, the ITR comprises the nucleotide sequence of SEQ ID NO: 1036 or a nucleotide sequence with at least 70%, 75%, 80%, 85%, 90%, 95% or 99% sequence identity thereto. In some embodiments, the ITR comprises the nucleotide sequence of SEQ ID NO: 1037 or a nucleotide sequence with at least 70%, 75%, 80%, 85%, 90%, 95% or 99% sequence identity thereto. In some embodiments, the ITR comprises the nucleotide sequence of SEQ ID NO: 1038 or a nucleotide sequence with at least 70%, 75%, 80%, 85%, 90%, 95% or 99% sequence identity thereto.

In some embodiments, the viral genome may have two ITRs. As a non-limiting example, the two ITRs are ITR1 and ITR3. As a non-limiting example, the two ITRs are ITR 1 and ITR4. As a non-limiting example, the two ITRs are ITR2 and ITR3. As a non-limiting example, the two ITRs are ITR2 and ITR4.

Viral Genome Component: Promoters

In some embodiments, the viral genome may comprise an element to enhance the transgene target specificity and/or expression (See e.g., Powell et al. Viral Expression Cassette Elements to Enhance Transgene Target Specificity and Expression in Gene Therapy, 2015; the contents of which are herein incorporated by reference in its entirety). In some embodiments, the AAV particle viral genome may comprise an element to enhance the transgene target specificity and/or expression comprise a promoter, an enhancer, e.g., a CMV enhancer, or both. In some embodiments, the AAV particle viral genome comprises a promoter operably linked to a transgene encoded by a nucleic acid molecule encoding a payload, e.g., antibody molecule (e.g., an anti-tau antibody molecule). In some embodiments, the AAV particle viral genome comprises an enhancer, e.g., a CMV enhancer. In some embodiment, the AAV particle viral genome comprises at least two promoters.

In some embodiments, the viral genome comprises a promoter that is species specific, inducible, tissue-specific, and/or cell cycle-specific (e.g., as described in Parr et al., *Nat. Med.* 3:1145-9 (1997); the contents of which are herein incorporated by reference in their entirety). In some embodiments, the viral genome comprises a promoter that is sufficient for expression, e.g., in a target cell, of a payload (e.g., an antibody molecule, e.g., an anti-tau antibody) encoded by a transgene.

In some embodiments, the promoter results in expression of the payload, e.g., an antibody molecule (e.g., an anti-tau antibody) for a sufficient period of time in a cell, tissue, and/or organ. In some embodiments, the promoter results in expression of the payload for at least 1 hour to 24 hours, e.g., 1-5 hours, 1-10 hours, 1-15 hours, 1-20 hours, 2-5 hours, 2-10 hours, 2-15 hours, 2-20 hours, or 2-24 hours, 3-5 hours, 3-15 hours, 3-20 hours, 3-24 hours, 4-5 hours, 4-15 hours, 4-20 hours, 4-24 hours, 5-15 hours, 5-20 hours, 5-23 hours, 6-15 hours, 6-20 hours 6-24 hours, 7-15 hours, 7-20 hours, 7-24 hours, 8-10 hours, 8-15 hours, 8-20 hours, 8-24 hours, 9-10 hours, 9-15 hours, 9-20 hours, 9-24 hours, 10-15 hours, 10-20 hours, 10-23 hours, 11-15 hours, 11-20 hours 11-24 hours, 12-15 hours, 12-20 hours, 12-24 hours, 13-15 hours, 13-20 hours, 13-24 hours, 14-15 hours, 14-20 hours, 14-23 hours, 15-20 hours, 15-24 hours, 16-20 hours, 16-24 hours, 17-20 hours, 17-24 hours, 18-20 hours, 18-24 hours, 19-20 hours, 19-24 hours, 20-24 hours, 21-24 hours, 22-24 hours, or 23-24 hours, e.g., 1 hour, 5 hours, 10 hours, 12 hours, 14 hours, 18 hours, 20 hours, or 24 hours. In some embodiments, the promoter results in expression of the payload for at least 1-7 days, e.g., 1-6 days, 1-5 days, 1-4 days, 1-3 days, 1-2 days, 2-7 days, 2-6 days, 2-5 days, 2-4 days, 2-3 days, 3-7 days, 3-6 days, 3-5 days, 3-4 days, 4-7 days, 4-6 days, 4-5 days, 5-7 days, 5-6 days, or 6-7 days, e.g., 1 day, 5 days, or 7 days. In some embodiments, the promoter results in expression of the payload for 1 week to 4 weeks, e.g., 1-3 weeks, 1-2 weeks, 2-4 weeks, 2-3 weeks, or 3-4 weeks. In some embodiments, the promoter results in expression of the payload for at least 1-12 months, at least 10-24 months, or at least 1-10 years, e.g., at least 1 year, at least 5 years, at least 10 years, or more than 10 years.

In some embodiments, the promoter may be a naturally occurring promoter, or a non-naturally occurring promoter. In some embodiments, the promoter is from a naturally expressed protein. In some embodiments, the promoter is an engineered promoter. In some embodiments, the promoter comprises a viral promoter, plant promoter, and/or a mammalian promoter. In some embodiments, the promoter may be a human promoter. In some embodiments, the promoter may be truncated. In some embodiments, the promoter is not a cell specific promoter.

In some embodiments, the promoter results in expression in one or more, e.g., multiple, cells and/or tissues, e.g., a ubiquitous promoter. In some embodiments, a promoter that results in expression in one or more tissues includes but is not limited to a human elongation factor 1α-subunit (EF1α) promoter, a cytomegalovirus (CMV) immediate-early enhancer and/or promoter, a chicken β-actin (CBA) promoter and its derivative CAG, a β glucuronidase (GUSB) promoter, or ubiquitin C (UBC) promoter. In some embodiments, a tissue-specific expression elements can be used to restrict expression to certain cell types such as, but not limited to, muscle specific promoters, B cell promoters, monocyte promoters, leukocyte promoters, macrophage promoters, pancreatic acinar cell promoters, endothelial cell promoters, lung tissue promoters, astrocyte promoters, or nervous system promoters which can be used to restrict expression to neurons, astrocytes, or oligodendrocytes. In some embodiments, the promoter is a ubiquitous promoter as described in Yu et al. (Molecular Pain 2011, 7:63), Soderblom et al. (E. Neuro 2015), Gill et al., (Gene Therapy 2001, Vol. 8, 1539-1546), and Husain et al. (Gene Therapy 2009), each of which are incorporated by reference in their entirety. In some embodiments, the promoter is a ubiquitous promoter chosen from CMV, CBA (including derivatives CAG, CB6, CBh, etc.), EF-1α, PGK, UBC, GUSB (hGBp), or UCOE (promoter of HNRPA2B1-CBX3).

In some embodiments, the promoter is a muscle-specific promoter, e.g., a promoter that results in expression in a muscle cell. In some embodiments, a muscle-specific promoter includes but is not limited to a mammalian muscle creatine kinase (MCK) promoter, a mammalian desmin (DES) promoter, a mammalian troponin I (TNNI2) promoter, a synthetic C5-12 promoter, and a mammalian skeletal alpha-actin (ASKA) promoter (see, e.g. U.S. Patent Publication US20110212529, the contents of which are herein incorporated by reference in their entirety).

In some embodiments, the promoter is a nervous system specific promoter, e.g., a promoter that results in expression of a payload in a neuron, an astrocyte, and/or an oligodendrocyte. In some embodiments, a nervous system specific promoter that results in expression in neurons includes but is not limited to a neuron-specific enolase (NSE) promoter, a platelet-derived growth factor (PDGF) promoter, a platelet-derived growth factor B-chain (PDGF-β) promoter, a synapsin (Syn) promoter, a methyl-CpG binding protein 2 (MeCP2) promoter, a $Ca^{2+}$/calmodulin-dependent protein kinase II (CaMKII) promoter, a metabotropic glutamate receptor 2 (mGluR2) promoter, a neurofilament light (NFL) or heavy (NFH) promoter, a β-globin minigene nβ2 promoter, a preproenkephalin (PPE) promoter, a enkephalin (Enk) promoter, and an excitatory amino acid transporter 2 (EAAT2) promoter. In some embodiments, a nervous system specific promoter that results in expression in astrocytes includes but is not limited to a glial fibrillary acidic protein (GFAP) promoter and a EAAT2 promoter. In some embodiments, a nervous system specific promoter that results in expression in oligodendrocytes includes but is not limited to a myelin basic protein (MBP) promoter. In some embodiments, the viral genome comprises a nervous system specific promoter as described in Husain et al. (Gene Therapy 2009), Passini and Wolfe (J. Virol. 2001, 12382-12392), Xu et al. (Gene Therapy 2001, 8, 1323-1332), Drews et al. (Mamm Genome (2007) 18:723-731), and Raymond et al. (Journal of Biological Chemistry (2004) 279(44) 46234-46241), each of which are incorporated by reference in their entirety.

In some embodiments, the promoter is a liver promoter, e.g. a promoter that results in expression a liver cell. In some embodiments, the liver promoter is chosen from human α-1-antitrypsin (hAAT) or thyroxine binding globulin (TBG). In some embodiments, the viral genome comprises an RNA pol III promoter. In some embodiments, the RNA pol III promoter is chosen from U6 or H1.

In some embodiments, the viral genome comprises two promoters. As a non-limiting example, the promoters are an EF1α promoter and a CMV promoter.

In some embodiments, the promoter is a ubiquitin c (UBC) promoter. The UBC promoter may have a size of 300-350 nucleotides. As a non-limiting example, the UBC promoter is 332 nucleotides. In some embodiments, the promoter is a β-glucuronidase (GUSB) promoter. The GUSB promoter may have a size of 350-400 nucleotides. As a non-limiting example, the GUSB promoter is 378 nucleotides. In some embodiments, the promoter is a neurofilament light (NFL) promoter. The NFL promoter may have a size of 600-700 nucleotides. As a non-limiting example, the NFL promoter is 650 nucleotides. In some embodiments, the promoter is a neurofilament heavy (NFH) promoter. The NFH promoter may have a size of 900-950 nucleotides. As a non-limiting example, the NFH promoter is 920 nucleotides. In some embodiments, the promoter is a scn8a promoter. The scn8a promoter may have a size of 450-500 nucleotides. As a non-limiting example, the scn8a promoter is 470 nucleotides. In some embodiments, the promoter is a phosphoglycerate kinase 1 (PGK) promoter.

In some embodiments, the promoter is chosen from a CAG promoter, a CBA promoter (e.g., a minimal CBA promoter), a CB promoter, a CMV (IE) promoter and/or enhancer, a GFAP promoter, a synapsin promoter, or a functional variant thereof.

In some embodiments, the viral genome comprises an enhancer element, a promoter and/or a 5'UTR intron. The enhancer element, also referred to herein as an "enhancer," may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter: (5) GUSB promoter: (6) NSE promoter: (7) Synapsin promoter; (8) MeCP2 promoter; and (9) GFAP promoter.

In some embodiments, the viral genome comprises a promoter that has a length between about 100-2000 nucleotides. In some embodiments, the promoter has a length between about 100-700 nucleotides, e.g., between about 100-600 nucleotides, 100-500 nucleotides, 100-400 nucleotides, 100-300 nucleotides, 100-200 nucleotides, 200-700 nucleotides, 200-600 nucleotides, 200-500 nucleotides, 200-400 nucleotides, 200-300 nucleotides, 300-700 nucleotides, 300-600 nucleotides, 300-500 nucleotides, 300-400 nucleotides, 400-700 nucleotides, 400-600 nucleotides, 400-500 nucleotides, 500-700 nucleotides, 500-600 nucleotides, or 600-700 nucleotides. In some embodiments, the promoter has a length between about 900-2000 nucleotides, e.g., between about 900-1000 nucleotides, 9000-1500 nucleotides, 1000-1500 nucleotides, 1000-2000 nucleotides, or 1500-2000 nucleotides. In some embodiments, the promoter has a length between about 1500 to about 1800 nucleotides, e.g., about 1715 nucleotides. In some embodiments, the promoter has a length of about 500 to about 750 nucleotides, e.g., about 557 nucleotides or about 699 nucleotides. In some embodiments, the promoter has a length of about 200 to about 450 nucleotides, e.g., about 260 nucleotides, about 283 nucleotides, about 299 nucleotides, about 380 nucleotides, or about 399 nucleotides.

In some embodiments, the viral genome comprises a promoter provided in Table 11. In some embodiments, the promoter is chosen from any one of Promoter 1-Promoter 12, or a functional variant thereof.

TABLE 11

| Promoter Sequence Regions | | |
|---|---|---|
| Sequence Region Name | Sequence Length | SEQ ID NO |
| Promoter 1 | 1715 | 1039 |
| Promoter 2 | 299 | 1040 |
| Promoter 3 | 283 | 1041 |
| Promoter 4 | 260 | 1042 |
| Promoter 5 | 654 | 1043 |
| Promoter 6 | 699 | 1044 |
| Promoter 7 | 557 | 1045 |
| Promoter 8 | 382 | 1046 |
| Promoter 9 | 1736 | 1047 |
| Promoter 10 | 365 | 1048 |
| Promoter 11 | 1714 | 1049 |
| Promoter 12 | 380 | 1050 |

In some embodiments, the viral genome comprises a promoter provided in Table 11. In some embodiments, the promoter is chosen from any one of Promoter 1-Promoter 12, or a functional variant thereof. In some embodiments, the promoter comprises the nucleotide sequence of any one of SEQ ID NOs: 1039-1050, or a sequence with at least 70%, 75%, 80%, 85%, 90%, 95% or 99% sequence identity thereto. In some embodiments, the promoter comprises the nucleotide sequence of SEQ ID NO: 1039 or a sequence with at least 70%, 75%, 80%, 85%, 90%, 95% or 99% sequence identity thereto. In some embodiments, the promoter comprises the nucleotide sequence of SEQ ID NO: 1040, or a sequence with at least 70%, 75%, 80%, 85%, 90%, 95% or 99% sequence identity thereto. In some embodiments, the promoter comprises the nucleotide sequence of SEQ ID NO: 1041, or a sequence with at least 70%, 75%, 80%, 85%, 90%, 95% or 99% sequence identity thereto. In some embodiments, the promoter comprises the nucleotide sequence of SEQ ID NO: 1042, or a sequence with at least 70%, 75%, 80%, 85%, 90%, 95% or 99% sequence identity thereto. In some embodiments, the promoter comprises the nucleotide sequence of SEQ ID NO: 1043, or a sequence with at least 70%, 75%, 80%, 85%, 90%, 95% or 99% sequence identity thereto. In some embodiments, the promoter comprises the nucleotide sequence of SEQ ID NO: 1044, or a sequence with at least 70%, 75%, 80%, 85%, 90%, 95% or 99% sequence identity thereto. In some embodiments, the promoter comprises the nucleotide sequence of SEQ ID NO: 1050, or a sequence with at least 70%, 75%, 80%, 85%, 90%, 95% or 99% sequence identity thereto.

In some embodiments, the viral genome comprises one promoter sequence region. In some embodiments, the promoter sequence region is Promoter 1. In some embodiments, the promoter sequence region is Promoter 2. In some embodiments, the promoter sequence region is Promoter 3. In some embodiments, the promoter sequence region is Promoter 4. In some embodiments, the promoter sequence region is Promoter 5. In some embodiments, the promoter sequence region is Promoter 6. In some embodiments, the promoter sequence region is Promoter 7. In some embodiments, the promoter sequence region is Promoter 8. In some embodiments, the promoter sequence region is Promoter 9. In some embodiments, the promoter sequence region is Promoter 10. In some embodiments, the promoter sequence region is Promoter 11. In some embodiments, the promoter sequence region is Promoter 12.

In some embodiments, the promoter sequence region further comprises at least one promoter sub-region. As a non-limiting example, the promoter sequence is Promoter 1, further comprising Promoter 2 and Promoter 3 sub-regions. In some embodiments, the viral genome comprises at least 2 or more promoters. In some embodiments, the viral genome comprises Promoter 12 and Promoter 4.

In some embodiments, the CAG promoter comprises the nucleotide sequence of SEQ ID NO: 1039 or nucleotide sequence with at least 70%, 75%, 80%, 85%, 90%, 95%, or 99% sequence identity thereto. In some embodiments, the CBA promoter (e.g., a minimal CBA promoter) comprises the nucleotide sequence of SEQ ID NO: 1041 or nucleotide sequence with at least 70%, 75%, 80%, 85%, 90%, 95%, or 99% sequence identity thereto. In some embodiments, the CB promoter comprises the nucleotide sequence of SEQ ID NO: 1042 or nucleotide sequence with at least 70%, 75%, 80%, 85%, 90%, 95%, or 99% sequence identity thereto. In some embodiments, the GFAP promoter comprises the nucleotide sequence of SEQ ID NO: 1044 or nucleotide sequence with at least 70%, 75%, 80%, 85%, 90%, 95%, or 99% sequence identity thereto. In some embodiments, the synapsin promoter comprises the nucleotide sequence of SEQ ID NO: 1045 or nucleotide sequence with at least 70%, 75%, 80%, 85%, 90%, 95%, or 99% sequence identity thereto. In some embodiments, the CMV (IE) promoter comprises the nucleotide sequence of SEQ ID NO: 1050 or nucleotide sequence with at least 70%, 75%, 80%, 85%, 90%, 95%, or 99% sequence identity thereto. In some embodiments, the CMV (ie) enhancer comprises e nucleotide sequence of SEQ ID NO: 1040 or nucleotide sequence with at least 70%, 75%, 80%, 85%, 90%, 95%, or 99% sequence identity thereto.

In some embodiments, the viral genome comprises more than one promoter sequence region. In some embodiments, the viral genome comprises two promoter sequence regions. In some embodiments, the viral genome comprises three promoter sequence regions.

Viral Genome Component: Untranslated Regions (UTRs)

In some embodiments, the viral genome comprises an untranslated region (UTR). In some embodiments, a wild type UTR of a gene are transcribed but not translated. In some embodiments, the 5' UTR starts at the transcription start site and ends at the start codon and the 3' UTR starts immediately following the stop codon and continues until the termination signal for transcription.

In some embodiments, a UTR comprises a feature found in abundantly expressed genes of specific target organs to enhance the stability and protein production. As a non-limiting example, a 5' UTR from mRNA normally expressed in the liver (e.g., albumin, serum amyloid A, Apolipoprotein A/B/E, transferrin, alpha fetoprotein, erythropoietin, or Factor VIII) may be used in the viral genome of an AAV particle described herein to enhance expression in hepatic cell lines or liver.

In some embodiments, the viral genome comprises a 5'UTR, e.g., a wild-type (e.g., naturally occurring) 5'UTR or a recombinant (e.g., non-naturally occurring) 5'UTR. In some embodiments, a 5' UTR comprises a feature which plays a role in translation initiation. In some embodiments, a UTR, e.g., a 5' UTR, comprises a Kozak sequence. In some embodiments, a Kozak sequence is involved in the process by which the ribosome initiates translation of many genes. In some embodiments, a Kozak sequence has the consensus sequence of CCR(A/G)CCAUGG, where R is a purine (adenine or guanine) three bases upstream of the start codon (ATG), which is followed by another 'G'. In some embodiments, a Kozak sequence comprises the nucleotide sequence of GAGGAGCCACC (SEQ ID NO: 1089) or a nucleotide sequence with at least 95-99% sequence identity thereto. In some embodiments, a Kozak sequence comprises the nucleotide sequence of GCCGCCACCATG (SEQ ID NO: 1079), or a nucleotide sequence with at least 95-99% sequence identity thereto. In some embodiments, a viral genome comprises a 5'UTR comprising a Kozak sequence. In some embodiments, a viral genome comprises a 5'UTR that does not comprise a Kozak sequence.

In some embodiments, the viral genome comprises a 3'UTR, e.g., a wild-type (e.g., naturally occurring) 3'UTR or a recombinant (e.g., non-naturally occurring) 3'UTR. In some embodiments, a 3' UTR comprises an element that modulates, e.g., increases or decreases, stability of a nucleic acid. In some embodiments, a 3' UTR comprises stretches of Adenosines and Uridines embedded therein, e.g., an AU rich signature. These AU rich signatures are generally prevalent in genes with high rates of turnover and are described, e.g., in Chen et al, 1995, the contents of which are herein incorporated by reference in its entirety. In some embodiments, an AR rich signature comprises an AU rich element (ARE). In some embodiments, a 3'UTR comprises an ARE chosen from a class I ARE (e.g., c-Myc and MyoD), a class II ARE (e.g., GM-CSF and TNF-$\alpha$), a class III ARE (e.g., c-Jun and Myogenin), or combination thereto. In some embodiments, a class I ARE comprises several dispersed copies of an AUUUA motif within U-rich regions. In some embodiments, a class II ARE comprises two or more overlapping UUAUUUA (U/A) (U/A) nonamers. In some embodiments, a class III ARE comprises U rich regions and/or do not contain an AUUUA motif. In some embodiments, an ARE destabilizes the messenger.

In some embodiments, a 3'UTR comprises a binding site for a protein member of the ELAV family. In some embodiments, a 3' UTR comprises a binding site for an HuR protein. In some embodiments, an HuR protein binds to an ARE of any one of classes I-III and/or increases the stability of mRNA. Without wishing to be bound by theory, it is believed in some embodiments, that a 3'UTR comprising an HuR specific binding sites will lead to HuR binding and, stabilization of a message in vivo.

In some embodiments, the 3' UTR of the viral genome comprises an oligo (dT) sequence for templated addition of a poly-A tail.

In some embodiments, the viral genome comprises a miRNA seed, binding site and/or full sequence. Generally, microRNAs (or miRNA or miR) are 19-25 nucleotide non-coding RNAs that bind to the sites of nucleic acid targets and down-regulate gene expression either by reducing nucleic acid molecule stability or by inhibiting translation. In some embodiments, the microRNA sequence comprises a seed region, e.g., a sequence in the region of positions 2-8 of the mature microRNA, which sequence has perfect Watson-Crick complementarity to the miRNA target sequence of the nucleic acid. In some embodiments, the viral genome may be engineered to include, alter or remove at least one miRNA binding site, sequence, or seed region.

In some embodiments, a UTR from any gene known in the art may be incorporated into the AAV particle viral genome described herein. These UTRs, or portions thereof, may be placed in the same orientation as in the gene from which they were selected, or they may be altered in orientation or location. In some embodiments, the UTR used in the viral genome may be inverted, shortened, lengthened, made with one or more other 5' UTRs or 3' UTRs known in the art. In some embodiments, an altered UTR, comprises a UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. In some embodiments, the viral genome comprises an artificial UTR, e.g., a UTR that is not a variant of a wild-type, e.g., a naturally occurring, UTR. In some embodiments, the viral genome comprises a UTR selected from a family of transcripts whose proteins share a common function, structure, feature or property.

Viral Genome Component: miR Binding Site

Tissue- or cell-specific expression of the AAV viral particles of the invention can be enhanced by introducing tissue- or cell-specific regulatory sequences, e.g., promoters, enhancers, microRNA binding sites, e.g., a detargeting site. Without wishing to be bound by theory, it is believed that an encoded miR binding site can modulate, e.g., prevent, suppress, or otherwise inhibit, the expression of a gene of interest on the viral genome of the invention, based on the expression of the corresponding endogenous microRNA (miRNA) or a corresponding controlled exogenous miRNA in a tissue or cell, e.g., a non-targeting cell or tissue. In some embodiments, a miR binding site modulates, e.g., reduces, expression of the payload encoded by a viral genome of an AAV particle described herein in a cell or tissue where the corresponding mRNA is expressed.

In some embodiments, the viral genome of an AAV particle described herein comprises a nucleotide sequence encoding a microRNA binding site, e.g., a detargeting site. In some embodiments, the viral genome of an AAV particle described herein comprises a nucleotide sequence encoding a miR binding site, a microRNA binding site series (miR BSs), or a reverse complement thereof.

In some embodiments, the nucleotide sequence encoding the miR binding site series or the miR binding site is located in the 3'-UTR region of the viral genome (e.g., 3' relative to the nucleic acid sequence encoding a payload), e.g., before the polyA sequence, 5'-UTR region of the viral genome (e.g., 5' relative to the nucleic acid sequence encoding a payload), or both.

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, all copies are identical, e.g., comprise the same miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is at least about 5 to 10 nucleotides, e.g., about 7-8 nucleotides, nucleotides in length. In some embodiments, the spacer coding sequence or reverse complement thereof comprises one or more of (i) GGAT: (ii) CACGTG; (iii) GCATGC, or a repeat of one or more of (i)-(iii).

In some embodiments, the encoded miR binding site series comprise at least 1-5 copies, e.g., at least 1-3, 2-4, 3-5, 1, 2, 3, 4, 5 or more copies of a miR binding site (miR BS). In some embodiments, at least 1, 2, 3, 4, 5, or all of the copies are different, e.g., comprise a different miR binding site. In some embodiments, the miR binding sites within the encoded miR binding site series are continuous and not separated by a spacer. In some embodiments, the miR binding sites within an encoded miR binding site series are separated by a spacer, e.g., a non-coding sequence. In some embodiments, the spacer is at least about 5 to 10 nucleotides, e.g., about 7-8 nucleotides, in length. In some embodiments, the spacer coding sequence or reverse complement thereof comprises one or more of (i) GGAT; (ii) CACGTG; (iii) GCATGC, or a repeat of one or more of (i)-(iii).

In some embodiments, the encoded miR binding site is substantially identical (e.g., at least 70%, 75%, 80%, 85%, 90%, 95%, 99% or 100% identical), to the miR in the host cell. In some embodiments, the encoded miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the encoded miR binding site is 100% identical to the miR in the host cell.

In some embodiments, the nucleotide sequence encoding the miR binding site is substantially complimentary (e.g., at least 70%, 75%, 80%, 85%, 90%, 95%, 99% or 100% identical), to the miR in the host cell. In some embodiments, to complementary sequence of the nucleotide sequence encoding the miR binding site comprises at least 1, 2, 3, 4, or 5 mismatches or no more than 6, 7, 8, 9, or 10 mismatches to a miR in the host cell. In some embodiments, the mismatched nucleotides are contiguous. In some embodiments, the mismatched nucleotides are non-contiguous. In some embodiments, the mismatched nucleotides occur outside the seed region-binding sequence of the miR binding site, such as at one or both ends of the miR binding site. In some embodiments, the encoded miR binding site is 100% identical to the miR in the host cell.

In some embodiments, an encoded miR binding site or sequence region is at least about 10 to about 125 nucleotides in length, e.g., at least about 10 to 50 nucleotides, 10 to 100 nucleotides, 50 to 100 nucleotides, 50 to 125 nucleotides, or 100 to 125 nucleotides in length. In some embodiments, an encoded miR binding site or sequence region is at least about 7 to about 28 nucleotides in length, e.g., at least about 8-28 nucleotides, 7-28 nucleotides, 8-18 nucleotides, 12-28 nucleotides, 20-26 nucleotides, 22 nucleotides, 24 nucleotides, or 26 nucleotides in length, and optionally comprises at least one consecutive region (e.g., 7 or 8 nucleotides) complementary to the seed sequence of a miRNA (e.g., a miR122, a miR142, a miR183).

In some embodiments, the encoded miR binding site is complementary to a miR expressed in liver or hepatocytes, such as miR122. In some embodiments, the encoded miR binding site or encoded miR binding site series comprises a miR122 binding site sequence. In some embodiments, the encoded miR122 binding site comprises the nucleotide sequence of ACAAACACCATTGTCACACTCCA (SEQ ID NO: 1029), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1029, e.g., wherein the modification can result in a mismatch between the encoded miR binding site and the corresponding miRNA. In some embodiments, the viral genome comprises at least 3, 4, or 5 copies of the encoded miR122 binding site, e.g., an encoded miR122 binding site series, optionally wherein the encoded miR122 binding site series comprises the nucleotide sequence of: ACAAACACCATTGT-CACACTCCACACAAACACCATTGTCACACTC-CACACAAACACCATTGT CACACTCCA (SEQ ID NO: 1030), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1030, e.g., wherein the modification can result in a mismatch between the encoded miR binding site and the corresponding miRNA. In some embodiments, at least two of the encoded miR122 binding sites are connected directly, e.g., without a spacer. In other embodiments, at least two of the encoded miR122 binding sites are separated by a spacer, e.g., 1, 2, 3, 4, 5, 6, 7, 8, 9, or 10 nucleotides in length, which is located between two or more consecutive encoded miR122 binding site sequences. In embodiments, the spacer is at least about 5 to 10 nucleotides, e.g., about 7-8, in length. In some embodiments, the spacer coding sequence or reverse complement thereof comprises one or more of (i) GGAT; (ii) CACGTG; (iii) GCATGC, or a repeat of one or more of (i)-(iii). In some embodiments, an encoded miR binding site series comprises at least 3-5 copies (e.g., 4 copies) of a miR122 binding site, with or without a spacer, wherein the spacer is at least about 5 to 10 nucleotides, e.g., about 7-8 nucleotides, in length.

In some embodiments, the encoded miR binding site is complementary to a miR expressed in hematopoietic lineage, including immune cells (e.g., antigen presenting cells or APC, including dendritic cells (DCs), macrophages, and B-lymphocytes). In some embodiments, the encoded miR binding site complementary to a miR expressed in hematopoietic lineage comprises a nucleotide sequence disclosed, e.g., in US 2018/0066279, the contents of which are incorporated by reference herein in its entirety.

In some embodiments, the encoded miR binding site or encoded miR binding site series comprises a miR-142-3p binding site sequence. In some embodiments, the encoded miR-142-3p binding site comprises the nucleotide sequence of TCCATAAAGTAGGAAACACTACA (SEQ ID NO: 1031), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1031, e.g., wherein the modification can result in a mismatch between the encoded miR binding site and the corresponding miRNA. In some embodiments, the viral genome comprises at least 3, 4, or 5 copies of the encoded miR-142-3p binding site, e.g., an encoded miR-142-3p binding site series. In some embodiments, an encoded miR binding site series comprises at least 3-5 copies (e.g., 4 copies) of a miR-142-3p binding site, with or without a spacer, wherein the spacer is at least about 5 to 10 nucleotides, e.g., about 7-8 nucleotides, in length.

In some embodiments, the encoded miR binding site is complementary to a miR expressed in a DRG (dorsal root ganglion) neuron, e.g., a miR183, a miR182, and/or miR96 binding site. In some embodiments, the encoded miR binding site complementary to a miR expressed in expressed in a DRG neuron comprises a nucleotide sequence disclosed, e.g., in WO2020/132455, the contents of which are incorporated by reference herein in its entirety.

In some embodiments, the encoded miR binding site or encoded miR binding site series comprises a miR183 binding site sequence. In some embodiments, the encoded miR183 binding site comprises the nucleotide sequence of AGTGAATTCTACCAGTGCCATA (SEQ ID NO: 1032), or a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1032, e.g., wherein the modification can result in a mismatch between the encoded miR binding site and the corresponding miRNA. In some embodiments, the sequence complementary to the seed sequence corresponds to the double underlined of the encoded miR-183 binding site sequence. In some embodiments, the viral genome comprises at least comprises at least 3, 4, or 5 copies of the encoded miR183 binding site, e.g. an encoded miR183 binding site. In some embodiments, an encoded miR binding site series comprises at least 3-5 copies (e.g., 4 copies) of a miR183 binding site, with or without a spacer, wherein the spacer is at least about 5 to 10 nucleotides, e.g., about 7-8 nucleotides, in length.

In some embodiments, the encoded miR binding site or encoded miR binding site series comprises a miR182 binding site sequence. In some embodiments, the encoded miR182 binding site comprises, the nucleotide sequence of AGTGTGAGTTCTACCATTGCCAAA (SEQ ID NO: 1033), a nucleotide sequence having at least 50%, 55%, 60%, 65%, 70%, 75%, 80%, 85%, 90%, at least 95%, at least 99%, or 100% sequence identity, or having at least one, two, three, four, five, six, or seven modifications but no more than ten modifications to SEQ ID NO: 1033, e.g., wherein the modification can result in a mismatch between the encoded miR binding site and the corresponding miRNA. In some embodiments, the viral genome comprises at least 3, 4, or 5 copies of the encoded miR182 binding site, e.g., an encoded miR182 binding site series. In some embodiments, an encoded miR binding site series comprises at least 3-5 copies (e.g., 4 copies) of a miR182 binding site, with or without a spacer, wherein the spacer is at least about 5 to 10 nucleotides, e.g., about 7-8 nucleotides, in length.

In some embodiments, the encoded miR binding site or encoded miR binding site series comprises a miR96 binding site sequence. In some embodiments, the encoded miR96 binding site comprises the nucleotide sequence of AGCAAAAATGTGCTAGTGCCAAA (SEQ ID NO: 1034), a sequence having at least 50%, 55%, 60%, 65%, 70%, 75%,80%,85%, 90%, at least 95%, at least 99%, or 100% sequence identity, or having at least one, two, three, four, five, six, or seven modifications but no more than ten modifications to SEQ ID NO: 1034, e.g., wherein the modification can result in a mismatch between the encoded miR binding site and the corresponding miRNA. In some embodiments, the viral genome comprises at least 3, 4, or 5 copies of the encoded miR96 binding site, e.g., an encoded miR96 binding site series. In some embodiments, an encoded miR binding site series comprises at least 3-5 copies (e.g., 4 copies) of a miR96 binding site, with or without a spacer, wherein the spacer is at least about 5 to 10 nucleotides, e.g., about 7-8, in length.

In some embodiments, the encoded miR binding site series comprises a miR122 binding site, a miR142 binding site, a miR183 binding site, a miR182 binding site, a miR96 binding site, or a combination thereof. In some embodiments, the encoded miR binding site series comprises at least 3, 4, or 5 copies of a miR122 binding site, a miR142 binding site, a miR183 binding site, a miR182 binding site, a miR96 binding site, or a combination thereof. In some embodiments, at least two of the encoded miR binding sites are connected directly, e.g., without a spacer. In other embodiments, at least two of the encoded miR binding sites are separated by a spacer, e.g., 1, 2, 3, 4, 5, 6, 7, 8, 9, or 10 nucleotides in length, which is located between two or more consecutive encoded miR binding site sequences. In embodiments, the spacer is at least about 5 to 10 nucleotides, e.g., about 7-8 nucleotides, in length. In some embodiments, the spacer coding sequence or reverse complement thereof comprises one or more of (i) GGAT: (ii) CACGTG; (iii) GCATGC, or a repeat of one or more of (i)-(iii). In some embodiments, an encoded miR binding site series comprises at least 3-5 copies (e.g., 4 copies) of a combination of at least two, three, four, five, or all of a miR122 binding site, a miR142 binding site, a miR183 binding site, a miR182 binding site, a miR96 binding site, with or without a spacer, wherein the spacer is at least about 5 to 10 nucleotides, e.g., about 7-8 nucleotides, in length.

Viral Genome Component: Exon Sequence Region

In some embodiments, the viral genome may comprise at least one exon sequence region. In some embodiments, the viral genome comprises at least 2, at least 3, at least 4, or at least 5 exon regions. In some embodiments, the viral genome comprises two Exon sequence regions. In some embodiments, the viral genome comprises three Exon sequence regions. In some embodiments, the viral genome comprises four Exon sequence regions. In some embodiments, the viral genome comprises more than four Exon sequence regions.

In some embodiments, the exon region(s) may, independently, have a length such as, but not limited to, about 50-150 nucleotides in length, e.g., about 50-140 nucleotides, about 50-130 nucleotides, about 50-120 nucleotides, about 50-110 nucleotides, about 50-100 nucleotides, about 50-90 nucleotides, about 50-80 nucleotides, about 50-80 nucleotides, about 50-70 nucleotides, about 50-60 nucleotides, about 60-150 nucleotides, about 60-140 nucleotides, about 60-130 nucleotides, about 60-120 nucleotides, about 60-110 nucleotides, about 60-100 nucleotides, about 60-90 nucleotides, about 60-80 nucleotides, about 60-80 nucleotides, about 60-70 nucleotides, about 70-150 nucleotides, about 70-140 nucleotides, about 70-130 nucleotides, about 70-120 nucleotides, about 70-110 nucleotides, about 70-100 nucleotides, about 70-90 nucleotides, about 70-80 nucleotides, about 80-150 nucleotides, about 80-140 nucleotides, about 80-130 nucleotides, about 80-120 nucleotides, about 80-110 nucleotides, about 80-100 nucleotides, about 80-90 nucleotides, about 90-150 nucleotides, about 90-140 nucleotides, about 90-130 nucleotides, about 90-120 nucleotides, about 90-110 nucleotides, about 90-100 nucleotides, about 100-150 nucleotides, about 100-140 nucleotides, about 100-130 nucleotides, about 100-120 nucleotides, about 100-110 nucleotides, about 110-150 nucleotides, about 110-140 nucleotides, about 110-130 nucleotides, about 110-120 nucleotides, about 120-150 nucleotides, about 120-140 nucleotides, about 120-130 nucleotides, about 130-150 nucleotides, about 130-140 nucleotides, or about 140-150 nucleotides. In some embodiments, the exon region comprises about 120 nucleotides to about 140 nucleotides in length, e.g., about 134 nucleotides. In some embodiments, the exon region comprises about 40 nucleotides to about 60 nucleotides in length, e.g., about 53 nucleotides.

In some embodiments, the exon region is provided in Table 12.

TABLE 12

Exon Sequence Regions

| Sequence Region Name | Sequence Length | SEQ ID NO |
|---|---|---|
| Exon1 | 134 | 1051 |
| Exon2 | 102 | 1052 |
| Exon3 | 59 | 1053 |
| Exon4 | 53 | 1054 |
| Exon5 | 54 | 1055 |

In some embodiments, the viral genome comprises an exon region chosen from Exon1, Exon2, Exon3, Exon4, or a function variant thereof. In some embodiments, the exon region comprises the nucleotide sequence of any one of SEQ ID NOs: 1051-1055, or a nucleotide sequence with at least 70%, 75%, 80%, 85%, 90%, 95%, or 99% sequence identity thereto.

In some embodiments, the viral genome comprises one Exon sequence region. In some embodiments, the Exon sequence region is the Exon1 sequence region. In some embodiments, the Exon sequence region is the Exon2 sequence region. In some embodiments, the Exon sequence region is the Exon3 sequence region. In some embodiments, the Exon sequence region is the Exon4 sequence region. In some embodiments, the Exon sequence region is the Exon5 sequence region.

Viral Genome Component: Intron Sequence Region

In some embodiments, the viral genome comprises at least one element to enhance the expression of a transgene encoding a payload. In some embodiments, an element that enhances expression of a transgene comprises an introns or functional variant thereof. In some embodiments, the viral genome comprises an intron or functional variant thereof. In some embodiments, the viral genome comprises at least two intron regions, e.g., at least 2 intron regions, at least 3 intron regions, at least 4 intron regions, or 5 or more intron regions.

In some embodiments, the viral genome comprises an intron chosen from a MVM intron (67-97 bps), an F.IX truncated intron 1 (300 bps), an β-globin SD/immunoglobulin heavy chain splice acceptor intron (250 bps), an adenovirus splice donor/immunoglobin splice acceptor intron (500 bps), SV40 late splice donor/splice acceptor intron (19S/16S) (180 bps), or a hybrid adenovirus splice donor/IgG splice acceptor intron (230 bps). In some embodiments, the viral genome comprises a human beta-globin intron region.

In some embodiments, the viral genome comprises an intron region comprising about 10 nucleotides to about 1200 nucleotides in length. In some embodiments, the intron region comprises about 10-100 nucleotides in length, e.g., about 10-90 nucleotides, about 10-80 nucleotides, about 10-70 nucleotides, about 10-60 nucleotides, about 10-50 nucleotides, about 10-40 nucleotides, about 10-30 nucleotides, about 10-20 nucleotides, about 20-100 nucleotides, about 20-90 nucleotides, about 20-80 nucleotides, about 20-70 nucleotides, about 20-60 nucleotides, about 20-50 nucleotides, about 20-40 nucleotides, about 20-30 nucleotides, about 30-100 nucleotides, about 30-90 nucleotides, about 30-80 nucleotides, about 30-70 nucleotides, about 30-60 nucleotides, about 30-50 nucleotides, about 30-40 nucleotides, about 40-100 nucleotides, about 40-90 nucleotides, about 40-80 nucleotides, about 40-70 nucleotides, about 40-60 nucleotides, about 40-50 nucleotides, about 50-100, about 50-90 nucleotides, about 50-80 nucleotides, about 50-70 nucleotides, about 50-60 nucleotides, about 60-100 nucleotides, about 60-90 nucleotides, about 60-80 nucleotides, about 60-70 nucleotides, about 70-100 nucleotides, about 70-90 nucleotides, about 70-80 nucleotides, about 80-100 nucleotides, about 80-90 nucleotides, or about 90-100 nucleotides in length. In some embodiments, the intron region comprises about 100-600 nucleotides in length, e.g., about 100-500 nucleotides, about 100-400 nucleotides, about 100-300 nucleotides, about 100-200 nucleotides, about 200-600 nucleotides, about 200-500 nucleotides, about 200-400 nucleotides, about 200-300 nucleotides, about 300-600 nucleotides, about 300-500 nucleotides, about 300-400 nucleotides, about 400-600 nucleotides, about 400-500 nucleotides, or about 500-600 nucleotides in length. In some embodiments, the intron region comprises about 900-1200 nucleotides in length, e.g., about 900-1100 nucleotides, about 900-1000 nucleotides, about 1000-1200 nucleotides, about 1000-1100 nucleotides, or about 1100-1200 nucleotides.

In some embodiments, the intron region comprises about 20 to about 40 nucleotides in length, e.g., about 32 nucleotides. In some embodiments, the intron region comprises about 340 to about 360 nucleotides in length, e.g., about 347 nucleotides. In some embodiments, the intron region comprises about 550 to about 570 nucleotides in length, e.g., about 566 nucleotides.

As a non-limiting example, the viral genome comprises an intron region that is about 15 nucleotides in length. As a non-limiting example, the viral genome comprises an intron region that is about 32 nucleotides in length. As a non-limiting example, the viral genome comprises an intron region that is about 41 nucleotides in length. As a non-limiting example, the viral genome comprises an intron region that is about 53 nucleotides in length. As a non-limiting example, the viral genome comprises an intron region that is about 73 nucleotides in length. As a non-limiting example, the viral genome comprises an intron region that is about 168 nucleotides in length. As a non-limiting example, the viral genome comprises an intron region that is about 172 nucleotides in length. As a non-limiting example, the viral genome comprises an intron region that is about 292 nucleotides in length. As a non-limiting example, the viral genome comprises an intron region that is about 347 nucleotides in length. As a non-limiting example, the viral genome comprises an intron region that is about 387 nucleotides in length. As a non-limiting example, the viral genome comprises an intron region that is about 491 nucleotides in length. As a non-limiting example, the viral genome comprises an intron region that is about 566 nucleotides in length. As a non-limiting example, the viral genome comprises an intron region that is about 1074 nucleotides in length.

In some embodiments, the viral genome comprises an intron region provided in Table 13.

TABLE 13

Intron Sequence Regions

| Sequence Region Name | Sequence Length | SEQ ID NO |
|---|---|---|
| Intron1 | 32 | 1056 |
| Intron2 | 15 | 1057 |
| Intron3 | 347 | 1058 |
| Intron4 | 168 | 1059 |
| Intron5 | 73 | 1060 |
| Intron6 | 73 | 1061 |
| Intron7 | 73 | 1062 |
| Intron8 | 53 | 1063 |
| Intron9 | 172 | 1064 |
| Intron10 | 1074 | 1065 |
| Intron11 | 41 | 1066 |
| Intron12 | 566 | 1067 |
| Intron13 | 491 | 1068 |
| Intron14 | 387 | 1069 |
| Intron15 | 292 | 1070 |

In some embodiments, the viral genome comprises an intron region chosen from any one of Intron1 to Intron15, or a functional variant thereof. In some embodiments, the viral genome comprises Intron1. In some embodiments, the viral genome comprises Intron3. In some embodiments, the viral genome comprises Intron12. In some embodiments, the viral genome comprises Intron12 and Intron3. In some embodiments, the viral genome comprises Intron1 and Intron12. In some embodiments, the viral genome comprises an intron region of any one of SEQ ID NOs: 1056-1070, or a sequence with at least 70%, 75%, 80%, 85%, 90%, 95%, or 99% sequence identity thereto.

In some embodiments, the viral genome comprises one intron sequence region. In some embodiments, the intron sequence region is the Intron 1 sequence region. In some embodiments, the intron sequence region is the Intron 2 sequence region. In some embodiments, the intron sequence region is the Intron3 sequence region. In some embodiments, the intron sequence region is the Intron4 sequence region. In some embodiments, the intron sequence region is the Intron5 sequence region. In some embodiments, the intron sequence region is the Intron6 sequence region. In some embodiments, the intron sequence region is the Intron7 sequence region. In some embodiments, the intron sequence region is the Intron8 sequence region. In some embodiments, the intron sequence region is the Intron9 sequence region. In some embodiments, the intron sequence region is the Intron 10 sequence region. In some embodiments, the intron sequence region is the Intron11 sequence region. In some embodiments, the intron sequence region is the Intron 12 sequence region. In some embodiments, the intron sequence region is the Intron 13 sequence region. In some embodiments, the intron sequence region is the Intron 14 sequence region. In some embodiments, the intron sequence region is the Intron 15 sequence region.

In some embodiments, the viral genome comprises two intron sequence regions. In some embodiments, the viral genome comprises three intron sequence regions. In some embodiments, the viral genome comprises more than three intron sequence regions.

Viral Genome Component: Signal Sequence Region

In some embodiments, the viral genome comprises a nucleotide sequence encoding a signal sequence region (e.g., one, two, or three signal sequence region(s)). In some embodiments, the nucleic acid sequence encoding the signal sequence is located 5' relative to the nucleic acid sequence encoding the VH and/or the heavy chain. In some embodiments, the nucleotide sequence encoding the signal sequence is located 5' relative to the nucleic acid sequence encoding the VL and/or the light chain. In some embodiments, the encoded VH, VL, heavy chain, and/or light chain of the encoded antibody molecule comprises a signal sequence at the N-terminus, wherein the signal sequence is optionally cleaved during cellular processing and/or localization of the antibody molecule.

In some embodiments, the signal sequence is derived from an antibody, variant or fragment thereof. In another embodiment, the signal sequence region may not be derived from an antibody. In some embodiments, the signal sequence is derived from the same antibody as the heavy and light chain. In some embodiments, the signal sequence is derived from the same antibody as one of the heavy or light chain sequences. In some embodiments, the signal sequence is derived from a different antibody than either the heavy or light chain sequences.

As a non-limiting example, a signal sequence or the nucleotide sequence encoding the signal sequence may be derived from the heavy chain or the light chain of an anti-tau antibody, such as, but not limited to, IPN002, PHF1 and/or MC1. While not wishing to be bound by theory, the first approximately 57 nucleotides of an antibody heavy chain or light chain sequence may be considered a signal sequence. Non-limiting examples of antibody derived signal sequences include Signal13-Signal18 (SEQ ID NO: 1083-1088, respectively).

In some embodiments, the signal sequence region may signal for transcription. In some embodiments, the signal sequence region may signal for translation. In some embodiments, the signal sequence region directs the payload out of the nucleus or out of the cell. In some embodiments, the signal sequence region directs the payload to a particular target, wherein the target may be an organ, tissue, cell, cellular compartment, cellular organelle or a component of any of the above.

The signal sequence region(s) may, independently, have a length such as, but not limited to, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, or more than 150 nucleotides. The length of the signal region in the viral genome may be 10-15, 15-25, 25-35, 25-50, 35-45, 45-55, 50-75, 55-65, 65-75, 75-85, 75-100, 85-95, 95-105, 100-125, 105-115, 115-125, 125-135, 125-150, 135-145, 145-155, 150-175, 155-165, 165-175, 175-185, 175-200, 185-195, 195-205, 200-225, 205-215, 215-225, 225-235, 225-250, 235-245, 245-255, 250-275, 255-265, 265-275, 275-285, 275-300, 285-295, 295-305, 300-325, 305-315, 315-325, 325-335, 325-350, 335-345, and 345-500 nucleotides.

In some embodiments, the viral genome comprises at least one signal sequence region. Non-limiting examples of signal sequence regions are listed in Table 14.

TABLE 14

Signal Sequence Regions

| Sequence Region Name | Sequence Length | SEQ ID NO |
|---|---|---|
| Signal1 | 84 | 1071 |
| Signal2 | 93 | 1072 |
| Signal3 | 96 | 1073 |
| Signal4 | 66 | 1074 |
| Signal5 | 72 | 1075 |
| Signal6 | 93 | 1076 |
| Signal7 | 69 | 1077 |
| Signal8 | 81 | 1078 |
| Signal9 | 12 | 1079 |
| Signal10 | 81 | 1080 |
| Signal11 | 66 | 1081 |
| Signal12 | 78 | 1082 |
| Signal13 | 57 | 1083 |
| Signal14 | 57 | 1084 |
| Signal15 | 57 | 1085 |
| Signal16 | 411 | 1086 |
| Signal17 | 57 | 1087 |
| Signal18 | 72 | 1088 |
| Signal19 | 11 | 1089 |

In some embodiments, the viral genome comprises one signal sequence region. In some embodiments, the viral genome comprises two signal sequence regions. In some embodiments, the viral genome comprises three signal sequence regions. In some embodiments, the viral genome comprises more than three signal sequence regions. In some embodiments, the signal sequences of a viral genome comprising more than one signal sequence, are the same. In another embodiment, the signal sequences of a viral genome comprising more than one signal sequence, are not the same.

In some embodiments, the viral genome comprises one signal sequence region. In some embodiments, the signal sequence region is the Signal1 sequence region. In some embodiments, the signal sequence region is the Signal2 sequence region. In some embodiments, the signal sequence region is the Signal3 sequence region. In some embodiments, the signal sequence region is the Signal4 sequence region. In some embodiments, the signal sequence region is the Signal5 sequence region. In some embodiments, the signal sequence region is the Signal6 sequence region. In some embodiments, the signal sequence region is the Signal7 sequence region. In some embodiments, the signal sequence region is the Signal8 sequence region. In some embodiments, the signal sequence region is the Signal9 sequence region. In some embodiments, the signal sequence region is the Signal10 sequence region. In some embodiments, the signal sequence region is the Signal11 sequence region. In some embodiments, the signal sequence region is the Signal12 sequence region. In some embodiments, the signal sequence region is the Signal13 sequence region. In some embodiments, the signal sequence region is the Signal14 sequence region. In some embodiments, the signal sequence region is the Signal15 sequence region. In some embodiments, the signal sequence region is the Signal16 sequence region. In some embodiments, the signal sequence region is the Signal17 sequence region. In some embodiments, the signal sequence region is the Signal18 sequence region. In some embodiments, the signal sequence region is the Signal19 sequence region.

In some embodiments, the signal sequence comprises any one of the signal sequences provided in Table 14 or a functional variant thereof. In some embodiments, the encoded signal sequence comprises an amino acid sequence encoded by any one of the nucleotide sequences provided in Table 14, or an amino acid sequence with at least 70%, 75%, 80%, 85%, 90%, 95%, or 99% sequence identity thereto. In some embodiments, the nucleic acid sequence encoding the signal sequence comprises any one of the nucleotide sequences provided in Table 14, or a nucleotide sequence with at least 70%, 75%, 80%, 85%, 90%, 95%, or 99% sequence identity thereto.

Viral Genome Component: Linkers

In some embodiments, the viral genome comprises or encodes a linker region or linker. In some embodiments, the linker connects two antibody sequence regions of the viral genome (e.g., a VH-linker-VL, VL-linker-VH heavy chain-linker-light chain or light chain-linker-heavy chain).

In some cases, the linker may be a peptide linker that may be used to connect the polypeptides encoded by the payload region (e.g., light and heavy antibody chains during expression). Some peptide linkers may be cleaved after expression to separate heavy and light chain domains, allowing assembly of mature antibodies or antibody fragments. Linker cleavage may be enzymatic. In some cases, linkers comprise an enzymatic cleavage site to facilitate intracellular or extracellular cleavage. Some payload regions encode linkers that interrupt polypeptide synthesis during translation of the linker sequence from an mRNA transcript. Such linkers may facilitate the translation of separate protein domains (e.g., heavy and light chain antibody domains) from a single transcript. In some cases, two or more linkers are encoded by a payload region of the viral genome.

In some embodiments, the encoded linker comprises a linker provided in Table 15. For those sequences described by their amino acid composition (e.g., G4S; SEQ ID NO: 1097) the SEQ ID NO: provided in parentheses represents the amino acid sequence while the SEQ ID NO: column lists DNA SEQ ID NO.

TABLE 15

| Linkers | | | |
|---|---|---|---|
| Linker ID | Description | Length | Nucleotide SEQ ID NO: |
| Linker 1 | Furin | 12 | 1090 |
| Linker2 | Furin | 12 | 1091 |
| Linker3 | T2A | 54 | 1092 |
| Linker4 | F2A | 75 | 1093 |
| Linker5 | P2A | 66 | 1094 |
| Linker6 | IRES | 609 | 1095 |
| Linker7 | IRES-2 | 623 | 1096 |
| Linker8 | G4S (SEQ ID NO:1097) | 15 | 1098 |
| Linker9 | SG4S (SEQ ID NO: 1099) | 18 | 1100 |
| Linker10 | (G4S)2 (SEQ ID NO: 1101) | 30 | 1102 |
| Linker11 | (G4S)3 (SEQ ID NO: 1103) | 45 | 1104 |
| Linker12 | (G4S)3 (SEQ ID NO: 1103) | 45 | 1105 |
| Linker13 | (G4S)4 (SEQ ID NO: 1106) | 60 | 1107 |
| Linker14 | (G4S)4 (SEQ ID NO: 1106) | 60 | 1108 |
| Linker15 | (G4S)5 (SEQ ID NO: 1109) | 75 | 1110 |
| Linker16 | (G4S)5 (SEQ ID NO: 1109) | 75 | 1111 |
| Linker17 | (G4S)5 (SEQ ID NO: 1109) | 75 | 1112 |
| Linker18 | (G4S)6 (SEQ ID NO: 1113) | 90 | 1114 |
| Linker19 | (G4S)6 (SEQ ID NO: 1113) | 90 | 1115 |
| Linker20 | (G4S)8 (SEQ ID NO: 1116) | 120 | 1117 |
| Linker21 | (G4S)8 (SEQ ID NO:1116) | 120 | 1118 |
| Linker22 | nxG4S, where n = 1-10 (SEQ ID NO: 1119) | 50 | — |
| Linker23 | hIgG2 hinge | 54 | 1120 |
| Linker24 | hIgG3 hinge | 108 | 1121 |
| Linker25 | hIgG3-2 hinge | 153 | 1122 |
| Linker26 | hIgG3-3 hinge | 198 | 1123 |
| Linker27 | msiGG-1 hinge | 45 | 1124 |
| Linker28 | msiGG1 hinge | 18 | 1125 |
| Linker29 | HigG3 hinge | 198 | 1126 |

In some embodiments, the encoded linker comprises an amino acid sequence encoded by any one of the nucleotide sequences provided in Table 15, or an amino acid sequence with at least 70%, 75%, 80%, 85%, 90%, 95%, or 99% sequence identity thereto. In some embodiments, the nucleic acid sequence encoding the linker comprises any one of the nucleotide sequences provided in Table 15, or a nucleotide sequence with at least 70%, 75%, 80%, 85%, 90%, 95%, or 99% sequence identity thereto.

In some embodiments, the encoded linker comprises an enzymatic cleavage site, e.g., for intracellular and/or extracellular cleavage. In some embodiments, the linker is cleaved to separate the VH and the VL of the antigen binding domain and/or the heavy chain and light chain of the antibody molecule (e.g., an anti-tau antibody).

In some embodiments, the encoded linker comprises a furin linker (furin cleavage sites) or a functional variant. In some embodiments, furin cleaves proteins just downstream of a basic amino acid target sequence (Arg-X-(Arg/Lys)-Arg). In some embodiments, the nucleotide sequence encoding the furin linker comprises the nucleotide sequence of SEQ ID NO: 1090 or 1091, or a nucleotide sequence with at least 70%, 75%, 80%, 85%, 90%, 95%, or 99% sequence identity thereto. In some embodiments, furin cleaves proteins downstream of a basic amino acid target sequence (e.g., Arg-X-(Arg/Lys)-Arg) (e.g., as described in Thomas, G., 2002. Nature Reviews Molecular Cell Biology 3(10): 753-66; the contents of which are herein incorporated by reference in its entirety).

In some embodiments, the encoded linker comprises a 2A self-cleaving peptide (e.g., a 2A peptide derived from foot-and-mouth disease virus (F2A), porcine teschovirus-1 (P2A), *Thosea asigna* virus (T2A), or equine rhinitis A virus (E2A)). The 2A designation refers specifically to a region of picornavirus polyproteins that lead to a ribosomal skip at the glycyl-prolyl bond in the C-terminus of the 2A peptide (Kim, J. H. et al., 2011. PLOS One 6(4): e18556; the contents of which are herein incorporated by reference in its entirety). This skip results in a cleavage between the 2A peptide and its immediate downstream peptide. Without wishing to be bound by theory, it is believed in some embodiments, that 2A peptides generate stoichiometric expression of proteins flanking the 2A peptide and their shorter length can be advantageous in generating viral expression vectors.

In some embodiments, the encoded linker comprises a T2A self-cleaving peptide linker. In some embodiments, the nucleotide sequence encoding the T2A linker comprises the nucleotide sequence of SEQ ID NO: 1092, or a nucleotide sequence with at least 70%, 75%, 80%, 85%, 90%, 95%, or 99% sequence identity thereto. In some embodiments, the nucleic acid encoding the payload encodes a furin linker and a T2A linker.

In some embodiments, the encoded linker comprises an internal ribosomal entry site (IRES) is a nucleotide sequence (>500 nucleotides) for initiation of translation in the middle of a nucleotide sequence, e.g., an mRNA sequence (Kim, J. H. et al., 2011. PLOS One 6(4): e18556; the contents of which are herein incorporated by reference in its entirety), which can be used, for example, to modulate expression of one or more transgenes. Use of an IRES sequence ensures co-expression of genes before and after the IRES, though the sequence following the IRES may be transcribed and translated at lower levels than the sequence preceding the IRES sequence.

In some embodiments, the encoded linker comprises a small and unbranched serine-rich peptide linker, such as those described by Huston et al. in U.S. Pat. No. 5,525,491, the contents of which are herein incorporated in their entirety. In some embodiments, polypeptides comprising a serine-rich linker has increased solubility. In some embodiments, the encoded linker comprises an artificial linker, such as those described by Whitlow and Filpula in U.S. Pat. No. 5,856,456 and Ladner et al. in U.S. Pat. No. 4,946,778, the contents of each of which are herein incorporated by their entirety.

In some embodiments, the viral genome comprises one more linkers such as, but not limited to, cathepsin, matrix metalloproteinases or legumain cleavage sites. Such linkers are described e.g. by Cizeau and Macdonald in International Publication No. WO2008052322, the contents of which are herein incorporated in their entirety.

In some embodiments, the viral genome may encode linkers that are not cleaved. In some embodiments, any of the antibody molecules described herein can have a flexible polypeptide linker, of varying lengths, connecting the variable domains (e.g., the VH and the VL) of the antigen binding domain of the antibody molecule. For example, a (Gly4-Ser)n linker (SEQ ID NO: 1214), wherein n is 0, 1, 2, 3, 4, 5, 6, 7, or 8 can be used (e.g., any one of SEQ ID NOs: 1098, 1100, 1102, 1104-1105, 1107-1108, 1110-1112, 1114-1115, 1117-1119). In some embodiments, such linkers may include a simple amino acid sequence, such as a glycine rich sequence. In some cases, the linkers comprise glycine and serine residues. In some embodiments, the linker may comprise flexible peptide linkers of different lengths, e.g. nxG4S, where n=1-10 (SEQ ID NO: 1119), and the length of the encoded linker varies between 5 and 50 amino acids. In a non-limiting example, the linker may be 5×G4S (SEQ ID NO: 1109). Without wishing to be bound by theory, it is believed in some embodiments, that these flexible linkers are small and without side chains so they tend not to influence secondary protein structure while providing a flexible linker between antibody segments (George, R. A., et al., 2002. Protein Engineering 15(11): 871-9; Huston, J. S. et al., 1988. PNAS 85:5879-83; and Shan, D. et al., 1999. Journal of Immunology. 162(11):6589-95; the contents of each of which are herein incorporated by reference in their entirety). Furthermore, the polarity of the serine residues improves solubility and prevents aggregation problems.

In some embodiments, the viral genome encodes at least one G4S3 linker ("G4S3" disclosed as SEQ ID NO: 1103). In some embodiments, the viral genome encodes at least one G4S linker ("G4S" disclosed as SEQ ID NO: 1097). In some embodiments, the viral genome encodes at least one furin site. In some embodiments, the viral genome encodes at least one G4S5 linker ("G4S5" disclosed as SEQ ID NO: 1109). In some embodiments, the viral genome encodes at least one T2A linker. In some embodiments, the viral genome encodes at least one F2A linker. In some embodiments, the viral genome encodes at least one P2A linker. In some embodiments, the viral genome encodes at least one furin and one 2A linker. As non-limiting examples, the viral genome may comprise furin and T2A linkers or furin and F2A linkers.

In some embodiments, the AAV particle viral genome encodes at least one IRES sequence. In some embodiments, the viral genome encodes at least one hinge region. As a non-limiting example, the hinge is an IgG hinge.

In some embodiments, the nucleic acid sequence encoding the linker comprises about 10 to about 700 nucleotides in length, e.g., about 10 to about 700 nucleotides, e.g. about 10 to about 100, e.g., about 50-200 nucleotides, about 150-300 nucleotides, about 250-400 nucleotides, about 350-500 nucleotides, about 450-600 nucleotides, about 550-700 nucleotides, about 650-700 nucleotides. In some embodiments, the nucleic acid sequence encoding the linker comprises about 5 to about 20 nucleotides in length, e.g., about 12 nucleotides in length. In some embodiments, the nucleic acid sequence encoding the linker comprises about 40 to about 60 nucleotides in length, e.g., about 54 nucleotides in length.

In some embodiments, the linker region may be 1-50, 1-100, 50-100, 50-150, 100-150, 100-200, 150-200, 150-250, 200-250, 200-300, 250-300, 250-350, 300-350, 300-400, 350-400, 350-450, 400-450, 400-500, 450-500, 450-550, 500-550, 500-600, 550-600, 550-650, or 600-650 nucleotides in length. The linker region may have a length of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73,74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 115, 120, 125, 130, 135, 140, 145, 150, 151, 152, 153, 154, 155, 156, 157, 158, 159, 160, 165, 170, 171, 172, 173, 174, 175, 176, 177, 178, 179, 180, 185, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 640, 650 or greater than 650. In some embodiments, the linker region may be 12 nucleotides in length. In some embodiments, the linker region may be 15 nucleotides in length, In some embodiments, the linker region may be 18 nucleotides in length. In some embodiments, the linker region may be 30 nucleotides in length. In some embodiments, the linker region may be 45 nucleotides in length. In some embodiments, the linker region may be 54 nucleotides in length. In some embodiments, the linker region may be 60 nucleotides in length. In some embodiments, the linker region may be 66 nucleotides in length. In some embodiments, the linker region may be 75 nucleotides in length. In some embodiments, the linker region may be 78 nucleotides in length. In some embodiments, the linker region may be 87 nucleotides in length. In some embodiments, the linker region may be 108 nucleotides in length. In some embodiments, the linker region may be 120 nucleotides in length. In some embodiments, the linker region may be 153 nucleotides in length. In some embodiments, the linker region may be 198 nucleotides in length. In some embodiments, the linker region may be 609 nucleotides in length. In some embodiments, the linker region may be 623 nucleotides in length.

Viral Genome Component: Tag

In some embodiments, the viral genome may comprise a tag polypeptide (e.g., a tag sequence or tag sequence region herein). As used herein, the term "tag" indicates a polynucleotide sequence appended to the payload, that once expressed may be used to identify the expressed payload. Alternatively, the term "tag" may indicate a polynucleotide sequence appended to the payload that signals for retention of the expressed payload in a particular region of the cell (e.g., endoplasmic reticulum).

In some embodiments, the nucleotide sequence encoding the tag polypeptide comprises about 10-50 nucleotides in length, e.g., about 10-40 nucleotides, about 10-30 nucleotides, about 10-20 nucleotides, about 20-50 nucleotides, about 20-40 nucleotides, about 20-30 nucleotides, about 30-50 nucleotides, about 30-40 nucleotides, or about 40 to 50 nucleotides. In some embodiments, the nucleotide sequence encoding the tag polypeptide comprises about 10 nucleotides to about 30 nucleotides, e.g., about 18 nucleotides or about 21 nucleotides. In some embodiments, the nucleotide sequence encoding the tag polypeptide comprises about 20 nucleotides to about 40 nucleotides, e.g., about 27 nucleotides.

TABLE 16

Tag Sequence Regions

| Sequence Region Name | Sequence Length | SEQ ID NO |
|---|---|---|
| Tag1 | 27 | 1127 |
| Tag2 | 21 | 1128 |
| Tag3 | 18 | 1129 |
| Tag4 | 18 | 1130 |
| Tag5 | 18 | 1131 |
| Tag6 | 4 | 1132 |
| Tag7 | 6 | 1133 |

In some embodiments, the viral genome comprises a tag sequence provided in Table 16. In some embodiments, the viral genome comprises any one of Tag1-Tag7 or a functional variant thereof. In some embodiments, the tag sequence comprises the nucleotide sequence of any one of SEQ ID NOs: 1127-1133, or a nucleotide sequence with at least 70%, 75%, 80%, 85%, 90%, 95% or 99% sequence identity thereto. In some embodiments, the encoded tag polypeptide comprises an amino acid sequence encoded by of any one of SEQ ID NOs: 1127-1133, or an amino acid sequence with at least 70%, 75%, 80%, 85%, 90%, 95% or 99% sequence identity thereto.

In some embodiments, the viral genome comprises one tag sequence region. In some embodiments, the tag sequence region is the Tag1 sequence region. In some embodiments, the tag sequence region is the Tag2 sequence region. In some embodiments, the tag sequence region is the Tag3 sequence region. In some embodiments, the tag sequence region is the Tag4 sequence region. In some embodiments, the tag sequence region is the Tag5 sequence region. In some embodiments, the encoded tag sequence region is the Tag6 sequence region. In some embodiments, the encoded tag sequence region is the Tag7 sequence region.

In some embodiments, the viral genome comprises more than one tag sequence region. In some embodiments, the viral genome comprises two tag sequence regions. In some embodiments, the viral genome comprises three tag sequence regions. In some embodiments, the viral genome comprises more than three tag sequence regions.

Viral Genome Component: Polyadenylation Sequence Region

In some embodiments, the viral genome may comprise at least one polyadenylation sequence region. In some embodiments, the viral genome comprises a polyadenylation (referred to herein as poly A, polyA, or poly-A) sequence between the 3' end of the transgene encoding the payload and the 5' end of the 3'ITR. In some embodiments, the viral genome comprises two or more polyA sequences. In some embodiments, the viral genome does not comprise a polyA sequence.

In some embodiments, the polyA signal region comprises a length of about 100-600 nucleotides, e.g., about 100-500 nucleotides, about 100-400 nucleotides, about 100-300 nucleotides, about 100-200 nucleotides, about 200-600 nucleotides, about 200-500 nucleotides, about 200-400 nucleotides, about 200-300 nucleotides, about 300-600 nucleotides, about 300-500 nucleotides, about 300-400 nucleotides, about 400-600 nucleotides, about 400-500 nucleotides, or about 500-600 nucleotides. In some embodiments, the polyA signal region comprises a length of about 100 to 150 nucleotides, e.g., about 127 nucleotides.

TABLE 17

Poly-A Signal Sequence Regions

| Sequence Region Name | Sequence Length | SEQ ID NO |
|---|---|---|
| PolyA1 | 127 | 1134 |
| PolyA2 | 477 | 1135 |
| PolyA3 | 552 | 1136 |

In some embodiments, the polyA signal region is provided in Table 17. In some embodiments, viral genome comprises a polyA sequence region chosen from polyA1, polyA2, polyA3, or a functional variant thereof. In some embodiments, the polyA signal region comprises the nucleotide sequence of any one of SEQ ID NOs: 1134-1136, or a sequence with at least 70%, 75%, 80%, 85%, 90%, 95%, or 99% sequence identity thereto.

In some embodiments, the viral genome comprises one polyA sequence region. In some embodiments, the polyA sequence region is the PolyA1 sequence. In some embodiments, the polyA sequence region is the PolyA2 sequence. In some embodiments, the polyA sequence region is the PolyA3 sequence.

In some embodiments, the viral genome comprises more than one polyA sequence region.

Viral Genome Component: Filler Sequence Region

In some embodiments, the viral genome may comprise at least one or multiple filler sequence regions.

In some embodiments, the filler sequence comprises about 100-2000, about 200 to 1900, about 300 to 1800, about 400 to 1700, about 500 to 1600, about 600 to 1500, about 700 to 1500, about 800 to 1500, about 900 to 1500, about 1000-1500 nucleotides in length, e.g., about 1000-1400 nucleotides, about 1000-1300 nucleotides, about 1000-1200 nucleotides, about 1200-1500 nucleotides, about 1200-1400 nucleotides, about 1200-1300 nucleotides, about 1300-1500 nucleotides, about 1300-1400 nucleotides, or about 1400-1500 nucleotides. In some embodiments, the filler sequence comprises about 1140 nucleotides to about 1160 nucleotides in length, e.g., about 1153 nucleotides. In some embodiments, the filler sequence comprises about 1230 nucleotides to about 1250 nucleotides in length, e.g., about 1240 nucleotides. As a non-limiting example, the viral genome comprises a filler region that is about 1153 nucleotides in length. As a non-limiting example, the viral genome comprises a filler region that is about 1240 nucleotides in length.

In some embodiments, the A viral genome comprises at least one filler sequence region. Non-limiting examples of filler sequence regions are described in Table 18.

TABLE 18

Filler Sequence Regions

| Sequence Region Name | Sequence Length | SEQ ID NO |
|---|---|---|
| FILLER1 | 1153 | 1137 |
| FILLER2 | 1240 | 1138 |

In some embodiments, the viral genome comprises two or more filler sequences. A filler sequence is provided in Table 18. In some embodiments, the viral genome comprises FILLER1, FILLER2, or a functional variant thereof. In some embodiments, the viral genome comprises FILLER 1 and FILLER2. In some embodiments, the filler sequence comprises the nucleotide sequence of SEQ ID NO: 1137, or a nucleotide sequence with at least 70%, 75%, 80%, 85%, 90%, 95%, 99% or 100% sequence identity thereto. In some embodiments, the filler sequence comprises the nucleotide sequence of SEQ ID NO: 1138, or a nucleotide sequence with at least 70%, 75%, 80%, 85%, 90%, 95%, 99% or 100% sequence identity thereto.

In some embodiments, the viral genome does not comprise a filler sequence region.

Viral Genome Component: Payload

The viral genomes of the present disclosure comprise at least one payload region. As used herein, "payload" or "payload region" refers to one or more polynucleotides or polynucleotide regions encoded by or within a viral genome, or an expression product of such polynucleotide or polynucleotide region, e.g., a transgene, a polynucleotide encoding a polypeptide or multi-polypeptide or a modulatory nucleic acid or regulatory nucleic acid. Payloads of the present disclosure typically encode polypeptides (e.g., antibodies or antibody-based compositions) or fragments or variants thereof.

The payload region may be constructed in such a way as to reflect a region similar to or mirroring the natural organization of an mRNA.

The payload region may comprise a combination of coding and non-coding nucleic acid sequences.

In some embodiments, the AAV payload region may encode a coding or non-coding RNA.

In some embodiments, the AAV particle comprises a viral genome with a payload region comprising nucleic acid sequences encoding more than one polypeptide of interest (e.g., heavy and light chains of an antibody). In such an embodiment, a viral genome encoding more than one polypeptide may be replicated and packaged into a viral particle. A target cell transduced with a viral particle comprising more than one polypeptides may express each of the polypeptides in a single cell.

In some embodiments, an AAV particle comprises a viral genome with a payload region comprising a nucleic acid sequence encoding a heavy chain and a light chain of an antibody, or fragments thereof. The heavy chain and light chain are expressed and assembled to form a functional antibody, which may then be secreted.

In some embodiments, the payload region may comprise at least one inverted terminal repeat (ITR), a promoter region, an intron region, and a coding region. In some embodiments, the coding region comprises a heavy chain region and/or a light chain region of an antibody, or a fragment thereof, and any two components may be separated by a linker region.

In some embodiments, the coding region may comprise a payload region with a heavy chain and light chain sequence separated by a linker and/or a cleavage site. In some embodiments, the heavy and light chain sequence is separated by an IRES sequence. In some embodiments, the heavy and light chain sequence is separated by a foot and mouth virus sequence. In some embodiments, the heavy and light chain sequence is separated by a foot and mouth virus sequence and a furin cleavage site. In some embodiments, the heavy and light chain sequence is separated by a porcine teschovirus-1 virus sequence. In some embodiments, the heavy and light chain sequence is separated by a porcine teschovirus-1 virus and a furin cleavage site. In some embodiments, the heavy and light chain sequence is separated by a 5×G4S sequence ("5×G4S" disclosed as SEQ ID NO: 1109).

In some embodiments, the payload region comprises one or more nucleic acid sequences encoding anti-tau antibodies, variants or fragments thereof. In some embodiments, the variant is a humanized variant, such as a humanized variant comprising any one or more (e.g., all 6) CDR regions of any one of the antibodies in any one of the Tables 1, 6, 2A-2C, 4 and 5.

In some embodiments, the payload region of the AAV particle comprises a nucleic acid sequence encoding a polypeptide or polypeptides comprising a heavy chain variable region (VH) and/or a light chain variable region (VL) sequences each listed in any of Tables 3 or 4, or variants or fragments thereof; optionally the polypeptide(s) further comprises a heavy chain constant region and/or a light chain constant region, such as those listed in Table X. The polypeptide may constitute a full-length antibody (e.g., comprising a VH and a heavy chain constant region, such as those listed in Table X; and a VL and a light chain constant region, such as those listed in Table X), or an antibody fragment thereof, such as Fab, $F(ab')_2$, scFv, etc. The payload region may also comprise a linker between the heavy and light chain sequences. In certain embodiments, the coding sequence for the heavy chain or VH is 5' to the coding sequence for the light chain or VL, or vice versa.

In some embodiments, the payload region of the AAV particle comprises a nucleic acid sequence encoding a polypeptide comprising a heavy chain variable region and a light chain variable region sequences listed in Table 3 or 4, or variants or fragments thereof, where the heavy chain variable region sequence is from a different antibody than the light chain variable region sequence. In certain embodiments, the payload region of the AAV particle comprises a nucleic acid sequence encoding a polypeptide comprising a heavy chain variable region and a light chain variable region sequences listed in Table 3 or 4, or variants or fragments thereof, where the VH and VL sequences are from the same antibody. The payload region may also comprise a linker between the heavy and light chain variable region sequences.

In some embodiments, the payload region comprises, in the 5' to 3' direction, an antibody light chain sequence, a linker and a heavy chain sequence (e.g., light-linker-heavy or L.Linker.H or LH). In another embodiment, the linker is not used or absent.

In some embodiments, the payload region comprises a nucleic acid sequence encoding, in the 5' to 3' direction, an antibody light chain sequence from Tables 3 or 4 (for VL sequence) and X (for constant region sequence), a linker and a heavy chain sequence from Tables 3 or 4 (for VH sequence) and X (for constant region sequence).

In some embodiments, the payload region comprises, in the 5' to 3' direction, an antibody heavy chain sequence, a linker region (may comprise one or more linkers) and a light chain sequence (i.e., heavy-linker-light or H.Linker.L or HL). In another embodiment, the linker is not used or absent.

In some embodiments, the payload region comprises a nucleic acid sequence encoding, in the 5' to 3' direction, an antibody heavy chain sequence from Tables 3 or 4 (for VH sequence) and X (for constant region sequence), one or more linkers, and a light chain sequence from Tables 3 or 4 (for VL sequence) and X (for constant region sequence).

In some embodiments, the payload region comprises a nucleic acid sequence encoding a single heavy chain. As a non-limiting example, the heavy chain comprises one or more amino acid sequences or fragments thereof described in Tables 3 (for VH), 2A-2C & 6 (for CDRH1-CDRH3), 7 (for FRH1-FRH4), 4 (for CDRH1-CDRH3 or VH), 5 (for CDRH1-CDRH3), and/or X (for heavy chain constant region).

In some embodiments, the payload region may further comprise a nucleic acid sequence encoding a light chain. As a non-limiting example, the light chain comprises one or more amino acid sequences or fragments thereof described in Tables 3 (for VL), 2A-2C & 6 (for CDRL1-CDRL3), 7 (for FRL1-FRL4), 4 (for CDRL1-CDRL3 or VL), 5 (for CDRL1-CDRL3), and/or X (for light chain constant region).

Shown in Tables 1, 3, 6, 7. X, 2A-2C, 4, and 5 are a listing of antibody components and their polynucleotides and/or polypeptides sequences. These sequences may be encoded by or included in the viral genomes of the present disclosure. Variants or fragments of the antibody sequences described in Tables 1, 3, 6, 7, X, 2A-2C, 4, and 5 may be utilized in the viral genomes of the present disclosure.

In some embodiments, the payload region of the AAV particle comprises one or more nucleic acid sequences encoding one or more of the payload antibody polypeptides listed in Tables 1, 3, 6, 7, 2A-2C, 4, and 5, or variants or fragments thereof. As used herein, "antibody polynucleotide" refers to a nucleic acid sequence encoding an antibody polypeptide.

In some embodiments, the payload region of the AAV particle comprises one or more nucleic acid sequences listed in Table 3, X or 4, or variants or fragments thereof.

In some embodiments, the payload region of the AAV particle comprises a nucleic acid sequence encoding a payload antibody with at least 50% identity to one or more payload antibody polypeptides or fragments thereof including framework region, constant region and antigen-binding fragments thereof (such as VH/VL, and CDRs) listed in any of Tables 1, 3, 6, 7. X, 2A-2C, 4, and 5. The encoded antibody polypeptide may have 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%,80%,81%,82%,83%,84%,85%, 86%, 87%, 88%, 89%, 90%, 91%, 92%, 93%, 94%, 95%, 96%, 97%, 98%, 99%, or 100% identity to one or more of the payload antibody polypeptides or fragments thereof listed in Tables 1,3, 6, 7. X. 2A-2C, 4, and 5, or variants or fragments thereof.

In some embodiments, the variable region sequence(s) (e.g., heavy or light chain) of the encoded antibody polypeptide may have 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%,80%,81%,82%,83%,84%,85%,86%,87%, 88%,89%, 90%, 91%, 92%, 93%, 94%, 95%, 96%, 97%, 98%, 99%, or 100% identity to one or more of the payload antibody polypeptides listed in Table 3 or 4, or variants or fragments thereof.

In some embodiments, any one or more of the CDR regions of the encoded antibody polypeptide may have 50%, 51%, 52%, 53%, 54%, 55%, 56%, 57%, 58%, 59%, 60%, 61%, 62%, 63%, 64%, 65%, 66%, 67%, 68%, 69%, 70%, 719%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, or contains at least or no more than 1, 2, 3, 4, 5, 6, 7, 8, 9, 10, 11, 12, 13, 14, 15, or 16 changes (e.g., substitutions including conservative substitutions, deletions, and/or insertions) compared to the CDRs of one or more of the payload antibody polypeptides listed in any of Tables 1, 2A-2C, 6, 4, and 5, or variants or fragments thereof.

In some embodiments, the framework region of the encoded antibody polypeptide may have 50%, 51%, 52%, 53%, 54%, 55%, 56%, 57%, 58%, 59%, 60%, 61%, 62%, 63%, 64%, 65%, 66%, 67%, 68%, 69%, 70%, 719%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, or contains at least or no more than 1, 2, 3, 4, 5, 6, 7, 8, 9, 10, 11, 12, 13, 14, 15, 16, 17, 18, 19, or 20 changes (e.g., substitutions including conservative substitutions, deletions, and/or insertions) compared to the framework sequences of one or more of the payload antibody polypeptides listed in Table 7 or 4, or variants or fragments thereof.

In some embodiments, the payload antibody (e.g., a full length heavy chain or a full-length light chain; or a VH or a VL thereof comprising the HC CDR1-3 or LC CDR1-3) has 90% identity to one or more of the antibody polypeptides (e.g., full-length antibody comprising a VH/VL region and a CH/CL region) listed in Tables 1, 2A-2C, 3, 6, 7, X, 4, and/or 5, or variants or fragments thereof.

In some embodiments, the payload antibody (e.g., a full length heavy chain or a full-length light chain; or a VH or a VL thereof comprising the HC CDR1-3 or LC CDR1-3) has 91% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 92% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 93% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 94% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 95% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 96% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 97% identity to one or more of the antibody polypeptides (e.g., full-length antibody comprising a VH/VL region and a CH/CL region) listed in Tables 1, 2A-2C. 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 98% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 99% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload antibody (e.g., a full length heavy chain or a full-length light chain; or a VH or a VL thereof comprising the HC CDR1-3 or LC CDR1-3) has 100% identity to one or more of the antibody polypeptides (e.g., full-length antibody comprising a VH/VL region and a CH/CL region) listed in Tables 1, 2A-2C, 3-7, and/or X, or variants or fragments thereof.

In some embodiments, the payload region of the AAV particle comprises a nucleic acid sequence with at least 50% identity to one or more nucleic acid sequences listed in Table 3 or 4, or variants or fragments thereof. The payload nucleic acid sequence may have 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%,80%,81%,82%, 83%, 84%, 85%, 86%, 87%, 88%, 89%, 90%, 91%, 92%, 93%, 94%, 95%, 96%, 97%, 98%, 99%, or 100% identity to one or more nucleic acid sequences listed in Table 3 or 4, or variants or fragments thereof.

In some embodiments, the payload nucleic acid sequence has 90% identity to one or more of the nucleic acid sequences listed in Table 3 or 4, or variants or fragments thereof.

In some embodiments, the payload nucleic acid sequence has 91% identity to one or more of the nucleic acid sequences listed in Table 3 or 4, or variants or fragments thereof.

In some embodiments, the payload nucleic acid sequence has 92% identity to one or more of the nucleic acid sequences listed in Table 3 or 4, or variants or fragments thereof.

In some embodiments, the payload nucleic acid sequence has 93% identity to one or more of the nucleic acid sequences listed in Table 3 or 4, or variants or fragments thereof.

In some embodiments, the payload nucleic acid sequence has 94% identity to one or more of the nucleic acid sequences listed in Table 3 or 4, or variants or fragments thereof.

In some embodiments, the payload nucleic acid sequence has 95% identity to one or more of the nucleic acid sequences listed in Table 3 or 4, or variants or fragments thereof.

In some embodiments, the payload nucleic acid sequence has 96% identity to one or more of the nucleic acid sequences listed in Table 3 or 4, or variants or fragments thereof.

In some embodiments, the payload nucleic acid sequence has 97% identity to one or more of the nucleic acid sequences listed in Table 3 or 4, or variants or fragments thereof.

In some embodiments, the payload nucleic acid sequence has 98% identity to one or more of the nucleic acid sequences listed in Table 3 or 4, or variants or fragments thereof.

In some embodiments, the payload nucleic acid sequence has 99% identity to one or more of the nucleic acid sequences listed in Table 3 or 4, or variants or fragments thereof.

In some embodiments, the payload nucleic acid sequence has 100% identity to one or more of the nucleic acid sequences listed in Table 3 or 4, or variants or fragments thereof. In some embodiments, the viral genome may comprise one or more components which have been codon-optimized. Codon-optimization may be achieved by any method known to one with skill in the art such as, but not limited to, by a method according to Genscript, EMBOSS, Bioinformatics, NUS, NUS2, Geneinfinity, IDT, NUS3, GregThatcher, Insilico, Molbio, N2P, Snapgene, and/or VectorNTI. Antibody heavy and/or light chain sequences within the same viral genome may be codon-optimized according to the same or according to different methods.

In some embodiments, the viral genome may comprise any combination of the components described herein, or generally known in the art. In some embodiments, the viral genome may comprise any combination of the following components, including, but not limited to, a 5' ITR, a promoter region (may comprise one or more component pieces), an exon region, an intronic region, a Kozak sequence, one or more signal sequences (antibody signal sequences or signal sequence derived from another protein), one or more furin cleavage sites, one or more linker sequences, one or more antibody light chain variable regions, one or more antibody light chain constant regions, one or more antibody heavy chain variable regions, one or more antibody heavy chain constant regions, a polyadenylation sequence, and/or a filler sequence.

In some embodiments, the AAV viral genome comprises, when read in the 5' to 3' direction, a 5' ITR, a promoter region, an optional intronic region, a signal sequence, an antibody light chain region, a linker region, a signal sequence, an antibody heavy chain region, a polyadenylation sequence, an optional filler sequence, and a 3' ITR. In some embodiments, the AAV viral genome comprises, when read in the 5' to 3' direction, an antibody construct in a light-linker-heavy format.

In some embodiments, the AAV viral genome comprises, when read in the 5' to 3' direction, a 5' ITR, a promoter region, an optional intronic region, a signal sequence, an antibody heavy chain region, a linker region, a signal sequence, an antibody light chain region, a polyadenylation sequence, an optional filler sequence, and a 3' ITR. In some embodiments, the AAV viral genome comprises, when read in the 5' to 3' direction, an antibody construct in a heavy-linker-light format.

The viral genome may encode an antibody fragment, such as, but not limited to Fab, $F(ab')^2$ or scFv fragments. In some embodiments, the viral genome encodes a Fab antibody fragment. In another embodiment, the viral genome encodes an $F(ab')_2$ antibody fragment. In some embodiments, the viral genome encodes an scFv.

In some embodiments, a viral genome described herein, or a fragment thereof, is packaged in a capsid having a serotype selected from Table 9 or described herein to generate an AAV particle. For example, the capsid serotype may be VOY101, VOY201, AAVPHP.B. AAVPHP.N, AAV1, AAV2, AAV2 variant, AAV3, AAV2/3 variant, AAV4, AAV5, AAV6, AAV7, AAV8, AAV9, AAV9.47, AAV9 (hu14), AAV9 K449R, AAV10, AAV11, AAV12, AAVrh8, AAVrh10, AAVDJ, or AAVDJ8, or any variant thereof. In some embodiments, the capsid serotype is AAVPHP.B, AAV9, AAV6, AAVrh10, and/or AAVDJ.

This disclosure also provides in some embodiments, nucleic acids, cells, AAV vectors, and AAV particles comprising the above viral genome.

AAV Production

The present disclosure provides methods for the generation of parvoviral particles, e.g. AAV particles, by viral genome replication in a viral replication cell.

In accordance with the disclosure, the viral genome comprising a payload region encoding an antibody, an antibody-based composition or fragment thereof, will be incorporated into the AAV particle produced in the viral replication cell. Methods of making AAV particles are well known in the art and are described in e.g., U.S. Pat. Nos. 6,204,059, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508, 5,064,764, 6,194,191, 6,566,118, 8,137,948; or International Publication Nos. WO1996039530, WO1998010088, WO1999014354, WO1999015685, WO1999047691, WO2000055342, WO2000075353, and WO2001023597; Methods In Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.,* 219:37-44 (1996); Zhao et al., *Vir.* 272:382-93 (2000); the contents of each of which are herein incorporated by reference in their entirety. In some embodiments, the AAV particles are made using the methods described in WO2015191508, the contents of which are herein incorporated by reference in their entirety.

Viral replication cells commonly used for production of recombinant AAV viral vectors include but are not limited to 293 cells, COS cells, HeLa cells, KB cells, and other mammalian cell lines as described in U.S. Pat. Nos. 6,156,303, 5,387,484, 5,741,683, 5,691,176, and 5,688,676; U.S. patent publication No. 2002/0081721, and International Patent Publication Nos. WO 00/47757. WO 00/24916, and WO 96/17947, the contents of each of which are herein incorporated by reference in their entireties.

In some embodiments, the AAV particles of the present disclosure may be produced in insect cells (e.g., Sf9 cells).

In some embodiments, the AAV particles of the present disclosure may be produced using triple transfection.

In some embodiments, the AAV particles of the present disclosure may be produced in mammalian cells.

In some embodiments, the AAV particles of the present disclosure may be produced by triple transfection in mammalian cells.

In some embodiments, the AAV particles of the present disclosure may be produced by triple transfection in HEK293 cells.

The present disclosure provides a method for producing an AAV particle comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In some embodiments, the present disclosure provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

In some embodiments, the viral construct vector(s) used for AAV production may contain a nucleotide sequence encoding the AAV capsid proteins where the initiation codon of the AAV VP1 capsid protein is a non-ATG, i.e., a suboptimal initiation codon, allowing the expression of a modified ratio of the viral capsid proteins in the production system, to provide improved infectivity of the host cell. In a non-limiting example, a viral construct vector may contain a nucleic acid construct comprising a nucleotide sequence encoding AAV VP1, VP2, and VP3 capsid proteins, wherein the initiation codon for translation of the AAV VP1 capsid protein is CTG, TTG, or GTG, as described in U.S. Pat. No. 8,163,543, the contents of which are herein incorporated by reference in its entirety.

In some embodiments, the viral construct vector(s) used for AAV production may contain a nucleotide sequence encoding the AAV rep proteins where the initiation codon of the AAV rep protein or proteins is a non-ATG. In some embodiments, a single coding sequence is used for the Rep78 and Rep52 proteins, wherein initiation codon for translation of the Rep78 protein is a suboptimal initiation codon, selected from the group consisting of ACG, TTG, CTG and GTG, that effects partial exon skipping upon expression in insect cells, as described in U.S. Pat. No. 8,512,981, the contents of which is herein incorporated by reference in its entirety, for example to promote less abundant expression of Rep78 as compared to Rep52, which may be advantageous in that it promotes high vector yields.

In some embodiments, the viral genome of the AAV particle optionally encodes a selectable marker. The selectable marker may comprise a cell-surface marker, such as any protein expressed on the surface of the cell including, but not limited to receptors, CD markers, lectins, integrins, or truncated versions thereof.

In some embodiments, selectable marker reporter genes are selected from those described in International Application No. WO 96/23810; Heim et al., Current Biology 2:178-182 (1996); Heim et al., Proc. Natl. Acad. Sci. USA (1995); or Heim et al., Science 373:663-664 (1995); WO 96/30540, the contents of each of which are incorporated herein by reference in their entireties).

The AAV viral genomes encoding an anti-tau antibody payload described herein may be useful in the fields of human disease, veterinary applications and a variety of in vivo and in vitro settings. The AAV particles of the present disclosure may be useful in the field of medicine for the treatment, prophylaxis, palliation or amelioration of neurological diseases and/or disorders. In some embodiments, the AAV particles are used for the prevention and/or treatment of a tauopathy.

Various embodiments herein provide a pharmaceutical composition comprising the AAV particles described herein and a pharmaceutically acceptable excipient.

Various embodiments herein provide a method of treating a subject in need thereof comprising administering to the subject a therapeutically effective amount of the pharmaceutical composition described herein.

Certain embodiments of the method provide that the subject is treated by a route of administration of the pharmaceutical composition selected from the group consisting of intravenous, intracerebroventricular, intraparenchymal, intrathecal, subpial and intramuscular, or a combination thereof. Certain embodiments of the method provide that the subject is treated for a tauopathy and/or other neurological disorder. In one aspect of the method, a pathological feature of the tauopathy or other neurological disorder is alleviated and/or the progression of the tauopathy or other neurological disorder is halted, slowed, ameliorated or reversed.

Various embodiments herein describe a method of decreasing the level of soluble tau in the central nervous system of a subject in need thereof comprising administering to said subject an effective amount of the pharmaceutical composition described herein.

Also described herein are compositions, methods, processes, kits and devices for the design, preparation, manufacture and/or formulation of AAV particles. In some embodiments, payloads, such as but not limited to anti-tau antibodies, may be encoded by payload constructs or contained within plasmids or vectors or recombinant adeno-associated viruses (AAVs).

The present disclosure also provides administration and/or delivery methods for vectors and viral particles, e.g., AAV particles, for the treatment or amelioration of neurological disease, such as, but not limited to tauopathy.

III. Formulation and Delivery

Pharmaceutical Compositions

Compounds and AAV particles disclosed herein may be prepared as pharmaceutical compositions. As used herein the term "pharmaceutical composition" refers to compositions including at least one active ingredient and, most often, a pharmaceutically acceptable excipient.

Relative amounts of the active ingredient (e.g. an antibody), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, at least 80% (w/w) active ingredient.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, rats, birds, including commercially relevant birds such as poultry, chickens, ducks, geese, and/or turkeys.

In some embodiments, compositions are administered to humans, human patients, or subjects.

Formulations

Compounds and AAV particles of the present disclosure can be formulated using one or more excipients to: (1) increase stability: (2) increase cell permeability; (3) permit the sustained or delayed release (e.g., from a sustained release formulation); and/or (4) alter the biodistribution (e.g., target an antibody to specific tissues or cell types). In addition to traditional excipients such as any and all solvents, dispersion media, diluents, or other liquid vehicles, dispersion or suspension aids, surface active agents, isotonic agents, thickening or emulsifying agents, preservatives, formulations of the present disclosure can include, without limitation, liposomes, lipid nanoparticles, polymers, lipoplexes, core-shell nanoparticles, peptides, proteins, transfected cells (e.g., for transplantation into a subject) and combinations thereof.

Pharmaceutical compositions described herein may be prepared by methods known or hereafter developed in the art of pharmacology. Such preparatory methods may include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition including a predetermined amount of the active ingredient. The amount of the active ingredient is generally equal to the dosage of the active ingredient which would be administered to a subject and/or a convenient fraction of such a dosage such as, for example, one-half or one-third of such a dosage.

In some embodiments, the AAV particles may be formulated in phosphate buffered saline (PBS), in combination with an ethylene oxide/propylene oxide copolymer (also known as Pluronic or poloxamer).

In some embodiments, the AAV particles may be formulated in PBS with 0.001% Pluronic acid (F-68) (poloxamer 188) at a pH of about 7.0.

In some embodiments, the AAV particles may be formulated in PBS with 0.001% Pluronic acid (F-68) (poloxamer 188) at a pH of about 7.3.

In some embodiments, the AAV particles may be formulated in PBS with 0.001% Pluronic acid (F-68) (poloxamer 188) at a pH of about 7.4.

In some embodiments, the AAV particles may be formulated in a solution comprising sodium chloride, sodium phosphate and an ethylene oxide/propylene oxide copolymer.

In some embodiments, the AAV particles may be formulated in a solution comprising sodium chloride, sodium phosphate dibasic, sodium phosphate monobasic and poloxamer 188/Pluronic acid (F-68).

In some embodiments, the AAV particles may be formulated in a solution comprising about 180 mM sodium chloride, about 10 mM sodium phosphate and about 0.001% poloxamer 188. In some embodiments, this formulation may be at a pH of about 7.3. The concentration of sodium chloride in the final solution may be 150 mM-200 mM. As non-limiting examples, the concentration of sodium chloride in the final solution may be 150 mM, 160 mM, 170 mM, 180 mM, 190 mM or 200 mM. The concentration of sodium phosphate in the final solution may be 1 mM-50 mM. As non-limiting examples, the concentration of sodium phosphate in the final solution may be 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, or 50 mM. The concentration of poloxamer 188 (Pluronic acid (F-68)) may be 0.0001%-1%. As non-limiting examples, the concentration of poloxamer 188 (Pluronic acid (F-68)) may be 0.0001%, 0.0005%, 0.001%, 0.005%, 0.01%, 0.05%,0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

In some embodiments, the AAV particles of the invention may be formulated in a solution comprising about 1.05% sodium chloride, about 0.212% sodium phosphate dibasic, heptahydrate, about 0.025% sodium phosphate monobasic, monohydrate, and 0.001% poloxamer 188, at a pH of about 7.4. As a non-limiting example, the concentration of AAV particle in this formulated solution may be about 0.001%. The concentration of sodium chloride in the final solution may be 0.1-2.0%, with non-limiting examples of 0.1%, 0.25%, 0.5%, 0.75%,0.95%,0.96%,0.97%,0.98%,0.99%, 1.00%,1.01%,1.02%,1.03%,1.04%. 1.05%, 1.06%, 1.07%, 1.08%, 1.09%, 1.10%, 1.25%, 1.5%,1.75%, or 2%. The concentration of sodium phosphate dibasic in the final solution may be 0.100-0.300% with non-limiting examples including 0.100%, 0.125%, 0.150%, 0.175%, 0.200%, 0.210%,0.211%,0.212%, 0.213%, 0.214%, 0.215%, 0.225%, 0.250%, 0.275%, 0.300%. The concentration of sodium phosphate monobasic in the final solution may be 0.010-0.050%, with non-limiting examples of 0.010%, 0.015%, 0.020%, 0.021%, 0.022%, 0.023%, 0.024%, 0.025%, 0.026%, 0.027%, 0.028%. 0.029%, 0.030%, 0.035%, 0.040%, 0.045%, or 0.050%. The concentration of poloxamer 188 (Pluronic acid (F-68)) may be 0.0001%-1%. As non-limiting examples, the concentration of poloxamer 188 (Pluronic acid (F-68)) may be 0.0001%, 0.0005%, 0.001%, 0.005%, 0.01%, 0.05%, 0.1%, 0.5%, or 1%. The final solution may have a pH of 6.8-7.7. Non-limiting examples for the pH of the final solution include a pH of 6.8, 6.9, 7.0, 7.1, 7.2, 7.3, 7.4, 7.5, 7.6, or 7.7.

Relative amounts of active ingredient (e.g. antibody), pharmaceutically acceptable excipients, and/or any additional ingredients in pharmaceutical compositions in accordance with the present disclosure may vary, depending upon the identity, size, and/or condition of subjects being treated and further depending upon route of administration. For example, compositions may include between 0.1% and 99% (w/w) of active ingredient. By way of example, compositions may include between 0.1% and 100%, e.g., between 0.5 and 50%, between 1-30%, between 5-80%, or at least 80% (w/w) active ingredient.

According to the present disclosure, compounds may be formulated for CNS delivery. Agents that cross the brain blood barrier may be used. For example, some cell penetrating peptides that can target molecules to the brain blood barrier endothelium may be used for formulation (e.g., Mathupala, *Expert Opin Ther Pat.,* 2009, 19, 137-140; the content of which is incorporated herein by reference in its entirety).

Excipients and Diluents

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by the United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparation are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of conventional excipient media may be contemplated within the scope of the present disclosure, except insofar as any conventional excipient media may be incompatible with certain substances or their derivatives, such as by producing any undesirable biological effects or otherwise interacting in a deleterious manner with any other component(s) of pharmaceutical compositions of the present disclosure.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Inactive Ingredients

In some embodiments, formulations of the present disclosure may include at least one inactive ingredient. As used herein, the term "inactive ingredient" refers to an agent that does not contribute to the activity of a pharmaceutical composition. In some embodiments, all, none or some of the inactive ingredients which may be used in formulations of the present disclosure may be approved by the US Food and Drug Administration (FDA).

Formulations disclosed herein may include cations or anions. Formulations may include $Zn^{2+}$, $Ca^{2+}$, $Cu^{2+}$, $Mn^{2+}$, $Mg^{+}$, or combinations thereof. As a non-limiting example, formulations may include polymers and complexes with metal cations (See e.g., U.S. Pat. Nos. 6,265,389 and 6,555,525, each of which is herein incorporated by reference in its entirety).

IV. Administration and Dosing

Administration

Compounds and compositions (e.g., AAV particles) of the present disclosure may be administered by any delivery route which results in a therapeutically effective outcome. These include, but are not limited to, enteral (into the intestine), gastroenteral, epidural (into the dura mater), oral (by way of the mouth), transdermal, intracerebral (into the cerebrum), intracerebroventricular (into the cerebral ventricles), epicutaneous (application onto the skin), intradermal (into the skin itself), subcutaneous (under the skin), nasal administration (through the nose), intravenous (into a vein), intravenous bolus, intravenous drip, intra-arterial (into an artery), intramuscular (into a muscle), intracardiac (into the heart), intraosseous infusion (into the bone marrow), intrathecal (into the spinal canal), intraparenchymal (into the substance of a tissue, e.g., brain tissue), intraperitoneal (infusion or injection into the peritoneum), intravesical infusion, intravitreal (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracoronal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis, and spinal.

In some embodiments, compositions may be administered in a way which allows them to cross the blood-brain barrier, vascular barrier, or other epithelial barrier. Compounds and compositions of the present disclosure may be administered in any suitable form, including, but not limited to, as a liquid solution, as a suspension, or as a solid form suitable for liquid solution or suspension in a liquid solution.

In some embodiments, delivery to a subject may be via a single route administration. In some embodiments, delivery to a subject may be via multi-site route of administration. Administration may include a bolus infusion. Administration may include sustained delivery over a period of minutes, hours, or days. Administration by infusion may include an infusion rate that may be changed depending on the subject, distribution, formulation, or other delivery parameter. Administration may be by more than one route of administration. As non-limiting examples, combination administrations may include intrathecal and intracerebroventricular administration, or intravenous and intraparenchymal administration.

Intravenous Administration

Compounds and compositions of the present disclosure may be administered to a subject by systemic administration. In some embodiments, systemic administration may include intravenous administration. Systemic administration may include intraarterial administration.

Compounds and compositions of the present disclosure may be administered to a subject by intravenous administration. In some embodiments, intravenous administration may be achieved by subcutaneous delivery. In some embodiments, the AAV particle is administered to the subject via focused ultrasound (FUS), e.g., coupled with the intravenous administration of microbubbles (FUS-MB), or MRI-guided FUS coupled with intravenous administration, e.g., as described in Terstappen et al. (Nat Rev Drug Discovery, doi.org/10.1038/s41573-021-00139-y (2021)), Burgess et al. (Expert Rev Neurother. 15(5): 477-491 (2015)), and/or Hsu et al. (PLOS One 8(2): 1-8), the contents of which are incorporated herein by reference in its entirety. In some embodiments, the AAV particle is administered to the subject intravenously. Intravenous administration may be achieved by a tail vein injection (e.g., in a mouse model). Intravenous administration may be achieved by retro-orbital injection.

Administration to the CNS

Compounds and compositions of the present disclosure may be administered to a subject by direct injection into the brain. As a non-limiting example, the brain delivery may be by intrahippocampal administration. Administration may be by intraparenchymal administration. In some embodiments, the intraparenchymal administration is to tissue of the central nervous system. Administration may be by intracranial delivery (See, e.g., U.S. Pat. No. 8,119,611; the content of which is incorporated herein by reference in its entirety). Administration may be by injection into the CSF pathway. Non-limiting examples of delivery to the CSF pathway include intrathecal and intracerebroventricular (e.g., intracisternal magna—ICM) administration. Administration to the brain may be by systemic delivery. As a non-limiting example, the systemic delivery may be by intravascular administration. As a non-limiting example, the systemic or intravascular administration may be intravenous. Administration may be by intraocular delivery route. A non-limiting example of intraocular administration includes an intravitreal injection.

Intramuscular Administration

In some embodiments, the AAV particles may be delivered by intramuscular administration. Whilst not wishing to be bound by theory, the multi-nucleated nature of muscle cells provides an advantage to gene transduction subsequent to AAV delivery. Cells of the muscle are capable of expressing recombinant proteins with the appropriate post-translational modifications. The enrichment of muscle tissue with vascular structures allows for transfer to the blood stream and whole-body delivery. Examples of intramuscular administration include systemic (e.g., intravenous), subcutaneous or directly into the muscle. In some embodiments, more than one injection is administered.

In some embodiments, the AAV particles of the present disclosure may be delivered by intramuscular delivery route. (See, e.g., U.S. Pat. No. 6,506,379; the content of which is incorporated herein by reference in its entirety). Non-limiting examples of intramuscular administration include an intravenous injection or a subcutaneous injection.

In some embodiments, the AAV particles of the present disclosure are administered to a subject and transduce muscle of a subject. As a non-limiting example, the AAV particles are administered by intramuscular administration.

In some embodiments, the AAV particles of the present disclosure may be administered to a subject by subcutaneous administration.

In some embodiments, the intramuscular administration is via systemic delivery.

In some embodiments, the intramuscular administration is via intravenous delivery.

In some embodiments, the intramuscular administration is via direct injection to the muscle.

In some embodiments, the muscle is transduced by administration, and this is referred to as intramuscular administration.

In some embodiments, the intramuscular delivery comprises administration at one site.

In some embodiments, the intramuscular delivery comprises administration at more than one site. In some embodiments, the intramuscular delivery comprises administration at two sites. In some embodiments, the intramuscular delivery comprises administration at three sites. In some embodiments, the intramuscular delivery comprises administration at four sites. In some embodiments, the intramuscular delivery comprises administration at more than four sites.

In some embodiments, intramuscular delivery is combined with at least one other method of administration.

In some embodiments, the AAV particles that may be administered to a subject by peripheral injections. Non-limiting examples of peripheral injections include intraperitoneal, intramuscular, intravenous, conjunctival, or joint injection. It was disclosed in the art that the peripheral administration of AAV vectors can be transported to the central nervous system, for example, to the motor neurons (e.g., U.S. Patent Publication Nos. US20100240739 and US20100130594; the content of each of which is incorporated herein by reference in their entirety).

In some embodiments, the AAV particles of the present disclosure may be administered to a subject by intraparenchymal administration. In some embodiments, the intraparenchymal administration is to muscle tissue.

In some embodiments, the AAV particles of the present disclosure are delivered as described in Bright et al 2015 (Neurobiol Aging. 36(2):693-709), the contents of which are herein incorporated by reference in their entirety.

In some embodiments, the AAV particles of the present disclosure are administered to the gastrocnemius muscle of a subject.

In some embodiments, the AAV particles of the present disclosure are administered to the bicep femorii of the subject.

In some embodiments, the AAV particles of the present disclosure are administered to the tibialis anterior muscles.

In some embodiments, the AAV particles of the present disclosure are administered to the soleus muscle.

Depot Administration

As described herein, in some embodiments, pharmaceutical compositions, AAV particles of the present disclosure are formulated in depots for extended release. Generally, specific organs or tissues ("target tissues") are targeted for administration.

In some aspects, pharmaceutical compositions, AAV particles of the present disclosure are spatially retained within or proximal to target tissues. Provided are methods of providing pharmaceutical compositions, AAV particles, to target tissues of mammalian subjects by contacting target tissues (which comprise one or more target cells) with pharmaceutical compositions, AAV particles, under conditions such that they are substantially retained in target tissues, meaning that at least 10, 20, 30, 40, 50, 60, 70, 80, 85, 90, 95, 96, 97, 98, 99, 99.9, 99.99 or greater than 99.99% of the composition is retained in the target tissues. Advantageously, retention is determined by measuring the amount of pharmaceutical compositions, AAV particles, that enter one or more target cells. For example, at least 1%, 5%, 10%, 20%, 30%, 40%, 50%, 60%, 70%, 80%, 85%, 90%, 95%, 96%, 97%, 98%, 99%, 99.9%, 99.99%, or greater than 99.99% of pharmaceutical compositions, AAV particles, administered to subjects are present intracellularly at a period of time following administration. For example, intramuscular injection to mammalian subjects may be performed using aqueous compositions comprising pharmaceutical compositions, AAV particles of the present disclosure and one or more transfection reagents, and retention is determined by measuring the amount of pharmaceutical compositions, AAV particles, present in muscle cells.

Certain aspects are directed to methods of providing pharmaceutical compositions, AAV particles of the present disclosure to a target tissues of mammalian subjects, by contacting target tissues (comprising one or more target cells) with pharmaceutical compositions, AAV particles under conditions such that they are substantially retained in such target tissues. Pharmaceutical compositions, AAV particles comprise enough active ingredient such that the effect of interest is produced in at least one target cell. In some embodiments, pharmaceutical compositions, AAV particles generally comprise one or more cell penetration agents, although "naked" formulations (such as without cell penetration agents or other agents) are also contemplated, with or without pharmaceutically acceptable carriers.

Dose and Regimen

The present disclosure provides methods of administering compounds and compositions in accordance with the disclosure to a subject in need thereof. Administration may be in any amount and by any route of administration effective for preventing, treating, managing, or diagnosing diseases, disorders, and/or conditions. The exact amount required may vary from subject to subject, depending on species, age, general condition of the subject, severity of disease, particular composition, mode of administration, mode of activity, and the like. Subjects may be, but are not limited to, humans, mammals, or animals. Compositions may be formulated in unit dosage form for ease of administration and uniformity of dosage. It will be understood, however, that the total daily usage of compositions of the present disclosure may be decided by an attending physician within the scope of sound medical judgment. Specific therapeutically effective, prophylactically effective, or appropriate diagnostic dose levels for any particular individual may vary depending upon a variety of factors including the disorder being treated and severity of the disorder; the activity of specific payloads employed; specific compositions employed; age, body weight, general health, sex, and diet of patients; time of administration, route of administration, and rate of excretion of compounds and compositions employed; duration of treatment; drugs used in combination or coincidental with compounds and compositions employed; and like factors well known in the medical arts.

In some embodiments, compounds and compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, or prophylactic, effect.

In some embodiments, the desired dosage may be delivered using multiple administrations (e.g., two, three, four, or more than four administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event.

Compounds and compositions of the present disclosure may be administered as a "pulse dose" or as a "continuous flow." As used herein, a "pulse dose" is a series of single unit doses of any therapeutic agent administered with a set frequency over a period of time. As used herein, a "continuous flow" is a dose of therapeutic agent administered continuously for a period of time in a single route/single point of contact, i.e., continuous administration event. A total daily dose, an amount given or prescribed in a 24-hour period, may be administered by any of these methods, or as a combination of these methods, or by any other methods suitable for pharmaceutical administration.

In some embodiments, delivery of AAV particles may comprise a total dose between about $1\times10^{6}$ VG and about $1\times10^{16}$ VG. In some embodiments, delivery may comprise a total dose of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $1.9\times10^{10}$, $2\times10^{10}$, $3\times10^{10}$, $3.73\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $2.5\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG. As a non-limiting example, the total dose is $1\times10^{13}$ VG. As another non-limiting example, the total dose is $2.1\times10^{12}$ VG.

In some embodiments, delivery of AAV particles may comprise a composition concentration between about $1\times10^{6}$ VG/mL and about $1\times10^{16}$ VG/mL. In some embodiments, delivery may comprise a composition concentration of about $1\times10^{6}$, $2\times10^{6}$, $3\times10^{6}$, $4\times10^{6}$, $5\times10^{6}$, $6\times10^{6}$, $7\times10^{6}$, $8\times10^{6}$, $9\times10^{6}$, $1\times10^{7}$, $2\times10^{7}$, $3\times10^{7}$, $4\times10^{7}$, $5\times10^{7}$, $6\times10^{7}$, $7\times10^{7}$, $8\times10^{7}$, $9\times10^{7}$, $1\times10^{8}$, $2\times10^{8}$, $3\times10^{8}$, $4\times10^{8}$, $5\times10^{8}$, $6\times10^{8}$, $7\times10^{8}$, $8\times10^{8}$, $9\times10^{8}$, $1\times10^{9}$, $2\times10^{9}$, $3\times10^{9}$, $4\times10^{9}$, $5\times10^{9}$, $6\times10^{9}$, $7\times10^{9}$, $8\times10^{9}$, $9\times10^{9}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/mL. In some embodiments, the delivery comprises a composition concentration of $1\times10^{13}$ VG/mL. In some embodiments, the delivery comprises a composition concentration of $2.1\times10^{12}$ VG/mL.

Combinations

Compounds and compositions of the present disclosure may be used in combination with one or more other therapeutic, prophylactic, research or diagnostic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, research, or diagnostic compositions in combination with agents that may improve their bioavailability, reduce and/or modify their metabolism, inhibit their excretion, and/or modify their distribution within the body.

V. Methods and Uses of the Compositions

In some embodiments, the present disclosure provides methods related to using and evaluating compounds and compositions for therapeutic and diagnostic applications.

Therapeutic Applications

In some embodiments, methods of the present disclosure include methods of treating therapeutic indications using compounds and/or compositions disclosed herein. As used herein, the term "therapeutic indication" refers to any symptom, condition, disorder, or disease that may be alleviated, stabilized, improved, cured, or otherwise addressed by some form of treatment or other therapeutic intervention. In some embodiments, methods of the present disclosure include treating therapeutic indications by administering antibodies disclosed herein.

As used herein the terms "treat," "treatment," and the like, refer to relief from or alleviation of pathological processes. In the context of the present disclosure insofar as it relates to any of the other conditions recited herein below, the terms "treat," "treatment." and the like mean to relieve or alleviate at least one symptom associated with such condition, or to slow or reverse the progression or anticipated progression of such condition.

By "lower" or "reduce" in the context of a disease marker or symptom is meant a significant decrease in such a level, often statistically significant. The decrease may be, for example, at least 10%, at least 20%, at least 30%, at least 40% or more, and is preferably down to a level accepted as within the range of normal for an individual without such a disorder.

By "increase" or "raise" in the context of a disease marker or symptom is meant a significant rise in such level, often statistically significant. The increase may be, for example, at least 10%, at least 20%, at least 30%, at least 40% or more, and is preferably up to a level accepted as within the range of normal for an individual without such disorder.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a compound or composition described herein, "effective against" a disease or disorder indicates that administration in a clinically appropriate manner results in a beneficial effect for at least a fraction of patients, such as an improvement of symptoms, a cure, a reduction in disease load, reduction in protein aggregation, reduction in neurofibrillary tangles, reduction in neurodegeneration, extension of life, improvement in quality of life, or other effect generally recognized as positive by medical doctors familiar with treating the particular type of disease or disorder.

A treatment or preventive effect is evident when there is a significant improvement, often statistically significant, in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more may be indicative of effective treatment. Efficacy for a given compound or composition may also be judged using an experimental animal model for the given disease as known in the art. When using an experimental animal model, efficacy of treatment is evidenced when a statistically significant modulation in a marker or symptom is observed.

Compounds of the present disclosure and additional therapeutic agents can be administered in combination. Such combinations may be in the same composition, or the additional therapeutic agents can be administered as part of a separate composition or by another method described herein.

In some embodiments, therapeutic indications that may be addressed by methods of the present disclosure include neurological indications. As used herein, a "neurological indication" refers to any therapeutic indication relating to the central nervous system (CNS). Methods of treating neurological indications according to the present disclosure may include administering compounds (e.g., antibodies) and/or compositions described herein. Neurological indications may include neurological diseases and/or disorders involving irregular expression or aggregation of tau. Such indications may include, but are not limited to neurodegenerative disease, Alzheimer's disease (AD), frontotemporal dementia and parkinsonism linked to chromosome 17 (FTDP-17), frontotemporal lobar degeneration (FTLD), frontotemporal dementia (FTD), chronic traumatic encephalopathy (CTE), progressive supranuclear palsy (PSP), Down's syndrome, Pick's disease, corticobasal degeneration (CBD), corticobasal syndrome, amyotrophic lateral sclerosis (ALS), a prion disease, Creutzfeldt-Jakob disease (CJD), multiple system atrophy, tangle-only dementia, stroke, and progressive subcortical gliosis.

In some embodiments, methods of treating neurological diseases and/or disorders in a subject in need thereof may include one or more of the steps of: (1) deriving, generating, and/or selecting an anti-tau antibody or fragment or composition thereof; and (2) administering the anti-tau antibody or fragment or composition thereof to the subject. Administration to the subject may slow, stop, or reverse disease progression. As a non-limiting example, disease progression may be measured by cognitive tests such as, but not limited to, the Mini-Mental State Exam (MMSE) or other similar diagnostic tool(s), known to those skilled in the art. As another non-limiting example, disease progression may be measured by change in the pathological features of the brain, CSF or other tissues of the subject, such as, but not limited to a decrease in levels of tau (either soluble or insoluble). In some embodiments, levels of insoluble hyperphosphorylated tau are decreased. In some embodiments, levels of soluble tau are decreased. In some embodiments, both soluble and insoluble tau are decreased. In some embodiments, levels of insoluble hyperphosphorylated tau are increased. In some embodiments, levels of soluble tau are increased. In some embodiments, both insoluble and soluble tau levels are increased. In some embodiments, neurofibrillary tangles are decreased in size, number, density, or combination thereof. In another embodiment, neurofibrillary tangles are increased in size, number, density or combination thereof.

Neurodegeneration

Neurodegenerative disease refers to a group of conditions characterized by progressive loss of neuronal structure and function, ultimately leading to neuronal cell death. Neurons are the building blocks of the nervous system(s) and are generally not able to reproduce and/or be replaced, and therefore neuron damage and/or death is especially devastating. Other, non-degenerating diseases that lead to neuronal cell loss, such as stroke, have similarly debilitating outcomes. Targeting molecules that contribute to deteriorating cell structure or function may prove beneficial generally for treatment of neurological indications, including neurodegenerative disease and stroke.

Certain molecules are believed to have inhibitory effects on neurite outgrowth, contributing to the limited ability of the central nervous system to repair damage. Such molecules include, but are not limited to, myelin associated proteins, such as, but not limited to, RGM (Repulsive guidance molecule), NOGO (Neurite outgrowth inhibitor), NOGO receptor, MAG (myelin associated glycoprotein), and MAI (myelin associated inhibitor). In some embodiments, anti-tau antibodies of the present disclosure may be utilized to target the aforementioned antigens (e.g., neurite outgrowth inhibitors).

Many neurodegenerative diseases are associated with aggregation of misfolded proteins, including, but not limited to, alpha synuclein, tau (as in tauopathies), amyloid B, prion proteins, TDP-43, and huntingtin (see, e.g. De Genst et al., 2014, Biochim Biophys Acta; 1844(11):1907-1919, and Yu et al., 2013, Neurotherapeutics.; 10(3): 459-472, references therein, all of which are herein incorporated by reference in their entirety). The aggregation results from disease-specific conversion of soluble proteins to an insoluble, highly ordered fibrillary deposit. This conversion is thought to prevent the proper disposal or degradation of misfolded proteins, thereby leading to further aggregation. Conditions associated with alpha synuclein misfolding and aggregation are referred to as "synucleinopathies." In some embodiments, anti-tau antibodies of the present disclosure may be utilized to target misfolded or aggregated proteins.

Alzheimer's Disease

Alzheimer Disease (AD) is a debilitating neurodegenerative disease currently afflicting more than 35 million people worldwide, with that number expected to double in coming decades. Symptomatic treatments have been available for many years but these treatments do not address the underlying pathophysiology. Recent clinical trials using these and other treatments have largely failed and, to date, no known cure has been identified.

The AD brain is characterized by the presence of two forms of pathological aggregates, the extracellular plaques composed of β-amyloid (AB) and the intracellular neurofibrillary tangles (NFT) comprised of hyperphosphorylated microtubule associated protein tau. Based on early genetic findings, B-amyloid alterations were thought to initiate disease, with changes in tau considered downstream. Thus, most clinical trials have been Aβ-centric. Although no mutations of the tau gene have been linked to AD, such alterations have been shown to result in a family of dementias known as tauopathies, demonstrating that changes in tau can contribute to neurodegenerative processes. Tau is normally a very soluble protein known to associate with microtubules based on the extent of its phosphorylation. Hyperphosphorylation of tau depresses its binding to microtubules and microtubule assembly activity. In tauopathies, the tau becomes hyperphosphorylated, misfolds and aggregates as NFT of paired helical filaments (PHF), twisted ribbons or straight filaments. In AD, NFT pathology, rather than plaque pathology, correlates more closely with neuropathological markers such as neuronal loss, synaptic deficits, severity of disease and cognitive decline. NFT pathology marches through the brain in a stereotyped manner and animal studies suggest a trans-cellular propagation mechanism along neuronal connections.

Several approaches have been proposed for therapeutically interfering with progression of tau pathology and preventing the subsequent molecular and cellular consequences. Given that NFT are composed of a hyperphosphorylated, misfolded and aggregated form of tau, interference at each of these stages has yielded the most avidly pursued set of targets. Introducing agents that limit phosphorylation, block misfolding or prevent aggregation have all generated promising results. Passive and active immunization with late stage anti-phospho-tau antibodies in mouse models have led to dramatic decreases in tau aggregation and improvements in cognitive parameters. It has also been suggested that introduction of anti-tau antibodies can prevent the trans-neuronal spread of tau pathology.

In some embodiments, anti-tau antibodies of the present disclosure may be used according to methods presented herein to treat subjects suffering from AD and other tauopathies. In some cases, methods of the present disclosure may be used to treat subjects suspected of developing AD or other tauopathies.

Frontotemporal Dementia and Parkinsonism Linked to Chromosome 17 (FTDP-17)

Although Alzheimer's disease is, in part, characterized by the presence of tau pathology, no known mutations in the tau gene have been causally linked to the disease. Mutations in the tau gene have been shown to lead to an autosomal dominantly inherited tauopathy known as frontotemporal dementia and parkinsonism linked to chromosome 17 (FTDP-17) and demonstrate that alterations in tau can lead to neurodegenerative changes in the brain. Mutations in the tau gene that lead to FTDP-17 are thought to influence splicing patterns, thereby leading to an elevated proportion of tau with four microtubule binding domains (rather than three). These molecules are considered to be more amyloidogenic, meaning they are more likely to become hyperphosphorylated and more likely to aggregate into NFT (Hutton, M. et al., 1998, Nature 393(6686):702-5, the contents of which are herein incorporated by reference in their entirety). Although physically and behaviorally, FTDP-17 patients can appear quite similar to Alzheimer's disease patients, at autopsy FTDP-17 brains lack the prominent Aβ plaque pathology of an AD brain (Gotz, J. et al., 2012, British Journal of Pharmacology 165(5):1246-59, the contents of which are herein incorporated by reference in their entirety). Therapeutically targeting the aggregates of tau protein may ameliorate and prevent degenerative changes in the brain and potentially lead to improved cognitive ability.

As of today, there is no treatment to prevent, slow the progression, or cure FTDP-17. Medication may be prescribed to reduce aggressive, agitated or dangerous behavior. There remains a need for therapy affecting the underlying pathophysiology, such as antibody therapies targeting tau protein.

In some embodiments, anti-tau antibodies of the present disclosure may be used to treat subjects suffering from FTDP-17. In some cases, methods of the present disclosure may be used to treat subjects suspected of developing FTDP-17.

Chronic Traumatic Encephalopathy

Unlike the genetically linked tauopathies, chronic traumatic encephalopathy is a degenerative tauopathy linked to repeated head injuries. The disease was first described in boxers whom behaved "punch drunk" and has since been identified primarily in athletes that play American football, ice hockey, wrestling and other contact sports. The brains of those suffering from CTE are characterized by distinctive patterns of brain atrophy accompanied by accumulation of hyperphosphorylated species of aggregated tau in NFT. In CTE, pathological changes in tau are accompanied by a number of other pathobiological processes, such as inflammation (Daneshvar, D. H. et al., 2015 Mol Cell Neurosci 66(Pt B): 81-90, the contents of which are herein incorporated by reference in their entirety). Targeting the tau aggregates may provide reprieve from the progression of the disease and may allow cognitive improvement.

As of today, there is no medical therapy to treat or cure CTE. The condition is only diagnosed after death, due to lack of in vivo techniques to identify CTE specific biomarkers. There remains a need for therapy affecting the underlying pathophysiology, such as antibody therapies targeting tau protein.

In some embodiments, anti-tau antibodies of the present disclosure may be used to treat subjects suffering from CTE. In some cases, methods of the present disclosure may be used to treat subjects suspected of developing CTE.

Prion Diseases

Prion diseases, also known as transmissible spongiform encephalopathies (TSEs), are a group of rare progressive conditions affecting the nervous system. The related conditions are rare and are typically caused by mutations in the PRNP gene which enables production of the prion protein. Gene mutations lead to an abnormally structured prion protein. Alternatively, the abnormal prion may be acquired by exposure from an outside source, e.g. by consumption of beef products containing the abnormal prion protein. Abnormal prions are misfolded, causing the brain tissue to degenerate rapidly. Prion diseases include, but are not limited to, Creutzfeldt-Jakob disease (CJD), Gerstmann-Sträussler-Scheinker syndrome (GSS), fatal insomnia (FFI), variably protease-sensitive prionopathy (VPSPr), and kuru. Prion diseases are rare. Approximately 350 cases of prion diseases are diagnosed in the US annually.

CJD is a degenerative brain disorder characterized by problems with muscular coordination, personality changes including mental impairment, impaired vision, involuntary muscle jerks, weakness and eventually coma. The most common categories of CJD are sporadic, hereditary due to a genetic mutation, and acquired. Sporadic CJD is the most common form affecting people with no known risk factors for the disease. The acquired form of CJD is transmitted by exposure of the brain and nervous system tissue to the prion. As an example, variant CJD (vCDJ) is linked to a bovine spongiform encephalopathy (BSE), also known as a 'mad cow' disease. CJD is fatal and patients typically die within one year of diagnosis.

Prion diseases are associated with an infectious agent consisting of an alternative conformational isoform of the prion protein, PrPSc. PrPSc replication is considered to occur through an induction of the infectious prion in the normal prion protein (PrPC). The replication occurs without a nucleic acid.

As of today, there is no therapy to manage or cure CJD, or other prion diseases. Typically, treatment is aimed at alleviating symptoms and increasing comfort of the patient, e.g. with pain relievers. There remains a need for therapy affecting the underlying pathophysiology.

In some embodiments, anti-tau antibodies of the present disclosure may be used to treat subjects suffering from a prion disease. In some cases, methods of the present disclosure may be used to treat subjects suspected of developing a prion disease.

Diagnostic Applications

In some embodiments, compounds (e.g., antibodies) and compositions of the present disclosure may be used as diagnostics. Anti-tau antibodies may be used to identify, label, or stain cells, tissues, organs, etc. expressing tau proteins. Anti-tau antibodies may be used to identify tau proteins present in tissue sections (e.g., histological tissue sections), including tissue known or suspected of having tau protein aggregates. Such antibodies may in some cases be used to identify subjects with neurological diseases and/or disorders. Tissue sections may be from CNS tissue.

In some embodiments, diagnostic methods of the present disclosure may include the analysis of one or more cells or tissues using immunohistochemical techniques. Such methods may include the use of one or more of any of the anti-tau antibodies described herein. Immunohistochemical methods may include staining tissue sections to determine the presence and/or level of one or more tau proteins or other markers. Tissue sections may be derived from subject CNS tissue (e.g., patient CNS, animal CNS, and CNS from animal models of disease). Tissue sections may come from formalin-fixed or unfixed fresh frozen tissues. In some cases, tissue sections come from formalin fixed paraffin-embedded (FFPE) tissues. Anti-tau antibodies described herein may be used as primary antibodies. Primary antibodies are used to contact tissue sections directly and bind to target epitopes. Primary antibodies may be directly conjugated with a detectable label or may be detected through the use of a detection agent such as a secondary antibody. In some embodiments, primary antibodies or detection agents include an enzyme that can be used to react with a substrate to generate a visible product (e.g., precipitate). Such enzymes may include, but are not limited to horse radish peroxidase, alkaline phosphatase, beta-galactosidase, and catalase.

Anti-tau antibodies described herein may be used according to immunohistochemical methods of the present disclosure to detect tau proteins in tissues or cells. In some cases, these antibodies are used to detect and/or determine the level of tau proteins in tissues. Levels of anti-tau antibodies used in immunohistochemical staining techniques may be varied to increase visible staining or to decrease background levels of staining. In some embodiments, antibody concentrations of from about 0.01 μg/ml to about 50 μg/ml are used. For example, antibody concentrations of from about 0.01 μg/ml to about 1 μg/ml, from about 0.05 ug/ml to about 5 μg/ml, from about 0.1 ug/ml to about 3 μg/ml, from about 1 μg/ml to about 10 μg/ml, from about 2 μg/ml to about 20 μg/ml, from about 3 μg/ml to about 25 μg/ml, from about 4 μg/ml to about 30 μg/ml, or from about 5 μg/ml to about 50 μg/ml may be used.

Levels and/or identities of tau proteins may be determined according to any methods known in the art for identifying proteins and/or quantitating protein levels. In some embodiments, such methods may include, but are not limited to mass spectrometry, array analysis (e.g., antibody array or protein array), Western blotting, flow cytometry, immunoprecipitation, surface plasmon resonance analysis, and ELISA. Tau proteins may in some cases be immunoprecipitated from samples prior to analysis. Such immunoprecipitation may be carried out using anti-tau antibodies disclosed herein. In some embodiments, tau proteins are immunoprecipitated from biological samples using anti-tau antibodies and then identified and/or quantitated using mass spectrometry.

In some embodiments, treatments are informed by diagnostic information generated using anti-tau antibodies. Accordingly, the present disclosure provides methods of treating neurological diseases and/or disorders that include obtaining a sample from a subject, diagnosing one or more neurological diseases and/or disorders using an anti-tau antibody, and administering a treatment selected based on the diagnosis. Such treatments may include treatment with anti-tau antibodies. Anti-tau antibodies administered according to such methods may include any of those described herein.

In some embodiments, the present disclosure provides methods of detecting and/or quantifying tau proteins in samples through the use of capture and detection antibodies. As used herein, a "capture antibody" is an antibody that binds an analyte in a way that it may be isolated or detected. Capture antibodies may be associated with surfaces or other carriers (e.g., beads). Detection antibodies are antibodies that facilitate observation of the presence or absence of an analyte. According to some methods of detecting and/or quantifying tau proteins, both capture antibodies and detection antibodies bind to tau proteins. Capture and detection antibodies may bind to different epitopes or regions of tau proteins to avoid competition for binding. In some embodiments, detection antibodies may be conjugated with a detectable label for direct detection. In some embodiments, binding of detection antibodies may be assessed using a secondary antibody that binds to a constant domain of the detection antibody or to a detectable label of the detection antibody. Capture, detection, and/or secondary antibodies may be derived from different species. This may prevent secondary antibodies from binding to both capture and detection antibodies.

VI. Kits and Devices

Kits

In some embodiments, compounds and composition of the present disclosure may be included in a kit. Such compounds and compositions may include anti-tau antibodies disclosed herein. In a non-limiting example, kits may include reagents for generating anti-tau antibodies, including tau protein antigens. Kits may include additional reagents and/or instructions for use, e.g., for creating or synthesizing anti-tau antibodies. Kits may include one or more buffers. Kits may include additional components, for example, solid supports or substrates for antibody or antigen attachment.

In some embodiments, the present disclosure includes kits for screening, monitoring, and/or diagnosis of a subject that include one or more anti-tau antibodies. Such kits may be used alone or in combination with one or more other methods of screening, monitoring, and/or diagnosis. Kits may include one or more of a buffer, a biological standard, a secondary antibody, a detection reagent, and a composition for sample pre-treatment (e.g., for antigen retrieval, blocking, etc.).

Kit components may be packaged. In some embodiments, kit components are packaged in aqueous media or in lyophilized form. Packaging may include one or more vial, test tube, flask, bottle, syringe or other container into which a component may be placed and/or suitably aliquoted. Where there are multiple kit components (labeling reagent and label may be packaged together), kits may include second, third or other additional containers into which additional components may be separately placed.

When kit components are provided in one and/or more liquid solutions, liquid solutions may be aqueous. Liquid solutions may be provided sterile. Kit components may be provided as dried powder(s). Dried powder components may be provided for reconstitution by kit users, e.g., by addition of suitable solvent. Solvents may also be provided in kits in one or more separate containers. In some embodiments, labeling dyes are provided in dried powder format.

Kits may include instructions for employing kit components as well other reagents not included in the kit. Instructions may include variations that can be implemented.

Devices

Any of the compounds and compositions described herein may be combined with, coated onto, or embedded in, or delivered by a device. Devices may include, but are not limited to, implants, stents, bone replacements, artificial joints, valves, pacemakers, or other implantable therapeutic devices.

VII. Definitions

At various places in the present specification, substituents of compounds of the present disclosure are disclosed in groups or in ranges. It is specifically intended that the present disclosure include each and every individual sub combination of the members of such groups and ranges.

About: As used herein, the term "about" means+/−10% of the recited value.

Activity: As used herein, the term "activity" refers to the condition in which things are happening or being done. Compositions may have activity and this activity may involve one or more biological events.

Adeno-associated virus: The term "adeno-associated virus" or "AAV" as used herein refers to members of the dependovirus genus comprising any particle, sequence, gene, protein, or component derived therefrom.

AAV Particle: As used herein, an "AAV particle" is a virus which comprises a viral genome with at least one payload region and at least one ITR region. AAV vectors of the present disclosure may be produced recombinantly and may be based on adeno-associated virus (AAV) parent or reference sequences. AAV particles may be derived from any serotype, described herein or known in the art, including combinations of serotypes (i.e., "pseudotyped" AAV) or from various genomes (e.g., single stranded or self-complementary). In addition, the AAV particle may be replication defective and/or targeted.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amelioration: As used herein, the term "amelioration" or "ameliorating" refers to a lessening of severity of at least one indicator of a condition or disease. For example, in the context of neurodegeneration disorder, amelioration includes the reduction of neuron loss.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about." as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached." and "tethered," when used with respect to two or more entities, means that the entities are physically associated or connected with one another, either directly or via a linker, to form a structure that is sufficiently stable so that the entities remain physically associated, e.g., under working conditions, e.g., under physiological conditions. An "association" need not be through covalent chemical bonding and may include other forms of association or bonding sufficiently stable such that the "associated" entities remain physically associated, e.g., ionic bonding, hydrostatic bonding, hydrophobic bonding, hydrogen bonding, or hybridization-based connectivity.

Bifunctional: As used herein, the term "bifunctional" refers to any substance, molecule or moiety which is capable of or maintains at least two functions. The functions may affect the same outcome or a different outcome. The structure that produces the function may be the same or different.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active.

Capsid: As used herein, the term "capsid" refers to the protein shell of a virus particle. In some embodiments, the term capsid may refer to the nucleic acid encoding the protein shell of the virus particle.

Chimeric antigen receptor (CAR): As used herein, the term "chimeric antigen receptor" or "CAR" refers to an artificial chimeric protein comprising at least one antigen specific targeting region (ASTR), a transmembrane domain and an intracellular signaling domain, wherein the antigen specific targeting region comprises a full-length antibody or a fragment thereof. As a non-limiting example, the ASTR of a CAR may be any of the antibodies presented herein or fragments thereof. Any molecule that is capable of binding a target antigen with high affinity can be used in the ASTR of a CAR. The CAR may optionally have an extracellular spacer domain and/or a co-stimulatory domain. A CAR may also be used to generate a cytotoxic cell carrying the CAR.

Compound: Compounds of the present disclosure include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Comprehensive Positional Evolution (CPE™): As used herein, the term "comprehensive positional evolution" refers to an antibody evolution technology that allows for mapping of the effects of amino acid changes at every position along an antibody variable domain's sequence. This comprehensive mutagenesis technology can be used to enhance one or more antibody properties or characteristics.

Comprehensive Protein Synthesis (CPS™): As used herein, the term "comprehensive protein synthesis" refers to a combinatorial protein synthesis technology that can be used to optimize antibody properties or characteristics by combining the best properties into a new, high-performance antibody.

Conditionally active: As used herein, the term "conditionally active" refers to a mutant or variant of a wild-type polypeptide, wherein the mutant or variant is more or less active at physiological conditions than the parent polypeptide. Further, the conditionally active polypeptide may have increased or decreased activity at aberrant conditions as compared to the parent polypeptide. A conditionally active polypeptide may be reversibly or irreversibly inactivated at normal physiological conditions or aberrant conditions.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of a polynucleotide or polypeptide or may apply to a portion, region or feature thereof.

Control Elements: As used herein, "control elements", "regulatory control elements", or "regulatory sequences" refers to promoter regions, polyadenylation signals, transcription termination sequences, upstream regulatory domains, origins of replication, internal ribosome entry sites ("IRES"), enhancers, and the like, which provide for the replication, transcription and translation of a coding sequence in a recipient cell. Not all of these control elements need always be present as long as the selected coding sequence is capable of being replicated, transcribed and/or translated in an appropriate host cell.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of providing a compound, substance, entity, moiety, cargo, or payload to a subject or destination.

Detectable label: As used herein, "detectable label" refers to one or more markers, signals, or moieties which are attached, incorporated or associated with another entity, which markers, signals or moieties are readily detected by methods known in the art including radiography, fluorescence, chemiluminescence, enzymatic activity, absorbance and the like. Detectable labels include, but are not limited to, radioisotopes, fluorophores, chemiluminescent compounds, chromophores, enzymes, enzyme co-factors, dyes, metal ions, ligands, biotin, avidin, streptavidin, haptens, quantum dots, and the like. Detectable labels may be located at any position in or on an entity with which they are conjugated or otherwise attached, incorporated, or associated. For example, when conjugated or otherwise attached, incorporated, or associated with a peptide or protein, detectable labels may be on, within, or between amino acids or may be attached or associated with the N- or C-termini.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Dosing regimen: As used herein, a "dosing regimen" is a schedule of administration or physician determined regimen of treatment, prophylaxis, or palliative care.

Encapsulate: As used herein, the term "encapsulate" means to enclose, surround or encase.

Engineered: As used herein, embodiments are "engineered" when they are designed to have a feature or property, whether structural or chemical, that varies from a starting compound, material or molecule (e.g., from a wild type or native molecule).

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment of a therapeutic indication as compared to the response obtained without administration of the agent.

Epitope: As used herein, an "epitope" refers to a surface or region on one or more entities that is capable of interacting with an antibody or other binding biomolecule. For example, a protein epitope may contain one or more amino acids and/or post-translational modifications (e.g., phosphorylated residues) which interact with an antibody. In some embodiments, an epitope may be a "conformational epitope," which refers to an epitope involving a specific three-dimensional arrangement of the entity(ies) having or forming the epitope. For example, conformational epitopes of proteins may include combinations of amino acids and/or post-translational modifications from folded, non-linear stretches of amino acid chains.

EvoMap™: As used herein, an EvoMap™ refers to a map of a polypeptide, wherein detailed informatics are presented about the effects of single amino acid mutations within the length of the polypeptide and their influence on the properties and characteristics of that polypeptide.

Expression: As used herein, "expression" of a gene, nucleic acid, or protein refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" refers to a material or mixture prepared according to a formula. Formulations may include a compound (e.g., an antibody) or substance combined with a carrier or excipient.

Fragment: A "fragment." as used herein, refers to a portion. For example, fragments of proteins may include polypeptides obtained by digesting full-length protein isolated from cultured cells.

Functional: As used herein, a "functional" biological molecule is a biological molecule in a form in which it exhibits a property and/or activity by which it is characterized. For example, a "functional" antibody may include an antibody that binds a specific target or that activates or inhibits a specific biological process.

Half maximal effective concentration: As used herein, the term "half maximal effective concentration" or "EC50" refers to the concentration of a substance necessary to increase a given reaction, activity or process by half. For example, when measuring binding of an antibody in a sample to a target using a binding assay (e.g., an ELISA assay), the EC50 is the concentration of antibody in the sample needed to yield 50% of the maximum binding that can be observed with that assay. Similarly, the term "half maximal inhibitory concentration" or "IC50" refers to a concentration necessary to reduce a given reaction or process by half. For example, the IC50 for an antibody capable of inhibiting a biological process is the concentration of antibody necessary in a sample to reduce the biological process by 50%. EC50 and IC50 values may be differ under specific time constraints and/or conditions.

Homology: As used herein, the term "homology" refers to the overall relatedness between polymeric molecules, e.g. between polynucleotide molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%,85%, 90%, 95%, or 99% identical or similar. The term "homologous" necessarily refers to a comparison between at least two sequences (polynucleotide or polypeptide sequences). In accordance with the disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the disclosure, two protein sequences are considered to be homologous if the proteins are at least about 50%, 60%, 70%, 80%, or 90% identical for at least one stretch of at least about 20 amino acids.

Heterologous Region: As used herein the term "heterologous region" refers to a region which would not be considered a homologous region.

Homologous Region: As used herein the term "homologous region" refers to a region which is similar in position, structure, evolution origin, character, form or function.

Identity: As used herein, the term "identity" refers to the overall relatedness between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H. and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)). In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that is altered or removed from the natural state, e.g., altered or removed from at least some of component with which it is associated in the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. Such polynucleotides could be part of a vector and/or such polynucleotides or polypeptides could be part of a composition, and still be isolated in that such vector or composition is not part of the environment in which it is found in nature. In some embodiments, an isolated nucleic acid is recombinant, e.g., incorporated into a vector.

Linker: As used herein "linker" refers to a molecule or group of molecules which connects two molecules. In some embodiments, linkers may be cleavable (e.g., through contact with an enzyme, change in pH, or change in temperature).

MicroRNA (miRNA or miR) binding site: As used herein, a "miR binding site" comprises a nucleic acid sequence (whether RNA or DNA, e.g., differ by "U" of RNA or "T" in DNA) that is capable of binding, or binds, in whole or in part to a microRNA (miR) through complete or partial hybridization. Typically, such binding occurs between the miR and the miR binding site in the reverse complement orientation. In some embodiments, the miR binding site is transcribed from the AAV vector genome encoding the miR binding site.

In some embodiments, a miR binding site may be encoded or transcribed in series. Such a "miR binding site series" or "miRBSs" may include two or more miR binding sites having the same or different nucleic acid sequence.

Modified: As used herein "modified" refers to a changed state or structure of a molecule. Molecules may be modified in many ways including chemically, structurally, and functionally.

Naturally occurring: As used herein, "naturally occurring" or "wild-type" means existing in nature without artificial aid, or involvement of the hand of man.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, primate, rabbit, reindeer, sheep, water buffalo, and yak.

Off-target: As used herein, "off-target" refers to unintended activity or binding to an entity other than an expected target.

Operably linked: As used herein, the phrase "operably linked" refers to a functional connection between two or more molecules, constructs, transcripts, entities, moieties or the like.

Particle: As used herein, a "particle" is a virus comprised of at least two components, a protein capsid and a polynucleotide sequence enclosed within the capsid (e.g., viral genome).

Patient: As used herein, "patient" refers to a subject who may seek or be in need of treatment, requires treatment, is receiving treatment, will receive treatment, or a subject who is under care by a trained professional for a particular disease or condition.

Payload: As used herein, "payload" refers to any substance being delivered by an agent. For example, payloads may include therapeutic agents conjugated to antibodies for delivery to a cell, tissue, or region harboring an epitope of the antibody.

Peptide: As used herein, "peptide" is less than or equal to 50 amino acids long, e.g., about 5, 10, 15, 20, 25, 30, 35, 40, 45, or 50 amino acids long.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient." as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspension or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* $17^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmaceutically acceptable solvate: The term "pharmaceutically acceptable solvate," as used herein, means a compound wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body: (M) Metabolism (or Biotransformation) is the irreversible transformation of parent compounds into daughter metabolites;

and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified." "purification" means to make substantially pure or clear from unwanted components, material defilement, admixture or imperfection. "Purified" refers to the state of being pure. "Purification" refers to the process of making pure.

Region: As used herein, the term "region" refers to a zone or general area. In some embodiments, when referring to a polypeptide or protein, a region may include a linear sequence of amino acids along the polypeptide or protein or may include a three-dimensional area, an epitope, or a cluster of epitopes. When referring to a polynucleotide, a region may include a linear sequence of nucleic acids along the polynucleotide or may include a three-dimensional area, secondary structure, or tertiary structure. Regions may include terminal regions. As used herein, the term "terminal region" refers to a region located at the end or "terminus" of a given entity. When referring to polypeptides, terminal regions may include N- and/or C-termini. N-terminus refers to the end of a polypeptide with a free amino acid amino group. C-terminus refers to the end of a polypeptide with a free amino acid carboxyl group. N- and/or C-terminal regions may refer to a single terminal functional group, single amino acid, or multiple amino acids located at either terminus. When referring to polynucleotides, terminal regions may include 5' and 3' termini. The 5' terminus refers to the end of a polynucleotide that includes a free nucleic acid phosphate group. The 3' terminus refers to the end of a polynucleotide that includes a free nucleic acid hydroxyl group. Polynucleotide terminal regions may refer to a single terminal functional group, single nucleotide, or multiple nucleotides located at a terminus.

RNA and DNA: As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. RNA and DNA can be single-stranded (i.e., ssRNA or ssDNA, respectively) or multi-stranded (e.g., double stranded, i.e., dsRNA and dsDNA, respectively). The term "messenger RNA" or "mRNA," as used herein, refers to a single stranded RNA that encodes an amino acid sequence of one or more polypeptide chains.

Sample: As used herein, the term "sample" refers to a portion or subset of larger entity. A sample from a biological organism or material is referred to herein as a "biological sample" and may include, but is not limited to, tissues, cells, and body fluids (e.g., blood, mucus, lymphatic fluid, synovial fluid, cerebrospinal fluid, saliva, amniotic fluid, amniotic cord blood, urine, vaginal fluid, and semen). Samples may further include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, and organs. Samples may further include a medium, such as a nutrient broth or gel, which may contain cellular components, such as proteins or nucleic acid molecules.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event. In some embodiments, a single unit dose is provided as a discrete dosage form (e.g., a tablet, capsule, patch, loaded syringe, vial, etc.).

Spacer: As used here, a "spacer" is generally any selected nucleic acid sequence of, e.g., 1, 2, 3, 4, 5, 6, 7, 8, 9, or 10 nucleotides in length, which is located between two or more consecutive miR binding site sequences. Spacers may also be more than 10 nucleotides in length, e.g., 20, 30, 40, or 50 or more than 50 nucleotides.

Split dose: As used herein, a "split dose" is the division of single unit dose or total daily dose into two or more doses.

Stable: As used herein "stable" refers to a state of an entity that is sufficiently robust to survive a certain degree of perturbation. For example, a stable compound or protein may remain intact during isolation to a useful degree of purity from a reaction mixture.

Stabilized: As used herein, the term "stabilize" or "stabilized" means to make or become stable.

Subject: As used herein, the term "subject" refers to any organism to which a compound, composition, method, kit, or device according to the present disclosure may be administered or applied, e.g., for experimental, diagnostic, prophylactic, and/or therapeutic purposes. Subjects can include animals (e.g., mammals such as mice, rats, rabbits, non-human primates, and humans) and plants. A subject receiving, requiring, eligible for, or seeking medical treatment is referred to herein as a "patient."

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially"

is therefore used herein to capture the potential lack of completeness inherent in many biological and chemical phenomena.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, neurodegenerative disease) may be characterized by one or more of the following: (1) a genetic mutation associated with development of the disease, disorder, and/or condition: (2) a genetic polymorphism associated with development of the disease, disorder, and/or condition: (3) increased and/or decreased expression and/or activity or disfunction of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to release of a compound or agent over a specific period of time, typically at a relatively controlled or consistent rate.

Synthetic: The term "synthetic" means produced, prepared, and/or manufactured by the hand of man. Synthetic polynucleotides, polypeptides, or other molecules of the present disclosure may be prepared using chemical or enzymatic processes.

Target: As used herein, the term "target" refers to an entity of interest or attention, which may include a subject, an organ, a tissue, a cell, a protein, a nucleic acid, biomolecule, or a group, complex, or portion of any of the foregoing. In some embodiments, a target may be a protein or epitope thereof for which an antibody has affinity or for which an antibody is desired, designed, or developed to have affinity for. As used herein, the term "target" may also be used to refer to an activity of an agent that is directed to a particular object. For example, an antibody that has affinity for a specific protein "X" may be said to target protein X or may be referred to as an antibody targeting protein X or referred to as a protein X-targeting antibody. Similarly, an object that is the subject of an agent's activity may be referred to as a "targeted" object. For example, where an antibody has affinity for a specific protein "X." protein X may be referred to as being targeted by the antibody.

Therapeutic Agent: The term "therapeutic agent" refers to any agent that, when administered to a subject, has a therapeutic, diagnostic, and/or prophylactic effect and/or elicits a desired biological and/or pharmacological effect. Therapeutic agents capable of producing a biological effect in living organisms are referred to herein as "drugs."

Therapeutically effective amount: As used herein, the term "therapeutically effective amount" means an amount of an agent (e.g., antibody or other therapeutic agent) to be delivered to a subject suffering from or susceptible to an infection, disease, disorder, and/or condition, that when delivered or administered in that amount is sufficient to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" neurodegenerative disease in a subject may refer to inhibiting neurodegeneration; promoting the health of neuronal cells; reversing, preventing, or reducing the formation of plaques or tangles in the brain; and/or reversing, preventing, or reducing memory loss or loss of other neurological functions or activities of the subject. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may refer to the wild type or native form of a biomolecule. Molecules may undergo a series of modifications whereby each modified molecule may serve as the "unmodified" starting molecule for a subsequent modification.

Vector: As used herein, a "vector" is any molecule or moiety which transports, transduces or otherwise acts as a carrier of a heterologous molecule. Vectors of the present disclosure may be produced recombinantly.

Viral genome: As used herein, a "viral genome" or "vector genome" is a polynucleotide comprising at least one inverted terminal repeat (ITR) and at least one encoded payload. A viral genome encodes at least one copy of the payload.

VIII. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a." "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

Examples

Example 1. Antigen Preparation

Antigen preparation was carried out to support mouse immunization and generation and characterization of anti-human tau antibodies. Enriched paired helical filament (ePHF; sarkosyl insoluble tau) including human microtubule-associated protein tau, isoform 2 (SEQ ID NO: 920) was prepared along with several tau protein antigens with different phosphorylated residues corresponding to pathological tau. Related sequences are presented in Table 19. Phosphorylated residues are double-underlined in the Table.

TABLE 19

Tau protein antigens

| Antigen | Sequence | SEQ ID NO |
|---|---|---|
| human microtubule-associated protein tau, isoform 2 | MAEPRQEFEVMEDHAGTYGLGDRKDQGGYTMHQDQEGDTDAGLKESPLQ TPTEDGSEEPGSETSDAKSTPTAEDVTAPLVDEGAPGKQAAAQPHTEIP EGTTAEEAGIGDTPSLEDEAAGHVTQARMVSKSKDGTGSDDKKAKGADG KTKIATPRGAAPPGQKGQANATRIPAKTPPAPKTPPSSGEPPKSGDRSG YSSPGSPGTPGSRSRTPSLPTPPTREPKKVAVVRTPPKSPSSAKSRLQT APVPMPDLKNVKSKIGSTENLKHQPGGGKVQI INKKLDLSNVQSKCGSK DNIKHVPGGGSVQIVYKPVDLSKVTSKCGSLGNIHHKP GGGQVEVKSEK LDFKDRVQSKIGSLDNITHVPGGGNKKIETHKLTFRENAKAKTDHGAEI VYKSPVVSGDTSPRHLSNVSSTGSIDMVDSPQLATLADEVSASLAKQGL | 920 |
| PT3 epitope peptide (pT212/pT217) | TPGSRSRIPSLPIPPTREPK | 921 |
| Peptide 5 (pT212/pS214/pT217) | GTPGSRSRIPSLPIPPTRE | 922 |
| Peptide 12 (pS396/pS404/pS409) | RENAKAKTDHGAEIVYKSPVVSGDTSPRHLSNVSSTG | 923 |
| Peptide 1 (AT120 epitope) | PTREPKKV | 924 |

Tau protein antigens were conjugated with keyhole limpet hemocyanin (KLH) for immunization. For ePHF antigen preparation, ePHF was isolated from fractions of AD or non-AD frontal cortical tissue. Cortical tissue fractions were prepared according to methods described by Greenberg and Davies (1990) with minor modification (Liu et al., J Neuroscience, 2016, the contents of which are herein incorporated by reference in their entirety). Briefly, brain tissue was homogenized with cold homogenization buffer (10 mM Tris/1 mM EDTA/0.8 M NaCl/10% sucrose, pH 7.4) with protease inhibitor (Roche Molecular Systems, Inc., Branchburg, NJ) and phosphatase inhibitors cocktail (ThermoFisher, Waltham, MA, catalog #78437) or 1 mM NaF/1 mM $Na_3VO_4$ in a Teflon glass homogenizer. Brain homogenate was then centrifuged at 27,000×g for 30 min at 4° C. The resulting supernatant was subjected to extraction with 1% (w/v)N-lauroylsarcosine in the presence of 1% (v/v) 2-mercaptoethanol at 37° C. for 2.5 h followed by centrifugation at 108,000×g for 30 min at room temperature. The pellet recovered from this centrifugation was quickly rinsed one time with 0.5 mL of PBS/tube. The rinsed PBS was discarded. Another 0.5 mL of PBS was added to each tube to dissolve PHF. PHF from 6 tubes were pooled and the pooled PHF solution was sonicated. The resulting solution was concentrated to ~5× and further sonicated. PHF samples were then analyzed by HT7 western for qualitative and PT3 ELISA quantitative assessment. PHF samples were then stored at −80° C.

Example 2. Immunization

Wild type and tau knockout mouse cohorts were immunized with ePHF or KLH-conjugated tau protein antigens described in Example 1. Sera from immunized mice were screened by enzyme-linked immunosorbent assay (ELISA) for the presence of antibodies binding to albumin-conjugated antigens. Immunized mice with sera testing positive for antigen-specific antibodies were used to prepare hybridoma cells. Supernatants from hybridoma cell culture medium were screened by direct ELISA to identify cells producing antigen-specific antibodies. Hybridoma clones producing antibodies with positive antigen binding were selected for subcloning and antibody sequence analysis.

Variable domain amino acid and nucleic acid sequences for selected clones are presented in Table 3, with each ID #corresponding to an antibody expressed by a selected hybridoma clone. Complementarity determining region (CDR) analysis was carried out to identify heavy chain CDRH1, CDRH2, and CDRH3 sequences and light chain CDRL1, CDRL2, and CDRL3 sequences. CDR amino acid sequences identified include those presented in Table 6.

Example 3. Tau Binding

Variable domain nucleic acid sequences from antibodies obtained from immunizations described above were used to prepare recombinant mouse IgG antibodies. These candidate antibodies were analyzed for binding to ePHF and specificity for ePHF over wild type tau by direct ELISA.

For direct ePHF and wildtype tau ELISA, plates were first coated with ePHF or wild type tau. Antigen solutions were prepared in PBS and 50 μL were pipetted into each well. Plates were covered and incubated for one hour at 37° C. or overnight at 4° C. Plates were then washed and blocked by addition of 150 μl of blocking buffer to each well and incubated one hour at room temperature. Plates were then washed before addition of serially diluted candidate antibody samples prepared in blocking buffer. Detection of candidate antibody binding was carried out by washing plates and adding a solution of enzyme-labeled secondary antibody in blocking buffer to each well. Secondary antibody binding was detected by addition of substrate and spectrophotometric analysis of resulting reaction product. Half maximal effective concentration (EC50) for antibody binding to ePHF and wild type tau are presented in Table 20.

TABLE 20

ELISA results

| ID# | ePHF EC50 (nM) | Wild type Tau EC50 (nM) |
|---|---|---|
| V0009 | 0.038 | No binding |
| V1004 | 0.069 | No binding |
| V0037 | 0.073 | No binding |
| V0004 | 0.083 | No binding |
| V0047 | 0.118 | No binding |
| V0024 | 0.125 | No binding |
| V00010 | 0.134 | No binding |
| V00011 | 0.171 | No binding |
| V0044 | 0.209 | No binding |
| V1003 | 0.234 | No binding |
| V2001 | 0.237 | No binding |
| V0020 | 0.351 | No binding |
| V1005 | 0.480 | No binding |
| V0021 | 0.571 | No binding |
| V0043 | 0.581 | No binding |
| V0045 | 0.618 | No binding |
| V0007 | 0.740 | No binding |
| V0006 | 0.861 | No binding |
| V0042 | 0.869 | No binding |
| V0008 | 1.541 | No binding |
| V0058 | 2.452 | No binding |
| V0003 | 2.833 | No binding |
| V0027 | 3.509 | No binding |
| V0026 | 5.610 | No binding |
| V0036 | 6.426 | No binding |
| V0031 | 8.800 | No binding |
| V0032 | 14.300 | No binding |
| V0050 | 17.950 | No binding |
| V0025 | 0.098 | Weak binding |
| V1001 | 0.401 | Weak binding |
| V0035 | 0.315 | 0.169 |
| V0034 | 0.351 | 0.140 |
| V00018 | 0.718 | 0.238 |
| V0049 | 0.053 | Not determined |
| V0022 | 0.070 | Not determined |
| V0023 | 0.110 | Not determined |
| V0001 | 0.126 | Not determined |
| V0028 | Weak binding | No binding |
| V0029 | Weak binding | No binding |
| V0046 | Weak binding | No binding |
| V0053 | Weak binding | No binding |
| V0054 | Weak binding | No binding |
| V0055 | Weak binding | No binding |
| V0059 | Weak binding | No binding |
| V0060 | Weak binding | No binding |
| V0062 | Weak binding | No binding |
| V0064 | Weak binding | No binding |
| V00019 | Weak binding | 0.285 |
| V0052 | Weak binding | Not determined |
| V0057 | Weak binding | Not determined |
| V2003 | Weak binding | Not determined |
| V00014 | No binding | No binding |
| V0038 | No binding | No binding |
| V0040 | No binding | No binding |
| V1002 | No binding | No binding |
| V2004 | No binding | No binding |
| V0002 | No binding | Not determined |
| V0030 | No binding | Not determined |
| V00016 | No binding | 0.141 |
| V0033 | No binding | 0.342 |

Follow up analysis of antibodies V0004, V0009, V0022, V0023, V0024, and V0052 indicated greater than 100-fold selectivity for ePHF over wild type tau. Further, these antibodies demonstrated low polyspecificity and good stability in solution at 1 mg/mL.

Example 4. Epitope Binning by Antibody Competition

Variable domain nucleic acid sequences from antibodies obtained from immunizations described above were used to prepare recombinant mouse IgG antibodies for iPHF affinity measurement and epitope binding competition analysis. Studies were carried out by Octet (ForteBio, Menlo Park, CA) analysis.

For iPHF affinity analysis, candidate antibodies were immobilized on anti-mouse IgG Fc capture (AMC) biosensor tips (ForteBio, cat #18-5088) in kinetic buffer (ForteBio, cat #18-1105). Biosensor tips were then washed before introduction of a solution of iPHF in kinetic buffer for analysis of iPHF association and dissociation with candidate antibodies. Affinity measurements were obtained using Data Analysis HT version 11.1 and corrected for background and high-frequency noise.

For epitope binding competition analysis, a process also referred to as "epitope binning." candidate antibodies were analyzed using a sandwich assay format, wherein a first "capture" antibody is attached to the Octet biosensor before antigen and a second antibody are sequentially introduced and biosensor readings are used to determine whether one or both antibodies bind to each antigen. Antibodies demonstrating competitive epitope binding were placed into the same or similar characterization category or "bin." Antibodies demonstrating simultaneous binding were placed into separate categories. PT3, IPN002, or C10.2 antibodies were used as capture antibodies and immobilized on AMC biosensor tips as described above. Biosensor tips were then washed and blocked in 10 g/ml MOPC. After a further wash, biosensor capture antibodies were associated with iPHF. Candidate antibodies were then analyzed for binding to iPHF. MOPC (non antigen-specific control) and PT3, IPN002, or C10.2 antibodies (in each case matching the biosensor antibody) were used as directly competing controls. Results are shown in Table 21.

TABLE 21

| Epitope binning results | |
|---|---|
| ID# | Antibody response |
| V0009 | Cross blocked by C10.2 |
| V0030 | Cross blocked by C10.2 |
| V0004 | Cross blocked by PT3 |
| V1003 | Cross blocked by PT3 |
| V1004 | Cross blocked by PT3 |
| V0001 | Cross blocked by PT3 and C10.2 |
| V0003 | Cross blocked by PT3 and C10.2 |
| V0006 | Cross blocked by PT3 and C10.2 |
| V0008 | Cross blocked by PT3 and C10.2 |
| V00010 | Cross blocked by PT3 and C10.2 |
| V0034 | Cross blocked by PT3 and C10.2 |
| V0038 | Cross blocked by PT3 and C10.2 |
| V0039 | Cross blocked by PT3 and C10.2 |
| V0040 | Cross blocked by PT3 and C10.2 |
| V0041 | Cross blocked by PT3 and C10.2 |
| V0042 | Cross blocked by PT3 and C10.2 |
| V0044 | Cross blocked by PT3 and C10.2 |
| V0045 | Cross blocked by PT3 and C10.2 |
| V0046 | Cross blocked by PT3 and C10.2 |
| V0047 | Cross blocked by PT3 and C10.2 |
| V0059 | Cross blocked by PT3 and C10.2 |
| V0060 | Cross blocked by PT3 and C10.2 |
| V2004 | Cross blocked by PT3 and C10.2 |

TABLE 21-continued

| Epitope binning results | |
|---|---|
| ID# | Antibody response |
| V0007 | Not cross blocked by IPN002, PT3, or C10.2 |
| V00011 | Not cross blocked by IPN002, PT3, or C10.2 |
| V00016 | Not cross blocked by IPN002, PT3, or C10.2 |
| V00018 | Not cross blocked by IPN002, PT3, or C10.2 |
| V00019 | Not cross blocked by IPN002, PT3, or C10.2 |
| V0020 | Not cross blocked by IPN002, PT3, or C10.2 |
| V0021 | Not cross blocked by IPN002, PT3, or C10.2 |
| V0022 | Not cross blocked by IPN002, PT3, or C10.2 |
| V0023 | Not cross blocked by IPN002, PT3, or C10.2 |
| V0024 | Not cross blocked by IPN002, PT3, or C10.2 |
| V0025 | Not cross blocked by IPN002, PT3, or C10.2 |
| V0026 | Not cross blocked by IPN002, PT3, or C10.2 |
| V0027 | Not cross blocked by IPN002, PT3, or C10.2 |
| V0031 | Not cross blocked by IPN002, PT3, or C10.2 |
| V0032 | Not cross blocked by IPN002, PT3, or C10.2 |
| V0035 | Not cross blocked by IPN002, PT3, or C10.2 |
| V0036 | Not cross blocked by IPN002, PT3, or C10.2 |
| V0049 | Not cross blocked by IPN002, PT3, or C10.2 |
| V0052 | Not cross blocked by IPN002, PT3, or C10.2 |
| V0054 | Not cross blocked by IPN002, PT3, or C10.2 |
| V0055 | Not cross blocked by IPN002, PT3, or C10.2 |
| V0057 | Not cross blocked by IPN002, PT3, or C10.2 |
| V0058 | Not cross blocked by IPN002, PT3, or C10.2 |
| V0002 | No binding to iPHF |
| V00014 | No binding to iPHF |
| V0028 | No binding to iPHF |
| V0029 | No binding to iPHF |
| V0033 | No binding to iPHF |
| V0061 | No binding to iPHF |
| V0062 | No binding to iPHF |
| V0063 | No binding to iPHF |
| V0064 | No binding to iPHF |

Candidate antibodies were identified that demonstrated cross blocking with PT3, C10.2, or both PT3 and C10.2. Further candidate antibodies were identified that did not demonstrate cross blocking with any of the antibodies tested or did not demonstrate binding to iPHF.

Example 5. Epitope Binning by Peptide Antigen

Variable domain nucleic acid sequences from antibodies obtained from immunizations described above were used to prepare recombinant mouse IgG antibodies for PHF tau epitope binning analysis by sandwich ELISA. Anti-tau antibodies AT120 (directed to peptide 1), PT3 (directed to peptide 5), C10.2 (directed to peptide 12), PT76, 6C5, and UCB D were used as capture antibodies in the assay. Capture antibodies were diluted in PBS at a concentration of 1 μg/ml and 50 μl of the solution was used to coat each assay plate well. Plates were covered and incubated overnight at 4° C. Plates were then washed and blocked by addition of 150 μl of blocking buffer to each well and incubated one hour at room temperature. Plates were again washed before coating with ePHF or wild type tau in blocking buffer followed by incubation for 1 hour at room temperature. Plates were then washed before addition of serially diluted candidate antibody samples prepared in blocking buffer. Detection of candidate antibody binding was carried out by washing plates and adding a solution of enzyme-labeled secondary antibody in blocking buffer to each well. Secondary antibody binding was detected by addition of substrate and spectrophotometric analysis of resulting reaction product. Epitope "bins" were determined for each candidate antibody tested based on observed competition (epitope blocking) by each anti-tau capture antibody tested. Results are shown in Table 22.

TABLE 22

| Epitope binning results | |
|---|---|
| ID# | Epitope bin |
| V0036 | C10.2 bin (Peptide 12) |
| V0049 | C10.2 bin (Peptide 12) |
| V0054 | C10.2 bin (Peptide 12) |
| V0055 | C10.2 bin (Peptide 12) |
| V0057 | C10.2 bin (Peptide 12) |
| V0058 | C10.2 bin (Peptide 12) |
| V0050 | C10.2 bin (Peptide 12); PT76-UCB D bin |
| V0004 | PT3 bin (Peptide 5) |
| V1001 | PT3 bin (Peptide 5) |
| V1003 | PT3 bin (Peptide 5) |
| V1004 | PT3 bin (Peptide 5) |
| V2001 | PT3 bin (Peptide 5) |
| V1005 | PT3 bin (Peptide 5); C10.2 bin (Peptide 12) |
| V00016 | PT76-UCB D bin |
| V00018 | PT76-UCB D bin |
| V00019 | PT76-UCB D bin |
| V0024 | PT76-UCB D bin |
| V0025 | PT76-UCB D bin |
| V0026 | PT76-UCB D bin |
| V0038 | PT76-UCB D bin |
| V0047 | PT76-UCB D bin |
| V00010 | PT76-UCB D bin |
| V0059 | Non-specific |
| V1002 | No binding |
| V2003 | No binding |
| V2004 | No binding |
| V2005 | No binding |
| V0001 | No binding |
| V0002 | No binding |
| V0003 | No binding |
| V0006 | No binding |
| V0007 | No binding |
| V0008 | No binding |
| V0009 | No binding |
| V00011 | No binding |
| V00014 | No binding |
| V0020 | No binding |
| V0021 | No binding |
| V0022 | No binding |
| V0023 | No binding |
| V0027 | No binding |
| V0028 | No binding |
| V0029 | No binding |
| V0030 | No binding |
| V0031 | No binding |
| V0032 | No binding |
| V0033 | No binding |
| V0034 | No binding |
| V0035 | No binding |
| V0037 | No binding |
| V0039 | No binding |
| V0040 | No binding |
| V0041 | No binding |
| V0042 | No binding |
| V0043 | No binding |
| V0044 | No binding |
| V0045 | No binding |
| V0046 | No binding |
| V0051 | No binding |
| V0052 | No binding |
| V0053 | No binding |
| V0060 | No binding |
| V0061 | No binding |
| V0062 | No binding |
| V0063 | No binding |
| V0064 | No binding |

Multiple antibodies competed for epitope binding with either C10.2 or PT3, with one antibody competing for epitope binding with both C10.2 and PT3. Multiple antibodies also competed for epitope binding with PT176 and UCB D, with one antibody competing for epitope binding with PT176, UCB D, and C10.2.

Example 6. Immunodepletion Screening

Variable domain nucleic acid sequences from antibodies obtained from immunizations described above were used to prepare recombinant mouse IgG antibodies for immunodepletion assay screening. Immunodepletion assays analyze the ability of antibody candidates to deplete target antigens from solution by assessing altered properties associated with the depleted solution. Here, tau RD Biosensor cells were used to analyze tau aggregation induced by ePHF in supernatants obtained from solutions subjected to immunodepletion with candidate antibodies. RD Biosensor cells yield a fluorescent signal in response to tau aggregation. For the assay, 500 nM to 0.8 nM antibody solutions (5 dilutions tested in total) were incubated for 30 minutes at room temperature with 10 mg/ml solutions of Protein G Dynabeads to yield antibody-coated beads. 10 nM ePHF was diluted in phosphate buffered saline and sonicated prior to incubation with antibody-coated bead preparations for 90 minutes at room temperature. Supernatant was then collected and diluted 1:5 before incubation at room temperature for 20 minutes with 1:1 lipofectamine 2000 (Thermo Fisher Scientific, Waltham, MA) in optimem (Thermo Fisher Scientific). 20 μl of the resulting solution was added to biosensor cell cultures (150 μl final medium volume). Cells were cultured for two days before fixation for fluorescence analysis. Nuclei were stained with Draq5 stain and nine 10× images per well (triplicate wells per condition) were captured by Cytation 5. Percentage of cells with tau aggregates was determined for each well and normalized against cells treated with MOPC-21 IgG control beads, which were used in parallel as a seeding control. Antibodies demonstrating tau aggregation inhibition in initial analyses were selected for dose response curve analysis to determine half maximal inhibitory concentration (IC50) for inhibiting tau aggregation. Average IC50 values (based on geometric mean) for each candidate antibody tested are shown in Table 23.

TABLE 23

| Aggregation inhibition | |
|---|---|
| ID# | Average IC50 (nM) |
| V0020 | 1.9 |
| V0052 | 3.0 |
| V0058 | 4.1 |
| V0021 | 4.7 |
| V0009 | 4.8 |
| V0031 | 5.8 |
| V0055 | 5.8 |
| V00016 | 6.1 |
| V0057 | 6.1 |
| V0054 | 6.3 |
| V0032 | 8.0 |
| V0050 | 9.0 |
| V0026 | 9.1 |
| V0027 | 9.3 |
| V0023 | 16.5 |
| V0022 | 18.2 |
| V0024 | 18.6 |
| V0036 | 20.4 |
| V0004 | 26.3 |
| V0053 | 26.4 |

Multiple antibodies demonstrated tau aggregation inhibition IC50 values of less than 30 nM, with 14 antibodies below 10 nM.

Example 7. Tissue Staining

Variable domain nucleic acid sequences from antibodies obtained from immunizations described above were used to prepare recombinant mouse IgG antibodies and tested for ability to bind pathological tau in human brain tissue sections. Cryo-preserved human brain tissue sections from patients with or without Alzheimer's Disease (AD) were mounted on glass slides and washed with PBS. Endogenous peroxidase activity in tissue sections was quenched for 30 minutes at room temperature using a solution of 0.9% hydrogen peroxide and 0.02% Triton-X 100 in 1×PBS. Tissue sections were then washed with PBS and incubated for 1 hour at room temperature with a blocking solution of 10% normal goat serum in PBS with 0.02% Triton-X 100. Candidate antibody solutions were prepared by 1:500 dilution in PBS with protein diluent. Tissue sections were incubated in candidate antibody solutions for 1 hour at room temperature before washing in PBS to remove unbound antibody. Tissue sections were then treated with solutions of biotinylated goat-anti mouse IgG in PBS with protein diluent and incubated for 1 hour at room temperature. Tissue sections were again washed in PBS and treated with a solution of avidin-peroxidase conjugate before incubation for 30 minutes at room temperature. Tissue sections were again washed in PBS prior to treatment with a 3,3' diaminobenzidine tetrahydrochloride (DAB) substrate solution to yield a brown enzymatic precipitate at sites of candidate antibody binding and peroxidase immunocomplex formation. Enzymatic reactions were allowed to proceed for about 1 minute before being halted by rinsing in PBS wash solution. Tissue sections were then mounted for microscopic evaluation of immunostaining (indicating candidate antibody binding). Immunostained tissue sections were ranked based on degree of staining observed. Results are shown in Table 24. In the Table, "−" indicates no staining, and "+," "+/++," "++," "++/+++," and "+++" indicate levels of positive staining from low to high. "+/−" indicates no staining, with the exception of some staining observed in non-disease tissue. Antibodies yielding stained cell nuclei are indicated.

TABLE 24

| Tissue staining results | | |
|---|---|---|
| ID# | Staining level in AD tissue | Staining level in non-AD tissue |
| V1003 | +++ | − |
| V0034 | +++ | − |
| V00016 | +++ | − |
| V0024 | +++ | − |
| V1001 | +++ | − |
| V1002 | +++ | − |
| V0009 | +++ | −/+ |
| V0004 | +++ | −/+ |
| V0007 | +++ | −/+ |
| V00018 | +++ | −/+ |
| V0022 | +++ | −/+ |
| V0023 | +++ | −/+ |
| V0025 | +++ | −/+ |
| V0033 | +++ | −/+ |
| V2001 | +++ | −/+ |
| V2003 | +++ | −/+ |
| V1005 | +++ | + (nuclear) |
| V1004 | +++ | +/− |
| V0037 | +++ | ++ |
| V0020 | ++ | + (nuclear) |
| V0021 | ++ | + (nuclear) |
| V0026 | ++ | ++ |
| V0053 | ++ | ++ |
| V0031 | +/++ | + |
| V0032 | +/++ | + |
| V0052 | +/++ | + |
| V0058 | +/++ | + |
| V0030 | +/++ | +/++ |
| V0057 | +/++ | +/++ |

TABLE 24-continued

| Tissue staining results | | |
|---|---|---|
| ID# | Staining level in AD tissue | Staining level in non-AD tissue |
| V0050 | +/++ | +/++ |
| V0027 | + | + |
| V0036 | + | + |
| V0054 | + | + |
| V0055 | + | + |
| V00010 | +++ | +++ |
| V0051 | ++ | + |
| V0043 | ++ | ++ |
| V0008 | +/++ | +/++ |
| V0061 | +/++ | +/++ |
| V00014 | +/− | +/− |
| V00019 | + | −/+ |
| V0063 | + | −/+ |
| V0064 | + | −/+ |
| V0001 | + | + |
| V0003 | + | + |
| V0006 | + | + |
| V0039 | + | + |
| V0040 | + | + |
| V0041 | + | + |
| V0042 | + | + |
| V0044 | + | + |
| V0045 | + | + |
| V0046 | + | + |
| V0047 | + | + |
| V0059 | + | + |
| V0060 | + | + |
| V00011 | + | + |
| V0035 | + | + |
| V0049 | + | + |
| V0002 | + | + |
| V0028 | + | + |
| V0029 | + | + |
| V0062 | + | + |
| V0038 | + | +/− |
| V2005 | −/+ | − |
| V2004 | −/+ | −/+ |

Multiple antibodies yielded positive staining in AD brain tissue sections with little or no positive staining observed in brain tissue sections from non-AD brain tissue.

Similar results were obtained using fixed human brain tissues when assessing antibodies V0004, V0009, V0022, V0023, V0024, and V0052. Similar results were also obtained for these antibodies when comparing brain tissue staining between wild type mice and FTD mutant tau transgenic mice carrying P301S tau mutations.

Example 8. iPHF Affinity Analysis

Anti-human tau antibodies were assessed for affinity for iPHF by Octet (ForteBio, Menlo Park, CA) analysis. Recombinant mouse IgG antibodies were prepared with clone-specific variable domain pairs selected from those presented in Table 3 and mouse IgG1 constant domains. Candidate antibodies were immobilized on biosensor tips (ForteBio) in kinetic buffer (ForteBio). Biosensor tips were then washed before introduction of a solution of iPHF in kinetic buffer for analysis of association and dissociation with candidate antibodies. Affinity measurements ($K_D$) were obtained using Data Analysis HT version 11.1 and corrected for background and high-frequency noise. Results are presented in Table 25.

TABLE 25

| Affinity analysis results | |
|---|---|
| ID# | iPHF $K_D$ (nM) |
| V0009 | 0.2 |
| V0022 | 0.3 |
| V0050 | 0.4 |
| V0052 | 0.6 |
| V0026 | 0.7 |
| V0058 | 1.0 |
| V0055 | 1.3 |
| V0024 | 2.8 |
| V0023 | 4.0 |
| V00016 | 5.5 |
| V0027 | 10.5 |
| V0021 | 15.1 |
| V0057 | 17.4 |
| V0032 | 17.5 |
| V0004 | 20.0 |
| V0020 | 32.7 |
| V0031 | 57.7 |
| V0054 | 105.0 |

The antibodies shown in Table 25 all demonstrated $K_D$ values less than 150 nM, with antibodies V0009, V0022, V0050, V0052, V0026, V0058, V0055, V0024, V0023, and V00016 demonstrating $K_D$ values less than 10 nM. Of the antibodies tested, all demonstrated weak or no affinity (greater than 200 nM $K_D$) for wild type tau, except for V00016, which demonstrated nearly equivalent affinity for wild type tau.

Example 9. Pepscan Epitope Analysis

Recombinant mouse IgG antibodies were prepared with clone-specific variable domain pairs selected from those presented in Table 3 and mouse IgG1 constant domains. Epitope analysis was carried out with different anti-tau antibodies using a peptide scanning approach (e.g., see Verelst, J. et al. Front Mol Biosci. 2020 Mar. 31; 7:48). Libraries of overlapping synthetic biotinylated peptides corresponding to phosphorylated human tau (Pepscan, Lelystad, NL) were obtained and used to coat assay plate wells, each with individual library members. Recombinant mouse IgG antibodies were prepared with clone-specific variable domain pairs selected from those presented in Table 3 and mouse IgG1 constant domains. Antibody binding to peptides in each well was analyzed using colorimetric detection of peptide-antibody complexes with labeled secondary antibody or by associating biotinylated peptides with streptavidin coated biosensors in assay wells and assessing antibody binding by bio-layer interferometry (BLI)-based detection.

Results indicated binding of V0022, V0023, and V0024 antibodies close to the tau C-terminus with affinity for peptides corresponding with residues 409-436 of human tau (SEQ ID NO: 920). These antibodies demonstrated the highest affinity (V0022 $K_D$=3.06×10$^{-10}$ M; V0023 $K_D$=2.07×10$^{-10}$ M; V0024 $K_D$=2.25×10$^{-10}$ M) for peptides corresponding with residues 413-430 of human tau (SEQ ID NO: 920).

Antibody V0052 demonstrated association with multiple regions of human tau indicating that the epitope on full length tau may be conformational (including multiple regions grouped together by protein folding). V0052 demonstrated affinity for peptides corresponding with residues 55-76, 159-194, 219-247, and 381-426 of human tau (SEQ ID NO: 920). Of these regions, V0052 affinity was greater for residues 57-72 ($K_D$=1.40×10$^{-8}$ M), 175-191 ($K_D$=7.24×10$^{-9}$ M), 223-238 ($K_D$=2.08×10$^{-9}$ M), and 383-400 ($K_D$=1.26×10$^{-8}$ M) of human tau (SEQ ID NO: 920), with the highest affinity for residues 223-238 of human tau (SEQ ID NO: 920) ($K_D$=2.08×10$^{-9}$ M).

V0009 demonstrated greatest affinity around residues 32-49 and 185-200 of human tau (SEQ ID NO: 920).

Example 10. CDR Sequence Analysis

CDR amino acid sequences associated with antibodies described above were aligned and assessed for relationship between sequence structure. Multiple sequence alignment in the corresponding CDR regions is performed using the web-based T-coffee program (suitable for multi-sequence alignment of relatively small sequences) at the EMBL-EBI website. A number of antibody groups were identified with high levels of sequence identity among CDR sequences analyzed, in some cases correlating with specific epitope and/or binding affinity.

Alignment Between Antibodies V0020 and V0021

Alignment between antibodies V0020 and V0021 is shown below.

| ID# | CDRH1 | CDRH2 | CDRH3 |
|---|---|---|---|
| V0020 | GYTFTSY (SEQ ID NO: 308) | NPNNSD (SEQ ID NO: 356) | ANYYGGSQFAY (SEQ ID NO: 409) |
| V0021 | GYTFTSN (SEQ ID NO: 313) | NPNNSE (SEQ ID NO: 357) | ANYYGGSQFAY (SEQ ID NO: 409) |

| ID# | CDRL1 | CDRL2 | CDRL3 |
|---|---|---|---|
| V0020 | RSSQSLVHSNGKTYLH (SEQ ID NO: 472) | KVSNRFS (SEQ ID NO: 525) | SQSTHVPFT (SEQ ID NO: 570) |
| V0021 | RSSQSLVHSNGKTYLH (SEQ ID NO: 472) | KVSNRFS (SEQ ID NO: 525) | SQSTHVPFT (SEQ ID NO: 570) |

VH CDR sequence alignment yielded a CDRH1 consensus sequence of GYTFTS [Y/N] (SEQ ID NO: 927), or more generally GYTFTSX (SEQ ID NO: 928), where X may be any amino acid, e.g., X is Y/F/N/Q; a CDRH2 consensus sequence of NPNNS [D/E] (SEQ ID NO: 929), or more generally NPNNSX (SEQ ID NO: 930), where X may be any amino acid, e.g., an amino acid with a negatively charged side chain; and a CDRH3 consensus sequence of ANYYGGSQFAY (SEQ ID NO: 409), which was conserved among antibodies in this group.

VL CDR sequence alignment demonstrated that light chain CDR sequences are completely conserved among antibodies in this group.

Alignment Between Antibodies V0022-V0024

As described above, antibodies V0022-V0024 demonstrated binding near the C-terminus of human tau, with highest affinity for peptides corresponding to residues 413-430 of human tau (SEQ ID NO: 920). In view of this overlap, CDR sequence alignment between antibodies V0022-V0024 was carried out and used to identify consensus sequences.

Alignment between antibodies V0022-V0024 is shown below.

| ID# | CDRH1 | CDRH2 | CDRH3 |
|---|---|---|---|
| V0022 | GFTFTRY (SEQ ID NO: 314) | NPNNGG (SEQ ID NO: 341) | GTGTGAMDY (SEQ ID NO: 410) |
| V0023 | GYTFTIF (SEQ ID NO: 315) | NPNNGG (SEQ ID NO: 341) | GTGTGAMDY (SEQ ID NO: 410) |
| V0024 | GYTFTRF (SEQ ID NO: 316) | NPNNGG (SEQ ID NO: 341) | GTGTGAMDY (SEQ ID NO: 410) |

| ID# | CDRL1 | CDRL2 | CDRL3 |
|---|---|---|---|
| V0022 | RSSQSLVHNNGITYLY (SEQ ID NO: 1154) | RVSNRFS (SEQ ID NO: 529) | FQGTHVPRT (SEQ ID NO: 571) |
| V0023 | RSSQSLVHSNGITHLY (SEQ ID NO: 474) | RVSNRFS (SEQ ID NO: 529) | FQGTHVPRT (SEQ ID NO: 571) |
| V0024 | RSSQSLVHSNGNTHLY (SEQ ID NO: 475) | RVSSRFS (SEQ ID NO: 530) | FQGTHVPRT (SEQ ID NO: 571) |

As described above, antibodies V0022-V0024 demonstrated binding near the C-terminus of human tau, with highest affinity for peptides corresponding to residues 413-430 of human tau (SEQ ID NO: 920).

VH CDR sequence alignment yielded a CDRH1 consensus sequence of G [F/Y] TFT [R/I] [Y/F] (SEQ ID NO: 931), or more generally G-X1-TFT-X2-X3 (SEQ ID NO: 932), where X1, X2, and X3 may be any amino acid, e.g., X1 and/or X3 may be an amino acid with a hydrophobic and/or aromatic side chain, such as F or Y, and/or X2 may be a positively charged residue (such as R, K, H) or a residue with aliphatic side chain (such as A, V, I, or L); a CDRH2 consensus sequence of NPNNGG (SEQ ID NO: 341), which was conserved among antibodies in this group; and a CDRH3 consensus sequence of GTGTGAMDY (SEQ ID NO: 410), which was conserved among antibodies in this group.

VL CDR sequence alignment yielded a CDRL1 consensus sequence of RSSQSLVH [N/S] NG [I/N] T [H/Y] LY (SEQ ID NO: 933), or more generally RSSQSLVH-X1-NG-X2-T-X3-LY (SEQ ID NO: 934), where X1, X2, and X3 may be any amino acid, e.g., X1 is Q/N/S/T and/or X2 is A/V/I/L/Q/N and/or X3 is H/R/K/Y/F; a CDRL2 consensus sequence of RVS [N/S] RFS (SEQ ID NO: 935), or more generally RVSXRFS (SEQ ID NO: 936), where X may be any amino acid, e.g., X is Q/N/S/T; and a CDRL3 consensus sequence of FQGTHVPRT (SEQ ID NO: 571), which was conserved among antibodies in this group.

Alignment Between Antibodies V0022-V0025

Alignment between antibodies V0022-V0025, and V0050 is shown below.

| ID# | CDRH1 | CDRH2 | CDRH3 |
|---|---|---|---|
| V0022 | GFTFTRY (SEQ ID NO: 314) | NPNNGG (SEQ ID NO: 341) | GTGTGAMDY (SEQ ID NO: 410) |
| V0023 | GYTFTIF (SEQ ID NO: 315) | NPNNGG (SEQ ID NO: 341) | GTGTGAMDY (SEQ ID NO: 410) |
| V0024 | GYTFTRF (SEQ ID NO: 316) | NPNNGG (SEQ ID NO: 341) | GTGTGAMDY (SEQ ID NO: 410) |
| V0025 | GFTFTRF (SEQ ID NO: 317) | NPNNGE (SEQ ID NO: 358) | GTGTGAMDY (SEQ ID NO: 410) |
| V0050 | GYTFTDY (SEQ ID NO: 297) | NPNNGG (SEQ ID NO: 341) | GRGMGYYALDY (SEQ ID NO: 433) |

| ID# | CDRL1 | CDRL2 | CDRL3 |
|---|---|---|---|
| V0022 | RSSQSLVHNNGITYLY (SEQ ID NO: 1154) | RVSNRFS (SEQ ID NO: 529) | FQGTHVPRT (SEQ ID NO: 571) |
| V0023 | RSSQSLVHSNGITHLY (SEQ ID NO: 474) | RVSNRFS (SEQ ID NO: 529) | FQGTHVPRT (SEQ ID NO: 571) |
| V0024 | RSSQSLVHSNGNTHLY (SEQ ID NO: 475) | RVSSRFS (SEQ ID NO: 530) | FQGTHVPRT (SEQ ID NO: 571) |
| V0025 | RSSQSLVHSTGNTYLY (SEQ ID NO: 476) | RVSTRFS (SEQ ID NO: 531) | FQGTHVPRT (SEQ ID NO: 571) |
| V0050 | GASENVYGALN (SEQ ID NO: 494) | GATNLAD (SEQ ID NO: 539) | QNVLTIPWT (SEQ ID NO: 586) |

VH CDR sequence alignment yielded a CDRH1 consensus sequence of G [F/Y] TFT [R/I/D] [Y/F] (SEQ ID NO: 937), or more generally G-X1-TFT-X2-X3 (SEQ ID NO: 938), where X1, X2 and X3 may be any amino acid, e.g., X1 and X3 are each independently F/Y and/or X2 is any residue (such as R/K/H/D/E/G/A/I/L/V); a CDRH2 consensus sequence of NPNNG [G/E] (SEQ ID NO: 939), or more generally NPNNGX (SEQ ID NO: 940), where X may be any amino acid, e.g., E/D/G/A/V/I/L; and a CDRH3 consensus sequence of G [T/R] G [T/M] G [absent/Y] [absent/Y] A [M/L] DY (SEQ ID NO: 941), or more generally G-X1-G-X2-G-X3-X4-A-X5-DY (SEQ ID NO: 942), where each of X1-X5 may be any amino acid and/or where X3 and/or X4 may be absent, e.g., X1 is S/T/R/K/H and/or X2 is S/T/V/L/A/I/M and/or X3 and X4 are each independently Y/F/absent and/or X5 is A/V/I/L/M.

VL CDR sequence alignment yielded a CDRL1 consensus sequence with from about 11 to about 17 amino acids with an amino acid sequence of [R/G] [S/A] S [Q/E] [S/N] [L/V] [V/Y] [H/G] [S/A/N] [N/T/L] [G/N] [I/N/absent] [T/absent] [H/Y/absent] [L/absent] [Y/absent], or more generally X1-X2-S-X3-X4-X5-X6-X7-X8-X9-X10-X11-X12-X13-X14-X15, where X1-X15 may be any amino acid and/or where X11, X12, X13, X14, and/or X15 may be absent, e.g., X1 is R/K/H/G/A/V/I/L and/or X2 is S/T/A/V/I/L and/or X3 is Q/N/E/D and/or X4 is S/T/N/Q and/or X5 is L/V/A/I and/or X6 is A/V/I/L/Y/F and/or X7 is H/R/K/G/A and/or X8 is S/T/A/V/I/L/N/Q and/or X9 is N/Q/A/I/L/V/M/S/T and/or X10 is G/A/N/Q and/or X11 is Q/N/A/V/I/L/absent and/or X12 is T/S/absent and/or X13 is H/R/K/Y/F/absent and/or X14 is A/V/I/L/absent and/or X15 is Y/F/absent; a CDRL2 consensus sequence with from about 3 to about 7 amino acids with an amino acid sequence of [R/G] [V/A] [S/T] [N/T/S] [R/L] [F/A] [S/D], or more generally X1-X2-X3-X4-X5-X6-X7, where X1, X2, X3, X4, X5, X6, and X7 may be any amino acid, e.g., X1 is R/K/H/G/A and/or X2 is V/A/I/L and/or X3 is S/T and/or X4 is N/Q/T/S and/or X5 is R/K/H/A/V/I/L and/or X6 is F/Y/A/V/I/L/G and/or X7 is S/T/D/E; and a CDRL3 consensus sequence with from about 9 amino acids with an amino acid sequence of [F/Q] [G/N] [G/V] [T/L] [H/T] [V/I] P [R/W] T, or more generally X1-X2-X3-X4-X5-X6-P-X7-T, where X1, X2, X3, X4, X5, X6, and X7 may be any amino acid, e.g., X1 is F/Y/Q/N and/or X2 is G/A/Q/N and/or X3 is G/A/V/I/L and/or X4 is T/S/A/V/I/L and/or X5 is H/R/K/T/S and/or X6 is V/I/A/L and/or X7 is R/K/H/W/F/Y.

Alignment Between Antibodies V0026, V0027, and V0032

Alignment between antibodies V0026, V0027, and V0032 is shown below.

| ID# | CDRH1 | CDRH2 | CDRH3 |
|---|---|---|---|
| V0026 | GYSFTDY (SEQ ID NO: 318) | FPGSDS (SEQ ID NO: 359) | PTVVARDYAMDY (SEQ ID NO: 411) |
| V0027 | GYTFTEY (SEQ ID NO: 319) | FPGRGS (SEQ ID NO: 360) | PTIVARDYAMDY (SEQ ID NO: 412) |
| V0032 | GYTFTDY (SEQ ID NO: 297) | YPGSGN (SEQ ID NO: 364) | PAYYSKDYAMEY (SEQ ID NO: 417) |

| ID# | CDRL1 | CDRL2 | CDRL3 |
|---|---|---|---|
| V0026 | RSSQSIVYSNGNTYLE (SEQ ID NO: 477) | KVSNRFS (SEQ ID NO: 525) | FQGSHVPYT (SEQ ID NO: 572) |
| V0027 | RSSQSIVHRNGNTYLE (SEQ ID NO: 478) | KVSNRFS (SEQ ID NO: 525) | FQGSHVPFT (SEQ ID NO: 573) |
| V0032 | RSSQSIVYTNGNTYLE (SEQ ID NO: 481) | KVSNRFS (SEQ ID NO: 525) | FQGSHVPYT (SEQ ID NO: 572) |

VH CDR sequence alignment yielded a CDRH1 consensus sequence of GY [S/T] FT [D/E] Y (SEQ ID NO: 949), or more generally GY-X1-FT-X2-Y (SEQ ID NO: 950), where X1 and X2 may be any amino acid, e.g., X1 is S/T and/or X2 is D/E/S/T; a CDRH2 consensus sequence of [F/Y] PG [S/R] [D/G] [S/N], or more generally X1-PG-X2-X3-X4, where X1-X4 may be any amino acid, e.g., X1 is F/Y and/or X2 is S/T/R/K/H and/or X3 is D/E/G/A and/or X4 is S/T/N/Q; and a CDRH3 consensus sequence of P [T/A] [V/V/Y] [V/Y] [A/S] [R/K] DYAM [D/E] Y (SEQ ID NO: 953), or more generally P-X1-X2-X3-X4-X5-DYAM-X6-Y (SEQ ID NO: 954), where X1-X6 may be any amino acid, e.g., X1 is T/S/A/V/I/L and/or X2 is V/I/A/L/Y/F and/or X3 is V/I/A/L/Y/F and/or X4 is A/V/I/L/S/T and/or X5 is R/K/H and/or X6 is D/E.

VL CDR sequence alignment yielded a CDRL1 consensus sequence of RSSQSIV [Y/H] [S/R/T] NGNTYLE (SEQ ID NO: 955), or more generally RSSQSIV-X1-X2-NGN-TYLE (SEQ ID NO: 956), where X1 and X2 may be any amino acid, e.g., X1 is Y/F/H/R/K and/or X2 is S/T/R/K/H; a CDRL2 consensus sequence of KVSNRFS (SEQ ID NO: 525), which was conserved among antibodies in this group; and a CDRL3 consensus sequence of FQGSHVP [Y/F] T (SEQ ID NO: 957), or more generally FQGSHVPXT (SEQ ID NO: 958), where X may be any amino acid, e.g., Y, F.

Alignment Between Antibodies V0026, V0027, V0031, and V0032

Alignment between antibodies V0026, V0027, V0031, and V0032 is shown below.

| ID# | CDRH1 | CDRH2 | CDRH3 |
|---|---|---|---|
| V0026 | GYSFTDY (SEQ ID NO: 318) | FPGSDS (SEQ ID NO: 359) | PTVVARDYAMDY (SEQ ID NO: 411) |
| V0027 | GYTFTEY (SEQ ID NO: 319) | FPGRGS (SEQ ID NO: 360) | PTIVARDYAMDY (SEQ ID NO: 412) |
| V0031 | GYTFTSY (SEQ ID NO: 308) | YPSNGG (SEQ ID NO: 363) | SSVVGRDYAMDY (SEQ ID NO: 416) |
| V0032 | GYTFTDY (SEQ ID NO: 297) | YPGSGN (SEQ ID NO: 364) | PAYYSKDYAMEY (SEQ ID NO: 417) |

| ID# | CDRL1 | CDRL2 | CDRL3 |
|---|---|---|---|
| V0026 | RSSQSIVYSNGNTYLE (SEQ ID NO: 477) | KVSNRFS (SEQ ID NO: 525) | FQGSHVPYT (SEQ ID NO: 572) |
| V0027 | RSSQSIVHRNGNTYLE (SEQ ID NO: 478) | KVSNRFS (SEQ ID NO: 525) | FQGSHVPFT (SEQ ID NO: 573) |
| V0031 | RSSQSIVHSNGNTYLE (SEQ ID NO: 479) | KVSNRFS (SEQ ID NO: 525) | FQGSHVPYT (SEQ ID NO: 572) |
| V0032 | RSSQSIVYTNGNTYLE (SEQ ID NO: 481) | KVSNRFS (SEQ ID NO: 525) | FQGSHVPYT (SEQ ID NO: 572) |

VH CDR sequence alignment yielded a CDRH1 consensus sequence of GY [S/T] FT [D/E/S] Y (SEQ ID NO: 959), or more generally GY-X1-FT-X2-Y (SEQ ID NO: 950), where X1 and X2 may be any amino acid, e.g., X1 is S/T and/or X2 is E/D/S/T; a CDRH2 consensus sequence of [F/Y] P [G/S] [S/R/N] [D/G] [S/G/N], or more generally X1-P-X2-X3-X4-X5, where X1-X5 may be any amino acid, e.g., X1 is F/Y and/or X2 is S/T/G/A/V/I/L and/or X3 is S/T/R/K/H/N/Q and/or X4 is D/E/G/A and/or X5 is S/T/N/Q/G/A; and a CDRH3 consensus sequence of [P/S] [T/A/S] [V/I/Y] [V/Y] [A/S/G] [R/K] DYAM [D/E] Y (SEQ ID NO: 962), or more generally X1-X2-X3-X4-X5-X6-DYAM-X7-Y (SEQ ID NO: 963), where X1-X7 may be any amino acid, e.g., X1 is S/T/P/A/I/L/V and/or X2 is T/S/A/V/I/L and/or X3 is A/V/I/L/Y/F and/or X4 is A/V/I/L/Y/F and/or X5 is A/V/I/L/G/S/T and/or X6 is R/K/H and/or X7 is E/D.

VL CDR sequence alignment yielded a CDRL1 consensus sequence of RSSQSIV [Y/H] [S/R/T] NGNTYLE (SEQ ID NO: 955), or more generally RSSQSIV-X1-X2-NGNTYLE (SEQ ID NO: 956), where X1 and X2 may be any amino acid, e.g., X1 is Y/F/H/R/K and/or X2 is S/T/R/K/H; a CDRL2 consensus sequence of KVSNRFS (SEQ ID NO: 525), which was conserved among antibodies in this group; and a CDRL3 consensus sequence of FQGSHVP [Y/F] T (SEQ ID NO: 957), or more generally FQGSHVPXT (SEQ ID NO: 958), where X may be any amino acid, e.g., Y and F.

Alignment Between Antibodies V0052, V0054, V0055, V0057, and V0058

As described in the Pepscan epitope analysis presented above, V0052 demonstrated affinity for peptides corresponding with residues 55-76, 159-194, 219-247, and 381-426 of human tau (SEQ ID NO: 920). Of these regions, V0052 affinity was greater for residues 57-72, 175-191, 223-238, and 383-400 of human tau (SEQ ID NO: 920). Binding of antibodies V0054, V0055, V0057, and V0058 to ePHF was shown by ELISA analysis to be blocked when ePHF was bound to plates coated with C10.2 capture antibody. C10.2 antibody is known to bind Peptide 12 (SEQ ID NO: 923) corresponding to amino acid residues 379-415 of human tau (SEQ ID NO: 920), which overlaps with residues involved in V0052 tau binding. In view of this overlap, CDR sequence alignment between antibodies V0052, V0054, V0055, V0057, and V0058 was carried out and used to identify consensus sequences.

Alignment between antibodies V0052, V0054, V0055, V0057, and V0058 is shown below.

| ID# | CDRH1 | CDRH2 | CDRH3 |
|---|---|---|---|
| V0052 | GFSLSTSAM (SEQ ID NO: 325) | YWDDD (SEQ ID NO: 362) | RRRGYGMDY (SEQ ID NO: 435) |
| V0054 | GFSLNTSGM (SEQ ID NO: 326) | YWDDD (SEQ ID NO: 362) | RVRGYGMDY (SEQ ID NO: 437) |
| V0055 | GFSLSTSGM (SEQ ID NO: 321) | YWDDD (SEQ ID NO: 362) | RVRYYAMDY (SEQ ID NO: 438) |
| V0057 | GFSLSTSGM (SEQ ID NO: 321) | YWDDD (SEQ ID NO: 362) | RVRYYAMDY (SEQ ID NO: 438) |
| V0058 | GFSLSTFGM (SEQ ID NO: 327) | YWDDD (SEQ ID NO: 362) | RKRSYGMDY (SEQ ID NO: 440) |

| ID# | CDRL1 | CDRL2 | CDRL3 |
|---|---|---|---|
| V0052 | KASQSVSNDVA (SEQ ID NO: 495) | YASNRCT (SEQ ID NO: 540) | QQDYRSPLT (SEQ ID NO: 587) |
| V0054 | KSSQSLLNSGNQKNYLA (SEQ ID NO: 496) | GTSTRES (SEQ ID NO: 542) | QNDHSHPYT (SEQ ID NO: 588) |
| V0055 | KSSQSLLNSGNQKNYLA (SEQ ID NO: 496) | GASTRES (SEQ ID NO: 543) | QNDHSHPYT (SEQ ID NO: 588) |
| V0057 | KSSQSLLNSGNQKNYLA (SEQ ID NO: 496) | GASTRES (SEQ ID NO: 543) | QNDHSHPYT (SEQ ID NO: 588) |
| V0058 | KSSQSLLSSGNQKNYLA (SEQ ID NO: 497) | GASTRES (SEQ ID NO: 543) | QNDHSHPYT (SEQ ID NO: 588) |

VH CDR sequence alignment yielded a CDRH1 consensus sequence of GFSL [S/N] T [S/F] [A/G] M (SEQ ID NO: 964), or more generally GFSL-X1-T-X2-X3-M (SEQ ID NO: 965), where X1-X3 may be any amino acid, e.g., X1 is S/T/N/Q and/or X2 is S/T/F/Y and/or X3 is A/V/I/L/G; a CDRH2 consensus sequence of YWDDD (SEQ ID NO: 362), which was conserved among antibodies of this group; and a CDRH3 consensus sequence of R [R/V/K] R [G/Y/S] Y [G/A] MDY (SEQ ID NO: 966), or more generally R-X1-R-X2-Y-X3-MDY (SEQ ID NO: 967), where X1-X3 may be any amino acid, e.g., X1 is R/K/H/A/V/I/L and/or X2 is G/A/V/I/L/S/T/Y/F and/or X3 is A/V/I/L/G.

VL CDR sequence alignment yielded a CDRL1 consensus sequence of K [A/S] SQS [V/L] [S/L] [N/S] [absent/S] [absent/G] [absent/N] [absent/Q] [absent/K] [absent/N] [D/Y] [V/L] A (SEQ ID NO: 968), or more generally K-X1-SQS-X2-X3-X4-X5-X6-X7-X8-X9-X10-X11-X12-A (SEQ ID NO: 969), where X1-X12 may be any amino acid and/or where one or more of X5-X10 may be absent, e.g., X1 is S/T/A/V/I/L and/or X2 is A/V/I/L and/or X3 is S/T/A/V/I/L and/or X4 is N/Q/S/T and/or X5 is S/T/absent and/or X6 is G/A/V/I/L/absent and/or X7 is N/Q/absent and/or X8 is N/Q/absent and/or X9 is K/R/H/absent and/or X10 is N/Q/absent and/or X11 is E/D/Y/F and/or X12 is A/V/I/L; a CDRL2 consensus sequence of [Y/G] [A/T] S [N/T] R [C/E] [T/S], or more generally X1-X2-S-X3-R-X4-X5, where X1-X5 may be any amino acid, e.g., X1 is Y/F/G/A/V/I/L and/or X2 is A/V/I/L/T/S and/or X3 is N/Q/T/S and/or X4 is C/S/E/D and/or X5 is T/S; and a CDRL3 consensus sequence of Q [Q/N] D [Y/H] [R/S] [S/H] P [L/Y] T (SEQ ID NO: 972), or more generally Q-X1-D-X3-X4-X5-P-X6-T (SEQ ID NO: 973), where X1-X6 may be any amino acid, e.g., X1 is Q/N and/or X2 is Y/F/H/R/K and/or X3 is R/K/H/S/T and/or X4 is S/T/H/K/R and/or A/V/I/L/Y/F.

Alignment Between Antibodies V0052, V0054, V0055, V0057, V0058, V0036, and V0049

As described in the Pepscan epitope analysis presented above, V0052 demonstrated affinity for peptides corresponding with residues 55-76, 159-194, 219-247, and 381-426 of human tau (SEQ ID NO: 920). Of these regions, V0052 affinity was greater for residues 57-72, 175-191, 223-238, and 383-400 of human tau (SEQ ID NO: 920). Binding of antibodies V0036, V0049, V0054, V0055, V0057, and V0058 to ePHF was shown by ELISA analysis to be blocked when ePHF was bound to plates coated with C10.2 capture antibody.

C10.2 antibody is known to bind Peptide 12 (SEQ ID NO: 923) corresponding to amino acid residues 379-415 of human tau (SEQ ID NO: 920), which overlaps with residues involved in V0052 tau binding. In view of this overlap, CDR sequence alignment between antibodies V0036, V0049, V0052, V0054, V0055, V0057, and V0058 was carried out and used to identify consensus sequences.

Alignment between antibodies V0052, V0054, V0055, V0057, V0058, V0036, and V0049 is shown below.

| ID# | CDRH1 | CDRH2 | CDRH3 |
|---|---|---|---|
| V0052 | GFSLSTSAM (SEQ ID NO: 325) | YWDDD (SEQ ID NO: 362) | RRRGYGMDY (SEQ ID NO: 435) |
| V0054 | GFSLNTSGM (SEQ ID NO: 326) | YWDDD (SEQ ID NO: 362) | RVRGYGMDY (SEQ ID NO: 437) |
| V0055 | GFSLSTSGM (SEQ ID NO: 321) | YWDDD (SEQ ID NO: 362) | RVRYYAMDY (SEQ ID NO: 438) |
| V0057 | GFSLSTSGM (SEQ ID NO: 321) | YWDDD (SEQ ID NO: 362) | RVRYYAMDY (SEQ ID NO: 438) |
| V0058 | GFSLSTFGM (SEQ ID NO: 327) | YWDDD (SEQ ID NO: 362) | RKRSYGMDY (SEQ ID NO: 440) |
| V0036 | GFSLSTSGM (SEQ ID NO: 321) | YWDDD (SEQ ID NO: 362) | RSRRGNYDY (SEQ ID NO: 421) |
| V0049 | GFSLSTSGM (SEQ ID NO: 321) | YWDDD (SEQ ID NO: 362) | RGYYSNGNYFDY (SEQ ID NO: 432) |

| ID# | CDRL1 | CDRL2 | CDRL3 |
|---|---|---|---|
| V0052 | KASQSVSNDVA (SEQ ID NO: 495) | YASNRCT (SEQ ID NO: 540) | QQDYRSPLT (SEQ ID NO: 587) |
| V0054 | KSSQSLLNSGNQKNYLA (SEQ ID NO: 496) | GTSTRES (SEQ ID NO: 542) | QNDHSHPYT (SEQ ID NO: 588) |
| V0055 | KSSQSLLNSGNQKNYLA (SEQ ID NO: 496) | GASTRES (SEQ ID NO: 543) | QNDHSHPYT (SEQ ID NO: 588) |
| V0057 | KSSQSLLNSGNQKNYLA (SEQ ID NO: 496) | GASTRES (SEQ ID NO: 543) | QNDHSHPYT (SEQ ID NO: 588) |
| V0058 | KSSQSLLSSGNQKNYLA (SEQ ID NO: 497) | GASTRES (SEQ ID NO: 543) | QNDHSHPYT (SEQ ID NO: 588) |
| V0036 | KSSQSLLDSDGKTYLN (SEQ ID NO: 484) | LVSKLDS (SEQ ID NO: 532) | WQGTHFPQT (SEQ ID NO: 576) |
| V0049 | SASSSISSTYLH (SEQ ID NO: 493) | RTSNLAS (SEQ ID NO: 538) | QQGSSIPRYT (SEQ ID NO: 585) |

VH CDR sequence alignment yielded a CDRH1 consensus sequence of GFSL [S/N] T [S/F] [A/G] M (SEQ ID NO: 964), or more generally GFSL-X1-T-X2-X3-M (SEQ ID NO: 965), where X1-X3 may be any amino acid, e.g., X1 is S/T/N/Q and/or X2 is S/T/F/Y and/or X3 is G/A/I/L/V; a CDRH2 consensus sequence of YWDDD (SEQ ID NO: 362), which was conserved among antibodies of this group; and a CDRH3 consensus sequence of R [R/V/K/S/G] [Y/R] [Y/absent] [S/absent] [absent/N] [G/S/Y/R] [Y/N/G] [G/A/Y/N] [M/F/Y] DY, or more generally R-X1-X2-X3-X4-X5-X6-X7-X8-X9-DY, where each of X1-X9 may be any amino acid and/or where one or more of X3-X5 may be absent, e.g., X1 is R/K/H/A/V/I/L/G/S/T and/or X2 is Y/F/R/K/H and/or X3 is Y/F/absent and/or X4 is S/T/absent and/or X5 is N/Q/absent and/or X6 is G/A/V/I/L/S/T/Y/F/R/K/H and/or X7 is Y/F/N/Q/G/A/V/I/L and/or X8 is G/A/V/I/L/Y/F/N/Q and/or X9 is M/F/Y.

VL CDR sequence alignment yielded a CDRL1 consensus sequence of [K/S] [S/A] S [Q/S] S [L/V/V] [L/S] [N/S/D] [D/S/T] [V/G/D/Y] [N/G/absent] [Q/absent] [K/absent] [N/T/absent] [Y/absent] [L/absent] [A/H/N], or more generally X1-X2-S-X3-S-X4-X5-X6-X7-X8-X9-X10-X11-X12-X13-X14-X15, where each of X1-X15 may be any amino acid and/or where one or more of X9-X14 may be absent, e.g., X1 is K/R/H/S/T and/or X2 is S/T/A/V/I/L and or X3 is Q/N/S/T and/or X4 is L/I/V/A and/or X5 is A/V/I/L/S/T and/or X6 is N/Q/S/T/D/E and/or X7 is D/E/S/T and/or X8 is G/A/V/I/L/D/E/Y/F and/or X9 is N/Q/G/A/absent and/or X10 is Q/N/absent and/or X11 is K/R/H/absent and/or X12 is N/Q/T/S/absent and/or X13 is Y/F/absent and/or X14 is A/V/I/L/absent and/or X15 is A/V/I/L/H/K/R/N/Q; a CDRL2 consensus sequence of [Y/G/L/R] [A/T/V] S [N/T/K] [R/L] [C/E/D/A] [T/S], or more generally X1-X2-S-X3-$X_4$-X5-X6, where X1-X6 may be any amino acid, e.g., X1 is Y/F/G/A/V/I/L/R/K/H and/or X2 is A/V/I/L/T/S and/or X3 is N/Q/T/S/K/R/H and/or X4 is R/K/H/A/V/I/L and/or X5 is C/S/E/D/A/V/I/L and/or X6 is T/S; and a CDRL3 consensus sequence of [W/Q] [Q/N] [G/D] [T/S/Y/H] [H/S/R] [F/I/S/H] P [Q/R/L/Y] [absent/Y] T, or more generally X1-X2-X3-X4-X5-X6-P-X7-X8-T, where each of X1-X8 may be any amino acid and/or where X8 may be absent, e.g., X1 is Q/N/W/F/Y and/or X2 is Q/N and/or X3 is G/A/V/I/L/D/E and/or X4 is T/S/Y/F/H/K/R and/or X5 is H/K/R/S/T and/or X6 is F/Y/A/V/I/L/S/T/H/K/R and/or X7 is Q/N/R/K/H/A/V/I/L/Y/F and/or X8 is Y/F/absent.

Example 11. Passive Immunotherapy Seeding Model Analysis

A passive immunotherapy seeding model was used to assess different anti-tau antibodies. For assessments, recombinant mouse IgG antibodies were prepared with clone-specific variable domain pairs selected from those presented in Table 3 and mouse IgG1 constant domains. In the model, FTD mutant tau transgenic mice carrying P301S tau mutations were used. Seeding was carried out by weekly intraparenchymal infusion of 75 ng ePHF to CAI hippocampal regions of study mice, beginning at 8 weeks of age and continuing for 6 weeks. Antibodies were administered to mice at a dose of 40 mg/kg by intraperitoneal injection. Administration was carried out 7 and 3 days prior to seeding and on days 4, 11, 18, 25, and 32 after initiation of seeding. Effect of antibody treatment on pathogenic tau level was determined in each case by ELISA analysis of ipsilateral hippocampal sample immunoreactivity with AT8 antibody, which is specific for pathogenic tau. Percent decrease in AT8 reactivity between samples from vehicle (control) treated mice and mice treated with various antibodies are presented in Table 26.

TABLE 26

| AT8 reactivity | |
|---|---|
| Treatment | % AT8 immunoreactivity relative to control |
| V0009 | 75% |
| V0023 | 49% |
| V0052 | 83% |
| PHF1 | 59% |

Each of the antibodies tested yielded samples with reduced AT8 reactivity, with V0023 and PHF1 yielding the greatest reductions over samples from control mice and V0023 demonstrating the greatest efficacy.

Example 12. Engineering Viral Genomes for the Expression of Anti-Tau Antibodies Viral genomes are designed for AAV delivery of anti-tau antibodies or variants thereof. Payload regions comprising or encoding antibody sequences provided in any of Tables 1-7 are cloned into viral genomes. The viral genomes may include, besides the antibody coding regions, any one or more of each of the following, a 5' ITR, a promoter (may have several components), one or more intron or exon sequences, one or more signal sequences, one or more linker sequences, a tag sequence, a polyadenylation sequence, a filler sequence and a 3'ITR. Sequence components may be selected from sequences provided in Tables 10-18.

A series of viral genomes are generated, wherein the order of heavy and light chains is alternated with respect to 5' to 3' direction. When read 5' to 3', viral genomes encoding a heavy chain antibody sequence, a linker region, and a light chain antibody sequence (heavy-linker-light) are prepared. Viral genomes encoding a light chain antibody sequence, a linker region, and a heavy chain antibody sequence (light-linker-heavy) are also prepared.

The viral genomes for expression of anti-tau antibodies are incorporated into AAV particles (e.g., using an AAV1, AAV2, AAV2 variant, AAV2/3 variant, or VOY101 capsid).

Example 13. Production and Purification of AAV Particles

Any of the viral genomes contemplated herein may be encapsulated in an AAV capsid to generate an AAV particle. AAV particles may be produced using methods known in the art, such as, for example, triple transfection or baculovirus mediated virus production. Any suitable permissive or packaging cell known in the art may be employed to produce the particles. Mammalian cells are often preferred. Also preferred are trans-complementing packaging cell lines that provide functions deleted from a replication-defective helper virus. e.g., 293 cells or other E1a trans-complementing cells.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes.

Recombinant AAV virus particles are, in some cases, produced and purified from culture supernatants according to the procedure as described in US20160032254, the contents of which are incorporated by reference. Production may also involve methods known in the art including those using 293T cells, sf9 insect cells, triple transfection or any suitable production method.

In some cases, 293T cells (adhesion/suspension) are transfected with polyethyleneimine (PEI) with plasmids required for production of AAV, i.e., AAV2 rep, an adenoviral helper construct and an ITR flanked transgene cassette. The AAV2 rep plasmid also contains the cap sequence of the particular virus being studied. Twenty-four hours after transfection (no medium changes for suspension), which occurs in DMEM/F17 with/without serum, the medium is replaced with fresh medium with or without serum. Three (3) days after transfection, a sample is taken from the culture medium of the 293 adherent cells. Subsequently cells are scraped, or suspension cells are pelleted, and transferred into a receptacle. For adhesion cells, after centrifugation to remove cellular pellet, a second sample is taken from the supernatant after scraping. Next, cell lysis is achieved by three consecutive freeze-thaw cycles (−80 C to 37 C) or adding detergent triton. Cellular debris is removed by centrifugation or depth filtration and sample 3 is taken from the medium. The samples are quantified for AAV particles by DNase resistant genome titration by DNA qPCR. The total production yield from such a transfection is equal to the particle concentration from sample 3 described above.

AAV particle titers are measured according to genome copy number (genome particles per milliliter). Genome particle concentrations are based on DNA qPCR of the vector DNA as previously reported (Clark et al. (1999) Hum. Gene Ther., 10:1031-1039; Veldwijk et al. (2002) Mol. Ther., 6:272-278).

What is claimed is:

1. An antibody that binds to tau comprising a heavy chain variable region (VH) comprising a heavy chain complementarity determining region 1 (HC CDR1), an HC CDR2, and an HC CDR3, and a light chain variable region (VL) comprising a light chain complementarity determining region 1 (LC CDR1), an LC CDR2, and an LC CDR3, wherein:

(i) the HC CDR1 comprises the amino acid sequence, $X_1X_2$WMH wherein $X_1$ is R or I; and $X_2$ is Y or F, the HC CDR2 comprises the amino acid sequence of SEQ ID NO: 1184, and the HC CDR3 comprises the amino acid sequence of SEQ ID NO: 410; and the LC CDR1 comprises the amino acid sequence of SEQ ID NO: 1185, the LC CDR2 comprises the amino acid sequence of SEQ ID NO: 1182, and the LC CDR3 comprises the amino acid sequence of SEQ ID NO: 571;

(ii) the HC CDR1 comprises the amino acid sequence of SEQ ID NO: 1186, the HC CDR2 comprises the amino acid sequence of SEQ ID NO: 1187, and the HC CDR3 comprises the amino acid sequence of SEQ ID NO: 1167; and the LC CDR1 comprises the amino acid sequence of SEQ ID NO: 1188, the LC CDR2 comprises the amino acid sequence of RVS, and the LC CDR3 comprises the amino acid sequence of SEQ ID NOs: 571; or (iii) the HC CDR1 comprises the amino acid sequence of SEQ ID NO: 1180, the HC CDR2 comprises the amino acid sequence of SEQ ID NO: 341, and the HC CDR3 comprises the amino acid sequence of SEQ ID NO: 410; and the LC CDR1 comprises the amino acid sequence of SEQ ID NO: 1181, the LC CDR2 comprises the amino acid sequence of SEQ ID NO: 1182, and the LC CDR3 comprises the amino acid sequence of SEQ ID NO: 571.

2. The antibody of claim 1, wherein the HC CDR1 comprises the amino acid sequence of SEQ ID NO: 1147, the HC CDR2 comprises the amino acid sequence of SEQ ID NO: 1148, and the HC CDR3 comprises the amino acid sequence of SEQ ID NO: 410; and the LC CDR1 comprises the amino acid sequence of SEQ ID NO: 474, the LC CDR2 comprises the amino acid sequence of SEQ ID NO: 529, and the LC CDR3 comprises the amino acid sequence of SEQ ID NO 571.

3. The antibody of claim 1, wherein the HC CDR1 comprises the amino acid sequence of SEQ ID NO: 1149, the HC CDR2 comprises the amino acid sequence of SEQ ID NO: 1150, and the HC CDR3 comprises the amino acid sequence of SEQ ID NO: 410; and the LC CDR1 comprises the amino acid sequence of SEQ ID NO: 475, the LC CDR2 comprises the amino acid sequence of SEQ ID NO: 530, and the LC CDR3 comprises the amino acid sequence of SEQ ID NO: 571.

4. The antibody of claim 1, wherein:

(i) the VH comprises the amino acid sequence of any one of SEQ ID NOs: 21, 22, or 23, or an amino acid sequence having at least 80% sequence identity thereto; or (ii) the VH comprises an amino acid sequence having no more than 30 modifications of the amino acid sequence of any one of SEQ ID NOs: 21, 22, or 23.

5. The antibody of claim 1, wherein:

(i) the VL comprises the amino acid sequence of any one of SEQ ID NOs: 93, 94, or 95, or an amino acid sequence at least 80% identical thereto; or (ii) the VL comprises an amino acid sequence having no more than 30 modifications of the amino acid sequence of any one of SEQ ID NOs: 93, 94, or 95.

6. The antibody of claim 1, wherein the VH comprises the amino acid sequence of SEQ ID NO: 22, or an amino acid sequence at least 80% identical thereto; and the VL comprises the amino acid sequence of SEQ ID NO: 94, or an amino acid sequence at least 80% identical thereto.

7. The antibody of claim 1, wherein the VH comprises the amino acid sequence of SEQ ID NO: 23, or an amino acid sequence at least 80% identical thereto; and the VL comprises the amino acid sequence of SEQ ID NO: 95, or an amino acid sequence at least 80% identical thereto.

8. The antibody of claim 1, wherein the nucleotide sequence encoding the VH comprises the nucleotide sequence of any one of SEQ ID NOs: 167, 168, or 169, or a nucleotide sequence at least 80% identical thereto.

9. The antibody of claim 1, wherein the nucleotide sequence encoding the VL comprises the nucleotide sequence of any one of SEQ ID NOs: 241, 242, or 243, or a nucleotide sequence at least 80% identical thereto.

10. The antibody of claim 1, wherein the nucleotide sequence encoding the VH comprises the nucleotide sequence of SEQ ID NO: 167, or a nucleotide sequence at least 80% identical thereto; and the nucleotide sequence encoding the VL comprises the nucleotide sequence of SEQ ID NO: 241, or a nucleotide sequence at least 80% identical thereto.

11. The antibody of claim 1, wherein the nucleotide sequence encoding the VH comprises the nucleotide sequence of SEQ ID NO: 168, or a nucleotide sequence at least 80% identical thereto; and the nucleotide sequence encoding the VL comprises the nucleotide sequence of SEQ ID NO: 242, or a nucleotide sequence at least 80% identical thereto.

12. The antibody of claim 1, wherein the nucleotide sequence encoding the VH comprises the nucleotide sequence of SEQ ID NO: 169, or a nucleotide sequence at least 80% identical thereto; and the nucleotide sequence encoding the VL comprises the nucleotide sequence of SEQ ID NO: 243, or a nucleotide sequence at least 80% identical thereto.

13. The antibody of claim 1, comprising:

(i) a heavy chain constant region selected from human IgG1, human IgG2, human IgG3, and human IgG4, murine IgG1, murine IgG2a, murine IgG2b, murine IgG2c, and murine IgG3; and (ii) a light chain constant region chosen from the light chain constant regions of kappa or lambda.

14. The antibody of claim 1, comprising a human IgG4 heavy chain constant region and a human kappa light chain constant region.

15. The antibody of claim 1, which binds the C-terminus of a tau protein.

16. The antibody of claim 1, which binds a tau protein comprising one or more phosphorylated residues.

17. The antibody of claim 1, which (i) binds enriched paired helical filament tau protein (ePHF);

(ii) binds an epitope comprising a region formed by a complex of at least two tau proteins;

(iii) binds to a tau protein with a dissociation constant ($K_D$) of less than about 120 nM; and/or (iv) reduces or inhibits aggregation of tau.

18. A vector comprising a nucleic acid encoding the antibody of claim 1.

19. A host cell comprising a nucleic acid encoding the antibody of claim 1.

20. The host cell of claim 19, wherein the host cell is an insect cell, a bacterial cell or a mammalian cell.

21. A method of producing an antibody, the method comprising culturing the host cell of claim 20 under conditions suitable for gene expression.

22. A pharmaceutical composition comprising the antibody of claim 1, and a pharmaceutically acceptable excipient.

23. An antibody that binds to tau comprising a heavy chain variable region (VH) comprising a heavy chain complementarity determining region 1 (HC CDR1), an HC CDR2, and an HC CDR3, and a light chain variable region (VL) comprising a light chain complementarity determining region 1 (LC CDR1), an LC CDR2, and an LC CDR3, wherein:

(i) the HC CDR1 comprises the amino acid sequence of SEQ ID NO: 1144, the HC CDR2 comprises the amino acid sequence of SEQ ID NO: 1145, and the HC CDR3 comprises the amino acid sequence of SEQ ID NO: 410; and the LC CDR1 comprises the amino acid sequence of SEQ ID NO: 1146, the LC CDR2 comprises the amino acid sequence of SEQ ID NO: 529, and the LC CDR3 comprises the amino acid sequence of SEQ ID NO: 571;

(ii) the HC CDR1 comprises the amino acid sequence of SEQ ID NO: 1165, the HC CDR2 comprises the amino acid sequence of SEQ ID NO: 1166, and the HC CDR3 comprises the amino acid sequence of SEQ ID NO: 1167; and the LC CDR1 comprises the amino acid sequence of SEQ ID NO: 473, the LC CDR2 comprises the amino acid sequence of RVS, and the LC CDR3 comprises the amino acid sequence of SEQ ID NO: 571; or (iii) the HC CDR1 comprises the amino acid sequence of SEQ ID NO: 314, the HC CDR2 comprises the amino acid sequence of SEQ ID NO: 341, and the HC CDR3 comprises the amino acid sequence of SEQ ID NO: 410; and the LC CDR1 comprises the amino acid sequence of SEQ ID NO: 1154, the LC CDR2 comprises the amino acid sequence of SEQ ID NO: 529, and the LC CDR3 comprises the amino acid sequence of SEQ ID NO: 571.

24. The antibody of claim 23, wherein the VH comprises the amino acid sequence of SEQ ID NO: 21, or an amino acid sequence at least 80% identical thereto; and the VL comprises the amino acid sequence of SEQ ID NO: 93, or an amino acid sequence at least 80% identical thereto.

25. The antibody of claim 23, which is a full length antibody, a bispecific antibody, an Fab, an $F(ab')_2$, an Fv, or a single chain Fv fragment (scFv).

26. The antibody of claim 23, which is a humanized antibody.

27. The antibody of claim 23, wherein the HC CDR1 comprises the amino acid sequence of SEQ ID NO: 1144, the HC CDR2 comprises the amino acid sequence of SEQ ID NO: 1145, and the HC CDR3 comprises the amino acid sequence of SEQ ID NO: 410; and the LC CDR1 comprises the amino acid sequence of SEQ ID NO: 1146, the LC CDR2 comprises the amino acid sequence of SEQ ID NO: 529, and the LC CDR3 comprises the amino acid sequence of SEQ ID NO: 571.

28. The antibody of claim 27, comprising a human IgG4 heavy chain constant region and a human kappa light chain constant region.

29. A vector comprising a nucleic acid encoding the antibody of claim 27.

30. A host cell comprising a nucleic acid encoding the antibody of claim 27.

31. The host cell of claim 30, wherein the host cell is an insect cell, a bacterial cell or a mammalian cell.

32. A method of producing an antibody, the method comprising culturing the host cell of claim 30 under conditions suitable for gene expression.

33. A pharmaceutical composition comprising the antibody of claim 27, and a pharmaceutically acceptable excipient.

34. A nucleic acid encoding the antibody of claim 23.

35. A nucleic acid encoding an antibody that binds to tau comprising a heavy chain variable region (VH) comprising a heavy chain complementarity determining region 1 (HC CDR1), an HC CDR2, and an HC CDR3, and a light chain variable region (VL) comprising a light chain complementarity determining region 1 (LC CDR1), an LC CDR2, and an LC CDR3, wherein:

(i) the HC CDR1 comprises the amino acid sequence of $X_1X_2$WMH wherein $X_1$ is R or I; and $X_2$ is Y or F, the HC CDR2 comprises the amino acid sequence of SEQ ID NO: 1184, and the HC CDR3 comprises the amino acid sequence of SEQ ID NO: 410; and the LC CDR1 comprises the amino acid sequence of SEQ ID NO: 1185, the LC CDR2 comprises the amino acid sequence of SEQ ID NO: 1182, and the LC CDR3 comprises the amino acid sequence of SEQ ID NO: 571;

(ii) the HC CDR1 comprises the amino acid sequence of SEQ ID NO: 1186, the HC CDR2 comprises the amino acid sequence of SEQ ID NO: 1187, and the HC CDR3 comprises the amino acid sequence of SEQ ID NO: 1167; and the LC CDR1 comprises the amino acid sequence of SEQ ID NO: 1188, the LC CDR2 comprises the amino acid sequence of RVS, and the LC CDR3 comprises the amino acid sequence of SEQ ID NO: 571; or (iii) the HC CDR1 comprises the amino acid sequence of SEQ ID NO: 1180, the HC CDR2 comprises the amino acid sequence of SEQ ID NO: 341, and the HC CDR3 comprises the amino acid sequence of SEQ ID NO: 410; and the LC CDR1 comprises the amino acid sequence of SEQ ID NO: 1181, the LC CDR2 comprises the amino acid sequence of SEQ ID NO: 1182, and the LC CDR3 comprises the amino acid sequence of SEQ ID NO: 571.

36. The nucleic acid of claim 35, wherein:

(i) the nucleotide sequence encoding the VH comprises any one of SEQ ID NOs: 167, 168, or 169, or a nucleotide sequence at least 80% identical thereto; and/or the nucleotide sequence encoding the VL comprises any one of SEQ ID NOs: 241, 242, or 243, or a nucleotide sequence at least 80% identical thereto;

(ii) the nucleotide sequence encoding the VH comprises SEQ ID NO: 167, or a nucleotide sequence at least 80% identical thereto; and/or the nucleotide sequence encoding the VL comprises SEQ ID NO: 241, or a nucleotide sequence at least 80% identical thereto;

(iii) the nucleotide sequence encoding the VH comprises SEQ ID NO: 168, or a nucleotide sequence at least 80% identical thereto; and/or the nucleotide sequence encoding the VL comprises SEQ ID NO: 242, or a nucleotide sequence at least 80% identical thereto; or (iv) the nucleotide sequence encoding the VH comprises SEQ ID NO: 169, or a nucleotide sequence at least 80% identical thereto; and/or the nucleotide sequence encoding the VL comprises SEQ ID NO: 243, or a nucleotide sequence at least 80% identical thereto.

37. The nucleic acid of claim 35, wherein the HC CDR1 comprises the amino acid sequence of SEQ ID NO: 1144, the HC CDR2 comprises the amino acid sequence of SEQ ID NO: 1145, and the HC CDR3 comprises the amino acid sequence of SEQ ID NO: 410; and the LC CDR1 comprises the amino acid sequence of SEQ ID NO: 1146, the LC CDR2 comprises the amino acid sequence of SEQ ID NO: 529, and the LC CDR3 comprises the amino acid sequence of SEQ ID NO: 571.

38. The nucleic acid of claim 37, wherein the encoded VH comprises the amino acid sequence of SEQ ID NO: 21, or an amino acid sequence at least 80% identical thereto; and the encoded VL comprises the amino acid sequence of SEQ ID NO: 93, or an amino acid sequence at least 80% identical thereto.

39. The nucleic acid of claim 35, wherein the HC CDR1 comprises the amino acid sequence of SEQ ID NO: 1147, the HC CDR2 comprises the amino acid sequence of SEQ ID NO: 1148, and the HC CDR3 comprises the amino acid sequence of SEQ ID NO: 410; and the LC CDR1 comprises the amino acid sequence of SEQ ID NO: 474, the LC CDR2 comprises the amino acid sequence of SEQ ID NO: 529, and the LC CDR3 comprises the amino acid sequence of SEQ ID NO 571.

40. The nucleic acid of claim 35, wherein the HC CDR1 comprises the amino acid sequence of SEQ ID NO: 1149, the HC CDR2 comprises the amino acid sequence of SEQ ID NO: 1150, and the HC CDR3 comprises the amino acid sequence of SEQ ID NO: 410; and the LC CDR1 comprises the amino acid sequence of SEQ ID NO: 475, the LC CDR2 comprises the amino acid sequence of SEQ ID NO: 530, and the LC CDR3 comprises the amino acid sequence of SEQ ID NO: 571.

41. The nucleic acid of claim 35, wherein:

(i) the encoded VH comprises the amino acid sequence of any one of SEQ ID NOs: 21, 22, or 23, or an amino acid sequence having at least 80% sequence identity thereto; and/or (ii) the encoded VL comprises the amino acid sequence of any one of SEQ ID NOs: 93, 94, or 95, or an amino acid sequence at least 80% identical thereto.

42. The nucleic acid of claim 35, wherein the encoded VH comprises the amino acid sequence of SEQ ID NO: 22, or an amino acid sequence at least 80% identical thereto; and the encoded VL comprises the amino acid sequence of SEQ ID NO: 94, or an amino acid sequence at least 80% identical thereto.

43. The nucleic acid of claim 35, wherein the encoded VH comprises the amino acid sequence of SEQ ID NO: 23, or an amino acid sequence at least 80% identical thereto; and the encoded VL comprises the amino acid sequence of SEQ ID NO: 95, or an amino acid sequence at least 80% identical thereto.

* * * * *

SEQUENCE LISTING

```
Sequence total quantity: 1226
SEQ ID NO: 1            moltype = AA  length = 120
FEATURE                 Location/Qualifiers
source                  1..120
                        mol_type = protein
                        organism = Mus musculus
SEQUENCE: 1
EVQLVESGGG LVQPKGSLKL SCAASGFTFN TYAMYWVRQA PGKGLEWVAR IRSKSSNYAT  60
YYADSVKDRF TISRDDSQSK LYLQMNNLKT EDTAMYYCVR EGLWYYFDYW GQGTTLTVSS  120

SEQ ID NO: 2            moltype = AA  length = 121
FEATURE                 Location/Qualifiers
source                  1..121
                        mol_type = protein
                        organism = Mus musculus
SEQUENCE: 2
EVQLQQSGPE LVKPGASVKI SCEASGYTFT DYYMNWVKQS HGKSLEWIGD INPNNGGTTY  60
NQKFKGKATL TVDKSSSTAH MELRSLTSED SAVYYCARGS SYYDFSWFAY WGQGTLVTVS  120
A                                                                 121

SEQ ID NO: 3            moltype = AA  length = 122
FEATURE                 Location/Qualifiers
source                  1..122
                        mol_type = protein
                        organism = Mus musculus
SEQUENCE: 3
QVQLQQPGTE LVKPGASVKL SCKASGYTFT KNWLHWVKQR PGQGLEWIGY INPSNGATNY  60
NERFKSKASL TVDKSSTTAY MQLSSLTSED SAVYYCARSG GWLLPYYAMD YWGHGTSVTV  120
SS                                                                122

SEQ ID NO: 4            moltype = AA  length = 113
FEATURE                 Location/Qualifiers
source                  1..113
                        mol_type = protein
                        organism = Mus musculus
SEQUENCE: 4
QVQLQQPGAE LVKPGASVKL SCKASDYTFT NYWMHWVKQR PGRGLEWIGR IDPNSGGTRY  60
NEKFKNKATL TVDKPSSTAY MHLSSLTSED SAVYYCAGDF DVWGTGTTVT VSS        113

SEQ ID NO: 5            moltype = AA  length = 120
FEATURE                 Location/Qualifiers
source                  1..120
                        mol_type = protein
                        organism = Mus musculus
SEQUENCE: 5
QVQLKESGPG LVAPSQSLSI TCTLSGFSLT DYGVSWIRQP PGKGLEWLGL MWGGGSTYYN  60
SALKSRLSIS KDNSKSQVFL KMNSLQTDDT AMYYCAKHGT YYGNYGIAYW GQGTLVTVSA  120

SEQ ID NO: 6            moltype = AA  length = 120
FEATURE                 Location/Qualifiers
source                  1..120
                        mol_type = protein
                        organism = Mus musculus
SEQUENCE: 6
```

```
QVQLKESGPG LVAPSQSLSI TCTVSGFSLT SYAISWVRQP PGKSLEWLGV IWTGGGSKYN  60
SALKSRLSIS KDNSKSQVFL KMNSLQTDDT ARYYCVRNYD YYRYEGFDYW GQGTLVTVSA  120

SEQ ID NO: 7            moltype = AA  length = 120
FEATURE                 Location/Qualifiers
source                  1..120
                        mol_type = protein
                        organism = Mus musculus
SEQUENCE: 7
EVQLVESGGD LVKPGGSLKL SCAASGFTFS SYGLSWVRQT PDKRLEWVAT ISSGGDYTYY  60
PDSVKGRFTI SRDNAKNILY LHMSSLKSED TAMYYCARED GYYVGTMDYW GQGTSVTVSS  120

SEQ ID NO: 8            moltype = AA  length = 126
FEATURE                 Location/Qualifiers
source                  1..126
                        mol_type = protein
                        organism = Mus musculus
SEQUENCE: 8
QVQLKESGPG LVAPSQSLSI TCTVSGFSLT TYAISWVRQP PGKGLEWLGV IWTGGGTDFN  60
SALKSRLSIS KDNSKSQVFL KMISLQTNDT ARYYCARKGG SYYSTTYVGL YAMDYWGQGT  120
SVTVSS                                                             126

SEQ ID NO: 9            moltype = AA  length = 115
FEATURE                 Location/Qualifiers
source                  1..115
                        mol_type = protein
                        organism = Mus musculus
SEQUENCE: 9
EVQLVESGGA LVQPGGSLSL SCAASGFTFT DYYMSWVRQP PGKALEWLAL IRNKAKGFTT  60
EYSASVKGRF TISRDNSQSI LLFQMNDLRA DDSATYYCVR DINYWGQGTT LTVSS       115

SEQ ID NO: 10           moltype = AA  length = 120
FEATURE                 Location/Qualifiers
source                  1..120
                        mol_type = protein
                        organism = Mus musculus
SEQUENCE: 10
QIQLVQSGPE LKKPGETVKI SCKASGYSFT TYGMSWVKQA PGKGLKWMGW INTYSGVPTY  60
ADDFKERFAF SLETSASTAY LQINNLKNED TSTYFCARRG GLYDGYYGYW GQGTTLTVSS  120

SEQ ID NO: 11           moltype = AA  length = 115
FEATURE                 Location/Qualifiers
source                  1..115
                        mol_type = protein
                        organism = Mus musculus
SEQUENCE: 11
EVQLVESGGG LVKPGGSLKL SCAASGFTFS DYGMYWVRQA PEKGLEWVAY ISSGSTTIYY  60
ADTVKGRFTI SRDNAKNTLF LQMTSLRSED TAMYYCAGHW YFDVWGTGTT VTVSS       115

SEQ ID NO: 12           moltype = AA  length = 114
FEATURE                 Location/Qualifiers
source                  1..114
                        mol_type = protein
                        organism = Mus musculus
SEQUENCE: 12
EVKLEESGGG LVQPGGSMKL SCVASGITFS HYWMNWVRQA PERGLEWVAQ IKLKSDNYAT  60
HYAESVKGRF TISRDDSKSS VYLQMNNLRA EDTGVYYCTG FYDWGQGTTL TVSS        114

SEQ ID NO: 13           moltype = AA  length = 114
FEATURE                 Location/Qualifiers
source                  1..114
                        mol_type = protein
                        organism = Mus musculus
SEQUENCE: 13
QAYLQQSGAE LVRPGASVKM SCKASGYTFT SYNMHWVKQT PRQGLEWIGA IYPGNGDTSY  60
NQKFKGKATL TVDKSSSTAY MQLSSLTSED SAVYFCARGG MDYWGQGTSV TVSS        114

SEQ ID NO: 14           moltype = AA  length = 114
FEATURE                 Location/Qualifiers
source                  1..114
                        mol_type = protein
                        organism = Mus musculus
SEQUENCE: 14
EVQLQQSGPE LVKPGASVKM SCKASGYTFS DYNMHWLKQS HGKSLEWIGY INPNNGGISY  60
NQKFKGKATL TVNKSSSTAY MELRSLTSED SALYYCARWS VSYWGQGTLV TVSA        114

SEQ ID NO: 15           moltype = AA  length = 117
FEATURE                 Location/Qualifiers
source                  1..117
```

```
                        mol_type = protein
                        organism = Mus musculus
SEQUENCE: 15
EVQLQQSGAE LVKPGASVKL SCTASGFNIK DYYIHWVKQR TEQGLEWIGR IDPEDGETKY  60
APKFQGKATI AADTSSNTAY LHLNSLTSED TAVYYCAREF SYAMDYWGQG TSVTVSS     117

SEQ ID NO: 16           moltype = AA  length = 117
FEATURE                 Location/Qualifiers
source                  1..117
                        mol_type = protein
                        organism = Mus musculus
SEQUENCE: 16
EVQLQQSGAE LVKPGASVKL SCTASGFNIK DYYMHWVKQR TEQGLEWIGR IDPEDDETKY  60
APKFQGKATI TADTSSNTVY LQLSSLTSED TAVYYCAREF SYAMDYWGQG TSVTVSS     117

SEQ ID NO: 17           moltype = AA  length = 117
FEATURE                 Location/Qualifiers
source                  1..117
                        mol_type = protein
                        organism = Mus musculus
SEQUENCE: 17
QVQLQQPGAD LVRPGSSVKL SCKASGYTFT RSWMHWVKQR PIEGLEWIGN IDPSDSEAHY  60
NQKFKDKATL TVDKFSNTAY MQLSSLTSED SAVYYCARWD DFYVAYWGQG TLVTVSA     117

SEQ ID NO: 18           moltype = AA  length = 117
FEATURE                 Location/Qualifiers
source                  1..117
                        mol_type = protein
                        organism = Mus musculus
SEQUENCE: 18
QVQLQQPGAA LVRPGSSVKL SCKASGYTFT SSWMHWVKQR PIQGLEWIGN IDPSDGETHY  60
NQKFKDKATL TVDKSSNTAY MQLSSLTSED SAVYYCARWD DYYVAYWGQG TLVTVSA     117

SEQ ID NO: 19           moltype = AA  length = 120
FEATURE                 Location/Qualifiers
source                  1..120
                        mol_type = protein
                        organism = Mus musculus
SEQUENCE: 19
QVQLQQPGTD LVKPGASVKL SCKASGYTFT SYWMHWLKQR PGQGLEWIGN INPNNSDANY  60
NEKFKSKATL TVDKSSSAAY MQLISLTSED SAVYYCARAN YYGGSQFAYW GQGTLVTVSA  120

SEQ ID NO: 20           moltype = AA  length = 120
FEATURE                 Location/Qualifiers
source                  1..120
                        mol_type = protein
                        organism = Mus musculus
SEQUENCE: 20
QVQLQQPGIE LVKTGASVKL SCKASGYTFT SNWMHWLKQR PGQGLEWIGN INPNNSETNY  60
NEKFRKKATL TVDKSSSAAY MQLISLTSED SAVYYCARAN YYGGSQFAYW GQGTLVTVSA  120

SEQ ID NO: 21           moltype = AA  length = 118
FEATURE                 Location/Qualifiers
source                  1..118
                        mol_type = protein
                        organism = Mus musculus
SEQUENCE: 21
QVQLQQPGTE LVKPGSSVNL SCKASGFTFT RYWMHWVKER PGHGLEWIGN INPNNGGTDF  60
NEKFKNKATL TVHKSSTTVF IQLSSLTSED SAVYYCARGT GTGAMDYWGQ GTSVTVSS    118

SEQ ID NO: 22           moltype = AA  length = 118
FEATURE                 Location/Qualifiers
source                  1..118
                        mol_type = protein
                        organism = Mus musculus
SEQUENCE: 22
QVQLQQPGTE LVKPGASVKL SCKASGYTFT IFWMHWVKQR PGHGLEWIGK INPNNGGGDY  60
NEKFKSKATL TVDKSSTTAY LQLSSLTSED SAVYYCARGT GTGAMDYWGQ GTSVTVSS    118

SEQ ID NO: 23           moltype = AA  length = 118
FEATURE                 Location/Qualifiers
source                  1..118
                        mol_type = protein
                        organism = Mus musculus
SEQUENCE: 23
QVQLQQPGTE LVKPGASVKL SCKASGYTFT RFWMHWVKQR PGQGLEWIGN INPNNGGTDN  60
NERFKSKATL TVDRSSSTAY MQLSSLTSED SAVYYCARGT GTGAMDYWGQ GTSVTVSS    118

SEQ ID NO: 24           moltype = AA  length = 118
```

```
FEATURE               Location/Qualifiers
source                1..118
                      mol_type = protein
                      organism = Mus musculus
SEQUENCE: 24
QVQLQQPGTE LVKPGASVKL SCKASGFTFT RFWMHWVKQR PGQGLEWIGN INPNNGETNY  60
NEKFKIKAAL TVDKSSTTAY MQLSSLTSED SAVYSCARGT GTGAMDYWGQ GTSVTVSS    118

SEQ ID NO: 25         moltype = AA  length = 121
FEATURE               Location/Qualifiers
source                1..121
                      mol_type = protein
                      organism = Mus musculus
SEQUENCE: 25
QVQLQQSGPE LVKPGASVKI SCKASGYSFT DYYINWVKQR PGQGLEWIGW IFPGSDSTYY  60
NEKFKGKATL TVDKSSSTAS MLLSSLTSED SAVYFCARPT VVARDYAMDY WGQGTSVTVS  120
S                                                                  121

SEQ ID NO: 26         moltype = AA  length = 121
FEATURE               Location/Qualifiers
source                1..121
                      mol_type = protein
                      organism = Mus musculus
SEQUENCE: 26
QVQLQQSGPE LVKPGASVKI SCKASGYTFT EYYLNWMKQR PGQGLEWIGW IFPGRGSTNY  60
NEKFKGKATL TVDKSSSTAY MLLSSLTSED SAVYFCARPT IVARDYAMDY WGQGTSVTVS  120
S                                                                  121

SEQ ID NO: 27         moltype = AA  length = 122
FEATURE               Location/Qualifiers
source                1..122
                      mol_type = protein
                      organism = Mus musculus
SEQUENCE: 27
QVQLQQSGPE LVKPGASVKI SCKASGYAFS SSWMNWVKQR PGKGLEWIGR IYPGDGDTNY  60
NGKFKGKATL TADKSSSTAY MQLSSLTSED SAVYFCARIG GRAGSGYAMD YWGQGTSVTV  120
SS                                                                 122

SEQ ID NO: 28         moltype = AA  length = 121
FEATURE               Location/Qualifiers
source                1..121
                      mol_type = protein
                      organism = Mus musculus
SEQUENCE: 28
QVSLKESGPG ILQSSQTLSL TCSFSGFSLS TSGMGVSWIR QPSGKGLEWL SHIYWDDDKW  60
YNPSLKSRLT ISKDTSRNQV FLKITSVDTA DTATYYCARR EIGKRDFFAY WGQGTLVTVS  120
A                                                                  121

SEQ ID NO: 29         moltype = AA  length = 121
FEATURE               Location/Qualifiers
source                1..121
                      mol_type = protein
                      organism = Mus musculus
SEQUENCE: 29
QVQLQQPGTE LVKPGASVKL SCKASGYTFT SYWMHWVKQR PGQGLEWIGN IYPSNGGTNY  60
NEKFKNKATL TVDKSSSTAS MQLSSLTSED SAVYYCARSS VVARDYAMDY WGQGTSVTVS  120
S                                                                  121

SEQ ID NO: 30         moltype = AA  length = 121
FEATURE               Location/Qualifiers
source                1..121
                      mol_type = protein
                      organism = Mus musculus
SEQUENCE: 30
QVQLQQPGTE LVKPGASVKL SCKASGYTFT SYWMHWVKQR PGQGLEWIGN IYPSNGGTYY  60
NEKFKSKATL TVDKSSSTAY MQLSSLTSED SAVYYCARSS VVGRDYAMDY WGQGTSVTVS  120
S                                                                  121

SEQ ID NO: 31         moltype = AA  length = 121
FEATURE               Location/Qualifiers
source                1..121
                      mol_type = protein
                      organism = Mus musculus
SEQUENCE: 31
QVQLKQSGAE LVRPGASVKL SCKTSGYTFT DYYIKWVKQR PGQGLEWIAR IYPGSGNTYY  60
NEKFKGKATL TAEKSSSTAY MQLSSLTSED SAVYFCARPA YYSKDYAMEY WGQGTSVTVS  120
S                                                                  121

SEQ ID NO: 32         moltype = AA  length = 116
```

```
FEATURE                 Location/Qualifiers
source                  1..116
                        mol_type = protein
                        organism = Mus musculus
SEQUENCE: 32
EVQLQQSGAE LVRPGSSVKM SCKTSGYTFT SYGINWVKQR PGQGLEWIGY IYIGNGHTEY  60
NEKFEGKATL TSDTSSSTAY MQLSSLTSED SAIYFCAGTG TLFDYWGQGT TLTVSS      116

SEQ ID NO: 33           moltype = AA  length = 116
FEATURE                 Location/Qualifiers
source                  1..116
                        mol_type = protein
                        organism = Mus musculus
SEQUENCE: 33
EVQLQQSGAE LVRPGSSVKM SCKTSGYTFT SYGINWVKQR PGQGLEWVGY IYIRDGNTAY  60
NEKFKGKATV TSDTSSSTVY MQLSSLTSED SAIYFCAGTG TSFAYWGQGT LVTVSA      116

SEQ ID NO: 34           moltype = AA  length = 116
FEATURE                 Location/Qualifiers
source                  1..116
                        mol_type = protein
                        organism = Mus musculus
SEQUENCE: 34
EAQLQQSGAE LVRPGSSVKM SCKTSGYTFT SYGINWVKQR PGQGLEWIGY IYIRNGNTAY  60
NEKFKGKATV TSDTSSSTVY MQLSSLTSED SAIYFCAGTG TSFTYWGQGT LVTVSA      116

SEQ ID NO: 35           moltype = AA  length = 119
FEATURE                 Location/Qualifiers
source                  1..119
                        mol_type = protein
                        organism = Mus musculus
SEQUENCE: 35
QVTLKESGPG ILQPSQTLNL TCSFSGFSLS TSGMGVSWIR QPSGKGLEWL AHIYWDDDKR  60
YNPSLKSRLT ISKDTSRNQV FLKITSVDTA DTATYYCVRR SRRGNYDYWG QGTTLTVSS   119

SEQ ID NO: 36           moltype = AA  length = 114
FEATURE                 Location/Qualifiers
source                  1..114
                        mol_type = protein
                        organism = Mus musculus
SEQUENCE: 36
QVQLQQSGAE LARPGASVKL SCKASGYTFT SYGINWVKQR TGQGLEWIGE IYPRSGKTYY  60
NEKFKGKATL TADKSSSTAY MELRSLTSED SAVYFCARGG GGYWGQGTTL TVSS        114

SEQ ID NO: 37           moltype = AA  length = 119
FEATURE                 Location/Qualifiers
source                  1..119
                        mol_type = protein
                        organism = Mus musculus
SEQUENCE: 37
QVQLQQSGPE LVKPGALVKI SCKASGYTFT SYDINWVKQR PGQGLEWIGW IYPGNGNTNY  60
NAKFKDKATL TADKSSSTAY MQLSSLTSET SAVYFCARGI RRSWYFDVWG AGTTVTVSS   119

SEQ ID NO: 38           moltype = AA  length = 119
FEATURE                 Location/Qualifiers
source                  1..119
                        mol_type = protein
                        organism = Mus musculus
SEQUENCE: 38
QVQLQQSGPE LVKPGALVKI SCKASGYTFT SYDINWVKQR PGQGLEWIGW IYPGDRNTKY  60
NEKFKGKATL TADKSSSTAY MQLISLTSEN SAVYFCARGI RRSWYFDVWG AGTTVTVSS   119

SEQ ID NO: 39           moltype = AA  length = 123
FEATURE                 Location/Qualifiers
source                  1..123
                        mol_type = protein
                        organism = Mus musculus
SEQUENCE: 39
QVQLKQSGPG LVQPSQSLSI TCTVSGFSLT SYGVHWVRQS PGKGLEWLGV IWSGGSTDYN  60
AAFISRLSIS KDNSKSQVFF KMNSLQADDT AIYYCARNSG GYYVDDYYAM DYWGQGISVT  120
VSS                                                                123

SEQ ID NO: 40           moltype = AA  length = 123
FEATURE                 Location/Qualifiers
source                  1..123
                        mol_type = protein
                        organism = Mus musculus
SEQUENCE: 40
QVQLKQSGPG LVQPSQSLSI TCTVSGFSLT SYGVHWVRQS PGKGLEWLGV IWSGGSTDYN  60
```

-continued

```
AAFISRLSIS KDNSKSQVFF KMNSLQADDT AIFYCARNSG GYYVDDYYAM DYWGQGTSVT  120
VSS                                                                123

SEQ ID NO: 41          moltype = AA  length = 115
FEATURE                Location/Qualifiers
source                 1..115
                       mol_type = protein
                       organism = Mus musculus
SEQUENCE: 41
DVQLQESGPG LVKPSQSLSL TCSVTGYSIT TNYYWNWIRQ FPGNKLEWMG YITYDGIKTY  60
NPSLNNRISI TRDTSKNQFF LKLNSVTTED TATYYCARGP GLDYWGQGTT LTVSS       115

SEQ ID NO: 42          moltype = AA  length = 115
FEATURE                Location/Qualifiers
source                 1..115
                       mol_type = protein
                       organism = Mus musculus
SEQUENCE: 42
DVQLQESGPG LVKPSQSLSL TCSVSGYSIT TNYFWNWIRL FPGNKLEWMG YISYDGSNVY  60
NPSLKNRISI TRDTSKNQFF LKLNSLTTED TATYYCARGP PSAYWGQGTL VTVSA       115

SEQ ID NO: 43          moltype = AA  length = 115
FEATURE                Location/Qualifiers
source                 1..115
                       mol_type = protein
                       organism = Mus musculus
SEQUENCE: 43
DVQLQESGPG LVKPSQSLSL TCSVTGYSIT TNYYWNWIRQ FPGNKLEWMG YITYDGSNNY  60
NPSLKNRISI TRDTSKNQFF LKLNSVTTED TATYYCARGP PTAYWGQGTL VTVSA       115

SEQ ID NO: 44          moltype = AA  length = 114
FEATURE                Location/Qualifiers
source                 1..114
                       mol_type = protein
                       organism = Mus musculus
SEQUENCE: 44
DVQLQESGPG LVKPSQSLSL TCSVTGYSIT TNYYWNWIRQ FPGNKLEWMG YISYDGSSNY  60
NPSLKNRISI TRDTSKNQFF LNLNSVTTED TATYYCARDL LGYWGQGTTL TVSS        114

SEQ ID NO: 45          moltype = AA  length = 116
FEATURE                Location/Qualifiers
source                 1..116
                       mol_type = protein
                       organism = Mus musculus
SEQUENCE: 45
EVQLVESGGG LVKPGGSLKL SCAASGFTFS DYGMHWVRQA PEKGLEWVAY ISSGSITIYY  60
ADTVKGRFTI SRDNAKNTLF LQMTSLRSED TAMYYCARSP YAMDSWGQGT SVTVSS      116

SEQ ID NO: 46          moltype = AA  length = 116
FEATURE                Location/Qualifiers
source                 1..116
                       mol_type = protein
                       organism = Mus musculus
SEQUENCE: 46
EVQLVESGGG LVKPGGSLKL SCAASGFTFS DYGMHWVRQA PEKGLEWVAY ISSGSRTIYY  60
ADTVKGRFTI SRDNAKNTLF LQMTSLRSED TAMYYCARSP YAMDYWGQGT SVTVSS      116

SEQ ID NO: 47          moltype = AA  length = 122
FEATURE                Location/Qualifiers
source                 1..122
                       mol_type = protein
                       organism = Mus musculus
SEQUENCE: 47
QVTLKESGPG ILQSSQTLSL TCSFSGFSLS TSGMGVSWLR QPSGKGLEWL AHIYWDDEER  60
YDPSLKSRLT ISKDTSRNQV FLKITSVDTA DTATYYCARR GYYSDGNYFD SWGQGTTLTV  120
SS                                                                 122

SEQ ID NO: 48          moltype = AA  length = 122
FEATURE                Location/Qualifiers
source                 1..122
                       mol_type = protein
                       organism = Mus musculus
SEQUENCE: 48
QVTLKESGPG ILQSSQTLSL TCSFSGFSLS TSGMGVSWIR QPSGKGLEWL AHIYWDDDKR  60
YNPSLKSRLK ISKDTSRNQV FLKITSVDTA DTATYYCARR GYYSNGNYFD YWGQGTTLTV  120
SS                                                                 122

SEQ ID NO: 49          moltype = AA  length = 120
FEATURE                Location/Qualifiers
```

```
source                  1..120
                        mol_type = protein
                        organism = Mus musculus
SEQUENCE: 49
EVQLQQSGPE LVKPGASVKI PCRASGYTFT DYNMDWVKQS HGKTLEWIGD INPNNGGTIY  60
NQKFKGKATL TVDKSSSTAY MELRSLTSED TAVYYCARGR GMGYYALDYW GQGTSVTVSS  120

SEQ ID NO: 50           moltype = AA  length = 119
FEATURE                 Location/Qualifiers
source                  1..119
                        mol_type = protein
                        organism = Mus musculus
SEQUENCE: 50
QVTLKESGPG ILQSSQTLSL TCSFSGFSLS TSTMGVSWIR QPSGKGLEWL AHIYWDDDKR  60
YNPSLKSRLT ISKDTSRNQV FLNITSVDTA DIATYYCARR ARGYGMDYWG QGTSVTVSS   119

SEQ ID NO: 51           moltype = AA  length = 119
FEATURE                 Location/Qualifiers
source                  1..119
                        mol_type = protein
                        organism = Mus musculus
SEQUENCE: 51
QITLKESGPG ILQSSQTLSL TCSFSGFSLS TSAMGVSWIR QPSGEGLEWL AHIYWDDDKR  60
YNPSLKSRLT ISKDTSRNQV FLKITSVDTA DTATYYCARR RRGYGMDYWG QGTSVTVSS   119

SEQ ID NO: 52           moltype = AA  length = 119
FEATURE                 Location/Qualifiers
source                  1..119
                        mol_type = protein
                        organism = Mus musculus
SEQUENCE: 52
QVTLKESGPG ILQSSQTLSL TCSFSGFSLS TSGMGVSWIR QPSGKGLEWL AHIYWDDDKR  60
YNPSLKSRLT ISKDTSRNQV FLKITSVDTA ETATYYCARR ARFYAMDYWG QGTSVTVSS   119

SEQ ID NO: 53           moltype = AA  length = 119
FEATURE                 Location/Qualifiers
source                  1..119
                        mol_type = protein
                        organism = Mus musculus
SEQUENCE: 53
QVTLKESGPG ILQSSQTLSL TCSFSGFSLN TSGMGVSWIR LPSGKGLEWL AHIYWDDDKR  60
YNPSLKSRLT ISKDTSRKQV FLKITSVDTA DTATYYCARR VRGYGMDYWG QGTSVTVSS   119

SEQ ID NO: 54           moltype = AA  length = 119
FEATURE                 Location/Qualifiers
source                  1..119
                        mol_type = protein
                        organism = Mus musculus
SEQUENCE: 54
QVTLKESGPG ILQSSQTLSL TCSFSGFSLS TSGMGVSWIR QPSGKGLEWL AHIYWDDDKR  60
YNPSLKSRLT ISKDTSRNQV FLKITSVDTA DTATYYCARR VRYYAMDYWG QGTSVTVSS   119

SEQ ID NO: 55           moltype = AA  length = 119
FEATURE                 Location/Qualifiers
source                  1..119
                        mol_type = protein
                        organism = Mus musculus
SEQUENCE: 55
QVTLKESGPG ILQSSQTLSL TCSFSGFSLS TSGMGVSWIR QPSGKGLEWL AHIYWDDDKR  60
YNPSLKSRLT ISKDTSRNQV FLKITSVDTE DTATYYCTRR VRSYAMDYWG QGTSVTVSS   119

SEQ ID NO: 56           moltype = AA  length = 119
FEATURE                 Location/Qualifiers
source                  1..119
                        mol_type = protein
                        organism = Mus musculus
SEQUENCE: 56
QVTLKESGPG ILQSSQTLSL TCSFSGFSLS TSGMGVSWIR QPSGKGLEWL AHIYWDDDKR  60
YNPSLKSRLT ISKDTSRNQV FLKITSVDTA DTATYYCTRR VRYYAMDYWG QGTSVTVSS   119

SEQ ID NO: 57           moltype = AA  length = 119
FEATURE                 Location/Qualifiers
source                  1..119
                        mol_type = protein
                        organism = Mus musculus
SEQUENCE: 57
QVTLKESGPG ILQSSQTLSL TCSFSGFSLS TFGMGVSWIR QPSGKGLEWL AHIYWDDDKR  60
YNPSLKSRLT ISKDTSRNQV FLKITSVDTA DTATYYCVRR KRSYGMDYWG QGTSVTVSS   119
```

```
SEQ ID NO: 58           moltype = AA  length = 120
FEATURE                 Location/Qualifiers
source                  1..120
                        mol_type = protein
                        organism = Mus musculus
SEQUENCE: 58
QIQLVQSGPE LKKPGETVKI SCKASVYTFT TYGMSWVKQA PGKGLKWMGW INTYSGVPTY  60
ADDFKGRFAF SLETSASTAY LQINNLKNED TATYFCARLG LRRGSYFDYW GQGTTLTVSS  120

SEQ ID NO: 59           moltype = AA  length = 120
FEATURE                 Location/Qualifiers
source                  1..120
                        mol_type = protein
                        organism = Mus musculus
SEQUENCE: 59
QIQLVQSGPE LKKPGETVKI SCKASGYTFT TYGMSWVKQA PGKGLKWMGW INTYSGVPTY  60
ADDFKGRFVF SLETSASTAY LQINNLKNED TATYFCARLG LRRGSYFDYW GQGTTLTVSS  120

SEQ ID NO: 60           moltype = AA  length = 120
FEATURE                 Location/Qualifiers
source                  1..120
                        mol_type = protein
                        organism = Mus musculus
SEQUENCE: 60
QVQLQQPGAE LVKPGVSVKM SCKASGYTFT SYWITWVKQR PGQGLEWVGD IFPGSGSTNY  60
NEKFKSKATL TVDTSSSTAY MQLSSLTSED SAVYYCARGG KGVIGYFDYW GQGTTLTVSS  120

SEQ ID NO: 61           moltype = AA  length = 115
FEATURE                 Location/Qualifiers
source                  1..115
                        mol_type = protein
                        organism = Mus musculus
SEQUENCE: 61
EVQLVESGGG LVKPGGSLKL SCAASGFTFS DYGMHWVRQA PEKGLEWVAY ISSGSSNIYY  60
TDTVKGRFTI SRDNAKNTLF LQMTSLRSED TAMYYCTRSW YFDVWGTGTT VTVSS       115

SEQ ID NO: 62           moltype = AA  length = 113
FEATURE                 Location/Qualifiers
source                  1..113
                        mol_type = protein
                        organism = Mus musculus
SEQUENCE: 62
QVQLQQSGAE LVRPGASVTL SCKASGYTFT DYEMHWVKQT PVHGLEWIGA IDPDTGGTAD  60
NQKFKGKAIL TADKSSSTAY MELRSLTSED SAVYYCSLRL YDWGQGTTLT VSS         113

SEQ ID NO: 63           moltype = AA  length = 121
FEATURE                 Location/Qualifiers
source                  1..121
                        mol_type = protein
                        organism = Mus musculus
SEQUENCE: 63
QVQLQQPGAE LVKPGASVKL SCKASGYTFT SYWMHWVKQR PGQGLEWIGV IHPNSGFTNN  60
NEKLKSKATL TVDKSSSTAY MQLSSLTSED SAVYYCAKSA VVERDYAMDY WGQGTSVTVS  120
S                                                                  121

SEQ ID NO: 64           moltype = AA  length = 122
FEATURE                 Location/Qualifiers
source                  1..122
                        mol_type = protein
                        organism = Mus musculus
SEQUENCE: 64
QVQLQQSGAE LARPGASVKL SCKASGYTFT SYGISWVKQR TGQGLEWIGE IYPRSGNTYY  60
NEKFKGEATL TADKSSSTAY MELRSLTSED SAVYFCARVY YYGSNYDGFA YWGQGTLVTV  120
SA                                                                 122

SEQ ID NO: 65           moltype = AA  length = 122
FEATURE                 Location/Qualifiers
source                  1..122
                        mol_type = protein
                        organism = Mus musculus
SEQUENCE: 65
EVQLVESGGG LVKPGGSLKL SCAASGFTFS SYAMSWVRQT PEKRLEWVAA INSNGGRTYY  60
PDTVKDRFTI SRDNAKNTLY LQMSSLRSED TALYYCARQG HSNYYEAWFA YWGQGTLVTV  120
SA                                                                 122

SEQ ID NO: 66           moltype = AA  length = 120
FEATURE                 Location/Qualifiers
source                  1..120
                        mol_type = protein
```

```
                         organism = Mus musculus
SEQUENCE: 66
LVQLQQSGAE LARPGASVKL SCKASGYTFT NHGLSWVKQR TGQGLEWIGE IYPRSGNTYY  60
NENCKGKATL TADRSSSAAY MELRSLTSED SAVYFCARRH SNNDYAMDYW GQGTSVTVSS  120

SEQ ID NO: 67            moltype = AA  length = 118
FEATURE                  Location/Qualifiers
source                   1..118
                         mol_type = protein
                         organism = Mus musculus
SEQUENCE: 67
EVKLVESGGG LVKPGGSLKL SCAASGFTFS SYAMSWVRQI PEKRLEWVAA INSNGGSTYY  60
PDTVKDRFTI SRDNAKNTLY LQMSSLRSED TALYYCVRQG WDAWFAYWGQ GTLVAVSA    118

SEQ ID NO: 68            moltype = AA  length = 118
FEATURE                  Location/Qualifiers
source                   1..118
                         mol_type = protein
                         organism = Mus musculus
SEQUENCE: 68
EVQLVESGGG LVKPGGSLKL SCAASGFTFS SYAMSWVRQT PEKRLEWVAA INSNGGSIYY  60
PDTVKDRFTI SRDNAKNTLY LQMISLRSED TALYYCARQG GSSWFVYWGQ GTLVTVSA    118

SEQ ID NO: 69            moltype = AA  length = 123
FEATURE                  Location/Qualifiers
source                   1..123
                         mol_type = protein
                         organism = Mus musculus
SEQUENCE: 69
QVTLKESGPG KLQPSQTLSL TCSFSGFSLS TSGMGVSWIR QPSGKGLEWL AHIYWDDDKR  60
YNPSLKSRLT ISKDTSRNQV FLKITSVDTA DTATYYCARG WLRRKDYSAM DYWGQGTSVT  120
VSS                                                               123

SEQ ID NO: 70            moltype = AA  length = 122
FEATURE                  Location/Qualifiers
source                   1..122
                         mol_type = protein
                         organism = Mus musculus
SEQUENCE: 70
DVQLVESGGG LVQPGGSRKL SCAASGFIFS SFGMHWVRQA PEKGLEWVAY ISSGSATIYY  60
ADTVKGRFTI SRDNPKNTLF LQMTSLRSED TAMYYCARKR GSGNYVSAMD FWGQGTSVTV  120
SS                                                                122

SEQ ID NO: 71            moltype = AA  length = 122
FEATURE                  Location/Qualifiers
source                   1..122
                         mol_type = protein
                         organism = Mus musculus
SEQUENCE: 71
DVQLVESGGG LVQPGGSRKL SCAASGFTFS NFGMHWVRQV PEKGLEWVAY ISSDISTIYY  60
VDTVKGRFTI SRDNSKNTLF LQMTSLRSED TAMYYCARKR GSGDYVSAMD YWGQGTSVTV  120
SS                                                                122

SEQ ID NO: 72            moltype = AA  length = 122
FEATURE                  Location/Qualifiers
source                   1..122
                         mol_type = protein
                         organism = Mus musculus
SEQUENCE: 72
EVKLVESGGG LVKPGGSLKL SCAASGFTFS DYSMYWVRQT PEKRLEWVAT ISNGGTFIYY  60
VDSVRGRFTI SRDDANNNVY LQMYSLKSED TAIYYCTRGG HYANKGDWFA YWGQGTLVTV  120
SA                                                                122

SEQ ID NO: 73            moltype = AA  length = 117
FEATURE                  Location/Qualifiers
source                   1..117
                         mol_type = protein
                         organism = Mus musculus
SEQUENCE: 73
QVQLQQSGAE LARPGASVKL SCKSSGYIFS SYWMQWVKQR PGQGLEWIGA IYPGDGDTRY  60
TPKFKGKATL TADKSSSTAY MQLTSLASED SAVYYCAKGY SQSFDYWGQG TTLTVSS     117

SEQ ID NO: 74            moltype = AA  length = 117
FEATURE                  Location/Qualifiers
source                   1..117
                         mol_type = protein
                         organism = Mus musculus
SEQUENCE: 74
QVQLKQSGAE LASPKTSVKL SCKASGYTFT SYWMQWIKQR PGQGLEWIGA IYPGDGDTRY  60
```

```
TQKFRGKATL TADKSSNTAY MQLSSLASED SAVYYCAKGY SNSFDYWGQG TSLTVSS     117

SEQ ID NO: 75          moltype = AA  length = 107
FEATURE                Location/Qualifiers
source                 1..107
                       mol_type = protein
                       organism = Mus musculus
SEQUENCE: 75
DIQMTQITSS LSASLGDRVT ISCRASQDIS NYLNWYQQKP DGTVKLLIYS TSRLHSGVPS  60
RFSGSGSGTD YSLTISNLEP EDIATYYCQQ YSKLLPTFGS GTKLEIK                107

SEQ ID NO: 76          moltype = AA  length = 107
FEATURE                Location/Qualifiers
source                 1..107
                       mol_type = protein
                       organism = Mus musculus
SEQUENCE: 76
DIQMTQTTSS LSASLGDRVT ISCSASQGIS NYLNWYQQKP DGTVKLLIYY TSSLHSGVPS  60
RFSGSGSGID YSLTISNLEP EDIATYYCQQ YSKFPWTFGG GTKLEIK                107

SEQ ID NO: 77          moltype = AA  length = 108
FEATURE                Location/Qualifiers
source                 1..108
                       mol_type = protein
                       organism = Mus musculus
SEQUENCE: 77
EIVLIQSPAL MAASPGEKVT ITCSVSSSIS SSNLHWYQQQ SGTSPKPWIL ATSNLASGVP  60
VRFSGSGSGT SYSLTISSME AEDAATYYCQ QWSSYPFTFG TGTKLEIK               108

SEQ ID NO: 78          moltype = AA  length = 107
FEATURE                Location/Qualifiers
source                 1..107
                       mol_type = protein
                       organism = Mus musculus
SEQUENCE: 78
DIQMTQSPAS LSASVGETVT ITCRASGNIH NYLAWYQQRQ GKSPQLLVYN AKTLPDGVPS  60
RFSGSGSGTQ YSLKINSLQP EDFGSYCCQH FWSTPLTFGA GTKLELK                107

SEQ ID NO: 79          moltype = AA  length = 108
FEATURE                Location/Qualifiers
source                 1..108
                       mol_type = protein
                       organism = Mus musculus
SEQUENCE: 79
QIVLTQSPAI MSASPGEKVT LTCSASSSVS SSYLYWYQQK PGSSPKLWIY STSNLASRVP  60
TRFSGSGSGT SYSLTISSME AEDAASYFCH QWSSYPLTFG AGTKLELK               108

SEQ ID NO: 80          moltype = AA  length = 107
FEATURE                Location/Qualifiers
source                 1..107
                       mol_type = protein
                       organism = Mus musculus
SEQUENCE: 80
DIKMTQSPSS LSASLGEGVS LTCRASQDIG SSLHWLQQKP DGTIKRLIYG TSTLDSDVPK  60
RFSGSRSGSD YSLTISSLES EDFVDYFCLQ YATSPPTFGG GTKLEIK                107

SEQ ID NO: 81          moltype = AA  length = 107
FEATURE                Location/Qualifiers
source                 1..107
                       mol_type = protein
                       organism = Mus musculus
SEQUENCE: 81
DIQMTQSPSS LSASLGERVS LTCRASQDIG SSLNWLQQEP DGTFKRLIYA TSSLDSGVPK  60
RFSGSRSGSD YSLTISSLES EDFVDYYCLQ YDSLPLTFGA GTKLELK                107

SEQ ID NO: 82          moltype = AA  length = 107
FEATURE                Location/Qualifiers
source                 1..107
                       mol_type = protein
                       organism = Mus musculus
SEQUENCE: 82
DIQMTQTTSS LSASLGDRVT ISCRASQDIS NYLNWYQQKP AGTVKLLIYY TSRLHSGVPS  60
RFSGSGSGTD YSLTISNLEQ EDVATYFCQQ GNTLPWTFGG GSKLEIK                107

SEQ ID NO: 83          moltype = AA  length = 113
FEATURE                Location/Qualifiers
source                 1..113
                       mol_type = protein
                       organism = Mus musculus
```

```
SEQUENCE: 83
DIVMSQSPSS LAVSVGEKVT MSCKSSQSLL YSTNQENYLA WYQQKPGQSP KLLIYWASSR  60
ESGVPDRFTG SGSGTDFTLT ISSVKAEDLA VYYCQQYYSY PRTFGGGTKL EIK         113

SEQ ID NO: 84          moltype = AA  length = 112
FEATURE                Location/Qualifiers
source                 1..112
                       mol_type = protein
                       organism = Mus musculus
SEQUENCE: 84
DIVMSQSPSS LAVSAGEKVT MSCKSSQSLL SSRTRKNYLA WYQQKPGQSP KLLIYWASTR  60
ESGVPDRFTG SGSGTDFTLT ITTVQAEDLA VYYCKQSYNL WTFGGGTKLE IK          112

SEQ ID NO: 85          moltype = AA  length = 112
FEATURE                Location/Qualifiers
source                 1..112
                       mol_type = protein
                       organism = Mus musculus
SEQUENCE: 85
DVLMTQTPVS LPVSLGDQAS ISCRSSQSIV HSNGNTHLEW YLQKPGQSPK LLIYKVSNRF  60
SGVPDRFSGS GSGTDFTLKI SRVEAEDLGV YYCFQDSHVP WTFGGGTKLE IK          112

SEQ ID NO: 86          moltype = AA  length = 107
FEATURE                Location/Qualifiers
source                 1..107
                       mol_type = protein
                       organism = Mus musculus
SEQUENCE: 86
DVQITQSPSY LAASPGETIT INCRASKSIS KYLAWYQEKP GKTNKVLIYS GSTLQSGIPS  60
RFSGSGSGTD FTLTISSLEP EDFAMYYCQQ YNEYPWTFGG GTKLEIK                107

SEQ ID NO: 87          moltype = AA  length = 112
FEATURE                Location/Qualifiers
source                 1..112
                       mol_type = protein
                       organism = Mus musculus
SEQUENCE: 87
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP YTFGGGTKLE IK          112

SEQ ID NO: 88          moltype = AA  length = 112
FEATURE                Location/Qualifiers
source                 1..112
                       mol_type = protein
                       organism = Mus musculus
SEQUENCE: 88
NIMMTQSPSS LAVSAGEKVT MSCKSSQSVL YSSNQKNYLA WYQQKPGQSP KLLIYWASTR  60
ESGVPDRFTG SGSGTDFTLT ISSVQAEDLA VYYCHQYLSS RTFGGGTKLE IK          112

SEQ ID NO: 89          moltype = AA  length = 111
FEATURE                Location/Qualifiers
source                 1..111
                       mol_type = protein
                       organism = Mus musculus
SEQUENCE: 89
DIVLTQSPAS LAVSLGQRAT ISCRASKSVS TSGYSYIHWY QQKPGQPPKL LIYLASNLES  60
GVPARFSGSG SGTDFTLNIH PVEEEDAATY YCQHSRELPW TFGGGTKLEI K           111

SEQ ID NO: 90          moltype = AA  length = 111
FEATURE                Location/Qualifiers
source                 1..111
                       mol_type = protein
                       organism = Mus musculus
SEQUENCE: 90
DIVLTQSPAS LAVSLGQRAT ISCRASKSVS TSGYSYMHWY QQKPGQPPKL LIYLASNLES  60
GVPARFSGSG SGTDFTLNIH PVEEEDAATY YCLHSRELPW TFGGGTKLEI K           111

SEQ ID NO: 91          moltype = AA  length = 112
FEATURE                Location/Qualifiers
source                 1..112
                       mol_type = protein
                       organism = Mus musculus
SEQUENCE: 91
DVVVTQTPLS LPVSLGDQAS ISCRSSQSLV HSNGKTYLHW YLQKPGQSPN LLIYKVSNRF  60
SGVPDRFSGS GSGTDFTLKI SRVEAEDLGV YFCSQSTHVP FTFGSGTKLE IK          112

SEQ ID NO: 92          moltype = AA  length = 112
FEATURE                Location/Qualifiers
source                 1..112
```

```
                        mol_type = protein
                        organism = Mus musculus
SEQUENCE: 92
DVVMTQTPLS LCVSLGDQAS ISCRSSQSLV HSNGKTYLHW YLQKPGQSPN LLIYKVSNRF  60
SGVPDRFSGS GSGTDFTLKI SRVEAEDLGV YFCSQSTHVP FTFGSGTKLE IK          112

SEQ ID NO: 93           moltype = AA  length = 112
FEATURE                 Location/Qualifiers
source                  1..112
                        mol_type = protein
                        organism = Mus musculus
SEQUENCE: 93
DVVMTQTPLS LPVSLGDQAS ISCRSSQSLV HNNGITYLYW YLQKPGQSPK LLIYRVSNRF  60
SGVPDRFGGS GSGTDFTLKI SRVEAEDLGV YFCFQGTHVP RTFGGGTKLE IK          112

SEQ ID NO: 94           moltype = AA  length = 112
FEATURE                 Location/Qualifiers
source                  1..112
                        mol_type = protein
                        organism = Mus musculus
SEQUENCE: 94
DVVMTQTPLS LPVSLGDHAS ISCRSSQSLV HSNGITHLYW YLQRPGQTPK LLIYRVSNRF  60
SGVPDRFSGS GSGTDFTLKI SSVEAEDLGV YFCFQGTHVP RTFGGGTKLE IE          112

SEQ ID NO: 95           moltype = AA  length = 112
FEATURE                 Location/Qualifiers
source                  1..112
                        mol_type = protein
                        organism = Mus musculus
SEQUENCE: 95
DVVMTQTPLS LPVSLGDQAS ISCRSSQSLV HSNGNTHLYW YLQKPGQSPK LLIYRVSSRF  60
SGVPDRFSGS GSGTDFTLKI SRVEAEDLGV YFCFQGTHVP RTFGGGTKLE IK          112

SEQ ID NO: 96           moltype = AA  length = 112
FEATURE                 Location/Qualifiers
source                  1..112
                        mol_type = protein
                        organism = Mus musculus
SEQUENCE: 96
DVVMTQTPLS LPVSLGDQAS ISCRSSQSLV HSTGNTYLYW YLQKPGQSPK LLIYRVSTRF  60
SGVPDRFSGS GSGTDFTLKI NRVEAEDLGV YFCFQGTHVP RTFGGGTKLE IK          112

SEQ ID NO: 97           moltype = AA  length = 112
FEATURE                 Location/Qualifiers
source                  1..112
                        mol_type = protein
                        organism = Mus musculus
SEQUENCE: 97
DVLMTQTPLS LPVSLGDQAS ISCRSSQSIV YSNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 98           moltype = AA  length = 112
FEATURE                 Location/Qualifiers
source                  1..112
                        mol_type = protein
                        organism = Mus musculus
SEQUENCE: 98
DVLMTQTPLS LPVSLGDQAS ISCRSSQSIV HRNGNTYLEW YLQKPGQSPK LLIYKVSNRF  60
SGVPDRFSGS GSGTDFTLKI SRVEAEDLGV YYCFQGSHVP FTFGSGTKLE IK          112

SEQ ID NO: 99           moltype = AA  length = 112
FEATURE                 Location/Qualifiers
source                  1..112
                        mol_type = protein
                        organism = Mus musculus
SEQUENCE: 99
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP FTFGSGTKLE IK          112

SEQ ID NO: 100          moltype = AA  length = 112
FEATURE                 Location/Qualifiers
source                  1..112
                        mol_type = protein
                        organism = Mus musculus
SEQUENCE: 100
DVLMTQTPLS LPVSLGDQAS ISCRSSQNIV HSNGNTYLEW YLQKPGQSPK LLIYRVSNRF  60
SGVPGRFSGS GSGTDFTLKI SRVEAEDLGV YYCFQGSRVP LTFGTGTKLE LK          112

SEQ ID NO: 101          moltype = AA  length = 112
```

```
FEATURE                Location/Qualifiers
source                 1..112
                       mol_type = protein
                       organism = Mus musculus
SEQUENCE: 101
DVLMTQTPLS LPVSLGDQAS ISCRSSQNIV HSNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 102         moltype = AA  length = 112
FEATURE                Location/Qualifiers
source                 1..112
                       mol_type = protein
                       organism = Mus musculus
SEQUENCE: 102
DVLMTQTPLS LPVSLGDQAS IACRSSQSIV HSNGNTYLEW YLQKPGQSPE LLIYKVSNRF  60
SGVPDRFSGS GSGTDFTLKI SRVEAEDLGV YYCFQGSHVP YTFGGGTKLE IK          112

SEQ ID NO: 103         moltype = AA  length = 112
FEATURE                Location/Qualifiers
source                 1..112
                       mol_type = protein
                       organism = Mus musculus
SEQUENCE: 103
DVLMTQTPLS LPVSLGDQAS ISCRSSQSIV YTNGNTYLEW YLQKPGQSPK LLIYKVSNRF  60
SGVPDRFSGS GSGTDFTLKI SRVEAEDLGV YYCFQGSHVP YTFGGGTKLE IK          112

SEQ ID NO: 104         moltype = AA  length = 112
FEATURE                Location/Qualifiers
source                 1..112
                       mol_type = protein
                       organism = Mus musculus
SEQUENCE: 104
DVVLTQTPLT LSVTIGQPAS ISCKSSQSLL HSDGKTYLNW LLQRPGQSPK RLFYLVSKLD  60
SGVPDRFTGS GSGTDFTLKI SSVEAEDLGV YYCWQGTHFP HTFGAGTKLE LK          112

SEQ ID NO: 105         moltype = AA  length = 112
FEATURE                Location/Qualifiers
source                 1..112
                       mol_type = protein
                       organism = Mus musculus
SEQUENCE: 105
DVVMTQTPLT LSVTIGQPAS ISCKSSQSLL HSDGKTFLNW LLQRPGQSPK RLIYLVSKLD  60
SGVPDRFTGS GSGTDFTLKI SRVEAEDLGV YYCWQGTHFP QTFGGGTKLE IK          112

SEQ ID NO: 106         moltype = AA  length = 112
FEATURE                Location/Qualifiers
source                 1..112
                       mol_type = protein
                       organism = Mus musculus
SEQUENCE: 106
DVVMIQTPLT LSVTSGQPAS ISCKSSQSLL HSDGKTYLNW LLQRPGQSPK RLMYLVSKLD  60
SGVPDRFTGS GSGTDFTLKI SRVEAEDLGV YYCWQGTHFP QTFGGGTKLE IK          112

SEQ ID NO: 107         moltype = AA  length = 112
FEATURE                Location/Qualifiers
source                 1..112
                       mol_type = protein
                       organism = Mus musculus
SEQUENCE: 107
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP QTFGGGTKLE IK          112

SEQ ID NO: 108         moltype = AA  length = 112
FEATURE                Location/Qualifiers
source                 1..112
                       mol_type = protein
                       organism = Mus musculus
SEQUENCE: 108
DVVMTQTPLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP RTFGGGTKLE IK          112

SEQ ID NO: 109         moltype = AA  length = 107
FEATURE                Location/Qualifiers
source                 1..107
                       mol_type = protein
                       organism = Mus musculus
SEQUENCE: 109
DVQITQSPSY LAASPGEIII INCRTSKSIN KYLAWYQEKP GKTNKLLIYS GSTLQSGIPS  60
RFSGSGSGTD FTLTISSLEP EDFAMYYCQQ HNEYPYTFGG GTKLEIK                107
```

```
SEQ ID NO: 110         moltype = AA  length = 107
FEATURE                Location/Qualifiers
source                 1..107
                       mol_type = protein
                       organism = Mus musculus
SEQUENCE: 110
DVQITQSPSY LAASPGETIT LNCRASKNIS KYLAWYQEKP GKTNKLLIYS GSTLQSGIPS  60
RFSGSGSGTD FTLTISSLEP EDFAMYFCQQ HNEYPYTFGG GTKLEMK                107

SEQ ID NO: 111         moltype = AA  length = 107
FEATURE                Location/Qualifiers
source                 1..107
                       mol_type = protein
                       organism = Mus musculus
SEQUENCE: 111
DIQMTQSPAS LSASVGETVT ITCRASENIY SYLAWYQQKQ GTSPQLLVYN AKALAEGVPS  60
RFSGSGSGTQ FSLKINSLQP EDFGSYYCQH HYGTPRTFGG GSKLEIK                107

SEQ ID NO: 112         moltype = AA  length = 107
FEATURE                Location/Qualifiers
source                 1..107
                       mol_type = protein
                       organism = Mus musculus
SEQUENCE: 112
DIQMTQSPAS LSASVGETVT ITCRASENIY SYLAWYQQKQ GKSPQLLVYN AKTLAEGVPS  60
RFSGSGSGTQ FSLKINSLQP EDFGSYYCQH HYGTPRTFGG GTKLEIK                107

SEQ ID NO: 113         moltype = AA  length = 107
FEATURE                Location/Qualifiers
source                 1..107
                       mol_type = protein
                       organism = Mus musculus
SEQUENCE: 113
SIVMTQTPKF LPVSAGDRVT MTCKASQSVG NNVAWYQQKP GQSPKLLIYY ASNRYTGVPD  60
RFTASGSGTD FTFTISSVQV EDLAVYFCQQ HYSSPYTFGS GTNLEIK                107

SEQ ID NO: 114         moltype = AA  length = 107
FEATURE                Location/Qualifiers
source                 1..107
                       mol_type = protein
                       organism = Mus musculus
SEQUENCE: 114
SIVMTQSPKF LPVSAGDRVT MTCKASQSVG NNVAWYQQKP GQSPKLLIYY ASNRYTGVPD  60
RFTGSGSGTD FTLTISSVQV EDLVVYFCQQ HYSSPLTFGA GTKLELK                107

SEQ ID NO: 115         moltype = AA  length = 107
FEATURE                Location/Qualifiers
source                 1..107
                       mol_type = protein
                       organism = Mus musculus
SEQUENCE: 115
NIVMTQTPKF LPIAAGDRVI MTCKASQSVG NNVGWYQLKP GQSPKLLIYF ASNRYTGVPD  60
RFTGSGSGTD FTFTISSVQV EDLAVYFCQQ HYSSPLTFGA GTKLELK                107

SEQ ID NO: 116         moltype = AA  length = 107
FEATURE                Location/Qualifiers
source                 1..107
                       mol_type = protein
                       organism = Mus musculus
SEQUENCE: 116
SIVMTQTPKF LPVSAGDRVT MTCKASQSLG NNVAWYQQKP GQSPKLLIYY ASNRYTGVPD  60
RFTGSGSGTD FTFTISSVQV EDLAVYFCQQ HYSSPRTFGG GTKLEIR                107

SEQ ID NO: 117         moltype = AA  length = 112
FEATURE                Location/Qualifiers
source                 1..112
                       mol_type = protein
                       organism = Mus musculus
SEQUENCE: 117
DVVMTQTPLS LPVSLGDQAS ISCRSSQSLV HSYRNTYLHW YLQKPGQSPK LLIYKVSNRF  60
SGVPDRFSGS GSGTDFTLKI SKVEAEDLGV YFCSQSTHVP WTFGGGTKLE IK          112

SEQ ID NO: 118         moltype = AA  length = 112
FEATURE                Location/Qualifiers
source                 1..112
                       mol_type = protein
                       organism = Mus musculus
SEQUENCE: 118
```

```
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP WTFGGGTKLE IK          112

SEQ ID NO: 119          moltype = AA  length = 109
FEATURE                 Location/Qualifiers
source                  1..109
                        mol_type = protein
                        organism = Mus musculus
SEQUENCE: 119
EIVLTQSPTT MAASPGENIT ITCSASSTIS SHYLHWYQQK PGFSPKLLIY RTYNLASGVP  60
TRFSGSGSGT SYSLTIGAME AEDVATYYCQ QGSTISRYTF GGGTKLEVK           109

SEQ ID NO: 120          moltype = AA  length = 109
FEATURE                 Location/Qualifiers
source                  1..109
                        mol_type = protein
                        organism = Mus musculus
SEQUENCE: 120
QIVLTQSPTT MAASPGEKIT ITCSASSSIS STYLHWYQQK PGFSPKLLIY RTSNLASGVP  60
ARFSGSGSGT SYSLTIGTME AEDVATYYCQ QGSSIPRYTF GGGTKLEIK           109

SEQ ID NO: 121          moltype = AA  length = 107
FEATURE                 Location/Qualifiers
source                  1..107
                        mol_type = protein
                        organism = Mus musculus
SEQUENCE: 121
DIQMTQSPAS LSASVGETVT FTCGASENVY GALNWYQRKQ GKSPQLLIYG ATNLADGMSS  60
RFSGSGSGRQ YSLKISSLHP DDVATYYCQN VLTIPWTFGG GAKLEIK             107

SEQ ID NO: 122          moltype = AA  length = 107
FEATURE                 Location/Qualifiers
source                  1..107
                        mol_type = protein
                        organism = Mus musculus
SEQUENCE: 122
SIVMTQTPKF LLVSAGDRVT ITCKASQSVS NDVAWYQQKP GQSPKLLIYY ASNRCTGVPD  60
RFTGSGYGTD FTFTISTVQA EDLAVYFCQQ DYRSPLTFGA GTKLELK             107

SEQ ID NO: 123          moltype = AA  length = 113
FEATURE                 Location/Qualifiers
source                  1..113
                        mol_type = protein
                        organism = Mus musculus
SEQUENCE: 123
DIVMTQSPSS LSVSAGEKVT MSCKSSQSLL NSGNQKNYLA WYQQKPGQPP KLLIYGASIR  60
ESGVPDRFTG SGSGTDFTLT ISSVQAEDLA VYYCQNDHSH PYTFGGGTKL EIK       113

SEQ ID NO: 124          moltype = AA  length = 113
FEATURE                 Location/Qualifiers
source                  1..113
                        mol_type = protein
                        organism = Mus musculus
SEQUENCE: 124
DIVMTQSPSS LSVSAGEKVT MSCKSSQSLL NSGNQKNYLA WYQQKPGQPP KLLIYGTSTR  60
ESGVPDRFTG SGSGTDFTLT ISSVQAEDLA VYYCQNDHSH PYTFGGGTKL EIK       113

SEQ ID NO: 125          moltype = AA  length = 113
FEATURE                 Location/Qualifiers
source                  1..113
                        mol_type = protein
                        organism = Mus musculus
SEQUENCE: 125
DIVMTQSPSS LSVSAGEKVT MSCKSSQSLL NSGNQKNYLA WYQQKPGQPP KLLIYGASTR  60
ESGVPDRFTG SGSGTDFTLT ISSVQAEDLA VYYCQNDHSH PYTFGGGTKL EIK       113

SEQ ID NO: 126          moltype = AA  length = 113
FEATURE                 Location/Qualifiers
source                  1..113
                        mol_type = protein
                        organism = Mus musculus
SEQUENCE: 126
DTVMTQSPSS LSVSAGEKVT MNCKSSQSLL NSGNQKNYLA WYQQKPGQPP KLLIYGASTR  60
ESGVPDRFTG SGSGTDFTLT ISSVQAEDLA VYYCQNDHSH PYTFGGGTKL EIK       113

SEQ ID NO: 127          moltype = AA  length = 113
FEATURE                 Location/Qualifiers
source                  1..113
                        mol_type = protein
```

```
                        organism = Mus musculus
SEQUENCE: 127
DIVMTQSPSS LSVSAGEKVT MSCKSSQSLL SSGNQKNYLA WYQQKPGQPP KLLIYGASTR  60
ESGVPDRFTG SGSGTDFTLT ISSVQAEDLA VYYCQNDHSH PYTFGGGTKL EIK         113

SEQ ID NO: 128          moltype = AA  length = 111
FEATURE                 Location/Qualifiers
source                  1..111
                        mol_type = protein
                        organism = Mus musculus
SEQUENCE: 128
DIVLTQSPAS LAVSLGQRAT ISCRASHSVS SSCYSYMHWY QQKPGQPPKL LIKYASNLES  60
GVPARFSGSG SGTDFTLNIH PVEEEDTATY YCQHSWEIPY TFGGGTKLEI K           111

SEQ ID NO: 129          moltype = AA  length = 111
FEATURE                 Location/Qualifiers
source                  1..111
                        mol_type = protein
                        organism = Mus musculus
SEQUENCE: 129
DIVLTQSPAS SAVSLGQRAT ISCRASQRVS TSSYSYMHWY QQKPGQPPKL LIKYASNLES  60
GVPARFSGSG SGTDFTLNIH PVEEEDTATY YCQHSWEIPY TFGGGTKLEI K           111

SEQ ID NO: 130          moltype = AA  length = 107
FEATURE                 Location/Qualifiers
source                  1..107
                        mol_type = protein
                        organism = Mus musculus
SEQUENCE: 130
DIQMTQTTSS LSASLGDRVT ISCSASQGIS NYLNWYQQKP DGTVTLLIYY TSSLHSGVPS  60
RFSGSGSGTD YSLTISNLEP EDIATYYCQQ YSKLPWTFGG GTKLEIK               107

SEQ ID NO: 131          moltype = AA  length = 112
FEATURE                 Location/Qualifiers
source                  1..112
                        mol_type = protein
                        organism = Mus musculus
SEQUENCE: 131
DVVMTQTPLS LPVSLGDQAS ISCRSSQSLL HSNGNTYLHW YLQKPGQSPE LLIYKVSNRF  60
FGVPDRFSGS GSGTDFTLKI SRVEAEDLGV YFCSQSTHVP WTFGGGTKLE IK          112

SEQ ID NO: 132          moltype = AA  length = 112
FEATURE                 Location/Qualifiers
source                  1..112
                        mol_type = protein
                        organism = Mus musculus
SEQUENCE: 132
DVLMTQTPLS LPVSLGDQAS ISCRSSQNIV QSNGNTYLEW YLQKPGQSPK LLIYKVFNRF  60
SGVPDRFSGS GSGTDFTLKI SRVEAEDLGV YYCFQGSHVP YTFGGGTKLE IK          112

SEQ ID NO: 133          moltype = AA  length = 112
FEATURE                 Location/Qualifiers
source                  1..112
                        mol_type = protein
                        organism = Mus musculus
SEQUENCE: 133
DVVMTQTPLS LPVSLGDQAS ISCRSSQSLV HSNGNTYLHW YLQKPGQSPK LLIYKVSNRF  60
SGVPDRFSGS GSGTDFTLKI SRVEAEDLGV YFCSQSTHVP LTFGAGTKLE LK          112

SEQ ID NO: 134          moltype = AA  length = 107
FEATURE                 Location/Qualifiers
source                  1..107
                        mol_type = protein
                        organism = Mus musculus
SEQUENCE: 134
DIVMTQSPAT LSVTPGDRVS LSCRASQSIS DYLHWYQQKL HESPRLLIKY ASQSISGSPS  60
RFSGSGSGSD FTLSINSVEP EDVGVYYCQN GHSFPPTFGG GTKLEIK               107

SEQ ID NO: 135          moltype = AA  length = 107
FEATURE                 Location/Qualifiers
source                  1..107
                        mol_type = protein
                        organism = Mus musculus
SEQUENCE: 135
DIKMTQSPSS MYASLGERLS ITCKASQDIN SYLNWFQQKP GKSPKTLIYR ANRLVDGVPS  60
RFSGSGSGQD YSLTISSLED EDMGIYYCLQ YDEFPLTFGA GTKLELR               107

SEQ ID NO: 136          moltype = AA  length = 107
FEATURE                 Location/Qualifiers
```

```
source                  1..107
                        mol_type = protein
                        organism = Mus musculus
SEQUENCE: 136
DILLTQSPAI LSVSPGERVS FSCRASQNIG TSIHWYQQRT NGSPRLLIKY ASESISGIPS  60
RFSGSGSGTD FTLSINSVES EDIADYYCQQ SNSWPTTFGG GTKLEIK               107

SEQ ID NO: 137          moltype = AA  length = 107
FEATURE                 Location/Qualifiers
source                  1..107
                        mol_type = protein
                        organism = Mus musculus
SEQUENCE: 137
DIKMTQSPSS MYASLGERVT ITCKASQDIN SYLSWFQQKP GKSPKTLIYR ANRLVDGVPS  60
RFSGSGSGQD YSLTISSLEY EDMGIYYCLQ YDEFPLTFGA GTKLELK               107

SEQ ID NO: 138          moltype = AA  length = 107
FEATURE                 Location/Qualifiers
source                  1..107
                        mol_type = protein
                        organism = Mus musculus
SEQUENCE: 138
DIKMIQSPSS MYASLGERVT ITCKASQDIN SYLSWFQQKP GKSPKTLIYR ANRLVDGVPS  60
RFSGSGSGQD YSLTISRLEY EDVGLYYCQQ YDEFPLTFGA GTKLELK               107

SEQ ID NO: 139          moltype = AA  length = 107
FEATURE                 Location/Qualifiers
source                  1..107
                        mol_type = protein
                        organism = Mus musculus
SEQUENCE: 139
NIVMTQSPKS MSMSVGERVT LSCKASEHVG PYVSWYQHKA EQSPKLLIYG ASNRYTGVPD  60
RFTGSGSATD FTLIISSVQA EDLADYHCGQ TYSYPLTFGA GTKLELK               107

SEQ ID NO: 140          moltype = AA  length = 107
FEATURE                 Location/Qualifiers
source                  1..107
                        mol_type = protein
                        organism = Mus musculus
SEQUENCE: 140
NIVMTQSPKS MSMSVGERVT LTCKASENVV TYVSWYQHKA EQSPKLLIYG ASNRYTGVPD  60
RFTGSGSATD FTLIISSVQA EDLADYHCGQ TYSYPLTFGA GTKLELK               107

SEQ ID NO: 141          moltype = AA  length = 107
FEATURE                 Location/Qualifiers
source                  1..107
                        mol_type = protein
                        organism = Mus musculus
SEQUENCE: 141
NIVMTQSPKS MSMSVGERVT LTCKASENVV TYVSWYQQKP EQSPKLLIYG ASNRYTGVPD  60
RFTGSGSATD FTLTISSVQA EDLADYHCGQ TYSYPLTFGA GTKLELK               107

SEQ ID NO: 142          moltype = AA  length = 112
FEATURE                 Location/Qualifiers
source                  1..112
                        mol_type = protein
                        organism = Mus musculus
SEQUENCE: 142
DVLMTQTPLS LPVSLGDQAS ISCRSGQSIV HSNGNTYLEW YLQKPGQSPK LLIYKVSNRF  60
SGVPDRFSGS GSGTDFTLKI SRVEAEDLGV YYCFQGSHVP WTFGGGTKLE IK          112

SEQ ID NO: 143          moltype = AA  length = 112
FEATURE                 Location/Qualifiers
source                  1..112
                        mol_type = protein
                        organism = Mus musculus
SEQUENCE: 143
DVLLTQSPLS LPVSLGDQVS ISCRSGQSIV HSNGNTYLGW YLQKPGQSPK LLIYKVSIRF  60
YGVPDRFSGS GSGTYFTLKI SRVEAEDLGV YHCFQGSHVP WTFGGGTKLE IK          112

SEQ ID NO: 144          moltype = AA  length = 112
FEATURE                 Location/Qualifiers
source                  1..112
                        mol_type = protein
                        organism = Mus musculus
SEQUENCE: 144
DVVMTQTPLT LSVIIGQPAS IYCKSSQSLL YSNGKTYLNW LLQRPGQSPK RLIYLVSKLD  60
SGVPDRFTGS GSGTDFALQI SRVEAEDLGI YYCVQGTHFP HTFGGGTKLE IK          112
```

```
SEQ ID NO: 145         moltype = AA  length = 112
FEATURE                Location/Qualifiers
source                 1..112
                       mol_type = protein
                       organism = Mus musculus
SEQUENCE: 145
DVVMTQTPLT LSVTIGQPAS ISCKSSQSLL DSDGKTYLSW LLQRPGQTPK RLIYMVSKLD  60
SGVPDRFTGS GSGTDFTLKI KRVEAEDLGV YYCWQGTHFP VTFGGGTKLE LK         112

SEQ ID NO: 146         moltype = AA  length = 112
FEATURE                Location/Qualifiers
source                 1..112
                       mol_type = protein
                       organism = Mus musculus
SEQUENCE: 146
DVEMTQTPLT LSVTIGQPAS ISCKSNQSLL DSDGKTYLSW LLQRPGQSPK RLIYMVSKLD  60
SGVPDRFTGS GSGTDFTLKI NRVVAEDLGV YSCWQGTHFP LTFGAGTKLE VK         112

SEQ ID NO: 147         moltype = DNA  length = 360
FEATURE                Location/Qualifiers
source                 1..360
                       mol_type = unassigned DNA
                       organism = Mus musculus
SEQUENCE: 147
gaggtgcagc ttgttgagtc tggtggagga ttggtgcagc ctaaaggatc attgaaactc  60
tcatgtgccg cctctggttt caccttcaat acctatgcca tgtattgggt ccgccaggct  120
ccaggaaagg gtttggaatg ggttgctcgc ataagaagta aaagtagtaa ttatgcaaca  180
tattatgccg attcagtgaa agacagattc accatctcca gagatgattc acaaagcaag  240
ctctatctgc aaatgaacaa cctgaaaact gaggacacag ccatgtatta ctgtgtgaga  300
gagggactat ggtactactt tgactactgg ggccaaggca ccactctcac agtctcctca  360

SEQ ID NO: 148         moltype = DNA  length = 363
FEATURE                Location/Qualifiers
source                 1..363
                       mol_type = unassigned DNA
                       organism = Mus musculus
SEQUENCE: 148
gaggtccagc tgcaacaatc tggacctgag ctggtgaagc ctggggcttc agtgaagata  60
tcctgtgagg cttctggata cacattcact gactactaca tgaactgggt gaagcagagc  120
catggaaaga gccttgagtg gattggagat attaatccta acaatggtgg tactacctac  180
aaccagaagt tcaagggcaa ggccacattg actgtagaca agtcctccag cacagcccac  240
atggaactcc gcagcctgac atctgaggac tctgcagtct attactgtgc aagaggatct  300
agttactatg atttttcctg gtttgcttac tggggccagg ggactctggt cactgtctct  360
gca                                                                363

SEQ ID NO: 149         moltype = DNA  length = 366
FEATURE                Location/Qualifiers
source                 1..366
                       mol_type = unassigned DNA
                       organism = Mus musculus
SEQUENCE: 149
caggtccaac tgcagcagcc tgggactgaa ctggtgaagc ctggggcttc agtgaagctg  60
tcctgcaagg cttctggcta caccttcacc aagaactggc tgcactgggt gaagcagagg  120
cctggacaag gccttgaatg gattggatat attaatccta gtaatggtgc tacaaactac  180
aatgagaggt tcaagagcaa ggcctcactg actgtagaca aatcctccac cacagcctac  240
atgcagctca gcagcctgac atctgaggac tctgcggtct attattgtgc aagatcaggg  300
ggatggttac taccctacta tgctatggac tactggggtc atggaacctc agtcaccgtc  360
tcctca                                                             366

SEQ ID NO: 150         moltype = DNA  length = 339
FEATURE                Location/Qualifiers
source                 1..339
                       mol_type = unassigned DNA
                       organism = Mus musculus
SEQUENCE: 150
caggtccaac tgcagcagcc tggggctgag cttgtgaagc ctggggcttc agtgaagctg  60
tcctgcaagg cttctgacta caccttcacc aactactgga tgcactgggt gaagcagagg  120
cctggacgag gccttgagtg gataggaagg attgatccta atagtggtgg tactaggtac  180
aatgagaagt tcaagaacaa ggccacactg actgttgaca aaccctccag cacagcctac  240
atgcatctca gcagcctgac atctgaggac tctgcggtct attattgtgc aggggacttc  300
gatgtctggg gcacagggac cacggtcacc gtctcctca                         339

SEQ ID NO: 151         moltype = DNA  length = 360
FEATURE                Location/Qualifiers
source                 1..360
                       mol_type = unassigned DNA
                       organism = Mus musculus
SEQUENCE: 151
caggtgcagc tgaaggagtc aggacctggc ctggtggcgc cctcacagag cctgtccatc  60
```

```
acatgcactc tctcagggtt ctcattaacc gactatggtg taagctggat tcgccagcct  120
ccaggaaagg gtctggagtg gctgggatta atgtggggtg gtggaagcac atactataat  180
tcagctctca aatccagact gagcatcagc aaggacaact ccaagagcca agttttctta  240
aaaatgaaca gtctgcaaac tgatgacaca gccatgtact actgtgccaa acatgggacc  300
tactatggta actacgggat tgcttactgg ggccaaggga ctctggtcac tgtctctgca  360

SEQ ID NO: 152          moltype = DNA  length = 360
FEATURE                 Location/Qualifiers
source                  1..360
                        mol_type = unassigned DNA
                        organism = Mus musculus
SEQUENCE: 152
caggtgcagc tgaaggagtc aggacctggc ctggtggcgc cctcacagag cctgtccatc  60
acatgcactg tctctgggtt ctcactaacc agctatgcta taagctgggt tcgccagcca  120
ccaggaaaga gtctggagtg gcttggagta atatggactg gtggaggctc aaaatataat  180
tcagctctca aatccagact gagcatcagc aaagacaact ccaagagtca ggtttttctta  240
aaaatgaaca gtctgcaaac tgatgataca gccaggtact attgtgtcag aaattacgac  300
tactataggt acgaggggtt tgattactgg ggccaaggga ctctggtcac tgtctctgca  360

SEQ ID NO: 153          moltype = DNA  length = 360
FEATURE                 Location/Qualifiers
source                  1..360
                        mol_type = unassigned DNA
                        organism = Mus musculus
SEQUENCE: 153
gaggtgcagc tggtggagtc tgggggagac ttagtgaagc ctggagggtc cctgaaactc  60
tcctgtgcag cctctggatt cactttcagt agctatggct tgtcttgggt tcgccagact  120
ccagacaaga ggctggagtg ggtcgcaacc attagtagtg gtggtgatta cacctactat  180
ccagacagtg tgaaggggcg attcaccatc tccagagaca atgccaagaa catcctgtac  240
ctgcacatga gcagtctgaa gtctgaggac acagccatgt attactgtgc aagagaggat  300
ggttattacg tggggactat ggactactgg ggtcaaggaa cctcagtcac cgtctcctca  360

SEQ ID NO: 154          moltype = DNA  length = 378
FEATURE                 Location/Qualifiers
source                  1..378
                        mol_type = unassigned DNA
                        organism = Mus musculus
SEQUENCE: 154
caggtgcagc tgaaggagtc aggacctggc ctggtggcgc cctcacagag cctgtccatc  60
acatgcactg tctctgggtt ctcattaacc acctatgcta taagctgggt tcgccagcca  120
ccaggaaagg gtctggagtg gcttggagta atatggactg gtggaggcac agattttaat  180
tcagctctca aatccagact gagcatcagc aaagacaact ccaagagtca agttttctta  240
aagatgatca gtctgcaaac taatgacaca gccaggtact actgtgccag aaagggagga  300
tcttactaca gtactaccta cgtcgggcta tatgctatgg actactgggg tcaaggaacc  360
tcagtcaccg tctcctca                                               378

SEQ ID NO: 155          moltype = DNA  length = 345
FEATURE                 Location/Qualifiers
source                  1..345
                        mol_type = unassigned DNA
                        organism = Mus musculus
SEQUENCE: 155
gaggtgcagc tggtggagtc tggaggagcc ttggtacagc ctgggggttc tctgagtctc  60
tcctgtgcag cttctggatt caccttcact gattactaca tgagctgggt ccgccagcct  120
ccagggaagg cacttgagtg gctggctttg attagaaaca aagctaaagg tttcacaaca  180
gaatacagtg catctgtgaa gggtcggttc accatctcca gagataattc ccaaagcatc  240
ctccttttc aaatgaatga cctgagagct gacgacagtg ccacttatta ctgtgtaaga  300
gatataaact actggggcca aggcaccact ctcacagtct cctca                 345

SEQ ID NO: 156          moltype = DNA  length = 360
FEATURE                 Location/Qualifiers
source                  1..360
                        mol_type = unassigned DNA
                        organism = Mus musculus
SEQUENCE: 156
cagatccagt tggtacagtc tggacctgag ctgaagaagc ctggagagac agtcaagatc  60
tcctgcaagg cttctgggta ttccttcaca acctatggaa tgagctgggt gaaacaggct  120
ccaggaaagg gtttaaagtg gatgggctgg ataaacacct actctggagt gccaacatat  180
gctgatgact tcaaggaacg gtttgccttc tctttggaaa cctctgccag cactgcctat  240
ttgcagatca acaacctcaa aaatgaggac acgtctacat atttctgtgc aagaagaggg  300
ggcctctatg atggttacta cggctactgg ggccaaggca ccactctcac agtctcctca  360

SEQ ID NO: 157          moltype = DNA  length = 345
FEATURE                 Location/Qualifiers
source                  1..345
                        mol_type = unassigned DNA
                        organism = Mus musculus
SEQUENCE: 157
gaggtgcagc tggtggagtc tgggggaggc ttagtgaagc ctggagggtc cctgaaactc  60
```

```
tcctgtgcag cctctggatt cactttcagt gactatggaa tgtattgggt tcgtcaggct  120
ccagagaagg ggctggagtg ggttgcatat attagtagtg gcagtactac catctactat  180
gcagacacag tgaagggccg attcaccatc tccagagaca atgccaagaa caccctgttc  240
ctgcaaatga ccagtctgag gtctgaggac acggccatgt attactgtgc cggtcactgg  300
tacttcgatg tctggggcac agggaccacg gtcaccgtct cctca                   345

SEQ ID NO: 158          moltype = DNA  length = 342
FEATURE                 Location/Qualifiers
source                  1..342
                        mol_type = unassigned DNA
                        organism = Mus musculus
SEQUENCE: 158
gaagtgaagc ttgaggagtc tggaggaggc ttggtgcaac ctggaggatc catgaaactc  60
tcctgtgttg cctctggaat cactttcagt cactactgga tgaactgggt ccgccaggct  120
ccagagaggg gccttgagtg ggttgctcaa attaaattga aatctgataa ttatgcaaca  180
cattatgcgg agtctgtgaa agggaggttt accatttcaa gagatgattc caaaagtagt  240
gtctacctgc aaatgaacaa cttaagggct gaagacactg gagtttatta ctgcacaggc  300
ttctatgatt ggggccaagg caccactctc acagtctcct ca                      342

SEQ ID NO: 159          moltype = DNA  length = 342
FEATURE                 Location/Qualifiers
source                  1..342
                        mol_type = unassigned DNA
                        organism = Mus musculus
SEQUENCE: 159
caggcttatc tacagcagtc tggggctgag ctggtgaggc ctggggcctc agtgaagatg  60
tcctgcaagg cttctggcta cacatttacc agttacaata tgcactgggt aaagcagaca  120
cctagacagg gcctggaatg gattggagct atttatccag gaaatggtga tacttcctac  180
aatcagaagt tcaagggcaa ggccacactg actgtagaca aatcctccag cacagcctac  240
atgcagctca gcagcctgac atctgaagac tctgcggtct atttctgtgc aagagggggg  300
atggactact ggggtcaagg aacctcagtc accgtctcct ca                      342

SEQ ID NO: 160          moltype = DNA  length = 342
FEATURE                 Location/Qualifiers
source                  1..342
                        mol_type = unassigned DNA
                        organism = Mus musculus
SEQUENCE: 160
gaggtccagc tacaacagtc tggacctgag ctggtgaagc ctggggcttc agtgaagatg  60
tcctgcaagg cttctggata cacattctct gactacaaca tgcactggtt gaagcagagc  120
catggaaaga gccttgagtg gattggatat attaacccta acaatggtgg tattagctac  180
aaccagaagt tcaagggcaa ggccacattg actgtaaaca agtcctccag cacagcctac  240
atggagctcc gcagcctgac atcggaggat tctgcactct attattgtgc aagatggagt  300
gtctcttact ggggccaagg gactctggtc actgtctccg ca                      342

SEQ ID NO: 161          moltype = DNA  length = 351
FEATURE                 Location/Qualifiers
source                  1..351
                        mol_type = unassigned DNA
                        organism = Mus musculus
SEQUENCE: 161
gaggttcagc tgcagcagtc tggggcagag cttgtgaagc caggggcctc agtcaagttg  60
tcctgcacag cttctggctt caacattaaa gactactata tacactgggt gaagcagagg  120
actgaacagg gcctggagtg gattggaagg attgatcctg aggatggtga aactaaatat  180
gccccgaaat tccagggcaa ggccactata gcagcagaca catcctccaa cacagcctac  240
ctacacctca acagcctgac atctgaggac actgccgtct attactgtgc tagggaattc  300
tcctatgcta tggactactg gggtcaagga acctcagtca ccgtctcctc a            351

SEQ ID NO: 162          moltype = DNA  length = 351
FEATURE                 Location/Qualifiers
source                  1..351
                        mol_type = unassigned DNA
                        organism = Mus musculus
SEQUENCE: 162
gaggttcagc tgcagcagtc tggggcagag cttgtgaagc caggggcctc agtcaagttg  60
tcctgcacag cttctggctt caacattaaa gactactata tgcactgggt gaagcagagg  120
actgaacagg gcctggagtg gattggaagg attgatcctg aggatgatga aactaaatat  180
gccccgaaat tccagggcaa ggccactata acagcagaca catcctccaa cacagtctac  240
ctgcagctca gcagcctgac atctgaggac actgccgtct attactgtgc tagggaattc  300
tcctatgcta tggactactg gggtcaagga acctcagtca ccgtctcctc a            351

SEQ ID NO: 163          moltype = DNA  length = 351
FEATURE                 Location/Qualifiers
source                  1..351
                        mol_type = unassigned DNA
                        organism = Mus musculus
SEQUENCE: 163
caggtccaac tgcagcagcc tggggctgac ctggtgaggc ctgggtcttc agtgaagctg  60
tcctgcaagg cttctggcta caccttcacc aggtcctgga tgcattgggt gaagcagagg  120
```

```
cctatagaag gccttgaatg gattggtaac attgaccctt ctgatagtga agctcactac  180
aatcaaaagt tcaaggacaa ggccacattg actgtagaca aattttccaa cacagcctac  240
atgcagctca gcagcctgac atctgaggac tctgcggtct attactgtgc aagatgggat  300
gatttctacg ttgcttactg gggccaaggg actctggtca ctgtctctgc a           351

SEQ ID NO: 164          moltype = DNA  length = 351
FEATURE                 Location/Qualifiers
source                  1..351
                        mol_type = unassigned DNA
                        organism = Mus musculus
SEQUENCE: 164
caggtccaac tgcagcagcc tggggctgcc ctggtgaggc ctgggtcttc agtgaagctg  60
tcctgcaagg cttctggcta caccttcacc agctcctgga tgcattgggt gaagcagagg  120
cctatacaag gccttgaatg gattggtaac attgaccctt ctgatggtga aactcactac  180
aatcaaaagt tcaaggacaa ggccacattg actgtagaca aatcctccaa cacagcctac  240
atgcagctca gcagcctgac atctgaggac tctgcggtct attactgtgc aagatgggat  300
gattactacg ttgcttactg gggccaaggg actctggtca ctgtctctgc a           351

SEQ ID NO: 165          moltype = DNA  length = 360
FEATURE                 Location/Qualifiers
source                  1..360
                        mol_type = unassigned DNA
                        organism = Mus musculus
SEQUENCE: 165
caggtccaac tgcagcagcc tgggactgac ctggtgaagc ctggggcttc agtgaagctg  60
tcctgcaagg cttctggcta caccttcacc agctactgga tgcactggtt gaagcagagg  120
cctggacaag gccttgagtg gattggaaat attaatccta acaatagtga tgctaactac  180
aatgagaagt tcaagagtaa ggccacactg actgtggaca aatcctccag tgcagcctac  240
atgcagctca tcagcctgac atctgaggac tctgcggtct attattgtgc aagagcgaat  300
tactacggtg gtagccagtt tgcttactgg ggccaaggga ctctggtcac tgtctctgca  360

SEQ ID NO: 166          moltype = DNA  length = 360
FEATURE                 Location/Qualifiers
source                  1..360
                        mol_type = unassigned DNA
                        organism = Mus musculus
SEQUENCE: 166
caggtccaac tgcagcagcc tgggattgaa ctggtgaaga ctggggcttc agtgaagctg  60
tcctgcaagg cttctggcta caccttcacc agcaactgga tgcactggtt gaagcagagg  120
cctggacaag gccttgagtg gattggaaat attaatccta acaatagtga aactaactac  180
aatgagaagt tcaggaaaaa ggccacactg actgtagaca aatcctccag tgcagcctac  240
atgcagctca tcagcctgac atctgaggac tctgcggtct attattgtgc aagagcgaat  300
tactacggtg gtagccagtt tgcttactgg ggccaaggga ctctggtcac tgtctctgca  360

SEQ ID NO: 167          moltype = DNA  length = 354
FEATURE                 Location/Qualifiers
source                  1..354
                        mol_type = unassigned DNA
                        organism = Mus musculus
SEQUENCE: 167
caggtccaac tgcagcagcc tgggactgaa ctggtgaagc ctgggtcttc agtgaacctg  60
tcctgcaagg cttctggctt caccttcacc aggtactgga tgcactgggt gaaggagagg  120
cctggacatg gccttgagtg gattggaaat attaatccta acaatggtgg tactgacttc  180
aatgagaagt tcaagaacaa ggccacactg actgtacaca agtcctccac cacagtcttc  240
atccaactca gcagcctgac atctgaggac tctgcggtct attattgtgc aagaggaact  300
gggacgggag ctatggacta ctggggtcaa ggaacctcag tcaccgtctc ctca        354

SEQ ID NO: 168          moltype = DNA  length = 354
FEATURE                 Location/Qualifiers
source                  1..354
                        mol_type = unassigned DNA
                        organism = Mus musculus
SEQUENCE: 168
caggtccaac tgcagcagcc tgggactgaa ctggtgaagc ctggggcttc agtgaagctg  60
tcctgcaagg cttctggcta caccttcacc atcttctgga tgcactgggt gaagcagagg  120
cctggacatg gccttgagtg gattggaaag attaatccta acaatggagg tggtgactac  180
aatgagaaat tcaagagtaa ggccacattg actgtagaca aatcctccac cacagcctac  240
ttgcagctca gcagcctgac atctgaggac tctgcggtct attattgtgc aagaggaact  300
gggacgggag ctatggacta ctggggtcaa ggaacctcag tcaccgtctc ctca        354

SEQ ID NO: 169          moltype = DNA  length = 354
FEATURE                 Location/Qualifiers
source                  1..354
                        mol_type = unassigned DNA
                        organism = Mus musculus
SEQUENCE: 169
caggtccaac tgcagcagcc tgggactgaa ctggtgaagc ctggggcttc agtgaagctg  60
tcctgcaagg cttctggcta caccttcacc aggttctgga tgcactgggt gaagcagagg  120
cctggacaag gccttgagtg gattggaaat attaatccta acaatggtgg tactgacaat  180
```

```
aatgagaggt tcaagagcaa ggccacactg actgtagaca gatcctccag cacagcctac  240
atgcagctca gcagcctgac atctgaggac tctgcggtct attattgtgc aagaggaact  300
gggacgggag ctatggacta ctggggtcaa ggaacctcag tcaccgtctc ctca        354

SEQ ID NO: 170         moltype = DNA  length = 354
FEATURE                Location/Qualifiers
source                 1..354
                       mol_type = unassigned DNA
                       organism = Mus musculus
SEQUENCE: 170
caggtccaac tgcagcagcc tgggactgaa ctggtgaagc ctggggcttc agtgaaactg  60
tcctgcaagg cttctggctt caccttcacc aggttctgga tgcactgggt gaagcagagg  120
cctggacaag gccttgagtg gattggaaat attaatccta acaatggtga aactaactac  180
aatgagaaat tcaaaatcaa ggccgctctg actgtagaca aatcctccac cacagcctac  240
atgcagctca gcagcctgac atctgaggac tctgcggtct attcttgtgc aagaggaact  300
gggacgggag ctatggacta ctggggtcaa ggaacctcag tcaccgtctc ctca        354

SEQ ID NO: 171         moltype = DNA  length = 363
FEATURE                Location/Qualifiers
source                 1..363
                       mol_type = unassigned DNA
                       organism = Mus musculus
SEQUENCE: 171
caggtccagc tacagcagtc tggacctgag ctggtgaagc ctggggcttc agtgaagata  60
tcctgcaagg cttctggcta cagcttcact gactactata taaactgggt gaagcagagg  120
cctggacagg gacttgagtg gattggatgg atttttcctg gaagtgatag tacttactac  180
aatgagaagt tcaagggcaa ggccacactt actgtagaca aatcctccag cacagcctcc  240
atgttgctca gcagcctgac ctctgaggac tctgcggtct atttctgtgc aagacctacg  300
gttgtagccc gggactatgc tatggactac tggggtcaag gaacctcagt caccgtctcc  360
tca                                                                 363

SEQ ID NO: 172         moltype = DNA  length = 363
FEATURE                Location/Qualifiers
source                 1..363
                       mol_type = unassigned DNA
                       organism = Mus musculus
SEQUENCE: 172
caggtccagc tacagcagtc tggacctgag ctggtgaagc ctggggcttc agtgaagata  60
tcctgcaagg cttctggcta caccttcact gagtactatc taaactggat gaaacagagg  120
cctggacagg gacttgagtg gattggatgg atttttcctg gacgtggtag tactaactac  180
aatgagaagt tcaagggcaa ggccacactt actgtagaca aatcttccag cacagcctac  240
atgttgctca gcagcctgac ctctgaggac tctgcggtct atttctgtgc aagacctacg  300
atagtagccc gggactatgc tatggactac tggggtcaag gaacctcagt caccgtctcc  360
tca                                                                 363

SEQ ID NO: 173         moltype = DNA  length = 366
FEATURE                Location/Qualifiers
source                 1..366
                       mol_type = unassigned DNA
                       organism = Mus musculus
SEQUENCE: 173
caggttcagc tgcagcagtc tggacctgag ctggtgaagc ctggggcctc agtgaagatt  60
tcctgcaagg cttctggcta cgcattcagt agctcctgga tgaactgggt gaagcagagg  120
cctggaaagg gtcttgagtg gattggacgg atttatcctg gagatggaga tactaactac  180
aatgggaagt tcaagggcaa ggccacactg actgcagaca aatcctccag cacagcctac  240
atgcaactca gcagcctgac atctgaggac tctgcggtct acttctgtgc aagaataggg  300
ggacgggccg ggtcggggta tgctatggac tactggggtc aaggaacctc agtcaccgtc  360
tcctca                                                              366

SEQ ID NO: 174         moltype = DNA  length = 363
FEATURE                Location/Qualifiers
source                 1..363
                       mol_type = unassigned DNA
                       organism = Mus musculus
SEQUENCE: 174
caggtttctc tgaaagagtc tggccctggg atattgcagt cctcccagac cctcagtctg  60
acttgttctt tctctgggtt ttcactgagc acttctggta tgggtgtgag ttggattcgt  120
cagccttctg gaaagggtct ggagtggctg tcacacattt actgggatga tgacaagtgg  180
tataacccat ccctgaagag ccggctcaca atctccaagg atacctccag aaaccaggta  240
ttcctcaaga tcaccagtgt ggacactgca gatactgcca catactactg tgctcgaaga  300
gaaattggga agagggattt ttttgcttac tggggccaag ggactctggt cactgtctct  360
gca                                                                 363

SEQ ID NO: 175         moltype = DNA  length = 363
FEATURE                Location/Qualifiers
source                 1..363
                       mol_type = unassigned DNA
                       organism = Mus musculus
SEQUENCE: 175
```

```
caggtccaac tgcagcagcc tgggactgaa ctggtgaagc ctggggcttc agtgaagctg  60
tcctgcaagg cttctggcta caccttcacc agctactgga tgcactgggt gaagcagagg 120
cctggacaag gccttgagtg gattggaaat atttatccta gcaatggtgg tactaactac 180
aatgagaaat tcaagaacaa ggccacactg actgttgaca aatcctccag cacagcctcc 240
atgcagctca gcagcctgac atctgaggac tctgcggtct attattgtgc aagatcttcg 300
gtcgtagcta gggactatgc tatggactac tggggtcaag gaacctcagt caccgtctcc 360
tca                                                               363

SEQ ID NO: 176         moltype = DNA  length = 363
FEATURE                Location/Qualifiers
source                 1..363
                       mol_type = unassigned DNA
                       organism = Mus musculus
SEQUENCE: 176
caggtccaac tgcagcagcc tgggactgaa ctggtgaagc ctggggcttc agtgaagctg  60
tcctgcaagg cttctggcta caccttcacc agctactgga tgcactgggt gaagcagagg 120
cctggacaag gccttgagtg gattggaaat atttatccta gcaatggtgg tacttactac 180
aatgagaagt tcaagagcaa ggccacactg actgtagaca aatcctccag cacagcctac 240
atgcagctca gcagcctgac atctgaggac tctgcggtct attattgtgc aagatcttcg 300
gtagtaggta gggactatgc tatggactac tggggtcaag gaacctcagt caccgtctcc 360
tca                                                               363

SEQ ID NO: 177         moltype = DNA  length = 363
FEATURE                Location/Qualifiers
source                 1..363
                       mol_type = unassigned DNA
                       organism = Mus musculus
SEQUENCE: 177
caggtccagc tgaagcagtc tggggctgag ctggtgaggc ctggggcttc agtgaagctg  60
tcctgcaaaa cttctggcta cactttcact gactactata taaaatgggt gaagcagagg 120
cctggacagg gacttgagtg gattgcaagg atttatcctg gaagtggtaa tacttactac 180
aatgagaagt tcaagggcaa ggccacactg actgcagaaa aatcctccag cacggcctac 240
atgcagctca gcagcctgac atctgaggac tctgctgtct atttctgtgc aagacccgcc 300
tactatagta aggactatgc tatggaatac tggggtcaag gaacctcagt caccgtctcc 360
tca                                                               363

SEQ ID NO: 178         moltype = DNA  length = 348
FEATURE                Location/Qualifiers
source                 1..348
                       mol_type = unassigned DNA
                       organism = Mus musculus
SEQUENCE: 178
gaggtccagc ttcagcagtc tggagctgag ctggtgaggc ctgggtcctc agtgaagatg  60
tcctgcaaga cttctggata tacattcaca agctacggta taaactgggt gaagcagagg 120
cctggacagg gcctggaatg gattggatat atttatattg gaaatggtca tactgagtac 180
aatgagaagt tcgagggcaa ggccacactg acttcagaca catcctccag cacagcctac 240
atgcagctca gcagcctgac atctgaggac tctgcaatct atttctgtgc aggaactggg 300
acactctttg actactgggg ccaaggcacc actctcacag tctcctca              348

SEQ ID NO: 179         moltype = DNA  length = 348
FEATURE                Location/Qualifiers
source                 1..348
                       mol_type = unassigned DNA
                       organism = Mus musculus
SEQUENCE: 179
gaggtccagc ttcagcagtc tggagctgag ctggtgaggc ctgggtcctc agtgaagatg  60
tcctgcaaga cttctggata tacattcaca agctacggta taaactgggt gaaacagagg 120
cctggacagg gcctggaatg ggttggatat atttatattc gagatggtaa tactgcgtat 180
aatgagaagt tcaagggcaa ggccacagtg acttcagaca catcctccag cacagtctac 240
atgcagctca gcagcctgac atctgaagac tctgcaatct atttctgtgc ggggactggg 300
acttcttttg cttactgggg ccaagggact ctggtcactg tctctgca              348

SEQ ID NO: 180         moltype = DNA  length = 348
FEATURE                Location/Qualifiers
source                 1..348
                       mol_type = unassigned DNA
                       organism = Mus musculus
SEQUENCE: 180
gaggcccagc ttcagcagtc tggagctgag ctggtgaggc ctgggtcctc agtgaagatg  60
tcctgcaaga cttctggata tacattcaca agctacggta taaactgggt gaaacagagg 120
cctggacagg gcctggaatg gattggatat atttatattc gaaatgggaa tactgcgtat 180
aatgagaagt tcaagggcaa ggccacagtg acttcagaca catcctccag cacagtctac 240
atgcagctca gcagcctgac atctgaggac tctgcaatct atttctgtgc ggggactggg 300
acttctttta cttactgggg ccaagggact ctggtcactg tctctgca              348

SEQ ID NO: 181         moltype = DNA  length = 357
FEATURE                Location/Qualifiers
source                 1..357
                       mol_type = unassigned DNA
```

```
                        organism = Mus musculus
SEQUENCE: 181
caggttactc tgaaagagtc tggccctggg atattgcagc cctcccagac cctcaatctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggtc  240
ttcctcaaga tcaccagtgt ggacactgca gatactgcca catactactg tgttcgaaga  300
agtaggagag gtaactacga ctactggggc caaggcacca ctctcacagt ctcctca     357

SEQ ID NO: 182          moltype = DNA  length = 342
FEATURE                 Location/Qualifiers
source                  1..342
                        mol_type = unassigned DNA
                        organism = Mus musculus
SEQUENCE: 182
caggttcagc tgcagcagtc tggagctgag ctggcgaggc ctggggcttc agtgaagttg  60
tcctgcaagg cttctggcta caccttcaca agctatggta taaactgggt gaagcagaga  120
actggacagg gccttgagtg gattggagag atttatccta gaagtggtaa aacttactac  180
aatgagaagt tcaagggcaa ggccacactg actgcagaca aatcctccag cacagcgtac  240
atggagctcc gcagcctgac atctgaggac tctgcggtct atttctgtgc aagagggggt  300
gggggctact ggggccaagg caccactctc acagtctcct ca                     342

SEQ ID NO: 183          moltype = DNA  length = 357
FEATURE                 Location/Qualifiers
source                  1..357
                        mol_type = unassigned DNA
                        organism = Mus musculus
SEQUENCE: 183
caggttcagc tgcagcagtc tggacctgag ctggtgaagc ctggggcttt agtgaagata  60
tcctgcaagg cttctggtta caccttcaca agctacgata taaactgggt gaaacagagg  120
cctggacagg gacttgagtg gattggatgg atttatcctg gaaatggtaa tactaactac  180
aatgcgaaat tcaaggacaa ggccacactg actgcagaca aatcctccag cacagcctac  240
atgcagctca gcagcctgac ttctgagacc tctgcagtct atttctgtgc aagaggaatt  300
aggaggtcct ggtacttcga tgtctggggc gcagggacca cggtcaccgt ctcctca     357

SEQ ID NO: 184          moltype = DNA  length = 357
FEATURE                 Location/Qualifiers
source                  1..357
                        mol_type = unassigned DNA
                        organism = Mus musculus
SEQUENCE: 184
caggttcagc tgcaacagtc tggacctgag ctggtgaagc ctggggcttt agtgaagata  60
tcctgcaagg cttctggtta caccttcaca agctacgata taaactgggt gaagcagcgg  120
cctggacagg gacttgagtg gattggatgg atttatcctg gagatcgtaa tactaagtac  180
aatgagaaat tcaagggcaa ggccacactg actgcagaca agtcctccag cacagcctac  240
atgcaactca tcagcctgac ttctgagaac tctgcagtct atttctgtgc aagagggatt  300
aggaggtcct ggtacttcga tgtctggggc gcagggacca cggtcaccgt ctcctca     357

SEQ ID NO: 185          moltype = DNA  length = 369
FEATURE                 Location/Qualifiers
source                  1..369
                        mol_type = unassigned DNA
                        organism = Mus musculus
SEQUENCE: 185
caggtgcagc tgaagcagtc aggacctggc ctagtgcagc cctcacagag cctgtccatc  60
acctgcacag tctctggttt ctcattaact agctatggtg tacactgggt tcgccagtct  120
ccaggaaagg gtctggagtg gctgggagtg atatggagtg gtggaagcac agactataat  180
gcagctttca tatccagact gagcatcagc aaggacaatt ccaagagcca agttttcttt  240
aaaatgaaca gtctgcaagc tgatgacaca gccatatatt actgtgccag aaattcgggt  300
ggttactacg tggatgatta ctatgctatg gactactggg gtcaaggaat ttcagtcacc  360
gtctcctca                                                          369

SEQ ID NO: 186          moltype = DNA  length = 369
FEATURE                 Location/Qualifiers
source                  1..369
                        mol_type = unassigned DNA
                        organism = Mus musculus
SEQUENCE: 186
caggtgcagc tgaagcagtc aggacctggc ctagtgcagc cctcacagag cctgtccatc  60
acctgcacag tctctggttt ctcattaact agctatggtg tacactgggt tcgccagtct  120
ccaggaaagg gtctggagtg gctgggagtg atatggagtg gtggaagcac agactataat  180
gcagctttca tatccagact gagcatcagc aaggacaatt ccaagagcca agttttcttt  240
aaaatgaaca gtctgcaagc tgatgacaca gccatatttt actgtgccag aaattcgggt  300
ggttactacg tggatgatta ctatgctatg gactactggg gtcaaggaac ctcagtcacc  360
gtctcctca                                                          369

SEQ ID NO: 187          moltype = DNA  length = 345
FEATURE                 Location/Qualifiers
source                  1..345
```

```
                        mol_type = unassigned DNA
                        organism = Mus musculus
SEQUENCE: 187
gatgtacagc ttcaggagtc aggacctggc ctcgtgaaac cttctcagtc tctgtcgctc  60
acctgctctg tcactggcta ctccatcacc actaattatt actggaactg gatccggcag  120
tttccaggaa acaaactgga atggatgggc tacataacct acgatggtat caaaacctac  180
aacccatctc tcaataatcg aatctccatc actcgtgaca catctaagaa ccagtttttc  240
ctgaagttga attctgtgac tactgaggac acagccacat attactgtgc aagaggaccg  300
gggcttgact actggggcca aggcaccact ctcacagtct cctca                  345

SEQ ID NO: 188          moltype = DNA  length = 345
FEATURE                 Location/Qualifiers
source                  1..345
                        mol_type = unassigned DNA
                        organism = Mus musculus
SEQUENCE: 188
gatgtacagc ttcaggagtc aggacctggc ctcgtaaaac cttctcagtc tctgtctctc  60
acctgctctg tctctggcta ctccatcacc actaattatt tctggaactg gatccggcta  120
tttcccggaa acaaactgga atggatgggc tacataagct acgatggttc caatgtctac  180
aacccatctc tcaaaaatcg aatctccatc actcgtgaca catctaagaa ccagtttttc  240
ctgaagttga attctctgac tactgaggac acagccacat attactgtgc cagaggcccg  300
ccttcggctt actggggcca agggactctg gtcactgtct ctgca                  345

SEQ ID NO: 189          moltype = DNA  length = 345
FEATURE                 Location/Qualifiers
source                  1..345
                        mol_type = unassigned DNA
                        organism = Mus musculus
SEQUENCE: 189
gatgtacagc ttcaggagtc aggacctggc ctcgtgaaac cttctcagtc tctgtctctc  60
acctgctctg tcactggcta ctccatcacc actaattatt actggaactg gatccggcag  120
tttccaggaa acaagctgga atggatgggc tacataacct acgatggtag caataactac  180
aacccatctc tcaaaaatcg aatctccatc actcgtgaca catctaagaa ccagtttttc  240
ctgaaattga attctgtgac tactgaggac acagccacat attactgtgc aagaggcccg  300
cctacggctt actggggcca agggactctg gtcactgtct ctgca                  345

SEQ ID NO: 190          moltype = DNA  length = 342
FEATURE                 Location/Qualifiers
source                  1..342
                        mol_type = unassigned DNA
                        organism = Mus musculus
SEQUENCE: 190
gatgtacagc ttcaggagtc aggacctggc ctcgtgaaac cttctcagtc tctgtctctc  60
acctgctctg tcactggtta ctccatcacc actaattatt actggaactg gatccggcag  120
tttccaggaa acaaactgga atggatgggc tacataagct acgatggtag cagtaactac  180
aacccatctc tcaaaaatcg aatctccatc actcgtgaca catctaagaa ccagtttttc  240
ctgaacttga attctgtgac tactgaggac acagccacat attactgtgc aagagaccta  300
ctaggttact ggggccaagg caccactctc acagtctcct ca                     342

SEQ ID NO: 191          moltype = DNA  length = 348
FEATURE                 Location/Qualifiers
source                  1..348
                        mol_type = unassigned DNA
                        organism = Mus musculus
SEQUENCE: 191
gaggtgcagc tggtggagtc tgggggaggc ttagtgaagc ctggagggtc cctgaaactc  60
tcctgtgcag cctctggatt cactttcagt gactatggaa tgcactgggt tcgtcaggct  120
ccagagaagg ggctggaatg ggttgcatac attagtagtg gcagtattac catctactat  180
gcagacacag tgaagggccg attcaccatc tccagagaca atgccaagaa caccctgttc  240
ctgcaaatga ccagtctgag gtctgaggac acggccatgt attactgtgc aaggagccca  300
tatgctatgg actcctgggg tcaaggaacc tcagtcaccg tctcctca               348

SEQ ID NO: 192          moltype = DNA  length = 348
FEATURE                 Location/Qualifiers
source                  1..348
                        mol_type = unassigned DNA
                        organism = Mus musculus
SEQUENCE: 192
gaggtgcagc tggtggagtc tgggggaggc ttagtgaagc ctggagggtc cctgaaactc  60
tcctgtgcag cctctggatt cactttcagt gactatggaa tgcactgggt tcgtcaggct  120
ccagagaagg ggctggagtg ggttgcatac attagtagtg gcagtagaac catctactat  180
gcagacacag tgaagggccg attcaccatc tccagagaca atgccaagaa caccctgttc  240
ctgcaaatga ccagtctgag gtctgaggac acggccatgt attactgtgc aaggagccca  300
tatgctatgg actactgggg tcaaggaacc tcagtcaccg tctcctca               348

SEQ ID NO: 193          moltype = DNA  length = 366
FEATURE                 Location/Qualifiers
source                  1..366
                        mol_type = unassigned DNA
```

```
                          organism = Mus musculus
SEQUENCE: 193
caggttactc tgaaagagtc tggccctggg atattgcagt cctcccagac cctcagtctg  60
acttgttctt tctctgggtt ttcactgagc acttctggta tgggtgtgag ctggcttcgt  120
cagccttcag gaaagggtct ggagtggctg gcacacattt actgggatga tgaggagcgc  180
tatgacccat ccctgaagag ccggctcaca atctccaagg atacctccag aaaccaggta  240
ttcctcaaga tcaccagtgt ggacactgca gatactgcca catactactg tgctcgaagg  300
ggctactata gtgacgggaa ctactttgac tcctggggcc aaggcaccac tctcacagtc  360
tcctca                                                             366

SEQ ID NO: 194            moltype = DNA  length = 366
FEATURE                   Location/Qualifiers
source                    1..366
                          mol_type = unassigned DNA
                          organism = Mus musculus
SEQUENCE: 194
caggttactc tgaaagagtc tggccctggg atattgcagt cctcccagac cctcagtctg  60
acatgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaaa atctccaagg atacctccag aaaccaggtt  240
ttcctcaaga tcaccagtgt ggacactgca gatactgcca catactactg tgctcgaagg  300
ggctactata gtaacgggaa ctactttgac tactggggcc aaggcaccac tctcacagtc  360
tcctca                                                             366

SEQ ID NO: 195            moltype = DNA  length = 360
FEATURE                   Location/Qualifiers
source                    1..360
                          mol_type = unassigned DNA
                          organism = Mus musculus
SEQUENCE: 195
gaggtccagc tgcaacagtc tggacctgag ctggtgaagc ctggggcttc agtgaagatc  60
ccctgcaggg cttctggata cacattcact gactacaaca tggactgggt gaagcagagc  120
catggaaaga cccttgagtg gattggagat attaatccta acaatggtgg tactatctac  180
aaccagaagt tcaagggcaa ggccacattg actgtagaca agtcctccag cacagcctac  240
atggagctcc gcagcctgac atctgaggac actgcagtct attactgtgc aagagggagg  300
ggtatgggtt actatgcttt ggactactgg ggtcaaggaa cctcagtcac cgtctcctca  360

SEQ ID NO: 196            moltype = DNA  length = 357
FEATURE                   Location/Qualifiers
source                    1..357
                          mol_type = unassigned DNA
                          organism = Mus musculus
SEQUENCE: 196
caggttactc tgaaagagtc tggccctggg atattgcagt cctcccagac cctcagtctg  60
acttgttctt tctctgggtt ttcactgagc acttctacta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaca tcaccagtgt ggacactgca gatattgcca catactactg tgctcgaaga  300
gctaggggct acggtatgga ctactggggt caaggaacct cagtcaccgt ctcctca     357

SEQ ID NO: 197            moltype = DNA  length = 357
FEATURE                   Location/Qualifiers
source                    1..357
                          mol_type = unassigned DNA
                          organism = Mus musculus
SEQUENCE: 197
cagattactc tgaaagagtc tggccctggg atattgcagt cctcccagac cctcagtctg  60
acttgttctt tctctgggtt ttcactgagc acttctgcta tgggtgtgag ttggattcgt  120
cagccttcag gagagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgca gatactgcca catactactg tgctcgaaga  300
aggagggggt atggtatgga ctactggggt caaggaacct cagtcaccgt ctcctca     357

SEQ ID NO: 198            moltype = DNA  length = 357
FEATURE                   Location/Qualifiers
source                    1..357
                          mol_type = unassigned DNA
                          organism = Mus musculus
SEQUENCE: 198
caggttactc tgaaagagtc tggccctggg atattgcagt cctcccagac cctcagtctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggtt  240
ttcctcaaga tcaccagtgt ggacactgca gagactgcca catactactg tgctcgaagg  300
gcccgtttct atgctatgga ctactggggt caaggaacct cagtcaccgt ctcctca     357

SEQ ID NO: 199            moltype = DNA  length = 357
FEATURE                   Location/Qualifiers
source                    1..357
```

```
                         mol_type = unassigned DNA
                         organism = Mus musculus
SEQUENCE: 199
caggttactc tgaaagagtc tggccctggg atattgcagt cctcccagac cctcagtctg  60
acttgttctt tctctgggtt ttcactgaac acttctggta tgggtgtgag ctggattcgt  120
ctgccttcag gaaagggtct ggagtggctg gcacacattt actgggatga tgacaagcgc  180
tataacccat cccttaagag ccggctcaca atctccaagg atacctccag aaagcaggta  240
ttcctcaaga tcaccagtgt ggacactgca gatactgcca catactactg tgctcgaaga  300
gttaggggtt atggtatgga ctactggggt caaggaacct cagtcaccgt ctcctca     357

SEQ ID NO: 200           moltype = DNA  length = 357
FEATURE                  Location/Qualifiers
source                   1..357
                         mol_type = unassigned DNA
                         organism = Mus musculus
SEQUENCE: 200
caggttactc tgaaagagtc tggccctggg atattgcagt cctcccagac cctcagtctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggtt  240
ttcctcaaga tcaccagtgt ggacactgca gatactgcca catactactg tgctcgaagg  300
gtccgttact atgctatgga ctactggggt caaggaacct cagtcaccgt ctcctca     357

SEQ ID NO: 201           moltype = DNA  length = 357
FEATURE                  Location/Qualifiers
source                   1..357
                         mol_type = unassigned DNA
                         organism = Mus musculus
SEQUENCE: 201
caggttactc tgaaagagtc tggccctggg atattgcagt cctcccagac cctcagtctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgaa gatactgcca catactactg tactcgaaga  300
gtccggtcct atgctatgga ctactggggt caaggaacct cagtcaccgt ctcctca     357

SEQ ID NO: 202           moltype = DNA  length = 357
FEATURE                  Location/Qualifiers
source                   1..357
                         mol_type = unassigned DNA
                         organism = Mus musculus
SEQUENCE: 202
caggttactc tgaaagagtc tggccctggg atattgcagt cctcccagac cctcagtctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgca gatactgcca catactactg tactcgaagg  300
gtccgttact atgctatgga ctactggggt caaggaacct cagtcaccgt ctcctca     357

SEQ ID NO: 203           moltype = DNA  length = 357
FEATURE                  Location/Qualifiers
source                   1..357
                         mol_type = unassigned DNA
                         organism = Mus musculus
SEQUENCE: 203
caggttactc tgaaagagtc tggccctggg atattgcagt cctcccagac cctcagtctg  60
acttgttctt tctctggatt ttcactgagc acttttggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgca gatactgcca catactactg tgttcgaagg  300
aagagatcct atggtatgga ctactggggt caaggaacct cagtcaccgt ctcctca     357

SEQ ID NO: 204           moltype = DNA  length = 360
FEATURE                  Location/Qualifiers
source                   1..360
                         mol_type = unassigned DNA
                         organism = Mus musculus
SEQUENCE: 204
cagatccagt tggtacagtc tggacctgag ctgaagaagc ctggagagac agtcaagatc  60
tcctgcaagg cttctgtgta taccttcaca acctatggaa tgagctgggt gaaacaggct  120
ccaggaaagg gtttaaagtg gatgggctgg ataaacacct actctggagt gccaacatat  180
gctgatgact tcaagggacg gtttgccttc tctttggaaa cctctgccag cactgcctat  240
ttgcagatca acaacctcaa aaatgaggac acggctacat atttctgtgc aagattggga  300
ttacgacgag gttcctactt tgactactgg ggccaaggca ccactctcac agtctcctca  360

SEQ ID NO: 205           moltype = DNA  length = 360
FEATURE                  Location/Qualifiers
source                   1..360
                         mol_type = unassigned DNA
```

```
                         organism = Mus musculus
SEQUENCE: 205
cagatccagt tggtacagtc tggacctgag ctgaagaagc ctggagagac agtcaagatc  60
tcctgcaagg cttctgggta taccttcaca acctatggaa tgagctgggt gaaacaggct  120
ccaggaaagg gtttaaagtg gatgggctgg ataaacacct actctggagt gccaacatat  180
gctgatgact tcaagggacg gtttgtcttc tctttggaaa cctctgccag cactgcctat  240
ttgcagatca acaacctcaa aaatgaggac acggctacat atttctgtgc aagattggga  300
ttacgacgag gttcctactt tgactactgg ggccaaggca ccactctcac agtctcctca  360

SEQ ID NO: 206           moltype = DNA  length = 360
FEATURE                  Location/Qualifiers
source                   1..360
                         mol_type = unassigned DNA
                         organism = Mus musculus
SEQUENCE: 206
caggtccaac tgcagcagcc tggggctgag cttgtgaagc ctggggtttc agtgaagatg  60
tcctgcaagg cttctggcta caccttcacc agctactgga taacctgggt gaagcagagg  120
cctggacaag gccttgagtg ggttggagat atttttcctg gtagtggtag tactaactac  180
aatgagaagt tcaagagcaa ggccacactg actgtagaca catcctccag cacagcctac  240
atgcagctca gcagcctgac atctgaggac tctgcggtct attactgtgc aagaggaggt  300
aaaggggtca tcggttactt tgactactgg ggccaaggca ccactctcac agtctcctca  360

SEQ ID NO: 207           moltype = DNA  length = 345
FEATURE                  Location/Qualifiers
source                   1..345
                         mol_type = unassigned DNA
                         organism = Mus musculus
SEQUENCE: 207
gaggtgcagc tggtggagtc tggggggaggc ctagtgaagc ctggagggtc cctgaaactc  60
tcctgtgcag cctctggatt cactttcagt gactatggaa tgcactgggt tcgtcaggct  120
ccagagaagg ggctggagtg ggttgcatac attagtagtg gcagtagtaa catctactat  180
acagacacag tgaagggccg attcaccatc tccagagaca atgccaagaa caccctgttc  240
ctgcaaatga ccagtctgag gtctgaggac acggccatgt attactgtac aaggtcctgg  300
tacttcgatg tctggggcac agggaccacg gtcaccgtct cctca                   345

SEQ ID NO: 208           moltype = DNA  length = 339
FEATURE                  Location/Qualifiers
source                   1..339
                         mol_type = unassigned DNA
                         organism = Mus musculus
SEQUENCE: 208
caggttcaac tgcagcagtc tggggctgag ctggtgaggc ctggggcttc agtgacgctg  60
tcctgcaagg cttcgggcta cacatttact gactatgaga tgcactgggt gaagcagaca  120
cctgtgcatg gcctggaatg gattggagct attgatcctg atactggtgg tactgccgac  180
aatcagaagt tcaagggcaa ggccatactg actgcagaca aatcctccag cacagcctac  240
atggagctcc gcagcctgac atctgaggac tctgccgtct attactgttc cctgcgcctc  300
tacgactggg gtcaaggcac cactctcaca gtctcctca                          339

SEQ ID NO: 209           moltype = DNA  length = 363
FEATURE                  Location/Qualifiers
source                   1..363
                         mol_type = unassigned DNA
                         organism = Mus musculus
SEQUENCE: 209
caggtccaac tgcagcagcc tggggctgag ctggtaaagc ctggggcttc agtgaagttg  60
tcctgcaagg cttctggcta cactttcacc agctactgga tgcactgggt gaagcagagg  120
cctggacaag gccttgagtg gattggagtg attcatccta atagtggttt tactaacaac  180
aatgagaagt tgaagagcaa ggccacactg actgttgaca aatcctccag cacagcctac  240
atgcaactca gcagcctgac atctgaggac tctgcggtct attactgtgc aaaatctgcg  300
gtagtggaga gagactatgc tatggactac tggggtcaag gaacctcagt caccgtctcc  360
tca                                                                 363

SEQ ID NO: 210           moltype = DNA  length = 366
FEATURE                  Location/Qualifiers
source                   1..366
                         mol_type = unassigned DNA
                         organism = Mus musculus
SEQUENCE: 210
caggttcagc tgcagcagtc tggagctgag ctggcgaggc ctggggcttc agtgaagctg  60
tcctgcaagg cttctggcta caccttcaca agctatggta taagctgggt gaagcagaga  120
actggacagg gccttgagtg gattggagag atttatccta gaagtggtaa tacttactac  180
aatgagaagt tcaagggcga ggccacactg actgcagaca aatcctccag cacagcgtac  240
atggagctcc gcagcctgac atctgaggac tctgcggtct atttctgtgc aagagtttat  300
tactacggta gtaactacga tggatttgct tactggggcc aagggactct ggtcactgtc  360
tctgca                                                              366

SEQ ID NO: 211           moltype = DNA  length = 366
FEATURE                  Location/Qualifiers
source                   1..366
```

```
                         mol_type = unassigned DNA
                         organism = Mus musculus
SEQUENCE: 211
gaggtgcagc tggtggagtc tgggggaggc ttagtgaagc ctggagggtc cctgaaactc  60
tcctgtgcag cctctggatt caccttcagt agctatgcca tgtcttgggt tcgccagact  120
ccagagaaga ggctggagtg ggtcgcagcc attaatagta atggtggtag gacctactat  180
ccagacactg tgaaggaccg attcaccatc tccagagaca atgccaagaa caccctgtat  240
ctgcaaatga gcagtctgag gtctgaggac acagccttgt attactgtgc aagacagggg  300
catagtaact actacgaggc ctggtttgct tactggggcc aagggactct ggtcactgtc  360
tctgca                                                              366

SEQ ID NO: 212           moltype = DNA  length = 360
FEATURE                  Location/Qualifiers
source                   1..360
                         mol_type = unassigned DNA
                         organism = Mus musculus
SEQUENCE: 212
ctggttcagc tgcagcagtc tggagctgag ctggcgaggc ctggggcttc agtgaagctg  60
tcctgcaagg cttctggcta caccttcaca aaccatggtt taagctgggt gaagcagaga  120
actggacagg gccttgagtg gattggagag atttatccta gaagtggtaa tacttactac  180
aatgagaatt gcaagggcaa ggccactctg actgcagaca gatcctccag cgcggcgtac  240
atggagctcc gcagcctgac atctgaggac tctgcggtct atttctgtgc aagaagacat  300
agtaacaacg actatgctat ggactactgg ggtcaaggaa cctcagtcac cgtctcctca  360

SEQ ID NO: 213           moltype = DNA  length = 354
FEATURE                  Location/Qualifiers
source                   1..354
                         mol_type = unassigned DNA
                         organism = Mus musculus
SEQUENCE: 213
gaagtgaagc tggtggagtc tgggggaggc ttagtgaagc ctggagggtc cctgaaactc  60
tcctgtgcag cctctggatt cactttcagt agctatgcca tgtcttgggt tcgccagatt  120
ccagagaaga ggctggagtg ggtcgcagcc attaatagta atggtggtag cacctactat  180
ccagacactg tgaaggaccg attcaccatc tccagagaca atgccaagaa caccctgtac  240
ctgcaaatga gcagtctgag gtctgaggac acagccttgt attactgtgt aagacaaggg  300
tgggatgcct ggtttgctta ctggggccaa gggactctgg tcgctgtctc tgca        354

SEQ ID NO: 214           moltype = DNA  length = 354
FEATURE                  Location/Qualifiers
source                   1..354
                         mol_type = unassigned DNA
                         organism = Mus musculus
SEQUENCE: 214
gaggtgcagc tggtggagtc tgggggaggc ttagtgaagc ctggagggtc cctgaaactc  60
tcctgtgcag cctctggatt cactttcagt agctatgcca tgtcttgggt tcgccagact  120
ccagaaaaga ggctggagtg ggtcgcagcc attaatagta atggtggtag tatttattat  180
ccagacaccg tgaaggaccg attcaccatc tccagagaca atgccaagaa caccctgtac  240
ctgcaaatga tcagtctgag gtctgaggac acagccttgt attactgtgc aagacagggg  300
ggttcctctt ggtttgttta ttggggccaa gggactctgg tcactgtctc tgca        354

SEQ ID NO: 215           moltype = DNA  length = 369
FEATURE                  Location/Qualifiers
source                   1..369
                         mol_type = unassigned DNA
                         organism = Mus musculus
SEQUENCE: 215
caggttactc tgaaagagtc tggccctggg aaattgcagc cctcccagac cctcagtctg  60
acttgttctt tctctgggtt ttcactgagc acttctggta tgggtgtgag ctggattcgt  120
cagccttcag gaaagggtct ggagtggctg gcacacattt actgggatga tgacaagcgc  180
tataacccat ccctgaagag ccggctcaca atctccaagg atacctccag aaaccaggta  240
ttcctcaaga tcaccagtgt ggacactgca gatactgcca catactactg tgctcgagga  300
tggttgcgac ggaaagatta ctctgctatg gactactggg gtcaaggaac ctcagtcacc  360
gtctcctca                                                           369

SEQ ID NO: 216           moltype = DNA  length = 366
FEATURE                  Location/Qualifiers
source                   1..366
                         mol_type = unassigned DNA
                         organism = Mus musculus
SEQUENCE: 216
gatgtgcaac tggttgagag cgggggcgga ctggtccagc ccggagggag caggaaactc  60
agctgcgccg cctctgggtt tatattttca tcctttggaa tgcactgggt caggcaagcc  120
cctgaaaaag gtctggaatg ggtcgcatac atatcctctg gatctgccac tatctattat  180
gctgatactg taaagggtcg gttcaccatc agtagggata acccaaagaa cacgctcttc  240
ctgcaaatga ctagtctgcg cagcgaggat accgccatgt attactgtgc tagaaagcgg  300
ggttccggaa attacgtatc agccatggac ttttggggcc aggggactag cgttacagtg  360
agctca                                                              366

SEQ ID NO: 217           moltype = DNA  length = 366
```

```
FEATURE                 Location/Qualifiers
source                  1..366
                        mol_type = unassigned DNA
                        organism = Mus musculus
SEQUENCE: 217
gacgtccagc tggtcgagtc aggcggcgga ctcgtgcaac caggaggctc ccggaagctg  60
agttgtgcag cctctgggtt cacctttagc aatttcggga tgcactgggt gcgacaggtg  120
ccagaaaaag gcctggaatg ggtggcctac atctcatctg atatcagtac tatctactac  180
gtcgatacag taaagggaag attcaccatc tcaagagata attcaaaaaa cactctgttc  240
ctgcagatga ccagcctcag aagtgaggat actgctatgt attactgtgc gcgaaagagg  300
gggtccggcg actacgtcag tgccatggac tactggggtc aggggacaag cgttaccgtg  360
tcctca                                                              366

SEQ ID NO: 218          moltype = DNA  length = 366
FEATURE                 Location/Qualifiers
source                  1..366
                        mol_type = unassigned DNA
                        organism = Mus musculus
SEQUENCE: 218
gaagttaaat tggtcgaaag tggtggaggg ctcgtgaagc caggaggctc tctgaagctg  60
agttgtgctg cctctggatt taccttctcc gattactcaa tgtattgggt gaggcagacc  120
cccgaaaaac ggcttgagtg ggttgccact ataagcaacg gtgggacctt tatctactat  180
gttgactccg ttcgaggacg gttcacgatc agccgggacg atgcgaataa caacgtttat  240
ctgcagatgt attcactgaa gagcgaagac actgcaatat actactgtac acgcggggga  300
cattacgcaa ataagggtga ctggttcgcc tattggggcc aagggacact tgtcacagta  360
tctgca                                                              366

SEQ ID NO: 219          moltype = DNA  length = 351
FEATURE                 Location/Qualifiers
source                  1..351
                        mol_type = unassigned DNA
                        organism = Mus musculus
SEQUENCE: 219
caggttcaac tgcagcaatc cggcgcagag cttgcaagac caggtgctag cgtgaaactc  60
tcctgcaaaa gctctggtta tatcttctct tcctactgga tgcaatgggt taagcagcga  120
ccaggacaag gtctcgagtg gatcggagcc atttatcctg gtgacggtga cactagatac  180
accccaaagt tcaaggggaa ggcaacactg accgctgaca agagttccag cacagcatat  240
atgcaattga cttcactggc ctcagaagat tctgccgtgt actactgcgc aaaaggttac  300
tcccagtcat tcgattattg ggtcaggggg accacactga cggtatcctc t           351

SEQ ID NO: 220          moltype = DNA  length = 351
FEATURE                 Location/Qualifiers
source                  1..351
                        mol_type = unassigned DNA
                        organism = Mus musculus
SEQUENCE: 220
caggtgcagt tgaagcagag cggtgcagag ctggcgtccc caaagacttc cgtcaaactc  60
tcatgtaagg ccagcggata taccttttaca agctattgga tgcaatggat caagcagagg  120
ccaggacaag gactcgaatg gatcggcgct atatacccag gagacggaga cactaggtac  180
acccagaagt ttagaggcaa ggcaactctg accgccgaca agtcttccaa cactgcctat  240
atgcagctgt ctagtcttgc atccgaggac agcgctgtat attactgtgc aaagggctac  300
tcaaattcct tcgactactg gggacagggc acttcactga ccgtctcttc c           351

SEQ ID NO: 221          moltype = DNA  length = 321
FEATURE                 Location/Qualifiers
source                  1..321
                        mol_type = unassigned DNA
                        organism = Mus musculus
SEQUENCE: 221
gatatccaga tgacacagat tacatcctcc ctgtctgcct ctctgggaga cagagtcacc  60
atcagttgca gggcaagtca ggatattagc aattatttaa attggtatca gcagaaacca  120
gacggaactg ttaaactcct gatctactcc acatcaagat tacactcagg agtcccatca  180
aggttcagtg gcagtgggtc tgggacagat tattctctca ccatcagcaa cctggaacct  240
gaagatattg ccacttacta ttgtcagcag tatagcaagc ttcttcctac gttcggatcg  300
gggaccaagc tggaaataaa a                                             321

SEQ ID NO: 222          moltype = DNA  length = 321
FEATURE                 Location/Qualifiers
source                  1..321
                        mol_type = unassigned DNA
                        organism = Mus musculus
SEQUENCE: 222
gatatccaga tgacacagac tacatcctcc ctgtctgcct ctctgggaga cagagtcacc  60
atcagttgca gtgcaagtca gggcattagc aattatttaa actggtatca gcagaaacca  120
gatggaactg ttaaactcct gatctattac acatcaagtt tacattcagg agtcccatca  180
aggttcagtg gcagtgggtc tgggatagat tattctctca ccatcagcaa cctggaacct  240
gaagatattg ccacttacta ttgtcagcaa tatagtaagt ttccgtggac gttcggtgga  300
ggcaccaagc tggaaatcaa a                                             321
```

```
SEQ ID NO: 223          moltype = DNA  length = 324
FEATURE                 Location/Qualifiers
source                  1..324
                        mol_type = unassigned DNA
                        organism = Mus musculus
SEQUENCE: 223
gaaattgtgc tcatccagtc tccagcactc atggctgcat ctccagggga gaaggtcacc  60
atcacctgca gtgtcagctc aagtattagt tccagcaact tacactggta ccagcagcag  120
tcaggaacct cccccaaacc ctggattctt gccacatcca accttgcttc tggagtccct  180
gttcgcttca gtggcagcgg atctgggacc tcttattctc tcacaatcag cagcatggag  240
gctgaagatg ctgccactta ttactgtcaa cagtggagta gttacccatt cacgttcggc  300
acggggacaa aattggaaat taaa                                         324

SEQ ID NO: 224          moltype = DNA  length = 321
FEATURE                 Location/Qualifiers
source                  1..321
                        mol_type = unassigned DNA
                        organism = Mus musculus
SEQUENCE: 224
gacatccaga tgactcagtc tccagcctcc ctatctgcat ctgtgggaga aactgtcacc  60
atcacatgtc gagcaagtgg gaatattcac aattatttag catggtatca gcagagacag  120
ggaaaatctc ctcagctcct ggtctataat gcaaaaacct taccagatgg tgtgccatca  180
aggttcagtg gcagtggatc aggaacacaa tattctctca agatcaacag cctgcagcct  240
gaagattttg ggagttattg ctgtcaacat tttggagta ctccgctcac gttcggtgct  300
gggaccaagt tggagctgaa a                                            321

SEQ ID NO: 225          moltype = DNA  length = 324
FEATURE                 Location/Qualifiers
source                  1..324
                        mol_type = unassigned DNA
                        organism = Mus musculus
SEQUENCE: 225
caaattgttc tcacccagtc tccagcaatc atgtctgcat ctcctgggga gaaggtcacc  60
ttgacctgca gtgccagctc aagtgtaagt tccagctact tgtattggta ccagcagaag  120
ccaggatcct cccccaaact ctggatttat agcacatcca acctggcttc tagagtccct  180
actcgcttca gtggcagtgg gtctgggacc tcttactctc tcacaatcag cagcatggag  240
gctgaagatg ctgcctctta tttctgccat cagtggagta gttacccccct cacgttcggt  300
gctgggacca agctggagct gaaa                                         324

SEQ ID NO: 226          moltype = DNA  length = 321
FEATURE                 Location/Qualifiers
source                  1..321
                        mol_type = unassigned DNA
                        organism = Mus musculus
SEQUENCE: 226
gacatcaaga tgacccagtc tccgtcctcc ttatctgcct ctctgggaga aggagtcagt  60
ctcacttgtc gggcaagtca ggacattggt agtagcttac actggcttca gcagaaaccg  120
gacggaacta ttaaacgcct gatctacggc acatccactt tagattctga tgtccccaaa  180
aggttcagtg gcagtaggtc tgggtcagat tattctctca ccatcagcag ccttgagtct  240
gaagattttg tagactattt ctgtctacaa tatgctactt ctcctccgac gttcggtgga  300
ggcaccaagc tggaaatcaa a                                            321

SEQ ID NO: 227          moltype = DNA  length = 321
FEATURE                 Location/Qualifiers
source                  1..321
                        mol_type = unassigned DNA
                        organism = Mus musculus
SEQUENCE: 227
gacatccaga tgacccagtc tccatcctcc ttatctgcct ctctgggaga aagagtcagt  60
ctcacttgtc gggcaagtca ggacattggt agtagcttaa actggcttca gcaggaacca  120
gatggaactt ttaaacgcct gatctacgcc acatccagtt tagattctgg tgtccccaaa  180
aggttcagtg gcagtaggtc tgggtcagat tattctctca ccatcagtag ccttgagtct  240
gaagattttg tagactatta ctgtctacaa tatgatagtt taccgctcac gttcggtgct  300
gggaccaagc tggagctgaa a                                            321

SEQ ID NO: 228          moltype = DNA  length = 321
FEATURE                 Location/Qualifiers
source                  1..321
                        mol_type = unassigned DNA
                        organism = Mus musculus
SEQUENCE: 228
gatatccaga tgacacagac tacatcctcc ctgtctgcct ctctgggaga cagagtcacc  60
atcagttgca gggcaagtca ggacattagc aattatttaa actggtatca gcagaaacca  120
gctggaactg ttaaactcct gatctactac acatcaagat tacactcagg agtcccatca  180
aggttcagtg gcagtgggtc tgggacagat tattctctca ccattagcaa cctggagcaa  240
gaggatgttg ccacttactt ttgccagcag ggtaatacgc ttccgtggac gttcggtgga  300
ggctccaagc tggaaatcaa a                                            321

SEQ ID NO: 229          moltype = DNA  length = 339
```

```
FEATURE                 Location/Qualifiers
source                  1..339
                        mol_type = unassigned DNA
                        organism = Mus musculus
SEQUENCE: 229
gacattgtga tgtcacagtc tccatcctcc ctagctgtgt cagttggaga gaaggttact  60
atgagctgca agtccagtca gagcctttta tatagtacca atcaagagaa ctacttggcc  120
tggtaccagc agaaaccagg gcagtctcct aaactgctga tttactgggc atcctctagg  180
gaatctgggg tccctgatcg ctttacaggc agtggatctg ggacagattt cactctcacc  240
atcagcagtg tgaaggctga agacctggca gtttattact gtcagcaata ttatagctat  300
cctcggacgt tcggtggagg caccaagctg gaaatcaaa                        339

SEQ ID NO: 230          moltype = DNA  length = 336
FEATURE                 Location/Qualifiers
source                  1..336
                        mol_type = unassigned DNA
                        organism = Mus musculus
SEQUENCE: 230
gacattgtga tgtcacagtc tccatcctcc ctggctgtgt cagcaggaga gaaggtcact  60
atgagctgca aatccagtca gagtctgctc agcagtagaa cccgaaagaa ctacttggct  120
tggtaccagc agaaaccagg gcagtctcct aaactgctga tctactgggc atccactagg  180
gaatctgggg tccctgatcg cttcacaggc agtggatctg ggacagattt cactctcacc  240
atcaccactg tgcaggctga agacctggca gtttattact gcaagcaatc ttataatctg  300
tggacgttcg gtggtggcac caagctggaa atcaaa                            336

SEQ ID NO: 231          moltype = DNA  length = 336
FEATURE                 Location/Qualifiers
source                  1..336
                        mol_type = unassigned DNA
                        organism = Mus musculus
SEQUENCE: 231
gatgttttga tgacccaaac tccagtctcc ctgcctgtca gtcttggaga tcaagcctcc  60
atctcttgca gatctagtca gagcattgta catagtaatg gaaacaccca tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaagattc acatgttccg  300
tggacgttcg gtggaggcac caagctggaa atcaaa                            336

SEQ ID NO: 232          moltype = DNA  length = 321
FEATURE                 Location/Qualifiers
source                  1..321
                        mol_type = unassigned DNA
                        organism = Mus musculus
SEQUENCE: 232
gatgtccaga taacccagtc tccatcttat cttgctgcat ctcctggaga aaccattact  60
attaattgca gggcaagtaa gagtattagc aaatatttag cctggtatca agagaaacct  120
gggaaaaacta ataaggttct tatctactct ggatccactt tgcaatctgg aattccatca  180
aggttcagtg gcagtggatc tggtacagat ttcactctca ccatcagtag cctggagcct  240
gaagattttg caatgtatta ctgtcaacag tataatgaat acccgtggac gttcggtgga  300
ggcaccaagc tggaaatcaa a                                            321

SEQ ID NO: 233          moltype = DNA  length = 336
FEATURE                 Location/Qualifiers
source                  1..336
                        mol_type = unassigned DNA
                        organism = Mus musculus
SEQUENCE: 233
gatgttgtga tgacccaaac tccactctcc ctgcctgtca gtcttggaga tcaagcctcc  60
atctcttgca gatctagtca gagccttgta cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
tacacgttcg gaggggggac caagctggaa ataaaa                            336

SEQ ID NO: 234          moltype = DNA  length = 336
FEATURE                 Location/Qualifiers
source                  1..336
                        mol_type = unassigned DNA
                        organism = Mus musculus
SEQUENCE: 234
gatgttgtga tgactcaaac tccactctcc ctgcctgtca gtcttggaga tcaagcctcc  60
atctcttgca gatctagtca gagccttgta cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgtt ctcaaagtac acatgttccg  300
tacacgttcg gaggggggac caagctggaa ataaaa                            336

SEQ ID NO: 235          moltype = DNA  length = 336
FEATURE                 Location/Qualifiers
```

```
source                  1..336
                        mol_type = unassigned DNA
                        organism = Mus musculus
SEQUENCE: 235
aacattatga tgacacagtc gccatcatct ctggctgtgt ctgcaggaga aaaggtcact  60
atgagctgta agtccagtca aagtgtttta tacagttcaa atcagaagaa ctacttggcc  120
tggtaccagc agaaaccagg gcagtctcct aaactgctga tctactgggc atccactagg  180
gaatctggtg tccctgatcg cttcacaggc agtggatctg ggacagattt tactcttacc  240
atcagcagtg tacaagctga agacctggca gtttattact gtcatcaata cctctcctcg  300
cggacgttcg gtggaggcac caagctggaa atcaaa                            336

SEQ ID NO: 236          moltype = DNA  length = 336
FEATURE                 Location/Qualifiers
source                  1..336
                        mol_type = unassigned DNA
                        organism = Mus musculus
SEQUENCE: 236
aacattatga tgacacagtc gccatcatct ctggctgtgt ctgcaggaga aaaggtcact  60
atgagctgta agtccagtca aagtgtttta tacagttcaa atcagaagaa ctacttggcc  120
tggtaccagc agaaaccagg gcaatctcct aaactgctga tctactgggc atccactagg  180
gaatctggtg tccctgatcg cttcacaggc agtggatctg ggacagattt tactcttacc  240
atcagcagtg tacaagctga agacctggca gtttattact gtcatcaata cctctcctcg  300
cggacgttcg gtggaggcac caagctggaa atcaaa                            336

SEQ ID NO: 237          moltype = DNA  length = 333
FEATURE                 Location/Qualifiers
source                  1..333
                        mol_type = unassigned DNA
                        organism = Mus musculus
SEQUENCE: 237
gacattgtgc tgacacagtc tcctgcttcc ttagctgtat ctctggggca gagggccacc  60
atctcatgca gggccagcaa aagtgtcagt acatctggct atagttatat tcactggtac  120
caacagaaac caggacagcc acccaaactc ctcatctatc ttgcatccaa cctagaatct  180
ggggtccctg ccaggttcag tggcagtggg tctgggacag acttcaccct caacatccat  240
cctgtggagg aggaggatgc tgcaacctat tactgtcagc acagtaggga gcttccgtgg  300
acgttcggtg gaggcaccaa gctggaaatc aaa                               333

SEQ ID NO: 238          moltype = DNA  length = 333
FEATURE                 Location/Qualifiers
source                  1..333
                        mol_type = unassigned DNA
                        organism = Mus musculus
SEQUENCE: 238
gacattgtgc tgacacagtc tcctgcttcc ttagctgtat ctctggggca gagggccacc  60
atctcatgca gggccagcaa aagtgtcagt acatctggct atagttatat gcactggtac  120
caacagaaac caggacagcc acccaaactc ctcatctatc ttgcatccaa cctagaatct  180
ggggtccctg ccaggttcag tggcagtggg tctgggacag acttcaccct caacatccat  240
cctgtggagg aggaggatgc tgcaacctat tactgtctgc acagtaggga gcttccgtgg  300
acgttcggtg gaggcaccaa gctggaaatc aaa                               333

SEQ ID NO: 239          moltype = DNA  length = 336
FEATURE                 Location/Qualifiers
source                  1..336
                        mol_type = unassigned DNA
                        organism = Mus musculus
SEQUENCE: 239
gatgttgtgg tgacccaaac tccactctcc ctgcctgtca gtcttggaga tcaagcctcc  60
atctcttgca gatctagtca gagccttgta cacagtaatg ggaaaacata tttacattgg  120
tacctgcaga agccaggcca gtctccaaac ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttcca  300
ttcacgttcg gctcggggac caagttggaa ataaaa                            336

SEQ ID NO: 240          moltype = DNA  length = 336
FEATURE                 Location/Qualifiers
source                  1..336
                        mol_type = unassigned DNA
                        organism = Mus musculus
SEQUENCE: 240
gatgttgtga tgacccaaac tccactctcc ctgtgtgtca gtcttggaga tcaagcctcc  60
atctcttgca gatctagtca gagccttgta cacagtaatg gaaaaacata tttacattgg  120
tacctgcaga agccaggcca gtctccaaac ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttcca  300
ttcacgttcg gctcggggac caagttggaa ataaaa                            336

SEQ ID NO: 241          moltype = DNA  length = 336
FEATURE                 Location/Qualifiers
source                  1..336
```

```
                        mol_type = unassigned DNA
                        organism = Mus musculus
SEQUENCE: 241
gatgttgtga tgacccaaac tccactctcc ctgcctgtca gtcttggaga tcaagcttcc  60
atctcttgca gatctagtca gagccttgta cacaacaatg gaatcaccta tttatattgg  120
tacctgcaga agccaggcca gtctccaaag ctcctgatct acagggtttc caaccgattt  180
tctggggtcc cagacaggtt cggtggcagt ggatcaggga cagatttcac actcaagatc  240
agcagagtgg aggctgagga tctgggagtt tatttctgct ttcaaggtac acatgttcct  300
cggacgttcg gtggaggcac caagctggaa atcaaa                            336

SEQ ID NO: 242          moltype = DNA  length = 336
FEATURE                 Location/Qualifiers
source                  1..336
                        mol_type = unassigned DNA
                        organism = Mus musculus
SEQUENCE: 242
gatgttgtga tgacccaaac tccactctcc ctgcctgtca gtcttggaga tcacgcttcc  60
atctcttgca gatctagtca gagccttgta cacagcaatg gaatcaccca tttatattgg  120
tacctgcaga ggccaggcca gactccaaag ctcctgatct acagggtttc caaccgattt  180
tctggggtcc cagacaggtt cagtggcagt ggatcaggga cagatttcac actcaagatc  240
agcagcgtgg aggctgagga tctgggagtt tatttctgct ttcaaggtac acatgttcct  300
cggacgttcg gtggaggcac caagctggaa atcgaa                            336

SEQ ID NO: 243          moltype = DNA  length = 336
FEATURE                 Location/Qualifiers
source                  1..336
                        mol_type = unassigned DNA
                        organism = Mus musculus
SEQUENCE: 243
gatgtggtga tgacccaaac tccactctcc ctgcctgtca gtcttggaga tcaggcttcc  60
atctcttgca gatctagtca gagccttgta cacagcaatg gaaacaccca tttatattgg  120
tacctgcaga agccaggcca gtctccaaag ctcctgatct acagggtttc cagccgattt  180
tctggggtcc cagacaggtt cagtggcagt ggatcaggga cagatttcac actcaagatc  240
agcagagtgg aggctgagga tctgggagtt tatttctgct ttcagggtac acatgttcct  300
cggacgttcg gtggaggcac caagctggaa atcaaa                            336

SEQ ID NO: 244          moltype = DNA  length = 336
FEATURE                 Location/Qualifiers
source                  1..336
                        mol_type = unassigned DNA
                        organism = Mus musculus
SEQUENCE: 244
gatgttgtga tgacccaaac tccactctcc ctgcctgtca gtcttggaga tcaagcttcc  60
atctcttgca gatctagtca gagccttgta cacagcactg gaaacaccta tttatattgg  120
tacctgcaga agccaggcca gtctccaaag ctcctgatct acagggtttc cacccgattt  180
tctggggtcc cagacaggtt cagtggcagt ggatcaggga cagatttcac actcaagatc  240
aacagagtgg aggctgagga tctgggagtt tatttctgct ttcaaggtac acatgttcct  300
cggacgttcg gtggaggcac caagctggaa atcaaa                            336

SEQ ID NO: 245          moltype = DNA  length = 336
FEATURE                 Location/Qualifiers
source                  1..336
                        mol_type = unassigned DNA
                        organism = Mus musculus
SEQUENCE: 245
gatgttttga tgacccaaac tccactctcc ctgcctgtca gtcttggaga tcaagcctcc  60
atctcttgca gatctagtca gagcattgta tatagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc acatgttccg  300
tacacgttcg gaggggggac caagctggaa ataaaa                            336

SEQ ID NO: 246          moltype = DNA  length = 336
FEATURE                 Location/Qualifiers
source                  1..336
                        mol_type = unassigned DNA
                        organism = Mus musculus
SEQUENCE: 246
gatgttttga tgacccaaac tccactctcc ctgcctgtca gtcttggaga tcaagcctcc  60
atctcttgca gatctagtca gagcattgta cataggaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc acatgttcca  300
ttcacgttcg gctcggggac aaagttggaa ataaaa                            336

SEQ ID NO: 247          moltype = DNA  length = 336
FEATURE                 Location/Qualifiers
source                  1..336
                        mol_type = unassigned DNA
```

```
                         organism = Mus musculus
SEQUENCE: 247
gatgttttga tgacccaaac tccactctcc ctgcctgtca gtcttggaga tcaagcctcc  60
atctcttgca gatctagtca gagcattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc acatgttcca  300
ttcacgttcg gctcggggac aaagttggaa ataaaa                            336

SEQ ID NO: 248           moltype = DNA  length = 336
FEATURE                  Location/Qualifiers
source                   1..336
                         mol_type = unassigned DNA
                         organism = Mus musculus
SEQUENCE: 248
gatgttttga tgacccaaac tccactctcc ctgcctgtca gtcttggaga tcaagcctcc  60
atctcttgca gatctagtca gaacattgta catagtaatg gaaacaccta tttagaatgg  120
tacctgcaga aaccaggcca gtctccaaag ctcctgatct acagagtttc caaccgattt  180
tctggggtcc cgggcaggtt cagtggcagt gggtcgggga cagatttcac actcaagatc  240
agcagagtgg aggctgagga tctgggagtt tattactgct ttcaaggttc acgtgttccg  300
ctcacgttcg gcactgggac caagctggag ctgaaa                            336

SEQ ID NO: 249           moltype = DNA  length = 336
FEATURE                  Location/Qualifiers
source                   1..336
                         mol_type = unassigned DNA
                         organism = Mus musculus
SEQUENCE: 249
gatgttttga tgacccaaac tccactctcc ctgcctgtca gtcttggaga tcaagcctcc  60
atctcttgca gatctagtca gaacattgta catagtaatg gaaacaccta tttagaatgg  120
tacctgcaga aaccaggcca gtctccaaag ctcctgatct acaaagtttc caaccgattt  180
tctggggtcc cagacaggtt cagtggcagt ggatcaggga cagatttcac actcaagatc  240
agcagggtgg aggctgagga tctgggagtt tattactgct ttcaaggttc acatgttccg  300
tacacgttcg gaggggggac caagctggaa ataaaa                            336

SEQ ID NO: 250           moltype = DNA  length = 336
FEATURE                  Location/Qualifiers
source                   1..336
                         mol_type = unassigned DNA
                         organism = Mus musculus
SEQUENCE: 250
gatgttttga tgacccagac tccactctcc ctgcctgtca gtcttggaga tcaagcctcc  60
atcgcttgca gatctagtca gagcattgta catagtaatg gaaacaccta tttagaatgg  120
tacctgcaga aaccaggcca gtctccagag ctcctgatct acaaagtttc caaccgattt  180
tctggggtcc cagacaggtt cagtggcagt ggatcaggga cagatttcac actcaagatc  240
agcagagtgg aggctgagga tctgggagtt tattactgct ttcaaggttc acatgttccg  300
tacacgttcg gaggggggac caagctggaa ataaaa                            336

SEQ ID NO: 251           moltype = DNA  length = 336
FEATURE                  Location/Qualifiers
source                   1..336
                         mol_type = unassigned DNA
                         organism = Mus musculus
SEQUENCE: 251
gatgttttga tgacccaaac tccactctcc ctgcctgtca gtcttggaga tcaagcctcc  60
atctcttgca gatctagtca gagcattgta tatactaatg gaaacaccta tttagaatgg  120
tacctgcaga aaccaggcca gtctccaaag ctcctgatct acaaagtttc caaccgattt  180
tctggggtcc cagacaggtt tagtggcagt ggatcaggga cagatttcac actcaagatc  240
agcagagtgg aggctgagga tctgggagtt tattactgct ttcaaggttc acatgttccg  300
tacacgttcg gaggggggac caagctggaa ataaaa                            336

SEQ ID NO: 252           moltype = DNA  length = 336
FEATURE                  Location/Qualifiers
source                   1..336
                         mol_type = unassigned DNA
                         organism = Mus musculus
SEQUENCE: 252
gatgttgtgc tgacccagac tccactcact ttgtcggtta ccattggaca accagcctcc  60
atctcttgca agtcaagtca gagcctctta catagtgatg gaaagacata tttgaattgg  120
ttgttacaga ggccaggcca gtctccaaag cgcctattct atctggtgtc taaactggac  180
tctggagtcc ctgacaggtt cactggcagt ggatcaggga cagatttcac actgaaaatc  240
agcagcgtgg aggctgagga tttgggagtt tattattgct ggcaaggtac acattttcct  300
cacacattcg gtgctgggac caagctggag ctgaaa                            336

SEQ ID NO: 253           moltype = DNA  length = 336
FEATURE                  Location/Qualifiers
source                   1..336
                         mol_type = unassigned DNA
                         organism = Mus musculus
```

```
SEQUENCE: 253
gatgttgtga tgacccagac tccactcact ttgtcggtta ccattggaca accagcctcc  60
atctcttgca agtcaagtca gagcctctta catagtgatg gaaagacatt tttgaattgg  120
ttgttacaga ggccaggcca gtctccaaag cgcctaatct atctggtgtc taaactggac  180
tctggagtcc ctgacaggtt cactggcagt ggatctggga cagatttcac actgaaaatc  240
agcagagtgg aggctgagga tttgggagtt tattattgct ggcaaggtac acattttcct  300
cagacgttcg gtggaggcac caagctggaa atcaaa                            336

SEQ ID NO: 254          moltype = DNA  length = 336
FEATURE                 Location/Qualifiers
source                  1..336
                        mol_type = unassigned DNA
                        organism = Mus musculus
SEQUENCE: 254
gatgttgtga tgatccagac tccactcact ttgtcggtta ccagtggaca accagcctcc  60
atctcttgca agtcaagtca gagcctctta catagtgatg gaaagacata tttgaattgg  120
ttgttacaga ggccaggcca gtctccaaag cgcctaatgt atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                            336

SEQ ID NO: 255          moltype = DNA  length = 336
FEATURE                 Location/Qualifiers
source                  1..336
                        mol_type = unassigned DNA
                        organism = Mus musculus
SEQUENCE: 255
gatgttgtga tgacccagac tccactcact ttgtcggtta ccattggaca accagcctcc  60
atctcttgca agtcaagtca gagcctctta gatagtgatg gaaagacata tttgaattgg  120
ttgttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cagacgttcg gtggaggcac caagctggaa atcaaa                            336

SEQ ID NO: 256          moltype = DNA  length = 336
FEATURE                 Location/Qualifiers
source                  1..336
                        mol_type = unassigned DNA
                        organism = Mus musculus
SEQUENCE: 256
gatgttgtga tgacccagac tccactcact ttgtcggtta ccattggaca accagcctcc  60
atctcttgca agtcaagtca gagcctctta gatagtgatg gaaagacata tttgaattgg  120
ttgttacaga ggccaggcca gtctccaaag cgcctaatct atctggtgtc taaactggac  180
tctggagtcc ctgacaggtt cactggcagt ggatcaggga cagatttcac actgaaaatc  240
agcagagtgg aggctgagga tttgggagtt tattattgct ggcaaggtac acattttcct  300
cggacgttcg gtggaggcac caagctggaa atcaaa                            336

SEQ ID NO: 257          moltype = DNA  length = 321
FEATURE                 Location/Qualifiers
source                  1..321
                        mol_type = unassigned DNA
                        organism = Mus musculus
SEQUENCE: 257
gatgtccaga taacccagtc tccatcttat cttgctgcat ctcctggaga aatcattatt  60
attaattgca gaacaagtaa gagcattaac aaatatttag cctggtatca agagaaacct  120
ggaaaaacta ataagcttct tatctactct ggatccactt tgcaatctgg aattccatca  180
aggttcagtg gcagtggatc tggtacagat ttcactctca ccatcagtag cctggagcct  240
gaagattttg caatgtatta ctgtcaacag cataatgaat acccgtacac gttcggaggg  300
gggaccaagc tggaaataaa a                                            321

SEQ ID NO: 258          moltype = DNA  length = 321
FEATURE                 Location/Qualifiers
source                  1..321
                        mol_type = unassigned DNA
                        organism = Mus musculus
SEQUENCE: 258
gatgtccaga taacccagtc tccatcttat cttgctgcat ctcctggaga aaccattact  60
cttaattgca gggcaagtaa gaacattagc aaatatttag cctggtatca agagaaacct  120
gggaaaacta ataagcttct tatctactct ggatccactt tgcaatctgg aattccatca  180
aggttcagtg gcagtggatc tggtacagat ttcactctca ccatcagtag cctggagcct  240
gaagattttg caatgtattt ctgtcaacag cataatgaat acccgtacac gttcggaggg  300
gggaccaagc tggaaatgaa a                                            321

SEQ ID NO: 259          moltype = DNA  length = 321
FEATURE                 Location/Qualifiers
source                  1..321
                        mol_type = unassigned DNA
                        organism = Mus musculus
SEQUENCE: 259
```

```
gacatccaga tgactcagtc tccagcctcc ctatctgcat ctgtgggaga aactgtcacc  60
atcacatgtc gagcaagtga gaatatttac agttatttag catggtatca gcagaaacag  120
ggaacatctc ctcaactcct ggtctataat gcaaaagcct tagcagaagg tgtgccatca  180
aggttcagtg gcagtggatc aggcacacag ttttctctga agatcaacag cctgcagcct  240
gaagattttg ggagttatta ctgtcaacat cattatggta ctcctcggac gttcggtgga  300
ggctccaagc tggaaatcaa a                                            321

SEQ ID NO: 260         moltype = DNA  length = 321
FEATURE                Location/Qualifiers
source                 1..321
                       mol_type = unassigned DNA
                       organism = Mus musculus
SEQUENCE: 260
gacatccaga tgactcagtc tccagcctcc ctatctgcat ctgtgggaga aactgtcacc  60
atcacatgtc gagcaagtga gaatatttac agttatttag catggtatca gcagaaacag  120
ggaaaatctc ctcagctcct ggtctataat gcaaaaacct tagcagaagg tgtgccatca  180
aggttcagtg gcagtggatc aggcacacag ttttctctga agatcaacag cctgcagcct  240
gaagattttg ggagttatta ctgtcaacat cattatggta ctcctcggac gttcggtgga  300
ggcaccaagc tggaaatcaa a                                            321

SEQ ID NO: 261         moltype = DNA  length = 321
FEATURE                Location/Qualifiers
source                 1..321
                       mol_type = unassigned DNA
                       organism = Mus musculus
SEQUENCE: 261
agtattgtga tgacccagac tcccaaattc ctgcctgtat cagcaggaga cagggttacc  60
atgacctgca aggccagtca gagtgtgggt aataatgtag cctggtacca acagaagcca  120
ggacagtctc ctaaactgct gatatactat gcatccaatc gttacactgg agtccctgat  180
cgcttcactg ccagtggatc tgggacagat ttcactttca ccatcagcag tgtgcaggtt  240
gaagacctgg cagtttattt ctgtcagcag cattatagct ctccgtatac gttcggatcg  300
gggaccaatc tggaaataaa a                                            321

SEQ ID NO: 262         moltype = DNA  length = 321
FEATURE                Location/Qualifiers
source                 1..321
                       mol_type = unassigned DNA
                       organism = Mus musculus
SEQUENCE: 262
agtattgtga tgacccagag tcccaaattc ctgcctgtat cagcaggaga cagggttacc  60
atgacctgca aggccagtca gagtgtgggt aataatgtag cctggtacca acagaagcca  120
ggacagtctc ccaaactgct gatatactat gcatccaatc gctacactgg agtccctgat  180
cgcttcactg gcagtggatc tgggacagat ttcactctca ccatcagcag tgtgcaggtt  240
gaagacctgg tagtttattt ctgtcagcag cattatagtt ctccgctcac gttcggtgct  300
gggaccaagc tggagctgaa a                                            321

SEQ ID NO: 263         moltype = DNA  length = 321
FEATURE                Location/Qualifiers
source                 1..321
                       mol_type = unassigned DNA
                       organism = Mus musculus
SEQUENCE: 263
aatattgtga tgacccagac tcccaaattc ctgcctatag cagcaggaga cagggttatt  60
atgacctgca aggccagtca gagtgtgggt aataatgtag gctggtacca gctgaagcca  120
ggacagtctc ctaaactgct gatatacttt gcatccaatc gctacactgg agtccctgat  180
cgcttcactg gcagtggatc tgggacagat ttcactttca ccatcagcag tgtgcaggtt  240
gaagacctgg cagtttattt ctgtcagcag cattatagct ctccgctcac gttcggtgct  300
gggaccaagc tggagctgaa a                                            321

SEQ ID NO: 264         moltype = DNA  length = 321
FEATURE                Location/Qualifiers
source                 1..321
                       mol_type = unassigned DNA
                       organism = Mus musculus
SEQUENCE: 264
agtattgtga tgacccagac tcccaaattc ctgcctgttt cagcaggaga cagggttacc  60
atgacctgca aggccagtca gagtttgggt aataatgtag cctggtacca acagaagcca  120
ggacagtctc ctaaactgct gatatactat gcatccaatc gctacactgg agtccctgat  180
cgcttcactg gcagtggatc tgggacagat ttcactttca ccatcagcag tgtgcaggtt  240
gaagacctgg cagtttattt ctgtcagcag cattatagct ctcctcggac gttcggtgga  300
ggcaccaagc tggaaatcag a                                            321

SEQ ID NO: 265         moltype = DNA  length = 336
FEATURE                Location/Qualifiers
source                 1..336
                       mol_type = unassigned DNA
                       organism = Mus musculus
SEQUENCE: 265
gatgttgtga tgacccaaac tccactctcc ctgcctgtca gtcttggaga tcaagcctcc  60
```

```
atctcttgca gatctagtca gagccttgta cacagttata gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcaaagtgg aagctgagga tctgggagtt tatttctgct ctcaaagtac acatgttccg  300
tggacgttcg gtggaggcac caagctggaa atcaaa                            336

SEQ ID NO: 266          moltype = DNA  length = 336
FEATURE                 Location/Qualifiers
source                  1..336
                        mol_type = unassigned DNA
                        organism = Mus musculus
SEQUENCE: 266
gatgttgtga tgacccaaac tccactctcc ctgcctgtca gtcttggaga tcaagcctcc  60
atctcttgca gatctagtca gagccttgta cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
tggacgttcg gtggaggcac caagctggaa atcaaa                            336

SEQ ID NO: 267          moltype = DNA  length = 327
FEATURE                 Location/Qualifiers
source                  1..327
                        mol_type = unassigned DNA
                        organism = Mus musculus
SEQUENCE: 267
gaaattgtgt taacccagtc tccaaccacc atggctgcat ctcccggaga gaatatcact  60
atcacctgca gtgccagctc aactataagt tcccattact tgcattggta tcagcagaag  120
ccaggattct cccctaaact cttgatttat aggacataca atctggcttc tggagtccca  180
actcgcttca gtggcagtgg gtctgggacc tcctactctc tcacaattgg cgccatggag  240
gctgaagatg ttgccactta ctactgccag cagggtagta ctatatcacg ctacacgttc  300
ggaggggga ccaagctgga agtaaaa                                       327

SEQ ID NO: 268          moltype = DNA  length = 327
FEATURE                 Location/Qualifiers
source                  1..327
                        mol_type = unassigned DNA
                        organism = Mus musculus
SEQUENCE: 268
caaattgtgc tcacccagtc tccaaccacc atggctgcat ctcccgggga gaagatcact  60
atcacgtgca gtgccagctc aagtataagt tccacttact tgcattggta tcagcagaag  120
ccaggattct cccctaaact cttgatttat aggacatcca atctggcttc tggagtccca  180
gctcgcttca gtggcagtgg gtctgggacc tcttactctc tcacaattgg caccatggag  240
gctgaagatg ttgccactta ctactgccag cagggtagta gtataccacg ctacacgttc  300
ggagggggga ccaagctgga aataaaa                                      327

SEQ ID NO: 269          moltype = DNA  length = 321
FEATURE                 Location/Qualifiers
source                  1..321
                        mol_type = unassigned DNA
                        organism = Mus musculus
SEQUENCE: 269
gacatccaga tgactcagtc tccagcttca ctgtctgcat ctgtgggaga aactgtcacc  60
ttcacatgtg gagcaagtga gaatgtttac ggtgctttaa attggtatca gcggaaacag  120
ggaaaatctc ctcagctcct gatctatggt gcaaccaact tggcagatgg catgtcatcg  180
aggttcagtg gcagtggatc tggtagacag tattctctca agatcagtag cctgcatcct  240
gacgatgttg caacgtatta ctgtcaaaat gtattaacta ttccgtggac gttcggtgga  300
ggcgccaagt tggaaatcaa a                                            321

SEQ ID NO: 270          moltype = DNA  length = 321
FEATURE                 Location/Qualifiers
source                  1..321
                        mol_type = unassigned DNA
                        organism = Mus musculus
SEQUENCE: 270
agtattgtga tgacccagac tcccaaattc ctgcttgtat cagcaggaga cagggttacc  60
ataacctgca aggccagtca gagtgtgagt aatgatgtag cttggtacca acagaagcca  120
gggcagtctc ctaaactgct aatatactat gcatccaatc gctgcactgg agtccctgat  180
cgcttcactg gcagtggata tgggacggat ttcactttca ccatcagcac tgtacaggct  240
gaagacctgg cagtttattt ctgtcagcag gattataggt ctccgctcac gttcggtgct  300
gggaccaagc tggagctgaa a                                            321

SEQ ID NO: 271          moltype = DNA  length = 339
FEATURE                 Location/Qualifiers
source                  1..339
                        mol_type = unassigned DNA
                        organism = Mus musculus
SEQUENCE: 271
gacattgtga tgacacagtc tccatcctcc ctgagtgtgt cagcaggaga gaaggtcact  60
atgagctgca agtccagtca gagtctgtta aacagtggaa atcaaaagaa ctacttggcc  120
```

```
tggtaccagc agaaaccagg gcagcctcct aaactgttga tctacggggc atccattagg  180
gaatctgggg tccctgatcg cttcacaggc agtggatctg gaaccgattt cactcttacc  240
atcagcagtg tgcaggctga agacctggca gtttattact gtcagaatga tcatagtcat  300
ccgtacacgt tcggaggggg gaccaagttg gaaataaaa                         339

SEQ ID NO: 272         moltype = DNA  length = 339
FEATURE                Location/Qualifiers
source                 1..339
                       mol_type = unassigned DNA
                       organism = Mus musculus
SEQUENCE: 272
gacattgtta tgacacagtc tccatcctcc ctgagtgtgt cagcaggaga gaaggtcact  60
atgagctgca agtccagtca gagtctgcta aacagtggaa atcaaaagaa ctacttggcc  120
tggtaccagc agaaaccagg gcagcctcct aaactgttga tctacgggac atccactagg  180
gaatctgggg tccctgatcg cttcacaggc agtggatctg gaaccgattt cactcttacc  240
atcagcagtg tgcaggctga agacctggca gtttattact gtcagaatga tcatagtcat  300
ccgtacacgt tcggaggggg gaccaagctg gaaataaaa                         339

SEQ ID NO: 273         moltype = DNA  length = 339
FEATURE                Location/Qualifiers
source                 1..339
                       mol_type = unassigned DNA
                       organism = Mus musculus
SEQUENCE: 273
gacattgtga tgacacagtc tccatcctcc ctgagtgtgt cagcaggaga gaaggtcact  60
atgagctgca agtccagtca gagtctgtta aacagtggaa atcaaaagaa ctacttggcc  120
tggtaccagc agaaaccagg gcagcctcct aaactgttga tctacggggc atccactagg  180
gaatctgggg tccctgatcg cttcacaggc agtggatctg gaaccgattt cactcttacc  240
atcagcagtg tgcaggctga agacctggca gtttattact gtcagaatga tcatagtcat  300
ccgtacacgt tcggaggggg gaccaagctg gaaataaaa                         339

SEQ ID NO: 274         moltype = DNA  length = 339
FEATURE                Location/Qualifiers
source                 1..339
                       mol_type = unassigned DNA
                       organism = Mus musculus
SEQUENCE: 274
gacactgtga tgacacagtc tccatcctcc ctgagtgtgt ctgcaggaga gaaggtcacc  60
atgaactgca agtccagtca gagtctgtta aacagtggaa atcaaaagaa ctacttggcc  120
tggtaccagc agaaacccgg gcagcctcct aaactgttga tctacggggc atccactagg  180
gaatctgggg tccctgatcg cttcacaggc agtggatctg gaaccgattt cactcttacc  240
atcagcagtg tgcaggctga agacctggca gtttattact gtcagaatga tcatagtcat  300
ccgtacacgt tcggaggggg gaccaagctg gaaataaaa                         339

SEQ ID NO: 275         moltype = DNA  length = 339
FEATURE                Location/Qualifiers
source                 1..339
                       mol_type = unassigned DNA
                       organism = Mus musculus
SEQUENCE: 275
gacattgtga tgacacagtc tccatcctcc ctgagtgtgt cagcaggaga gaaggtcact  60
atgagctgca agtccagtca gagtctttta aacagtggaa atcaaaagaa ctacctggcc  120
tggtaccagc agaaaccagg gcagcctcct aaactgttga tctacggggc atccactagg  180
gaatctgggg tccctgatcg cttcacaggc agtggatctg gaaccgattt cactcttacc  240
atcagcagtg tgcaggctga agacctggca gtttattact gtcagaatga tcatagtcat  300
ccgtatacgt tcggaggggg gaccaagctg gaaataaaa                         339

SEQ ID NO: 276         moltype = DNA  length = 339
FEATURE                Location/Qualifiers
source                 1..339
                       mol_type = unassigned DNA
                       organism = Mus musculus
SEQUENCE: 276
gacattgtga tgacacagtc tccatcctcc ctgagtgtgt cagcaggaga gaaggtcact  60
atgagctgca agtccagtca gagtctgtta agtagtggaa atcaaaagaa ctacttggcc  120
tggtaccagc agaaaccagg gcagcctcct aaactgttga tctacggggc atccactagg  180
gaatctgggg tccctgatcg cttcacaggc agtggatctg gaaccgattt cactcttacc  240
atcagcagtg ttcaggctga agacctggca gtttattact gtcagaatga tcattctcat  300
ccgtacacgt tcggaggggg gaccaagctg gaaataaaa                         339

SEQ ID NO: 277         moltype = DNA  length = 333
FEATURE                Location/Qualifiers
source                 1..333
                       mol_type = unassigned DNA
                       organism = Mus musculus
SEQUENCE: 277
gacattgtgc tgacacagtc tcctgcttcc ttagctgtat ctctggggca gagggccacc  60
atctcatgca gggccagcca tagtgtcagt tcatcttgct atagttatat gcactggtac  120
caacagaaac caggacagcc acccaaactc ctcatcaagt atgcatccaa cctagaatct  180
```

```
ggggtccctg ccaggttcag tggcagtggg tctgggacag acttcaccct caacatccat  240
cctgtggagg aggaggatac tgcaacatat tactgtcagc acagttggga gattccgtac  300
acgttcggag gggggaccaa gctggaaata aaa                               333

SEQ ID NO: 278          moltype = DNA  length = 333
FEATURE                 Location/Qualifiers
source                  1..333
                        mol_type = unassigned DNA
                        organism = Mus musculus
SEQUENCE: 278
gacattgtgc tgacacagtc tcctgcttcc tcagctgtat ctctggggca gagggccacc  60
atctcatgca gggccagcca aagggtcagt acatctagct atagttatat gcactggtac  120
caacagaaac caggacagcc acccaaactc ctcatcaagt atgcatccaa cctagaatct  180
ggggtccctg ccaggttcag tggcagtggg tctgggacag acttcaccct caacatccat  240
cctgtggagg aggaggatac tgcaacatat tactgtcagc acagttggga gattccgtac  300
acgttcggag gggggaccaa gctggaaata aaa                               333

SEQ ID NO: 279          moltype = DNA  length = 321
FEATURE                 Location/Qualifiers
source                  1..321
                        mol_type = unassigned DNA
                        organism = Mus musculus
SEQUENCE: 279
gatatccaga tgacacagac tacatcctcc ctgtctgcct ctctgggaga cagagtcacc  60
atcagttgca gtgcaagtca gggcattagc aattatttaa actggtatca gcagaaacca  120
gatggaactg ttacactcct gatctattac acttcaagtt tacactcagg agtcccatca  180
aggttcagtg gcagtgggtc tgggacagat tattctctca ccatcagcaa cctggaacct  240
gaagatattg ccacttacta ttgtcagcag tatagtaagc ttccgtggac gttcggtgga  300
ggcaccaagc tggaaatcaa a                                            321

SEQ ID NO: 280          moltype = DNA  length = 336
FEATURE                 Location/Qualifiers
source                  1..336
                        mol_type = unassigned DNA
                        organism = Mus musculus
SEQUENCE: 280
gatgttgtga tgacccaaac tccactctcc ctgcctgtca gtcttggaga tcaagcctcc  60
atctcttgca gatctagtca gagccttcta cacagtaatg gaaacaccta tttacattgg  120
tacctgcaga agccaggcca gtctccagag ctcctgatct acaaagtttc caaccgattt  180
tttggggtcc cagacaggtt cagtggcagt ggatcaggga cagatttcac actcaagatc  240
agtagagtgg aggctgagga tctgggagtt tatttctgct ctcaaagtac acatgttccg  300
tggacgttcg gtggaggcac caagctggaa atcaaa                            336

SEQ ID NO: 281          moltype = DNA  length = 336
FEATURE                 Location/Qualifiers
source                  1..336
                        mol_type = unassigned DNA
                        organism = Mus musculus
SEQUENCE: 281
gatgttttga tgacccaaac tccactctcc ctgcctgtca gtcttggaga tcaagcctcc  60
atctcttgca gatctagtca gaacattgta caaagtaatg gaaacaccta tttagaatgg  120
tacttgcaga aaccaggcca gtctccaaag ctcctgatct acaaagtttt caaccgattt  180
tctggggtcc cagacaggtt cagtggcagt ggatcaggga cagatttcac actcaagatc  240
agcagagtgg aggctgagga tctgggagtt tattactgct ttcaaggttc acatgttccg  300
tacacgttcg gaggggggac taagctggaa ataaaa                            336

SEQ ID NO: 282          moltype = DNA  length = 336
FEATURE                 Location/Qualifiers
source                  1..336
                        mol_type = unassigned DNA
                        organism = Mus musculus
SEQUENCE: 282
gatgttgtga tgacccaaac tccactctcc ctgcctgtca gtcttggaga tcaagcctcc  60
atctcttgca gatctagtca gagccttgta cacagtaatg gaaacaccta tttacattgg  120
tacctgcaga agccaggcca gtctccaaag ctcctgatct acaaagtttc caaccgattt  180
tctggggtcc cagacaggtt cagtggcagt ggatcaggga cagatttcac actcaagatc  240
agcagagtgg aggctgagga tctgggagtt tatttctgct ctcaaagtac acatgttccg  300
ctcacgttcg gtgctgggac caagctggag ctgaaa                            336

SEQ ID NO: 283          moltype = DNA  length = 321
FEATURE                 Location/Qualifiers
source                  1..321
                        mol_type = unassigned DNA
                        organism = Mus musculus
SEQUENCE: 283
gacattgtga tgactcagtc tccagccacc ctgtctgtga ctccaggaga tagagtctct  60
ctttcctgca gggccagcca gagtattagc gactacttac actggtatca acaaaaatta  120
catgagtctc caaggcttct catcaaatat gcttcccaat ccatctctgg gagcccctcc  180
aggttcagtg gcagtggatc agggtcagat ttcactctca gtatcaacag tgtggaacct  240
```

```
gaagatgttg gagtgtatta ctgtcaaaat ggtcacagct ttcctccgac gttcggtgga  300
ggcaccaagc tggaaatcaa a                                            321

SEQ ID NO: 284          moltype = DNA  length = 321
FEATURE                 Location/Qualifiers
source                  1..321
                        mol_type = unassigned DNA
                        organism = Mus musculus
SEQUENCE: 284
gacatcaaga tgacccagtc tccatcttcc atgtatgcat ctctaggaga gagactctct  60
atcacttgca aggcgagtca ggacattaat agctatttaa actggttcca gcagaaacca  120
gggaaatctc ctaagaccct gatctatcgt gcaaacagat tggtagatgg ggtcccatca  180
aggttcagtg gcagtggatc tgggcaagat tattctctca ccatcagcag cctggaggat  240
gaagatatgg gaatttatta ttgtctacag tatgatgagt ttccgctcac gttcggtgct  300
gggaccaagc tggagctgag a                                            321

SEQ ID NO: 285          moltype = DNA  length = 321
FEATURE                 Location/Qualifiers
source                  1..321
                        mol_type = unassigned DNA
                        organism = Mus musculus
SEQUENCE: 285
gacatcttgc tgactcagtc tccagccatc ctgtctgtga gtccaggaga aagagtcagt  60
ttctcctgca gggccagtca gaatattggc acaagcatac actggtatca gcaaagaaca  120
aatggttctc caaggcttct cataaagtat gcttctgagt ctatctctgg gatcccttcc  180
aggtttagtg gcagtggatc agggacagat tttactctta gtatcaacag tgtggagtct  240
gaagatattg cagattatta ctgtcaacaa agtaatagct ggccaacgac gttcggtgga  300
ggcaccaagc tggaaatcaa a                                            321

SEQ ID NO: 286          moltype = DNA  length = 321
FEATURE                 Location/Qualifiers
source                  1..321
                        mol_type = unassigned DNA
                        organism = Mus musculus
SEQUENCE: 286
gacatcaaga tgacccagtc tccatcttcc atgtatgcat ctctaggaga gagagtcact  60
atcacttgca aggcgagtca ggacattaat agctatttaa gctggttcca gcagaaacca  120
gggaaatctc ctaagaccct gatctatcgt gcaaacagat tggtagatgg ggtcccatca  180
aggttcagtg gcagtggatc tgggcaagat tattctctca ccatcagcag cctggagtat  240
gaagatatgg gaatttatta ttgtctacag tatgatgagt ttcctctcac gttcggtgct  300
gggaccaagc tggagctgaa a                                            321

SEQ ID NO: 287          moltype = DNA  length = 321
FEATURE                 Location/Qualifiers
source                  1..321
                        mol_type = unassigned DNA
                        organism = Mus musculus
SEQUENCE: 287
gacatcaaga tgatccagtc tccatcttcc atgtatgcat ctctaggaga gagagtcact  60
atcacttgca aggcgagtca ggacattaat agctatttaa gctggttcca gcagaaacca  120
gggaaatctc ctaagaccct gatctatcgt gcaaacagat tggtagatgg ggtcccatca  180
aggttcagtg gcagtggatc tgggcaagat tattctctca ccatcagcag gctggaatat  240
gaagatgtgg gactttatta ttgtcaacag tatgatgagt ttcctctcac gttcggtgct  300
gggaccaagc tggagctgaa a                                            321

SEQ ID NO: 288          moltype = DNA  length = 321
FEATURE                 Location/Qualifiers
source                  1..321
                        mol_type = unassigned DNA
                        organism = Mus musculus
SEQUENCE: 288
aacattgtaa tgacccaatc tcccaaatcc atgtccatgt cagtaggaga gagggtcacc  60
ttgagctgca aggccagtga gcatgtgggt ccttatgtat cctggtatca acataaagca  120
gagcagtctc ctaaactgct gatatacggg gcatccaacc ggtacactgg ggtccctgat  180
cgcttcacag gcagtggatc tgcaacagat ttcactctga tcatcagcag tgttcaggct  240
gaagaccttg cagattatca ctgtggacag acttacagct atcctctcac gttcggtgct  300
gggaccaagc tggagctgaa a                                            321

SEQ ID NO: 289          moltype = DNA  length = 321
FEATURE                 Location/Qualifiers
source                  1..321
                        mol_type = unassigned DNA
                        organism = Mus musculus
SEQUENCE: 289
aacattgtaa tgacccaatc tcccaaatcc atgtccatgt cagtaggaga gagggtcacc  60
ttgacctgca aggccagtga gaatgtggtt acttatgttt cctggtatca acataaagca  120
gagcagtctc ctaaactgct gatatacggg gcatccaacc ggtacactgg ggtccctgat  180
cgcttcacag gcagtggatc tgcaacagat ttcactctga tcatcagcag tgttcaggct  240
gaagaccttg cagattatca ctgtggacag acttacagct atcctctcac gttcggtgct  300
```

```
gggaccaagc tggagctgaa a                                          321

SEQ ID NO: 290          moltype = DNA  length = 321
FEATURE                 Location/Qualifiers
source                  1..321
                        mol_type = unassigned DNA
                        organism = Mus musculus
SEQUENCE: 290
aacattgtaa tgacccaatc tcccaaatcc atgtccatgt cagtaggaga gagggtcacc  60
ttgacctgca aggccagtga gaatgtggtt acttatgttt cctggtatca acagaaacca  120
gagcagtctc ctaaactgct gatatacggg gcatccaacc ggtacactgg ggtccccgat  180
cgcttcacag gcagtggatc tgcaacagat ttcactctga ccatcagcag tgtgcaggct  240
gaagaccttg cagattatca ctgtggacag acttacagct atcctctcac gttcggtgct  300
gggaccaagc tggagctgaa a                                          321

SEQ ID NO: 291          moltype = DNA  length = 336
FEATURE                 Location/Qualifiers
source                  1..336
                        mol_type = unassigned DNA
                        organism = Mus musculus
SEQUENCE: 291
gacgtcctca tgacacagac ccctctcagc cttcctgtgt ccctcgggga tcaagcaagc  60
atcagttgcc gcagtggcca gagcatcgtg catagcaatg gaaacaccta tctcgaatgg  120
tacctccaaa agccaggcca gtcaccaaag ctcctgattt acaaggtctc aaatagattt  180
tcaggcgtcc ccgatcgatt ctctggaagt ggttcaggga ctgacttcac actcaaaatc  240
tcccgggtcg aggcagagga cttgggagtt tactattgtt ttcagggaag ccacgtgcca  300
tggacattcg gagggggaac caaactggaa atcaaa                           336

SEQ ID NO: 292          moltype = DNA  length = 336
FEATURE                 Location/Qualifiers
source                  1..336
                        mol_type = unassigned DNA
                        organism = Mus musculus
SEQUENCE: 292
gatgtcctgc tgactcagag cccactgagc ctgccggtgt ccctgggcga tcaggtaagc  60
atcagttgcc gaagcggcca gagtattgtc cacagcaacg gcaacacgta tctggggtgg  120
tatctgcaga aacctgggca gagcccaaaa cttctgattt ataaggtcag tataaggttt  180
tatggggtac ccgaccggtt ctccggaagt ggcagcggga catatttcac cctcaaaatt  240
agccgggtgg aggcggagga tcttggagtg taccactgct ttcagggttc tcatgtccct  300
tggaccttcg gcggcgggac caagctggag atcaaa                           336

SEQ ID NO: 293          moltype = DNA  length = 336
FEATURE                 Location/Qualifiers
source                  1..336
                        mol_type = unassigned DNA
                        organism = Mus musculus
SEQUENCE: 293
gacgtggtga tgacacaaac tccccttaca ctgagtgtga tcattggaca gccagcaagt  60
atctactgca agtcatccca gagcctgctc tactctaatg gcaaaacata tctcaattgg  120
ctgctgcaga ggccaggtca gagccctaag cgactgatct atctggttag caagcttgat  180
agcggtgtcc ccgatcggtt cacaggatca gggtccggca ctgacttcgc cctgcagatt  240
tccagagtgg aggccgaaga cctcggcatt tattattgtg tccagggaac ccactttcct  300
catacattcg gcggggggac gaagttggag attaag                           336

SEQ ID NO: 294          moltype = DNA  length = 336
FEATURE                 Location/Qualifiers
source                  1..336
                        mol_type = unassigned DNA
                        organism = Mus musculus
SEQUENCE: 294
gatgtggtga tgacacagac ccccctcact cttagcgtga ccataggaca acctgcctca  60
atatcctgca agtctagcca atcactgctt gattctgacg gaaagacgta ccttagctgg  120
ctgctccaga ggcccggaca gacgccgaaa cgcctcattt acatggtatc aaaactcgac  180
tccggcgtcc ccgacagatt tacaggatcc gggagcggaa ccgattttac tctgaagatc  240
aagagagtcg aggcggaaga cctcggggtg tattactgtt ggcagggaac ccattttcca  300
gtgacattcg gcggcggaac aaaattggag ctcaag                           336

SEQ ID NO: 295          moltype = DNA  length = 336
FEATURE                 Location/Qualifiers
source                  1..336
                        mol_type = unassigned DNA
                        organism = Mus musculus
SEQUENCE: 295
gacgtggaaa tgacccagac ccccctcaca ctgtccgtga cgatcggcca gcctgcctct  60
atctcttgca agtctaatca gagtcttctg gattctgatg gtaaaaccta cctgagctgg  120
ttgctgcagc gccctgggca gtcacctaaa cggttgatct acatggtgtc taagctggat  180
agcggggtgc ccgaccgctt taccggttca ggcagcggta cggactttac tctgaagatt  240
aatcgggtag tggcggagga cctgggagtg tactcatgtt ggcaaggaac ccacttcccg  300
ttgacattcg gcgcagggac caagctcgaa gtgaaa                           336
```

```
SEQ ID NO: 296          moltype = AA  length = 7
FEATURE                 Location/Qualifiers
source                  1..7
                        mol_type = protein
                        organism = Mus musculus
SEQUENCE: 296
GFTFNTY                                                                    7

SEQ ID NO: 297          moltype = AA  length = 7
FEATURE                 Location/Qualifiers
source                  1..7
                        mol_type = protein
                        organism = Mus musculus
SEQUENCE: 297
GYTFTDY                                                                    7

SEQ ID NO: 298          moltype = AA  length = 7
FEATURE                 Location/Qualifiers
source                  1..7
                        mol_type = protein
                        organism = Mus musculus
SEQUENCE: 298
GYTFTKN                                                                    7

SEQ ID NO: 299          moltype = AA  length = 7
FEATURE                 Location/Qualifiers
source                  1..7
                        mol_type = protein
                        organism = Mus musculus
SEQUENCE: 299
DYTFTNY                                                                    7

SEQ ID NO: 300          moltype = AA  length = 7
FEATURE                 Location/Qualifiers
source                  1..7
                        mol_type = protein
                        organism = Mus musculus
SEQUENCE: 300
GFSLTDY                                                                    7

SEQ ID NO: 301          moltype = AA  length = 7
FEATURE                 Location/Qualifiers
source                  1..7
                        mol_type = protein
                        organism = Mus musculus
SEQUENCE: 301
GFSLTSY                                                                    7

SEQ ID NO: 302          moltype = AA  length = 7
FEATURE                 Location/Qualifiers
source                  1..7
                        mol_type = protein
                        organism = Mus musculus
SEQUENCE: 302
GFTFSSY                                                                    7

SEQ ID NO: 303          moltype = AA  length = 7
FEATURE                 Location/Qualifiers
source                  1..7
                        mol_type = protein
                        organism = Mus musculus
SEQUENCE: 303
GFSLTTY                                                                    7

SEQ ID NO: 304          moltype = AA  length = 7
FEATURE                 Location/Qualifiers
source                  1..7
                        mol_type = protein
                        organism = Mus musculus
SEQUENCE: 304
GFTFTDY                                                                    7

SEQ ID NO: 305          moltype = AA  length = 7
FEATURE                 Location/Qualifiers
source                  1..7
                        mol_type = protein
                        organism = Mus musculus
SEQUENCE: 305
```

```
GYSFTTY                                                                     7

SEQ ID NO: 306          moltype = AA  length = 7
FEATURE                 Location/Qualifiers
source                  1..7
                        mol_type = protein
                        organism = Mus musculus
SEQUENCE: 306
GFTFSDY                                                                     7

SEQ ID NO: 307          moltype = AA  length = 7
FEATURE                 Location/Qualifiers
source                  1..7
                        mol_type = protein
                        organism = Mus musculus
SEQUENCE: 307
GITFSHY                                                                     7

SEQ ID NO: 308          moltype = AA  length = 7
FEATURE                 Location/Qualifiers
source                  1..7
                        mol_type = protein
                        organism = Mus musculus
SEQUENCE: 308
GYTFTSY                                                                     7

SEQ ID NO: 309          moltype = AA  length = 7
FEATURE                 Location/Qualifiers
source                  1..7
                        mol_type = protein
                        organism = Mus musculus
SEQUENCE: 309
GYTFSDY                                                                     7

SEQ ID NO: 310          moltype = AA  length = 7
FEATURE                 Location/Qualifiers
source                  1..7
                        mol_type = protein
                        organism = Mus musculus
SEQUENCE: 310
GFNIKDY                                                                     7

SEQ ID NO: 311          moltype = AA  length = 7
FEATURE                 Location/Qualifiers
source                  1..7
                        mol_type = protein
                        organism = Mus musculus
SEQUENCE: 311
GYTFTRS                                                                     7

SEQ ID NO: 312          moltype = AA  length = 7
FEATURE                 Location/Qualifiers
source                  1..7
                        mol_type = protein
                        organism = Mus musculus
SEQUENCE: 312
GYTFTSS                                                                     7

SEQ ID NO: 313          moltype = AA  length = 7
FEATURE                 Location/Qualifiers
source                  1..7
                        mol_type = protein
                        organism = Mus musculus
SEQUENCE: 313
GYTFTSN                                                                     7

SEQ ID NO: 314          moltype = AA  length = 7
FEATURE                 Location/Qualifiers
source                  1..7
                        mol_type = protein
                        organism = Mus musculus
SEQUENCE: 314
GFTFTRY                                                                     7

SEQ ID NO: 315          moltype = AA  length = 7
FEATURE                 Location/Qualifiers
source                  1..7
                        mol_type = protein
                        organism = Mus musculus
```

```
SEQUENCE: 315
GYTFTIF                                                         7

SEQ ID NO: 316          moltype = AA  length = 7
FEATURE                 Location/Qualifiers
source                  1..7
                        mol_type = protein
                        organism = Mus musculus
SEQUENCE: 316
GYTFTRF                                                         7

SEQ ID NO: 317          moltype = AA  length = 7
FEATURE                 Location/Qualifiers
source                  1..7
                        mol_type = protein
                        organism = Mus musculus
SEQUENCE: 317
GFTFTRF                                                         7

SEQ ID NO: 318          moltype = AA  length = 7
FEATURE                 Location/Qualifiers
source                  1..7
                        mol_type = protein
                        organism = Mus musculus
SEQUENCE: 318
GYSFTDY                                                         7

SEQ ID NO: 319          moltype = AA  length = 7
FEATURE                 Location/Qualifiers
source                  1..7
                        mol_type = protein
                        organism = Mus musculus
SEQUENCE: 319
GYTFTEY                                                         7

SEQ ID NO: 320          moltype = AA  length = 7
FEATURE                 Location/Qualifiers
source                  1..7
                        mol_type = protein
                        organism = Mus musculus
SEQUENCE: 320
GYAFSSS                                                         7

SEQ ID NO: 321          moltype = AA  length = 9
FEATURE                 Location/Qualifiers
source                  1..9
                        mol_type = protein
                        organism = Mus musculus
SEQUENCE: 321
GFSLSTSGM                                                       9

SEQ ID NO: 322          moltype = AA  length = 8
FEATURE                 Location/Qualifiers
source                  1..8
                        mol_type = protein
                        organism = Mus musculus
SEQUENCE: 322
GYSITTNY                                                        8

SEQ ID NO: 323          moltype = AA  length = 9
FEATURE                 Location/Qualifiers
source                  1..9
                        mol_type = protein
                        organism = Mus musculus
SEQUENCE: 323
GYSITTNYF                                                       9

SEQ ID NO: 324          moltype = AA  length = 9
FEATURE                 Location/Qualifiers
source                  1..9
                        mol_type = protein
                        organism = Mus musculus
SEQUENCE: 324
GFSLSTSTM                                                       9

SEQ ID NO: 325          moltype = AA  length = 9
FEATURE                 Location/Qualifiers
source                  1..9
                        mol_type = protein
```

```
                        organism = Mus musculus
SEQUENCE: 325
GFSLSTSAM                                                9

SEQ ID NO: 326          moltype = AA  length = 9
FEATURE                 Location/Qualifiers
source                  1..9
                        mol_type = protein
                        organism = Mus musculus
SEQUENCE: 326
GFSLNTSGM                                                9

SEQ ID NO: 327          moltype = AA  length = 9
FEATURE                 Location/Qualifiers
source                  1..9
                        mol_type = protein
                        organism = Mus musculus
SEQUENCE: 327
GFSLSTFGM                                                9

SEQ ID NO: 328          moltype = AA  length = 7
FEATURE                 Location/Qualifiers
source                  1..7
                        mol_type = protein
                        organism = Mus musculus
SEQUENCE: 328
VYTFTTY                                                  7

SEQ ID NO: 329          moltype = AA  length = 7
FEATURE                 Location/Qualifiers
source                  1..7
                        mol_type = protein
                        organism = Mus musculus
SEQUENCE: 329
GYTFTTY                                                  7

SEQ ID NO: 330          moltype = AA  length = 8
FEATURE                 Location/Qualifiers
source                  1..8
                        mol_type = protein
                        organism = Mus musculus
SEQUENCE: 330
GYTFTSYW                                                 8

SEQ ID NO: 331          moltype = AA  length = 8
FEATURE                 Location/Qualifiers
source                  1..8
                        mol_type = protein
                        organism = Mus musculus
SEQUENCE: 331
GFTFSDYG                                                 8

SEQ ID NO: 332          moltype = AA  length = 8
FEATURE                 Location/Qualifiers
source                  1..8
                        mol_type = protein
                        organism = Mus musculus
SEQUENCE: 332
GYTFTDYE                                                 8

SEQ ID NO: 333          moltype = AA  length = 8
FEATURE                 Location/Qualifiers
source                  1..8
                        mol_type = protein
                        organism = Mus musculus
SEQUENCE: 333
GYTFTSYG                                                 8

SEQ ID NO: 334          moltype = AA  length = 5
FEATURE                 Location/Qualifiers
source                  1..5
                        mol_type = protein
                        organism = Mus musculus
SEQUENCE: 334
SYAMS                                                    5

SEQ ID NO: 335          moltype = AA  length = 5
FEATURE                 Location/Qualifiers
source                  1..5
```

```
                        mol_type = protein
                        organism = Mus musculus
SEQUENCE: 335
NHGLS                                                                    5

SEQ ID NO: 336          moltype = AA  length = 7
FEATURE                 Location/Qualifiers
source                  1..7
                        mol_type = protein
                        organism = Mus musculus
SEQUENCE: 336
TSGMGVS                                                                  7

SEQ ID NO: 337          moltype = AA  length = 7
FEATURE                 Location/Qualifiers
source                  1..7
                        mol_type = protein
                        organism = Mus musculus
SEQUENCE: 337
GFIFSSF                                                                  7

SEQ ID NO: 338          moltype = AA  length = 7
FEATURE                 Location/Qualifiers
source                  1..7
                        mol_type = protein
                        organism = Mus musculus
SEQUENCE: 338
GFTFSNF                                                                  7

SEQ ID NO: 339          moltype = AA  length = 7
FEATURE                 Location/Qualifiers
source                  1..7
                        mol_type = protein
                        organism = Mus musculus
SEQUENCE: 339
GYIFSSY                                                                  7

SEQ ID NO: 340          moltype = AA  length = 8
FEATURE                 Location/Qualifiers
source                  1..8
                        mol_type = protein
                        organism = Mus musculus
SEQUENCE: 340
RSKSSNYA                                                                 8

SEQ ID NO: 341          moltype = AA  length = 6
FEATURE                 Location/Qualifiers
source                  1..6
                        mol_type = protein
                        organism = Mus musculus
SEQUENCE: 341
NPNNGG                                                                   6

SEQ ID NO: 342          moltype = AA  length = 6
FEATURE                 Location/Qualifiers
source                  1..6
                        mol_type = protein
                        organism = Mus musculus
SEQUENCE: 342
NPSNGA                                                                   6

SEQ ID NO: 343          moltype = AA  length = 6
FEATURE                 Location/Qualifiers
source                  1..6
                        mol_type = protein
                        organism = Mus musculus
SEQUENCE: 343
DPNSGG                                                                   6

SEQ ID NO: 344          moltype = AA  length = 5
FEATURE                 Location/Qualifiers
source                  1..5
                        mol_type = protein
                        organism = Mus musculus
SEQUENCE: 344
WGGGS                                                                    5

SEQ ID NO: 345          moltype = AA  length = 5
FEATURE                 Location/Qualifiers
```

```
source                1..5
                      mol_type = protein
                      organism = Mus musculus
SEQUENCE: 345
WTGGG                                                                       5

SEQ ID NO: 346        moltype = AA  length = 6
FEATURE               Location/Qualifiers
source                1..6
                      mol_type = protein
                      organism = Mus musculus
SEQUENCE: 346
SSGGDY                                                                      6

SEQ ID NO: 347        moltype = AA  length = 8
FEATURE               Location/Qualifiers
source                1..8
                      mol_type = protein
                      organism = Mus musculus
SEQUENCE: 347
RNKAKGFT                                                                    8

SEQ ID NO: 348        moltype = AA  length = 6
FEATURE               Location/Qualifiers
source                1..6
                      mol_type = protein
                      organism = Mus musculus
SEQUENCE: 348
NTYSGV                                                                      6

SEQ ID NO: 349        moltype = AA  length = 6
FEATURE               Location/Qualifiers
source                1..6
                      mol_type = protein
                      organism = Mus musculus
SEQUENCE: 349
SSGSTT                                                                      6

SEQ ID NO: 350        moltype = AA  length = 8
FEATURE               Location/Qualifiers
source                1..8
                      mol_type = protein
                      organism = Mus musculus
SEQUENCE: 350
KLKSDNYA                                                                    8

SEQ ID NO: 351        moltype = AA  length = 6
FEATURE               Location/Qualifiers
source                1..6
                      mol_type = protein
                      organism = Mus musculus
SEQUENCE: 351
YPGNGD                                                                      6

SEQ ID NO: 352        moltype = AA  length = 6
FEATURE               Location/Qualifiers
source                1..6
                      mol_type = protein
                      organism = Mus musculus
SEQUENCE: 352
DPEDGE                                                                      6

SEQ ID NO: 353        moltype = AA  length = 6
FEATURE               Location/Qualifiers
source                1..6
                      mol_type = protein
                      organism = Mus musculus
SEQUENCE: 353
DPEDDE                                                                      6

SEQ ID NO: 354        moltype = AA  length = 6
FEATURE               Location/Qualifiers
source                1..6
                      mol_type = protein
                      organism = Mus musculus
SEQUENCE: 354
DPSDSE                                                                      6

SEQ ID NO: 355        moltype = AA  length = 6
```

```
FEATURE                 Location/Qualifiers
source                  1..6
                        mol_type = protein
                        organism = Mus musculus
SEQUENCE: 355
DPSDGE                                                                      6

SEQ ID NO: 356          moltype = AA  length = 6
FEATURE                 Location/Qualifiers
source                  1..6
                        mol_type = protein
                        organism = Mus musculus
SEQUENCE: 356
NPNNSD                                                                      6

SEQ ID NO: 357          moltype = AA  length = 6
FEATURE                 Location/Qualifiers
source                  1..6
                        mol_type = protein
                        organism = Mus musculus
SEQUENCE: 357
NPNNSE                                                                      6

SEQ ID NO: 358          moltype = AA  length = 6
FEATURE                 Location/Qualifiers
source                  1..6
                        mol_type = protein
                        organism = Mus musculus
SEQUENCE: 358
NPNNGE                                                                      6

SEQ ID NO: 359          moltype = AA  length = 6
FEATURE                 Location/Qualifiers
source                  1..6
                        mol_type = protein
                        organism = Mus musculus
SEQUENCE: 359
FPGSDS                                                                      6

SEQ ID NO: 360          moltype = AA  length = 6
FEATURE                 Location/Qualifiers
source                  1..6
                        mol_type = protein
                        organism = Mus musculus
SEQUENCE: 360
FPGRGS                                                                      6

SEQ ID NO: 361          moltype = AA  length = 6
FEATURE                 Location/Qualifiers
source                  1..6
                        mol_type = protein
                        organism = Mus musculus
SEQUENCE: 361
YPGDGD                                                                      6

SEQ ID NO: 362          moltype = AA  length = 5
FEATURE                 Location/Qualifiers
source                  1..5
                        mol_type = protein
                        organism = Mus musculus
SEQUENCE: 362
YWDDD                                                                       5

SEQ ID NO: 363          moltype = AA  length = 6
FEATURE                 Location/Qualifiers
source                  1..6
                        mol_type = protein
                        organism = Mus musculus
SEQUENCE: 363
YPSNGG                                                                      6

SEQ ID NO: 364          moltype = AA  length = 6
FEATURE                 Location/Qualifiers
source                  1..6
                        mol_type = protein
                        organism = Mus musculus
SEQUENCE: 364
YPGSGN                                                                      6
```

```
SEQ ID NO: 365          moltype = AA  length = 6
FEATURE                 Location/Qualifiers
source                  1..6
                        mol_type = protein
                        organism = Mus musculus
SEQUENCE: 365
YIGNGH                                                                    6

SEQ ID NO: 366          moltype = AA  length = 6
FEATURE                 Location/Qualifiers
source                  1..6
                        mol_type = protein
                        organism = Mus musculus
SEQUENCE: 366
YIRDGN                                                                    6

SEQ ID NO: 367          moltype = AA  length = 6
FEATURE                 Location/Qualifiers
source                  1..6
                        mol_type = protein
                        organism = Mus musculus
SEQUENCE: 367
YIRNGN                                                                    6

SEQ ID NO: 368          moltype = AA  length = 6
FEATURE                 Location/Qualifiers
source                  1..6
                        mol_type = protein
                        organism = Mus musculus
SEQUENCE: 368
YPRSGK                                                                    6

SEQ ID NO: 369          moltype = AA  length = 6
FEATURE                 Location/Qualifiers
source                  1..6
                        mol_type = protein
                        organism = Mus musculus
SEQUENCE: 369
YPGNGN                                                                    6

SEQ ID NO: 370          moltype = AA  length = 6
FEATURE                 Location/Qualifiers
source                  1..6
                        mol_type = protein
                        organism = Mus musculus
SEQUENCE: 370
YPGDRN                                                                    6

SEQ ID NO: 371          moltype = AA  length = 5
FEATURE                 Location/Qualifiers
source                  1..5
                        mol_type = protein
                        organism = Mus musculus
SEQUENCE: 371
WSGGS                                                                     5

SEQ ID NO: 372          moltype = AA  length = 5
FEATURE                 Location/Qualifiers
source                  1..5
                        mol_type = protein
                        organism = Mus musculus
SEQUENCE: 372
TYDGI                                                                     5

SEQ ID NO: 373          moltype = AA  length = 7
FEATURE                 Location/Qualifiers
source                  1..7
                        mol_type = protein
                        organism = Mus musculus
SEQUENCE: 373
ISYDGSN                                                                   7

SEQ ID NO: 374          moltype = AA  length = 5
FEATURE                 Location/Qualifiers
source                  1..5
                        mol_type = protein
                        organism = Mus musculus
SEQUENCE: 374
TYDGS                                                                     5
```

```
SEQ ID NO: 375          moltype = AA  length = 5
FEATURE                 Location/Qualifiers
source                  1..5
                        mol_type = protein
                        organism = Mus musculus
SEQUENCE: 375
SYDGS                                                                5

SEQ ID NO: 376          moltype = AA  length = 6
FEATURE                 Location/Qualifiers
source                  1..6
                        mol_type = protein
                        organism = Mus musculus
SEQUENCE: 376
SSGSIT                                                               6

SEQ ID NO: 377          moltype = AA  length = 6
FEATURE                 Location/Qualifiers
source                  1..6
                        mol_type = protein
                        organism = Mus musculus
SEQUENCE: 377
SSGSRT                                                               6

SEQ ID NO: 378          moltype = AA  length = 5
FEATURE                 Location/Qualifiers
source                  1..5
                        mol_type = protein
                        organism = Mus musculus
SEQUENCE: 378
YWDDE                                                                5

SEQ ID NO: 379          moltype = AA  length = 8
FEATURE                 Location/Qualifiers
source                  1..8
                        mol_type = protein
                        organism = Mus musculus
SEQUENCE: 379
IFPGSGST                                                             8

SEQ ID NO: 380          moltype = AA  length = 8
FEATURE                 Location/Qualifiers
source                  1..8
                        mol_type = protein
                        organism = Mus musculus
SEQUENCE: 380
ISSGSSNI                                                             8

SEQ ID NO: 381          moltype = AA  length = 8
FEATURE                 Location/Qualifiers
source                  1..8
                        mol_type = protein
                        organism = Mus musculus
SEQUENCE: 381
IDPDTGGT                                                             8

SEQ ID NO: 382          moltype = AA  length = 8
FEATURE                 Location/Qualifiers
source                  1..8
                        mol_type = protein
                        organism = Mus musculus
SEQUENCE: 382
IHPNSGFT                                                             8

SEQ ID NO: 383          moltype = AA  length = 8
FEATURE                 Location/Qualifiers
source                  1..8
                        mol_type = protein
                        organism = Mus musculus
SEQUENCE: 383
IYPRSGNT                                                             8

SEQ ID NO: 384          moltype = AA  length = 17
FEATURE                 Location/Qualifiers
source                  1..17
                        mol_type = protein
                        organism = Mus musculus
SEQUENCE: 384
```

```
AINSNGGRTY YPDTVKD                                                  17

SEQ ID NO: 385           moltype = AA  length = 17
FEATURE                  Location/Qualifiers
source                   1..17
                         mol_type = protein
                         organism = Mus musculus
SEQUENCE: 385
EIYPRSGNTY YNENCKG                                                  17

SEQ ID NO: 386           moltype = AA  length = 17
FEATURE                  Location/Qualifiers
source                   1..17
                         mol_type = protein
                         organism = Mus musculus
SEQUENCE: 386
AINSNGGSTY YPDTVKD                                                  17

SEQ ID NO: 387           moltype = AA  length = 17
FEATURE                  Location/Qualifiers
source                   1..17
                         mol_type = protein
                         organism = Mus musculus
SEQUENCE: 387
AINSNGGSIY YPDTVKD                                                  17

SEQ ID NO: 388           moltype = AA  length = 16
FEATURE                  Location/Qualifiers
source                   1..16
                         mol_type = protein
                         organism = Mus musculus
SEQUENCE: 388
HIYWDDDKRY NPSLKS                                                   16

SEQ ID NO: 389           moltype = AA  length = 6
FEATURE                  Location/Qualifiers
source                   1..6
                         mol_type = protein
                         organism = Mus musculus
SEQUENCE: 389
SSGSAT                                                              6

SEQ ID NO: 390           moltype = AA  length = 6
FEATURE                  Location/Qualifiers
source                   1..6
                         mol_type = protein
                         organism = Mus musculus
SEQUENCE: 390
SSDIST                                                              6

SEQ ID NO: 391           moltype = AA  length = 6
FEATURE                  Location/Qualifiers
source                   1..6
                         mol_type = protein
                         organism = Mus musculus
SEQUENCE: 391
SNGGTF                                                              6

SEQ ID NO: 392           moltype = AA  length = 9
FEATURE                  Location/Qualifiers
source                   1..9
                         mol_type = protein
                         organism = Mus musculus
SEQUENCE: 392
EGLWYYFDY                                                           9

SEQ ID NO: 393           moltype = AA  length = 12
FEATURE                  Location/Qualifiers
source                   1..12
                         mol_type = protein
                         organism = Mus musculus
SEQUENCE: 393
GSSYYDFSWF AY                                                       12

SEQ ID NO: 394           moltype = AA  length = 13
FEATURE                  Location/Qualifiers
source                   1..13
                         mol_type = protein
                         organism = Mus musculus
```

```
SEQUENCE: 394
SGGWLLPYYA MDY                                                    13

SEQ ID NO: 395          moltype = AA  length = 4
FEATURE                 Location/Qualifiers
source                  1..4
                        mol_type = protein
                        organism = Mus musculus
SEQUENCE: 395
DFDV                                                              4

SEQ ID NO: 396          moltype = AA  length = 12
FEATURE                 Location/Qualifiers
source                  1..12
                        mol_type = protein
                        organism = Mus musculus
SEQUENCE: 396
HGTYYGNYGI AY                                                     12

SEQ ID NO: 397          moltype = AA  length = 12
FEATURE                 Location/Qualifiers
source                  1..12
                        mol_type = protein
                        organism = Mus musculus
SEQUENCE: 397
NYDYYRYEGF DY                                                     12

SEQ ID NO: 398          moltype = AA  length = 11
FEATURE                 Location/Qualifiers
source                  1..11
                        mol_type = protein
                        organism = Mus musculus
SEQUENCE: 398
EDGYYVGTMD Y                                                      11

SEQ ID NO: 399          moltype = AA  length = 18
FEATURE                 Location/Qualifiers
source                  1..18
                        mol_type = protein
                        organism = Mus musculus
SEQUENCE: 399
KGGSYYSTTY VGLYAMDY                                               18

SEQ ID NO: 400          moltype = AA  length = 4
FEATURE                 Location/Qualifiers
source                  1..4
                        mol_type = protein
                        organism = Mus musculus
SEQUENCE: 400
DINY                                                              4

SEQ ID NO: 401          moltype = AA  length = 11
FEATURE                 Location/Qualifiers
source                  1..11
                        mol_type = protein
                        organism = Mus musculus
SEQUENCE: 401
RGGLYDGYYG Y                                                      11

SEQ ID NO: 402          moltype = AA  length = 6
FEATURE                 Location/Qualifiers
source                  1..6
                        mol_type = protein
                        organism = Mus musculus
SEQUENCE: 402
HWYFDV                                                            6

SEQ ID NO: 403          moltype =   length =
SEQUENCE: 403
000

SEQ ID NO: 404          moltype = AA  length = 5
FEATURE                 Location/Qualifiers
source                  1..5
                        mol_type = protein
                        organism = Mus musculus
SEQUENCE: 404
GGMDY                                                             5
```

```
SEQ ID NO: 405          moltype = AA  length = 5
FEATURE                 Location/Qualifiers
source                  1..5
                        mol_type = protein
                        organism = Mus musculus
SEQUENCE: 405
WSVSY                                                                5

SEQ ID NO: 406          moltype = AA  length = 8
FEATURE                 Location/Qualifiers
source                  1..8
                        mol_type = protein
                        organism = Mus musculus
SEQUENCE: 406
EFSYAMDY                                                             8

SEQ ID NO: 407          moltype = AA  length = 8
FEATURE                 Location/Qualifiers
source                  1..8
                        mol_type = protein
                        organism = Mus musculus
SEQUENCE: 407
WDDFYVAY                                                             8

SEQ ID NO: 408          moltype = AA  length = 8
FEATURE                 Location/Qualifiers
source                  1..8
                        mol_type = protein
                        organism = Mus musculus
SEQUENCE: 408
WDDYYVAY                                                             8

SEQ ID NO: 409          moltype = AA  length = 11
FEATURE                 Location/Qualifiers
source                  1..11
                        mol_type = protein
                        organism = Mus musculus
SEQUENCE: 409
ANYYGGSQFA Y                                                         11

SEQ ID NO: 410          moltype = AA  length = 9
FEATURE                 Location/Qualifiers
source                  1..9
                        mol_type = protein
                        organism = Mus musculus
SEQUENCE: 410
GTGTGAMDY                                                            9

SEQ ID NO: 411          moltype = AA  length = 12
FEATURE                 Location/Qualifiers
source                  1..12
                        mol_type = protein
                        organism = Mus musculus
SEQUENCE: 411
PTVVARDYAM DY                                                        12

SEQ ID NO: 412          moltype = AA  length = 12
FEATURE                 Location/Qualifiers
source                  1..12
                        mol_type = protein
                        organism = Mus musculus
SEQUENCE: 412
PTIVARDYAM DY                                                        12

SEQ ID NO: 413          moltype = AA  length = 13
FEATURE                 Location/Qualifiers
source                  1..13
                        mol_type = protein
                        organism = Mus musculus
SEQUENCE: 413
IGGRAGSGYA MDY                                                       13

SEQ ID NO: 414          moltype = AA  length = 11
FEATURE                 Location/Qualifiers
source                  1..11
                        mol_type = protein
                        organism = Mus musculus
SEQUENCE: 414
REIGKRDFFA Y                                                         11
```

```
SEQ ID NO: 415          moltype = AA  length = 12
FEATURE                 Location/Qualifiers
source                  1..12
                        mol_type = protein
                        organism = Mus musculus
SEQUENCE: 415
SSVVARDYAM DY                                                         12

SEQ ID NO: 416          moltype = AA  length = 12
FEATURE                 Location/Qualifiers
source                  1..12
                        mol_type = protein
                        organism = Mus musculus
SEQUENCE: 416
SSVVGRDYAM DY                                                         12

SEQ ID NO: 417          moltype = AA  length = 12
FEATURE                 Location/Qualifiers
source                  1..12
                        mol_type = protein
                        organism = Mus musculus
SEQUENCE: 417
PAYYSKDYAM EY                                                         12

SEQ ID NO: 418          moltype = AA  length = 7
FEATURE                 Location/Qualifiers
source                  1..7
                        mol_type = protein
                        organism = Mus musculus
SEQUENCE: 418
TGTLFDY                                                               7

SEQ ID NO: 419          moltype = AA  length = 7
FEATURE                 Location/Qualifiers
source                  1..7
                        mol_type = protein
                        organism = Mus musculus
SEQUENCE: 419
TGTSFAY                                                               7

SEQ ID NO: 420          moltype = AA  length = 7
FEATURE                 Location/Qualifiers
source                  1..7
                        mol_type = protein
                        organism = Mus musculus
SEQUENCE: 420
TGTSFTY                                                               7

SEQ ID NO: 421          moltype = AA  length = 9
FEATURE                 Location/Qualifiers
source                  1..9
                        mol_type = protein
                        organism = Mus musculus
SEQUENCE: 421
RSRRGNYDY                                                             9

SEQ ID NO: 422          moltype = AA  length = 5
FEATURE                 Location/Qualifiers
source                  1..5
                        mol_type = protein
                        organism = Mus musculus
SEQUENCE: 422
GGGGY                                                                 5

SEQ ID NO: 423          moltype = AA  length = 10
FEATURE                 Location/Qualifiers
source                  1..10
                        mol_type = protein
                        organism = Mus musculus
SEQUENCE: 423
GIRRSWYFDV                                                            10

SEQ ID NO: 424          moltype = AA  length = 15
FEATURE                 Location/Qualifiers
source                  1..15
                        mol_type = protein
                        organism = Mus musculus
SEQUENCE: 424
```

```
NSGGYYVDDY YAMDY                                                    15

SEQ ID NO: 425          moltype = AA  length = 6
FEATURE                 Location/Qualifiers
source                  1..6
                        mol_type = protein
                        organism = Mus musculus
SEQUENCE: 425
GPGLDY                                                              6

SEQ ID NO: 426          moltype = AA  length = 8
FEATURE                 Location/Qualifiers
source                  1..8
                        mol_type = protein
                        organism = Mus musculus
SEQUENCE: 426
ARGPPSAY                                                            8

SEQ ID NO: 427          moltype = AA  length = 6
FEATURE                 Location/Qualifiers
source                  1..6
                        mol_type = protein
                        organism = Mus musculus
SEQUENCE: 427
GPPTAY                                                              6

SEQ ID NO: 428          moltype = AA  length = 5
FEATURE                 Location/Qualifiers
source                  1..5
                        mol_type = protein
                        organism = Mus musculus
SEQUENCE: 428
DLLGY                                                               5

SEQ ID NO: 429          moltype = AA  length = 7
FEATURE                 Location/Qualifiers
source                  1..7
                        mol_type = protein
                        organism = Mus musculus
SEQUENCE: 429
SPYAMDS                                                             7

SEQ ID NO: 430          moltype = AA  length = 7
FEATURE                 Location/Qualifiers
source                  1..7
                        mol_type = protein
                        organism = Mus musculus
SEQUENCE: 430
SPYAMDY                                                             7

SEQ ID NO: 431          moltype = AA  length = 12
FEATURE                 Location/Qualifiers
source                  1..12
                        mol_type = protein
                        organism = Mus musculus
SEQUENCE: 431
RGYYSDGNYF DS                                                       12

SEQ ID NO: 432          moltype = AA  length = 12
FEATURE                 Location/Qualifiers
source                  1..12
                        mol_type = protein
                        organism = Mus musculus
SEQUENCE: 432
RGYYSNGNYF DY                                                       12

SEQ ID NO: 433          moltype = AA  length = 11
FEATURE                 Location/Qualifiers
source                  1..11
                        mol_type = protein
                        organism = Mus musculus
SEQUENCE: 433
GRGMGYYALD Y                                                        11

SEQ ID NO: 434          moltype = AA  length = 9
FEATURE                 Location/Qualifiers
source                  1..9
                        mol_type = protein
                        organism = Mus musculus
```

```
SEQUENCE: 434
RARGYGMDY                                                     9

SEQ ID NO: 435          moltype = AA  length = 9
FEATURE                 Location/Qualifiers
source                  1..9
                        mol_type = protein
                        organism = Mus musculus
SEQUENCE: 435
RRRGYGMDY                                                     9

SEQ ID NO: 436          moltype = AA  length = 9
FEATURE                 Location/Qualifiers
source                  1..9
                        mol_type = protein
                        organism = Mus musculus
SEQUENCE: 436
RARFYAMDY                                                     9

SEQ ID NO: 437          moltype = AA  length = 9
FEATURE                 Location/Qualifiers
source                  1..9
                        mol_type = protein
                        organism = Mus musculus
SEQUENCE: 437
RVRGYGMDY                                                     9

SEQ ID NO: 438          moltype = AA  length = 9
FEATURE                 Location/Qualifiers
source                  1..9
                        mol_type = protein
                        organism = Mus musculus
SEQUENCE: 438
RVRYYAMDY                                                     9

SEQ ID NO: 439          moltype = AA  length = 9
FEATURE                 Location/Qualifiers
source                  1..9
                        mol_type = protein
                        organism = Mus musculus
SEQUENCE: 439
RVRSYAMDY                                                     9

SEQ ID NO: 440          moltype = AA  length = 9
FEATURE                 Location/Qualifiers
source                  1..9
                        mol_type = protein
                        organism = Mus musculus
SEQUENCE: 440
RKRSYGMDY                                                     9

SEQ ID NO: 441          moltype = AA  length = 11
FEATURE                 Location/Qualifiers
source                  1..11
                        mol_type = protein
                        organism = Mus musculus
SEQUENCE: 441
LGLRRGSYFD Y                                                  11

SEQ ID NO: 442          moltype = AA  length = 13
FEATURE                 Location/Qualifiers
source                  1..13
                        mol_type = protein
                        organism = Mus musculus
SEQUENCE: 442
ARGGKGVIGY FDY                                                13

SEQ ID NO: 443          moltype = AA  length = 8
FEATURE                 Location/Qualifiers
source                  1..8
                        mol_type = protein
                        organism = Mus musculus
SEQUENCE: 443
TRSWYFDV                                                      8

SEQ ID NO: 444          moltype = AA  length = 6
FEATURE                 Location/Qualifiers
source                  1..6
                        mol_type = protein
```

```
                        organism = Mus musculus
SEQUENCE: 444
SLRLYD                                                          6

SEQ ID NO: 445          moltype = AA  length = 14
FEATURE                 Location/Qualifiers
source                  1..14
                        mol_type = protein
                        organism = Mus musculus
SEQUENCE: 445
AKSAVVERDY AMDY                                                 14

SEQ ID NO: 446          moltype = AA  length = 15
FEATURE                 Location/Qualifiers
source                  1..15
                        mol_type = protein
                        organism = Mus musculus
SEQUENCE: 446
ARVYYYGSNY DGFAY                                                15

SEQ ID NO: 447          moltype = AA  length = 13
FEATURE                 Location/Qualifiers
source                  1..13
                        mol_type = protein
                        organism = Mus musculus
SEQUENCE: 447
QGHSNYYEAW FAY                                                  13

SEQ ID NO: 448          moltype = AA  length = 11
FEATURE                 Location/Qualifiers
source                  1..11
                        mol_type = protein
                        organism = Mus musculus
SEQUENCE: 448
RHSNNDYAMD Y                                                    11

SEQ ID NO: 449          moltype = AA  length = 9
FEATURE                 Location/Qualifiers
source                  1..9
                        mol_type = protein
                        organism = Mus musculus
SEQUENCE: 449
QGWDAWFAY                                                       9

SEQ ID NO: 450          moltype = AA  length = 9
FEATURE                 Location/Qualifiers
source                  1..9
                        mol_type = protein
                        organism = Mus musculus
SEQUENCE: 450
QGGSSWFVY                                                       9

SEQ ID NO: 451          moltype = AA  length = 13
FEATURE                 Location/Qualifiers
source                  1..13
                        mol_type = protein
                        organism = Mus musculus
SEQUENCE: 451
GWLRRKDYSA MDY                                                  13

SEQ ID NO: 452          moltype = AA  length = 13
FEATURE                 Location/Qualifiers
source                  1..13
                        mol_type = protein
                        organism = Mus musculus
SEQUENCE: 452
KRGSGNYVSA MDF                                                  13

SEQ ID NO: 453          moltype = AA  length = 13
FEATURE                 Location/Qualifiers
source                  1..13
                        mol_type = protein
                        organism = Mus musculus
SEQUENCE: 453
KRGSGDYVSA MDY                                                  13

SEQ ID NO: 454          moltype = AA  length = 13
FEATURE                 Location/Qualifiers
source                  1..13
```

```
                     mol_type = protein
                     organism = Mus musculus
SEQUENCE: 454
GGHYANKGDW FAY                                                          13

SEQ ID NO: 455       moltype = AA  length = 8
FEATURE              Location/Qualifiers
source               1..8
                     mol_type = protein
                     organism = Mus musculus
SEQUENCE: 455
GYSQSFDY                                                                8

SEQ ID NO: 456       moltype = AA  length = 8
FEATURE              Location/Qualifiers
source               1..8
                     mol_type = protein
                     organism = Mus musculus
SEQUENCE: 456
GYSNSFDY                                                                8

SEQ ID NO: 457       moltype = AA  length = 11
FEATURE              Location/Qualifiers
source               1..11
                     mol_type = protein
                     organism = Mus musculus
SEQUENCE: 457
RASQDISNYL N                                                            11

SEQ ID NO: 458       moltype = AA  length = 11
FEATURE              Location/Qualifiers
source               1..11
                     mol_type = protein
                     organism = Mus musculus
SEQUENCE: 458
SASQGISNYL N                                                            11

SEQ ID NO: 459       moltype = AA  length = 12
FEATURE              Location/Qualifiers
source               1..12
                     mol_type = protein
                     organism = Mus musculus
SEQUENCE: 459
SVSSSISSSN LH                                                           12

SEQ ID NO: 460       moltype = AA  length = 11
FEATURE              Location/Qualifiers
source               1..11
                     mol_type = protein
                     organism = Mus musculus
SEQUENCE: 460
RASGNIHNYL A                                                            11

SEQ ID NO: 461       moltype = AA  length = 12
FEATURE              Location/Qualifiers
source               1..12
                     mol_type = protein
                     organism = Mus musculus
SEQUENCE: 461
SASSSVSSSY LY                                                           12

SEQ ID NO: 462       moltype = AA  length = 11
FEATURE              Location/Qualifiers
source               1..11
                     mol_type = protein
                     organism = Mus musculus
SEQUENCE: 462
RASQDIGSSL H                                                            11

SEQ ID NO: 463       moltype = AA  length = 11
FEATURE              Location/Qualifiers
source               1..11
                     mol_type = protein
                     organism = Mus musculus
SEQUENCE: 463
RASQDIGSSL N                                                            11

SEQ ID NO: 464       moltype = AA  length = 17
FEATURE              Location/Qualifiers
```

```
source                  1..17
                        mol_type = protein
                        organism = Mus musculus
SEQUENCE: 464
KSSQSLLYST NQENYLA                                                  17

SEQ ID NO: 465          moltype = AA  length = 17
FEATURE                 Location/Qualifiers
source                  1..17
                        mol_type = protein
                        organism = Mus musculus
SEQUENCE: 465
KSSQSLLSSR TRKNYLA                                                  17

SEQ ID NO: 466          moltype = AA  length = 16
FEATURE                 Location/Qualifiers
source                  1..16
                        mol_type = protein
                        organism = Mus musculus
SEQUENCE: 466
RSSQSIVHSN GNTHLE                                                   16

SEQ ID NO: 467          moltype = AA  length = 11
FEATURE                 Location/Qualifiers
source                  1..11
                        mol_type = protein
                        organism = Mus musculus
SEQUENCE: 467
RASKSISKYL A                                                        11

SEQ ID NO: 468          moltype = AA  length = 16
FEATURE                 Location/Qualifiers
source                  1..16
                        mol_type = protein
                        organism = Mus musculus
SEQUENCE: 468
RSSQSLVHSN GNTYLH                                                   16

SEQ ID NO: 469          moltype = AA  length = 17
FEATURE                 Location/Qualifiers
source                  1..17
                        mol_type = protein
                        organism = Mus musculus
SEQUENCE: 469
KSSQSVLYSS NQKNYLA                                                  17

SEQ ID NO: 470          moltype = AA  length = 15
FEATURE                 Location/Qualifiers
source                  1..15
                        mol_type = protein
                        organism = Mus musculus
SEQUENCE: 470
RASKSVSTSG YSYIH                                                    15

SEQ ID NO: 471          moltype = AA  length = 15
FEATURE                 Location/Qualifiers
source                  1..15
                        mol_type = protein
                        organism = Mus musculus
SEQUENCE: 471
RASKSVSTSG YSYMH                                                    15

SEQ ID NO: 472          moltype = AA  length = 16
FEATURE                 Location/Qualifiers
source                  1..16
                        mol_type = protein
                        organism = Mus musculus
SEQUENCE: 472
RSSQSLVHSN GKTYLH                                                   16

SEQ ID NO: 473          moltype = AA  length = 11
FEATURE                 Location/Qualifiers
source                  1..11
                        mol_type = protein
                        organism = Mus musculus
SEQUENCE: 473
QSLVHNNGIT Y                                                        11

SEQ ID NO: 474          moltype = AA  length = 16
```

```
FEATURE                Location/Qualifiers
source                 1..16
                       mol_type = protein
                       organism = Mus musculus
SEQUENCE: 474
RSSQSLVHSN GITHLY                                                  16

SEQ ID NO: 475         moltype = AA  length = 16
FEATURE                Location/Qualifiers
source                 1..16
                       mol_type = protein
                       organism = Mus musculus
SEQUENCE: 475
RSSQSLVHSN GNTHLY                                                  16

SEQ ID NO: 476         moltype = AA  length = 16
FEATURE                Location/Qualifiers
source                 1..16
                       mol_type = protein
                       organism = Mus musculus
SEQUENCE: 476
RSSQSLVHST GNTYLY                                                  16

SEQ ID NO: 477         moltype = AA  length = 16
FEATURE                Location/Qualifiers
source                 1..16
                       mol_type = protein
                       organism = Mus musculus
SEQUENCE: 477
RSSQSIVYSN GNTYLE                                                  16

SEQ ID NO: 478         moltype = AA  length = 16
FEATURE                Location/Qualifiers
source                 1..16
                       mol_type = protein
                       organism = Mus musculus
SEQUENCE: 478
RSSQSIVHRN GNTYLE                                                  16

SEQ ID NO: 479         moltype = AA  length = 16
FEATURE                Location/Qualifiers
source                 1..16
                       mol_type = protein
                       organism = Mus musculus
SEQUENCE: 479
RSSQSIVHSN GNTYLE                                                  16

SEQ ID NO: 480         moltype = AA  length = 16
FEATURE                Location/Qualifiers
source                 1..16
                       mol_type = protein
                       organism = Mus musculus
SEQUENCE: 480
RSSQNIVHSN GNTYLE                                                  16

SEQ ID NO: 481         moltype = AA  length = 16
FEATURE                Location/Qualifiers
source                 1..16
                       mol_type = protein
                       organism = Mus musculus
SEQUENCE: 481
RSSQSIVYTN GNTYLE                                                  16

SEQ ID NO: 482         moltype = AA  length = 16
FEATURE                Location/Qualifiers
source                 1..16
                       mol_type = protein
                       organism = Mus musculus
SEQUENCE: 482
KSSQSLLHSD GKTYLN                                                  16

SEQ ID NO: 483         moltype = AA  length = 16
FEATURE                Location/Qualifiers
source                 1..16
                       mol_type = protein
                       organism = Mus musculus
SEQUENCE: 483
KSSQSLLHSD GKTFLN                                                  16
```

```
SEQ ID NO: 484          moltype = AA  length = 16
FEATURE                 Location/Qualifiers
source                  1..16
                        mol_type = protein
                        organism = Mus musculus
SEQUENCE: 484
KSSQSLLDSD GKTYLN                                                    16

SEQ ID NO: 485          moltype = AA  length = 11
FEATURE                 Location/Qualifiers
source                  1..11
                        mol_type = protein
                        organism = Mus musculus
SEQUENCE: 485
RTSKSINKYL A                                                         11

SEQ ID NO: 486          moltype = AA  length = 11
FEATURE                 Location/Qualifiers
source                  1..11
                        mol_type = protein
                        organism = Mus musculus
SEQUENCE: 486
RASKNISKYL A                                                         11

SEQ ID NO: 487          moltype = AA  length = 11
FEATURE                 Location/Qualifiers
source                  1..11
                        mol_type = protein
                        organism = Mus musculus
SEQUENCE: 487
RASENIYSYL A                                                         11

SEQ ID NO: 488          moltype = AA  length = 11
FEATURE                 Location/Qualifiers
source                  1..11
                        mol_type = protein
                        organism = Mus musculus
SEQUENCE: 488
KASQSVGNNV A                                                         11

SEQ ID NO: 489          moltype = AA  length = 11
FEATURE                 Location/Qualifiers
source                  1..11
                        mol_type = protein
                        organism = Mus musculus
SEQUENCE: 489
KASQSVGNNV G                                                         11

SEQ ID NO: 490          moltype = AA  length = 11
FEATURE                 Location/Qualifiers
source                  1..11
                        mol_type = protein
                        organism = Mus musculus
SEQUENCE: 490
KASQSLGNNV A                                                         11

SEQ ID NO: 491          moltype = AA  length = 16
FEATURE                 Location/Qualifiers
source                  1..16
                        mol_type = protein
                        organism = Mus musculus
SEQUENCE: 491
RSSQSLVHSY RNTYLH                                                    16

SEQ ID NO: 492          moltype = AA  length = 12
FEATURE                 Location/Qualifiers
source                  1..12
                        mol_type = protein
                        organism = Mus musculus
SEQUENCE: 492
SASSTISSHY LH                                                        12

SEQ ID NO: 493          moltype = AA  length = 12
FEATURE                 Location/Qualifiers
source                  1..12
                        mol_type = protein
                        organism = Mus musculus
SEQUENCE: 493
SASSSISSTY LH                                                        12
```

```
SEQ ID NO: 494          moltype = AA  length = 11
FEATURE                 Location/Qualifiers
source                  1..11
                        mol_type = protein
                        organism = Mus musculus
SEQUENCE: 494
GASENVYGAL N                                                          11

SEQ ID NO: 495          moltype = AA  length = 11
FEATURE                 Location/Qualifiers
source                  1..11
                        mol_type = protein
                        organism = Mus musculus
SEQUENCE: 495
KASQSVSNDV A                                                          11

SEQ ID NO: 496          moltype = AA  length = 17
FEATURE                 Location/Qualifiers
source                  1..17
                        mol_type = protein
                        organism = Mus musculus
SEQUENCE: 496
KSSQSLLNSG NQKNYLA                                                    17

SEQ ID NO: 497          moltype = AA  length = 17
FEATURE                 Location/Qualifiers
source                  1..17
                        mol_type = protein
                        organism = Mus musculus
SEQUENCE: 497
KSSQSLLSSG NQKNYLA                                                    17

SEQ ID NO: 498          moltype = AA  length = 15
FEATURE                 Location/Qualifiers
source                  1..15
                        mol_type = protein
                        organism = Mus musculus
SEQUENCE: 498
RASHSVSSSC YSYMH                                                      15

SEQ ID NO: 499          moltype = AA  length = 15
FEATURE                 Location/Qualifiers
source                  1..15
                        mol_type = protein
                        organism = Mus musculus
SEQUENCE: 499
RASQRVSTSS YSYMH                                                      15

SEQ ID NO: 500          moltype = AA  length = 6
FEATURE                 Location/Qualifiers
source                  1..6
                        mol_type = protein
                        organism = Mus musculus
SEQUENCE: 500
QGISNY                                                                6

SEQ ID NO: 501          moltype = AA  length = 11
FEATURE                 Location/Qualifiers
source                  1..11
                        mol_type = protein
                        organism = Mus musculus
SEQUENCE: 501
QSLLHSNGNT Y                                                          11

SEQ ID NO: 502          moltype = AA  length = 11
FEATURE                 Location/Qualifiers
source                  1..11
                        mol_type = protein
                        organism = Mus musculus
SEQUENCE: 502
QNIVQSNGNT Y                                                          11

SEQ ID NO: 503          moltype = AA  length = 11
FEATURE                 Location/Qualifiers
source                  1..11
                        mol_type = protein
                        organism = Mus musculus
SEQUENCE: 503
```

```
QSLVHSNGNT Y                                                    11

SEQ ID NO: 504          moltype = AA  length = 6
FEATURE                 Location/Qualifiers
source                  1..6
                        mol_type = protein
                        organism = Mus musculus
SEQUENCE: 504
QSISDY                                                          6

SEQ ID NO: 505          moltype = AA  length = 11
FEATURE                 Location/Qualifiers
source                  1..11
                        mol_type = protein
                        organism = Mus musculus
SEQUENCE: 505
KASQDINSYL N                                                    11

SEQ ID NO: 506          moltype = AA  length = 11
FEATURE                 Location/Qualifiers
source                  1..11
                        mol_type = protein
                        organism = Mus musculus
SEQUENCE: 506
RASQNIGTSI H                                                    11

SEQ ID NO: 507          moltype = AA  length = 11
FEATURE                 Location/Qualifiers
source                  1..11
                        mol_type = protein
                        organism = Mus musculus
SEQUENCE: 507
KASQDINSYL S                                                    11

SEQ ID NO: 508          moltype = AA  length = 11
FEATURE                 Location/Qualifiers
source                  1..11
                        mol_type = protein
                        organism = Mus musculus
SEQUENCE: 508
KASEHVGPYV S                                                    11

SEQ ID NO: 509          moltype = AA  length = 11
FEATURE                 Location/Qualifiers
source                  1..11
                        mol_type = protein
                        organism = Mus musculus
SEQUENCE: 509
KASENVVTYV S                                                    11

SEQ ID NO: 510          moltype = AA  length = 16
FEATURE                 Location/Qualifiers
source                  1..16
                        mol_type = protein
                        organism = Mus musculus
SEQUENCE: 510
RSGQSIVHSN GNTYLE                                               16

SEQ ID NO: 511          moltype = AA  length = 16
FEATURE                 Location/Qualifiers
source                  1..16
                        mol_type = protein
                        organism = Mus musculus
SEQUENCE: 511
RSGQSIVHSN GNTYLG                                               16

SEQ ID NO: 512          moltype = AA  length = 16
FEATURE                 Location/Qualifiers
source                  1..16
                        mol_type = protein
                        organism = Mus musculus
SEQUENCE: 512
KSSQSLLYSN GKTYLN                                               16

SEQ ID NO: 513          moltype = AA  length = 16
FEATURE                 Location/Qualifiers
source                  1..16
                        mol_type = protein
                        organism = Mus musculus
```

```
SEQUENCE: 513
KSSQSLLDSD GKTYLS                                                   16

SEQ ID NO: 514          moltype = AA  length = 16
FEATURE                 Location/Qualifiers
source                  1..16
                        mol_type = protein
                        organism = Mus musculus
SEQUENCE: 514
KSNQSLLDSD GKTYLS                                                   16

SEQ ID NO: 515          moltype = AA  length = 7
FEATURE                 Location/Qualifiers
source                  1..7
                        mol_type = protein
                        organism = Mus musculus
SEQUENCE: 515
STSRLHS                                                             7

SEQ ID NO: 516          moltype = AA  length = 7
FEATURE                 Location/Qualifiers
source                  1..7
                        mol_type = protein
                        organism = Mus musculus
SEQUENCE: 516
YTSSLHS                                                             7

SEQ ID NO: 517          moltype = AA  length = 7
FEATURE                 Location/Qualifiers
source                  1..7
                        mol_type = protein
                        organism = Mus musculus
SEQUENCE: 517
ATSNLAS                                                             7

SEQ ID NO: 518          moltype = AA  length = 7
FEATURE                 Location/Qualifiers
source                  1..7
                        mol_type = protein
                        organism = Mus musculus
SEQUENCE: 518
NAKTLPD                                                             7

SEQ ID NO: 519          moltype = AA  length = 7
FEATURE                 Location/Qualifiers
source                  1..7
                        mol_type = protein
                        organism = Mus musculus
SEQUENCE: 519
STSNLAS                                                             7

SEQ ID NO: 520          moltype = AA  length = 7
FEATURE                 Location/Qualifiers
source                  1..7
                        mol_type = protein
                        organism = Mus musculus
SEQUENCE: 520
GTSTLDS                                                             7

SEQ ID NO: 521          moltype = AA  length = 7
FEATURE                 Location/Qualifiers
source                  1..7
                        mol_type = protein
                        organism = Mus musculus
SEQUENCE: 521
ATSSLDS                                                             7

SEQ ID NO: 522          moltype = AA  length = 7
FEATURE                 Location/Qualifiers
source                  1..7
                        mol_type = protein
                        organism = Mus musculus
SEQUENCE: 522
YTSRLHS                                                             7

SEQ ID NO: 523          moltype = AA  length = 7
FEATURE                 Location/Qualifiers
source                  1..7
                        mol_type = protein
```

```
                        organism = Mus musculus
SEQUENCE: 523
WASSRES                                                                      7

SEQ ID NO: 524          moltype = AA  length = 7
FEATURE                 Location/Qualifiers
source                  1..7
                        mol_type = protein
                        organism = Mus musculus
SEQUENCE: 524
WASTRES                                                                      7

SEQ ID NO: 525          moltype = AA  length = 7
FEATURE                 Location/Qualifiers
source                  1..7
                        mol_type = protein
                        organism = Mus musculus
SEQUENCE: 525
KVSNRFS                                                                      7

SEQ ID NO: 526          moltype = AA  length = 7
FEATURE                 Location/Qualifiers
source                  1..7
                        mol_type = protein
                        organism = Mus musculus
SEQUENCE: 526
SGSTLQS                                                                      7

SEQ ID NO: 527          moltype = AA  length = 7
FEATURE                 Location/Qualifiers
source                  1..7
                        mol_type = protein
                        organism = Mus musculus
SEQUENCE: 527
LASNLES                                                                      7

SEQ ID NO: 528          moltype =   length =
SEQUENCE: 528
000

SEQ ID NO: 529          moltype = AA  length = 7
FEATURE                 Location/Qualifiers
source                  1..7
                        mol_type = protein
                        organism = Mus musculus
SEQUENCE: 529
RVSNRFS                                                                      7

SEQ ID NO: 530          moltype = AA  length = 7
FEATURE                 Location/Qualifiers
source                  1..7
                        mol_type = protein
                        organism = Mus musculus
SEQUENCE: 530
RVSSRFS                                                                      7

SEQ ID NO: 531          moltype = AA  length = 7
FEATURE                 Location/Qualifiers
source                  1..7
                        mol_type = protein
                        organism = Mus musculus
SEQUENCE: 531
RVSTRFS                                                                      7

SEQ ID NO: 532          moltype = AA  length = 7
FEATURE                 Location/Qualifiers
source                  1..7
                        mol_type = protein
                        organism = Mus musculus
SEQUENCE: 532
LVSKLDS                                                                      7

SEQ ID NO: 533          moltype = AA  length = 7
FEATURE                 Location/Qualifiers
source                  1..7
                        mol_type = protein
                        organism = Mus musculus
SEQUENCE: 533
NAKALAE                                                                      7
```

```
SEQ ID NO: 534          moltype = AA  length = 7
FEATURE                 Location/Qualifiers
source                  1..7
                        mol_type = protein
                        organism = Mus musculus
SEQUENCE: 534
NAKTLAE                                                                     7

SEQ ID NO: 535          moltype = AA  length = 7
FEATURE                 Location/Qualifiers
source                  1..7
                        mol_type = protein
                        organism = Mus musculus
SEQUENCE: 535
YASNRYT                                                                     7

SEQ ID NO: 536          moltype = AA  length = 7
FEATURE                 Location/Qualifiers
source                  1..7
                        mol_type = protein
                        organism = Mus musculus
SEQUENCE: 536
FASNRYT                                                                     7

SEQ ID NO: 537          moltype = AA  length = 7
FEATURE                 Location/Qualifiers
source                  1..7
                        mol_type = protein
                        organism = Mus musculus
SEQUENCE: 537
RTYNLAS                                                                     7

SEQ ID NO: 538          moltype = AA  length = 7
FEATURE                 Location/Qualifiers
source                  1..7
                        mol_type = protein
                        organism = Mus musculus
SEQUENCE: 538
RTSNLAS                                                                     7

SEQ ID NO: 539          moltype = AA  length = 7
FEATURE                 Location/Qualifiers
source                  1..7
                        mol_type = protein
                        organism = Mus musculus
SEQUENCE: 539
GATNLAD                                                                     7

SEQ ID NO: 540          moltype = AA  length = 7
FEATURE                 Location/Qualifiers
source                  1..7
                        mol_type = protein
                        organism = Mus musculus
SEQUENCE: 540
YASNRCT                                                                     7

SEQ ID NO: 541          moltype = AA  length = 7
FEATURE                 Location/Qualifiers
source                  1..7
                        mol_type = protein
                        organism = Mus musculus
SEQUENCE: 541
GASIRES                                                                     7

SEQ ID NO: 542          moltype = AA  length = 7
FEATURE                 Location/Qualifiers
source                  1..7
                        mol_type = protein
                        organism = Mus musculus
SEQUENCE: 542
GTSTRES                                                                     7

SEQ ID NO: 543          moltype = AA  length = 7
FEATURE                 Location/Qualifiers
source                  1..7
                        mol_type = protein
                        organism = Mus musculus
SEQUENCE: 543
```

```
GASTRES                                                                 7

SEQ ID NO: 544          moltype = AA  length = 7
FEATURE                 Location/Qualifiers
source                  1..7
                        mol_type = protein
                        organism = Mus musculus
SEQUENCE: 544
YASNLES                                                                 7

SEQ ID NO: 545          moltype =   length =
SEQUENCE: 545
000

SEQ ID NO: 546          moltype =   length =
SEQUENCE: 546
000

SEQ ID NO: 547          moltype =   length =
SEQUENCE: 547
000

SEQ ID NO: 548          moltype =   length =
SEQUENCE: 548
000

SEQ ID NO: 549          moltype = AA  length = 7
FEATURE                 Location/Qualifiers
source                  1..7
                        mol_type = protein
                        organism = Mus musculus
SEQUENCE: 549
RANRLVD                                                                 7

SEQ ID NO: 550          moltype = AA  length = 7
FEATURE                 Location/Qualifiers
source                  1..7
                        mol_type = protein
                        organism = Mus musculus
SEQUENCE: 550
YASESIS                                                                 7

SEQ ID NO: 551          moltype = AA  length = 7
FEATURE                 Location/Qualifiers
source                  1..7
                        mol_type = protein
                        organism = Mus musculus
SEQUENCE: 551
GASNRYT                                                                 7

SEQ ID NO: 552          moltype = AA  length = 7
FEATURE                 Location/Qualifiers
source                  1..7
                        mol_type = protein
                        organism = Mus musculus
SEQUENCE: 552
KVSIRFY                                                                 7

SEQ ID NO: 553          moltype = AA  length = 7
FEATURE                 Location/Qualifiers
source                  1..7
                        mol_type = protein
                        organism = Mus musculus
SEQUENCE: 553
MVSKLDS                                                                 7

SEQ ID NO: 554          moltype = AA  length = 9
FEATURE                 Location/Qualifiers
source                  1..9
                        mol_type = protein
                        organism = Mus musculus
SEQUENCE: 554
QQYSKLLPT                                                               9

SEQ ID NO: 555          moltype = AA  length = 9
FEATURE                 Location/Qualifiers
source                  1..9
                        mol_type = protein
                        organism = Mus musculus
```

```
SEQUENCE: 555
QQYSKFPWT                                                              9

SEQ ID NO: 556         moltype = AA  length = 9
FEATURE                Location/Qualifiers
source                 1..9
                       mol_type = protein
                       organism = Mus musculus
SEQUENCE: 556
QQWSSYPFT                                                              9

SEQ ID NO: 557         moltype = AA  length = 9
FEATURE                Location/Qualifiers
source                 1..9
                       mol_type = protein
                       organism = Mus musculus
SEQUENCE: 557
QHFWSTPLT                                                              9

SEQ ID NO: 558         moltype = AA  length = 9
FEATURE                Location/Qualifiers
source                 1..9
                       mol_type = protein
                       organism = Mus musculus
SEQUENCE: 558
HQWSSYPLT                                                              9

SEQ ID NO: 559         moltype = AA  length = 9
FEATURE                Location/Qualifiers
source                 1..9
                       mol_type = protein
                       organism = Mus musculus
SEQUENCE: 559
LQYATSPPT                                                              9

SEQ ID NO: 560         moltype = AA  length = 9
FEATURE                Location/Qualifiers
source                 1..9
                       mol_type = protein
                       organism = Mus musculus
SEQUENCE: 560
LQYDSLPLT                                                              9

SEQ ID NO: 561         moltype = AA  length = 9
FEATURE                Location/Qualifiers
source                 1..9
                       mol_type = protein
                       organism = Mus musculus
SEQUENCE: 561
QQGNTLPWT                                                              9

SEQ ID NO: 562         moltype = AA  length = 9
FEATURE                Location/Qualifiers
source                 1..9
                       mol_type = protein
                       organism = Mus musculus
SEQUENCE: 562
QQYYSYPRT                                                              9

SEQ ID NO: 563         moltype = AA  length = 8
FEATURE                Location/Qualifiers
source                 1..8
                       mol_type = protein
                       organism = Mus musculus
SEQUENCE: 563
KQSYNLWT                                                               8

SEQ ID NO: 564         moltype = AA  length = 9
FEATURE                Location/Qualifiers
source                 1..9
                       mol_type = protein
                       organism = Mus musculus
SEQUENCE: 564
FQDSHVPWT                                                              9

SEQ ID NO: 565         moltype = AA  length = 9
FEATURE                Location/Qualifiers
source                 1..9
                       mol_type = protein
```

```
                        organism = Mus musculus
SEQUENCE: 565
QQYNEYPWT                                                                   9

SEQ ID NO: 566          moltype = AA  length = 9
FEATURE                 Location/Qualifiers
source                  1..9
                        mol_type = protein
                        organism = Mus musculus
SEQUENCE: 566
SQSTHVPYT                                                                   9

SEQ ID NO: 567          moltype = AA  length = 8
FEATURE                 Location/Qualifiers
source                  1..8
                        mol_type = protein
                        organism = Mus musculus
SEQUENCE: 567
HQYLSSRT                                                                    8

SEQ ID NO: 568          moltype = AA  length = 9
FEATURE                 Location/Qualifiers
source                  1..9
                        mol_type = protein
                        organism = Mus musculus
SEQUENCE: 568
QHSRELPWT                                                                   9

SEQ ID NO: 569          moltype = AA  length = 9
FEATURE                 Location/Qualifiers
source                  1..9
                        mol_type = protein
                        organism = Mus musculus
SEQUENCE: 569
LHSRELPWT                                                                   9

SEQ ID NO: 570          moltype = AA  length = 9
FEATURE                 Location/Qualifiers
source                  1..9
                        mol_type = protein
                        organism = Mus musculus
SEQUENCE: 570
SQSTHVPFT                                                                   9

SEQ ID NO: 571          moltype = AA  length = 9
FEATURE                 Location/Qualifiers
source                  1..9
                        mol_type = protein
                        organism = Mus musculus
SEQUENCE: 571
FQGTHVPRT                                                                   9

SEQ ID NO: 572          moltype = AA  length = 9
FEATURE                 Location/Qualifiers
source                  1..9
                        mol_type = protein
                        organism = Mus musculus
SEQUENCE: 572
FQGSHVPYT                                                                   9

SEQ ID NO: 573          moltype = AA  length = 9
FEATURE                 Location/Qualifiers
source                  1..9
                        mol_type = protein
                        organism = Mus musculus
SEQUENCE: 573
FQGSHVPFT                                                                   9

SEQ ID NO: 574          moltype = AA  length = 9
FEATURE                 Location/Qualifiers
source                  1..9
                        mol_type = protein
                        organism = Mus musculus
SEQUENCE: 574
FQGSRVPLT                                                                   9

SEQ ID NO: 575          moltype = AA  length = 9
FEATURE                 Location/Qualifiers
source                  1..9
```

```
                          mol_type = protein
                          organism = Mus musculus
SEQUENCE: 575
WQGTHFPHT                                                                  9

SEQ ID NO: 576            moltype = AA  length = 9
FEATURE                   Location/Qualifiers
source                    1..9
                          mol_type = protein
                          organism = Mus musculus
SEQUENCE: 576
WQGTHFPQT                                                                  9

SEQ ID NO: 577            moltype = AA  length = 9
FEATURE                   Location/Qualifiers
source                    1..9
                          mol_type = protein
                          organism = Mus musculus
SEQUENCE: 577
WQGTHFPRT                                                                  9

SEQ ID NO: 578            moltype = AA  length = 9
FEATURE                   Location/Qualifiers
source                    1..9
                          mol_type = protein
                          organism = Mus musculus
SEQUENCE: 578
QQHNEYPYT                                                                  9

SEQ ID NO: 579            moltype = AA  length = 9
FEATURE                   Location/Qualifiers
source                    1..9
                          mol_type = protein
                          organism = Mus musculus
SEQUENCE: 579
QHHYGTPRT                                                                  9

SEQ ID NO: 580            moltype = AA  length = 9
FEATURE                   Location/Qualifiers
source                    1..9
                          mol_type = protein
                          organism = Mus musculus
SEQUENCE: 580
QQHYSSPYT                                                                  9

SEQ ID NO: 581            moltype = AA  length = 9
FEATURE                   Location/Qualifiers
source                    1..9
                          mol_type = protein
                          organism = Mus musculus
SEQUENCE: 581
QQHYSSPLT                                                                  9

SEQ ID NO: 582            moltype = AA  length = 9
FEATURE                   Location/Qualifiers
source                    1..9
                          mol_type = protein
                          organism = Mus musculus
SEQUENCE: 582
QQHYSSPRT                                                                  9

SEQ ID NO: 583            moltype = AA  length = 9
FEATURE                   Location/Qualifiers
source                    1..9
                          mol_type = protein
                          organism = Mus musculus
SEQUENCE: 583
SQSTHVPWT                                                                  9

SEQ ID NO: 584            moltype = AA  length = 10
FEATURE                   Location/Qualifiers
source                    1..10
                          mol_type = protein
                          organism = Mus musculus
SEQUENCE: 584
QQGSTISRYT                                                                 10

SEQ ID NO: 585            moltype = AA  length = 10
FEATURE                   Location/Qualifiers
```

```
source                  1..10
                        mol_type = protein
                        organism = Mus musculus
SEQUENCE: 585
QQGSSIPRYT                                                                10

SEQ ID NO: 586          moltype = AA  length = 9
FEATURE                 Location/Qualifiers
source                  1..9
                        mol_type = protein
                        organism = Mus musculus
SEQUENCE: 586
QNVLTIPWT                                                                 9

SEQ ID NO: 587          moltype = AA  length = 9
FEATURE                 Location/Qualifiers
source                  1..9
                        mol_type = protein
                        organism = Mus musculus
SEQUENCE: 587
QQDYRSPLT                                                                 9

SEQ ID NO: 588          moltype = AA  length = 9
FEATURE                 Location/Qualifiers
source                  1..9
                        mol_type = protein
                        organism = Mus musculus
SEQUENCE: 588
QNDHSHPYT                                                                 9

SEQ ID NO: 589          moltype = AA  length = 9
FEATURE                 Location/Qualifiers
source                  1..9
                        mol_type = protein
                        organism = Mus musculus
SEQUENCE: 589
QHSWEIPYT                                                                 9

SEQ ID NO: 590          moltype = AA  length = 9
FEATURE                 Location/Qualifiers
source                  1..9
                        mol_type = protein
                        organism = Mus musculus
SEQUENCE: 590
QQYSKLPWT                                                                 9

SEQ ID NO: 591          moltype = AA  length = 9
FEATURE                 Location/Qualifiers
source                  1..9
                        mol_type = protein
                        organism = Mus musculus
SEQUENCE: 591
SQSTHVPLT                                                                 9

SEQ ID NO: 592          moltype = AA  length = 9
FEATURE                 Location/Qualifiers
source                  1..9
                        mol_type = protein
                        organism = Mus musculus
SEQUENCE: 592
QNGHSFPPT                                                                 9

SEQ ID NO: 593          moltype = AA  length = 9
FEATURE                 Location/Qualifiers
source                  1..9
                        mol_type = protein
                        organism = Mus musculus
SEQUENCE: 593
LQYDEFPLT                                                                 9

SEQ ID NO: 594          moltype = AA  length = 9
FEATURE                 Location/Qualifiers
source                  1..9
                        mol_type = protein
                        organism = Mus musculus
SEQUENCE: 594
QQSNSWPTT                                                                 9

SEQ ID NO: 595          moltype = AA  length = 9
```

```
FEATURE                Location/Qualifiers
source                 1..9
                       mol_type = protein
                       organism = Mus musculus
SEQUENCE: 595
QQYDEFPLT                                                            9

SEQ ID NO: 596         moltype = AA  length = 9
FEATURE                Location/Qualifiers
source                 1..9
                       mol_type = protein
                       organism = Mus musculus
SEQUENCE: 596
GQTYSYPLT                                                            9

SEQ ID NO: 597         moltype = AA  length = 9
FEATURE                Location/Qualifiers
source                 1..9
                       mol_type = protein
                       organism = Mus musculus
SEQUENCE: 597
FQGSHVPWT                                                            9

SEQ ID NO: 598         moltype = AA  length = 9
FEATURE                Location/Qualifiers
source                 1..9
                       mol_type = protein
                       organism = Mus musculus
SEQUENCE: 598
VQGTHFPHT                                                            9

SEQ ID NO: 599         moltype = AA  length = 9
FEATURE                Location/Qualifiers
source                 1..9
                       mol_type = protein
                       organism = Mus musculus
SEQUENCE: 599
WQGTHFPVT                                                            9

SEQ ID NO: 600         moltype = AA  length = 9
FEATURE                Location/Qualifiers
source                 1..9
                       mol_type = protein
                       organism = Mus musculus
SEQUENCE: 600
WQGTHFPLT                                                            9

SEQ ID NO: 601         moltype = AA  length = 25
FEATURE                Location/Qualifiers
source                 1..25
                       mol_type = protein
                       organism = Mus musculus
SEQUENCE: 601
EVQLVESGGG LVQPKGSLKL SCAAS                                          25

SEQ ID NO: 602         moltype = AA  length = 25
FEATURE                Location/Qualifiers
source                 1..25
                       mol_type = protein
                       organism = Mus musculus
SEQUENCE: 602
EVQLQQSGPE LVKPGASVKI SCEAS                                          25

SEQ ID NO: 603         moltype = AA  length = 25
FEATURE                Location/Qualifiers
source                 1..25
                       mol_type = protein
                       organism = Mus musculus
SEQUENCE: 603
QVQLQQPGTE LVKPGASVKL SCKAS                                          25

SEQ ID NO: 604         moltype = AA  length = 25
FEATURE                Location/Qualifiers
source                 1..25
                       mol_type = protein
                       organism = Mus musculus
SEQUENCE: 604
QVQLQQPGAE LVKPGASVKL SCKAS                                          25
```

```
SEQ ID NO: 605          moltype = AA  length = 25
FEATURE                 Location/Qualifiers
source                  1..25
                        mol_type = protein
                        organism = Mus musculus
SEQUENCE: 605
QVQLKESGPG LVAPSQSLSI TCTLS                                              25

SEQ ID NO: 606          moltype = AA  length = 25
FEATURE                 Location/Qualifiers
source                  1..25
                        mol_type = protein
                        organism = Mus musculus
SEQUENCE: 606
QVQLKESGPG LVAPSQSLSI TCTVS                                              25

SEQ ID NO: 607          moltype = AA  length = 25
FEATURE                 Location/Qualifiers
source                  1..25
                        mol_type = protein
                        organism = Mus musculus
SEQUENCE: 607
EVQLVESGGD LVKPGGSLKL SCAAS                                              25

SEQ ID NO: 608          moltype = AA  length = 25
FEATURE                 Location/Qualifiers
source                  1..25
                        mol_type = protein
                        organism = Mus musculus
SEQUENCE: 608
EVQLVESGGA LVQPGGSLSL SCAAS                                              25

SEQ ID NO: 609          moltype = AA  length = 25
FEATURE                 Location/Qualifiers
source                  1..25
                        mol_type = protein
                        organism = Mus musculus
SEQUENCE: 609
QIQLVQSGPE LKKPGETVKI SCKAS                                              25

SEQ ID NO: 610          moltype = AA  length = 25
FEATURE                 Location/Qualifiers
source                  1..25
                        mol_type = protein
                        organism = Mus musculus
SEQUENCE: 610
EVQLVESGGG LVKPGGSLKL SCAAS                                              25

SEQ ID NO: 611          moltype = AA  length = 25
FEATURE                 Location/Qualifiers
source                  1..25
                        mol_type = protein
                        organism = Mus musculus
SEQUENCE: 611
EVKLEESGGG LVQPGGSMKL SCVAS                                              25

SEQ ID NO: 612          moltype = AA  length = 25
FEATURE                 Location/Qualifiers
source                  1..25
                        mol_type = protein
                        organism = Mus musculus
SEQUENCE: 612
QAYLQQSGAE LVRPGASVKM SCKAS                                              25

SEQ ID NO: 613          moltype = AA  length = 25
FEATURE                 Location/Qualifiers
source                  1..25
                        mol_type = protein
                        organism = Mus musculus
SEQUENCE: 613
EVQLQQSGPE LVKPGASVKM SCKAS                                              25

SEQ ID NO: 614          moltype = AA  length = 25
FEATURE                 Location/Qualifiers
source                  1..25
                        mol_type = protein
                        organism = Mus musculus
SEQUENCE: 614
EVQLQQSGAE LVKPGASVKL SCTAS                                              25
```

```
SEQ ID NO: 615          moltype = AA  length = 25
FEATURE                 Location/Qualifiers
source                  1..25
                        mol_type = protein
                        organism = Mus musculus
SEQUENCE: 615
QVQLQQPGAD LVRPGSSVKL SCKAS                                          25

SEQ ID NO: 616          moltype = AA  length = 25
FEATURE                 Location/Qualifiers
source                  1..25
                        mol_type = protein
                        organism = Mus musculus
SEQUENCE: 616
QVQLQQPGAA LVRPGSSVKL SCKAS                                          25

SEQ ID NO: 617          moltype = AA  length = 25
FEATURE                 Location/Qualifiers
source                  1..25
                        mol_type = protein
                        organism = Mus musculus
SEQUENCE: 617
QVQLQQPGTD LVKPGASVKL SCKAS                                          25

SEQ ID NO: 618          moltype = AA  length = 25
FEATURE                 Location/Qualifiers
source                  1..25
                        mol_type = protein
                        organism = Mus musculus
SEQUENCE: 618
QVQLQQPGIE LVKTGASVKL SCKAS                                          25

SEQ ID NO: 619          moltype = AA  length = 25
FEATURE                 Location/Qualifiers
source                  1..25
                        mol_type = protein
                        organism = Mus musculus
SEQUENCE: 619
QVQLQQPGTE LVKPGSSVNL SCKAS                                          25

SEQ ID NO: 620          moltype = AA  length = 25
FEATURE                 Location/Qualifiers
source                  1..25
                        mol_type = protein
                        organism = Mus musculus
SEQUENCE: 620
QVQLQQSGPE LVKPGASVKI SCKAS                                          25

SEQ ID NO: 621          moltype = AA  length = 25
FEATURE                 Location/Qualifiers
source                  1..25
                        mol_type = protein
                        organism = Mus musculus
SEQUENCE: 621
QVSLKESGPG ILQSSQTLSL TCSFS                                          25

SEQ ID NO: 622          moltype = AA  length = 25
FEATURE                 Location/Qualifiers
source                  1..25
                        mol_type = protein
                        organism = Mus musculus
SEQUENCE: 622
QVQLKQSGAE LVRPGASVKL SCKTS                                          25

SEQ ID NO: 623          moltype = AA  length = 25
FEATURE                 Location/Qualifiers
source                  1..25
                        mol_type = protein
                        organism = Mus musculus
SEQUENCE: 623
EVQLQQSGAE LVRPGSSVKM SCKTS                                          25

SEQ ID NO: 624          moltype = AA  length = 25
FEATURE                 Location/Qualifiers
source                  1..25
                        mol_type = protein
                        organism = Mus musculus
SEQUENCE: 624
```

```
EAQLQQSGAE LVRPGSSVKM SCKTS                                      25

SEQ ID NO: 625          moltype = AA  length = 25
FEATURE                 Location/Qualifiers
source                  1..25
                        mol_type = protein
                        organism = Mus musculus
SEQUENCE: 625
QVTLKESGPG ILQPSQTLNL TCSFS                                      25

SEQ ID NO: 626          moltype = AA  length = 25
FEATURE                 Location/Qualifiers
source                  1..25
                        mol_type = protein
                        organism = Mus musculus
SEQUENCE: 626
QVQLQQSGAE LARPGASVKL SCKAS                                      25

SEQ ID NO: 627          moltype = AA  length = 25
FEATURE                 Location/Qualifiers
source                  1..25
                        mol_type = protein
                        organism = Mus musculus
SEQUENCE: 627
QVQLQQSGPE LVKPGALVKI SCKAS                                      25

SEQ ID NO: 628          moltype = AA  length = 25
FEATURE                 Location/Qualifiers
source                  1..25
                        mol_type = protein
                        organism = Mus musculus
SEQUENCE: 628
QVQLKQSGPG LVQPSQSLSI TCTVS                                      25

SEQ ID NO: 629          moltype = AA  length = 25
FEATURE                 Location/Qualifiers
source                  1..25
                        mol_type = protein
                        organism = Mus musculus
SEQUENCE: 629
DVQLQESGPG LVKPSQSLSL TCSVT                                      25

SEQ ID NO: 630          moltype = AA  length = 25
FEATURE                 Location/Qualifiers
source                  1..25
                        mol_type = protein
                        organism = Mus musculus
SEQUENCE: 630
DVQLQESGPG LVKPSQSLSL TCSVS                                      25

SEQ ID NO: 631          moltype = AA  length = 25
FEATURE                 Location/Qualifiers
source                  1..25
                        mol_type = protein
                        organism = Mus musculus
SEQUENCE: 631
QVTLKESGPG ILQSSQTLSL TCSFS                                      25

SEQ ID NO: 632          moltype = AA  length = 25
FEATURE                 Location/Qualifiers
source                  1..25
                        mol_type = protein
                        organism = Mus musculus
SEQUENCE: 632
EVQLQQSGPE LVKPGASVKI PCRAS                                      25

SEQ ID NO: 633          moltype = AA  length = 25
FEATURE                 Location/Qualifiers
source                  1..25
                        mol_type = protein
                        organism = Mus musculus
SEQUENCE: 633
QITLKESGPG ILQSSQTLSL TCSFS                                      25

SEQ ID NO: 634          moltype = AA  length = 25
FEATURE                 Location/Qualifiers
source                  1..25
                        mol_type = protein
                        organism = Mus musculus
```

```
SEQUENCE: 634
QVQLQQPGAE LVKPGVSVKM SCKAS                                          25

SEQ ID NO: 635          moltype = AA  length = 25
FEATURE                 Location/Qualifiers
source                  1..25
                        mol_type = protein
                        organism = Mus musculus
SEQUENCE: 635
QVQLQQSGAE LVRPGASVTL SCKAS                                          25

SEQ ID NO: 636          moltype = AA  length = 30
FEATURE                 Location/Qualifiers
source                  1..30
                        mol_type = protein
                        organism = Mus musculus
SEQUENCE: 636
EVQLVESGGG LVKPGGSLKL SCAASGFTFS                                     30

SEQ ID NO: 637          moltype = AA  length = 30
FEATURE                 Location/Qualifiers
source                  1..30
                        mol_type = protein
                        organism = Mus musculus
SEQUENCE: 637
LVQLQQSGAE LARPGASVKL SCKASGYTFT                                     30

SEQ ID NO: 638          moltype = AA  length = 30
FEATURE                 Location/Qualifiers
source                  1..30
                        mol_type = protein
                        organism = Mus musculus
SEQUENCE: 638
EVKLVESGGG LVKPGGSLKL SCAASGFTFS                                     30

SEQ ID NO: 639          moltype = AA  length = 30
FEATURE                 Location/Qualifiers
source                  1..30
                        mol_type = protein
                        organism = Mus musculus
SEQUENCE: 639
QVTLKESGPG KLQPSQTLSL TCSFSGFSLS                                     30

SEQ ID NO: 640          moltype = AA  length = 25
FEATURE                 Location/Qualifiers
source                  1..25
                        mol_type = protein
                        organism = Mus musculus
SEQUENCE: 640
DVQLVESGGG LVQPGGSRKL SCAAS                                          25

SEQ ID NO: 641          moltype = AA  length = 25
FEATURE                 Location/Qualifiers
source                  1..25
                        mol_type = protein
                        organism = Mus musculus
SEQUENCE: 641
EVKLVESGGG LVKPGGSLKL SCAAS                                          25

SEQ ID NO: 642          moltype = AA  length = 25
FEATURE                 Location/Qualifiers
source                  1..25
                        mol_type = protein
                        organism = Mus musculus
SEQUENCE: 642
QVQLQQSGAE LARPGASVKL SCKSS                                          25

SEQ ID NO: 643          moltype = AA  length = 25
FEATURE                 Location/Qualifiers
source                  1..25
                        mol_type = protein
                        organism = Mus musculus
SEQUENCE: 643
QVQLKQSGAE LASPKTSVKL SCKAS                                          25

SEQ ID NO: 644          moltype = AA  length = 19
FEATURE                 Location/Qualifiers
source                  1..19
                        mol_type = protein
```

```
                       organism = Mus musculus
SEQUENCE: 644
AMYWVRQAPG KGLEWVARI                                                19

SEQ ID NO: 645         moltype = AA  length = 19
FEATURE                Location/Qualifiers
source                 1..19
                       mol_type = protein
                       organism = Mus musculus
SEQUENCE: 645
YMNWVKQSHG KSLEWIGDI                                                19

SEQ ID NO: 646         moltype = AA  length = 19
FEATURE                Location/Qualifiers
source                 1..19
                       mol_type = protein
                       organism = Mus musculus
SEQUENCE: 646
WLHWVKQRPG QGLEWIGYI                                                19

SEQ ID NO: 647         moltype = AA  length = 19
FEATURE                Location/Qualifiers
source                 1..19
                       mol_type = protein
                       organism = Mus musculus
SEQUENCE: 647
WMHWVKQRPG RGLEWIGRI                                                19

SEQ ID NO: 648         moltype = AA  length = 19
FEATURE                Location/Qualifiers
source                 1..19
                       mol_type = protein
                       organism = Mus musculus
SEQUENCE: 648
GVSWIRQPPG KGLEWLGLM                                                19

SEQ ID NO: 649         moltype = AA  length = 19
FEATURE                Location/Qualifiers
source                 1..19
                       mol_type = protein
                       organism = Mus musculus
SEQUENCE: 649
AISWVRQPPG KSLEWLGVI                                                19

SEQ ID NO: 650         moltype = AA  length = 19
FEATURE                Location/Qualifiers
source                 1..19
                       mol_type = protein
                       organism = Mus musculus
SEQUENCE: 650
GLSWVRQTPD KRLEWVATI                                                19

SEQ ID NO: 651         moltype = AA  length = 19
FEATURE                Location/Qualifiers
source                 1..19
                       mol_type = protein
                       organism = Mus musculus
SEQUENCE: 651
AISWVRQPPG KGLEWLGVI                                                19

SEQ ID NO: 652         moltype = AA  length = 19
FEATURE                Location/Qualifiers
source                 1..19
                       mol_type = protein
                       organism = Mus musculus
SEQUENCE: 652
YMSWVRQPPG KALEWLALI                                                19

SEQ ID NO: 653         moltype = AA  length = 19
FEATURE                Location/Qualifiers
source                 1..19
                       mol_type = protein
                       organism = Mus musculus
SEQUENCE: 653
GMSWVKQAPG KGLKWMGWI                                                19

SEQ ID NO: 654         moltype = AA  length = 19
FEATURE                Location/Qualifiers
source                 1..19
```

```
                        mol_type = protein
                        organism = Mus musculus
SEQUENCE: 654
GMYWVRQAPE KGLEWVAYI                                            19

SEQ ID NO: 655          moltype = AA  length = 19
FEATURE                 Location/Qualifiers
source                  1..19
                        mol_type = protein
                        organism = Mus musculus
SEQUENCE: 655
WMNWVRQAPE RGLEWVAQI                                            19

SEQ ID NO: 656          moltype = AA  length = 19
FEATURE                 Location/Qualifiers
source                  1..19
                        mol_type = protein
                        organism = Mus musculus
SEQUENCE: 656
NMHWVKQTPR QGLEWIGAI                                            19

SEQ ID NO: 657          moltype = AA  length = 19
FEATURE                 Location/Qualifiers
source                  1..19
                        mol_type = protein
                        organism = Mus musculus
SEQUENCE: 657
NMHWLKQSHG KSLEWIGYI                                            19

SEQ ID NO: 658          moltype = AA  length = 19
FEATURE                 Location/Qualifiers
source                  1..19
                        mol_type = protein
                        organism = Mus musculus
SEQUENCE: 658
YIHWVKQRTE QGLEWIGRI                                            19

SEQ ID NO: 659          moltype = AA  length = 19
FEATURE                 Location/Qualifiers
source                  1..19
                        mol_type = protein
                        organism = Mus musculus
SEQUENCE: 659
YMHWVKQRTE QGLEWIGRI                                            19

SEQ ID NO: 660          moltype = AA  length = 19
FEATURE                 Location/Qualifiers
source                  1..19
                        mol_type = protein
                        organism = Mus musculus
SEQUENCE: 660
WMHWVKQRPI EGLEWIGNI                                            19

SEQ ID NO: 661          moltype = AA  length = 19
FEATURE                 Location/Qualifiers
source                  1..19
                        mol_type = protein
                        organism = Mus musculus
SEQUENCE: 661
WMHWVKQRPI QGLEWIGNI                                            19

SEQ ID NO: 662          moltype = AA  length = 19
FEATURE                 Location/Qualifiers
source                  1..19
                        mol_type = protein
                        organism = Mus musculus
SEQUENCE: 662
WMHWLKQRPG QGLEWIGNI                                            19

SEQ ID NO: 663          moltype = AA  length = 19
FEATURE                 Location/Qualifiers
source                  1..19
                        mol_type = protein
                        organism = Mus musculus
SEQUENCE: 663
WMHWVKERPG HGLEWIGNI                                            19

SEQ ID NO: 664          moltype = AA  length = 19
FEATURE                 Location/Qualifiers
```

```
source                  1..19
                        mol_type = protein
                        organism = Mus musculus
SEQUENCE: 664
WMHWVKQRPG HGLEWIGKI                                          19

SEQ ID NO: 665          moltype = AA  length = 19
FEATURE                 Location/Qualifiers
source                  1..19
                        mol_type = protein
                        organism = Mus musculus
SEQUENCE: 665
WMHWVKQRPG QGLEWIGNI                                          19

SEQ ID NO: 666          moltype = AA  length = 19
FEATURE                 Location/Qualifiers
source                  1..19
                        mol_type = protein
                        organism = Mus musculus
SEQUENCE: 666
YINWVKQRPG QGLEWIGWI                                          19

SEQ ID NO: 667          moltype = AA  length = 19
FEATURE                 Location/Qualifiers
source                  1..19
                        mol_type = protein
                        organism = Mus musculus
SEQUENCE: 667
YLNWMKQRPG QGLEWIGWI                                          19

SEQ ID NO: 668          moltype = AA  length = 19
FEATURE                 Location/Qualifiers
source                  1..19
                        mol_type = protein
                        organism = Mus musculus
SEQUENCE: 668
WMNWVKQRPG KGLEWIGRI                                          19

SEQ ID NO: 669          moltype = AA  length = 19
FEATURE                 Location/Qualifiers
source                  1..19
                        mol_type = protein
                        organism = Mus musculus
SEQUENCE: 669
GVSWIRQPSG KGLEWLSHI                                          19

SEQ ID NO: 670          moltype = AA  length = 19
FEATURE                 Location/Qualifiers
source                  1..19
                        mol_type = protein
                        organism = Mus musculus
SEQUENCE: 670
YIKWVKQRPG QGLEWIARI                                          19

SEQ ID NO: 671          moltype = AA  length = 19
FEATURE                 Location/Qualifiers
source                  1..19
                        mol_type = protein
                        organism = Mus musculus
SEQUENCE: 671
GINWVKQRPG QGLEWIGYI                                          19

SEQ ID NO: 672          moltype = AA  length = 19
FEATURE                 Location/Qualifiers
source                  1..19
                        mol_type = protein
                        organism = Mus musculus
SEQUENCE: 672
GINWVKQRPG QGLEWVGYI                                          19

SEQ ID NO: 673          moltype = AA  length = 19
FEATURE                 Location/Qualifiers
source                  1..19
                        mol_type = protein
                        organism = Mus musculus
SEQUENCE: 673
GVSWIRQPSG KGLEWLAHI                                          19

SEQ ID NO: 674          moltype = AA  length = 19
```

```
FEATURE                Location/Qualifiers
source                 1..19
                       mol_type = protein
                       organism = Mus musculus
SEQUENCE: 674
GINWVKQRTG QGLEWIGEI                                          19

SEQ ID NO: 675         moltype = AA  length = 19
FEATURE                Location/Qualifiers
source                 1..19
                       mol_type = protein
                       organism = Mus musculus
SEQUENCE: 675
DINWVKQRPG QGLEWIGWI                                          19

SEQ ID NO: 676         moltype = AA  length = 19
FEATURE                Location/Qualifiers
source                 1..19
                       mol_type = protein
                       organism = Mus musculus
SEQUENCE: 676
GVHWVRQSPG KGLEWLGVI                                          19

SEQ ID NO: 677         moltype = AA  length = 19
FEATURE                Location/Qualifiers
source                 1..19
                       mol_type = protein
                       organism = Mus musculus
SEQUENCE: 677
YWNWIRQFPG NKLEWMGYI                                          19

SEQ ID NO: 678         moltype = AA  length = 17
FEATURE                Location/Qualifiers
source                 1..17
                       mol_type = protein
                       organism = Mus musculus
SEQUENCE: 678
WNWIRLFPGN KLEWMGY                                            17

SEQ ID NO: 679         moltype = AA  length = 19
FEATURE                Location/Qualifiers
source                 1..19
                       mol_type = protein
                       organism = Mus musculus
SEQUENCE: 679
GMHWVRQAPE KGLEWVAYI                                          19

SEQ ID NO: 680         moltype = AA  length = 19
FEATURE                Location/Qualifiers
source                 1..19
                       mol_type = protein
                       organism = Mus musculus
SEQUENCE: 680
GVSWLRQPSG KGLEWLAHI                                          19

SEQ ID NO: 681         moltype = AA  length = 19
FEATURE                Location/Qualifiers
source                 1..19
                       mol_type = protein
                       organism = Mus musculus
SEQUENCE: 681
NMDWVKQSHG KTLEWIGDI                                          19

SEQ ID NO: 682         moltype = AA  length = 19
FEATURE                Location/Qualifiers
source                 1..19
                       mol_type = protein
                       organism = Mus musculus
SEQUENCE: 682
GVSWIRQPSG EGLEWLAHI                                          19

SEQ ID NO: 683         moltype = AA  length = 19
FEATURE                Location/Qualifiers
source                 1..19
                       mol_type = protein
                       organism = Mus musculus
SEQUENCE: 683
GVSWIRLPSG KGLEWLAHI                                          19
```

```
SEQ ID NO: 684          moltype = AA  length = 17
FEATURE                 Location/Qualifiers
source                  1..17
                        mol_type = protein
                        organism = Mus musculus
SEQUENCE: 684
ITWVKQRPGQ GLEWVGD                                                      17

SEQ ID NO: 685          moltype = AA  length = 17
FEATURE                 Location/Qualifiers
source                  1..17
                        mol_type = protein
                        organism = Mus musculus
SEQUENCE: 685
MHWVRQAPEK GLEWVAY                                                      17

SEQ ID NO: 686          moltype = AA  length = 17
FEATURE                 Location/Qualifiers
source                  1..17
                        mol_type = protein
                        organism = Mus musculus
SEQUENCE: 686
MHWVKQTPVH GLEWIGA                                                      17

SEQ ID NO: 687          moltype = AA  length = 17
FEATURE                 Location/Qualifiers
source                  1..17
                        mol_type = protein
                        organism = Mus musculus
SEQUENCE: 687
MHWVKQRPGQ GLEWIGV                                                      17

SEQ ID NO: 688          moltype = AA  length = 17
FEATURE                 Location/Qualifiers
source                  1..17
                        mol_type = protein
                        organism = Mus musculus
SEQUENCE: 688
ISWVKQRTGQ GLEWIGE                                                      17

SEQ ID NO: 689          moltype = AA  length = 14
FEATURE                 Location/Qualifiers
source                  1..14
                        mol_type = protein
                        organism = Mus musculus
SEQUENCE: 689
WVRQTPEKRL EWVA                                                         14

SEQ ID NO: 690          moltype = AA  length = 14
FEATURE                 Location/Qualifiers
source                  1..14
                        mol_type = protein
                        organism = Mus musculus
SEQUENCE: 690
WVKQRTGQGL EWIG                                                         14

SEQ ID NO: 691          moltype = AA  length = 14
FEATURE                 Location/Qualifiers
source                  1..14
                        mol_type = protein
                        organism = Mus musculus
SEQUENCE: 691
WVRQIPEKRL EWVA                                                         14

SEQ ID NO: 692          moltype = AA  length = 14
FEATURE                 Location/Qualifiers
source                  1..14
                        mol_type = protein
                        organism = Mus musculus
SEQUENCE: 692
WIRQPSGKGL EWLA                                                         14

SEQ ID NO: 693          moltype = AA  length = 19
FEATURE                 Location/Qualifiers
source                  1..19
                        mol_type = protein
                        organism = Mus musculus
SEQUENCE: 693
GMHWVRQVPE KGLEWVAYI                                                    19
```

```
SEQ ID NO: 694          moltype = AA  length = 19
FEATURE                 Location/Qualifiers
source                  1..19
                        mol_type = protein
                        organism = Mus musculus
SEQUENCE: 694
SMYWVRQTPE KRLEWVATI                                              19

SEQ ID NO: 695          moltype = AA  length = 19
FEATURE                 Location/Qualifiers
source                  1..19
                        mol_type = protein
                        organism = Mus musculus
SEQUENCE: 695
WMQWVKQRPG QGLEWIGAI                                              19

SEQ ID NO: 696          moltype = AA  length = 19
FEATURE                 Location/Qualifiers
source                  1..19
                        mol_type = protein
                        organism = Mus musculus
SEQUENCE: 696
WMQWIKQRPG QGLEWIGAI                                              19

SEQ ID NO: 697          moltype = AA  length = 41
FEATURE                 Location/Qualifiers
source                  1..41
                        mol_type = protein
                        organism = Mus musculus
SEQUENCE: 697
TYYADSVKDR FTISRDDSQS KLYLQMNNLK TEDTAMYYCV R                     41

SEQ ID NO: 698          moltype = AA  length = 41
FEATURE                 Location/Qualifiers
source                  1..41
                        mol_type = protein
                        organism = Mus musculus
SEQUENCE: 698
TTYNQKFKGK ATLTVDKSSS TAHMELRSLT SEDSAVYYCA R                     41

SEQ ID NO: 699          moltype = AA  length = 41
FEATURE                 Location/Qualifiers
source                  1..41
                        mol_type = protein
                        organism = Mus musculus
SEQUENCE: 699
TNYNERFKSK ASLTVDKSST TAYMQLSSLT SEDSAVYYCA R                     41

SEQ ID NO: 700          moltype = AA  length = 41
FEATURE                 Location/Qualifiers
source                  1..41
                        mol_type = protein
                        organism = Mus musculus
SEQUENCE: 700
TRYNEKFKNK ATLTVDKPSS TAYMHLSSLT SEDSAVYYCA G                     41

SEQ ID NO: 701          moltype = AA  length = 41
FEATURE                 Location/Qualifiers
source                  1..41
                        mol_type = protein
                        organism = Mus musculus
SEQUENCE: 701
TYYNSALKSR LSISKDNSKS QVFLKMNSLQ TDDTAMYYCA K                     41

SEQ ID NO: 702          moltype = AA  length = 41
FEATURE                 Location/Qualifiers
source                  1..41
                        mol_type = protein
                        organism = Mus musculus
SEQUENCE: 702
SKYNSALKSR LSISKDNSKS QVFLKMNSLQ TDDTARYYCV R                     41

SEQ ID NO: 703          moltype = AA  length = 41
FEATURE                 Location/Qualifiers
source                  1..41
                        mol_type = protein
                        organism = Mus musculus
SEQUENCE: 703
```

```
TYYPDSVKGR FTISRDNAKN ILYLHMSSLK SEDTAMYYCA R                       41

SEQ ID NO: 704          moltype = AA  length = 41
FEATURE                 Location/Qualifiers
source                  1..41
                        mol_type = protein
                        organism = Mus musculus
SEQUENCE: 704
TDFNSALKSR LSISKDNSKS QVFLKMISLQ TNDTARYYCA R                       41

SEQ ID NO: 705          moltype = AA  length = 41
FEATURE                 Location/Qualifiers
source                  1..41
                        mol_type = protein
                        organism = Mus musculus
SEQUENCE: 705
TEYSASVKGR FTISRDNSQS ILLFQMNDLR ADDSATYYCV R                       41

SEQ ID NO: 706          moltype = AA  length = 41
FEATURE                 Location/Qualifiers
source                  1..41
                        mol_type = protein
                        organism = Mus musculus
SEQUENCE: 706
PTYADDFKER FAFSLETSAS TAYLQINNLK NEDTSTYFCA R                       41

SEQ ID NO: 707          moltype = AA  length = 41
FEATURE                 Location/Qualifiers
source                  1..41
                        mol_type = protein
                        organism = Mus musculus
SEQUENCE: 707
IYYADTVKGR FTISRDNAKN TLFLQMTSLR SEDTAMYYCA G                       41

SEQ ID NO: 708          moltype = AA  length = 41
FEATURE                 Location/Qualifiers
source                  1..41
                        mol_type = protein
                        organism = Mus musculus
SEQUENCE: 708
THYAESVKGR FTISRDDSKS SVYLQMNNLR AEDTGVYYCT G                       41

SEQ ID NO: 709          moltype = AA  length = 41
FEATURE                 Location/Qualifiers
source                  1..41
                        mol_type = protein
                        organism = Mus musculus
SEQUENCE: 709
TSYNQKFKGK ATLTVDKSSS TAYMQLSSLT SEDSAVYFCA R                       41

SEQ ID NO: 710          moltype = AA  length = 41
FEATURE                 Location/Qualifiers
source                  1..41
                        mol_type = protein
                        organism = Mus musculus
SEQUENCE: 710
ISYNQKFKGK ATLTVNKSSS TAYMELRSLT SEDSALYYCA R                       41

SEQ ID NO: 711          moltype = AA  length = 41
FEATURE                 Location/Qualifiers
source                  1..41
                        mol_type = protein
                        organism = Mus musculus
SEQUENCE: 711
TKYAPKFQGK ATIAADTSSN TAYLHLNSLT SEDTAVYYCA R                       41

SEQ ID NO: 712          moltype = AA  length = 41
FEATURE                 Location/Qualifiers
source                  1..41
                        mol_type = protein
                        organism = Mus musculus
SEQUENCE: 712
TKYAPKFQGK ATITADTSSN TVYLQLSSLT SEDTAVYYCA R                       41

SEQ ID NO: 713          moltype = AA  length = 41
FEATURE                 Location/Qualifiers
source                  1..41
                        mol_type = protein
                        organism = Mus musculus
```

```
SEQUENCE: 713
AHYNQKFKDK ATLTVDKFSN TAYMQLSSLT SEDSAVYYCA R                          41

SEQ ID NO: 714          moltype = AA  length = 41
FEATURE                 Location/Qualifiers
source                  1..41
                        mol_type = protein
                        organism = Mus musculus
SEQUENCE: 714
THYNQKFKDK ATLTVDKSSN TAYMQLSSLT SEDSAVYYCA R                          41

SEQ ID NO: 715          moltype = AA  length = 41
FEATURE                 Location/Qualifiers
source                  1..41
                        mol_type = protein
                        organism = Mus musculus
SEQUENCE: 715
ANYNEKFKSK ATLTVDKSSS AAYMQLISLT SEDSAVYYCA R                          41

SEQ ID NO: 716          moltype = AA  length = 41
FEATURE                 Location/Qualifiers
source                  1..41
                        mol_type = protein
                        organism = Mus musculus
SEQUENCE: 716
TNYNEKFRKK ATLTVDKSSS AAYMQLISLT SEDSAVYYCA R                          41

SEQ ID NO: 717          moltype = AA  length = 41
FEATURE                 Location/Qualifiers
source                  1..41
                        mol_type = protein
                        organism = Mus musculus
SEQUENCE: 717
TDFNEKFKNK ATLTVHKSST TVFIQLSSLT SEDSAVYYCA R                          41

SEQ ID NO: 718          moltype = AA  length = 41
FEATURE                 Location/Qualifiers
source                  1..41
                        mol_type = protein
                        organism = Mus musculus
SEQUENCE: 718
GDYNEKFKSK ATLTVDKSST TAYLQLSSLT SEDSAVYYCA R                          41

SEQ ID NO: 719          moltype = AA  length = 41
FEATURE                 Location/Qualifiers
source                  1..41
                        mol_type = protein
                        organism = Mus musculus
SEQUENCE: 719
TDNNERFKSK ATLTVDRSSS TAYMQLSSLT SEDSAVYYCA R                          41

SEQ ID NO: 720          moltype = AA  length = 41
FEATURE                 Location/Qualifiers
source                  1..41
                        mol_type = protein
                        organism = Mus musculus
SEQUENCE: 720
TNYNEKFKIK AALTVDKSST TAYMQLSSLT SEDSAVYSCA R                          41

SEQ ID NO: 721          moltype = AA  length = 41
FEATURE                 Location/Qualifiers
source                  1..41
                        mol_type = protein
                        organism = Mus musculus
SEQUENCE: 721
TYYNEKFKGK ATLTVDKSSS TASMLLSSLT SEDSAVYFCA R                          41

SEQ ID NO: 722          moltype = AA  length = 41
FEATURE                 Location/Qualifiers
source                  1..41
                        mol_type = protein
                        organism = Mus musculus
SEQUENCE: 722
TNYNEKFKGK ATLTVDKSSS TAYMLLSSLT SEDSAVYFCA R                          41

SEQ ID NO: 723          moltype = AA  length = 41
FEATURE                 Location/Qualifiers
source                  1..41
                        mol_type = protein
```

```
                        organism = Mus musculus
SEQUENCE: 723
TNYNGKFKGK ATLTADKSSS TAYMQLSSLT SEDSAVYFCA R                        41

SEQ ID NO: 724          moltype = AA  length = 41
FEATURE                 Location/Qualifiers
source                  1..41
                        mol_type = protein
                        organism = Mus musculus
SEQUENCE: 724
KWYNPSLKSR LTISKDTSRN QVFLKITSVD TADTATYYCA R                        41

SEQ ID NO: 725          moltype = AA  length = 41
FEATURE                 Location/Qualifiers
source                  1..41
                        mol_type = protein
                        organism = Mus musculus
SEQUENCE: 725
TNYNEKFKNK ATLTVDKSSS TASMQLSSLT SEDSAVYYCA R                        41

SEQ ID NO: 726          moltype = AA  length = 41
FEATURE                 Location/Qualifiers
source                  1..41
                        mol_type = protein
                        organism = Mus musculus
SEQUENCE: 726
TYYNEKFKSK ATLTVDKSSS TAYMQLSSLT SEDSAVYYCA R                        41

SEQ ID NO: 727          moltype = AA  length = 41
FEATURE                 Location/Qualifiers
source                  1..41
                        mol_type = protein
                        organism = Mus musculus
SEQUENCE: 727
TYYNEKFKGK ATLTAEKSSS TAYMQLSSLT SEDSAVYFCA R                        41

SEQ ID NO: 728          moltype = AA  length = 41
FEATURE                 Location/Qualifiers
source                  1..41
                        mol_type = protein
                        organism = Mus musculus
SEQUENCE: 728
TEYNEKFEGK ATLTSDTSSS TAYMQLSSLT SEDSAIYFCA G                        41

SEQ ID NO: 729          moltype = AA  length = 41
FEATURE                 Location/Qualifiers
source                  1..41
                        mol_type = protein
                        organism = Mus musculus
SEQUENCE: 729
TAYNEKFKGK ATVTSDTSSS TVYMQLSSLT SEDSAIYFCA G                        41

SEQ ID NO: 730          moltype = AA  length = 41
FEATURE                 Location/Qualifiers
source                  1..41
                        mol_type = protein
                        organism = Mus musculus
SEQUENCE: 730
KRYNPSLKSR LTISKDTSRN QVFLKITSVD TADTATYYCV R                        41

SEQ ID NO: 731          moltype = AA  length = 41
FEATURE                 Location/Qualifiers
source                  1..41
                        mol_type = protein
                        organism = Mus musculus
SEQUENCE: 731
TYYNEKFKGK ATLTADKSSS TAYMELRSLT SEDSAVYFCA R                        41

SEQ ID NO: 732          moltype = AA  length = 41
FEATURE                 Location/Qualifiers
source                  1..41
                        mol_type = protein
                        organism = Mus musculus
SEQUENCE: 732
TNYNAKFKDK ATLTADKSSS TAYMQLSSLT SETSAVYFCA R                        41

SEQ ID NO: 733          moltype = AA  length = 41
FEATURE                 Location/Qualifiers
source                  1..41
```

```
                        mol_type = protein
                        organism = Mus musculus
SEQUENCE: 733
TKYNEKFKGK ATLTADKSSS TAYMQLISLT SENSAVYFCA R                        41

SEQ ID NO: 734          moltype = AA  length = 41
FEATURE                 Location/Qualifiers
source                  1..41
                        mol_type = protein
                        organism = Mus musculus
SEQUENCE: 734
TDYNAAFISR LSISKDNSKS QVFFKMNSLQ ADDTAIYYCA R                        41

SEQ ID NO: 735          moltype = AA  length = 41
FEATURE                 Location/Qualifiers
source                  1..41
                        mol_type = protein
                        organism = Mus musculus
SEQUENCE: 735
TDYNAAFISR LSISKDNSKS QVFFKMNSLQ ADDTAIFYCA R                        41

SEQ ID NO: 736          moltype = AA  length = 41
FEATURE                 Location/Qualifiers
source                  1..41
                        mol_type = protein
                        organism = Mus musculus
SEQUENCE: 736
KTYNPSLNNR ISITRDTSKN QFFLKLNSVT TEDTATYYCA R                        41

SEQ ID NO: 737          moltype = AA  length = 38
FEATURE                 Location/Qualifiers
source                  1..38
                        mol_type = protein
                        organism = Mus musculus
SEQUENCE: 737
VYNPSLKNRI SITRDTSKNQ FFLKLNSLTT EDTATYYC                            38

SEQ ID NO: 738          moltype = AA  length = 41
FEATURE                 Location/Qualifiers
source                  1..41
                        mol_type = protein
                        organism = Mus musculus
SEQUENCE: 738
NNYNPSLKNR ISITRDTSKN QFFLKLNSVT TEDTATYYCA R                        41

SEQ ID NO: 739          moltype = AA  length = 41
FEATURE                 Location/Qualifiers
source                  1..41
                        mol_type = protein
                        organism = Mus musculus
SEQUENCE: 739
SNYNPSLKNR ISITRDTSKN QFFLNLNSVT TEDTATYYCA R                        41

SEQ ID NO: 740          moltype = AA  length = 41
FEATURE                 Location/Qualifiers
source                  1..41
                        mol_type = protein
                        organism = Mus musculus
SEQUENCE: 740
IYYADTVKGR FTISRDNAKN TLFLQMTSLR SEDTAMYYCA R                        41

SEQ ID NO: 741          moltype = AA  length = 41
FEATURE                 Location/Qualifiers
source                  1..41
                        mol_type = protein
                        organism = Mus musculus
SEQUENCE: 741
ERYDPSLKSR LTISKDTSRN QVFLKITSVD TADTATYYCA R                        41

SEQ ID NO: 742          moltype = AA  length = 41
FEATURE                 Location/Qualifiers
source                  1..41
                        mol_type = protein
                        organism = Mus musculus
SEQUENCE: 742
KRYNPSLKSR LKISKDTSRN QVFLKITSVD TADTATYYCA R                        41

SEQ ID NO: 743          moltype = AA  length = 41
FEATURE                 Location/Qualifiers
```

```
source                 1..41
                       mol_type = protein
                       organism = Mus musculus
SEQUENCE: 743
TIYNQKFKGK ATLTVDKSSS TAYMELRSLT SEDTAVYYCA R                      41

SEQ ID NO: 744         moltype = AA  length = 41
FEATURE                Location/Qualifiers
source                 1..41
                       mol_type = protein
                       organism = Mus musculus
SEQUENCE: 744
KRYNPSLKSR LTISKDTSRN QVFLNITSVD TADIATYYCA R                      41

SEQ ID NO: 745         moltype = AA  length = 41
FEATURE                Location/Qualifiers
source                 1..41
                       mol_type = protein
                       organism = Mus musculus
SEQUENCE: 745
KRYNPSLKSR LTISKDTSRN QVFLKITSVD TADTATYYCA R                      41

SEQ ID NO: 746         moltype = AA  length = 41
FEATURE                Location/Qualifiers
source                 1..41
                       mol_type = protein
                       organism = Mus musculus
SEQUENCE: 746
KRYNPSLKSR LTISKDTSRN QVFLKITSVD TAETATYYCA R                      41

SEQ ID NO: 747         moltype = AA  length = 41
FEATURE                Location/Qualifiers
source                 1..41
                       mol_type = protein
                       organism = Mus musculus
SEQUENCE: 747
KRYNPSLKSR LTISKDTSRK QVFLKITSVD TADTATYYCA R                      41

SEQ ID NO: 748         moltype = AA  length = 41
FEATURE                Location/Qualifiers
source                 1..41
                       mol_type = protein
                       organism = Mus musculus
SEQUENCE: 748
KRYNPSLKSR LTISKDTSRN QVFLKITSVD TEDTATYYCT R                      41

SEQ ID NO: 749         moltype = AA  length = 41
FEATURE                Location/Qualifiers
source                 1..41
                       mol_type = protein
                       organism = Mus musculus
SEQUENCE: 749
KRYNPSLKSR LTISKDTSRN QVFLKITSVD TADTATYYCT R                      41

SEQ ID NO: 750         moltype = AA  length = 41
FEATURE                Location/Qualifiers
source                 1..41
                       mol_type = protein
                       organism = Mus musculus
SEQUENCE: 750
PTYADDFKGR FAFSLETSAS TAYLQINNLK NEDTATYFCA R                      41

SEQ ID NO: 751         moltype = AA  length = 41
FEATURE                Location/Qualifiers
source                 1..41
                       mol_type = protein
                       organism = Mus musculus
SEQUENCE: 751
PTYADDFKGR FVFSLETSAS TAYLQINNLK NEDTATYFCA R                      41

SEQ ID NO: 752         moltype = AA  length = 38
FEATURE                Location/Qualifiers
source                 1..38
                       mol_type = protein
                       organism = Mus musculus
SEQUENCE: 752
NYNEKFKSKA TLTVDTSSST AYMQLSSLTS EDSAVYYC                          38

SEQ ID NO: 753         moltype = AA  length = 38
```

```
FEATURE                Location/Qualifiers
source                 1..38
                       mol_type = protein
                       organism = Mus musculus
SEQUENCE: 753
YYTDTVKGRF TISRDNAKNT LFLQMTSLRS EDTAMYYC                              38

SEQ ID NO: 754         moltype = AA  length = 38
FEATURE                Location/Qualifiers
source                 1..38
                       mol_type = protein
                       organism = Mus musculus
SEQUENCE: 754
ADNQKFKGKA ILTADKSSST AYMELRSLTS EDSAVYYC                              38

SEQ ID NO: 755         moltype = AA  length = 38
FEATURE                Location/Qualifiers
source                 1..38
                       mol_type = protein
                       organism = Mus musculus
SEQUENCE: 755
NNNEKLKSKA TLTVDKSSST AYMQLSSLTS EDSAVYYC                              38

SEQ ID NO: 756         moltype = AA  length = 38
FEATURE                Location/Qualifiers
source                 1..38
                       mol_type = protein
                       organism = Mus musculus
SEQUENCE: 756
YYNEKFKGEA TLTADKSSST AYMELRSLTS EDSAVYFC                              38

SEQ ID NO: 757         moltype = AA  length = 32
FEATURE                Location/Qualifiers
source                 1..32
                       mol_type = protein
                       organism = Mus musculus
SEQUENCE: 757
RFTISRDNAK NTLYLQMSSL RSEDTALYYC AR                                    32

SEQ ID NO: 758         moltype = AA  length = 32
FEATURE                Location/Qualifiers
source                 1..32
                       mol_type = protein
                       organism = Mus musculus
SEQUENCE: 758
KATLTADRSS SAAYMELRSL TSEDSAVYFC AR                                    32

SEQ ID NO: 759         moltype = AA  length = 32
FEATURE                Location/Qualifiers
source                 1..32
                       mol_type = protein
                       organism = Mus musculus
SEQUENCE: 759
RFTISRDNAK NTLYLQMSSL RSEDTALYYC VR                                    32

SEQ ID NO: 760         moltype = AA  length = 32
FEATURE                Location/Qualifiers
source                 1..32
                       mol_type = protein
                       organism = Mus musculus
SEQUENCE: 760
RFTISRDNAK NTLYLQMISL RSEDTALYYC AR                                    32

SEQ ID NO: 761         moltype = AA  length = 32
FEATURE                Location/Qualifiers
source                 1..32
                       mol_type = protein
                       organism = Mus musculus
SEQUENCE: 761
RLTISKDTSR NQVFLKITSV DTADTATYYC AR                                    32

SEQ ID NO: 762         moltype = AA  length = 41
FEATURE                Location/Qualifiers
source                 1..41
                       mol_type = protein
                       organism = Mus musculus
SEQUENCE: 762
IYYADTVKGR FTISRDNPKN TLFLQMTSLR SEDTAMYYCA R                          41
```

```
SEQ ID NO: 763          moltype = AA  length = 41
FEATURE                 Location/Qualifiers
source                  1..41
                        mol_type = protein
                        organism = Mus musculus
SEQUENCE: 763
IYYVDTVKGR FTISRDNSKN TLFLQMTSLR SEDTAMYYCA R                    41

SEQ ID NO: 764          moltype = AA  length = 41
FEATURE                 Location/Qualifiers
source                  1..41
                        mol_type = protein
                        organism = Mus musculus
SEQUENCE: 764
IYYVDSVRGR FTISRDDANN NVYLQMYSLK SEDTAIYYCT R                    41

SEQ ID NO: 765          moltype = AA  length = 41
FEATURE                 Location/Qualifiers
source                  1..41
                        mol_type = protein
                        organism = Mus musculus
SEQUENCE: 765
TRYTPKFKGK ATLTADKSSS TAYMQLTSLA SEDSAVYYCA K                    41

SEQ ID NO: 766          moltype = AA  length = 41
FEATURE                 Location/Qualifiers
source                  1..41
                        mol_type = protein
                        organism = Mus musculus
SEQUENCE: 766
TRYTQKFRGK ATLTADKSSN TAYMQLSSLA SEDSAVYYCA K                    41

SEQ ID NO: 767          moltype = AA  length = 11
FEATURE                 Location/Qualifiers
source                  1..11
                        mol_type = protein
                        organism = Mus musculus
SEQUENCE: 767
WGQGTTLTVS S                                                     11

SEQ ID NO: 768          moltype = AA  length = 11
FEATURE                 Location/Qualifiers
source                  1..11
                        mol_type = protein
                        organism = Mus musculus
SEQUENCE: 768
WGQGTLVTVS A                                                     11

SEQ ID NO: 769          moltype = AA  length = 11
FEATURE                 Location/Qualifiers
source                  1..11
                        mol_type = protein
                        organism = Mus musculus
SEQUENCE: 769
WGHGTSVTVS S                                                     11

SEQ ID NO: 770          moltype = AA  length = 11
FEATURE                 Location/Qualifiers
source                  1..11
                        mol_type = protein
                        organism = Mus musculus
SEQUENCE: 770
WGTGTTVTVS S                                                     11

SEQ ID NO: 771          moltype = AA  length = 11
FEATURE                 Location/Qualifiers
source                  1..11
                        mol_type = protein
                        organism = Mus musculus
SEQUENCE: 771
WGQGTSVTVS S                                                     11

SEQ ID NO: 772          moltype = AA  length = 11
FEATURE                 Location/Qualifiers
source                  1..11
                        mol_type = protein
                        organism = Mus musculus
SEQUENCE: 772
WGAGTTVTVS S                                                     11
```

```
SEQ ID NO: 773          moltype = AA  length = 11
FEATURE                 Location/Qualifiers
source                  1..11
                        mol_type = protein
                        organism = Mus musculus
SEQUENCE: 773
WGQGISVTVS S                                                  11

SEQ ID NO: 774          moltype = AA  length = 11
FEATURE                 Location/Qualifiers
source                  1..11
                        mol_type = protein
                        organism = Mus musculus
SEQUENCE: 774
WGQGTLVAVS A                                                  11

SEQ ID NO: 775          moltype = AA  length = 11
FEATURE                 Location/Qualifiers
source                  1..11
                        mol_type = protein
                        organism = Mus musculus
SEQUENCE: 775
WGQGTSLTVS S                                                  11

SEQ ID NO: 776          moltype = AA  length = 23
FEATURE                 Location/Qualifiers
source                  1..23
                        mol_type = protein
                        organism = Mus musculus
SEQUENCE: 776
DIQMTQITSS LSASLGDRVT ISC                                     23

SEQ ID NO: 777          moltype = AA  length = 23
FEATURE                 Location/Qualifiers
source                  1..23
                        mol_type = protein
                        organism = Mus musculus
SEQUENCE: 777
DIQMTQTTSS LSASLGDRVT ISC                                     23

SEQ ID NO: 778          moltype = AA  length = 23
FEATURE                 Location/Qualifiers
source                  1..23
                        mol_type = protein
                        organism = Mus musculus
SEQUENCE: 778
EIVLIQSPAL MAASPGEKVT ITC                                     23

SEQ ID NO: 779          moltype = AA  length = 23
FEATURE                 Location/Qualifiers
source                  1..23
                        mol_type = protein
                        organism = Mus musculus
SEQUENCE: 779
DIQMTQSPAS LSASVGETVT ITC                                     23

SEQ ID NO: 780          moltype = AA  length = 23
FEATURE                 Location/Qualifiers
source                  1..23
                        mol_type = protein
                        organism = Mus musculus
SEQUENCE: 780
QIVLTQSPAI MSASPGEKVT LTC                                     23

SEQ ID NO: 781          moltype = AA  length = 23
FEATURE                 Location/Qualifiers
source                  1..23
                        mol_type = protein
                        organism = Mus musculus
SEQUENCE: 781
DIKMTQSPSS LSASLGEGVS LTC                                     23

SEQ ID NO: 782          moltype = AA  length = 23
FEATURE                 Location/Qualifiers
source                  1..23
                        mol_type = protein
                        organism = Mus musculus
SEQUENCE: 782
```

```
DIQMTQSPSS LSASLGERVS LTC                                         23

SEQ ID NO: 783          moltype = AA  length = 23
FEATURE                 Location/Qualifiers
source                  1..23
                        mol_type = protein
                        organism = Mus musculus
SEQUENCE: 783
DIVMSQSPSS LAVSVGEKVT MSC                                         23

SEQ ID NO: 784          moltype = AA  length = 23
FEATURE                 Location/Qualifiers
source                  1..23
                        mol_type = protein
                        organism = Mus musculus
SEQUENCE: 784
DIVMSQSPSS LAVSAGEKVT MSC                                         23

SEQ ID NO: 785          moltype = AA  length = 23
FEATURE                 Location/Qualifiers
source                  1..23
                        mol_type = protein
                        organism = Mus musculus
SEQUENCE: 785
DVLMTQTPVS LPVSLGDQAS ISC                                         23

SEQ ID NO: 786          moltype = AA  length = 23
FEATURE                 Location/Qualifiers
source                  1..23
                        mol_type = protein
                        organism = Mus musculus
SEQUENCE: 786
DVQITQSPSY LAASPGETIT INC                                         23

SEQ ID NO: 787          moltype = AA  length = 23
FEATURE                 Location/Qualifiers
source                  1..23
                        mol_type = protein
                        organism = Mus musculus
SEQUENCE: 787
DVVMTQTPLS LPVSLGDQAS ISC                                         23

SEQ ID NO: 788          moltype = AA  length = 23
FEATURE                 Location/Qualifiers
source                  1..23
                        mol_type = protein
                        organism = Mus musculus
SEQUENCE: 788
NIMMTQSPSS LAVSAGEKVT MSC                                         23

SEQ ID NO: 789          moltype = AA  length = 23
FEATURE                 Location/Qualifiers
source                  1..23
                        mol_type = protein
                        organism = Mus musculus
SEQUENCE: 789
DIVLTQSPAS LAVSLGQRAT ISC                                         23

SEQ ID NO: 790          moltype = AA  length = 23
FEATURE                 Location/Qualifiers
source                  1..23
                        mol_type = protein
                        organism = Mus musculus
SEQUENCE: 790
DVVVTQTPLS LPVSLGDQAS ISC                                         23

SEQ ID NO: 791          moltype = AA  length = 23
FEATURE                 Location/Qualifiers
source                  1..23
                        mol_type = protein
                        organism = Mus musculus
SEQUENCE: 791
DVVMTQTPLS LCVSLGDQAS ISC                                         23

SEQ ID NO: 792          moltype = AA  length = 26
FEATURE                 Location/Qualifiers
source                  1..26
                        mol_type = protein
                        organism = Mus musculus
```

```
SEQUENCE: 792
DVVMTQTPLS LPVSLGDQAS ISCRSS                                    26

SEQ ID NO: 793          moltype = AA  length = 23
FEATURE                 Location/Qualifiers
source                  1..23
                        mol_type = protein
                        organism = Mus musculus
SEQUENCE: 793
DVVMTQTPLS LPVSLGDHAS ISC                                       23

SEQ ID NO: 794          moltype = AA  length = 23
FEATURE                 Location/Qualifiers
source                  1..23
                        mol_type = protein
                        organism = Mus musculus
SEQUENCE: 794
DVLMTQTPLS LPVSLGDQAS ISC                                       23

SEQ ID NO: 795          moltype = AA  length = 23
FEATURE                 Location/Qualifiers
source                  1..23
                        mol_type = protein
                        organism = Mus musculus
SEQUENCE: 795
DVLMTQTPLS LPVSLGDQAS IAC                                       23

SEQ ID NO: 796          moltype = AA  length = 23
FEATURE                 Location/Qualifiers
source                  1..23
                        mol_type = protein
                        organism = Mus musculus
SEQUENCE: 796
DVVLTQTPLT LSVTIGQPAS ISC                                       23

SEQ ID NO: 797          moltype = AA  length = 23
FEATURE                 Location/Qualifiers
source                  1..23
                        mol_type = protein
                        organism = Mus musculus
SEQUENCE: 797
DVVMTQTPLT LSVTIGQPAS ISC                                       23

SEQ ID NO: 798          moltype = AA  length = 23
FEATURE                 Location/Qualifiers
source                  1..23
                        mol_type = protein
                        organism = Mus musculus
SEQUENCE: 798
DVVMIQTPLT LSVTSGQPAS ISC                                       23

SEQ ID NO: 799          moltype = AA  length = 23
FEATURE                 Location/Qualifiers
source                  1..23
                        mol_type = protein
                        organism = Mus musculus
SEQUENCE: 799
DVQITQSPSY LAASPGEIII INC                                       23

SEQ ID NO: 800          moltype = AA  length = 23
FEATURE                 Location/Qualifiers
source                  1..23
                        mol_type = protein
                        organism = Mus musculus
SEQUENCE: 800
DVQITQSPSY LAASPGETIT LNC                                       23

SEQ ID NO: 801          moltype = AA  length = 23
FEATURE                 Location/Qualifiers
source                  1..23
                        mol_type = protein
                        organism = Mus musculus
SEQUENCE: 801
SIVMTQTPKF LPVSAGDRVT MTC                                       23

SEQ ID NO: 802          moltype = AA  length = 23
FEATURE                 Location/Qualifiers
source                  1..23
                        mol_type = protein
```

```
                        organism = Mus musculus
SEQUENCE: 802
SIVMTQSPKF LPVSAGDRVT MTC                                          23

SEQ ID NO: 803          moltype = AA  length = 23
FEATURE                 Location/Qualifiers
source                  1..23
                        mol_type = protein
                        organism = Mus musculus
SEQUENCE: 803
NIVMTQTPKF LPIAAGDRVI MTC                                          23

SEQ ID NO: 804          moltype = AA  length = 23
FEATURE                 Location/Qualifiers
source                  1..23
                        mol_type = protein
                        organism = Mus musculus
SEQUENCE: 804
EIVLTQSPTT MAASPGENIT ITC                                          23

SEQ ID NO: 805          moltype = AA  length = 23
FEATURE                 Location/Qualifiers
source                  1..23
                        mol_type = protein
                        organism = Mus musculus
SEQUENCE: 805
QIVLTQSPTT MAASPGEKIT ITC                                          23

SEQ ID NO: 806          moltype = AA  length = 23
FEATURE                 Location/Qualifiers
source                  1..23
                        mol_type = protein
                        organism = Mus musculus
SEQUENCE: 806
DIQMTQSPAS LSASVGETVT FTC                                          23

SEQ ID NO: 807          moltype = AA  length = 23
FEATURE                 Location/Qualifiers
source                  1..23
                        mol_type = protein
                        organism = Mus musculus
SEQUENCE: 807
SIVMTQTPKF LLVSAGDRVT ITC                                          23

SEQ ID NO: 808          moltype = AA  length = 23
FEATURE                 Location/Qualifiers
source                  1..23
                        mol_type = protein
                        organism = Mus musculus
SEQUENCE: 808
DIVMTQSPSS LSVSAGEKVT MSC                                          23

SEQ ID NO: 809          moltype = AA  length = 23
FEATURE                 Location/Qualifiers
source                  1..23
                        mol_type = protein
                        organism = Mus musculus
SEQUENCE: 809
DTVMTQSPSS LSVSAGEKVT MNC                                          23

SEQ ID NO: 810          moltype = AA  length = 23
FEATURE                 Location/Qualifiers
source                  1..23
                        mol_type = protein
                        organism = Mus musculus
SEQUENCE: 810
DIVLTQSPAS SAVSLGQRAT ISC                                          23

SEQ ID NO: 811          moltype = AA  length = 26
FEATURE                 Location/Qualifiers
source                  1..26
                        mol_type = protein
                        organism = Mus musculus
SEQUENCE: 811
DIQMTQTTSS LSASLGDRVT ISCSAS                                       26

SEQ ID NO: 812          moltype = AA  length = 26
FEATURE                 Location/Qualifiers
source                  1..26
```

```
                          mol_type = protein
                          organism = Mus musculus
SEQUENCE: 812
DVLMTQTPLS LPVSLGDQAS ISCRSS                                      26

SEQ ID NO: 813            moltype = AA  length = 26
FEATURE                   Location/Qualifiers
source                    1..26
                          mol_type = protein
                          organism = Mus musculus
SEQUENCE: 813
DIVMTQSPAT LSVTPGDRVS LSCRAS                                      26

SEQ ID NO: 814            moltype = AA  length = 23
FEATURE                   Location/Qualifiers
source                    1..23
                          mol_type = protein
                          organism = Mus musculus
SEQUENCE: 814
DIKMTQSPSS MYASLGERLS ITC                                         23

SEQ ID NO: 815            moltype = AA  length = 23
FEATURE                   Location/Qualifiers
source                    1..23
                          mol_type = protein
                          organism = Mus musculus
SEQUENCE: 815
DILLTQSPAI LSVSPGERVS FSC                                         23

SEQ ID NO: 816            moltype = AA  length = 23
FEATURE                   Location/Qualifiers
source                    1..23
                          mol_type = protein
                          organism = Mus musculus
SEQUENCE: 816
DIKMTQSPSS MYASLGERVT ITC                                         23

SEQ ID NO: 817            moltype = AA  length = 23
FEATURE                   Location/Qualifiers
source                    1..23
                          mol_type = protein
                          organism = Mus musculus
SEQUENCE: 817
DIKMIQSPSS MYASLGERVT ITC                                         23

SEQ ID NO: 818            moltype = AA  length = 23
FEATURE                   Location/Qualifiers
source                    1..23
                          mol_type = protein
                          organism = Mus musculus
SEQUENCE: 818
NIVMTQSPKS MSMSVGERVT LSC                                         23

SEQ ID NO: 819            moltype = AA  length = 23
FEATURE                   Location/Qualifiers
source                    1..23
                          mol_type = protein
                          organism = Mus musculus
SEQUENCE: 819
NIVMTQSPKS MSMSVGERVT LTC                                         23

SEQ ID NO: 820            moltype = AA  length = 23
FEATURE                   Location/Qualifiers
source                    1..23
                          mol_type = protein
                          organism = Mus musculus
SEQUENCE: 820
DVLLTQSPLS LPVSLGDQVS ISC                                         23

SEQ ID NO: 821            moltype = AA  length = 23
FEATURE                   Location/Qualifiers
source                    1..23
                          mol_type = protein
                          organism = Mus musculus
SEQUENCE: 821
DVVMTQTPLT LSVIIGQPAS IYC                                         23

SEQ ID NO: 822            moltype = AA  length = 23
FEATURE                   Location/Qualifiers
```

```
source                  1..23
                        mol_type = protein
                        organism = Mus musculus
SEQUENCE: 822
DVEMTQTPLT LSVTIGQPAS ISC                                                  23

SEQ ID NO: 823          moltype = AA  length = 15
FEATURE                 Location/Qualifiers
source                  1..15
                        mol_type = protein
                        organism = Mus musculus
SEQUENCE: 823
WYQQKPDGTV KLLIY                                                           15

SEQ ID NO: 824          moltype = AA  length = 15
FEATURE                 Location/Qualifiers
source                  1..15
                        mol_type = protein
                        organism = Mus musculus
SEQUENCE: 824
WYQQQSGTSP KPWIL                                                           15

SEQ ID NO: 825          moltype = AA  length = 15
FEATURE                 Location/Qualifiers
source                  1..15
                        mol_type = protein
                        organism = Mus musculus
SEQUENCE: 825
WYQQRQGKSP QLLVY                                                           15

SEQ ID NO: 826          moltype = AA  length = 15
FEATURE                 Location/Qualifiers
source                  1..15
                        mol_type = protein
                        organism = Mus musculus
SEQUENCE: 826
WYQQKPGSSP KLWIY                                                           15

SEQ ID NO: 827          moltype = AA  length = 15
FEATURE                 Location/Qualifiers
source                  1..15
                        mol_type = protein
                        organism = Mus musculus
SEQUENCE: 827
WLQQKPDGTI KRLIY                                                           15

SEQ ID NO: 828          moltype = AA  length = 15
FEATURE                 Location/Qualifiers
source                  1..15
                        mol_type = protein
                        organism = Mus musculus
SEQUENCE: 828
WLQQEPDGTF KRLIY                                                           15

SEQ ID NO: 829          moltype = AA  length = 15
FEATURE                 Location/Qualifiers
source                  1..15
                        mol_type = protein
                        organism = Mus musculus
SEQUENCE: 829
WYQQKPAGTV KLLIY                                                           15

SEQ ID NO: 830          moltype = AA  length = 15
FEATURE                 Location/Qualifiers
source                  1..15
                        mol_type = protein
                        organism = Mus musculus
SEQUENCE: 830
WYQQKPGQSP KLLIY                                                           15

SEQ ID NO: 831          moltype = AA  length = 15
FEATURE                 Location/Qualifiers
source                  1..15
                        mol_type = protein
                        organism = Mus musculus
SEQUENCE: 831
WYLQKPGQSP KLLIY                                                           15

SEQ ID NO: 832          moltype = AA  length = 15
```

```
FEATURE                Location/Qualifiers
source                 1..15
                       mol_type = protein
                       organism = Mus musculus
SEQUENCE: 832
WYQEKPGKTN KVLIY                                                   15

SEQ ID NO: 833         moltype = AA  length = 15
FEATURE                Location/Qualifiers
source                 1..15
                       mol_type = protein
                       organism = Mus musculus
SEQUENCE: 833
WYQQKPGQPP KLLIY                                                   15

SEQ ID NO: 834         moltype = AA  length = 15
FEATURE                Location/Qualifiers
source                 1..15
                       mol_type = protein
                       organism = Mus musculus
SEQUENCE: 834
WYLQKPGQSP NLLIY                                                   15

SEQ ID NO: 835         moltype = AA  length = 17
FEATURE                Location/Qualifiers
source                 1..17
                       mol_type = protein
                       organism = Mus musculus
SEQUENCE: 835
LYWYLQKPGQ SPKLLIY                                                 17

SEQ ID NO: 836         moltype = AA  length = 15
FEATURE                Location/Qualifiers
source                 1..15
                       mol_type = protein
                       organism = Mus musculus
SEQUENCE: 836
WYLQRPGQTP KLLIY                                                   15

SEQ ID NO: 837         moltype = AA  length = 15
FEATURE                Location/Qualifiers
source                 1..15
                       mol_type = protein
                       organism = Mus musculus
SEQUENCE: 837
WYLQKPGQSP ELLIY                                                   15

SEQ ID NO: 838         moltype = AA  length = 15
FEATURE                Location/Qualifiers
source                 1..15
                       mol_type = protein
                       organism = Mus musculus
SEQUENCE: 838
WLLQRPGQSP KRLFY                                                   15

SEQ ID NO: 839         moltype = AA  length = 15
FEATURE                Location/Qualifiers
source                 1..15
                       mol_type = protein
                       organism = Mus musculus
SEQUENCE: 839
WLLQRPGQSP KRLIY                                                   15

SEQ ID NO: 840         moltype = AA  length = 15
FEATURE                Location/Qualifiers
source                 1..15
                       mol_type = protein
                       organism = Mus musculus
SEQUENCE: 840
WLLQRPGQSP KRLMY                                                   15

SEQ ID NO: 841         moltype = AA  length = 15
FEATURE                Location/Qualifiers
source                 1..15
                       mol_type = protein
                       organism = Mus musculus
SEQUENCE: 841
WYQEKPGKTN KLLIY                                                   15
```

```
SEQ ID NO: 842          moltype = AA  length = 15
FEATURE                 Location/Qualifiers
source                  1..15
                        mol_type = protein
                        organism = Mus musculus
SEQUENCE: 842
WYQQKQGTSP QLLVY                                                    15

SEQ ID NO: 843          moltype = AA  length = 15
FEATURE                 Location/Qualifiers
source                  1..15
                        mol_type = protein
                        organism = Mus musculus
SEQUENCE: 843
WYQQKQGKSP QLLVY                                                    15

SEQ ID NO: 844          moltype = AA  length = 15
FEATURE                 Location/Qualifiers
source                  1..15
                        mol_type = protein
                        organism = Mus musculus
SEQUENCE: 844
WYQLKPGQSP KLLIY                                                    15

SEQ ID NO: 845          moltype = AA  length = 15
FEATURE                 Location/Qualifiers
source                  1..15
                        mol_type = protein
                        organism = Mus musculus
SEQUENCE: 845
WYQQKPGFSP KLLIY                                                    15

SEQ ID NO: 846          moltype = AA  length = 15
FEATURE                 Location/Qualifiers
source                  1..15
                        mol_type = protein
                        organism = Mus musculus
SEQUENCE: 846
WYQRKQGKSP QLLIY                                                    15

SEQ ID NO: 847          moltype = AA  length = 15
FEATURE                 Location/Qualifiers
source                  1..15
                        mol_type = protein
                        organism = Mus musculus
SEQUENCE: 847
WYQQKPGQPP KLLIK                                                    15

SEQ ID NO: 848          moltype = AA  length = 17
FEATURE                 Location/Qualifiers
source                  1..17
                        mol_type = protein
                        organism = Mus musculus
SEQUENCE: 848
LNWYQQKPDG TVTLLIY                                                  17

SEQ ID NO: 849          moltype = AA  length = 17
FEATURE                 Location/Qualifiers
source                  1..17
                        mol_type = protein
                        organism = Mus musculus
SEQUENCE: 849
LHWYLQKPGQ SPELLIY                                                  17

SEQ ID NO: 850          moltype = AA  length = 17
FEATURE                 Location/Qualifiers
source                  1..17
                        mol_type = protein
                        organism = Mus musculus
SEQUENCE: 850
LEWYLQKPGQ SPKLLIY                                                  17

SEQ ID NO: 851          moltype = AA  length = 17
FEATURE                 Location/Qualifiers
source                  1..17
                        mol_type = protein
                        organism = Mus musculus
SEQUENCE: 851
LHWYLQKPGQ SPKLLIY                                                  17
```

```
SEQ ID NO: 852          moltype = AA  length = 17
FEATURE                 Location/Qualifiers
source                  1..17
                        mol_type = protein
                        organism = Mus musculus
SEQUENCE: 852
LHWYQQKLHE SPRLLIK                                                   17

SEQ ID NO: 853          moltype = AA  length = 15
FEATURE                 Location/Qualifiers
source                  1..15
                        mol_type = protein
                        organism = Mus musculus
SEQUENCE: 853
WFQQKPGKSP KTLIY                                                     15

SEQ ID NO: 854          moltype = AA  length = 15
FEATURE                 Location/Qualifiers
source                  1..15
                        mol_type = protein
                        organism = Mus musculus
SEQUENCE: 854
WYQQRTNGSP RLLIK                                                     15

SEQ ID NO: 855          moltype = AA  length = 15
FEATURE                 Location/Qualifiers
source                  1..15
                        mol_type = protein
                        organism = Mus musculus
SEQUENCE: 855
WYQHKAEQSP KLLIY                                                     15

SEQ ID NO: 856          moltype = AA  length = 15
FEATURE                 Location/Qualifiers
source                  1..15
                        mol_type = protein
                        organism = Mus musculus
SEQUENCE: 856
WYQQKPEQSP KLLIY                                                     15

SEQ ID NO: 857          moltype = AA  length = 15
FEATURE                 Location/Qualifiers
source                  1..15
                        mol_type = protein
                        organism = Mus musculus
SEQUENCE: 857
WLLQRPGQTP KRLIY                                                     15

SEQ ID NO: 858          moltype = AA  length = 32
FEATURE                 Location/Qualifiers
source                  1..32
                        mol_type = protein
                        organism = Mus musculus
SEQUENCE: 858
GVPSRFSGSG SGTDYSLTIS NLEPEDIATY YC                                  32

SEQ ID NO: 859          moltype = AA  length = 32
FEATURE                 Location/Qualifiers
source                  1..32
                        mol_type = protein
                        organism = Mus musculus
SEQUENCE: 859
GVPSRFSGSG SGIDYSLTIS NLEPEDIATY YC                                  32

SEQ ID NO: 860          moltype = AA  length = 32
FEATURE                 Location/Qualifiers
source                  1..32
                        mol_type = protein
                        organism = Mus musculus
SEQUENCE: 860
GVPVRFSGSG SGTSYSLTIS SMEAEDAATY YC                                  32

SEQ ID NO: 861          moltype = AA  length = 32
FEATURE                 Location/Qualifiers
source                  1..32
                        mol_type = protein
                        organism = Mus musculus
SEQUENCE: 861
```

```
GVPSRFSGSG SGTQYSLKIN SLQPEDFGSY CC                              32

SEQ ID NO: 862          moltype = AA  length = 32
FEATURE                 Location/Qualifiers
source                  1..32
                        mol_type = protein
                        organism = Mus musculus
SEQUENCE: 862
RVPTRFSGSG SGTSYSLTIS SMEAEDAASY FC                              32

SEQ ID NO: 863          moltype = AA  length = 32
FEATURE                 Location/Qualifiers
source                  1..32
                        mol_type = protein
                        organism = Mus musculus
SEQUENCE: 863
DVPKRFSGSR SGSDYSLTIS SLESEDFVDY FC                              32

SEQ ID NO: 864          moltype = AA  length = 32
FEATURE                 Location/Qualifiers
source                  1..32
                        mol_type = protein
                        organism = Mus musculus
SEQUENCE: 864
GVPKRFSGSR SGSDYSLTIS SLESEDFVDY YC                              32

SEQ ID NO: 865          moltype = AA  length = 32
FEATURE                 Location/Qualifiers
source                  1..32
                        mol_type = protein
                        organism = Mus musculus
SEQUENCE: 865
GVPSRFSGSG SGTDYSLTIS NLEQEDVATY FC                              32

SEQ ID NO: 866          moltype = AA  length = 32
FEATURE                 Location/Qualifiers
source                  1..32
                        mol_type = protein
                        organism = Mus musculus
SEQUENCE: 866
GVPDRFTGSG SGTDFTLTIS SVKAEDLAVY YC                              32

SEQ ID NO: 867          moltype = AA  length = 32
FEATURE                 Location/Qualifiers
source                  1..32
                        mol_type = protein
                        organism = Mus musculus
SEQUENCE: 867
GVPDRFTGSG SGTDFTLTIT TVQAEDLAVY YC                              32

SEQ ID NO: 868          moltype = AA  length = 32
FEATURE                 Location/Qualifiers
source                  1..32
                        mol_type = protein
                        organism = Mus musculus
SEQUENCE: 868
GVPDRFSGSG SGTDFTLKIS RVEAEDLGVY YC                              32

SEQ ID NO: 869          moltype = AA  length = 32
FEATURE                 Location/Qualifiers
source                  1..32
                        mol_type = protein
                        organism = Mus musculus
SEQUENCE: 869
GIPSRFSGSG SGTDFTLTIS SLEPEDFAMY YC                              32

SEQ ID NO: 870          moltype = AA  length = 32
FEATURE                 Location/Qualifiers
source                  1..32
                        mol_type = protein
                        organism = Mus musculus
SEQUENCE: 870
GVPDRFSGSG SGTDFTLKIS RVEAEDLGVY FC                              32

SEQ ID NO: 871          moltype = AA  length = 32
FEATURE                 Location/Qualifiers
source                  1..32
                        mol_type = protein
                        organism = Mus musculus
```

```
SEQUENCE: 871
GVPDRFTGSG SGTDFTLTIS SVQAEDLAVY YC                                32

SEQ ID NO: 872          moltype = AA  length = 32
FEATURE                 Location/Qualifiers
source                  1..32
                        mol_type = protein
                        organism = Mus musculus
SEQUENCE: 872
GVPARFSGSG SGTDFTLNIH PVEEEDAATY YC                                32

SEQ ID NO: 873          moltype = AA  length = 36
FEATURE                 Location/Qualifiers
source                  1..36
                        mol_type = protein
                        organism = Mus musculus
SEQUENCE: 873
NRFSGVPDRF GGSGSGTDFT LKISRVEAED LGVYFC                            36

SEQ ID NO: 874          moltype = AA  length = 32
FEATURE                 Location/Qualifiers
source                  1..32
                        mol_type = protein
                        organism = Mus musculus
SEQUENCE: 874
GVPDRFSGSG SGTDFTLKIS SVEAEDLGVY FC                                32

SEQ ID NO: 875          moltype = AA  length = 32
FEATURE                 Location/Qualifiers
source                  1..32
                        mol_type = protein
                        organism = Mus musculus
SEQUENCE: 875
GVPDRFSGSG SGTDFTLKIN RVEAEDLGVY FC                                32

SEQ ID NO: 876          moltype = AA  length = 32
FEATURE                 Location/Qualifiers
source                  1..32
                        mol_type = protein
                        organism = Mus musculus
SEQUENCE: 876
GVPGRFSGSG SGTDFTLKIS RVEAEDLGVY YC                                32

SEQ ID NO: 877          moltype = AA  length = 32
FEATURE                 Location/Qualifiers
source                  1..32
                        mol_type = protein
                        organism = Mus musculus
SEQUENCE: 877
GVPDRFTGSG SGTDFTLKIS SVEAEDLGVY YC                                32

SEQ ID NO: 878          moltype = AA  length = 32
FEATURE                 Location/Qualifiers
source                  1..32
                        mol_type = protein
                        organism = Mus musculus
SEQUENCE: 878
GVPDRFTGSG SGTDFTLKIS RVEAEDLGVY YC                                32

SEQ ID NO: 879          moltype = AA  length = 32
FEATURE                 Location/Qualifiers
source                  1..32
                        mol_type = protein
                        organism = Mus musculus
SEQUENCE: 879
GIPSRFSGSG SGTDFTLTIS SLEPEDFAMY FC                                32

SEQ ID NO: 880          moltype = AA  length = 32
FEATURE                 Location/Qualifiers
source                  1..32
                        mol_type = protein
                        organism = Mus musculus
SEQUENCE: 880
GVPSRFSGSG SGTQFSLKIN SLQPEDFGSY YC                                32

SEQ ID NO: 881          moltype = AA  length = 32
FEATURE                 Location/Qualifiers
source                  1..32
                        mol_type = protein
```

```
                         organism = Mus musculus
SEQUENCE: 881
GVPDRFTASG SGTDFTFTIS SVQVEDLAVY FC                                    32

SEQ ID NO: 882           moltype = AA  length = 32
FEATURE                  Location/Qualifiers
source                   1..32
                         mol_type = protein
                         organism = Mus musculus
SEQUENCE: 882
GVPDRFTGSG SGTDFTLTIS SVQVEDLVVY FC                                    32

SEQ ID NO: 883           moltype = AA  length = 32
FEATURE                  Location/Qualifiers
source                   1..32
                         mol_type = protein
                         organism = Mus musculus
SEQUENCE: 883
GVPDRFTGSG SGTDFTFTIS SVQVEDLAVY FC                                    32

SEQ ID NO: 884           moltype = AA  length = 32
FEATURE                  Location/Qualifiers
source                   1..32
                         mol_type = protein
                         organism = Mus musculus
SEQUENCE: 884
GVPDRFSGSG SGTDFTLKIS KVEAEDLGVY FC                                    32

SEQ ID NO: 885           moltype = AA  length = 32
FEATURE                  Location/Qualifiers
source                   1..32
                         mol_type = protein
                         organism = Mus musculus
SEQUENCE: 885
GVPTRFSGSG SGTSYSLTIG AMEAEDVATY YC                                    32

SEQ ID NO: 886           moltype = AA  length = 32
FEATURE                  Location/Qualifiers
source                   1..32
                         mol_type = protein
                         organism = Mus musculus
SEQUENCE: 886
GVPARFSGSG SGTSYSLTIG TMEAEDVATY YC                                    32

SEQ ID NO: 887           moltype = AA  length = 32
FEATURE                  Location/Qualifiers
source                   1..32
                         mol_type = protein
                         organism = Mus musculus
SEQUENCE: 887
GMSSRFSGSG SGRQYSLKIS SLHPDDVATY YC                                    32

SEQ ID NO: 888           moltype = AA  length = 32
FEATURE                  Location/Qualifiers
source                   1..32
                         mol_type = protein
                         organism = Mus musculus
SEQUENCE: 888
GVPDRFTGSG YGTDFTFTIS TVQAEDLAVY FC                                    32

SEQ ID NO: 889           moltype = AA  length = 32
FEATURE                  Location/Qualifiers
source                   1..32
                         mol_type = protein
                         organism = Mus musculus
SEQUENCE: 889
GVPARFSGSG SGTDFTLNIH PVEEEDTATY YC                                    32

SEQ ID NO: 890           moltype = AA  length = 36
FEATURE                  Location/Qualifiers
source                   1..36
                         mol_type = protein
                         organism = Mus musculus
SEQUENCE: 890
SLHSGVPSRF SGSGSGTDYS LTISNLEPED IATYYC                                36

SEQ ID NO: 891           moltype = AA  length = 36
FEATURE                  Location/Qualifiers
source                   1..36
```

```
                        mol_type = protein
                        organism = Mus musculus
SEQUENCE: 891
NRFFGVPDRF SGSGSGTDFT LKISRVEAED LGVYFC                          36

SEQ ID NO: 892          moltype = AA  length = 36
FEATURE                 Location/Qualifiers
source                  1..36
                        mol_type = protein
                        organism = Mus musculus
SEQUENCE: 892
NRFSGVPDRF SGSGSGTDFT LKISRVEAED LGVYYC                          36

SEQ ID NO: 893          moltype = AA  length = 36
FEATURE                 Location/Qualifiers
source                  1..36
                        mol_type = protein
                        organism = Mus musculus
SEQUENCE: 893
NRFSGVPDRF SGSGSGTDFT LKISRVEAED LGVYFC                          36

SEQ ID NO: 894          moltype = AA  length = 36
FEATURE                 Location/Qualifiers
source                  1..36
                        mol_type = protein
                        organism = Mus musculus
SEQUENCE: 894
QSISGSPSRF SGSGSGSDFT LSINSVEPED VGVYYC                          36

SEQ ID NO: 895          moltype = AA  length = 32
FEATURE                 Location/Qualifiers
source                  1..32
                        mol_type = protein
                        organism = Mus musculus
SEQUENCE: 895
GVPSRFSGSG SGQDYSLTIS SLEDEDMGIY YC                              32

SEQ ID NO: 896          moltype = AA  length = 32
FEATURE                 Location/Qualifiers
source                  1..32
                        mol_type = protein
                        organism = Mus musculus
SEQUENCE: 896
GIPSRFSGSG SGTDFTLSIN SVESEDIADY YC                              32

SEQ ID NO: 897          moltype = AA  length = 32
FEATURE                 Location/Qualifiers
source                  1..32
                        mol_type = protein
                        organism = Mus musculus
SEQUENCE: 897
GVPSRFSGSG SGQDYSLTIS SLEYEDMGIY YC                              32

SEQ ID NO: 898          moltype = AA  length = 32
FEATURE                 Location/Qualifiers
source                  1..32
                        mol_type = protein
                        organism = Mus musculus
SEQUENCE: 898
GVPSRFSGSG SGQDYSLTIS RLEYEDVGLY YC                              32

SEQ ID NO: 899          moltype = AA  length = 32
FEATURE                 Location/Qualifiers
source                  1..32
                        mol_type = protein
                        organism = Mus musculus
SEQUENCE: 899
GVPDRFTGSG SATDFTLIIS SVQAEDLADY HC                              32

SEQ ID NO: 900          moltype = AA  length = 32
FEATURE                 Location/Qualifiers
source                  1..32
                        mol_type = protein
                        organism = Mus musculus
SEQUENCE: 900
GVPDRFTGSG SATDFTLTIS SVQAEDLADY HC                              32

SEQ ID NO: 901          moltype = AA  length = 32
FEATURE                 Location/Qualifiers
```

```
source                1..32
                      mol_type = protein
                      organism = Mus musculus
SEQUENCE: 901
GVPDRFSGSG SGTYFTLKIS RVEAEDLGVY HC                              32

SEQ ID NO: 902        moltype = AA  length = 32
FEATURE               Location/Qualifiers
source                1..32
                      mol_type = protein
                      organism = Mus musculus
SEQUENCE: 902
GVPDRFTGSG SGTDFALQIS RVEAEDLGIY YC                              32

SEQ ID NO: 903        moltype = AA  length = 32
FEATURE               Location/Qualifiers
source                1..32
                      mol_type = protein
                      organism = Mus musculus
SEQUENCE: 903
GVPDRFTGSG SGTDFTLKIK RVEAEDLGVY YC                              32

SEQ ID NO: 904        moltype = AA  length = 32
FEATURE               Location/Qualifiers
source                1..32
                      mol_type = protein
                      organism = Mus musculus
SEQUENCE: 904
GVPDRFTGSG SGTDFTLKIN RVVAEDLGVY SC                              32

SEQ ID NO: 905        moltype = AA  length = 10
FEATURE               Location/Qualifiers
source                1..10
                      mol_type = protein
                      organism = Mus musculus
SEQUENCE: 905
FGSGTKLEIK                                                       10

SEQ ID NO: 906        moltype = AA  length = 10
FEATURE               Location/Qualifiers
source                1..10
                      mol_type = protein
                      organism = Mus musculus
SEQUENCE: 906
FGGGTKLEIK                                                       10

SEQ ID NO: 907        moltype = AA  length = 10
FEATURE               Location/Qualifiers
source                1..10
                      mol_type = protein
                      organism = Mus musculus
SEQUENCE: 907
FGTGTKLEIK                                                       10

SEQ ID NO: 908        moltype = AA  length = 10
FEATURE               Location/Qualifiers
source                1..10
                      mol_type = protein
                      organism = Mus musculus
SEQUENCE: 908
FGAGTKLELK                                                       10

SEQ ID NO: 909        moltype = AA  length = 10
FEATURE               Location/Qualifiers
source                1..10
                      mol_type = protein
                      organism = Mus musculus
SEQUENCE: 909
FGGGSKLEIK                                                       10

SEQ ID NO: 910        moltype = AA  length = 10
FEATURE               Location/Qualifiers
source                1..10
                      mol_type = protein
                      organism = Mus musculus
SEQUENCE: 910
FGGGTKLEIE                                                       10

SEQ ID NO: 911        moltype = AA  length = 10
```

```
FEATURE                Location/Qualifiers
source                 1..10
                       mol_type = protein
                       organism = Mus musculus
SEQUENCE: 911
FGTGTKLELK                                                          10

SEQ ID NO: 912         moltype = AA  length = 10
FEATURE                Location/Qualifiers
source                 1..10
                       mol_type = protein
                       organism = Mus musculus
SEQUENCE: 912
FGGGTKLEMK                                                          10

SEQ ID NO: 913         moltype = AA  length = 10
FEATURE                Location/Qualifiers
source                 1..10
                       mol_type = protein
                       organism = Mus musculus
SEQUENCE: 913
FGSGTNLEIK                                                          10

SEQ ID NO: 914         moltype = AA  length = 10
FEATURE                Location/Qualifiers
source                 1..10
                       mol_type = protein
                       organism = Mus musculus
SEQUENCE: 914
FGGGTKLEIR                                                          10

SEQ ID NO: 915         moltype = AA  length = 10
FEATURE                Location/Qualifiers
source                 1..10
                       mol_type = protein
                       organism = Mus musculus
SEQUENCE: 915
FGGGTKLEVK                                                          10

SEQ ID NO: 916         moltype = AA  length = 10
FEATURE                Location/Qualifiers
source                 1..10
                       mol_type = protein
                       organism = Mus musculus
SEQUENCE: 916
FGGGAKLEIK                                                          10

SEQ ID NO: 917         moltype = AA  length = 10
FEATURE                Location/Qualifiers
source                 1..10
                       mol_type = protein
                       organism = Mus musculus
SEQUENCE: 917
FGAGTKLELR                                                          10

SEQ ID NO: 918         moltype = AA  length = 10
FEATURE                Location/Qualifiers
source                 1..10
                       mol_type = protein
                       organism = Mus musculus
SEQUENCE: 918
FGGGTKLELK                                                          10

SEQ ID NO: 919         moltype = AA  length = 10
FEATURE                Location/Qualifiers
source                 1..10
                       mol_type = protein
                       organism = Mus musculus
SEQUENCE: 919
FGAGTKLEVK                                                          10

SEQ ID NO: 920         moltype = AA  length = 441
FEATURE                Location/Qualifiers
source                 1..441
                       mol_type = protein
                       organism = Homo sapiens
SEQUENCE: 920
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
```

```
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIINK KLDLSNVQSK CGSKDNIKHV  300
PGGGSVQIVY KPVDLSKVTS KCGSLGNIHH KPGGGQVEVK SEKLDFKDRV QSKIGSLDNI  360
THVPGGGNKK IETHKLTFRE NAKAKTDHGA EIVYKSPVVS GDTSPRHLSN VSSTGSIDMV  420
DSPQLATLAD EVSASLAKQG L                                            441

SEQ ID NO: 921         moltype = AA  length = 20
FEATURE                Location/Qualifiers
SITE                   8
                       note = Phosphorylated Thr
SITE                   13
                       note = Phosphorylated Thr
source                 1..20
                       mol_type = protein
                       organism = Homo sapiens
SEQUENCE: 921
TPGSRSRTPS LPTPPTREPK                                              20

SEQ ID NO: 922         moltype = AA  length = 19
FEATURE                Location/Qualifiers
SITE                   9
                       note = Phosphorylated Thr
SITE                   11
                       note = Phosphorylated Ser
SITE                   14
                       note = Phosphorylated Thr
source                 1..19
                       mol_type = protein
                       organism = Homo sapiens
SEQUENCE: 922
GTPGSRSRTP SLPTPPTRE                                               19

SEQ ID NO: 923         moltype = AA  length = 37
FEATURE                Location/Qualifiers
SITE                   18
                       note = Phosphorylated Ser
SITE                   26
                       note = Phosphorylated Ser
SITE                   31
                       note = Phosphorylated Ser
source                 1..37
                       mol_type = protein
                       organism = Homo sapiens
SEQUENCE: 923
RENAKAKTDH GAEIVYKSPV VSGDTSPRHL SNVSSTG                           37

SEQ ID NO: 924         moltype = AA  length = 8
FEATURE                Location/Qualifiers
source                 1..8
                       mol_type = protein
                       organism = Homo sapiens
SEQUENCE: 924
PTREPKKV                                                           8

SEQ ID NO: 925         moltype = AA  length = 7
FEATURE                Location/Qualifiers
source                 1..7
                       mol_type = protein
                       organism = Homo sapiens
SEQUENCE: 925
ARMVSKS                                                            7

SEQ ID NO: 926         moltype = AA  length = 24
FEATURE                Location/Qualifiers
source                 1..24
                       mol_type = protein
                       organism = Homo sapiens
SEQUENCE: 926
SPSSAKSRLQ TAPVPMPDLK NVKS                                         24

SEQ ID NO: 927         moltype = AA  length = 7
FEATURE                Location/Qualifiers
REGION                 1..7
                       note = Description of Artificial Sequence: Synthetic
                        consensus sequence
VARIANT                7
                       note = Tyr or Asn
source                 1..7
```

```
                        mol_type = protein
                        organism = synthetic construct
SEQUENCE: 927
GYTFTSX                                                                 7

SEQ ID NO: 928          moltype = AA  length = 7
FEATURE                 Location/Qualifiers
REGION                  1..7
                        note = Description of Artificial Sequence: Synthetic
                         consensus sequence
VARIANT                 7
                        note = Any amino acid
source                  1..7
                        mol_type = protein
                        organism = synthetic construct
SEQUENCE: 928
GYTFTSX                                                                 7

SEQ ID NO: 929          moltype = AA  length = 6
FEATURE                 Location/Qualifiers
REGION                  1..6
                        note = Description of Artificial Sequence: Synthetic
                         consensus sequence
VARIANT                 6
                        note = Asp or Glu
source                  1..6
                        mol_type = protein
                        organism = synthetic construct
SEQUENCE: 929
NPNNSX                                                                  6

SEQ ID NO: 930          moltype = AA  length = 6
FEATURE                 Location/Qualifiers
REGION                  1..6
                        note = Description of Artificial Sequence: Synthetic
                         consensus sequence
VARIANT                 6
                        note = Any amino acid
source                  1..6
                        mol_type = protein
                        organism = synthetic construct
SEQUENCE: 930
NPNNSX                                                                  6

SEQ ID NO: 931          moltype = AA  length = 7
FEATURE                 Location/Qualifiers
REGION                  1..7
                        note = Description of Artificial Sequence: Synthetic
                         consensus sequence
VARIANT                 2
                        note = Phe or Tyr
VARIANT                 6
                        note = Arg or Ile
VARIANT                 7
                        note = Tyr or Phe
source                  1..7
                        mol_type = protein
                        organism = synthetic construct
SEQUENCE: 931
GXTFTXX                                                                 7

SEQ ID NO: 932          moltype = AA  length = 7
FEATURE                 Location/Qualifiers
REGION                  1..7
                        note = Description of Artificial Sequence: Synthetic
                         consensus sequence
VARIANT                 2
                        note = Any amino acid
VARIANT                 6
                        note = Any amino acid
VARIANT                 7
                        note = Any amino acid
source                  1..7
                        mol_type = protein
                        organism = synthetic construct
SEQUENCE: 932
GXTFTXX                                                                 7

SEQ ID NO: 933          moltype = AA  length = 16
```

```
FEATURE               Location/Qualifiers
REGION                1..16
                      note = Description of Artificial Sequence: Synthetic
                       consensus sequence
VARIANT               9
                      note = Asn or Ser
VARIANT               12
                      note = Ile or Asn
VARIANT               14
                      note = His or Tyr
source                1..16
                      mol_type = protein
                      organism = synthetic construct
SEQUENCE: 933
RSSQSLVHXN GXTXLY                                                  16

SEQ ID NO: 934        moltype = AA  length = 16
FEATURE               Location/Qualifiers
REGION                1..16
                      note = Description of Artificial Sequence: Synthetic
                       consensus sequence
VARIANT               9
                      note = Any amino acid
VARIANT               12
                      note = Any amino acid
VARIANT               14
                      note = Any amino acid
source                1..16
                      mol_type = protein
                      organism = synthetic construct
SEQUENCE: 934
RSSQSLVHXN GXTXLY                                                  16

SEQ ID NO: 935        moltype = AA  length = 7
FEATURE               Location/Qualifiers
REGION                1..7
                      note = Description of Artificial Sequence: Synthetic
                       consensus sequence
VARIANT               4
                      note = Asn or Ser
source                1..7
                      mol_type = protein
                      organism = synthetic construct
SEQUENCE: 935
RVSXRFS                                                            7

SEQ ID NO: 936        moltype = AA  length = 7
FEATURE               Location/Qualifiers
REGION                1..7
                      note = Description of Artificial Sequence: Synthetic
                       consensus sequence
VARIANT               4
                      note = Any amino acid
source                1..7
                      mol_type = protein
                      organism = synthetic construct
SEQUENCE: 936
RVSXRFS                                                            7

SEQ ID NO: 937        moltype = AA  length = 7
FEATURE               Location/Qualifiers
REGION                1..7
                      note = Description of Artificial Sequence: Synthetic
                       consensus sequence
VARIANT               2
                      note = Phe or Tyr
VARIANT               6
                      note = Arg, Ile, or Asp
VARIANT               7
                      note = Tyr or Phe
source                1..7
                      mol_type = protein
                      organism = synthetic construct
SEQUENCE: 937
GXTFTXX                                                            7

SEQ ID NO: 938        moltype = AA  length = 7
FEATURE               Location/Qualifiers
REGION                1..7
```

```
                     note = Description of Artificial Sequence: Synthetic
                      consensus sequence
VARIANT              2
                     note = Any amino acid
VARIANT              6..7
                     note = Any amino acid
source               1..7
                     mol_type = protein
                     organism = synthetic construct
SEQUENCE: 938
GXTFTXX                                                                    7

SEQ ID NO: 939       moltype = AA  length = 6
FEATURE              Location/Qualifiers
REGION               1..6
                     note = Description of Artificial Sequence: Synthetic
                      consensus sequence
VARIANT              6
                     note = Gly or Glu
source               1..6
                     mol_type = protein
                     organism = synthetic construct
SEQUENCE: 939
NPNNGX                                                                     6

SEQ ID NO: 940       moltype = AA  length = 6
FEATURE              Location/Qualifiers
REGION               1..6
                     note = Description of Artificial Sequence: Synthetic
                      consensus sequence
VARIANT              6
                     note = Any amino acid
source               1..6
                     mol_type = protein
                     organism = synthetic construct
SEQUENCE: 940
NPNNGX                                                                     6

SEQ ID NO: 941       moltype = AA  length = 11
FEATURE              Location/Qualifiers
REGION               1..11
                     note = Description of Artificial Sequence: Synthetic
                      consensus sequence
VARIANT              2
                     note = Thr or Arg
VARIANT              4
                     note = Thr or Met
VARIANT              6
                     note = Tyr or absent
VARIANT              7
                     note = Tyr or absent
VARIANT              9
                     note = Met or Leu
source               1..11
                     mol_type = protein
                     organism = synthetic construct
SEQUENCE: 941
GXGXGXXAXD Y                                                               11

SEQ ID NO: 942       moltype = AA  length = 11
FEATURE              Location/Qualifiers
REGION               1..11
                     note = Description of Artificial Sequence: Synthetic
                      consensus sequence
VARIANT              2
                     note = Any amino acid
VARIANT              4
                     note = Any amino acid
VARIANT              6
                     note = Any amino acid or absent
VARIANT              7
                     note = Any amino acid or absent
VARIANT              9
                     note = Any amino acid
source               1..11
                     mol_type = protein
                     organism = synthetic construct
SEQUENCE: 942
GXGXGXXAXD Y                                                               11
```

```
SEQ ID NO: 943          moltype =   length =
SEQUENCE: 943
000

SEQ ID NO: 944          moltype =   length =
SEQUENCE: 944
000

SEQ ID NO: 945          moltype =   length =
SEQUENCE: 945
000

SEQ ID NO: 946          moltype =   length =
SEQUENCE: 946
000

SEQ ID NO: 947          moltype =   length =
SEQUENCE: 947
000

SEQ ID NO: 948          moltype =   length =
SEQUENCE: 948
000

SEQ ID NO: 949          moltype = AA  length = 7
FEATURE                 Location/Qualifiers
REGION                  1..7
                        note = Description of Artificial Sequence: Synthetic
                         consensus sequence
VARIANT                 3
                        note = Ser or Thr
VARIANT                 6
                        note = Asp or Glu
source                  1..7
                        mol_type = protein
                        organism = synthetic construct
SEQUENCE: 949
GYXFTXY                                                                    7

SEQ ID NO: 950          moltype = AA  length = 7
FEATURE                 Location/Qualifiers
REGION                  1..7
                        note = Description of Artificial Sequence: Synthetic
                         consensus sequence
VARIANT                 3
                        note = Any amino acid
VARIANT                 6
                        note = Any amino acid
source                  1..7
                        mol_type = protein
                        organism = synthetic construct
SEQUENCE: 950
GYXFTXY                                                                    7

SEQ ID NO: 951          moltype =   length =
SEQUENCE: 951
000

SEQ ID NO: 952          moltype =   length =
SEQUENCE: 952
000

SEQ ID NO: 953          moltype = AA  length = 12
FEATURE                 Location/Qualifiers
REGION                  1..12
                        note = Description of Artificial Sequence: Synthetic
                         consensus sequence
VARIANT                 2
                        note = Thr or Ala
VARIANT                 3
                        note = Val, Ile, or Tyr
VARIANT                 4
                        note = Val or Tyr
VARIANT                 5
                        note = Ala or Ser
VARIANT                 6
                        note = Arg or Lys
VARIANT                 11
```

```
                        note = Asp or Glu
source                  1..12
                        mol_type = protein
                        organism = synthetic construct
SEQUENCE: 953
PXXXXXDYAM XY                                                12

SEQ ID NO: 954          moltype = AA  length = 12
FEATURE                 Location/Qualifiers
REGION                  1..12
                        note = Description of Artificial Sequence: Synthetic
                         consensus sequence
VARIANT                 2..6
                        note = Any amino acid
VARIANT                 11
                        note = Any amino acid
source                  1..12
                        mol_type = protein
                        organism = synthetic construct
SEQUENCE: 954
PXXXXXDYAM XY                                                12

SEQ ID NO: 955          moltype = AA  length = 16
FEATURE                 Location/Qualifiers
REGION                  1..16
                        note = Description of Artificial Sequence: Synthetic
                         consensus sequence
VARIANT                 8
                        note = Tyr or His
VARIANT                 9
                        note = Ser, Arg, or Thr
source                  1..16
                        mol_type = protein
                        organism = synthetic construct
SEQUENCE: 955
RSSQSIVXXN GNTYLE                                            16

SEQ ID NO: 956          moltype = AA  length = 16
FEATURE                 Location/Qualifiers
REGION                  1..16
                        note = Description of Artificial Sequence: Synthetic
                         consensus sequence
VARIANT                 8..9
                        note = Any amino acid
source                  1..16
                        mol_type = protein
                        organism = synthetic construct
SEQUENCE: 956
RSSQSIVXXN GNTYLE                                            16

SEQ ID NO: 957          moltype = AA  length = 9
FEATURE                 Location/Qualifiers
REGION                  1..9
                        note = Description of Artificial Sequence: Synthetic
                         consensus sequence
VARIANT                 8
                        note = Tyr or Phe
source                  1..9
                        mol_type = protein
                        organism = synthetic construct
SEQUENCE: 957
FQGSHVPXT                                                    9

SEQ ID NO: 958          moltype = AA  length = 9
FEATURE                 Location/Qualifiers
REGION                  1..9
                        note = Description of Artificial Sequence: Synthetic
                         consensus sequence
VARIANT                 8
                        note = Any amino acid
source                  1..9
                        mol_type = protein
                        organism = synthetic construct
SEQUENCE: 958
FQGSHVPXT                                                    9

SEQ ID NO: 959          moltype = AA  length = 7
FEATURE                 Location/Qualifiers
REGION                  1..7
```

```
                        note = Description of Artificial Sequence: Synthetic
                         consensus sequence
VARIANT                 3
                        note = Ser or Thr
VARIANT                 6
                        note = Asp, Glu, or Ser
source                  1..7
                        mol_type = protein
                        organism = synthetic construct
SEQUENCE: 959
GYXFTXY                                                                   7

SEQ ID NO: 960          moltype =   length =
SEQUENCE: 960
000

SEQ ID NO: 961          moltype =   length =
SEQUENCE: 961
000

SEQ ID NO: 962          moltype = AA  length = 12
FEATURE                 Location/Qualifiers
REGION                  1..12
                        note = Description of Artificial Sequence: Synthetic
                         consensus sequence
VARIANT                 1
                        note = Pro or Ser
VARIANT                 2
                        note = Thr, Ala, or Ser
VARIANT                 3
                        note = Val, Ile, or Tyr
VARIANT                 4
                        note = Val or Tyr
VARIANT                 5
                        note = Ala, Ser, or Gly
VARIANT                 6
                        note = Arg or Lys
VARIANT                 11
                        note = Asp or Glu
source                  1..12
                        mol_type = protein
                        organism = synthetic construct
SEQUENCE: 962
XXXXXXDYAM XY                                                             12

SEQ ID NO: 963          moltype = AA  length = 12
FEATURE                 Location/Qualifiers
REGION                  1..12
                        note = Description of Artificial Sequence: Synthetic
                         consensus sequence
VARIANT                 1..6
                        note = Any amino acid
VARIANT                 11
                        note = Any amino acid
source                  1..12
                        mol_type = protein
                        organism = synthetic construct
SEQUENCE: 963
XXXXXXDYAM XY                                                             12

SEQ ID NO: 964          moltype = AA  length = 9
FEATURE                 Location/Qualifiers
REGION                  1..9
                        note = Description of Artificial Sequence: Synthetic
                         consensus sequence
VARIANT                 5
                        note = Ser or Asn
VARIANT                 7
                        note = Ser or Phe
VARIANT                 8
                        note = Ala or Gly
source                  1..9
                        mol_type = protein
                        organism = synthetic construct
SEQUENCE: 964
GFSLXTXXM                                                                 9

SEQ ID NO: 965          moltype = AA  length = 9
FEATURE                 Location/Qualifiers
```

```
REGION                  1..9
                        note = Description of Artificial Sequence: Synthetic
                         consensus sequence
VARIANT                 5
                        note = Any amino acid
VARIANT                 7..8
                        note = Any amino acid
source                  1..9
                        mol_type = protein
                        organism = synthetic construct
SEQUENCE: 965
GFSLXTXXM                                                                    9

SEQ ID NO: 966          moltype = AA  length = 9
FEATURE                 Location/Qualifiers
REGION                  1..9
                        note = Description of Artificial Sequence: Synthetic
                         consensus sequence
VARIANT                 2
                        note = Arg, Val, or Lys
VARIANT                 4
                        note = Gly, Tyr, or Ser
VARIANT                 6
                        note = Gly or Ala
source                  1..9
                        mol_type = protein
                        organism = synthetic construct
SEQUENCE: 966
RXRXYXMDY                                                                    9

SEQ ID NO: 967          moltype = AA  length = 9
FEATURE                 Location/Qualifiers
REGION                  1..9
                        note = Description of Artificial Sequence: Synthetic
                         consensus sequence
VARIANT                 2
                        note = Any amino acid
VARIANT                 4
                        note = Any amino acid
VARIANT                 6
                        note = Any amino acid
source                  1..9
                        mol_type = protein
                        organism = synthetic construct
SEQUENCE: 967
RXRXYXMDY                                                                    9

SEQ ID NO: 968          moltype = AA  length = 17
FEATURE                 Location/Qualifiers
REGION                  1..17
                        note = Description of Artificial Sequence: Synthetic
                         consensus sequence
VARIANT                 2
                        note = Ala or Ser
VARIANT                 6
                        note = Val or Leu
VARIANT                 7
                        note = Ser or Leu
VARIANT                 8
                        note = Asn or Ser
VARIANT                 9
                        note = Ser or absent
VARIANT                 10
                        note = Gly or absent
VARIANT                 11
                        note = Asn or absent
VARIANT                 12
                        note = Gln or absent
VARIANT                 13
                        note = Lys or absent
VARIANT                 14
                        note = Asn or absent
VARIANT                 15
                        note = Asp or Tyr
VARIANT                 16
                        note = Val or Leu
source                  1..17
                        mol_type = protein
                        organism = synthetic construct
```

```
SEQUENCE: 968
KXSQSXXXXX XXXXXXA                                                17

SEQ ID NO: 969          moltype = AA  length = 17
FEATURE                 Location/Qualifiers
REGION                  1..17
                        note = Description of Artificial Sequence: Synthetic
                         consensus sequence
VARIANT                 2
                        note = Any amino acid
VARIANT                 6..8
                        note = Any amino acid
VARIANT                 9..14
                        note = Any amino acid or absent
VARIANT                 15..16
                        note = Any amino acid
source                  1..17
                        mol_type = protein
                        organism = synthetic construct
SEQUENCE: 969
KXSQSXXXXX XXXXXXA                                                17

SEQ ID NO: 970          moltype =   length =
SEQUENCE: 970
000

SEQ ID NO: 971          moltype =   length =
SEQUENCE: 971
000

SEQ ID NO: 972          moltype = AA  length = 9
FEATURE                 Location/Qualifiers
REGION                  1..9
                        note = Description of Artificial Sequence: Synthetic
                         consensus sequence
VARIANT                 2
                        note = Gln or Asn
VARIANT                 4
                        note = Tyr or His
VARIANT                 5
                        note = Arg or Ser
VARIANT                 6
                        note = Ser or His
VARIANT                 8
                        note = Leu or Tyr
source                  1..9
                        mol_type = protein
                        organism = synthetic construct
SEQUENCE: 972
QXDXXXPXT                                                         9

SEQ ID NO: 973          moltype = AA  length = 9
FEATURE                 Location/Qualifiers
REGION                  1..9
                        note = Description of Artificial Sequence: Synthetic
                         consensus sequence
VARIANT                 2
                        note = Any amino acid
VARIANT                 4..6
                        note = Any amino acid
VARIANT                 8
                        note = Any amino acid
source                  1..9
                        mol_type = protein
                        organism = synthetic construct
SEQUENCE: 973
QXDXXXPXT                                                         9

SEQ ID NO: 974          moltype =   length =
SEQUENCE: 974
000

SEQ ID NO: 975          moltype =   length =
SEQUENCE: 975
000

SEQ ID NO: 976          moltype =   length =
SEQUENCE: 976
000
```

SEQ ID NO: 977 moltype = length =
SEQUENCE: 977
000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = DNA length = 4718
FEATURE Location/Qualifiers
source 1..4718
mol_type = unassigned DNA
organism = Adeno-associated virus 1
SEQUENCE: 982

```
ttgcccactc cctctctgcg cgctcgctcg ctcggtgggg cctgcggacc aaaggtccgc  60
agacggcaga gctctgctct gccggcccca ccgagcgagc gagcgcgcag agagggagtg  120
ggcaactcca tcactagggg taatcgcgaa gcgcctccca cgctgccgcg tcagcgctga  180
cgtaaattac gtcatagggg agtggtcctg tattagctgt cacgtgagtg cttttgcgac  240
attttgcgac accacgtggc catttagggt atatatggcc gagtgagcga gcaggatctc  300
cattttgacc gcgaaatttg aacgagcagc agccatgccg ggcttctacg agatcgtgat  360
caaggtgccg agcgacctgg acgagcacct gccgggcatt tctgactcgt ttgtgagctg  420
ggtggccgag aaggaatggg agctgccccc ggattctgac atggatctga atctgattga  480
gcaggcaccc ctgaccgtgg ccgagaagct gcagcgcgac ttcctggtcc aatggcgccg  540
cgtgagtaag gccccggagg ccctcttctt tgttcagttc gagaagggcg agtcctactt  600
ccacctccat attctggtgg agaccacggg ggtcaaatcc atggtgctgg gccgcttcct  660
gagtcagatt agggacaagc tggtgcagac catctaccgc gggatcgagc cgaccctgcc  720
caactggttc gcggtgacca agacgcgtaa tggcgccgga ggggggaaca aggtggtgga  780
cgagtgctac atccccaact acctcctgcc caagactcag cccgagctgc agtgggcgtg  840
gactaacatg gaggagtata taagcgcctg tttgaacctg gccgagcgca aacggctcgt  900
ggcgcagcac ctgacccacg tcagccagac ccaggagcag aacaaggaga atctgaaccc  960
caattctgac gcgcctgtca tccggtcaaa aacctccgcg cgctacatgg agctggtcgg  1020
gtggctggtg gaccggggca tcacctccga gaagcagtgg atccaggagg accaggcctc  1080
gtacatctcc ttcaacgccg cttccaactc gcggtcccag atcaaggccg ctctggacaa  1140
tgccggcaag atcatggcgc tgaccaaatc cgcgcccgac tacctggtag gccccgctcc  1200
gcccgcggac attaaaacca accgcatcta ccgcatcctg gagctgaacg gctacgaacc  1260
tgcctacgcc ggctccgtct ttctcggctg ggcccagaaa aggttcggga agcgcaacac  1320
catctggctg tttgggccgg ccaccacggg caagaccaac atcgcggaag ccatcgccca  1380
cgccgtgccc ttctacggct gcgtcaactg gaccaatgag aactttccct tcaatgattg  1440
cgtcgacaag atggtgatct ggtgggagga gggcaagatg acggccaagg tcgtggagtc  1500
cgccaaggcc attctcggcg gcagcaaggt gcgcgtggac caaaagtgca agtcgtccgc  1560
ccagatcgac cccacccccg tgatcgtcac ctccaacacc aacatgtgcg ccgtgattga  1620
cgggaacagc accaccttcg agcaccagca gccgttgcag gaccggatgt tcaaatttga  1680
actcacccgc cgtctggagc atgactttgg caaggtgaca aagcaggaag tcaaagagtt  1740
cttccgctgg gcgcaggatc acgtgaccga ggtggcgcat gagttctacg tcagaaaggg  1800
tggagccaac aaaagacccg cccccgatga cgcggataaa agcgagccca agcgggcctg  1860
cccctcagtc gcggatccat cgacgtcaga cgcggaagga gctccggtgg actttgccga  1920
caggtaccaa aacaaatgtt ctcgtcacgc gggcatgctt cagatgctgt ttccctgcaa  1980
gacatgcgag agaatgaatc agaatttcaa catttgcttc acgcacggga cgagagactg  2040
ttcagagtgc ttccccggcg tgtcagaatc tcaaccggtc gtcagaaaga ggacgtatcg  2100
gaaactctgt gccattcatc atctgctggg gcgggctccc gagattgctt gctcggcctg  2160
cgatctggtc aacgtggacc tggatgactg tgtttctgag caataaatga cttaaaccag  2220
gtatggctgc cgatggttat cttccagatt ggctcgagga caacctctct gagggcattc  2280
gcgagtggtg ggacttgaaa cctggagccc cgaagcccaa agccaaccag caaaagcagg  2340
acgacggccg gggtctggtg cttcctggct acaagtacct cggacccttc aacggactcg  2400
acaaggggga gcccgtcaac gcggcggacg cagcggccct cgagcacgac aaggcctacg  2460
accagcagct caaagcgggt gacaatccgt acctgcggta taaccacgcc gacgccgagt  2520
ttcaggagcg tctgcaagaa gatacgtctt ttgggggcaa cctcgggcga gcagtcttcc  2580
aggccaagaa gcgggttctc gaacctctcg gtctggttga ggaaggcgct aagacggctc  2640
ctggaaagaa acgtccggta gagcagtcgc cacaagagcc agactcctcc tcgggcatcg  2700
gcaagacagg ccagcagccc gctaaaaaga gactcaattt tggtcagact ggcgactcag  2760
agtcagtccc cgatccacaa cctctcggag aacctccagc aacccccgct gctgtgggac  2820
ctactacaat ggcttcaggc ggtggcgcac caatggcaga caataacgaa ggcgccgacg  2880
gagtgggtaa tgcctcagga aattggcatt gcgattccac atggctgggc gacagagtca  2940
tcaccaccag cacccgcacc tgggccttgc ccacctacaa taaccacctc tacaagcaaa  3000
tctccagtgc ttcaacgggg gccagcaacg acaaccacta cttcggctac agcaccccct  3060
gggggtattt tgatttcaac agattccact gccacttttc accacgtgac tggcagcgac  3120
```

```
tcatcaacaa caattgggga ttccggccca agagactcaa cttcaaactc ttcaacatcc  3180
aagtcaagga ggtcacgacg aatgatggcg tcacaaccat cgctaataac cttaccagca  3240
cggttcaagt cttctcggac tcggagtacc agcttccgta cgtcctcggc tctgcgcacc  3300
agggctgcct ccctccgttc ccggcggacg tgttcatgat tccgcaatac ggctacctga  3360
cgctcaacaa tggcagccaa gccgtgggac gttcatcctt ttactgcctg gaatatttcc  3420
cttctcagat gctgagaacg ggcaacaact ttaccttcag ctacaccttt gaggaagtgc  3480
ctttccacag cagctacgcg cacagccaga gcctggaccg gctgatgaat cctctcatcg  3540
accaatacct gtattacctg aacagaactc aaaatcagtc cggaagtgcc caaaacaagg  3600
acttgctgtt tagccgtggg tctccagctg gcatgtctgt tcagcccaaa aactggctac  3660
ctggaccctg ttatcggcag cagcgcgttt ctaaaacaaa aacagacaac aacaacagca  3720
attttacctg gactggtgct tcaaaatata acctcaatgg gcgtgaatcc atcatcaacc  3780
ctggcactgc tatggcctca cacaaagacg acgaagacaa gttctttccc atgagcggtg  3840
tcatgatttt tggaaaagag agcgccggag cttcaaacac tgcattggac aatgtcatga  3900
ttacagacga agaggaaatt aaagccacta accctgtggc caccgaaaga tttgggaccg  3960
tggcagtcaa tttccagagc agcagcacag accctgcgac cggagatgtg catgctatgg  4020
gagcattacc tggcatggtg tggcaagata gagacgtgta cctgcagggt cccatttggg  4080
ccaaaattcc tcacacagat ggacactttc acccgtctcc tcttatgggc ggctttggac  4140
tcaagaaccc gcctcctcag atcctcatca aaaacacgcc tgttcctgcg aatcctccgg  4200
cggagttttc agctacaaag tttgcttcat tcatcaccca atactccaca ggacaagtga  4260
gtgtggaaat tgaatgggag ctgcagaaag aaaacagcaa gcgctggaat cccgaagtgc  4320
agtacacatc caattatgca aaatctgcca acgttgattt tactgtggac aacaatggac  4380
tttatactga gcctcgcccc attggcaccc gttaccttac ccgtcccctg taattacgtg  4440
ttaatcaata aaccggttga ttcgtttcag ttgaactttg gtctcctgtc cttcttatct  4500
tatcggttac catggttata gcttacacat taactgcttg gttgcgcttc gcgataaaag  4560
acttacgtca tcgggttacc cctagtgatg gagttgccca ctccctctct gcgcgctcgc  4620
tcgctcggtg gggcctgcgg accaaaggtc cgcagacggc agagctctgc tctgccggcc  4680
ccaccgagcg agcgagcgcg cagagaggga gtgggcaa                         4718

SEQ ID NO: 983          moltype = AA  length = 736
FEATURE                 Location/Qualifiers
source                  1..736
                        mol_type = protein
                        organism = Adeno-associated virus 1
SEQUENCE: 983
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                 736

SEQ ID NO: 984          moltype = DNA  length = 2208
FEATURE                 Location/Qualifiers
source                  1..2208
                        mol_type = unassigned DNA
                        organism = Adeno-associated virus 2
SEQUENCE: 984
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgcggagttt  300
caggagcgcc ttaaagaaga tacgtctttt gggggcaacc tcggacgagc agtcttccag  360
gcgaaaaaga gggttcttga acctctgggc ctggttgagg aacctgttaa gacggctccg  420
ggaaaaaaga ggccggtaga gcactctcct gtggagccag actcctcctc gggaaccgga  480
aaggcgggcc agcagcctgc aagaaaaaga ttgaattttg gtcagactgg agacgcagac  540
tcagtacctg acccccagcc tctcggacag ccaccagcag ccccctctgg tctgggaact  600
aatacgatgg ctacaggcag tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caaacaaatt  780
tccagccaat caggagcctc gaacgacaat cactactttg gctacagcac cccttggggg  840
tattttgact tcaacagatt ccactgccac ttttcaccac gtgactggca aagactcatc  900
aacaacaact ggggattccg acccaagaga ctcaacttca agctctttaa cattcaagtc  960
aaagaggtca cgcagaatga cggtacgacg acgattgcca ataaccttac cagcacggtt  1020
caggtgttta ctgactcgga gtaccagctc ccgtacgtcc tcggctcggc gcatcaagga  1080
tgcctcccgc cgttcccagc agacgtcttc atggtgccac agtatggata cctcaccctg  1140
aacaacggga gtcaggcagt aggacgctct tcattttact gcctggagta ctttccttct  1200
cagatgctgc gtaccggaaa caactttacc ttcagctaca cttttgagga cgttcctttc  1260
cacagcagct acgctcacag ccagagtctg gaccgtctca tgaatcctct catcgaccag  1320
tacctgtatt acttgagcag aacaaacact ccaagtggaa ccaccacgca gtcaaggctt  1380
cagttttctc aggccggagc gagtgacatt cgggaccagt ctaggaactg gcttcctgga  1440
ccctgttacc gccagcagcg agtatcaaag acatctgcgg ataacaacaa cagtgaatac  1500
```

```
tcgtggactg gagctaccaa gtaccacctc aatggcagag actctctggt gaatccgggc  1560
ccggccatgg caagccacaa ggacgatgaa gaaaagtttt ttcctcagag cggggttctc  1620
atctttggga agcaaggctc agagaaaaca aatgtggaca ttgaaaaggt catgattaca  1680
gacgaagagg aaatcaggac aaccaatccc gtggctacgg agcagtatgg ttctgtatct  1740
accaacctcc agagaggcaa cagacaagca gctaccgcag atgtcaacac acaaggcgtt  1800
cttccaggca tggtctggca ggacagagat gtgtaccttc aggggcccat ctgggcaaag  1860
attccacaca cggacggaca ttttcacccc tctcccctca tgggtggatt cggacttaaa  1920
caccctcctc cacagattct catcaagaac accccggtac ctgcgaatcc ttcgaccacc  1980
ttcagtgcgg caaagtttgc ttccttcatc acacagtact ccacgggaca ggtcagcgtg  2040
gagatcgagt gggagctgca gaaggaaaac agcaaacgct ggaatcccga aattcagtac  2100
acttccaact acaacaagtc tgttaatgtg gactttactg tggacactaa tggcgtgtat  2160
tcagagcctc gccccattgg caccagatac ctgactcgta atctgtaa              2208

SEQ ID NO: 985         moltype = AA  length = 735
FEATURE                Location/Qualifiers
source                 1..735
                       mol_type = protein
                       organism = Adeno-associated virus 2
SEQUENCE: 985
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                  735

SEQ ID NO: 986         moltype = DNA  length = 4726
FEATURE                Location/Qualifiers
source                 1..4726
                       mol_type = unassigned DNA
                       organism = Adeno-associated virus 3
SEQUENCE: 986
ttggccactc cctctatgcg cactcgctcg ctcggtgggg cctggcgacc aaaggtcgcc  60
agacggacgt gctttgcacg tccggcccca ccgagcgagc gagtgcgcat agagggagtg  120
gccaactcca tcactagagg tatggcagtg acgtaacgcg aagcgcgcga agcgagacca  180
cgcctaccag ctgcgtcagc agtcaggtga cccttttgcg acagtttgcg acaccacgtg  240
gccgctgagg gtatatattc tcgagtgagc gaaccaggag ctccattttg accgcgaaat  300
ttgaacgagc agcagccatg ccggggttct acgagattgt cctgaaggtc ccgagtgacc  360
tggacgagcg cctgccgggc atttctaact cgtttgttaa ctgggtggcc gagaaggaat  420
gggacgtgcc gccggattct gacatggatc cgaatctgat tgagcaggca cccctgaccg  480
tggccgaaaa gcttcagcgc gagttcctgg tggagtggcg ccgcgtgagt aaggccccgg  540
aggccctctt ttttgtccag ttcgaaaagg gggagaccta cttccacctg cacgtgctga  600
ttgagaccat cggggtcaaa tccatggtgg tcggccgcta cgtgagccag attaaagaga  660
agctggtgac ccgcatctac cgcggggtcg agccgcagct tccgaactgg ttcgcggtga  720
ccaaaacgcg aaatggcgcc gggggcggga acaaggtggt ggacgactgc tacatcccca  780
actacctgct ccccaagacc cagcccgagc tccagtgggc gtggactaac atggaccagt  840
atttaagcgc ctgtttgaat ctcgcggagc gtaaacggct ggtggcgcag catctgacgc  900
acgtgtcgca gacgcaggag cagaacaaag agaatcagaa ccccaattct gacgcgccgg  960
tcatcaggtc aaaaacctca gccaggtaca tggagctggt cgggtggctg gtggaccgcg  1020
ggatcacgtc agaaaagcaa tggattcagg aggaccaggc ctcgtacatc tccttcaacg  1080
ccgcctccaa ctcgcggtcc cagatcaagg ccgcgctgga caatgcctcc aagatcatga  1140
gcctgacaaa gacggctccg gactacctgg tgggcagcaa cccgccggag gacattacca  1200
aaaatcggat ctaccaaatc ctggagctga acgggtacga tccgcagtac gcggcctccg  1260
tcttcctggg ctgggcgcaa aagaagttcg ggaagaggaa caccatctgg ctctttgggc  1320
cggccacgac gggtaaaacc aacatcgcgg aagccatcgc ccacgccgtg cccttctacg  1380
gctgcgtaaa ctggaccaat gagaactttc ccttcaacga ttgcgtcgac aagatggtga  1440
tctggtggga ggagggcaag atgacggcca aggtcgtgga gagcgccaag gccattctgg  1500
gcggaagcaa ggtgcgcgtg gaccaaaagt gcaagtcatc ggcccagatc gaacccactc  1560
ccgtgatcgt cacctccaac accaacatgt gcgccgtgat tgacgggaac agcaccacct  1620
tcgagcatca gcagccgctg caggaccgga tgtttgaatt tgaacttacc cgccgtttgg  1680
accatgactt tgggaaggtc accaaacagg aagtaaagga ctttttccgg tgggcttccg  1740
atcacgtgac tgacgtggct catgagttct acgtcagaaa gggtggagct aagaaacgcc  1800
ccgcctccaa tgacgcggat gtaagcgagc caaaacggga gtgcacgtca cttgcgcagc  1860
cgacaacgtc agacgcggaa gcaccggcgg actacgcgga caggtaccaa aacaaatgtt  1920
ctcgtcacgt gggcatgaat ctgatgcttt ttccctgtaa aacatgcgag agaatgaatc  1980
aaatttccaa tgtctgtttt acgcatggtc aaagagactg tggggaatgc ttccctggaa  2040
tgtcagaatc tcaacccgtt tctgtcgtca aaaagaagac ttatcagaaa ctgtgtccaa  2100
ttcatcatat cctgggaagg gcacccgaga ttgcctgttc ggcctgcgat ttggccaatg  2160
tggacttgga tgactgtgtt tctgagcaat aaatgactta aaccaggtat ggctgctgac  2220
ggttatcttc cagattggct cgaggacaac ctttctgaag gcattcgtga gtggtgggct  2280
ctgaaacctg gagtccctca acccaaagcg aaccaacaac accaggacaa ccgtcggggt  2340
cttgtgcttc cgggttacaa atacctcgga cccggtaacg gactcgacaa aggagagccg  2400
```

```
gtcaacgagg cggacgcggc agccctcgaa cacgacaaag cttacgacca gcagctcaag  2460
gccggtgaca acccgtacct caagtacaac cacgccgacg ccgagtttca ggagcgtctt  2520
caagaagata cgtcttttgg gggcaacctt ggcagagcag tcttccaggc caaaaagagg  2580
atccttgagc ctcttggtct ggttgaggaa gcagctaaaa cggctcctgg aaagaagggg  2640
gctgtagatc agtctcctca ggaaccggac tcatcatctg gtgttggcaa atcgggcaaa  2700
cagcctgcca gaaaaagact aaatttcggt cagactggag actcagagtc agtcccagac  2760
cctcaacctc tcggagaacc accagcagcc cccacaagtt tgggatctaa tacaatggct  2820
tcaggcggtg gcgcaccaat ggcagacaat aacgagggtg ccgatggagt gggtaattcc  2880
tcaggaaatt ggcattgcga ttcccaatgg ctgggcgaca gagtcatcac caccagcacc  2940
agaacctggg ccctgcccac ttacaacaac catctctaca agcaaatctc cagccaatca  3000
ggagcttcaa acgacaacca ctactttggc tacagcaccc cttgggggta ttttgacttt  3060
aacagattcc actgccactt ctcaccacgt gactggcagc gactcattaa caacaactgg  3120
ggattccggc ccaagaaact cagcttcaag ctcttcaaca tccaagttag aggggtcacg  3180
cagaacgatg gcacgacgac tattgccaat aaccttacca gcacggttca agtgtttacg  3240
gactcggagt atcagctccc gtacgtgctc gggtcggcgc accaaggctg tctcccgccg  3300
tttccagcgg acgtcttcat ggtccctcag tatggatacc tcaccctgaa caacggaagt  3360
caagcggtgg gacgctcatc cttttactgc ctggagtact tcccttcgca gatgctaagg  3420
actggaaata acttccaatt cagctatacc ttcgaggatg taccttttca cagcagctac  3480
gctcacagcc agagtttgga tcgcttgatg aatcctctta ttgatcagta tctgtactac  3540
ctgaacagaa cgcaaggaac aacctctgga acaaccaacc aatcacggct gctttttagc  3600
caggctgggc ctcagtctat gtctttgcag gccagaaatt ggctacctgg gccctgctac  3660
cggcaacaga gactttcaaa gactgctaac gacaacaaca acagtaactt tccttggaca  3720
gcggccagca aatatcatct caatggccgc gactcgctgg tgaatccagg accagctatg  3780
gccagtcaca aggacgatga agaaaaattt ttccctatgc acggcaatct aatatttggc  3840
aaagaaggga caacggcaag taacgcagaa ttagataatg taatgattac ggatgaagaa  3900
gagattcgta ccaccaatcc tgtggcaaca gagcagtatg gaactgtggc aaataacttg  3960
cagagctcaa atacagctcc cacgactgga actgtcaatc atcagggggc cttacctggc  4020
atggtgtggc aagatcgtga cgtgtacctt caaggaccta tctgggcaaa gattcctcac  4080
acggatggac actttcatcc ttctcctctg atgggaggct ttggactgaa acatccgcct  4140
cctcaaatca tgatcaaaaa tactccggta ccggcaaatc ctccgacgac tttcagcccg  4200
gccaagtttg cttcatttat cactcagtac tccactggac aggtcagcgt ggaaattgag  4260
tgggagctac agaaagaaaa cagcaaacgt tggaatccag agattcagta cacttccaac  4320
tacaacaagt ctgttaatgt ggactttact gtagacacta atggtgttta tagtgaacct  4380
cgccctattg gaacccggta tctcacacga aacttgtgaa tcctggttaa tcaataaacc  4440
gtttaattcg tttcagttga actttggctc ttgtgcactt ctttatcttt atcttgtttc  4500
catggctact gcgtagataa gcagcggcct gcggcgcttg cgcttcgcgg tttacaactg  4560
ctggttaata tttaactctc gccatacctc tagtgatgga gttggccact ccctctatgc  4620
gcactcgctc gctcggtggg gcctggcgac caaaggtcgc cagacggacg tgctttgcac  4680
gtccggcccc accgagcgag cgagtgcgca tagagggagt ggccaa                4726
```

```
SEQ ID NO: 987         moltype = AA  length = 736
FEATURE                Location/Qualifiers
source                 1..736
                       mol_type = protein
                       organism = Adeno-associated virus 3
SEQUENCE: 987
MAADGYLPDW LEDNLSEGIR EWWALKPGVP QPKANQQHQD NRRGLVLPGY KYLGPGNGLD  60
KGEPVNEADA AALEHDKAYD QQLKAGDNPY LKYNHADAEF QERLQEDTSF GGNLGRAVFQ  120
AKKRILEPLG LVEEAAKTAP GKKGAVDQSP QEPDSSSGVG KSGKQPARKR LNFGQTGDSE  180
SVPDPQPLGE PPAAPTSLGS NTMASGGGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKK LSFKLFNIQV RGVTQNDGTT TIANNLTSTV QVFTDSEYQL PYVLGSAHQG  360
CLPPFPADVF MVPQYGYLTL NNGSQAVGRS SFYCLEYFPS QMLRTGNNFQ FSYTFEDVPF  420
HSSYAHSQSL DRLMNPLIDQ YLYYLNRTQG TTSGTTNQSR LLFSQAGPQS MSLQARNWLP  480
GPCYRQQRLS KTANDNNNSN FPWTAASKYH LNGRDSLVNP GPAMASHKDD EEKFFPMHGN  540
LIFGKEGTTA SNAELDNVMI TDEEEIRTTN PVATEQYGTV ANNLQSSNTA PTTGTVNHQG  600
ALPGMVWQDR DVYLQGPIWA KIPHTDGHFH PSPLMGGFGL KHPPPQIMIK NTPVPANPPT  660
TFSPAKFASF ITQYSTGQVS VEIEWELQKE NSKRWNPEIQ YTSNYNKSVN VDFTVDTNGV  720
YSEPRPIGTR YLTRNL                                                   736
```

```
SEQ ID NO: 988         moltype = DNA  length = 4768
FEATURE                Location/Qualifiers
misc_difference        3009
                       note = Unknown
source                 1..4768
                       mol_type = unassigned DNA
                       organism = Adeno-associated virus 4
SEQUENCE: 988
ttggccactc cctctatgcg cgctcgctca ctcactcggc cctggagacc aaaggtctcc  60
agactgccgg cctctggccg gcagggccga gtgagtgagc gagcgcgcat agagggagtg  120
gccaactcca tcatctaggt ttgcccactg acgtcaatgt gacgtcctag ggttagggag  180
gtccctgtat tagcagtcac gtgagtgtcg tatttcgcgg agcgtagcgg agcgcatacc  240
aagctgccac gtcacagcca cgtggtccgt ttgcgacagt ttgcgacacc atgtggtcag  300
gagggtatat aaccgcgagt gagccagcga ggagctccat tttgcccgcg aattttgaac  360
gagcagcagc catgccgggg ttctacgaga tcgtgctgaa ggtgcccagc gacctggacg  420
agcacctgcc cggcatttct gactcttttg tgagctgggt ggccgagaag gaatgggagc  480
tgccgccgga ttctgacatg gacttgaatc tgattgagca ggcacccctg accgtggccg  540
aaaagctgca acgcgagttc ctggtcgagt ggcgccgcgt gagtaaggcc ccggaggccc  600
tcttctttgt ccagttcgag aagggggaca gctacttcca cctgcacatc ctggtggaga  660
```

```
ccgtgggcgt caaatccatg gtggtgggcc gctacgtgag ccagattaaa gagaagctgg  720
tgacccgcat ctaccgcggg gtcgagccgc agcttccgaa ctggttcgcg gtgaccaaga  780
cgcgtaatgg cgccggaggc gggaacaagg tggtggacga ctgctacatc cccaactacc  840
tgctccccaa gacccagccc gagctccagt gggcgtggac taacatggac cagtatataa  900
gcgcctgttt gaatctcgcg gagcgtaaac ggctggtggc gcagcatctg acgcacgtgt  960
cgcagacgca ggagcagaac aaggaaaacc agaaccccaa ttctgacgcg ccggtcatca  1020
ggtcaaaaac ctccgccagg tacatggagc tggtcgggtg gctggtggac cgcgggatca  1080
cgtcagaaaa gcaatggatc caggaggacc aggcgtccta catctccttc aacgccgcct  1140
ccaactcgcg gtcacaaatc aaggccgcgc tggacaatgc ctccaaaatc atgagcctga  1200
caaagacggc tccggactac ctggtgggcc agaacccgcc ggaggacatt tccagcaacc  1260
gcatctaccg aatcctcgag atgaacgggt acgatccgca gtacgcggcc tccgtcttcc  1320
tgggctgggc gcaaaagaag ttcgggaaga ggaacaccat ctggctcttt gggccggcca  1380
cgacgggtaa aaccaacatc gcggaagcca tcgcccacgc cgtgcccttc tacggctgcg  1440
tgaactggac caatgagaac tttccgttca acgattgcgt cgacaagatg gtgatctggt  1500
gggaggaggg caagatgacg gccaaggtcg tagagagcgc caaggccatc ctgggcggaa  1560
gcaaggtgcg cgtggaccaa aagtgcaagt catcggccca gatcgaccca actcccgtga  1620
tcgtcacctc caacaccaac atgtgcgcgg tcatcgacgg aaactcgacc accttcgagc  1680
accaacaacc actccaggac cggatgttca agttcgagct caccaagcgc ctggagcacg  1740
actttggcaa ggtcaccaag caggaagtca aagacttttt ccggtgggcg tcagatcacg  1800
tgaccgaggt gactcacgag ttttacgtca gaaagggtgg agctagaaag aggcccgccc  1860
ccaatgacgc agatataagt gagcccaagc gggcctgtcc gtcagttgcg cagccatcga  1920
cgtcagacgc ggaagctccg gtggactacg cggacaggta ccaaaacaaa tgttctcgtc  1980
acgtgggtat gaatctgatg ctttttccct gccggcaatg cgagagaatg aatcagaatg  2040
tggacatttg cttcacgcac ggggtcatgg actgtgccga gtgcttcccc gtgtcagaat  2100
ctcaacccgt gtctgtcgtc agaaagcgga cgtatcagaa actgtgtccg attcatcaca  2160
tcatggggag ggcgcccgag gtggcctgct cggcctgcga actggccaat gtggacttgg  2220
atgactgtga catggaacaa taaatgactc aaaccagata tgactgacgg ttaccttcca  2280
gattggctag aggacaacct ctctgaaggc gttcgagagt ggtgggcgct gcaacctgga  2340
gcccctaaac ccaaggcaaa tcaacaacat caggacaacg ctcggggtct tgtgcttccg  2400
ggttacaaat acctcggacc cggcaacgga ctcgacaagg gggaacccgt caacgcagcg  2460
gacgcggcag ccctcgagca cgacaaggcc tacgaccagc agctcaaggc cggtgacaac  2520
ccctacctca agtacaacca cgccgacgcg gagttccagc agcggcttca gggcgacaca  2580
ccgtttgggg gcaacctcgg cagagcagtc ttccaggcca aaaagagggt tcttgaacct  2640
cttggtctgg ttgagcaagc gggtgagacg gctcctggaa agaagagacc gttgattgaa  2700
tccccccagc agcccgactc ctccacgggt atcggcaaaa aaggcaagca gccggctaaa  2760
aagaagctcg ttttcgaaga cgaaactgga gcaggcgacg gaccccctga gggatcaact  2820
tccggagcca tgtctgatga cagtgagatg cgtgcagcag ctggcggagc tgcagtcgag  2880
ggsggacaag gtgccgatgg agtgggtaat gcctcgggtg attggcattg cgattccacc  2940
tggtctgagg gccacgtcac gaccaccagc accagaacct gggtcttgcc cacctacaac  3000
aaccacctnt acaagcgact cggagagagc ctgcagtcca acacctacaa cggattctcc  3060
acccccctggg gatactttga cttcaaccgc ttccactgcc acttctcacc acgtgactgg  3120
cagcgactca tcaacaacaa ctggggcatg cgacccaaag ccatgcgggt caaaatcttc  3180
aacatccagg tcaaggaggt cacgacgtcg aacggcgaga caacggtggc taataacctt  3240
accagcacgg ttcagatctt tgcggactcg tcgtacgaac tgccgtacgt gatggatgcg  3300
ggtcaagagg gcagcctgcc tccttttccc aacgacgtct ttatggtgcc ccagtacggc  3360
tactgtggac tggtgaccgg caacacttcg cagcaacaga ctgacagaaa tgccttctac  3420
tgcctggagt actttccttc gcagatgctg cggactggca acaactttga aattacgtac  3480
agttttgaga aggtgccttt ccactcgatg tacgcgcaca gccagagcct ggaccggctg  3540
atgaaccctc tcatcgacca gtacctgtgg ggactgcaat cgaccaccac cggaaccacc  3600
ctgaatgccg ggactgccac caccaacttt accaagctgc ggcctaccaa cttttccaac  3660
tttaaaaaga actggctgcc cgggccttca atcaagcagc agggcttctc aaagactgcc  3720
aatcaaaact acaagatccc tgccaccggg tcagacagtc tcatcaaata cgagacgcac  3780
agcactctgg acggaagatg gagtgccctg acccccggac ctccaatggc cacggctgga  3840
cctgcggaca gcaagttcag caacagccag ctcatctttg cggggcctaa acagaacggc  3900
aacacggcca ccgtacccgg gactctgatc ttcacctctg aggaggagct ggcagccacc  3960
aacgccaccg atacggacat gtggggcaac ctacctggcg gtgaccagag caacagcaac  4020
ctgccgaccg tggacagact gacagccttg ggagccgtgc ctggaatggt ctggcaaaac  4080
agagacattt actaccaggg tcccatttgg gccaagattc ctcataccga tggacacttt  4140
cacccctcac cgctgattgg tgggtttggg ctgaaacacc cgcctcctca aatttttatc  4200
aagaacaccc cggtacctgc gaatcctgca acgaccttca gctctactcc ggtaaactcc  4260
ttcattactc agtacagcac tggccaggtg tcggtgcaga ttgactggga gatccagaag  4320
gagcggtcca aacgctggaa ccccgaggtc cagtttacct ccaactacgg acagcaaaac  4380
tctctgttgt gggctcccga tgcggctggg aaatacactg agcctagggc tatcggtacc  4440
cgctacctca cccaccacct gtaataacct gttaatcaat aaaccggttt attcgtttca  4500
gttgaacttt ggtctccgtg tccttcttat cttatctcgt ttccatggct actgcgtaca  4560
taagcagcgg cctgcggcgc ttgcgcttcg cggtttacaa ctgccggtta atcagtaact  4620
tctggcaaac catgatgatg gagttggcca ctccctctat gcgcgctcgc tcactcactc  4680
ggccctggag accaaaggtc tccagactgc cggcctctgg ccggcagggc cgagtgagtg  4740
agcgagcgcg catagaggga gtggccaa                                  4768

SEQ ID NO: 989          moltype = DNA  length = 2205
FEATURE                 Location/Qualifiers
source                  1..2205
                        mol_type = unassigned DNA
                        organism = Adeno-associated virus 4
SEQUENCE: 989
atgactgacg gttaccttcc agattggcta gaggacaacc tctctgaagg cgttcgagag  60
tggtgggcgc tgcaacctgg agcccctaaa cccaaggcaa atcaacaaca tcaggacaac  120
gctcggggtc ttgtgcttcc gggttacaaa tacctcggac ccggcaacgg actcgacaag  180
```

```
ggggaacccg tcaacgcagc ggacgcggca gccctcgagc acgacaaggc ctacgaccag  240
cagctcaagg ccggtgacaa cccctacctc aagtacaacc acgccgacgc ggagttccag  300
cagcggcttc agggcgacac atcgtttggg ggcaacctcg gcagagcagt cttccaggcc  360
aaaaagaggg ttcttgaacc tcttggtctg gttgagcaag cgggtgagac ggctcctgga  420
aagaagagac cgttgattga atcccccag cagcccgact cctccacggg tatcggcaaa  480
aaaggcaagc agccggctaa aaagaagctc gttttcgaag acgaaactgg agcaggcgac  540
ggacccccctg agggatcaac ttccggagcc atgtctgatg acagtgagat gcgtgcagca  600
gctggcggag ctgcagtcga gggcggacaa ggtgccgatg gagtgggtaa tgcctcgggt  660
gattggcatt gcgattccac ctggtctgag ggccacgtca cgaccaccag caccagaacc  720
tgggtcttgc ccacctacaa caaccacctc tacaagcgac tcggagagag cctgcagtcc  780
aacacctaca acggattctc cacccctgg ggatactttg acttcaaccg cttccactgc  840
cacttctcac cacgtgactg gcagcgactc atcaacaaca actggggcat gcgacccaaa  900
gccatgcggg tcaaaatctt caacatccag gtcaaggagg tcacgacgtc gaacggcgag  960
acaacggtgg ctaataacct taccagcacg gttcagatct ttgcggactc gtcgtacgaa  1020
ctgccgtacg tgatggatgc gggtcaagag ggcagcctgc ctccttttcc caacgacgtc  1080
tttatggtgc cccagtacgg ctactgtgga ctggtgaccg gcaacacttc gcagcaacag  1140
actgacagaa atgccttcta ctgcctggag tactttcctt cgcagatgct gcggactggc  1200
aacaactttg aaattacgta cagttttgag aaggtgcctt tccactcgat gtacgcgcac  1260
agccagagcc tggaccggct gatgaaccct ctcatcgacc agtacctgtg gggactgcaa  1320
tcgaccacca ccggaaccac cctgaatgcc gggactgcca ccaccaactt taccaagctg  1380
cggcctacca acttttccaa ctttaaaaag aactggctgc ccgggccttc aatcaagcag  1440
cagggcttct caaagactgc caatcaaaac tacaagatcc ctgccaccgg gtcagacagt  1500
ctcatcaaat acgagacgca cagcactctg gacggaagat ggagtgccct gacccccgga  1560
cctccaatgg ccacggctgg acctgcggac agcaagttca gcaacagcca gctcatcttt  1620
gcggggccta aacagaacgg caacacggcc accgtacccg ggactctgat cttcacctct  1680
gaggaggagc tggcagccac caacgccacc gatacggaca tgtggggcaa cctacctggc  1740
ggtgaccaga gcaacagcaa cctgccgacc gtggacagac tgacagcctt gggagccgtg  1800
cctggaatgg tctggcaaaa cagagacatt tactaccagg gtcccatttg ggccaagatt  1860
cctcataccg atggacactt tcacccctca ccgctgattg gtgggtttgg gctgaaacac  1920
ccgcctcctc aaatttttat caagaacacc ccggtacctg cgaatcctgc aacgaccttc  1980
agctctactc cggtaaactc cttcattact cagtacagca ctggccaggt gtcggtgcag  2040
attgactggg agatccagaa ggagcggtcc aaacgctgga accccgaggt ccagtttacc  2100
tccaactacg gacagcaaaa ctctctgttg tgggctcccg atgcggctgg gaaatacact  2160
gagcctaggg ctatcggtac ccgctacctc acccaccacc tgtaa                  2205
```

```
SEQ ID NO: 990          moltype = AA  length = 734
FEATURE                 Location/Qualifiers
source                  1..734
                        mol_type = protein
                        organism = Adeno-associated virus 4
SEQUENCE: 990
MTDGYLPDWL EDNLSEGVRE WWALQPGAPK PKANQQHQDN ARGLVLPGYK YLGPGNGLDK  60
GEPVNAADAA ALEHDKAYDQ QLKAGDNPYL KYNHADAEFQ QRLQGDTSFG GNLGRAVFQA  120
KKRVLEPLGL VEQAGETAPG KKRPLIESPQ QPDSSTGIGK KGKQPAKKKL VFEDETGAGD  180
GPPEGSTSGA MSDDSEMRAA AGGAAVEGGQ GADGVGNASG DWHCDSTWSE GHVTTTSTRT  240
WVLPTYNNHL YKRLGESLQS NTYNGFSTPW GYFDFNRFHC HFSPRDWQRL INNNWGMRPK  300
AMRVKIFNIQ VKEVTTSNGE TTVANNLTST VQIFADSSYE LPYVMDAGQE GSLPPFPNDV  360
FMVPQYGYCG LVTGNTSQQQ TDRNAFYCLE YFPSQMLRTG NNFEITYSFE KVPFHSMYAH  420
SQSLDRLMNP LIDQYLWGLQ STTTGTTLNA GTATTNFTKL RPTNFSNFKK NWLPGPSIKQ  480
QGFSKTANQN YKIPATGSDS LIKYETHSTL DGRWSALTPG PPMATAGPAD SKFSNSQLIF  540
AGPKQNGNTA TVPGTLIFTS EEELAATNAT DTDMWGNLPG GDQSNSNLPT VDRLTALGAV  600
PGMVWQNRDI YYQGPIWAKI PHTDGHFHPS PLIGGFGLKH PPPQIFIKNT PVPANPATTF  660
SSTPVNSFIT QYSTGQVSVQ IDWEIQKERS KRWNPEVQFT SNYGQQNSLL WAPDAAGKYT  720
EPRAIGTRYL THHL                                                    734
```

```
SEQ ID NO: 991          moltype = DNA  length = 2172
FEATURE                 Location/Qualifiers
source                  1..2172
                        mol_type = unassigned DNA
                        organism = Adeno-associated virus 5
SEQUENCE: 991
atgtcttttg ttgatcaccc tccagattgg ttggaagaag ttggtgaagg tcttcgcgag  60
tttttgggcc ttgaagcggg cccaccgaaa ccaaaaccca atcagcagca tcaagatcaa  120
gcccgtggtc ttgtgctgcc tggttataac tatctcggac ccggaaacgg tctcgatcga  180
ggagagcctg tcaacagggc agacgaggtc gcgcgagagc acgacatctc gtacaacgag  240
cagcttgagg cgggagacaa cccctacctc aagtacaacc acgcggacgc cgagtttcag  300
gagaagctcg ccgacgacac atccttcggg ggaaacctcg gaaaggcagt ctttcaggcc  360
aagaaaaggg ttctcgaacc ttttggcctg gttgaagagg gtgctaagac ggcccctacc  420
ggaaagcgga tagacgacca ctttccaaaa agaaagaagg ctcggaccga agaggactcc  480
aagccttcca cctcgtcaga cgccgaagct ggacccagcg gatcccagca gctgcaaatc  540
ccagcccaac cagcctcaag tttgggagct gatacaatgt ctgcgggagg tggcggccca  600
ttgggcgaca ataaccaagg tgccgatgga gtgggcaatg cctcgggaga ttggcattgc  660
gattccacgt ggatggggga cagagtcgtc accaagtcca cccgaacctg ggtgctgccc  720
agctacaaca accaccagta ccgagagatc aaaagcggct ccgtcgacgg aagcaacgcc  780
aacgcctact ttggatacag cacccctgg gggtactttg actttaaccg cttccacagc  840
cactggagcc cccgagactg gcaaagactc atcaacaact actggggctt cagaccccgg  900
tccctcagag tcaaaatctt caacattcaa gtcaaagagg tcacggtgca ggactccacc  960
accaccatcg ccaacaacct cacctccacc gtccaagtgt ttacggacga cgactaccag  1020
ctgccctacg tcgtcggcaa cgggaccgag ggatgcctgc cggccttccc tccgcaggtc  1080
```

```
tttacgctgc cgcagtacgg ttacgcgacg ctgaaccgcg acaacacaga aaatcccacc  1140
gagaggagca gcttcttctg cctagagtac tttcccagca agatgctgag aacgggcaac  1200
aactttgagt ttacctacaa ctttgaggag gtgcccttcc actccagctt cgctcccagt  1260
cagaacctgt tcaagctggc caacccgctg gtggaccagt acttgtaccg cttcgtgagc  1320
acaaataaca ctggcggagt ccagttcaac aagaacctgg ccgggagata cgccaacacc  1380
tacaaaaact ggttcccggg gcccatgggc cgaacccagg gctggaacct gggctccggg  1440
gtcaaccgcg ccagtgtcag cgccttcgcc acgaccaata ggatggagct cgagggcgcg  1500
agttaccagg tgcccccgca gccgaacggc atgaccaaca acctccaggg cagcaacacc  1560
tatgccctgg agaacactat gatcttcaac agccagccgg cgaacccggg caccaccgcc  1620
acgtacctcg agggcaacat gctcatcacc agcgagagcg agacgcagcc ggtgaaccgc  1680
gtggcgtaca acgtcggcgg gcagatggcc accaacaacc agagctccac cactgccccc  1740
gcgaccggca cgtacaacct ccaggaaatc gtgcccggca gcgtgtggat ggagagggac  1800
gtgtacctcc aaggacccat ctgggccaag atcccagaga cgggggcgca ctttcacccc  1860
tctccggcca tgggcggatt cggactcaaa cacccaccgc ccatgatgct catcaagaac  1920
acgcctgtgc ccggaaatat caccagcttc tcggacgtgc ccgtcagcag cttcatcacc  1980
cagtacagca ccgggcaggt caccgtggag atggagtggg agctcaagaa ggaaaactcc  2040
aagaggtgga acccagagat ccagtacaca aacaactaca acgaccccca gtttgtggac  2100
tttgccccgg acagcaccgg ggaatacaga accaccagac ctatcggaac ccgatacctt  2160
acccgacccc tt                                                      2172

SEQ ID NO: 992          moltype = AA  length = 724
FEATURE                 Location/Qualifiers
source                  1..724
                        mol_type = protein
                        organism = Adeno-associated virus 5
SEQUENCE: 992
MSFVDHPPDW LEEVGEGLRE FLGLEAGPPK PKPNQQHQDQ ARGLVLPGYN YLGPGNGLDR  60
GEPVNRADEV AREHDISYNE QLEAGDNPYL KYNHADAEFQ EKLADDTSFG GNLGKAVFQA  120
KKRVLEPFGL VEEGAKTAPT GKRIDDHFPK RKKARTEEDS KPSTSSDAEA GPSGSQQLQI  180
PAQPASSLGA DTMSAGGGGP LGDNNQGADG VGNASGDWHC DSTWMGDRVV TKSTRTWVLP  240
SYNNHQYREI KSGSVDGSNA NAYFGYSTPW GYFDFNRFHS HWSPRDWQRL INNYWGFRPR  300
SLRVKIFNIQ VKEVTVQDST TTIANNLTST VQVFTDDDYQ LPYVVGNGTE GCLPAFPPQV  360
FTLPQYGYAT LNRDNTENPT ERSSFFCLEY FPSKMLRTGN NFEFTYNFEE VPFHSSFAPS  420
QNLFKLANPL VDQYLYRFVS TNNTGGVQFN KNLAGRYANT YKNWFPGPMG RTQGWNLGSG  480
VNRASVSAFA TTNRMELEGA SYQVPPQPNG MTNNLQGSNT YALENTMIFN SQPANPGTTA  540
TYLEGNMLIT SESETQPVNR VAYNVGGQMA TNNQSSTTAP ATGTYNLQEI VPGSVWMERD  600
VYLQGPIWAK IPETGAHFHP SPAMGGFGLK HPPPMMLIKN TPVPGNITSF SDVPVSSFIT  660
QYSTGQVTVE MEWELKKENS KRWNPEIQYT NNYNDPQFVD FAPDSTGEYR TTRPIGTRYL  720
TRPL                                                               724

SEQ ID NO: 993          moltype = DNA  length = 4683
FEATURE                 Location/Qualifiers
source                  1..4683
                        mol_type = unassigned DNA
                        organism = Adeno-associated virus 6
SEQUENCE: 993
ttggccactc cctctctgcg cgctcgctcg ctcactgagg ccgggcgacc aaaggtcgcc  60
cgacgcccgg gctttgcccg ggcggcctca gtgagcgagc gagcgcgcag agagggagtg  120
gccaactcca tcactagggg ttcctggagg ggtggagtcg tgacgtgaat tacgtcatag  180
ggttagggag gtcctgtatt agaggtcacg tgagtgtttt gcgacatttt gcgacaccat  240
gtggtcacgc tgggtattta agcccgagtg agcacgcagg gtctccattt tgaagcggga  300
ggtttgaacg cgcagcgcca tgccggggtt ttacgagatt gtgattaagg tccccagcga  360
ccttgacgag catctgcccg gcatttctga cagctttgtg aactgggtgg ccgagaagga  420
atgggagttg ccgccagatt ctgacatgga tctgaatctg attgagcagg cacccctgac  480
cgtggccgag aagctgcagc gcgacttcct ggtccagtgg cgccgcgtga gtaaggcccc  540
ggaggccctc ttctttgttc agttcgagaa gggcgagtcc tacttccacc tccatattct  600
ggtggagacc acgggggtca aatccatggt gctgggccgc ttcctgagtc agattaggga  660
caagctggtg cagaccatct accgcgggat cgagccgacc ctgcccaact ggttcgcggt  720
gaccaagacg cgtaatggcg ccggaggggg ggaacaaggtg gtggacgagt gctacatccc  780
caactacctc ctgcccaaga ctcagcccga gctgcagtgg gcgtggacta acatggagga  840
gtatataagc gcgtgtttaa acctggccga gcgcaaacgg ctcgtggcgc acgacctgac  900
ccacgtcagc cagacccagg agcagaacaa ggagaatctg aaccccaatt ctgacgcgcc  960
tgtcatccgg tcaaaaacct ccgcacgcta catggagctg gtcgggtggc tggtggaccg  1020
gggcatcacc tccgagaagc agtggatcca ggaggaccag gcctcgtaca tctccttcaa  1080
cgccgcctcc aactcgcggt cccagatcaa ggccgctctg gacaatgccg gcaagatcat  1140
ggcgctgacc aaatccgcgc ccgactacct ggtaggcccc gctccgcccg ccgacattaa  1200
aaccaaccgc atttaccgca tcctggagct gaacggctac gaccctgcct acgccggctc  1260
cgtctttctc ggctgggccc agaaaaggtt cggaaaacgc aacaccatct ggctgtttgg  1320
gccggccacc acgggcaaga ccaacatcgc ggaagccatc gcccacgccg tgcccttcta  1380
cggctgcgtc aactggacca atgagaactt tcccttcaac gattgcgtcg acaagatggt  1440
gatctggtgg gaggagggca agatgacggc caaggtcgtg gagtccgcca aggccattct  1500
cggcggcagc aaggtgcgcg tggaccaaaa gtgcaagtcg tccgcccaga tcgatcccac  1560
ccccgtgatc gtcacctcca acaccaacat gtgcgccgtg attgacggga acagcaccac  1620
cttcgagcac cagcagccgt tgcaggaccg gatgttcaaa tttgaactca cccgccgtct  1680
ggagcatgac tttggcaagg tgacaaagca ggaagtcaaa gagttcttcc gctgggcgca  1740
ggatcacgtg accgaggtgg cgcatgagtt ctacgtcaga aagggtggag ccaacaagag  1800
acccgccccc gatgacgcgg ataaaagcga gcccaagcgg gcctgcccct cagtcgcgga  1860
tccatcgacg tcagacgcgg aaggagctcc ggtggacttt gccgacaggt accaaaacaa  1920
atgttctcgt cacgcgggca tgcttcagat gctgtttccc tgcaaaacat gcgagagaat  1980
```

```
gaatcagaat ttcaacattt gcttcacgca cgggaccaga gactgttcag aatgtttccc  2040
cggcgtgtca gaatctcaac cggtcgtcag aaagaggacg tatcggaaac tctgtgccat  2100
tcatcatctg ctggggcggg ctcccgagat tgcttgctcg gcctgcgatc tggtcaacgt  2160
ggatctggat gactgtgttt ctgagcaata aatgacttaa accaggtatg gctgccgatg  2220
gttatcttcc agattggctc gaggacaacc tctctgaggg cattcgcgag tggtgggact  2280
tgaaacctgg agccccgaaa cccaaagcca accagcaaaa gcaggacgac ggccggggtc  2340
tggtgcttcc tggctacaag tacctcggac ccttcaacgg actcgacaag ggggagcccg  2400
tcaacgcggc ggatgcagcg gccctcgagc acgacaaggc ctacgaccag cagctcaaag  2460
cgggtgacaa tccgtacctg cggtataacc acgccgacgc cgagtttcag gagcgtctgc  2520
aagaagatac gtcttttggg ggcaacctcg ggcgagcagt cttccaggcc aagaagaggg  2580
ttctcgaacc ttttggtctg gttgaggaag gtgctaagac ggctcctgga aagaaacgtc  2640
cggtagagca gtcgccacaa gagccagact cctcctcggg cattggcaag acaggccagc  2700
agcccgctaa aaagagactc aattttggtc agactggcga ctcagagtca gtccccgacc  2760
cacaacctct cggagaacct ccagcaaccc ccgctgctgt gggacctact acaatggctt  2820
caggcggtgg cgcaccaatg gcagacaata acgaaggcgc cgacggagtg ggtaatgcct  2880
caggaaattg gcattgcgat tccacatggc tgggcgacag agtcatcacc accagcaccc  2940
gaacatgggc cttgcccacc tataacaacc acctctacaa gcaaatctcc agtgcttcaa  3000
cgggggccag caacgacaac cactacttcg gctacagcac cccctggggg tattttgatt  3060
tcaacagatt ccactgccat ttctcaccac gtgactggca gcgactcatc aacaacaatt  3120
ggggattccg gcccaagaga ctcaacttca agctcttcaa catccaagtc aaggaggtca  3180
cgacgaatga tggcgtcacg accatcgcta ataaccttac cagcacggtt caagtcttct  3240
cggactcgga gtaccagttg ccgtacgtcc tcggctctgc gcaccagggc tgcctccctc  3300
cgttcccggc ggacgtgttc atgattccgc agtacggcta cctaacgctc aacaatggca  3360
gccaggcagt gggacggtca tccttttact gcctggaata tttcccatcg cagatgctga  3420
gaacgggcaa taactttacc ttcagctaca ccttcgagga cgtgcctttc cacagcagct  3480
acgcgcacag ccagagcctg gaccggctga tgaatcctct catcgaccag tacctgtatt  3540
acctgaacag aactcagaat cagtccggaa gtgcccaaaa caaggacttg ctgtttagcc  3600
gggggtctcc agctggcatg tctgttcagc ccaaaaactg gctacctgga ccctgttacc  3660
ggcagcagcg cgtttctaaa acaaaaacag acaacaacaa cagcaacttt acctggactg  3720
gtgcttcaaa atataacctt aatgggcgtg aatctataat caaccctggc actgctatgg  3780
cctcacacaa agacgacaaa gacaagttct ttcccatgag cggtgtcatg atttttggaa  3840
aggagagcgc cggagcttca aacactgcat tggacaatgt catgatcaca gacgaagagg  3900
aaatcaaagc cactaacccc gtggccaccg aaagatttgg gactgtggca gtcaatctcc  3960
agagcagcag cacagaccct gcgaccggag atgtgcatgt tatgggagcc ttacctggaa  4020
tggtgtggca agacagagac gtatacctgc agggtcctat ttgggccaaa attcctcaca  4080
cggatggaca ctttcacccg tctcctctca tgggcggctt tggacttaag cacccgcctc  4140
ctcagatcct catcaaaaac acgcctgttc ctgcgaatcc tccggcagag ttttcggcta  4200
caaagtttgc ttcattcatc acccagtatt ccacaggaca agtgagcgtg gagattgaat  4260
gggagctgca gaaagaaaac agcaaacgct ggaatcccga agtgcagtat acatctaact  4320
atgcaaaatc tgccaacgtt gatttcactg tggacaacaa tggactttat actgagcctc  4380
gccccattgg cacccgttac ctcacccgtc ccctgtaatt gtgtgttaat caataaaccg  4440
gttaattcgt gtcagttgaa ctttggtctc atgtcgttat tatcttatct ggtcaccata  4500
gcaaccggtt acacattaac tgcttagttg cgcttcgcga atacccctag tgatggagtt  4560
gcccactccc tctatgcgcg ctcgctcgct cggtggggcc ggcagagcag agctctgccg  4620
tctgcggacc tttggtccgc aggccccacc gagcgagcga gcgcgcatag agggagtggg  4680
caa                                                                4683
```

```
SEQ ID NO: 994          moltype = DNA  length = 2211
FEATURE                 Location/Qualifiers
source                  1..2211
                        mol_type = unassigned DNA
                        organism = Adeno-associated virus 6
SEQUENCE: 994
atggctgccg atggttatct tccagattgg ctcgaggaca acctctctga gggcattcgc  60
gagtggtggg acttgaaacc tggagccccg aaacccaaag ccaaccagca aaagcaggac  120
gacggccggg gtctggtgct tcctggctac aagtacctcg gacccttcaa cggactcgac  180
aagggggagc ccgtcaacgc ggcggatgca gcggccctcg agcacgacaa ggcctacgac  240
cagcagctca aagcgggtga caatccgtac ctgcggtata accacgccga cgccgagttt  300
caggagcgtc tgcaagaaga tacgtctttt gggggcaacc tcgggcgagc agtcttccag  360
gccaagaaga gggttctcga accttttggt ctggttgagg aaggtgctaa gacggctcct  420
ggaaagaaac gtccggtaga gcagtcgcca caagagccag actcctcctc gggcattggc  480
aagacaggcc agcagcccgc taaaaagaga ctcaattttg gtcagactgg cgactcagag  540
tcagtccccg acccacaacc tctcggagaa cctccagcaa cccccgctgc tgtgggacct  600
actacaatgg cttcaggcgg tggcgcacca atggcagaca ataacgaagg cgccgacgga  660
gtgggtaatg cctcaggaaa ttggcattgc gattccacat ggctgggcga cagagtcatc  720
accaccagca cccgaacatg ggccttgccc acctataaca accacctcta caagcaaatc  780
tccagtgctt caacgggggc cagcaacgac aaccactact tcggctacag caccccctgg  840
gggtattttg atttcaacag attccactgc catttctcac cacgtgactg gcagcgactc  900
atcaacaaca attggggatt ccggcccaag agactcaact tcaagctctt caacatccaa  960
gtcaaggagg tcacgacgaa tgatggcgtc acgaccatcg ctaataacct taccagcacg  1020
gttcaagtct tctcggactc ggagtaccag ttgccgtacg tcctcggctc tgcgcaccag  1080
ggctgcctcc ctccgttccc ggcggacgtg ttcatgattc cgcagtacgg ctacctaacg  1140
ctcaacaatg gcagccaggc agtgggacgg tcatcctttt actgcctgga atatttccca  1200
tcgcagatgc tgagaacggg caataacttt accttcagct acaccttcga ggacgtgcct  1260
ttccacagca gctacgcgca cagccagagc ctggaccggc tgatgaatcc tctcatcgac  1320
cagtacctgt attacctgaa cagaactcag aatcagtccg gaagtgccca aaacaaggac  1380
ttgctgttta gccgggggtc tccagctggc atgtctgttc agcccaaaaa ctggctacct  1440
ggaccctgtt accggcagca gcgcgtttct aaaacaaaaa cagacaacaa caacagcaac  1500
tttacctgga ctggtgcttc aaaatataac cttaatgggc gtgaatctat aatcaaccct  1560
```

```
ggcactgcta tggcctcaca caaagacgac aaagacaagt tctttcccat gagcggtgtc  1620
atgatttttg gaaaggagag cgccggagct tcaaacactg cattggacaa tgtcatgatc  1680
acagacgaag aggaaatcaa agccactaac cccgtggcca ccgaaagatt tgggactgtg  1740
gcagtcaatc tccagagcag cagcacagac cctgcgaccg gagatgtgca tgttatggga  1800
gccttacctg gaatggtgtg gcaagacaga gacgtatacc tgcagggtcc tatttgggcc  1860
aaaattcctc acacggatgg acactttcac ccgtctcctc tcatgggcgg ctttggactt  1920
aagcacccgc ctcctcagat cctcatcaaa aacacgcctg ttcctgcgaa tcctccggca  1980
gagttttcgg ctacaaagtt tgcttcattc atcacccagt attccacagg acaagtgagc  2040
gtggagattg aatgggagct gcagaaagaa aacagcaaac gctggaatcc cgaagtgcag  2100
tatacatcta actatgcaaa atctgccaac gttgatttca ctgtggacaa caatggactt  2160
tatactgagc ctcgccccat tggcacccgt tacctcaccc gtcccctgta a           2211

SEQ ID NO: 995         moltype = AA  length = 736
FEATURE                Location/Qualifiers
source                 1..736
                       mol_type = protein
                       organism = Adeno-associated virus 6
SEQUENCE: 995
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPFG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEDVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD KDKFFPMSGV  540
MIFGKESAGA SNTALDNVMI TDEEEIKATN PVATERFGTV AVNLQSSSTD PATGDVHVMG  600
ALPGMVWQDR DVYLQGPIWA KIPHTDGHFH PSPLMGGFGL KHPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                  736

SEQ ID NO: 996         moltype = DNA  length = 2214
FEATURE                Location/Qualifiers
source                 1..2214
                       mol_type = unassigned DNA
                       organism = Adeno-associated virus 7
SEQUENCE: 996
atggctgccg atggttatct tccagattgg ctcgaggaca acctctctga gggcattcgc  60
gagtggtggg acctgaaacc tggagccccg aaacccaaag ccaaccagca aaagcaggac  120
aacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctca aagcgggtga caatccgtac ctgcggtata accacgccga cgccgagttt  300
caggagcgtc tgcaagaaga tacgtcattt gggggcaacc tcgggcgagc agtcttccag  360
gccaagaagc gggttctcga acctctcggt ctggttgagg aaggcgctaa gacggctcct  420
gcaaagaaga gaccggtaga gccgtcacct cagcgttccc ccgactcctc cacgggcatc  480
ggcaagaaag gccagcagcc cgccagaaag agactcaatt tcggtcagac tggcgactca  540
gagtcagtcc ccgaccctca acctctcgga gaacctccag cagcgccctc tagtgtggga  600
tctggtacag tggctgcagg cggtggcgca ccaatggcag acaataacga aggtgccgac  660
ggagtgggta atgcctcagg aaattggcat tgcgattcca catggctggg cgacagagtc  720
attaccacca gcacccgaac ctgggccctg cccacctaca acaaccacct ctacaagcaa  780
atctccagtg aaactgcagg tagtaccaac gacaacacct acttcggcta cagcaccccc  840
tgggggtatt ttgactttaa cagattccac tgccacttct caccacgtga ctggcagcga  900
ctcatcaaca acaactgggg attccggccc aagaagctgc ggttcaagct cttcaacatc  960
caggtcaagg aggtcacgac gaatgacggc gttacgacca tcgctaataa ccttaccagc  1020
acgattcagg tattctcgga ctcggaatac cagctgccgt acgtcctcgg ctctgcgcac  1080
cagggctgcc tgcctccgtt cccggcggac gtcttcatga ttcctcagta cggctacctg  1140
actctcaaca atggcagtca gtctgtggga cgttcctcct tctactgcct ggagtacttc  1200
ccctctcaga tgctgagaac gggcaacaac tttgagttca gctacagctt cgaggacgtg  1260
cctttccaca gcagctacgc acacagccag agcctggacc ggctgatgaa tcccctcatc  1320
gaccagtact tgtactacct ggccagaaca cagagtaacc caggaggcac agctggcaat  1380
cgggaactgc agttttacca gggcgggcct tcaactatgg ccgaacaagc caagaattgg  1440
ttacctggac cttgcttccg gcaacaaaga gtctccaaaa cgctggatca aaacaacaac  1500
agcaactttg cttggactgg tgccaccaaa tatcacctga acggcagaaa ctcgttggtt  1560
aatcccggcg tcgccatggc aactcacaag gacgacgagg accgcttttt cccatccagc  1620
ggagtcctga tttttggaaa aactggagca actaacaaaa ctacattgga aaatgtgtta  1680
atgacaaatg aagaagaaat tcgtcctact aatcctgtag ccacggaaga atacgggata  1740
gtcagcagca acttacaagc ggctaatact gcagcccaga cacaagttgt caacaaccag  1800
ggagccttac ctggcatggt ctggcagaac cgggacgtgt acctgcaggg tcccatctgg  1860
gccaagattc ctcacacgga tggcaacttt cacccgtctc ctttgatggg cggctttgga  1920
cttaaacatc cgcctcctca gatcctgatc aagaacactc ccgttcccgc taatcctccg  1980
gaggtgttta ctcctgccaa gtttgcttcg ttcatcacac agtacagcac cggacaagtc  2040
agcgtggaaa tcgagtggga gctgcagaag gaaaacagca agcgctggaa cccggagatt  2100
cagtacacct ccaactttga aaagcagact ggtgtggact ttgccgttga cagccagggt  2160
gtttactctg agcctcgccc tattggcact cgttacctca cccgtaatct gtaa        2214

SEQ ID NO: 997         moltype = DNA  length = 4721
FEATURE                Location/Qualifiers
source                 1..4721
```

```
                         mol_type = unassigned DNA
                         organism = Adeno-associated virus 7
SEQUENCE: 997
ttggccactc cctctatgcg cgctcgctcg ctcggtgggg cctgcggacc aaaggtccgc  60
agacggcaga gctctgctct gccggcccca ccgagcgagc gagcgcgcat agagggagtg  120
gccaactcca tcactagggg taccgcgaag cgcctcccac gctgccgcgt cagcgctgac  180
gtaaatcacg tcataggggg gtggtcctgt attagctgtc acgtgagtgc ttttgcgaca  240
ttttgcgaca ccacgtggcc atttgaggta tatatggccg agtgagcgag caggatctcc  300
attttgaccg cgaaatttga acgagcagca gccatgccgg gtttctacga gatcgtgatc  360
aaggtgccga gcgacctgga cgagcacctg ccgggcattt ctgactcgtt tgtgaactgg  420
gtggccgaga aggaatggga gctgccccgg gattctgaca tggatctgaa tctgatcgag  480
caggcacccc tgaccgtggc cgagaagctg cagcgcgact tcctggtcca atggcgccgc  540
gtgagtaagg ccccggaggc cctgttcttt gttcagttcg agaagggcga gagctacttc  600
caccttcacg ttctggtgga gaccacgggg gtcaagtcca tggtgctagg ccgcttcctg  660
agtcagattc gggagaagct ggtccagacc atctaccgcg gggtcgagcc cacgctgccc  720
aactggttcg cggtgaccaa gacgcgtaat ggcgccggcg gggggaacaa ggtggtggac  780
gagtgctaca tccccaacta cctcctgccc aagacccagc ccgagctgca gtgggcgtgg  840
actaacatgg aggagtatat aagcgcgtgt ttgaacctgg ccgaacgcaa acggctcgtg  900
gcgcagcacc tgacccacgt cagccagacg caggagcaga acaaggagaa tctgaacccc  960
aattctgacg cgcccgtgat caggtcaaaa acctccgcgc gctacatgga gctggtcggg  1020
tggctggtgg accggggcat cacctccgag aagcagtgga tccaggagga ccaggcctcg  1080
tacatctcct tcaacgccgc ctccaactcg cggtcccaga tcaaggccgc gctggacaat  1140
gccggcaaga tcatggcgct gaccaaatcc gcgcccgact acctggtggg gccctcgctg  1200
cccgcggaca ttaaaaccaa ccgcatctac cgcatcctgg agctgaacgg gtacgatcct  1260
gcctacgccg gctccgtctt tctcggctgg gcccagaaaa agttcgggaa gcgcaacacc  1320
atctggctgt ttgggcccgc caccaccggc aagaccaaca ttgcggaagc catcgcccac  1380
gccgtgccct tctacggctg cgtcaactgg accaatgaga actttccctt caacgattgc  1440
gtcgacaaga tggtgatctg gtgggaggag ggcaagatga cggccaaggt cgtggagtcc  1500
gccaaggcca ttctcggcgg cagcaaggtg cgcgtggacc aaaagtgcaa gtcgtccgcc  1560
cagatcgacc ccaccccccgt gatcgtcacc tccaacacca acatgtgcgc cgtgattgac  1620
gggaacagca ccaccttcga gcaccagcag ccgttgcagg accggatgtt caaatttgaa  1680
ctcacccgcc gtctggagca cgactttggc aaggtgacga agcaggaagt caaagagttc  1740
ttccgctggg ccagtgatca cgtgaccgag gtggcgcatg agttctacgt cagaaagggc  1800
ggagccagca aaagacccgc ccccgatgac gcggatataa gcgagcccaa gcgggcctgc  1860
ccctcagtcg cggatccatc gacgtcagac gcggaaggag ctccggtgga ctttgccgac  1920
aggtaccaaa acaaatgttc tcgtcacgcg ggcatgattc agatgctgtt tccctgcaaa  1980
acgtgcgaga gaatgaatca gaatttcaac atttgcttca cacacggggt cagagactgt  2040
ttagagtgtt tccccggcgt gtcagaatct caaccggtcg tcagaaaaaa gacgtatcgg  2100
aaactctgcg cgattcatca tctgctgggg cgggcgcccg agattgcttg ctcggcctgc  2160
gacctggtca acgtggacct ggacgactgc gtttctgagc aataaatgac ttaaaccagg  2220
tatggctgcc gatggttatc ttccagattg gctcgaggac aacctctctg agggcattcg  2280
cgagtggtgg gacctgaaac ctggagcccc gaaacccaaa gccaaccagc aaaagcagga  2340
caacggccgg ggtctggtgc ttcctggcta caagtacctc ggacccttca acggactcga  2400
caagggggag cccgtcaacg cggcggacgc agcggccctc gagcacgaca aggcctacga  2460
ccagcagctc aaagcgggtg acaatccgta cctgcggtat aaccacgccg acgccgagtt  2520
tcaggagcgt ctgcaagaag atacgtcatt tgggggcaac ctcgggcgag cagtcttcca  2580
ggccaagaag cgggttctcg aacctctcgg tctggttgag gaaggcgcta agacggctcc  2640
tgcaaagaag agaccggtag agccgtcacc tcagcgttcc cccgactcct ccacgggcat  2700
cggcaagaaa ggccagcagc ccgccagaaa gagactcaat ttcggtcaga ctggcgactc  2760
agagtcagtc cccgaccctc aacctctcgg agaacctcca gcagcgccct ctagtgtggg  2820
atctggtaca gtggctgcag gcggtggcgc accaatggca gacaataacg aaggtgccga  2880
cggagtgggt aatgcctcag gaaattggca ttgcgattcc acatggctgg gcgacagagt  2940
cattaccacc agcacccgaa cctgggccct gcccacctac aacaaccacc tctacaagca  3000
aatctccagt gaaactgcag gtagtaccaa cgacaacacc tacttcggct acagcacccc  3060
ctgggggtat tttgacttta acagattcca ctgccacttc tcaccacgtg actggcagcg  3120
actcatcaac aacaactggg gattccggcc caagaagctg cggttcaagc tcttcaacat  3180
ccaggtcaag gaggtcacga cgaatgacgg cgttacgacc atcgctaata accttaccag  3240
cacgattcag gtattctcgg actcggaata ccagctgccg tacgtcctcg gctctgcgca  3300
ccagggctgc ctgcctccgt tcccggcgga cgtcttcatg attcctcagt acggctacct  3360
gactctcaac aatggcagtc agtctgtggg acgttcctcc ttctactgcc tggagtactt  3420
cccctctcag atgctgagaa cgggcaacaa ctttgagttc agctacagct tcgaggacgt  3480
gcctttccac agcagctacg cacacagcca gagcctggac cggctgatga atcccctcat  3540
cgaccagtac ttgtactacc tggccagaac acagagtaac ccaggaggca cagctggcaa  3600
tcgggaactg cagttttacc agggcgggcc ttcaactatg gccgaacaag ccaagaattg  3660
gttacctgga ccttgcttcc ggcaacaaag agtctccaaa acgctggatc aaaacaacaa  3720
cagcaacttt gcttggactg gtgccaccaa atatcacctg aacggcagaa actcgttggt  3780
taatcccggc gtcgccatgg caactcacaa ggacgacgag gaccgctttt tcccatccag  3840
cggagtcctg atttttggaa aaactggagc aactaacaaa actacattgg aaaatgtgtt  3900
aatgacaaat gaagaagaaa ttcgtcctac taatcctgta gccacggaag aatacgggat  3960
agtcagcagc aacttacaag cggctaatac tgcagcccag acacaagttg tcaacaacca  4020
gggagcctta cctggcatgg tctggcagaa ccgggacgtg tacctgcagg gtcccatctg  4080
ggccaagatt cctcacacgg atggcaactt tcacccgtct cctttgatgg gcggctttgg  4140
acttaaacat ccgcctcctc agatcctgat caagaacact cccgttcccg ctaatcctcc  4200
ggaggtgttt actcctgcca agtttgcttc gttcatcaca cagtacagca ccggacaagt  4260
cagcgtggaa atcgagtggg agctgcagaa ggaaaacagc aagcgctgga acccggagat  4320
tcagtacacc tccaactttg aaaagcagac tggtgtggac tttgccgttg acagccaggg  4380
tgtttactct gagcctcgcc ctattggcac tcgttacctc acccgtaatc tgtaattgca  4440
tgttaatcaa taaaccggtt gattcgtttc agttgaactt tggtctcctg tgcttcttat  4500
cttatcggtt tccatagcaa ctggttacac attaactgct tgggtgcgct tcacgataag  4560
```

```
aacactgacg tcaccgcggt acccctagtg atggagttgg ccactccctc tatgcgcgct  4620
cgctcgctcg gtggggcctg cggaccaaag gtccgcagac ggcagagctc tgctctgccg  4680
gccccaccga gcgagcgagc gcgcatagag ggagtggcca a                      4721

SEQ ID NO: 998         moltype = AA  length = 737
FEATURE                Location/Qualifiers
source                 1..737
                       mol_type = protein
                       organism = Adeno-associated virus 7
SEQUENCE: 998
MAADGYLPDW LEDNLSEGIR EWWDLKPGAP KPKANQQKQD NGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP AKKRPVEPSP QRSPDSSTGI GKKGQQPARK RLNFGQTGDS  180
ESVPDPQPLG EPPAAPSSVG SGTVAAGGGA PMADNNEGAD GVGNASGNWH CDSTWLGDRV  240
ITTSTRTWAL PTYNNHLYKQ ISSETAGSTN DNTYFGYSTP WGYFDFNRFH CHFSPRDWQR  300
LINNNWGFRP KKLRFKLFNI QVKEVTTNDG VTTIANNLTS TIQVFSDSEY QLPYVLGSAH  360
QGCLPPFPAD VFMIPQYGYL TLNNGSQSVG RSSFYCLEYF PSQMLRTGNN FEFSYSFEDV  420
PFHSSYAHSQ SLDRLMNPLI DQYLYYLART QSNPGGTAGN RELQFYQGGP STMAEQAKNW  480
LPGPCFRQQR VSKTLDQNNN SNFAWTGATK YHLNGRNSLV NPGVAMATHK DDEDRFFPSS  540
GVLIFGKTGA TNKTTLENVL MTNEEEIRPT NPVATEEYGI VSSNLQAANT AAQTQVVNNQ  600
GALPGMVWQN RDVYLQGPIW AKIPHTDGNF HPSPLMGGFG LKHPPPQILI KNTPVPANPP  660
EVFTPAKFAS FITQYSTGQV SVEIEWELQK ENSKRWNPEI QYTSNFEKQT GVDFAVDSQG  720
VYSEPRPIGT RYLTRNL                                                 737

SEQ ID NO: 999         moltype = DNA  length = 4393
FEATURE                Location/Qualifiers
source                 1..4393
                       mol_type = unassigned DNA
                       organism = Adeno-associated virus 8
SEQUENCE: 999
cagagaggga gtggccaact ccatcactag gggtagcgcg aagcgcctcc cacgctgccg  60
cgtcagcgct gacgtaaatt acgtcatagg ggagtggtcc tgtattagct gtcacgtgag  120
tgcttttgcg gcattttgcg acaccacgtg gccatttgag gtatatatgg ccgagtgagc  180
gagcaggatc tccattttga ccgcgaaatt tgaacgagca gcagccatgc cgggcttcta  240
cgagatcgtg atcaaggtgc cgagcgacct ggacgagcac ctgccgggca tttctgactc  300
gtttgtgaac tgggtggccg agaaggaatg ggagctgccc ccggattctg acatggatcg  360
gaatctgatc gagcaggcac ccctgaccgt ggccgagaag ctgcagcgcg acttcctggt  420
ccaatggcgc cgcgtgagta aggccccgga ggccctcttc tttgttcagt tcgagaaggg  480
cgagagctac tttcacctgc acgttctggt cgagaccacg gggtcaagt ccatggtgct  540
aggccgcttc ctgagtcaga ttcgggaaaa gcttggtcca gaccatctac ccgcggggtc  600
gagccccacc ttgcccaact ggttcgcggt gaccaaagac gcggtaatgg cgccggcggg  660
ggggaacaag gtggtggacg agtgctacat ccccaactac ctcctgccca agactcagcc  720
cgagctgcag tgggcgtgga ctaacatgga ggagtatata agcgcgtgct tgaacctggc  780
cgagcgcaaa cggctcgtgg cgcagcacct gacccacgtc agccagacgc aggagcagaa  840
caaggagaat ctgaacccca attctgacgc gcccgtgatc aggtcaaaaa cctccgcgcg  900
ctatatggag ctggtcgggt ggctggtgga ccggggcatc acctccgaga agcagtggat  960
ccaggaggac caggcctcgt acatctcctt caacgccgcc tccaactcgc ggtcccagat  1020
caaggccgcg ctggacaatg ccggcaagat catggcgctg accaaatccg cgcccgacta  1080
cctggtgggg ccctcgctgc ccgcggacat tacccagaac cgcatctacc gcatcctcgc  1140
tctcaacggc tacgaccctg cctacgccgg ctccgtcttt ctcggctggg ctcagaaaaa  1200
gttcgggaaa cgcaacacca tctggctgtt tggacccgcc accaccggca agaccaacat  1260
tgcggaagcc atcgcccacg ccgtgccctt ctacggctgc gtcaactgga ccaatgagaa  1320
ctttcccttc aatgattgcg tcgacaagat ggtgatctgg tgggaggagg gcaagatgac  1380
ggccaaggtc gtggagtccg ccaaggccat tctcggcggc agcaaggtgc gcgtggacca  1440
aaagtgcaag tcgtccgccc agatcgaccc cacccccgtg atcgtcacct ccaacaccaa  1500
catgtgcgcc gtgattgacg ggaacagcac caccttcgag caccagcagc ctctccagga  1560
ccggatgttt aagttcgaac tcacccgccg tctggagcac gactttggca aggtgacaaa  1620
gcaggaagtc aaagagttct tccgctgggc cagtgatcac gtgaccgagg tggcgcatga  1680
gttttacgtc agaaagggcg gagccagcaa aagacccgcc cccgatgacg cggataaaag  1740
cgagcccaag cgggcctgcc cctcagtcgc ggatccatcg acgtcagacg cggaaggagc  1800
tccggtggac tttgccgaca ggtaccaaaa caaatgttct cgtcacgcgg gcatgcttca  1860
gatgctgttt ccctgcaaaa cgtgcgagag aatgaatcag aatttcaaca tttgcttcac  1920
acacggggtc agagactgct cagagtgttt ccccggcgtg tcagaatctc aaccggtcgt  1980
cagaaagagg acgtatcgga aactctgtgc gattcatcat ctgctggggc gggctcccga  2040
gattgcttgc tcggcctgcg atctggtcaa cgtggacctg gatgactgtg tttctgagca  2100
ataaatgact taaaccaggt atggctgccg atggttatct tccagattgg ctcgaggaca  2160
acctctctga gggcattcgc gagtggtggg cgctgaaacc tggagccccg aagcccaaag  2220
ccaaccagca aaagcaggac gacggccggg gtctggtgct tcctggctac aagtacctcg  2280
gacccttcaa cggactcgac aagggggagc ccgtcaacgc ggcggacgca gcggccctcg  2340
agcacgacaa ggcctacgac cagcagctgc aggcgggtga caatccgtac ctgcggtata  2400
accacgccga cgccgagttt caggagcgtc tgcaagaaga tacgtctttt gggggcaacc  2460
tcgggcgagc agtcttccag gccaagaagc gggttctcga acctctcggt ctggttgagg  2520
aaggcgctaa gacggctcct ggaaagaaga gaccggtaga gccatcaccc cagcgttctc  2580
cagactcctc tacgggcatc ggcaagaaag gccaacagcc cgccagaaaa agactcaatt  2640
ttggtcagac tggcgactca gagtcagttc cagaccctca acctctcgga gaacctccag  2700
cagcgccctc tggtgtggga cctaatacaa tggctgcagg cggtggcgca ccaatggcag  2760
acaataacga aggcgccgac ggagtgggta gttcctcggg aaattggcat tgcgattcca  2820
catggctggg cgacagagtc atcaccacca gcacccgaac ctgggccctg cccacctaca  2880
acaaccacct ctacaagcaa atctccaacg ggacatcggg aggagccacc aacgacaaca  2940
```

```
cctacttcgg ctacagcacc ccctgggggt attttgactt taacagattc cactgccact  3000
tttcaccacg tgactggcag cgactcatca acaacaactg ggattccgg cccaagagac   3060
tcagcttcaa gctcttcaac atccaggtca aggaggtcac gcagaatgaa ggcaccaaga  3120
ccatcgccaa taacctcacc agcaccatcc aggtgtttac ggactcggag taccagctgc  3180
cgtacgttct cggctctgcc caccagggct gcctgcctcc gttcccggcg gacgtgttca  3240
tgattcccca gtacggctac ctaacactca acaacggtag tcaggccgtg ggacgctcct  3300
ccttctactg cctggaatac tttccttcgc agatgctgag aaccggcaac aacttccagt  3360
ttacttacac cttcgaggac gtgcctttcc acagcagcta cgcccacagc cagagcttgg  3420
accggctgat gaatcctctg attgaccagt acctgtacta cttgtctcgg actcaaacaa  3480
caggaggcac ggcaaatacg cagactctgg gcttcagcca aggtgggcct aatacaatgg  3540
ccaatcaggc aaagaactgg ctgccaggac cctgttaccg ccaacaacgc gtctcaacga  3600
caaccgggca aaacaacaat agcaactttg cctggactgc tgggaccaaa taccatctga  3660
atggaagaaa ttcattggct aatcctggca tcgctatggc aacacacaaa gacgacgagg  3720
agcgtttttt tcccagtaac gggatcctga tttttggcaa acaaaatgct gccagagaca  3780
atgcggatta cagcgatgtc atgctcacca gcgaggaaga aatcaaaacc actaaccctg  3840
tggctacaga ggaatacggt atcgtggcag ataacttgca gcagcaaaac acggctcctc  3900
aaattggaac tgtcaacagc cagggggcct tacccggtat ggtctggcag aaccgggacg  3960
tgtacctgca gggtcccatc tgggccaaga ttcctcacac ggacggcaac ttccacccgt  4020
ctccgctgat gggcggcttt ggcctgaaac atcctccgcc tcagatcctg atcaagaaca  4080
cgcctgtacc tgcggatcct ccgaccacct tcaaccagtc aaagctgaac tctttcatca  4140
cgcaatacag caccggacag gtcagcgtgg aaattgaatg ggagctgcag aaggaaaaca  4200
gcaagcgctg gaaccccgag atccagtaca cctccaacta ctacaaatct acaagtgtgg  4260
actttgctgt taatacagaa ggcgtgtact ctgaaccccg ccccattggc acccgttacc  4320
tcacccgtaa tctgtaattg cctgttaatc aataaaccgg ttgattcgtt tcagttgaac  4380
tttggtctct gcg                                                    4393
```

```
SEQ ID NO: 1000         moltype = DNA  length = 2217
FEATURE                 Location/Qualifiers
source                  1..2217
                        mol_type = unassigned DNA
                        organism = Adeno-associated virus 8
SEQUENCE: 1000
atggctgccg atggttatct tccagattgg ctcgaggaca acctctctga gggcattcgc  60
gagtggtggg cgctgaaacc tggagccccg aagcccaaag ccaaccagca aaagcaggac  120
gacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctgc aggcgggtga caatccgtac ctgcggtata accacgccga cgccgagttt  300
caggagcgtc tgcaagaaga tacgtctttt gggggcaacc tcgggcgagc agtcttccag  360
gccaagaagc gggttctcga acctctcggt ctggttgagg aaggcgctaa gacggctcct  420
ggaaagaaga gaccggtaga gccatcaccc cagcgttctc cagactcctc tacgggcatc  480
ggcaagaaag gccaacagcc cgccagaaaa agactcaatt ttggtcagac tggcgactca  540
gagtcagttc cagaccctca acctctcgga gaacctccag cagcgccctc tggtgtggga  600
cctaatacaa tggctgcagg cggtggcgca ccaatggcag acaataacga aggcgccgac  660
ggagtgggta gttcctcggg aaattggcat tgcgattcca catggctggg cgacagagtc  720
atcaccacca gcacccgaac ctgggccctg cccacctaca acaaccacct ctacaagcaa  780
atctccaacg ggacatcggg aggagccacc aacgacaaca cctacttcgg ctacagcacc  840
ccctgggggt attttgactt taacagattc cactgccact tttcaccacg tgactggcag  900
cgactcatca acaacaactg ggattccgg cccaagagac tcagcttcaa gctcttcaac   960
atccaggtca aggaggtcac gcagaatgaa ggcaccaaga ccatcgccaa taacctcacc  1020
agcaccatcc aggtgtttac ggactcggag taccagctgc cgtacgttct cggctctgcc  1080
caccagggct gcctgcctcc gttcccggcg gacgtgttca tgattcccca gtacggctac  1140
ctaacactca acaacggtag tcaggccgtg ggacgctcct ccttctactg cctggaatac  1200
tttccttcgc agatgctgag aaccggcaac aacttccagt ttacttacac cttcgaggac  1260
gtgcctttcc acagcagcta cgcccacagc cagagcttgg accggctgat gaatcctctg  1320
attgaccagt acctgtacta cttgtctcgg actcaaacaa caggaggcac ggcaaatacg  1380
cagactctgg gcttcagcca aggtgggcct aatacaatgg ccaatcaggc aaagaactgg  1440
ctgccaggac cctgttaccg ccaacaacgc gtctcaacga caaccgggca aaacaacaat  1500
agcaactttg cctggactgc tgggaccaaa taccatctga atggaagaaa ttcattggct  1560
aatcctggca tcgctatggc aacacacaaa gacgacgagg agcgtttttt tcccagtaac  1620
gggatcctga tttttggcaa acaaaatgct gccagagaca atgcggatta cagcgatgtc  1680
atgctcacca gcgaggaaga aatcaaaacc actaaccctg tggctacaga ggaatacggt  1740
atcgtggcag ataacttgca gcagcaaaac acggctcctc aaattggaac tgtcaacagc  1800
cagggggcct tacccggtat ggtctggcag aaccgggacg tgtacctgca gggtcccatc  1860
tgggccaaga ttcctcacac ggacggcaac ttccacccgt ctccgctgat gggcggcttt  1920
ggcctgaaac atcctccgcc tcagatcctg atcaagaaca cgcctgtacc tgcggatcct  1980
ccgaccacct tcaaccagtc aaagctgaac tctttcatca cgcaatacag caccggacag  2040
gtcagcgtgg aaattgaatg ggagctgcag aaggaaaaca gcaagcgctg gaaccccgag  2100
atccagtaca cctccaacta ctacaaatct acaagtgtgg actttgctgt taatacagaa  2160
ggcgtgtact ctgaaccccg ccccattggc acccgttacc tcacccgtaa tctgtaa     2217
```

```
SEQ ID NO: 1001         moltype = AA  length = 738
FEATURE                 Location/Qualifiers
source                  1..738
                        mol_type = protein
                        organism = Adeno-associated virus 8
SEQUENCE: 1001
MAADGYLPDW LEDNLSEGIR EWWALKPGAP KPKANQQKQD DGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVEEGAKTAP GKKRPVEPSP QRSPDSSTGI GKKGQQPARK RLNFGQTGDS  180
```

```
ESVPDPQPLG EPPAAPSGVG PNTMAAGGGA PMADNNEGAD GVGSSSGNWH CDSTWLGDRV  240
ITTSTRTWAL PTYNNHLYKQ ISNGTSGGAT NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFQFTYTFED  420
VPFHSSYAHS QSLDRLMNPL IDQYLYYLSR TQTTGGTANT QTLGFSQGGP NTMANQAKNW  480
LPGPCYRQQR VSTTTGQNNN SNFAWTAGTK YHLNGRNSLA NPGIAMATHK DDEERFFPSN  540
GILIFGKQNA ARDNADYSDV MLTSEEEIKT TNPVATEEYG IVADNLQQQN TAPQIGTVNS  600
QGALPGMVWQ NRDVYLQGPI WAKIPHTDGN FHPSPLMGGF GLKHPPPQIL IKNTPVPADP  660
PTTFNQSKLN SFITQYSTGQ VSVEIEWELQ KENSKRWNPE IQYTSNYYKS TSVDFAVNTE  720
GVYSEPRPIG TRYLTRNL                                               738

SEQ ID NO: 1002         moltype = DNA  length = 2211
FEATURE                 Location/Qualifiers
source                  1..2211
                        mol_type = unassigned DNA
                        organism = Adeno-associated virus 9
SEQUENCE: 1002
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgc tgatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa aacagcaagc gctggaaccc ggagatccag  2100
tacacttcca actattacaa gtctaataat gttgaatttg ctgttaatac tgaaggtgta  2160
tatagtgaac ccgcgcccat tggcaccaga tacctgactc gtaatctgta a          2211

SEQ ID NO: 1003         moltype = AA  length = 736
FEATURE                 Location/Qualifiers
source                  1..736
                        mol_type = protein
                        organism = Adeno-associated virus 9
SEQUENCE: 1003
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 1004         moltype = DNA  length = 2232
FEATURE                 Location/Qualifiers
misc_feature            1..2232
                        note = Description of Artificial Sequence: Synthetic
```

```
                          polynucleotide
source                   1..2232
                         mol_type = other DNA
                         organism = synthetic construct
SEQUENCE: 1004
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctctagaact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaattttg gcaaacaagg taccggcaga gacaacgtgg atgcggacaa agtcatgata  1680
accaacgaag aagaaattaa aactactaac ccggtagcaa cggagtccta tggacaagtg  1740
gccacaaacc accagagtgc ccaaactttg gcggtgcctt ttaaggcaca ggcgcagacc  1800
ggttgggttc aaaaccaagg aatacttccg ggtatggttt ggcaggacag agatgtgtac  1860
ctgcaaggac ccatttgggc caaaattcct cacacggacg gcaactttca cccttctccg  1920
ctgatgggag ggtttggaat gaagcacccg cctcctcaga tcctcatcaa aaacacacct  1980
gtacctgcgg atcctccaac ggccttcaac aaggacaagc tgaactcttt catcacccag  2040
tattctactg gccaagtcag cgtggagatc gagtgggagc tgcagaagga aaacagcaag  2100
cgctggaacc cggagatcca gtacacttcc aactattaca agtctaataa tgttgaattt  2160
gctgttaata ctgaaggtgt atatagtgaa ccccgcccca ttggcaccag atacctgact  2220
cgtaatctgt aa                                                      2232

SEQ ID NO: 1005          moltype = AA  length = 743
FEATURE                  Location/Qualifiers
REGION                   1..743
                         note = Description of Artificial Sequence: Synthetic
                          polypeptide
source                   1..743
                         mol_type = protein
                         organism = synthetic construct
SEQUENCE: 1005
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                          743

SEQ ID NO: 1006          moltype = AA  length = 736
FEATURE                  Location/Qualifiers
REGION                   1..736
                         note = Description of Artificial Sequence: Synthetic
                          polypeptide
source                   1..736
                         mol_type = protein
                         organism = synthetic construct
SEQUENCE: 1006
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
```

-continued

```
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT IQSSQTPRQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                 736

SEQ ID NO: 1007        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
SEQUENCE: 1007
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT IILGTGTSQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTR TNPEAAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 1008        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
SEQUENCE: 1008
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT IILGTGTSQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQNG GTSSSAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743

SEQ ID NO: 1009        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
SEQUENCE: 1009
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSDGTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                         743
```

```
SEQ ID NO: 1010        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
SEQUENCE: 1010
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQQA VRTSLAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                        743

SEQ ID NO: 1011        moltype = AA  length = 736
FEATURE                Location/Qualifiers
REGION                 1..736
                       note = Description of Artificial Sequence: Synthetic
                        polypeptide
source                 1..736
                       mol_type = protein
                       organism = synthetic construct
SEQUENCE: 1011
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSRT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                736

SEQ ID NO: 1012        moltype = DNA  length = 3129
FEATURE                Location/Qualifiers
source                 1..3129
                       mol_type = unassigned DNA
                       organism = Adeno-associated virus
SEQUENCE: 1012
gaattcgccc tttctacggc tgcgtcaact ggaccaatga gaactttccc ttcaacgatt  60
gcgtcgacaa gatggtgatc tggtgggagg agggcaagat gacggccaag gtcgtggagt  120
ccgccaaggc cattctcggc ggcagcaaag tgcgcgtgga ccaaaagtgc aagtcgtccg  180
cccagatcga ccccaccccc gtgatcgtca cctccaacac caacatgtgc gccgtgattg  240
acgggaacag caccaccttc gagcaccagc agccgttgca ggaccggatg ttcaagtttg  300
aactcacccg ccgtctggag cacgactttg gcaaggtgac aaagcaggaa gtcagagagt  360
tcttccgctg ggcgcaggat cacgtgaccg aggtggcgca cgagttctac gtcagaaagg  420
gtggagccaa caagagaccc gcccccgatg acgcggataa aagcgagccc aagcgggcct  480
gcccctcagt cgcggatcca tcgacgtcag acgcggaagg agctccggtg gactttgccg  540
acaggtacca aaacaaatgt tctcgtcacg cgggcatgct tcagatgctg tttccctgca  600
aaacatgcga gagaatgaat cagaatttca acatttgctt cacgcacggg accagagact  660
gttcagaatg tttccccggc gtgtcagaat ctcaaccggt cgtcagaaaa aagacgtatc  720
ggaaactctg tgcgattcat catctgctgg gggcgggcac ccgagattgc ttgctcggcc  780
tgcgatctgg tcaacgtgga cctagatgac tgtgtttctg agcaataaat gacttaaacc  840
aggtatggct gccgatggtt atcttccaga ttggctcgag gacaacctct ctgagggcat  900
tcgcgagtgg tgggacttga aacctggagc cccgaaaccc aaagccaacc agcaaaagca  960
ggacgacggc cggggtctgg tgcttcctgg ctacaagtac ctcggaccct tcaacggact  1020
cgacaagggg gagcccgtca acgcggcgga cgcagcggcc ctcgagcacg acaaggccta  1080
cgaccagcag ctcaaagcgg gtgacaatcc gtacctgcgg tataaccacg ccgacgccga  1140
gtttcaggag cgtctgcaag aagatacgtc ttttgggggc aacctcgggc gagcagtctt  1200
ccaggccaag aagcgggttc tcgaacctct cggtctggtt gaggaaggcg ctaagacggc  1260
tcctggaaag aagagaccgg tagagccatc accccagcgt tctccagact cctctacggg  1320
catcggcaag aaaggccagc agcccgcgaa aaagagactc aactttgggc agactggcga  1380
ctcagagtca gtgcccgacc ctcaaccaat cggagaaccc cccgcaggcc cctctggtct  1440
gggatctggt acaatggctg caggcggtgg cgctccaatg gcagacaata acgaaggcgc  1500
cgacggagtg ggtagttcct caggaaattg gcattgcgat tccacatggc tgggcgacag  1560
```

```
agtcatcacc accagcaccc gaacctgggc cctccccacc tacaacaacc acctctacaa  1620
gcaaatctcc aacgggactt cgggaggaag caccaacgac aacacctact tcggctacag  1680
cacccccctgg gggtattttg actttaacag attccactgc cacttctcac cacgtgactg  1740
gcagcgactc atcaacaaca actggggatt ccggcccaag agactcaact tcaagctctt  1800
caacatccag gtcaaggagg tcacgcagaa tgaaggcacc aagaccatcg ccaataacct  1860
taccagcacg attcaggtct ttacggactc ggaataccag ctcccgtacg tcctcggctc  1920
tgcgcaccag ggctgcctgc ctccgttccc ggcggacgtc ttcatgattc ctcagtacgg  1980
gtacctgact ctgaacaatg gcagtcaggc cgtgggccgt tcctccttct actgcctgga  2040
gtactttcct tctcaaatgc tgagaacggg caacaacttt gagttcagct accagtttga  2100
ggacgtgcct tttcacagca gctacgcgca cagccaaagc ctggaccggc tgatgaaccc  2160
cctcatcgac cagtacctgt actacctgtc tcggactcag tccacgggag gtaccgcagg  2220
aactcagcag ttgctatttt ctcaggccgg gcctaataac atgtcggctc aggccaaaaa  2280
ctggctaccc gggccctgct accggcagca acgcgtctcc acgacactgt cgcaaaataa  2340
caacagcaac tttgcctgga ccggtgccac caagtatcat ctgaatggca gagactctct  2400
ggtaaatccc ggtgtcgcta tggcaaccca caaggacgac gaagagcgat tttttccgtc  2460
cagcggagtc ttaatgtttg ggaaacaggg agctggaaaa gacaacgtgg actatagcag  2520
cgttatgcta accagtgagg aagaaattaa aaccaccaac ccagtggcca cagaacagta  2580
cggcgtggtg gccgataacc tgcaacagca aaacgccgct cctattgtag gggccgtcaa  2640
cagtcaagga gccttacctg gcatggtctg gcagaaccgg gacgtgtacc tgcagggtcc  2700
tatctgggcc aagattcctc acacggacgg aaactttcat ccctcgccgc tgatgggagg  2760
ctttggactg aaacacccgc ctcctcagat cctgattaag aatacacctg ttcccgcgga  2820
tcctccaact accttcagtc aagctaagct ggcgtcgttc atcacgcagt acagcaccgg  2880
acaggtcagc gtggaaattg aatgggagct gcagaaagaa aacagcaaac gctggaaccc  2940
agagattcaa tacacttcca actactacaa atctacaaat gtggactttg ctgttaacac  3000
agatggcact tattctgagc ctcgccccat cggcacccgt tacctcaccc gtaatctgta  3060
attgcttgtt aatcaataaa ccggttgatt cgtttcagtt gaactttggt ctctgcgaag  3120
ggcgaattc                                                        3129

SEQ ID NO: 1013        moltype = AA  length = 738
FEATURE                Location/Qualifiers
source                 1..738
                       mol_type = protein
                       organism = Adeno-associated virus
SEQUENCE: 1013
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                               738

SEQ ID NO: 1014        moltype = DNA  length = 2215
FEATURE                Location/Qualifiers
misc_feature           1..2215
                       note = Description of Artificial Sequence: Synthetic
                        polynucleotide
source                 1..2215
                       mol_type = other DNA
                       organism = synthetic construct
SEQUENCE: 1014
atggctgccg atggttatct tccagattgg ctcgaggaca ctctctctga aggaataaga  60
cagtggtgga agctcaaacc tggcccacca ccaccaaagc ccgcagagcg gcataaggac  120
gacagcaggg gtcttgtgct tcctgggtac aagtacctcg gacccttcaa cggactcgac  180
aagggagagc cggtcaacga ggcagacgcc gcggccctcg agcacgacaa agcctacgac  240
cggcagctcg acagcggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc aatcggagaa cctcccgcag ccccctcagg tgtgggatct  600
cttacaatgg ctgcaggcgg tggcgcacca atggcagaca ataacgaggg cgccgacgga  660
gtgggtaatt cctcgggaaa ttggcattgc gattccacat ggatgggcga cagagtcatc  720
accaccagca cccgaacctg ggccctgccc acctacaaca accacctcta caagcaaatc  780
tccaacagca catctggagg atcttcaaat gacaacgcct acttcggcta cagcaccccc  840
tgggggtatt ttgactttaa cagattccac tgccactttt caccacgtga ctggcagcga  900
ctcatcaaca acaactgggg attccggccc aagagactca gcttcaagct cttcaacatc  960
caggtcaagg aggtcacgca gaatgaaggc accaagacca tcgccaataa cctcaccagc  1020
accatccagg tgtttacgga ctcggagtac cagctgccgt acgttctcgg ctctgcccac  1080
cagggctgcc tgcctccgtt cccggcggac gtgttcatga ttccccagta cggctaccta  1140
acactcaaca acggtagtca ggccgtggga cgctcctcct tctactgcct ggaatacttt  1200
ccttcgcaga tgctgagaac cggcaacaac ttccagttta cttacacctt cgaggacgtg  1260
cctttccaca gcagctacgc ccacagccag agcttggacc ggctgatgaa tcctctgatt  1320
```

```
gaccagtacc tgtactactt gtctcggact caaacaacag gaggcacgac aaatacgcag  1380
actctgggct tcagccaagg tgggcctaat acaatggcca atcaggcaaa gaactggctg  1440
ccaggaccct gttaccgcca gcagcgagta tcaaagacat ctgcggataa caacaacagt  1500
gaatactcgt ggactggagc taccaagtac cacctcaatg gcagagactc tctggtgaat  1560
ccgggcccgg ccatggcaag ccacaaggac gatgaagaaa agtttttttc ctcagagcgg  1620
ggttctcatc tttgggaagc aaggctcaga gaaaacaaat gtggacattg aaaaggtcat  1680
gattacagac gaagaggaaa tcaggacaac caatcccgtg gctacggagc agtatggttc  1740
tgtatctacc aacctccaga gaggcaacag acaagcagct accgcagatg tcaacacaca  1800
aggcgttctt ccaggcatgg tctggcagga cagagatgtg taccttcagg ggcccatctg  1860
ggcaaagatt ccacacacgg acggacattt tcacccctct cccctcatgg gtggattcgg  1920
acttaaacac cctccgcctc agatcctgat caagaacacg cctgtacctg cggatcctcc  1980
gaccaccttc aaccagtcaa agctgaactc tttcatcacc cagtattcta ctggccaagt  2040
cagcgtggag atcgagtggg agctgcagaa ggaaaacagc aagcgctgga accccgagat  2100
ccagtacacc tccaactact acaaatctac aagtgtggac tttgctgtta atacagaagg  2160
cgtgtactct gaaccccgcc ccattggcac ccgttacctc acccgtaatc tgtaa       2215

SEQ ID NO: 1015        moltype = AA  length = 737
FEATURE                Location/Qualifiers
REGION                 1..737
                       note = Description of Artificial Sequence: Synthetic
                        polypeptide
source                 1..737
                       mol_type = protein
                       organism = synthetic construct
SEQUENCE: 1015
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRLLEPLG LVEEAAKTAP GKKRPVEHSP VEPDSSSGTG KAGQQPARKR LNFGQTGDAD  180
SVPDPQPIGE PPAAPSGVGS LTMAAGGGAP MADNNEGADG VGNSSGNWHC DSTWMGDRVI  240
TTSTRTWALP TYNNHLYKQI SNSTSGGSSN DNAYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLKTGNN FQFTYTFEDV  420
PFHSSYAHSQ SLDRLMNPLI DQYLYYLSRT QTTGGTTNTQ TLGFSQGGPN TMANQAKNWL  480
PGPCYRQQRV SKTSADNNNS EYSWTGATKY HLNGRDSLVN PGPAMASHKD DEEKFFPQSG  540
VLIFGKQGSE KTNVDIEKVM ITDEEEIRTT NPVATEQYGS VSTNLQRGNR QAATADVNTQ  600
GVLPGMVWQD RDVYLQGPIW AKIPHTDGHF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 1016        moltype = AA  length = 737
FEATURE                Location/Qualifiers
REGION                 1..737
                       note = Description of Artificial Sequence: Synthetic
                        polypeptide
source                 1..737
                       mol_type = protein
                       organism = synthetic construct
SEQUENCE: 1016
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRLLEPLG LVEEAAKTAP GKKRPVEHSP VEPDSSSGTG KAGQQPARKR LNFGQTGDAD  180
SVPDPQPIGE PPAAPSGVGS LTMAAGGGAP MADNNEGADG VGNSSGNWHC DSTWMGDRVI  240
TTSTRTWALP TYNNHLYKQI SNSTSGGSSN DNAYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLKTGNN FQFTYTFEDV  420
PFHSSYAHSQ SLDRLMNPLI DQYLYYLSRT QTTGGTTNTQ TLGFSQGGPN TMANQAKNWL  480
PGPCYRQQRV SKTSADNNNS EYSWTGATKY HLNGRDSLVN PGPAMASHKD DEEKFFPQSG  540
VLIFGKQGSE KTNVDIEKVM ITDEEEIRTT NPVATEQYGS VSTNLQQGNT QAATADVNTQ  600
GVLPGMVWQD RDVYLQGPIW AKIPHTDGHF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 1017        moltype = AA  length = 737
FEATURE                Location/Qualifiers
REGION                 1..737
                       note = Description of Artificial Sequence: Synthetic
                        polypeptide
source                 1..737
                       mol_type = protein
                       organism = synthetic construct
SEQUENCE: 1017
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRLLEPLG LVEEAAKTAP GKKRPVEHSP VEPDSSSGTG KAGQQPARKR LNFGQTGDAD  180
SVPDPQPIGE PPAAPSGVGS LTMAAGGGAP MADNNEGADG VGNSSGNWHC DSTWMGDRVI  240
TTSTRTWALP TYNNHLYKQI SNSTSGGSSN DNAYFGYSTP WGYFDFNRFH CHFSPRDWQR  300
LINNNWGFRP KRLSFKLFNI QVKEVTQNEG TKTIANNLTS TIQVFTDSEY QLPYVLGSAH  360
QGCLPPFPAD VFMIPQYGYL TLNNGSQAVG RSSFYCLEYF PSQMLRTGNN FQFTYTFEDV  420
PFHSSYAHSQ SLDRLMNPLI DQYLYYLSRT QTTGGTTNTQ TLGFSQGGPN TMANQAKNWL  480
```

```
PGPCYRQQRV SKTSADNNNS EYSWTGATKY HLNGRDSLVN PGPAMASHKD DEEKFFPQSG  540
VLIFGKQGSE KTNVDIEKVM ITDEEEIRTT NPVATEQYGS VSTNLQQGNT QAATADVNTQ  600
GVLPGMVWQD RDVYLQGPIW AKIPHTDGHF HPSPLMGGFG LKHPPPQILI KNTPVPADPP  660
TTFNQSKLNS FITQYSTGQV SVEIEWELQK ENSKRWNPEI QYTSNYYKST SVDFAVNTEG  720
VYSEPRPIGT RYLTRNL                                                 737

SEQ ID NO: 1018        moltype = DNA  length = 2217
FEATURE                Location/Qualifiers
source                 1..2217
                       mol_type = unassigned DNA
                       organism = Adeno-associated virus
SEQUENCE: 1018
atggctgccg atggttatct tccagattgg ctcgaggaca acctctctga gggcattcgc  60
gagtggtggg acctgaaacc tggagccccg aaacccaaag ccaaccagca aaagcaggac  120
aacggccggg gtctggtgct tcctggctac aagtacctcg gacccttcaa cggactcgac  180
aagggggagc ccgtcaacgc ggcggacgca gcggccctcg agcacgacaa ggcctacgac  240
cagcagctcc aagcgggtga caatccgtac ctgcggtata atcacgccga cgccgagttt  300
caggagcgtc tgcaagaaga tacgtctttt gggggcaacc tcgggcgcgc agtcttccag  360
gccaaaaagc gggttctcga acctctgggc ctggttgaat cgccggttaa gacggctcct  420
ggaaagaaga gaccggtaga gccatcaccc cagcgctctc cagactcctc tacgggcatc  480
ggcaagaaag gccagcagcc cgcaaaaaag agactcaatt ttgggcagac tggcgactca  540
gagtcagtcc ccgaccctca accaatcgga gaaccaccag caggcccctc tggtctggga  600
tctggtacaa tggctgcagg cggtggcgct ccaatggcag acaataacga aggcgccgac  660
ggagtgggta gttcctcagg aaattggcat tgcgattcca catggctggg cgacagagtc  720
atcaccacca gcacccgcac ctgggccctg cccacctaca acaaccacct ctacaagcaa  780
atctccaacg ggacctcggg aggaagcacc aacgacaaca cctacttcgg ctacagcacc  840
ccctgggggt attttgactt caacagattc cactgccact tttcaccacg tgactggcag  900
cgactcatca acaacaactg gggattccgg cccaagaggc tcaacttcaa gctcttcaac  960
atccaagtca aggaggtcac gcagaatgaa ggcaccaaga ccatcgccaa taaccttacc  1020
agcacgattc aggtctttac ggactcggaa taccagctcc cgtacgtgct cggctcggcg  1080
caccagggct gcctgcctcc gttcccggcg gacgtcttca tgattcctca gtacgggtac  1140
ctgactctga acaatggcag tcaggctgtg ggccggtcgt ccttctactg cctggagtac  1200
tttccttctc aaatgctgag aacgggcaac aactttgaat tcagctacaa cttcgaggac  1260
gtgcccttcc acagcagcta cgcgcacagc cagagcctgg accggctgat gaaccctctc  1320
atcgaccagt acttgtacta cctgtcccgg actcaaagca cgggcggtac tgcaggaact  1380
cagcagttgc tattttctca ggccgggcct aacaacatgt cggctcaggc caagaactgg  1440
ctacccggtc cctgctaccg gcagcaacgc gtctccacga cactgtcgca gaacaacaac  1500
agcaactttg cctggacggg tgccaccaag tatcatctga atggcagaga ctctctggtg  1560
aatcctggcg ttgccatggc tacccacaag gacgacgaag agcgattttt tccatccagc  1620
ggagtcttaa tgtttgggaa acagggagct ggaaaagaca acgtggacta tagcagcgtg  1680
atgctaacca gcgaggaaga aataaagacc accaacccag tggccacaga acagtacggc  1740
gtggtggccg ataacctgca acagcaaaac gccgctccta ttgtaggggc cgtcaatagt  1800
caaggagcct tacctggcat ggtgtggcag aaccgggacg tgtacctgca gggtcccatc  1860
tgggccaaga ttcctcatac ggacggcaac tttcatccct cgccgctgat gggaggcttt  1920
ggactgaagc atccgcctcc tcagatcctg attaaaaaca cacctgttcc cgcggatcct  1980
ccgaccacct tcaatcaggc caagctggct tctttcatca cgcagtacag taccggccag  2040
gtcagcgtgg agatcgagtg ggagctgcag aaggagaaca gcaaacgctg gaacccagag  2100
attcagtaca cttccaacta ctacaaatct acaaatgtgg actttgctgt caatactgag  2160
ggtacttatt ccgagcctcg ccccattggc acccgttacc tcacccgtaa tctgtaa     2217

SEQ ID NO: 1019        moltype = AA  length = 738
FEATURE                Location/Qualifiers
source                 1..738
                       mol_type = protein
                       organism = Adeno-associated virus
SEQUENCE: 1019
MAADGYLPDW LEDNLSEGIR EWWDLKPGAP KPKANQQKQD NGRGLVLPGY KYLGPFNGLD  60
KGEPVNAADA AALEHDKAYD QQLQAGDNPY LRYNHADAEF QERLQEDTSF GGNLGRAVFQ  120
AKKRVLEPLG LVESPVKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYNFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFNQAKLA SFITQYSTGQ VSVEIEWELQ KENSKRWNPE IQYTSNYYKS TNVDFAVNTE  720
GTYSEPRPIG TRYLTRNL                                                738

SEQ ID NO: 1020        moltype = AA  length = 738
FEATURE                Location/Qualifiers
source                 1..738
                       mol_type = protein
                       organism = Adeno-associated virus 10
SEQUENCE: 1020
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEAAKTAP GKKRPVEPSP QRSPDSSTGI GKKGQQPAKK RLNFGQTGES  180
```

```
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLSFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYTFED  420
VPFHSSYAHS QSLDRLMNPL IDQYLYYLSR TQSTGGTQGT QQLLFSQAGP ANMSAQAKNW  480
LPGPCYRQQR VSTTLSQNNN SNFAWTGATK YHLNGRDSLV NPGVAMATHK DDEERFFPSS  540
GVLMFGKQGA GRDNVDYSSV MLTSEEEIKT TNPVATEQYG VVADNLQQAN TGPIVGNVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTE  720
GTYSEPRPIG TRYLTRNL                                               738

SEQ ID NO: 1021        moltype = AA  length = 738
FEATURE                Location/Qualifiers
source                 1..738
                       mol_type = protein
                       organism = Adeno-associated virus 10
SEQUENCE: 1021
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEPSP QRSPDSSTGI GKKGQQPAKK RLNFGQTGDS  180
ESVPDPQPIG EPPAGPSGLG SGTMAAGGGA PMADNNEGAD GVGSSSGNWH CDSTWLGDRV  240
ITTSTRTWAL PTYNNHLYKQ ISNGTSGGST NDNTYFGYST PWGYFDFNRF HCHFSPRDWQ  300
RLINNNWGFR PKRLNFKLFN IQVKEVTQNE GTKTIANNLT STIQVFTDSE YQLPYVLGSA  360
HQGCLPPFPA DVFMIPQYGY LTLNNGSQAV GRSSFYCLEY FPSQMLRTGN NFEFSYQFED  420
VPFHSSYAHS QSLDRLMNPL IDQYLYYLSR TQSTGGTAGT QQLLFSQAGP NNMSAQAKNW  480
LPGPCYRQQR VSTTLSQNNN SNFAWTGATK YHLNGRDSLV NPGVAMATHK DDEERFFPSS  540
GVLMFGKQGA GKDNVDYSSV MLTSEEEIKT TNPVATEQYG VVADNLQQQN AAPIVGAVNS  600
QGALPGMVWQ NRDVYLQGPI WAKIPHTDGN FHPSPLMGGF GLKHPPPQIL IKNTPVPADP  660
PTTFSQAKLA SFITQYSTGQ VSVEIEWELQ KENSKRWNPE IQYTSNYYKS TNVDFAVNTD  720
GTYSEPRPIG TRYLTRNL                                               738

SEQ ID NO: 1022        moltype = DNA  length = 2232
FEATURE                Location/Qualifiers
misc_feature           1..2232
                       note = Description of Artificial Sequence: Synthetic
                        polynucleotide
source                 1..2232
                       mol_type = other DNA
                       organism = synthetic construct
SEQUENCE: 1022
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctgggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtga tgggactttg gcggtgcctt ttaaggcaca ggcgcagacc  1800
ggctgggttc aaaaccaagg aatacttccg ggtatggttt ggcaggacag agatgtgtac  1860
ctgcaaggac ccatttgggc caaaattcct cacacggacg gcaactttca cccttctccg  1920
ctgatgggag ggtttggaat gaagcacccg cctcctcaga tcctcatcaa aaacacacct  1980
gtacctgcgg atcctccaac ggccttcaac aaggacaagc tgaactcttt catcacccag  2040
tattctactg gccaagtcag cgtggagatc gagtgggagc tgcagaagga aaacagcaag  2100
cgctggaacc cggagatcca gtacacttcc aactattaca agtctaataa tgttgaattt  2160
gctgttaata ctgaaggtgt atatagtgaa ccccgcccca ttggcaccag atacctgact  2220
cgtaatctgt aa                                                     2232
```

```
SEQ ID NO: 1023        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
SEQUENCE: 1023
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSDGTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                          743

SEQ ID NO: 1024        moltype = DNA  length = 2232
FEATURE                Location/Qualifiers
misc_feature           1..2232
                       note = Description of Artificial Sequence: Synthetic
                        polynucleotide
source                 1..2232
                       mol_type = other DNA
                       organism = synthetic construct
SEQUENCE: 1024
atggctgccg atggttatct tccagattgg ctcgaggaca accttagtga aggaattcgc  60
gagtggtggg ctttgaaacc tggagcccct caacccaagg caaatcaaca acatcaagac  120
aacgctcgag gtcttgtgct tccgggttac aaataccttg gacccggcaa cggactcgac  180
aagggggagc cggtcaacgc agcagacgcg gcggccctcg agcacgacaa ggcctacgac  240
cagcagctca aggccggaga caacccgtac ctcaagtaca accacgccga cgccgagttc  300
caggagcggc tcaaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcagtctcct caggaaccgg actcctccgc gggtattggc  480
aaatcgggtg cacagcccgc taaaaagaga ctcaatttcg gtcagactgg cgacacagag  540
tcagtcccag accctcaacc aatcggagaa cctcccgcag ccccctcagg tgtgggatct  600
cttacaatgg cttcaggtgg tggcgcacca gtggcagaca ataacgaagg tgccgatgga  660
gtgggtagtt cctcgggaaa ttggcattgc gattcccaat ggctggggga cagagtcatc  720
accaccagca cccgaacctg ggccctgccc acctacaaca atcacctcta caagcaaatc  780
tccaacagca catctggagg atcttcaaat gacaacgcct acttcggcta cagcaccccc  840
tgggggtatt ttgacttcaa cagattccac tgccacttct caccacgtga ctggcagcga  900
ctcatcaaca acaactgggg attccggcct aagcgactca acttcaagct cttcaacatt  960
caggtcaaag aggttacgga caacaatgga gtcaagacca tcgccaataa ccttaccagc  1020
acggtccagg tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcct tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacatacct  1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caaagaagga gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaaactttg gcggtgcctt ttaaggcaca ggcgcagacc  1800
ggctgggttc aaaaccaagg aatacttccg ggtatggttt ggcaggacag agatgtgtac  1860
ctgcaaggac ccatttgggc caaaattcct cacacggacg gcaactttca cccttctccg  1920
ctgatgggag ggtttggaat gaagcacccg cctcctcaga tcctcatcaa aaacacacct  1980
gtacctgcgg atcctccaac ggccttcaac aaggacaagc tgaactcttt catcacccag  2040
tattctactg gccaagtcag cgtggagatc gagtgggagc tgcagaagga aaacagcaag  2100
cgctggaacc cggagatcca gtacacttcc aactattaca agtctaataa tgttgaattt  2160
gctgttaata ctgaaggtgt atatagtgaa ccccgcccca ttggcaccag atacctgact  2220
cgtaatctgt aa                                                      2232

SEQ ID NO: 1025        moltype = AA  length = 743
FEATURE                Location/Qualifiers
REGION                 1..743
                       note = Description of Artificial Sequence: Synthetic
                        polypeptide
source                 1..743
                       mol_type = protein
                       organism = synthetic construct
```

```
SEQUENCE: 1025
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQTL AVPFKAQAQT  600
GWVQNQGILP GMVWQDRDVY LQGPIWAKIP HTDGNFHPSP LMGGFGMKHP PPQILIKNTP  660
VPADPPTAFN KDKLNSFITQ YSTGQVSVEI EWELQKENSK RWNPEIQYTS NYYKSNNVEF  720
AVNTEGVYSE PRPIGTRYLT RNL                                          743

SEQ ID NO: 1026        moltype = AA  length = 735
FEATURE                Location/Qualifiers
REGION                 1..735
                       note = Description of Artificial Sequence: Synthetic
                        polypeptide
source                 1..735
                       mol_type = protein
                       organism = synthetic construct
SEQUENCE: 1026
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VESDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LSFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSKTNA PSGTTTMSRL QFSQAGASDI RDQSRNWLPG  480
PCYRQQRVSK TAADNNNSDY SWTGATKYHL NGRDSLVNPG PAMASHKDDE EKYFPQSGVL  540
IFGKQGSNKT NVDIEKVMIT DEEEIRTTNP VATEQYGSVS TNLQSGNTQA ATSDVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                   735

SEQ ID NO: 1027        moltype = AA  length = 734
FEATURE                Location/Qualifiers
REGION                 1..734
                       note = Description of Artificial Sequence: Synthetic
                        polypeptide
source                 1..734
                       mol_type = protein
                       organism = synthetic construct
SEQUENCE: 1027
MAADGYLPDW LEDTLSEGIR QWWKLKPGPP PPKPAERHQD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP AEPDSSSGTG KAGQQPARKR LNFGQTGDAD  180
SVPDPQPLGQ PPAAPTSLGS TTMATGSGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLNRTQS NSGTLQQSRL LFSQAGPTSM SLQAKNWLPG  480
PCYRQQRLSK QANDNNSNFP WTAATKYHLN GRDSLVNPGP AMASHKDDEE KFFPMHGTLI  540
FGKQGTNAND ADLEHVMITD EEEIRTTNPV ATEQYGNVSN NLQNSNTGPT TENVNHQGAL  600
PGMVWQDRDV YLQGPIWAKI PHTDGHFHPS PLMGGFGLKH PPPQIMIKNT PVPANPPTNF  660
SAAKFASFIT QYSTGQVSVE IEWELQKENS KRWNPEIQYT SNYNKSVNVD FTVDTNGVYS  720
EPRPIGTRYL TRNL                                                    734

SEQ ID NO: 1028        moltype = AA  length = 735
FEATURE                Location/Qualifiers
REGION                 1..735
                       note = Description of Artificial Sequence: Synthetic
                        polypeptide
source                 1..735
                       mol_type = protein
                       organism = synthetic construct
SEQUENCE: 1028
MAADGYLPDW LEDTLSEGIR QWWKLKPGPP PPRPAERHQD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP AEPDSSSGTG KAGQQPARKR LNFGQTGDAD  180
SVPDPQPLGQ PPAAPTSLGS TTMATGSGAP MADNNEGADG VGNSSGNWHC DSQWLGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLNRTQS NSGTLQQSRL LFSQAGPTSM SLQAKNWLPG  480
PCYRQQRLSK QANDNNNSNF PWTAATKYHL NGRDSLVNPG PAMASHKDDE EKFFPMHGTL  540
```

```
IFGKQGTNAN DADLEHVMIT DEEEIRTTNP VATEQYGNVS NNLQNSNTGP TTENVNRQGA  600
LPGMVWQDRD VYLQGPIWAK IPHTDGHFHP SPLMGGFGLK HPPPQIMIKN TPVPANPPTN  660
FSAAKFASFI TQYSTGQVSV EIEWELQKEN SKRWNPEIQY TSNYNKSVNV DFTVDANGVY  720
SEPRPIGTRY LTRNL                                                   735

SEQ ID NO: 1029        moltype = DNA  length = 23
FEATURE                Location/Qualifiers
misc_feature           1..23
                       note = Description of Artificial Sequence: Synthetic miR
                        binding site
source                 1..23
                       mol_type = other DNA
                       organism = synthetic construct
SEQUENCE: 1029
acaaacacca ttgtcacact cca                                          23

SEQ ID NO: 1030        moltype = DNA  length = 71
FEATURE                Location/Qualifiers
misc_feature           1..71
                       note = Description of Artificial Sequence: Synthetic miR
                        binding site
source                 1..71
                       mol_type = other DNA
                       organism = synthetic construct
SEQUENCE: 1030
acaaacacca ttgtcacact ccacacaaac accattgtca cactccacac aaacaccatt  60
gtcacactcc a                                                       71

SEQ ID NO: 1031        moltype = DNA  length = 23
FEATURE                Location/Qualifiers
misc_feature           1..23
                       note = Description of Artificial Sequence: Synthetic miR
                        binding site
source                 1..23
                       mol_type = other DNA
                       organism = synthetic construct
SEQUENCE: 1031
tccataaagt aggaaacact aca                                          23

SEQ ID NO: 1032        moltype = DNA  length = 22
FEATURE                Location/Qualifiers
misc_feature           1..22
                       note = Description of Artificial Sequence: Synthetic miR
                        binding site
source                 1..22
                       mol_type = other DNA
                       organism = synthetic construct
SEQUENCE: 1032
agtgaattct accagtgcca ta                                           22

SEQ ID NO: 1033        moltype = DNA  length = 24
FEATURE                Location/Qualifiers
misc_feature           1..24
                       note = Description of Artificial Sequence: Synthetic miR
                        binding site
source                 1..24
                       mol_type = other DNA
                       organism = synthetic construct
SEQUENCE: 1033
agtgtgagtt ctaccattgc caaa                                         24

SEQ ID NO: 1034        moltype = DNA  length = 23
FEATURE                Location/Qualifiers
misc_feature           1..23
                       note = Description of Artificial Sequence: Synthetic miR
                        binding site
source                 1..23
                       mol_type = other DNA
                       organism = synthetic construct
SEQUENCE: 1034
agcaaaaatg tgctagtgcc aaa                                          23

SEQ ID NO: 1035        moltype = DNA  length = 130
FEATURE                Location/Qualifiers
misc_feature           1..130
                       note = Description of Artificial Sequence: Synthetic
                        polynucleotide
source                 1..130
                       mol_type = other DNA
```

```
                          organism = synthetic construct
SEQUENCE: 1035
ctgcgcgctc gctcgctcac tgaggccgcc cgggcaaagc ccgggcgtcg ggcgaccttt  60
ggtcgcccgg cctcagtgag cgagcgagcg cgcagagagg gagtggccaa ctccatcact  120
aggggttcct                                                         130

SEQ ID NO: 1036           moltype = DNA  length = 141
FEATURE                   Location/Qualifiers
misc_feature              1..141
                          note = Description of Artificial Sequence: Synthetic
                           polynucleotide
source                    1..141
                          mol_type = other DNA
                          organism = synthetic construct
SEQUENCE: 1036
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc t                                            141

SEQ ID NO: 1037           moltype = DNA  length = 130
FEATURE                   Location/Qualifiers
misc_feature              1..130
                          note = Description of Artificial Sequence: Synthetic
                           polynucleotide
source                    1..130
                          mol_type = other DNA
                          organism = synthetic construct
SEQUENCE: 1037
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag                                                         130

SEQ ID NO: 1038           moltype = DNA  length = 141
FEATURE                   Location/Qualifiers
misc_feature              1..141
                          note = Description of Artificial Sequence: Synthetic
                           polynucleotide
source                    1..141
                          mol_type = other DNA
                          organism = synthetic construct
SEQUENCE: 1038
aggaacccct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ctgcctgcag g                                            141

SEQ ID NO: 1039           moltype = DNA  length = 1715
FEATURE                   Location/Qualifiers
misc_feature              1..1715
                          note = Description of Artificial Sequence: Synthetic
                           polynucleotide
source                    1..1715
                          mol_type = other DNA
                          organism = synthetic construct
SEQUENCE: 1039
ctagttatta atagtaatca attacggggt cattagttca tagcccatat atggagttcc  60
gcgttacata acttacggta aatggcccgc ctggctgacc gcccaacgac ccccgcccat  120
tgacgtcaat aatgacgtat gttcccatag taacgccaat agggactttc cattgacgtc  180
aatgggtgga gtatttacgg taaactgccc acttggcagt acatcaagtg tatcatatgc  240
caagtacgcc ccctattgac gtcaatgacg gtaaatggcc cgcctggcat tatgcccagt  300
acatgacctt atgggacttt cctacttggc agtacatcta cgtattagtc atcgctatta  360
ccatggtcga ggtgagcccc acgttctgct tcactctccc catctccccc ccctccccac  420
ccccaatttt gtatttattt atttttaat tattttgtgc agcgatgggg gcgggggggg  480
gggggggcg cgcgccaggc ggggcggggc ggggcgaggg gcggggcggg gcgaggcgga  540
gaggtgcggc ggcagccaat cagagcggcg cgctccgaaa gtttcctttt atggcgaggc  600
ggcggcggcg gcggccctat aaaaagcgaa gcgcgcggcg ggcgggagtc gctgcgcgct  660
gccttcgccc cgtgccccgc tccgccgccg cctcgcgccg cccgccccgg ctctgactga  720
ccgcgttact cccacaggtg agcgggcggg acggcccttc tcctccgggc tgtaattagc  780
gcttggttta atgacggctt gtttcttttc tgtggctgcg tgaaagcctt gaggggctcc  840
gggagggccc tttgtgcggg gggagcggct cggggggtgc gtgcgtgtgt gtgtgcgtgg  900
ggagcgccgc gtgcggctcc gcgctgcccg gcggctgtga gcgctgcggg cgcggcgcgg  960
ggctttgtgc gctccgcagt gtgcgcgagg ggagcgcggc cgggggcggt gccccgcggt  1020
gcggggggg ctgcgagggg aacaaaggct gcgtgcgggg tgtgtgcgtg ggggggtgag  1080
cagggggtgt gggcgcgtcg gtcgggctgc aacccccct gcaccccct ccccgagttg  1140
ctgagcacgg cccggcttcg ggtgcggggc tccgtacggg gcgtggcgcg gggctcgccg  1200
tgccgggcgg ggggtggcgg caggtggggg tgccgggcgg ggcggggccg cctcgggccg  1260
gggagggctc gggggagggg cgcggcggcc cccggagcgc cggcggctgt cgaggcgcgg  1320
cgagccgcag ccattgcctt ttatggtaat cgtgcgagag ggcgcaggga cttcctttgt  1380
cccaaatctg tgcggagccg aaatctggga ggcgccgccg caccccctct agcgggcgcg  1440
gggcgaagcg gtgcggcgcc ggcaggaagg aaatgggcgg ggagggcctt cgtgcgtcgc  1500
```

```
cgcgccgccg tccccttctc cctctccagc ctcggggctg tccgcggggg gacggctgcc  1560
ttcggggggg acggggcagg gcggggttcg gcttctggcg tgtgaccggc ggctctagag  1620
cctctgctaa ccatgttcat gccttcttct ttttcctaca gctcctgggc aacgtgctgg  1680
ttattgtgct gtctcatcat tttggcaaag aattc                             1715

SEQ ID NO: 1040         moltype = DNA  length = 299
FEATURE                 Location/Qualifiers
misc_feature            1..299
                        note = Description of Artificial Sequence: Synthetic
                         polynucleotide
source                  1..299
                        mol_type = other DNA
                        organism = synthetic construct
SEQUENCE: 1040
tagcccatat atggagttcc gcgttacata acttacggta aatggcccgc ctggctgacc  60
gcccaacgac ccccgcccat tgacgtcaat aatgacgtat gttcccatag taacgccaat  120
agggactttc cattgacgtc aatgggtgga gtatttacgg taaactgccc acttggcagt  180
acatcaagtg tatcatatgc caagtacgcc ccctattgac gtcaatgacg gtaaatggcc  240
cgcctggcat tatgcccagt acatgacctt atgggacttt cctacttggc agtacatct   299

SEQ ID NO: 1041         moltype = DNA  length = 283
FEATURE                 Location/Qualifiers
misc_feature            1..283
                        note = Description of Artificial Sequence: Synthetic
                         polynucleotide
source                  1..283
                        mol_type = other DNA
                        organism = synthetic construct
SEQUENCE: 1041
catggtcgag gtgagcccca cgttctgctt cactctcccc atctcccccc cctccccacc  60
cccaattttg tatttattta tttttttaatt attttgtgca gcgatggggg cggggggggg  120
gggggggcgc gcgccaggcg gggcggggcg gggcgagggg cggggcgggg cgaggcggag  180
aggtgcggcg gcagccaatc agagcggcgc gctccgaaag tttcctttta tggcgaggcg  240
gcggcggcgg cggccctata aaaagcgaag cgcgcggcgg gcg                    283

SEQ ID NO: 1042         moltype = DNA  length = 260
FEATURE                 Location/Qualifiers
misc_feature            1..260
                        note = Description of Artificial Sequence: Synthetic
                         polynucleotide
source                  1..260
                        mol_type = other DNA
                        organism = synthetic construct
SEQUENCE: 1042
ccacgttctg cttcactctc cccatctccc cccccctcccc acccccaatt ttgtatttat  60
ttattttttta attattttgt gcagcgatgg gggcgggggg gggggggcgcg cgccaggcgg  120
ggcggggcgg ggcgaggggc ggggcggggc gaggcggaga ggtgcggcgg cagccaatca  180
gagcggcgcg ctccgaaagt ttccttttat ggcgaggcgg cggcggcggc ggccctataa  240
aaagcgaagc gcgcggcggg                                              260

SEQ ID NO: 1043         moltype = DNA  length = 654
FEATURE                 Location/Qualifiers
misc_feature            1..654
                        note = Description of Artificial Sequence: Synthetic
                         polynucleotide
source                  1..654
                        mol_type = other DNA
                        organism = synthetic construct
SEQUENCE: 1043
cgacattgat tattgactag ttattaatag taatcaatta cggggtcatt agttcatagc  60
ccatatatgg agttccgcgt tacataactt acggtaaatg gcccgcctgg ctgaccgccc  120
aacgaccccc gcccattgac gtcaataatg acgtatgttc ccatagtaac gccaataggg  180
actttccatt gacgtcaatg ggtggagtat ttacggtaaa ctgcccactt ggcagtacat  240
caagtgtatc atatgccaag tacgccccct attgacgtca atgacggtaa atggcccgcc  300
tggcattatg cccagtacat gaccttatgg gactttccta cttggcagta catctacgta  360
ttagtcatcg ctattaccat gtcgaggcca cgttctgctt cactctcccc atctcccccc  420
cctccccacc cccaattttg tatttattta ttttttaatt attttgtgca gcgatggggg  480
cggggggggg gggcgcgcgc caggcggggc ggggcggggc gaggggcggg gcggggcgag  540
gcggagaggt gcggcggcag ccaatcagag cggcgcgctc cgaaagtttc cttttatggc  600
gaggcggcgg cggcggcggc cctataaaaa gcgaagcgcg cggcgggcgg gagc        654

SEQ ID NO: 1044         moltype = DNA  length = 699
FEATURE                 Location/Qualifiers
misc_feature            1..699
                        note = Description of Artificial Sequence: Synthetic
                         polynucleotide
source                  1..699
                        mol_type = other DNA
                        organism = synthetic construct
```

```
SEQUENCE: 1044
gatctaacat atcctggtgt ggagtagcgg acgctgctat gacagaggct cgggggcctg  60
agctggctct gtgagctggg gaggaggcag acagccaggc cttgtctgca agcagacctg  120
gcagcattgg gctggccgcc ccccagggcc tcctcttcat gcccagtgaa tgactcacct  180
tggcacagac acaatgttcg ggtgggcac agtgcctgct tcccgccgca ccccagcccc  240
cctcaaatgc cttccgagaa gcccattgag caggggggctt gcattgcacc ccagcctgac  300
agcctggcat cttgggataa aagcagcaca gccccctagg ggctgccctt gctgtgtggc  360
gccaccggcg gtggagaaca aggctctatt cagcctgtgc ccaggaaagg ggatcagggg  420
atgcccaggc atggacagtg ggtggcaggg ggggagagga gggctgtctg cttcccagaa  480
gtccaaggac acaaatgggt gaggggagag ctctccccat agctgggctg cggcccaacc  540
ccaccccctc aggctatgcc agggggtgtt gccaggggca cccgggcatc gccagtctag  600
cccactcctt cataaagccc tcgcatccca ggagcgagca gagccagagc aggttggaga  660
ggagacgcat cacctccgct gctcgcgggg atcctctag                        699

SEQ ID NO: 1045        moltype = DNA  length = 557
FEATURE                Location/Qualifiers
misc_feature           1..557
                       note = Description of Artificial Sequence: Synthetic
                        polynucleotide
source                 1..557
                       mol_type = other DNA
                       organism = synthetic construct
SEQUENCE: 1045
tagtatctgc agagggccct gcgtatgagt gcaagtgggt tttaggacca ggatgaggcg  60
gggtgggggt gcctacctga cgaccgaccc cgacccactg gacaagcacc caaccccccat  120
tccccaaatt gcgcatcccc tatcagagag ggggaggggga aacaggatgc ggcgaggcgc  180
gtgcgcactg ccagcttcag caccgcggac agtgccttcg cccccgcctg gcggcgcgcg  240
ccaccgccgc ctcagcactg aaggcgcgct gacgtcactc gccggtcccc cgcaaactcc  300
ccttcccggc caccttggtc gcgtccgcgc cgccgccggc ccagccggac cgcaccacgc  360
gaggcgcgag atagggggggc acgggcgcga ccatctgcgc tgcggcgccg gcgactcagc  420
gctgcctcag tctgcggtgg gcagcggagg agtcgtgtcg tgcctgagag cgcagctgtg  480
ctcctgggca ccgcgcagtc cgcccccgcg gctcctggcc agaccacccc taggaccccc  540
tgccccaagt cgcagcc                                                557

SEQ ID NO: 1046        moltype = DNA  length = 382
FEATURE                Location/Qualifiers
misc_feature           1..382
                       note = Description of Artificial Sequence: Synthetic
                        polynucleotide
source                 1..382
                       mol_type = other DNA
                       organism = synthetic construct
SEQUENCE: 1046
ctagtcgaca ttgattattg actagttatt aatagtaatc aattacgggg tcattagttc  60
atagcccata tatggagttc cgcgttacat aacttacggt aaatggcccg cctggctgac  120
cgcccaacga cccccgccca ttgacgtcaa taatgacgta tgttcccata gtaacgccaa  180
tagggacttt ccattgacgt caatgggtgg agtatttacg gtaaactgcc cacttggcag  240
tacatcaagt gtatcatatg ccaagtacgc cccctattga cgtcaatgac ggtaaatggc  300
ccgcctggca ttatgcccag tacatgacct tatgggactt tcctacttgg cagtacatct  360
acgtattagt catcgctatt ac                                          382

SEQ ID NO: 1047        moltype = DNA  length = 1736
FEATURE                Location/Qualifiers
misc_feature           1..1736
                       note = Description of Artificial Sequence: Synthetic
                        polynucleotide
source                 1..1736
                       mol_type = other DNA
                       organism = synthetic construct
SEQUENCE: 1047
ctagtcgaca ttgattattg actagttatt aatagtaatc aattacgggg tcattagttc  60
atagcccata tatggagttc cgcgttacat aacttacggt aaatggcccg cctggctgac  120
cgcccaacga cccccgccca ttgacgtcaa taatgacgta tgttcccata gtaacgccaa  180
tagggacttt ccattgacgt caatgggtgg agtatttacg gtaaactgcc cacttggcag  240
tacatcaagt gtatcatatg ccaagtacgc cccctattga cgtcaatgac ggtaaatggc  300
ccgcctggca ttatgcccag tacatgacct tatgggactt tcctacttgg cagtacatct  360
acgtattagt catcgctatt accatggtcg aggtgagccc cacgttctgc ttcactctcc  420
ccatctcccc cccctcccca cccccaattt tgtatttatt tattttttaa ttattttgtg  480
cagcgatggg ggcggggggg gggggggggc gcgcgccagg cggggcgggg cggggcgagg  540
ggcggggcgg ggcgaggcgg agaggtgcgg cggcagccaa tcagagcggc gcgctccgaa  600
agtttccttt tatggcgagg cggcggcggc ggcggcccta taaaaagcga agcgcgcggc  660
gggcgggagt cgctgcgcgc tgccttcgcc ccgtgccccg ctccgccgcc gcctcgcgcc  720
gcccgccccg gctctgactg accgcgttac tcccacaggt gagcgggcgg gacggccctt  780
ctcctccggg ctgtaattag cgcttggttt aatgacggct tgtttctttt ctgtggctgc  840
gtgaaagcct tgaggggctc cgggagggcc ctttgtgcgg ggggagcggc tcggggggtg  900
cgtgcgtgtg tgtgtgcgtg gggagcgccg cgtgcggctc cgcgctgccc ggcggctgtg  960
agcgctgcgg gcgcggcgcg gggctttgtg cgctccgcag tgtgcgcgag gggagcgcgg  1020
ccgggggcgg tgccccgcgg tgcggggggg gctgcgaggg gaacaaaggc tgcgtgcggg  1080
gtgtgtgcgt gggggggtga gcagggggtg tgggcgcgtc ggtcgggctg caacccccc  1140
```

```
tgcacccccc tccccgagtt gctgagcacg gcccggcttc gggtgcgggg ctccgtacgg  1200
ggcgtggcgc ggggctcgcc gtgccgggcg gggggtggcg gcaggtgggg gtgccgggcg  1260
gggcggggcc gcctcgggcc ggggagggct cgggggaggg gcgcggcggc cccggagcg   1320
ccggcggctg tcgaggcgcg gcgagccgca gccattgcct tttatggtaa tcgtgcgaga  1380
gggcgcaggg acttcctttg tcccaaatct gtgcggagcc gaaatctggg aggcgccgcc  1440
gcacccccctc tagcgggcgc ggggcgaagc ggtgcggcgc cggcaggaag gaaatgggcg  1500
gggagggcct tcgtgcgtcg ccgcgccgcc gtccccttct ccctctccag cctcggggct  1560
gtccgcgggg ggacggctgc cttcgggggg gacggggcag ggcggggttc ggcttctggc  1620
gtgtgaccgg cggctctaga gcctctgcta accatgttca tgccttcttc tttttcctac  1680
agctcctggg caacgtgctg gttattgtgc tgtctcatca ttttggcaaa gaattc      1736
```

```
SEQ ID NO: 1048        moltype = DNA  length = 365
FEATURE                Location/Qualifiers
misc_feature           1..365
                       note = Description of Artificial Sequence: Synthetic
                        polynucleotide
source                 1..365
                       mol_type = other DNA
                       organism = synthetic construct
SEQUENCE: 1048
ctagtcgaca ttgattattg actagttatt aatagtaatc aattacgggg tcattagttc  60
atagcccata tatggagttc cgcgttacat aacttacggt aaatggcccg cctggctgac  120
cgcccaacga cccccgccca ttgacgtcaa taatgacgta tgttcccata gtaacgccaa  180
tagggacttt ccattgacgt caatgggtgg agtatttacg gtaaactgcc cacttggcag  240
tacatcaagt gtatcatatg ccaagtacgc cccctattga cgtcaatgac ggtaaatggc  300
ccgcctggca ttatgcccag tacatgacct tatgggactt tcctacttgg cagtacatct  360
acgta                                                              365
```

```
SEQ ID NO: 1049        moltype = DNA  length = 1714
FEATURE                Location/Qualifiers
misc_feature           1..1714
                       note = Description of Artificial Sequence: Synthetic
                        polynucleotide
source                 1..1714
                       mol_type = other DNA
                       organism = synthetic construct
SEQUENCE: 1049
ctagttatta atagtaatca attacggggt cattagttca tagcccatat atggagttcc  60
gcgttacata acttacggta aatggcccgc ctggctgacc gcccaacgac ccccgcccat  120
tgacgtcaat aatgacgtat gttcccatag taacgccaat agggactttc cattgacgtc  180
aatgggtgga gtatttacgg taaactgccc acttggcagt acatcaagtg tatcatatgc  240
caagtacgcc ccctattgac gtcaatgacg gtaaatggcc cgcctggcat tatgcccagt  300
acatgacctt atgggacttt cctacttggc agtacatcta cgtattagtc atcgctatta  360
ccatggtcga ggtgagcccc acgttctgct tcactctccc catctccccc ccctccccac  420
ccccaatttt gtatttattt atttttaat tattttgtgc agcgatgggg gcgggggggg   480
gggggggcg cgcgccaggc ggggcggggc ggggcgaggg gcggggcggg gcgaggcgga   540
gaggtgcggc ggcagccaat cagagcggcg cgctccgaaa gtttcctttt atggcgaggc  600
ggcggcggcg gcggccctat aaaaagcgaa gcgcgcggcg ggcgggagtc gctgcgcgct  660
gccttcgccc cgtgccccgc tccgccgccg cctcgcgccg cccgccccgg ctctgactga  720
ccgcgttact cccacaggtg agcgggcggg acggcccttc tcctccgggc tgtaattagc  780
gcttggttta atgacggctt gtttcttttc tgtggctgcg tgaaagcctt gaggggctcc  840
gggagggccc tttgtgcggg gggagcggct cgggggtgc gtgcgtgtgt gtgtgcgtgg   900
ggagcgccgc gtgcggctcc gcgctgcccg gcggctgtga gcgctgcggg cgcggcgcgg  960
ggctttgtgc gctccgcagt gtgcgcgagg ggagcgcggc cggggcggt gccccgcggt   1020
gcgggggggg ctgcgagggg aacaaaggct gcgtgcgggg tgtgtgcgtg ggggggtgag  1080
cagggggtgt gggcgcgtcg gtcgggctgc aacccccccct gcacccccct ccccgagttg  1140
ctgagcacgg cccggcttcg ggtgcggggc tccgtacggg gcgtggcgcg gggctcgccg  1200
tgccgggcgg ggggtggcgg caggtggggg tgccgggcgg ggcggggccg cctcgggccg  1260
gggagggctc gggggagggg cgcggcggcc cccggagcgc cggcggctgt cgaggcgcgg  1320
cgagccgcag ccattgcctt ttatggtaat cgtgcgagag ggcgcaggga cttcctttgt  1380
cccaaatctg tgcggagccg aaatctggga ggcgccgccg caccccctct agcgggcgcg  1440
gggcgaagcg gtgcggcgcc ggcaggaagg aaatgggcgg ggagggcctt cgtgcgtcgc  1500
cgcgccgccg tccccttctc cctctccagc ctcggggctg tccgcggggg gacggctgcc  1560
ttcggggggg acggggcagg gcggggttcg gcttctggcg tgtgaccggc ggctctagag  1620
cctctgctaa ccatgttcat gccttcttct ttttcctaca gctcctgggc aacgtgctgg  1680
ttattgtgct gtctcatcat tttggcaaag aatt                              1714
```

```
SEQ ID NO: 1050        moltype = DNA  length = 380
FEATURE                Location/Qualifiers
misc_feature           1..380
                       note = Description of Artificial Sequence: Synthetic
                        polynucleotide
source                 1..380
                       mol_type = other DNA
                       organism = synthetic construct
SEQUENCE: 1050
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
```

```
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg                                              380

SEQ ID NO: 1051        moltype = DNA  length = 134
FEATURE                Location/Qualifiers
misc_feature           1..134
                       note = Description of Artificial Sequence: Synthetic
                        polynucleotide
source                 1..134
                       mol_type = other DNA
                       organism = synthetic construct
SEQUENCE: 1051
tcagatcgcc tggagacgcc atccacgctg ttttgacctc catagaagac accgggaccg  60
atccagcctc cgcggattcg aatcccggcc gggaacggtg cattggaacg cggattcccc  120
gtgccaagag tgac                                                    134

SEQ ID NO: 1052        moltype = DNA  length = 102
FEATURE                Location/Qualifiers
misc_feature           1..102
                       note = Description of Artificial Sequence: Synthetic
                        polynucleotide
source                 1..102
                       mol_type = other DNA
                       organism = synthetic construct
SEQUENCE: 1052
ttgacctcca tagaagacac cgggaccgat ccagcctccg cggattcgaa tcccggccgg  60
gaacggtgca ttggaacgcg gattccccgt gccaagagtg ac                     102

SEQ ID NO: 1053        moltype = DNA  length = 59
FEATURE                Location/Qualifiers
misc_feature           1..59
                       note = Description of Artificial Sequence: Synthetic
                        oligonucleotide
source                 1..59
                       mol_type = other DNA
                       organism = synthetic construct
SEQUENCE: 1053
attcgaatcc cggccgggaa cggtgcattg gaacgcggat tccccgtgcc aagagtgac   59

SEQ ID NO: 1054        moltype = DNA  length = 53
FEATURE                Location/Qualifiers
misc_feature           1..53
                       note = Description of Artificial Sequence: Synthetic
                        oligonucleotide
source                 1..53
                       mol_type = other DNA
                       organism = synthetic construct
SEQUENCE: 1054
ctcctgggca acgtgctggt ctgtgtgctg gcccatcact ttggcaaaga att         53

SEQ ID NO: 1055        moltype = DNA  length = 54
FEATURE                Location/Qualifiers
misc_feature           1..54
                       note = Description of Artificial Sequence: Synthetic
                        oligonucleotide
source                 1..54
                       mol_type = other DNA
                       organism = synthetic construct
SEQUENCE: 1055
ctcctgggca acgtgctggt tattgtgctg tctcatcatt ttggcaaaga attc        54

SEQ ID NO: 1056        moltype = DNA  length = 32
FEATURE                Location/Qualifiers
misc_feature           1..32
                       note = Description of Artificial Sequence: Synthetic
                        oligonucleotide
source                 1..32
                       mol_type = other DNA
                       organism = synthetic construct
SEQUENCE: 1056
gtaagtaccg cctatagagt ctataggccc ac                                32

SEQ ID NO: 1057        moltype = DNA  length = 15
FEATURE                Location/Qualifiers
misc_feature           1..15
                       note = Description of Artificial Sequence: Synthetic
                        oligonucleotide
```

```
source                  1..15
                        mol_type = other DNA
                        organism = synthetic construct
SEQUENCE: 1057
gtaagtaccg cctat                                                  15

SEQ ID NO: 1058         moltype = DNA  length = 347
FEATURE                 Location/Qualifiers
misc_feature            1..347
                        note = Description of Artificial Sequence: Synthetic
                         polynucleotide
source                  1..347
                        mol_type = other DNA
                        organism = synthetic construct
SEQUENCE: 1058
aaaaaatgct ttcttctttt aatatacttt tttgtttatc ttatttctaa tactttccct  60
aatctctttc tttcagggca ataatgatac aatgtatcat gcctctttgc accattctaa  120
agaataacag tgataatttc tgggttaagg caatagcaat atttctgcat ataaatattt  180
ctgcatataa attgtaactg atgtaagagg tttcatattg ctaatagcag ctacaatcca  240
gctaccattc tgcttttatt ttatggttgg gataaggctg gattattctg agtccaagct  300
aggccctttt gctaatcatg ttcatacctc ttatcttcct cccacag                347

SEQ ID NO: 1059         moltype = DNA  length = 168
FEATURE                 Location/Qualifiers
misc_feature            1..168
                        note = Description of Artificial Sequence: Synthetic
                         polynucleotide
source                  1..168
                        mol_type = other DNA
                        organism = synthetic construct
SEQUENCE: 1059
tctgcatata aattgtaact gatgtaagag gtttcatatt gctaatagca gctacaatcc  60
agctaccatt ctgcttttat tttatggttg ggataaggct ggattattct gagtccaagc  120
taggcccttt tgctaatcat gttcatacct cttatcttcc tcccacag               168

SEQ ID NO: 1060         moltype = DNA  length = 73
FEATURE                 Location/Qualifiers
misc_feature            1..73
                        note = Description of Artificial Sequence: Synthetic
                         oligonucleotide
source                  1..73
                        mol_type = other DNA
                        organism = synthetic construct
SEQUENCE: 1060
aaaaaatgct ttcttctttt aatatacttt tcttttgcta atcatgttca tacctcttat  60
cttcctccca cag                                                    73

SEQ ID NO: 1061         moltype = DNA  length = 73
FEATURE                 Location/Qualifiers
misc_feature            1..73
                        note = Description of Artificial Sequence: Synthetic
                         oligonucleotide
source                  1..73
                        mol_type = other DNA
                        organism = synthetic construct
SEQUENCE: 1061
aggctggatt attctgagtc caagctaggc ccttttgcta atcatgttca tacctcttat  60
cttcctccca cag                                                    73

SEQ ID NO: 1062         moltype = DNA  length = 73
FEATURE                 Location/Qualifiers
misc_feature            1..73
                        note = Description of Artificial Sequence: Synthetic
                         oligonucleotide
source                  1..73
                        mol_type = other DNA
                        organism = synthetic construct
SEQUENCE: 1062
aaaaaatgct ttcttctttt caagctaggc ccttttgcta atcatgttca tacctcttat  60
cttcctccca cag                                                    73

SEQ ID NO: 1063         moltype = DNA  length = 53
FEATURE                 Location/Qualifiers
misc_feature            1..53
                        note = Description of Artificial Sequence: Synthetic
                         oligonucleotide
source                  1..53
                        mol_type = other DNA
                        organism = synthetic construct
```

```
SEQUENCE: 1063
caagctaggc cctttttgcta atcatgttca tacctcttat cttcctccca cag        53

SEQ ID NO: 1064        moltype = DNA  length = 172
FEATURE                Location/Qualifiers
misc_feature           1..172
                       note = Description of Artificial Sequence: Synthetic
                        polynucleotide
source                 1..172
                       mol_type = other DNA
                       organism = synthetic construct
SEQUENCE: 1064
gaactgaaaa accagaaagt taactggtaa gtttagtctt tttgtctttt atttcaggtc  60
ccggatccgg tggtggtgca aatcaaagaa ctgctcctca gtggatgttg cctttacttc  120
taggcctgta cggaagtgtt acttctgctc taaaagctgc ggaattgtac cc          172

SEQ ID NO: 1065        moltype = DNA  length = 1074
FEATURE                Location/Qualifiers
misc_feature           1..1074
                       note = Description of Artificial Sequence: Synthetic
                        polynucleotide
source                 1..1074
                       mol_type = other DNA
                       organism = synthetic construct
SEQUENCE: 1065
ggagtcgctg cgcgctgcct tcgccccgtg ccccgctccg ccgccgcctc gcgccgcccg  60
ccccggctct gactgaccgc gttactccca caggtgagcg ggcgggacgg cccttctcct  120
ccgggctgta attagcgctt ggtttaatga cggcttgttt cttttctgtg gctgcgtgaa  180
agccttgagg ggctccggga gggccctttg tgcgggggga gcggctcggg gggtgcgtgc  240
gtgtgtgtgt gcgtggggag cgccgcgtgc ggctccgcgc tgcccggcgg ctgtgagcgc  300
tgcgggcgcg gcgcggggct ttgtgcgctc cgcagtgtgc gcgaggggag cgcggccggg  360
ggcggtgccc cgcggtgcgg ggggggctgc gaggggaaca aaggctgcgt gcggggtgtg  420
tgcgtggggg ggtgagcagg gggtgtgggc gcgtcggtcg ggctgcaacc ccccctgcac  480
ccccctcccc gagttgctga gcacggcccg gcttcgggtg cggggctccg tacggggcgt  540
ggcgcggggc tcgccgtgcc gggcgggggg tggcggcagg tgggggtgcc gggcggggcg  600
gggccgcctc gggccgggga gggctcgggg gaggggcgcg gcggcccccg gagcgccggc  660
ggctgtcgag gcgcggcgag ccgcagccat tgccttttat ggtaatcgtg cgagagggcg  720
cagggacttc ctttgtccca aatctgtgcg gagccgaaat ctgggaggcg ccgccgcacc  780
ccctctagcg ggcgcggggc gaagcggtgc ggcgccggca ggaaggaaat gggcggggag  840
ggccttcgtg cgtcgccgcg ccgccgtccc cttctccctc tccagcctcg gggctgtccg  900
cggggggacg gctgccttcg ggggggacgg ggcagggcgg ggttcggctt ctggcgtgtg  960
accggcggct ctagagcctc tgctaaccat gttcatgcct tcttcttttt cctacagctc  1020
ctgggcaacg tgctggttat tgtgctgtct catcattttg gcaaagaatt cgag        1074

SEQ ID NO: 1066        moltype = DNA  length = 41
FEATURE                Location/Qualifiers
misc_feature           1..41
                       note = Description of Artificial Sequence: Synthetic
                        oligonucleotide
source                 1..41
                       mol_type = other DNA
                       organism = synthetic construct
SEQUENCE: 1066
cctctgctaa ccatgttcat gccttcttct ttttcctaca g                    41

SEQ ID NO: 1067        moltype = DNA  length = 566
FEATURE                Location/Qualifiers
misc_feature           1..566
                       note = Description of Artificial Sequence: Synthetic
                        polynucleotide
source                 1..566
                       mol_type = other DNA
                       organism = synthetic construct
SEQUENCE: 1067
tcagatcgcc tggagacgcc atccacgctg ttttgacctc catagaagac accgggaccg  60
atccagcctc cgcggattcg aatcccggcc gggaacggtg cattggaacg cggattcccc  120
gtgccaagag tgacgtaagt accgcctata gagtctatag gcccacaaaa aatgctttct  180
tcttttaata tactttttttg tttatcttat ttctaatact ttccctaatc tctttctttc  240
agggcaataa tgatacaatg tatcatgcct ctttgcacca ttctaaagaa taacagtgat  300
aatttctggg ttaaggcaat agcaatattt ctgcatataa atatttctgc atataaattg  360
taactgatgt aagaggtttc atattgctaa tagcagctac aatccagcta ccattctgct  420
tttattttat ggttgggata aggctggatt attctgagtc caagctaggc cctttttgcta  480
atcatgttca tacctcttat cttcctccca cagctcctgg gcaacgtgct ggtctgtgtg  540
ctggcccatc actttggcaa agaatt                                     566

SEQ ID NO: 1068        moltype = DNA  length = 491
FEATURE                Location/Qualifiers
misc_feature           1..491
                       note = Description of Artificial Sequence: Synthetic
```

```
                         polynucleotide
source                  1..491
                        mol_type = other DNA
                        organism = synthetic construct
SEQUENCE: 1068
attcgaatcc cggccgggaa cggtgcattg gaacgcggat tccccgtgcc aagagtgacg  60
taagtaccgc ctatagagtc tataggccca caaaaaatgc tttcttcttt taatatactt  120
ttttgtttat cttatttcta atactttccc taatctcttt ctttcagggc aataatgata  180
caatgtatca tgcctctttg caccattcta aagaataaca gtgataattt ctgggttaag  240
gcaatagcaa tatttctgca tataaatatt tctgcatata aattgtaact gatgtaagag  300
gtttcatatt gctaatagca gctacaatcc agctaccatt ctgcttttat tttatggttg  360
ggataaggct ggattattct gagtccaagc taggcccttt tgctaatcat gttcatacct  420
cttatcttcc tcccacagct cctgggcaac gtgctggtct gtgtgctggc ccatcacttt  480
ggcaaagaat t                                                       491

SEQ ID NO: 1069         moltype = DNA  length = 387
FEATURE                 Location/Qualifiers
misc_feature            1..387
                        note = Description of Artificial Sequence: Synthetic
                         polynucleotide
source                  1..387
                        mol_type = other DNA
                        organism = synthetic construct
SEQUENCE: 1069
tcagatcgcc tggagacgcc atccacgctg ttttgacctc catagaagac accgggaccg  60
atccagcctc cgcggattcg aatcccggcc gggaacggtg cattggaacg cggattcccc  120
gtgccaagag tgacgtaagt accgcctata gagtctatag gcccactctg catataaatt  180
gtaactgatg taagaggttt catattgcta atagcagcta caatccagct accattctgc  240
ttttatttta tggttgggat aaggctggat tattctgagt ccaagctagg ccctttgct  300
aatcatgttc atacctctta tcttcctccc acagctcctg ggcaacgtgc tggtctgtgt  360
gctggcccat cactttggca aagaatt                                      387

SEQ ID NO: 1070         moltype = DNA  length = 292
FEATURE                 Location/Qualifiers
misc_feature            1..292
                        note = Description of Artificial Sequence: Synthetic
                         polynucleotide
source                  1..292
                        mol_type = other DNA
                        organism = synthetic construct
SEQUENCE: 1070
tcagatcgcc tggagacgcc atccacgctg ttttgacctc catagaagac accgggaccg  60
atccaggtaa gtaccgccta tagagtctat aggcccacaa aaaatgcttt cttcttttaa  120
tatacttttt tgtttatctt atttctaata ctttccctaa tctctttcgc tggattattc  180
tgagtccaag ctaggccctt ttgctaatca tgttcatacc tcttatcttc ctcccacagc  240
tcctgggcaa cgtgctggtc tgtgtgctgg cccatcactt tggcaaagaa tt          292

SEQ ID NO: 1071         moltype = DNA  length = 84
FEATURE                 Location/Qualifiers
misc_feature            1..84
                        note = Description of Artificial Sequence: Synthetic
                         oligonucleotide
source                  1..84
                        mol_type = other DNA
                        organism = synthetic construct
SEQUENCE: 1071
atggcgacgg gttcaagaac ttccctactt cttgcatttg gcctgctttg tttgccgtgg  60
ttacaggagg gctcggcagc tgcc                                         84

SEQ ID NO: 1072         moltype = DNA  length = 93
FEATURE                 Location/Qualifiers
misc_feature            1..93
                        note = Description of Artificial Sequence: Synthetic
                         oligonucleotide
source                  1..93
                        mol_type = other DNA
                        organism = synthetic construct
SEQUENCE: 1072
gccgccacca tggcgacggg ttcaagaact tccctacttc ttgcatttgg cctgctttgt  60
ttgccgtggt tacaggaggg ctcggcagct gcc                               93

SEQ ID NO: 1073         moltype = DNA  length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
```

```
SEQUENCE: 1073
gccgccacca tgggggtgca cgaatgtcct gcctggctgt ggcttctcct gtccctgctg  60
tcgctccctc tgggcctccc agtcctgggc gctgcc                            96

SEQ ID NO: 1074        moltype = DNA  length = 66
FEATURE                Location/Qualifiers
misc_feature           1..66
                       note = Description of Artificial Sequence: Synthetic
                        oligonucleotide
source                 1..66
                       mol_type = other DNA
                       organism = synthetic construct
SEQUENCE: 1074
gccgccacca tgggagtcaa agttctgttt gccctgatct gcatcgctgt ggccgaggcc  60
gctgcc                                                             66

SEQ ID NO: 1075        moltype = DNA  length = 72
FEATURE                Location/Qualifiers
misc_feature           1..72
                       note = Description of Artificial Sequence: Synthetic
                        oligonucleotide
source                 1..72
                       mol_type = other DNA
                       organism = synthetic construct
SEQUENCE: 1075
gccgccacca tgaaacacct gtggttcttc ctcctgctgg tggcagctcc cagatgggtc  60
ctgtccgctg cc                                                      72

SEQ ID NO: 1076        moltype = DNA  length = 93
FEATURE                Location/Qualifiers
misc_feature           1..93
                       note = Description of Artificial Sequence: Synthetic
                        oligonucleotide
source                 1..93
                       mol_type = other DNA
                       organism = synthetic construct
SEQUENCE: 1076
gccgccacca tggacctcct gcacaagaac atgaaacacc tgtggttctt cctcctcctg  60
gtggcagctc ccagatgggt gctgtccgct gcc                               93

SEQ ID NO: 1077        moltype = DNA  length = 69
FEATURE                Location/Qualifiers
misc_feature           1..69
                       note = Description of Artificial Sequence: Synthetic
                        oligonucleotide
source                 1..69
                       mol_type = other DNA
                       organism = synthetic construct
SEQUENCE: 1077
gccgccacca tggctttcct ctggctcctc tcctgctggg ccctcctggg taccaccttc  60
ggcgctgcc                                                          69

SEQ ID NO: 1078        moltype = DNA  length = 81
FEATURE                Location/Qualifiers
misc_feature           1..81
                       note = Description of Artificial Sequence: Synthetic
                        oligonucleotide
source                 1..81
                       mol_type = other DNA
                       organism = synthetic construct
SEQUENCE: 1078
gccgccacca tgccccccaa gaagtgcctg ctgctgctgc tgaccctgct gctgctgatc  60
tccaccacct tcggcgctgc c                                            81

SEQ ID NO: 1079        moltype = DNA  length = 12
FEATURE                Location/Qualifiers
misc_feature           1..12
                       note = Description of Artificial Sequence: Synthetic
                        oligonucleotide
source                 1..12
                       mol_type = other DNA
                       organism = synthetic construct
SEQUENCE: 1079
gccgccacca tg                                                      12

SEQ ID NO: 1080        moltype = DNA  length = 81
FEATURE                Location/Qualifiers
misc_feature           1..81
                       note = Description of Artificial Sequence: Synthetic
```

```
                         oligonucleotide
source                  1..81
                        mol_type = other DNA
                        organism = synthetic construct
SEQUENCE: 1080
gccgccacca tggacatgag ggtccctgct cagctcctgg ggctcctgct gctctggctc  60
tcaggtgcca gatgtgctgc c                                            81

SEQ ID NO: 1081         moltype = DNA  length = 66
FEATURE                 Location/Qualifiers
misc_feature            1..66
                        note = Description of Artificial Sequence: Synthetic
                         oligonucleotide
source                  1..66
                        mol_type = other DNA
                        organism = synthetic construct
SEQUENCE: 1081
gccgccacca tggaaatcaa ggtgctgttt gccctcatct gtattgctgt tgctgaggca  60
gctgcc                                                             66

SEQ ID NO: 1082         moltype = DNA  length = 78
FEATURE                 Location/Qualifiers
misc_feature            1..78
                        note = Description of Artificial Sequence: Synthetic
                         oligonucleotide
source                  1..78
                        mol_type = other DNA
                        organism = synthetic construct
SEQUENCE: 1082
gccgccacca tggagacaga cacactcctg ctatgggtac tgctgctctg ggttccaggt  60
tccactggtg acgctgcc                                                78

SEQ ID NO: 1083         moltype = DNA  length = 57
FEATURE                 Location/Qualifiers
misc_feature            1..57
                        note = Description of Artificial Sequence: Synthetic
                         oligonucleotide
source                  1..57
                        mol_type = other DNA
                        organism = synthetic construct
SEQUENCE: 1083
atgaacttcg ggctcagctt gattttcctt gtccttgttt taaaaggtgt ccagtgt     57

SEQ ID NO: 1084         moltype = DNA  length = 57
FEATURE                 Location/Qualifiers
misc_feature            1..57
                        note = Description of Artificial Sequence: Synthetic
                         oligonucleotide
source                  1..57
                        mol_type = other DNA
                        organism = synthetic construct
SEQUENCE: 1084
atgggatgga gctggatctt tctctttctc ctgtcaggaa ctacaggtgt cctctct     57

SEQ ID NO: 1085         moltype = DNA  length = 57
FEATURE                 Location/Qualifiers
misc_feature            1..57
                        note = Description of Artificial Sequence: Synthetic
                         oligonucleotide
source                  1..57
                        mol_type = other DNA
                        organism = synthetic construct
SEQUENCE: 1085
atgaagttgc ctgttaggct gttggtgctg atgttctgga ttcctgcttc cagcagt     57

SEQ ID NO: 1086         moltype = DNA  length = 411
FEATURE                 Location/Qualifiers
misc_feature            1..411
                        note = Description of Artificial Sequence: Synthetic
                         polynucleotide
source                  1..411
                        mol_type = other DNA
                        organism = synthetic construct
SEQUENCE: 1086
atgaacttcg ggctcagctt gattttcctt gtccttgttt taaaaggtgt ccagtgtgag  60
gtgaagctgg tggagagcgg cggcgacctg gtgaagcctg gcggcagcct gaagctgagc  120
tgcgccgcca gcggcttcac cttcagcagc tacgccatga gctgggtgag acagaaccct  180
gagaagagac tggagtgggt ggccagcatc agcaagggcg gcaacaccta ctaccctaac  240
agcgtgaagg gcagattcac catcagcaga gacaacgcca gaaacatcct gtacctgcag  300
```

```
atgagcagcc tgagaagcga ggacaccgcc ctgtactact gcgccagagg ctggggcgac  360
tacggctggt tcgcctactg gggccaggtg accctggtga ccgtgagcgc c           411

SEQ ID NO: 1087        moltype = DNA  length = 57
FEATURE                Location/Qualifiers
misc_feature           1..57
                       note = Description of Artificial Sequence: Synthetic
                        oligonucleotide
source                 1..57
                       mol_type = other DNA
                       organism = synthetic construct
SEQUENCE: 1087
atgagtcctg cccagttcct gtttctgtta gtgctctgga ttcgggaaac caacggt     57

SEQ ID NO: 1088        moltype = DNA  length = 72
FEATURE                Location/Qualifiers
misc_feature           1..72
                       note = Description of Artificial Sequence: Synthetic
                        oligonucleotide
source                 1..72
                       mol_type = other DNA
                       organism = synthetic construct
SEQUENCE: 1088
gccgccacca tgagtcctgc ccagttcctg tttctgttag tgctctggat tcgggaaacc  60
aacggtgctg cc                                                      72

SEQ ID NO: 1089        moltype = DNA  length = 11
FEATURE                Location/Qualifiers
misc_feature           1..11
                       note = Description of Artificial Sequence: Synthetic
                        oligonucleotide
source                 1..11
                       mol_type = other DNA
                       organism = synthetic construct
SEQUENCE: 1089
gaggagccac c                                                       11

SEQ ID NO: 1090        moltype = DNA  length = 12
FEATURE                Location/Qualifiers
misc_feature           1..12
                       note = Description of Artificial Sequence: Synthetic
                        oligonucleotide
source                 1..12
                       mol_type = other DNA
                       organism = synthetic construct
SEQUENCE: 1090
agaaagaggc ga                                                      12

SEQ ID NO: 1091        moltype = DNA  length = 12
FEATURE                Location/Qualifiers
misc_feature           1..12
                       note = Description of Artificial Sequence: Synthetic
                        oligonucleotide
source                 1..12
                       mol_type = other DNA
                       organism = synthetic construct
SEQUENCE: 1091
cgggccaagc gg                                                      12

SEQ ID NO: 1092        moltype = DNA  length = 54
FEATURE                Location/Qualifiers
misc_feature           1..54
                       note = Description of Artificial Sequence: Synthetic
                        oligonucleotide
source                 1..54
                       mol_type = other DNA
                       organism = synthetic construct
SEQUENCE: 1092
gagggcagag gaagtcttct aacatgcggt gacgtggagg agaatcccgg ccct        54

SEQ ID NO: 1093        moltype = DNA  length = 75
FEATURE                Location/Qualifiers
misc_feature           1..75
                       note = Description of Artificial Sequence: Synthetic
                        oligonucleotide
source                 1..75
                       mol_type = other DNA
                       organism = synthetic construct
SEQUENCE: 1093
```

```
ggaagcggag tgaaacagac tttgaatttt gaccttctca agttggcggg agacgtggag  60
tccaaccctg gacct                                                   75

SEQ ID NO: 1094        moltype = DNA  length = 66
FEATURE                Location/Qualifiers
misc_feature           1..66
                       note = Description of Artificial Sequence: Synthetic
                        oligonucleotide
source                 1..66
                       mol_type = other DNA
                       organism = synthetic construct
SEQUENCE: 1094
ggaagcggag ctactaactt cagcctgctg aagcaggctg gagacgtgga ggagaaccct  60
ggacct                                                             66

SEQ ID NO: 1095        moltype = DNA  length = 609
FEATURE                Location/Qualifiers
misc_feature           1..609
                       note = Description of Artificial Sequence: Synthetic
                        polynucleotide
source                 1..609
                       mol_type = other DNA
                       organism = synthetic construct
SEQUENCE: 1095
aattccgccc ctctcccccc cccccctctc cctccccccc ccctaacgtt actggccgaa  60
gccgcttgga ataaggccgg tgtgcgtttg tctatatgtt attttccacc atattgccgt  120
cttttggcaa tgtgagggcc cggaaacctg gccctgtctt cttgacgagc attcctaggg  180
gtctttcccc tctcgccaaa ggaatgcaag gtctgttgaa tgtcgtgaag gaagcagttc  240
ctctggaagc ttcttgaaga caaacaacgt ctgtagcgac cctttgcagg cagcggaacc  300
ccccacctgg cgacaggtgc ctctgcggcc aaaagccacg tgtataagat acacctgcaa  360
aggcggcaca accccagtgc cacgttgtga gttggatagt tgtggaaaga gtcaaatggc  420
tctcctcaag cgtattcaac aaggggctga aggatgccca gaaggtaccc cattgtatgg  480
gatctgatct ggggcctcgg tgcacatgct ttacatgtgt ttagtcgagg ttaaaaaaac  540
gtctaggccc cccgaaccac ggggacgtgg ttttcctttg aaaaacacga tgataatatg  600
gccacaacc                                                          609

SEQ ID NO: 1096        moltype = DNA  length = 623
FEATURE                Location/Qualifiers
misc_feature           1..623
                       note = Description of Artificial Sequence: Synthetic
                        polynucleotide
source                 1..623
                       mol_type = other DNA
                       organism = synthetic construct
SEQUENCE: 1096
taacgaattc cgcccctctc cccccccccc ctctccctcc ccccccccta acgttactgg  60
ccgaagccgc ttggaataag gccggtgtgc gtttgtctat atgttatttt ccaccatatt  120
gccgtctttt ggcaatgtga gggcccggaa acctggccct gtcttcttga cgagcattcc  180
taggggtctt tcccctctcg ccaaaggaat gcaaggtctg ttgaatgtcg tgaaggaagc  240
agttcctctg gaagcttctt gaagacaaac aacgtctgta gcgacccttt gcaggcagcg  300
gaacccccca cctggcgaca ggtgcctctg cggccaaaag ccacgtgtat aagatacacc  360
tgcaaaggcg gcacaacccc agtgccacgt tgtgagttgg atagttgtgg aaagagtcaa  420
atggctctcc tcaagcgtat tcaacaaggg gctgaaggat gcccagaagg taccccattg  480
tatgggatct gatctggggc ctcggtgcac atgctttaca tgtgtttagt cgaggttaaa  540
aaaacgtcta ggccccccga accacgggga cgtggttttc ctttgaaaaa cacgatgata  600
atatggccac aaccgccgcc acc                                          623

SEQ ID NO: 1097        moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1097
GGGGS                                                              5

SEQ ID NO: 1098        moltype = DNA  length = 15
FEATURE                Location/Qualifiers
misc_feature           1..15
                       note = Description of Artificial Sequence: Synthetic
                        oligonucleotide
source                 1..15
                       mol_type = other DNA
                       organism = synthetic construct
SEQUENCE: 1098
ggtggtggtg gatcc                                                   15

SEQ ID NO: 1099        moltype = AA  length = 6
```

```
FEATURE                Location/Qualifiers
REGION                 1..6
                       note = Description of Artificial Sequence: Synthetic peptide
source                 1..6
                       mol_type = protein
                       organism = synthetic construct
SEQUENCE: 1099
SGGGGS                                                                   6

SEQ ID NO: 1100        moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 1100
tccggaggcg gcggcagc                                                      18

SEQ ID NO: 1101        moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 1101
GGGGSGGGGS                                                               10

SEQ ID NO: 1102        moltype = DNA  length = 30
FEATURE                Location/Qualifiers
misc_feature           1..30
                       note = Description of Artificial Sequence: Synthetic
                        oligonucleotide
source                 1..30
                       mol_type = other DNA
                       organism = synthetic construct
SEQUENCE: 1102
ggtggtggtg gatccggtgg tggtggatcc                                         30

SEQ ID NO: 1103        moltype = AA  length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 1103
GGGGSGGGGS GGGGS                                                         15

SEQ ID NO: 1104        moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 1104
ggtggtggtg gtagcggcgg cggcggctct ggtggtggtg gatcc                        45

SEQ ID NO: 1105        moltype = DNA  length = 45
FEATURE                Location/Qualifiers
misc_feature           1..45
                       note = Description of Artificial Sequence: Synthetic
                        oligonucleotide
source                 1..45
                       mol_type = other DNA
                       organism = synthetic construct
SEQUENCE: 1105
ggtggtggtg gatccggtgg tggtggatcc ggtggtggtg gatcc                        45

SEQ ID NO: 1106        moltype = AA  length = 20
FEATURE                Location/Qualifiers
REGION                 1..20
                       note = Description of Artificial Sequence: Synthetic peptide
source                 1..20
                       mol_type = protein
```

```
                        organism = synthetic construct
SEQUENCE: 1106
GGGGSGGGGS GGGGSGGGGS                                              20

SEQ ID NO: 1107         moltype = DNA  length = 60
FEATURE                 Location/Qualifiers
misc_feature            1..60
                        note = Description of Artificial Sequence: Synthetic
                         oligonucleotide
source                  1..60
                        mol_type = other DNA
                        organism = synthetic construct
SEQUENCE: 1107
ggtggtggtg gatccggtgg tggtggatcc ggtggtggtg gatccggtgg tggtggatcc  60

SEQ ID NO: 1108         moltype = DNA  length = 60
FEATURE                 Location/Qualifiers
misc_feature            1..60
                        note = Description of Artificial Sequence: Synthetic
                         oligonucleotide
source                  1..60
                        mol_type = other DNA
                        organism = synthetic construct
SEQUENCE: 1108
ggtggtggtg gtagcggcgg cggcggctct ggtggtggtg gatccggtgg tggtggatcc  60

SEQ ID NO: 1109         moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 1109
GGGGSGGGGS GGGGSGGGGS GGGGS                                        25

SEQ ID NO: 1110         moltype = DNA  length = 75
FEATURE                 Location/Qualifiers
misc_feature            1..75
                        note = Description of Artificial Sequence: Synthetic
                         oligonucleotide
source                  1..75
                        mol_type = other DNA
                        organism = synthetic construct
SEQUENCE: 1110
ggcggaggtg gctccggagg cggaggcagc ggcggaggtg ggtctggcgg aggcgggtgc  60
ggcggaggtg gctcc                                                   75

SEQ ID NO: 1111         moltype = DNA  length = 75
FEATURE                 Location/Qualifiers
misc_feature            1..75
                        note = Description of Artificial Sequence: Synthetic
                         oligonucleotide
source                  1..75
                        mol_type = other DNA
                        organism = synthetic construct
SEQUENCE: 1111
ggtggtggtg gtagcggcgg cggcggctct ggtggtggtg gatccggtgg tggtggatcc  60
ggtggtggtg gatcc                                                   75

SEQ ID NO: 1112         moltype = DNA  length = 75
FEATURE                 Location/Qualifiers
misc_feature            1..75
                        note = Description of Artificial Sequence: Synthetic
                         oligonucleotide
source                  1..75
                        mol_type = other DNA
                        organism = synthetic construct
SEQUENCE: 1112
ggtggtggtg gatccggtgg tggtggatcc ggtggtggtg gatccggtgg tggtggatcc  60
ggtggtggtg gatcc                                                   75

SEQ ID NO: 1113         moltype = AA  length = 30
FEATURE                 Location/Qualifiers
REGION                  1..30
                        note = Description of Artificial Sequence: Synthetic
                         polypeptide
source                  1..30
                        mol_type = protein
```

```
                        organism = synthetic construct
SEQUENCE: 1113
GGGGSGGGGS GGGGSGGGGS GGGGSGGGGS                                   30

SEQ ID NO: 1114         moltype = DNA  length = 90
FEATURE                 Location/Qualifiers
misc_feature            1..90
                        note = Description of Artificial Sequence: Synthetic
                         oligonucleotide
source                  1..90
                        mol_type = other DNA
                        organism = synthetic construct
SEQUENCE: 1114
ggtggtggtg gtagcggcgg cggcggctct ggtggtggtg gatccggtgg tggtggatcc  60
ggtggtggtg gatccggtgg tggtggatcc                                   90

SEQ ID NO: 1115         moltype = DNA  length = 90
FEATURE                 Location/Qualifiers
misc_feature            1..90
                        note = Description of Artificial Sequence: Synthetic
                         oligonucleotide
source                  1..90
                        mol_type = other DNA
                        organism = synthetic construct
SEQUENCE: 1115
ggtggtggtg gatccggtgg tggtggatcc ggtggtggtg gatccggtgg tggtggatcc  60
ggtggtggtg gatccggtgg tggtggatcc                                   90

SEQ ID NO: 1116         moltype = AA  length = 40
FEATURE                 Location/Qualifiers
REGION                  1..40
                        note = Description of Artificial Sequence: Synthetic
                         polypeptide
source                  1..40
                        mol_type = protein
                        organism = synthetic construct
SEQUENCE: 1116
GGGGSGGGGS GGGGSGGGGS GGGGSGGGGS GGGGSGGGGS                        40

SEQ ID NO: 1117         moltype = DNA  length = 120
FEATURE                 Location/Qualifiers
misc_feature            1..120
                        note = Description of Artificial Sequence: Synthetic
                         polynucleotide
source                  1..120
                        mol_type = other DNA
                        organism = synthetic construct
SEQUENCE: 1117
ggtggtggtg gtagcggcgg cggcggctct ggtggtggtg gatccggtgg tggtggatcc  60
ggtggtggtg gatccggtgg tggtggatcc ggtggtggtg gatccggtgg tggtggatcc  120

SEQ ID NO: 1118         moltype = DNA  length = 120
FEATURE                 Location/Qualifiers
misc_feature            1..120
                        note = Description of Artificial Sequence: Synthetic
                         polynucleotide
source                  1..120
                        mol_type = other DNA
                        organism = synthetic construct
SEQUENCE: 1118
ggtggtggtg gatccggtgg tggtggatcc ggtggtggtg gatccggtgg tggtggatcc  60
ggtggtggtg gatccggtgg tggtggatcc ggtggtggtg gatccggtgg tggtggatcc  120

SEQ ID NO: 1119         moltype = AA  length = 50
FEATURE                 Location/Qualifiers
REGION                  1..50
                        note = Description of Artificial Sequence: Synthetic
                         polypeptide
VARIANT                 1..50
                        note = This sequence may encompass 1-10 GGGGS repeating
                         units
source                  1..50
                        mol_type = protein
                        organism = synthetic construct
SEQUENCE: 1119
GGGGSGGGGS GGGGSGGGGS GGGGSGGGGS GGGGSGGGGS GGGGSGGGGS             50

SEQ ID NO: 1120         moltype = DNA  length = 54
FEATURE                 Location/Qualifiers
```

```
misc_feature            1..54
                        note = Description of Artificial Sequence: Synthetic
                         oligonucleotide
source                  1..54
                        mol_type = other DNA
                        organism = synthetic construct
SEQUENCE: 1120
gtggagagga agtgctgcgt ggagtgccca ccatgccctg cccctcctgt ggcc       54

SEQ ID NO: 1121         moltype = DNA  length = 108
FEATURE                 Location/Qualifiers
misc_feature            1..108
                        note = Description of Artificial Sequence: Synthetic
                         polynucleotide
source                  1..108
                        mol_type = other DNA
                        organism = synthetic construct
SEQUENCE: 1121
gagctcaaaa ccccacttgg tgacacaact cacacatgcc cacggtgccc agagcccaaa  60
tcttgtgaca cacctccccc gtgcccacgg tgcccagcac ctgaactc              108

SEQ ID NO: 1122         moltype = DNA  length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 1122
gagctcaaaa ccccacttgg tgacacaact cacacatgcc cacggtgccc agagcccaaa  60
tcttgtgaca cacctccccc gtgcccacgg tgcccagagc ccaaatcttg tgacacacct  120
cccccatgcc cacggtgccc agcacctgaa ctc                               153

SEQ ID NO: 1123         moltype = DNA  length = 198
FEATURE                 Location/Qualifiers
misc_feature            1..198
                        note = Description of Artificial Sequence: Synthetic
                         polynucleotide
source                  1..198
                        mol_type = other DNA
                        organism = synthetic construct
SEQUENCE: 1123
gagctcaaaa ccccacttgg tgacacaact cacacatgcc cacggtgccc agagcccaaa  60
tcttgtgaca cacctccccc gtgcccacgg tgcccagagc ccaaatcttg tgacacacct  120
cccccatgcc cacggtgccc agagcccaaa tcttgtgaca cacctccccc gtgcccaagg  180
tgcccagcac ctgaactc                                                198

SEQ ID NO: 1124         moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 1124
gtgcccaggg attgtggttg taagccttgc atatgtacag tccca                 45

SEQ ID NO: 1125         moltype = DNA  length = 18
FEATURE                 Location/Qualifiers
misc_feature            1..18
                        note = Description of Artificial Sequence: Synthetic
                         oligonucleotide
source                  1..18
                        mol_type = other DNA
                        organism = synthetic construct
SEQUENCE: 1125
gtgcccaggg attgtggt                                               18

SEQ ID NO: 1126         moltype = DNA  length = 198
FEATURE                 Location/Qualifiers
misc_feature            1..198
                        note = Description of Artificial Sequence: Synthetic
                         polynucleotide
source                  1..198
                        mol_type = other DNA
                        organism = synthetic construct
SEQUENCE: 1126
```

```
gagctcaaaa ccccacttgg tgacacaact cacacatgcc cacggtgccc agagcccaaa  60
tcttgtgaca cacctccccc gtgcccacgg tgcccagagc ccaaatcttg tgacacaact  120
cacacatgcc cacggtgccc agagcccaaa tcttgtgaca cacctccccc gtgcccaagg  180
tgcccagcac ctgaactc                                                198

SEQ ID NO: 1127        moltype = DNA  length = 27
FEATURE                Location/Qualifiers
misc_feature           1..27
                       note = Description of Artificial Sequence: Synthetic
                        oligonucleotide
source                 1..27
                       mol_type = other DNA
                       organism = synthetic construct
SEQUENCE: 1127
tacccatacg atgttccaga ttacgct                                      27

SEQ ID NO: 1128        moltype = DNA  length = 21
FEATURE                Location/Qualifiers
misc_feature           1..21
                       note = Description of Artificial Sequence: Synthetic
                        oligonucleotide
source                 1..21
                       mol_type = other DNA
                       organism = synthetic construct
SEQUENCE: 1128
agcgagaagg acgagctgta g                                            21

SEQ ID NO: 1129        moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 1129
agcgagaagg acgagctg                                                18

SEQ ID NO: 1130        moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 1130
catcaccatc accatcac                                                18

SEQ ID NO: 1131        moltype = DNA  length = 18
FEATURE                Location/Qualifiers
misc_feature           1..18
                       note = Description of Artificial Sequence: Synthetic
                        oligonucleotide
source                 1..18
                       mol_type = other DNA
                       organism = synthetic construct
SEQUENCE: 1131
catcatcacc atcaccat                                                18

SEQ ID NO: 1132        moltype = AA  length = 4
FEATURE                Location/Qualifiers
REGION                 1..4
                       note = Description of Unknown: KDEL ER retention motif
source                 1..4
                       mol_type = protein
                       organism = unidentified
SEQUENCE: 1132
KDEL                                                               4

SEQ ID NO: 1133        moltype = AA  length = 6
FEATURE                Location/Qualifiers
REGION                 1..6
                       note = Description of Unknown: SEKDEL ER retention motif
source                 1..6
                       mol_type = protein
                       organism = unidentified
SEQUENCE: 1133
SEKDEL                                                             6
```

```
SEQ ID NO: 1134        moltype = DNA  length = 127
FEATURE                Location/Qualifiers
misc_feature           1..127
                       note = Description of Artificial Sequence: Synthetic
                        polynucleotide
source                 1..127
                       mol_type = other DNA
                       organism = synthetic construct
SEQUENCE: 1134
gatctttttc cctctgccaa aaattatggg gacatcatga agccccttga gcatctgact  60
tctggctaat aaaggaaatt tattttcatt gcaatagtgt gttggaattt tttgtgtctc  120
tcactcg                                                            127

SEQ ID NO: 1135        moltype = DNA  length = 477
FEATURE                Location/Qualifiers
misc_feature           1..477
                       note = Description of Artificial Sequence: Synthetic
                        polynucleotide
source                 1..477
                       mol_type = other DNA
                       organism = synthetic construct
SEQUENCE: 1135
gggtggcatc cctgtgaccc ctccccagtg cctctcctgg ccctggaagt tgccactcca  60
gtgcccacca gccttgtcct aataaaatta agttgcatca ttttgtctga ctaggtgtcc  120
ttctataata ttatggggtg gaggggggtg gtatggagca aggggcaagt tgggaagaca  180
acctgtaggg cctgcggggt ctattgggaa ccaagctgga gtgcagtggc acaatcttgg  240
ctcactgcaa tctccgcctc ctgggttcaa gcgattctcc tgcctcagcc tcccgagttg  300
ttgggattcc aggcatgcat gaccaggctc agctaatttt tgttttttg gtagagacgg  360
ggtttcacca tattggccag gctggtctcc aactcctaat ctcaggtgat ctacccacct  420
tggcctccca aattgctggg attacaggcg tgaaccactg ctcccttccc tgtcctt     477

SEQ ID NO: 1136        moltype = DNA  length = 552
FEATURE                Location/Qualifiers
misc_feature           1..552
                       note = Description of Artificial Sequence: Synthetic
                        polynucleotide
source                 1..552
                       mol_type = other DNA
                       organism = synthetic construct
SEQUENCE: 1136
gaattcactc ctcaggtgca ggctgcctat cagaaggtgg tggctggtgt ggccaatgcc  60
ctggctcaca aataccactg agatcttttt ccctctgcca aaaattatgg ggacatcatg  120
aagccccttg agcatctgac ttctggctaa taaaggaaat ttattttcat tgcaatagtg  180
tgttggaatt ttttgtgtct ctcactcgga aggacatatg ggagggcaaa tcatttaaaa  240
catcagaatg agtatttggt ttagagtttg gcaacatatg cccatatgct ggctgccatg  300
aacaaaggtt ggctataaag aggtcatcag tatatgaaac agccccctgc tgtccattcc  360
ttattccata gaaaagcctt gacttgaggt tagatttttt ttatattttg ttttgtgtta  420
tttttttctt taacatccct aaaattttcc ttacatgttt tactagccag atttttcctc  480
ctctcctgac tactcccagt catagctgtc cctcttctct tatggagatc cctcgacctg  540
cagcccaagc tt                                                      552

SEQ ID NO: 1137        moltype = DNA  length = 1153
FEATURE                Location/Qualifiers
misc_feature           1..1153
                       note = Description of Artificial Sequence: Synthetic
                        polynucleotide
source                 1..1153
                       mol_type = other DNA
                       organism = synthetic construct
SEQUENCE: 1137
cctaggtttc ttgagacctc tacaagagtt ggagttgaca cttggggtac tttcttggtg  60
taacgaacta atagcctgaa aaaaagaagt catgtgtttt cagcaaggca agaaactgtc  120
taacatagta gataaaacag agaacacttg gccggaatca actaagatgt tgctatgttc  180
cattcatcat attatctcca tctgcagagt agtgggttag tggagggtag aaaacattct  240
cctgaacaac tagttaaact tggctttgag ttccacctgt accacttgca taatcttggg  300
aaagtgagtt gcctaattca gtgacattaa taaatttatt aatttcttct ttcaataaaa  360
cctggagaga gcttcatatg tatcagcata tgctaaactt gaaagataca agtagaaaat  420
ggaaggaaat atatctgact caatagggat agttcaaggg ttaaattaaa agtagtaaag  480
tattataatt aatctgacat ggtacctaat atataataat catgtattaa gaatgccagt  540
caccattaaa agtcaatgta tgactttaat ctactcgagg aaagaaacta tgtcttgttc  600
actgttatta tctctaaaat ccataatcag aagagcacca tgtgtatgag ccacacaata  660
aatatctact gtataatatg tctcttcttg tttttaacct tcatagataa gactctattg  720
aattgggaca ttagtccagc aagccattct gtctctgtct cttctatgga gggaaaggtt  780
taaccatcaa agactaggtg catctcccaa acaacctgaa tttaatattc aaatatgtat  840
ctaaattcat ttgttacatt tttgtgttca gcttacatat tactttttga gcgacatcta  900
ttcaaggcct actacttgct gctctacaaa atattgccat gctctatttg cccattaact  960
atttcttaac cttcaaggga catgctcagt tctgatatac caagatttgg tatttaccct  1020
cccagcctac atacttccaa tcttaagaga acaattttta gactacattc aaatatagac  1080
```

```
ctctccaccc catcaactat tttatctctc ctctcctatc tttcttgaca aagagtgatt  1140
agaaatatgc aat                                                     1153

SEQ ID NO: 1138        moltype = DNA  length = 1240
FEATURE                Location/Qualifiers
misc_feature           1..1240
                       note = Description of Artificial Sequence: Synthetic
                        polynucleotide
source                 1..1240
                       mol_type = other DNA
                       organism = synthetic construct
SEQUENCE: 1138
attatatttt tttaaagact cacatagtct tctgcacagg gcattctttt tgcttcagga  60
tgtttacaac atttgctgcc cacttttcct aggtttcttg agacctctac aagagttgga  120
gttgacactt ggggtacttt cttggtgtaa cgaactaata gcctgaaaaa aagaagtcat  180
gtgttttcag caaggcaaga aactgtctaa catagtagat aaaacagaga acacttggcc  240
ggaatcaact aagatgttgc tatgttccat tcatcatatt atctccatct gcagagtagt  300
gggttagtgg agggtagaaa acattctcct gaacaactag ttaaacttgg ctttgagttc  360
cacctgtacc acttgcataa tcttgggaaa gtgagttgcc taattcagtg acattaataa  420
atttattaat ttcttctttc aataaaacct ggagagagct tcatatgtat cagcatatgc  480
taaacttgaa agatacaagt agaaaatgga aggaaatata tctgactcaa tagggatagt  540
tcaagggtta aattaaaagt agtaaagtat tataattaat ctgacatggt acctaatata  600
taataatcat gtattaagaa tgccagtcac cattaaaagt caatgtatga ctttaatcta  660
ctcgaggaaa gaaactatgt cttgttcact gttattatct ctaaaatcca taatcagaag  720
agcaccatgt gtatgagcca cacaataaat atctactgta taatatgtct cttcttgttt  780
ttaaccttca tagataagac tctattgaat tgggacatta gtccagcaag ccattctgtc  840
tctgtctctt ctatggaggg aaaggtttaa ccatcaaaga ctaggtgcat ctcccaaaca  900
acctgaattt aatattcaaa tatgtatcta aattcatttg ttacattttt gtgttcagct  960
tacatattac tttttgagcg acatctattc aaggcctact acttgctgct ctacaaaata  1020
ttgccatgct ctatttgccc attaactatt tcttaacctt caagggacat gctcagttct  1080
gatataccaa gatttggtat ttaccctccc agcctacata cttccaatct taagagaaca  1140
atttttagac tacattcaaa tatagacctc tccaccccat caactatttt atctctcctc  1200
tcctatcttt cttgacaaag agtgattaga aatatgcaat                        1240

SEQ ID NO: 1139        moltype =   length =
SEQUENCE: 1139
000

SEQ ID NO: 1140        moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1140
NYWMH                                                              5

SEQ ID NO: 1141        moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 1141
RIDPNSGGTR YNEKFKN                                                 17

SEQ ID NO: 1142        moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1142
DYYMS                                                              5

SEQ ID NO: 1143        moltype = AA  length = 19
FEATURE                Location/Qualifiers
REGION                 1..19
                       note = Description of Artificial Sequence: Synthetic peptide
source                 1..19
                       mol_type = protein
                       organism = synthetic construct
SEQUENCE: 1143
LIRNKAKGFT TEYSASVKG                                               19

SEQ ID NO: 1144        moltype = AA  length = 5
```

```
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1144
RYWMH                                                                        5

SEQ ID NO: 1145        moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 1145
NINPNNGGTD FNEKFKN                                                           17

SEQ ID NO: 1146        moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 1146
RSSQSLVHNN GITYLY                                                            16

SEQ ID NO: 1147        moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1147
IFWMH                                                                        5

SEQ ID NO: 1148        moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 1148
KINPNNGGGD YNEKFKS                                                           17

SEQ ID NO: 1149        moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 1149
RFWMH                                                                        5

SEQ ID NO: 1150        moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 1150
NINPNNGGTD NNERFKS                                                           17

SEQ ID NO: 1151        moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 1151
TLAVPFK                                                                      7
```

```
SEQ ID NO: 1152         moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 1152
TSAMGVS                                                                    7

SEQ ID NO: 1153         moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 1153
HIYWDDDKRY NPSLKS                                                          16

SEQ ID NO: 1154         moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 1154
RSSQSLVHNN GITYLY                                                          16

SEQ ID NO: 1155         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1155
DYTFTNYW                                                                   8

SEQ ID NO: 1156         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1156
IDPNSGGT                                                                   8

SEQ ID NO: 1157         moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 1157
AGDFDV                                                                     6

SEQ ID NO: 1158         moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 1158
GNIHNY                                                                     6

SEQ ID NO: 1159         moltype =   length =
SEQUENCE: 1159
000

SEQ ID NO: 1160         moltype = AA  length = 8
FEATURE                 Location/Qualifiers
REGION                  1..8
                        note = Description of Artificial Sequence: Synthetic peptide
source                  1..8
```

```
                        mol_type = protein
                        organism = synthetic construct
SEQUENCE: 1160
GFTFTDYY                                                        8

SEQ ID NO: 1161         moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 1161
IRNKAKGFTT                                                      10

SEQ ID NO: 1162         moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 1162
VRDINY                                                          6

SEQ ID NO: 1163         moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 1163
QSLLYSTNQE NY                                                   12

SEQ ID NO: 1164         moltype =   length =
SEQUENCE: 1164
000

SEQ ID NO: 1165         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1165
GFTFTRYW                                                        8

SEQ ID NO: 1166         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1166
INPNNGGT                                                        8

SEQ ID NO: 1167         moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1167
ARGTGTGAMD Y                                                    11

SEQ ID NO: 1168         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1168
GYTFTIFW                                                        8
```

```
SEQ ID NO: 1169         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1169
INPNNGGG                                                                8

SEQ ID NO: 1170         moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1170
QSLVHSNGIT H                                                            11

SEQ ID NO: 1171         moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 1171
GYTFTRFW                                                                8

SEQ ID NO: 1172         moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1172
QSLVHSNGNT H                                                            11

SEQ ID NO: 1173         moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 1173
GFSLSTSAMG                                                              10

SEQ ID NO: 1174         moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 1174
IYWDDDK                                                                 7

SEQ ID NO: 1175         moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 1175
ARRRRGYGMD Y                                                            11

SEQ ID NO: 1176         moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 1176
QSVSND                                                                  6
```

```
SEQ ID NO: 1177        moltype =   length =
SEQUENCE: 1177
000

SEQ ID NO: 1178        moltype = AA  length = 23
FEATURE                Location/Qualifiers
REGION                 1..23
                       note = Description of Artificial Sequence: Synthetic peptide
source                 1..23
                       mol_type = protein
                       organism = synthetic construct
SEQUENCE: 1178
DVVMTQTPLS LPVSLGDQAS ISC                                          23

SEQ ID NO: 1179        moltype = AA  length = 32
FEATURE                Location/Qualifiers
REGION                 1..32
                       note = Description of Artificial Sequence: Synthetic
                        polypeptide
source                 1..32
                       mol_type = protein
                       organism = synthetic construct
SEQUENCE: 1179
GVPDRFGGSG SGTDFTLKIS RVEAEDLGVY FC                                32

SEQ ID NO: 1180        moltype = AA  length = 7
FEATURE                Location/Qualifiers
REGION                 1..7
                       note = Description of Artificial Sequence: Synthetic peptide
VARIANT                2
                       note = Phe or Tyr
VARIANT                6
                       note = Arg or Ile
VARIANT                7
                       note = Tyr or Phe
source                 1..7
                       mol_type = protein
                       organism = synthetic construct
SEQUENCE: 1180
GXTFTXX                                                            7

SEQ ID NO: 1181        moltype = AA  length = 16
FEATURE                Location/Qualifiers
REGION                 1..16
                       note = Description of Artificial Sequence: Synthetic peptide
VARIANT                9
                       note = Asn or Ser
VARIANT                12
                       note = Ile or Asn
VARIANT                14
                       note = Tyr or His
source                 1..16
                       mol_type = protein
                       organism = synthetic construct
SEQUENCE: 1181
RSSQSLVHXN GXTXLY                                                  16

SEQ ID NO: 1182        moltype = AA  length = 7
FEATURE                Location/Qualifiers
REGION                 1..7
                       note = Description of Artificial Sequence: Synthetic peptide
VARIANT                4
                       note = Asn or Ser
source                 1..7
                       mol_type = protein
                       organism = synthetic construct
SEQUENCE: 1182
RVSXRFS                                                            7

SEQ ID NO: 1183        moltype =   length =
SEQUENCE: 1183
000

SEQ ID NO: 1184        moltype = AA  length = 17
FEATURE                Location/Qualifiers
REGION                 1..17
                       note = Description of Artificial Sequence: Synthetic peptide
VARIANT                1
```

```
                         note = Asn or Lys
VARIANT                  9
                         note = Thr or Gly
VARIANT                  11
                         note = Phe, Tyr, or Asn
VARIANT                  14
                         note = Lys or Arg
VARIANT                  17
                         note = Asn or Ser
source                   1..17
                         mol_type = protein
                         organism = synthetic construct
SEQUENCE: 1184
XINPNNGGXD XNEXFKX                                              17

SEQ ID NO: 1185          moltype = AA  length = 16
FEATURE                  Location/Qualifiers
REGION                   1..16
                         note = Description of Artificial Sequence: Synthetic peptide
VARIANT                  9
                         note = Asn or Ser
VARIANT                  12
                         note = Ile or Asn
VARIANT                  14
                         note = Tyr or His
source                   1..16
                         mol_type = protein
                         organism = synthetic construct
SEQUENCE: 1185
RSSQSLVHXN GXTXLY                                               16

SEQ ID NO: 1186          moltype = AA  length = 8
FEATURE                  Location/Qualifiers
REGION                   1..8
                         note = Description of Artificial Sequence: Synthetic peptide
VARIANT                  2
                         note = Phe or Tyr
VARIANT                  6
                         note = Arg or Ile
VARIANT                  7
                         note = Tyr or Phe
source                   1..8
                         mol_type = protein
                         organism = synthetic construct
SEQUENCE: 1186
GXTFTXXW                                                        8

SEQ ID NO: 1187          moltype = AA  length = 8
FEATURE                  Location/Qualifiers
REGION                   1..8
                         note = Description of Artificial Sequence: Synthetic peptide
VARIANT                  8
                         note = Thr or Gly
source                   1..8
                         mol_type = protein
                         organism = synthetic construct
SEQUENCE: 1187
INPNNGGX                                                        8

SEQ ID NO: 1188          moltype = AA  length = 11
FEATURE                  Location/Qualifiers
REGION                   1..11
                         note = Description of Artificial Sequence: Synthetic peptide
VARIANT                  6
                         note = Asn or Ser
VARIANT                  9
                         note = Ile or Asn
VARIANT                  11
                         note = Tyr or His
source                   1..11
                         mol_type = protein
                         organism = synthetic construct
SEQUENCE: 1188
QSLVHXNGXT X                                                    11

SEQ ID NO: 1189          moltype = AA  length = 324
FEATURE                  Location/Qualifiers
REGION                   1..324
                         note = Description of Artificial Sequence: Synthetic
```

```
                        polypeptide
source                  1..324
                        mol_type = protein
                        organism = synthetic construct
SEQUENCE: 1189
AKTTPPSVYP LAPGSAAQTN SMVTLGCLVK GYFPEPVTVT WNSGSLSSGV HTFPAVLQSD  60
LYTLSSSVTV PSSPRPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMNTNGS YFVYSKLNVQ KSNWEAGNTF  300
TCSVLHEGLH NHHTEKSLSH SPGK                                        324

SEQ ID NO: 1190         moltype = AA  length = 393
FEATURE                 Location/Qualifiers
REGION                  1..393
                        note = Description of Artificial Sequence: Synthetic
                        polypeptide
source                  1..393
                        mol_type = protein
                        organism = synthetic construct
SEQUENCE: 1190
AKTTPPSVYP LAPGSAAQTN SMVTLGCLVK GYFPEPVTVT WNSGSLSSGV HTFPAVLQSD  60
LYTLSSSVTV PSSPRPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMNTNGS YFVYSKLNVQ KSNWEAGNTF  300
TCSVLHEGLH NHHTEKSLSH SPGLQLDETC AEAQDGELDG LWTTITIFIS LFLLSVCYSA  360
AVTLFKVKWI FSSVVELKQT LVPEYKNMIG QAP                              393

SEQ ID NO: 1191         moltype = AA  length = 330
FEATURE                 Location/Qualifiers
REGION                  1..330
                        note = Description of Artificial Sequence: Synthetic
                        polypeptide
source                  1..330
                        mol_type = protein
                        organism = synthetic construct
SEQUENCE: 1191
AKTTAPSVYP LAPVCGDTTG SSVTLGCLVK GYFPEPVTLT WNSGSLSSGV HTFPAVLQSD  60
LYTLSSSVTV TSSTWPSQSI TCNVAHPASS TKVDKKIEPR GPTIKPCPPC KCPAPNLLGG  120
PSVFIFPPKI KDVLMISLSP IVTCVVVDVS EDDPDVQISW FVNNVEVHTA QTQTHREDYN  180
STLRVVSALP IQHQDWMSGK EFKCKVNNKD LPAPIERTIS KPKGSVRAPQ VYVLPPPEEE  240
MTKKQVTLTC MVTDFMPEDI YVEWTNNGKT ELNYKNTEPV LDSDGSYFMY SKLRVEKKNW  300
VERNSYSCSV VHEGLHNHHT TKSFSRTPGK                                  330

SEQ ID NO: 1192         moltype = DNA  length = 990
FEATURE                 Location/Qualifiers
misc_feature            1..990
                        note = Description of Artificial Sequence: Synthetic
                        polynucleotide
source                  1..990
                        mol_type = other DNA
                        organism = synthetic construct
SEQUENCE: 1192
gctaaaacaa cagccccatc ggtctatcca ctggcccctg tgtgtggaga tacaactggc  60
tcctcggtga ctctaggatg cctggtcaag ggttatttcc ctgagccagt gaccttgacc  120
tggaactctg gatccctgtc cagtggtgtg cacaccttcc cagctgtcct gcagtctgac  180
ctctacaccc tcagcagctc agtgactgta acctcgagca cctggcccag ccagtccatc  240
acctgcaatg tggcccaccc ggcaagcagc accaaggtgg acaagaaaat tgagcccaga  300
gggcccacaa tcaagccctg tcctccatgc aaatgcccag cacctaacct cttgggtgga  360
ccatccgtct tcatcttccc tccaaagatc aaggatgtac tcatgatctc cctgagcccc  420
atagtcacat gtgtggtggt ggatgtgagc gaggatgacc cagatgtcca gatcagctgg  480
tttgtgaaca acgtggaagt acacacagct cagacacaaa cccatagaga ggattacaac  540
agtactctcc gggtggtcag tgccctcccc atccagcacc aggactggat gagtggcaag  600
gagttcaaat gcaaggtcaa caacaaagac ctcccagcgc ccatcgagag aaccatctca  660
aaacccaaag ggtcagtaag agctccacag gtatatgtct tgcctccacc agaagaagag  720
atgactaaga aacaggtcac tctgacctgc atggtcacag acttcatgcc tgaagacatt  780
tacgtggagt ggaccaacaa cgggaaaaca gagctaaact acaagaacac tgaaccagtc  840
ctggactctg atggttctta cttcatgtac agcaagctga gagtggaaaa gaagaactgg  900
gtggaaagaa atagctactc ctgttcagtg gtccacgagg gtctgcacaa tcaccacacg  960
actaagagct tctcccggac tccgggtaaa                                  990

SEQ ID NO: 1193         moltype = AA  length = 335
FEATURE                 Location/Qualifiers
REGION                  1..335
                        note = Description of Artificial Sequence: Synthetic
                        polypeptide
source                  1..335
                        mol_type = protein
```

```
                        organism = synthetic construct
SEQUENCE: 1193
AKTTAPSVYP LVPVCGGTTG SSVTLGCLVK GYFPEPVTLT WNSGSLSSGV HTFPALLQSG  60
LYTLSSSVTV TSNTWPSQTI TCNVAHPASS TKVDKKIEPR VPITQNPCPP HQRVPPCAAP  120
DLLGGPSVFI FPPKIKDVLM ISLSPMVTCV VVDVSEDDPD VQISWFVNNV EVHTAQTQTH  180
REDYNSTLRV VSALPIQHQD WMSGKEFKCK VNNRALPSPI EKTISKPRGP VRAPQVYVLP  240
PPAEEMTKKE FSLTCMITGF LPAEIAVDWT SNGRTEQNYK NTATVLDSDG SYFMYSKLRV  300
QKSTWERGSL FACSVVHEVL HNHLTTKTIS RSLGK                            335

SEQ ID NO: 1194         moltype = AA  length = 404
FEATURE                 Location/Qualifiers
REGION                  1..404
                        note = Description of Artificial Sequence: Synthetic
                         polypeptide
source                  1..404
                        mol_type = protein
                        organism = synthetic construct
SEQUENCE: 1194
KTTPPSVYPL APGCGDTTGS SVTLGCLVKG YFPESVTVTW NSGSLSSSVH TFPALLQSGL  60
YTMSSSVTVP SSTWPSQTVT CSVAHPASST TVDKKLEPSG PISTINPCPP CKECHKCPAP  120
NLEGGPSVFI FPPNIKDVLM ISLTPKVTCV VVDVSEDDPD VQISWFVNNV EVHTAQTQTH  180
REDYNSTIRV VSTLPIQHQD WMSGKEFKCK VNNKDLPSPI ERTISKIKGL VRAPQVYILP  240
PPAEQLSRKD VSLTCLVVGF NPGDISVEWT SNGHTEENYK DTAPVLDSDG SYFIYSKLNM  300
KTSKWEKTDS FSCNVRHEGL KNYYLKKTIS RSPGLDLDDI CAEAKDGELD GLWTTITIFI  360
SLFLLSVCYS ASVTLFKVKW IFSSVVELKQ KISPDYRNMI GQGA                  404

SEQ ID NO: 1195         moltype = AA  length = 403
FEATURE                 Location/Qualifiers
REGION                  1..403
                        note = Description of Artificial Sequence: Synthetic
                         polypeptide
source                  1..403
                        mol_type = protein
                        organism = synthetic construct
SEQUENCE: 1195
KTTAPSVYPL APVCGGTTGS SVTLGCLVKG YFPEPVTLTW NSGSLSSGVH TFPALLQSGL  60
YTLSSSVTVT SNTWPSQTIT CNVAHPASST KVDKKIEPRV PITQNPCPPL KECPPCAAPD  120
LLGGPSVFIF PPKIKDVLMI SLSPMVTCVV VDVSEDDPDV QISWFVNNVE VHTAQTQTHR  180
EDYNSTLRVV SALPIQHQDW MSGKEFKCKV NNRALPSPIE KTISKPRGPV RAPQVYVLPP  240
PAEEMTKKEF SLTCMITGFL PAEIAVDWTS NGRTEQNYKN TATVLDSDGS YFMYSKLRVQ  300
KSTWERGSLF ACSVVHEGLH NHLTTKTISR SLGLDLDDVC TEAQDGELDG LWTTITIFIS  360
LFLLSVCYSA SVTLFKVKWI FSSVVELKQK ISPDYRNMIG QGA                   403

SEQ ID NO: 1196         moltype = AA  length = 398
FEATURE                 Location/Qualifiers
REGION                  1..398
                        note = Description of Artificial Sequence: Synthetic
                         polypeptide
source                  1..398
                        mol_type = protein
                        organism = synthetic construct
SEQUENCE: 1196
TTTAPSVYPL VPGCSDTSGS SVTLGCLVKG YFPEPVTVKW NYGALSSGVR TVSSVLQSGF  60
YSLSSLVTVP SSTWPSQTVI CNVAHPASKT ELIKRIEPRI PKPSTPPGSS CPPGNILGGP  120
SVFIFPPKPK DALMISLTPK VTCVVVDVSE DDPDVHVSWF VDNKEVHTAW TQPREAQYNS  180
TFRVVSALPI QHQDWMRGKE FKCKVNNKAL PAPIERTISK PKGRAQTPQV YTIPPPREQM  240
SKKKVSLTCL VTNFFSEAIS VEWERNGELE QDYKNTPPIL DSDGTYFLYS KLTVDTDSWL  300
QGEIFTCSVV HEALHNHHTQ KNLSRSPELE LNETCAEAQD GELDGLWTTI TIFISLFLLS  360
VCYSASVTLF KVKWIFSSVV QVKQTAIPDY RNMIGQGA                         398

SEQ ID NO: 1197         moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 1197
ADAAPTVSIF PPSSEQLTSG GASVVCFLNN FYPKDINVKW KIDGSERQNG VLNSWTDQDS  60
KDSTYSMSST LTLTKDEYER HNSYTCEATH KTSTSPIVKS FNRNEC                106

SEQ ID NO: 1198         moltype = DNA  length = 318
FEATURE                 Location/Qualifiers
misc_feature            1..318
                        note = Description of Artificial Sequence: Synthetic
                         polynucleotide
source                  1..318
                        mol_type = other DNA
```

```
                         organism = synthetic construct
SEQUENCE: 1198
gcagatgctg caccaactgt atccatcttc ccaccatcca gtgagcagtt aacatctgga  60
ggtgcctcag tcgtgtgctt cttgaacaac ttctacccca aagacatcaa tgtcaagtgg  120
aagattgatg gcagtgaacg acaaaatggc gtcctgaaca gttggactga tcaggacagc  180
aaagacagca cctacagcat gagcagcacc ctcacgttga ccaaggacga gtatgaacga  240
cataacagct atacctgtga ggccactcac aagacatcaa cttcacccat tgtcaagagc  300
ttcaacagga atgagtgt                                                318

SEQ ID NO: 1199          moltype = AA  length = 105
FEATURE                  Location/Qualifiers
REGION                   1..105
                         note = Description of Artificial Sequence: Synthetic
                          polypeptide
source                   1..105
                         mol_type = protein
                         organism = synthetic construct
SEQUENCE: 1199
QPKSSPSVTL FPPSSEELET NKATLVCTIT DFYPGVVTVD WKVDGTPVTQ GMETTQPSKQ  60
SNNKYMASSY LTLTARAWER HSSYSCQVTH EGHTVEKSLS RADCS                  105

SEQ ID NO: 1200          moltype = AA  length = 104
FEATURE                  Location/Qualifiers
REGION                   1..104
                         note = Description of Artificial Sequence: Synthetic
                          polypeptide
source                   1..104
                         mol_type = protein
                         organism = synthetic construct
SEQUENCE: 1200
QPKSTPTLTV FPPSSEELKE NKATLVCLIS NFSPSGVTVA WKANGTPITQ GVDTSNPTKE  60
GNKFMASSFL HLTSDQWRSH NSFTCQVTHE GDTVEKSLSP AECL                   104

SEQ ID NO: 1201          moltype = AA  length = 104
FEATURE                  Location/Qualifiers
REGION                   1..104
                         note = Description of Artificial Sequence: Synthetic
                          polypeptide
source                   1..104
                         mol_type = protein
                         organism = synthetic construct
SEQUENCE: 1201
QPKSTPTLTM FPPSPEELQE NKATLVCLIS NFSPSGVTVA WKANGTPITQ GVDTSNPTKE  60
DNKYMASSFL HLTSDQWRSH NSFTCQVTHE GDTVEKSLSP AECL                   104

SEQ ID NO: 1202          moltype = AA  length = 329
FEATURE                  Location/Qualifiers
REGION                   1..329
                         note = Description of Artificial Sequence: Synthetic
                          polypeptide
source                   1..329
                         mol_type = protein
                         organism = synthetic construct
SEQUENCE: 1202
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 1203          moltype = DNA  length = 987
FEATURE                  Location/Qualifiers
misc_feature             1..987
                         note = Description of Artificial Sequence: Synthetic
                          polynucleotide
source                   1..987
                         mol_type = other DNA
                         organism = synthetic construct
SEQUENCE: 1203
gccagcacaa aagggcccag tgtgttcccg ctcgcaccaa gcagcaaatc aacgtcaggc  60
ggcacagccg cgttgggttg ccttgtaaaa gactacttcc cagaaccagt tacggtgtca  120
tggaacagtg gtgcactcac gagcggcgtt cataccttcc ccgccgtact tcagagttca  180
ggtctttact cactttccag cgtggtcaca gtaccgtcaa gctctcttgg aacacagaca  240
tatatctgta acgtaaatca taagcctagc aataccaaag tcgataaacg agtggaaccc  300
aagagttgtg ataaaaccca cacctgtccc ccttgcccgg caccggaact gctgggtggt  360
ccatcagtat tcttgtttcc gcctaagcca aaggacacac tgatgatatc cagaactcca  420
gaggttacgt gcgtagtcgt ggacgtcagt catgaagacc ccgaagttaa gttcaactgg  480
tacgtggatg gtgtggaagt acataatgcg aagacgaaac ccagggaaga acaatataac  540
```

```
tcaacttata gggtagtcag cgtcttgact gtacttcacc aagattggtt gaatggcaaa  600
gagtacaaat gcaaggtaag caacaaagca ttgcctgcgc caatcgaaaa gactatctca  660
aaagcaaagg gccagccacg cgaaccacaa gtgtatacat tgccgcccag tcgggaagaa  720
atgacgaaaa atcaagtcag tctcacatgc ctcgtgaaag gattttatcc ctctgacata  780
gctgtggagt gggaaagtaa tggccaaccc gaaaataatt acaaaacgac gcctcccgtt  840
ttggactcag atgggagttt tttcctttac agtaagctga cggttgacaa aagcaggtgg  900
caacaaggga acgtcttttc ttgtagtgtg atgcatgagg cgctccacaa tcattacact  960
caaaaatcct tgagcctgtc tccaggc                                      987

SEQ ID NO: 1204        moltype = AA  length = 326
FEATURE                Location/Qualifiers
REGION                 1..326
                       note = Description of Artificial Sequence: Synthetic
                        polypeptide
source                 1..326
                       mol_type = protein
                       organism = synthetic construct
SEQUENCE: 1204
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDISVEW ESNGQPENNY KTTPPMLDSD GSFFLYSKLT VDKSRWQQGN  300
VFSCSVMHEA LHNHYTQKSL SLSPGK                                       326

SEQ ID NO: 1205        moltype = AA  length = 377
FEATURE                Location/Qualifiers
REGION                 1..377
                       note = Description of Artificial Sequence: Synthetic
                        polypeptide
source                 1..377
                       mol_type = protein
                       organism = synthetic construct
SEQUENCE: 1205
ASTKGPSVFP LAPCSRSTSG GTAALGCLVK DYFPEPVTVS WNSGALTSGV HTFPAVLQSS  60
GLYSLSSVVT VPSSSLGTQT YTCNVNHKPS NTKVDKRVEL KTPLGDTTHT CPRCPEPKSC  120
DTPPPCPRCP EPKSCDTPPP CPRCPEPKSC DTPPPCPRCP APELLGGPSV FLFPPKPKDT  180
LMISRTPEVT CVVVDVSHED PEVQFKWYVD GVEVHNAKTK PREEQYNSTF RVVSVLTVLH  240
QDWLNGKEYK CKVSNKALPA PIEKTISKTK GQPREPQVYT LPPSREEMTK NQVSLTCLVK  300
GFYPSDIAVE WESSGQPENN YNTTPPMLDS DGSFFLYSKL TVDKSRWQQG NIFSCSVMHE  360
ALHNRFTQKS LSLSPGK                                                 377

SEQ ID NO: 1206        moltype = AA  length = 327
FEATURE                Location/Qualifiers
REGION                 1..327
                       note = Description of Artificial Sequence: Synthetic
                        polypeptide
source                 1..327
                       mol_type = protein
                       organism = synthetic construct
SEQUENCE: 1206
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 1207        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1207
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                 106

SEQ ID NO: 1208        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1208
```

```
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                106

SEQ ID NO: 1209        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1209
GQPKAAPSVT LFPPSSEELQ ANKATLVCLI SDFYPGAVTV AWKADSSPVK AGVETTTPSK  60
QSNNKYAASS YLSLTPEQWK SHKSYSCQVT HEGSTVEKTV APTECS                106

SEQ ID NO: 1210        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1210
GQPKAAPSVT LFPPSSEELQ ANKATLVCLI SDFYPGAVKV AWKADGSPVN TGVETTTPSK  60
QSNNKYAASS YLSLTPEQWK SHRSYSCQVT HEGSTVEKTV APAECS                106

SEQ ID NO: 1211        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1211
GQPKAAPSVT LFPPSSEELQ ANKATLVCLV SDFNPGAVTV AWKADGSPVK VGVETTKPSK  60
QSNNKYAASS YLSLTPEQWK SHRSYSCRVT HEGSTVEKTV APAECS                106

SEQ ID NO: 1212        moltype = AA  length = 106
FEATURE                Location/Qualifiers
REGION                 1..106
                       note = Description of Artificial Sequence: Synthetic
                        polypeptide
source                 1..106
                       mol_type = protein
                       organism = synthetic construct
SEQUENCE: 1212
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                106

SEQ ID NO: 1213        moltype = DNA  length = 318
FEATURE                Location/Qualifiers
misc_feature           1..318
                       note = Description of Artificial Sequence: Synthetic
                        polynucleotide
source                 1..318
                       mol_type = other DNA
                       organism = synthetic construct
SEQUENCE: 1213
actgtcgcag caccttctgt cttcatcttt ccgccaagcg atgaacagtt gaaatctgga  60
acagcgtccg tggtgtgcct gctcaacaac ttctatcctc gggaagcgaa ggtgcaatgg  120
aaggtagata atgctcttca gagtggcaat tcccaagagt cagttacgga gcaagatagc  180
aaggacagca cgtattccct gtctagtacg ttgactcttt ccaaggctga ctatgaaaag  240
cacaaggtgt atgcctgtga agtaacccac caaggtctct caagtcctgt aactaagagc  300
tttaatcgag gagaatgc                                                318

SEQ ID NO: 1214        moltype = AA  length = 40
FEATURE                Location/Qualifiers
REGION                 1..40
                       note = Description of Artificial Sequence: Synthetic
                        polypeptide
VARIANT                1..40
                       note = This sequence may encompass 0 to 8 GGGGS repeating
                        units
source                 1..40
                       mol_type = protein
                       organism = synthetic construct
SEQUENCE: 1214
```

```
GGGGSGGGGS GGGGSGGGGS GGGGSGGGGS GGGGSGGGGS                       40

SEQ ID NO: 1215        moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 1215
DIQMTQSPAS LSASVGETVT ITCRASGNIH NYLAWYQQRQ GKSPQLLVYN AKTLPDGVPS  60
RFSGSGSGTQ YSLKINSLQP EDFGSYCCQH FWSTPLTFGA GTKLELK                107

SEQ ID NO: 1216        moltype = AA  length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 1216
DIVMSQSPSS LAVSVGEKVT MSCKSSQSLL YSTNQENYLA WYQQKPGQSP KLLIYWASSR  60
ESGVPDRFTG SGSGTDFTLT ISSVKAEDLA VYYCQQYYSY PRTFGGGTKL EIK         113

SEQ ID NO: 1217        moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 1217
DVVMTQTPLS LPVSLGDQAS ISCRSSQSLV HNNGITYLYW YLQKPGQSPK LLIYRVSNRF  60
SGVPDRFGGS GSGTDFTLKI SRVEAEDLGV YFCFQGTHVP RTFGGGTKLE IK          112

SEQ ID NO: 1218        moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 1218
DVVMTQTPLS LPVSLGDHAS ISCRSSQSLV HSNGITHLYW YLQRPGQTPK LLIYRVSNRF  60
SGVPDRFSGS GSGTDFTLKI SSVEAEDLGV YFCFQGTHVP RTFGGGTKLE IE          112

SEQ ID NO: 1219        moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 1219
DVVMTQTPLS LPVSLGDQAS ISCRSSQSLV HSNGNTHLYW YLQKPGQSPK LLIYRVSSRF  60
SGVPDRFSGS GSGTDFTLKI SRVEAEDLGV YFCFQGTHVP RTFGGGTKLE IK          112

SEQ ID NO: 1220        moltype = AA  length = 107
FEATURE                Location/Qualifiers
REGION                 1..107
                       note = Description of Artificial Sequence: Synthetic
                        polypeptide
source                 1..107
                       mol_type = protein
                       organism = synthetic construct
SEQUENCE: 1220
SIVMTQTPKF LLVSAGDRVT ITCKASQSVS NDVAWYQQKP GQSPKLLIYY ASNRCTGVPD  60
RFTGSGYGTD FTFTISTVQA EDLAVYFCQQ DYRSPLTFGA GTKLELK                107

SEQ ID NO: 1221        moltype = AA  length = 113
FEATURE                Location/Qualifiers
REGION                 1..113
                       note = Description of Artificial Sequence: Synthetic
                        polypeptide
```

```
source                  1..113
                        mol_type = protein
                        organism = synthetic construct
SEQUENCE: 1221
QVQLQQPGAE LVKPGASVKL SCKASDYTFT NYWMHWVKQR PGRGLEWIGR IDPNSGGTRY  60
NEKFKNKATL TVDKPSSTAY MHLSSLTSED SAVYYCAGDF DVWGTGTTVT VSS         113

SEQ ID NO: 1222         moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 1222
EVQLVESGGA LVQPGGSLSL SCAASGFTFT DYYMSWVRQP PGKALEWLAL IRNKAKGFTT  60
EYSASVKGRF TISRDNSQSI LLFQMNDLRA DDSATYYCVR DINYWGQGTT LTVSS       115

SEQ ID NO: 1223         moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 1223
QVQLQQPGTE LVKPGSSVNL SCKASGFTFT RYWMHWVKER PGHGLEWIGN INPNNGGTDF  60
NEKFKNKATL TVHKSSTTVF IQLSSLTSED SAVYYCARGT GTGAMDYWGQ GTSVT       115

SEQ ID NO: 1224         moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 1224
QVQLQQPGTE LVKPGASVKL SCKASGYTFT IFWMHWVKQR PGHGLEWIGK INPNNGGGDY  60
NEKFKSKATL TVDKSSTTAY LQLSSLTSED SAVYYCARGT GTGAMDYWGQ GTSVT       115

SEQ ID NO: 1225         moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 1225
QVQLQQPGTE LVKPGASVKL SCKASGYTFT RFWMHWVKQR PGQGLEWIGN INPNNGGTDN  60
NERFKSKATL TVDRSSSTAY MQLSSLTSED SAVYYCARGT GTGAMDYWGQ GTSVT       115

SEQ ID NO: 1226         moltype = AA  length = 115
FEATURE                 Location/Qualifiers
REGION                  1..115
                        note = Description of Artificial Sequence: Synthetic
                         polypeptide
source                  1..115
                        mol_type = protein
                        organism = synthetic construct
SEQUENCE: 1226
QITLKESGPG ILQSSQTLSL TCSFSGFSLS TSAMGVSWIR QPSGEGLEWL AHIYWDDDKR  60
YNPSLKSRLT ISKDTSRNQV FLKITSVDTA DTATYYCARR RRGYGMDYWG QGTSV       115
```